United States Patent
Amann et al.

(10) Patent No.: US 11,453,722 B2
(45) Date of Patent: Sep. 27, 2022

(54) BISPECIFIC ANTIGEN BINDING MOLECULE FOR A COSTIMULATORY TNF RECEPTOR

(71) Applicant: Hoffmann-La Roche Inc., Little Falls, NJ (US)

(72) Inventors: Maria Amann, Schlieren (CH); Sandra Grau-Richards, Schlieren (CH); Christian Klein, Schlieren (CH); Mudita Pincha, Schlieren (CH); Pablo Umaña, Schlieren (CH)

(73) Assignee: Hoffmann La-Roche Inc., Little Falls, NJ (US)

(*) Notice: Subject to any disclaimer, the term of this patent is extended or adjusted under 35 U.S.C. 154(b) by 0 days.

(21) Appl. No.: 16/584,931

(22) Filed: Sep. 26, 2019

(65) Prior Publication Data

US 2020/0277392 A1   Sep. 3, 2020

Related U.S. Application Data

(63) Continuation of application No. PCT/EP2018/057769, filed on Mar. 27, 2018.

(30) Foreign Application Priority Data

Mar. 29, 2017   (EP) .................................. 17163561

(51) Int. Cl.
*C07K 16/28* (2006.01)
*C07K 16/18* (2006.01)

(52) U.S. Cl.
CPC .......... *C07K 16/2878* (2013.01); *C07K 16/18* (2013.01); *C07K 2317/31* (2013.01); *C07K 2317/35* (2013.01); *C07K 2317/515* (2013.01); *C07K 2317/52* (2013.01); *C07K 2317/522* (2013.01); *C07K 2317/55* (2013.01); *C07K 2317/565* (2013.01); *C07K 2317/64* (2013.01); *C07K 2317/92* (2013.01)

(58) Field of Classification Search
None
See application file for complete search history.

(56) References Cited

U.S. PATENT DOCUMENTS

| | | | |
|---|---|---|---|
| 5,731,168 A | 3/1998 | Carter et al. | |
| 7,695,936 B2 | 4/2010 | Carter et al. | |
| 10,464,981 B2 | 5/2019 | Amann et al. | |
| 10,392,445 B2 | 8/2019 | Amann et al. | |
| 10,526,413 B2 | 7/2020 | Amann. et al. | |
| 11,306,154 B2 | 4/2022 | Amann et al. | |
| 11,267,903 B2 | 8/2022 | Amann et al. | |
| 2010/0291549 A1* | 11/2010 | Ramakrishnan | ............................ G01N 33/57407 435/6.16 |
| 2015/0001056 A1 | 1/2015 | Bourquin et al. | |
| 2015/0010567 A1* | 1/2015 | Bourquin | ............... C07K 16/32 424/136.1 |
| 2015/0196663 A1* | 7/2015 | Shusta | .................. A61K 9/0085 424/178.1 |
| 2015/0284416 A1 | 8/2015 | Zhao | |
| 2015/0266947 A1* | 9/2015 | Sierks | ................ G01N 33/6896 424/135.1 |
| 2016/0002357 A1* | 1/2016 | May | ..................... C07K 16/468 424/136.1 |
| 2017/0073395 A1 | 3/2017 | Finlay et al. | |
| 2017/0107285 A1 | 4/2017 | Jensen | |
| 2017/0247467 A1 | 8/2017 | Amann et al. | |
| 2017/0355756 A1* | 12/2017 | Julien | ..................... C12N 15/86 |
| 2019/0016771 A1 | 1/2019 | Amann et al. | |
| 2019/0211113 A1 | 11/2019 | Amann et al. | |
| 2019/0352387 A1* | 11/2019 | Sampei | .................. C07K 16/18 |
| 2020/0071411 A1 | 3/2020 | Amann et al. | |
| 2020/0231691 A1 | 7/2020 | Grau-Richards et al. | |
| 2020/0270321 A1 | 8/2020 | Amann et al. | |
| 2020/0392237 A1 | 12/2020 | Bacac et al. | |
| 2021/0324108 A1 | 10/2021 | Amann et al. | |
| 2022/0025046 A1 | 1/2022 | Amann et al. | |
| 2022/0073646 A1 | 3/2022 | Amann et al. | |

FOREIGN PATENT DOCUMENTS

| | | |
|---|---|---|
| CN | 103328632 | 9/2013 |
| CN | 104203981 | 10/2014 |
| CN | 109153728 | 4/2019 |
| EP | 1173766 B1 | 9/2004 |
| EP | 1817345 B1 | 5/2009 |
| JP | 2013-543373 | 5/2013 |
| JP | 2016-525551 | 8/2016 |
| WO | 02/020565 A2 | 3/2002 |
| WO | WO 2008068048 * | 6/2008 |
| WO | 2009/089998 A1 | 7/2009 |
| WO | 2010/145792 A1 | 12/2010 |

(Continued)

OTHER PUBLICATIONS

Chen "Enhancement and destruction of antibody function by somatic mutation: unequal occurrence is controlled by V gene combinatorial associations" EMBO 14(12):2784-2794 (Year: 1995).*
Kussie "A Single Engineered Amino Acid Substitution Changes Antibody Fine Specificity" J immunol 152(1):146-52 (Year: 1994).*
Koenig "Mutational landscape of antibody variable domains reveals a switch modulating the interdomain conformational dynamics and antigen binding" PNAS E486-E495 (Year: 2017).*
Stamova "Cancer Immunotherapy by Retargeting of Immune Effector Cells via Recombinant Bispecific Antibody Constructs" Antibodies 2012, 1, 172-198; (Year: 2012).*

(Continued)

*Primary Examiner* — Adam Weidner
(74) *Attorney, Agent, or Firm* — Yan Qi

(57) ABSTRACT

The invention relates to novel bispecific antigen binding molecules comprising (a) at least one moiety capable of specific binding to OX40, and (b) at least one moiety capable of specific binding to tenascin C (TnC), and to methods of producing these molecules and to methods of using the same.

13 Claims, 17 Drawing Sheets

Specification includes a Sequence Listing.

(56) References Cited

FOREIGN PATENT DOCUMENTS

| WO | 2012/020038 A1 | 2/2012 |
| WO | 2012/130831 A1 | 10/2012 |
| WO | 2013/123061 A1 | 8/2013 |
| WO | 2015/155753 A2 | 10/2015 |
| WO | 2016/120216 A1 | 8/2016 |
| WO | 2017/055398 A2 | 4/2017 |
| WO | 2017/060144 A1 | 4/2017 |
| WO | 2012/198335 A1 | 10/2021 |

OTHER PUBLICATIONS

Brinkmann "The making of bispecific antibodies" MABS 2017, vol. 9, No. 2, 182-212 (Year: 2017).*

Balza, E., et al., "Production and characterization of monoclonal antibodies specific for different epitopes of human tenascin" FEBS LETT 332(1-2):39-43 (Oct 1, 1993).

Baumann, R., et al., "Functional expression of CD134 by neutrophils" Eur J Immunol 34(8):2268-2275 (Aug. 1, 2004).

Borsi, L., et al., "Expression of different tenascin isoforms in normal, hyperplastic and neoplastic human breast tissues" Int J Cancer 52(5):688-692 (Nov 11, 1992).

Brack, S., et al., "Tumor-Targeting Properties of Novel Antibodies Specific to the Large Isoform of Tenascin-C" Clin Cancer Res 12(10):3200-3208 (May 15, 2006).

Carnemolla, B., et al., "Comparison of human tenascin expression in normal, Simian-virus-40-transformed and tumor-derived cell lines" Eur J Biochem 205(2):561-567 (Apr 15, 1992).

Chiquet-Ehrismann, R., et al., "Tenascins: regulation and putative functions during pathological stress" J Pathol 200(4):488-499 (Jul. 1, 2003).

Croft, M. et al., "The significance of OX40 and OX40L to T-cell biology and immune disease" Immunol Rev 229(1):173-191 (May 1, 2009).

Gramaglia, I., et al., "Ox-40 Ligand: A Potent Costimulatory Molecule for Sustaining Primary CD4 T Cell Responses" J Immunol 161(12):6510-6517 (Aug. 13, 1998).

Hanamura, N., et al., "Expression of fibronectin and tenascin-C mRNA by myofibroblasts, vascular cells and epithelial cells in human colon adenomas and carcinomas" Int J Cancer 73(1):10-15 (Aug. 31, 1997).

Hsia, H., et al., "Meet the Tenascins: Multifunctional and Mysterious" J Biol Chem 280(29):26641-26644 (Jul. 22, 2005).

"International Preliminary Report on Patentability—PCT/EP2018/057769":pp. 1-12 (Oct. 10, 2019).

"International Search Report—PCT/EP2018/057769":pp. 1-22 (Jul. 27, 2018).

Jensen, S.M., et al., "Signaling Through OX40 Enhances Antitumor Immunity" Semin Oncol 37(5):524-532 (Oct. 1, 2010).

Orend, G., et al., "Tenascin-C induced signaling in cancer" Cancer Lett 244(2):143-163 (Dec. 8, 2006).

Silacci, M., et al., "Human monoclonal antibodies to domain C of tenascin-C selectively target solid tumors in vivo" Protein Eng Des Sel 19(10):471-478 (Oct. 19, 2006).

Song, J. et al., "Activation of NF-kB1 by OX40 Contributes to Antigen-Driven T Cell Expansion and Survival" J Immunol 180(11):7240-7248 (Jun. 1, 2008).

Wang, Yu-Cai, et al., "Generation and Identification of Monoclonal Antibodies Against FNIII Domain D of Human Tenascin-C" Hybridoma 29(1):13-16 (Jan. 31, 2010).

Watts, T., "TNF/TNFR family members in costimulation of T cell responses" Annu Rev Immunol 23:23-68 (Sep. 2005).

Weinberg, A., et al., "Engagement of the OX-40 Receptor In Vivo Enhances Antitumor Immunity" J Immunol 164(4):2160-2169 (Feb. 15, 2000).

Weinberg, A., et al., "The generation of T cell memory: a review describing the molecular and cellular events following OX40 (CD134) engagement" J Leukocyte Biol 75(6):962-972 (Jun. 1, 2004).

Yoshida, T., et al., "Co-expression of tenascin and fibronectin in epithelial and stromal cells of benign lesions and ductal carcinomas in the human breast" J Pathol 182(4):421-428 (Mar. 6, 1997).

Kussie et al., "A Single Engineered Amino Acid Substitution Changes Antibody Fine Specificity" J Immunol 152:146-152 (1994).

Brinkmann et al., "The making of bispecific antibodies" MABS 9(2):182-212 (2017).

Chen et al., "Enhancement and destruction of antibody function by somatic mutation: unequal occurrence is controlled by V gene combinatorial associations" The EMBO Journal 14(12):2784-2794 (1995).

Horning et al., "Evaluation Combinations of costimulatory antibody—ligand fusion proteins for targeted cancer immunotherapy" Cancer Immunol Immunother 63:1369-1380 (2013).

* cited by examiner

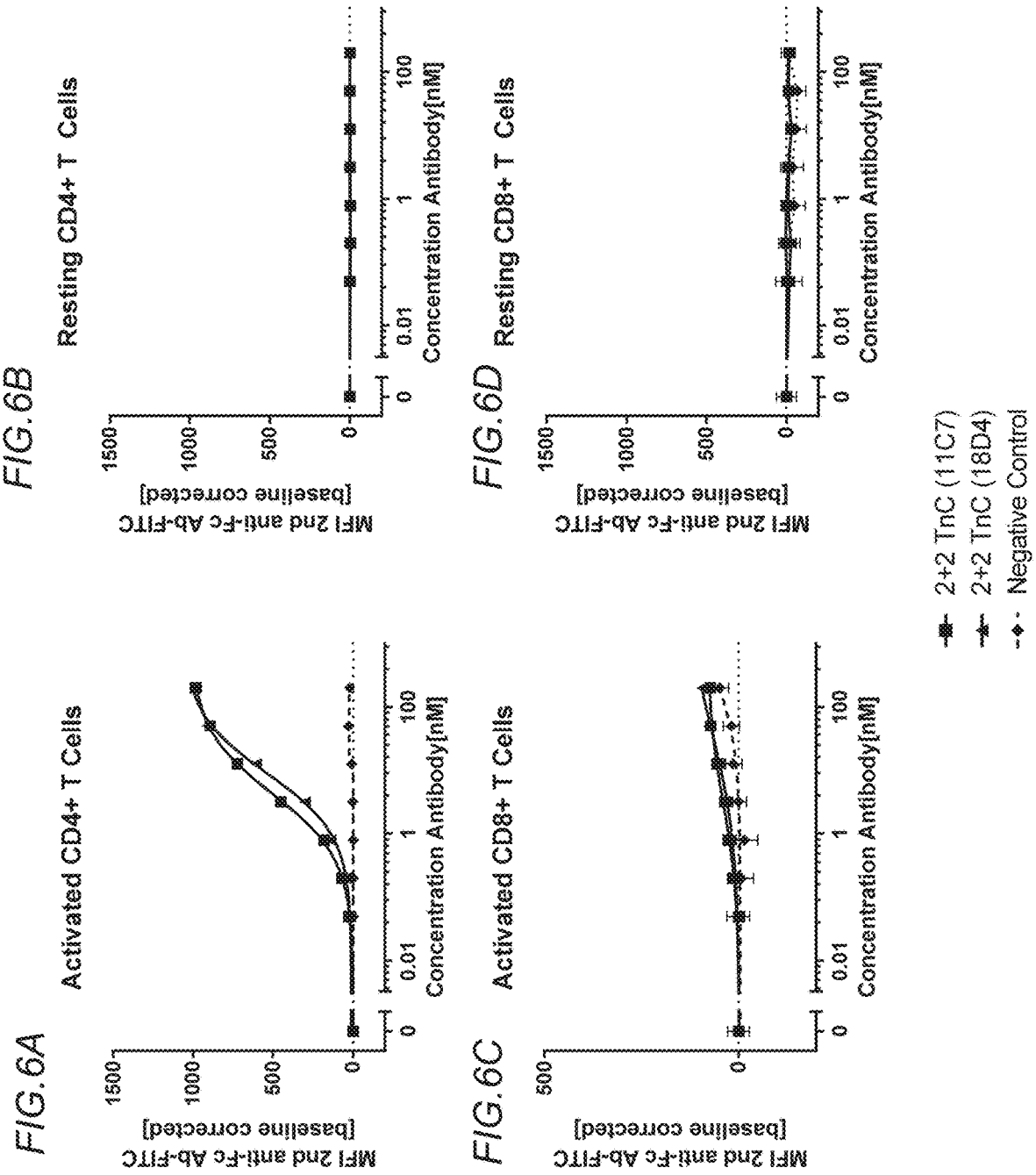

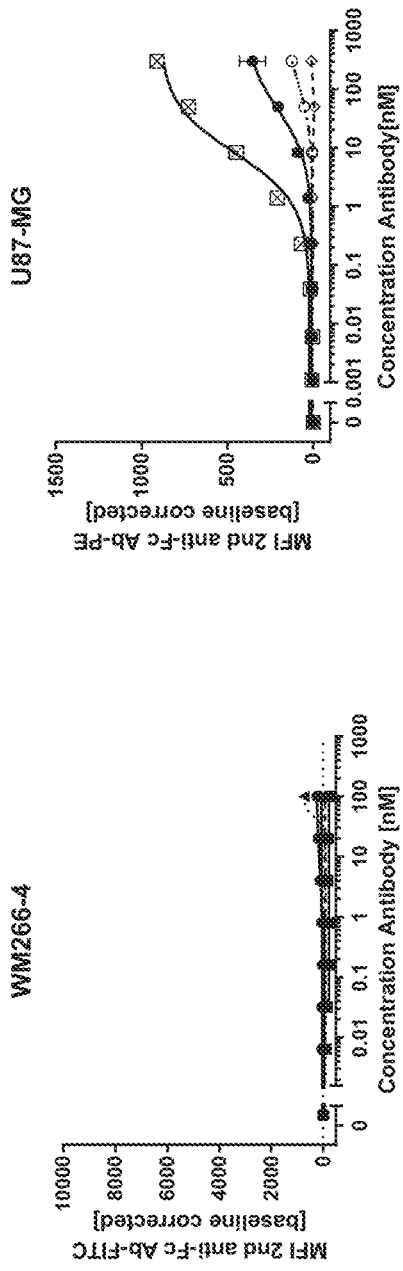
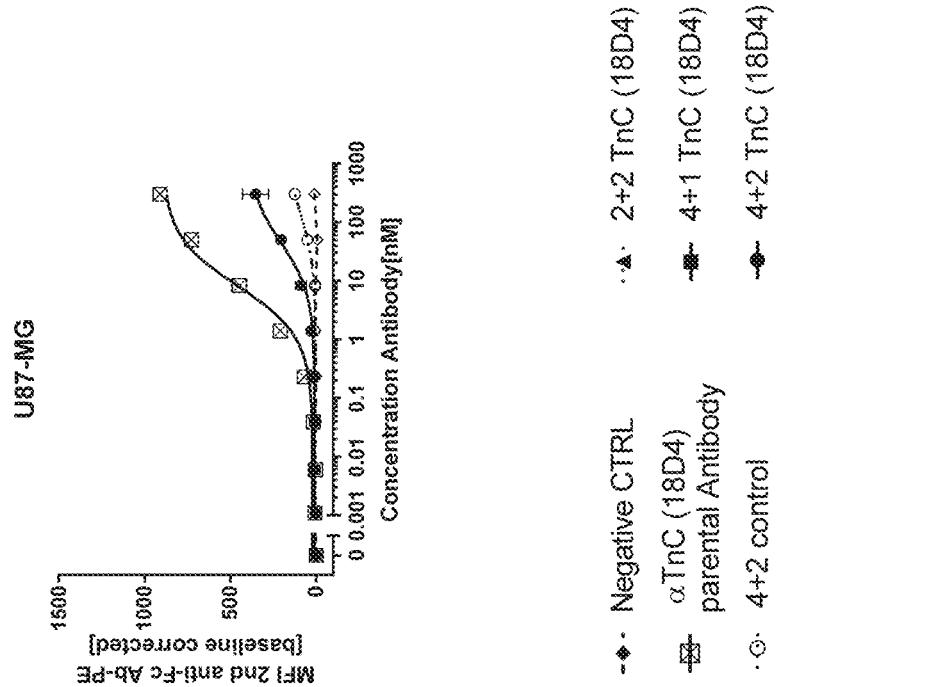
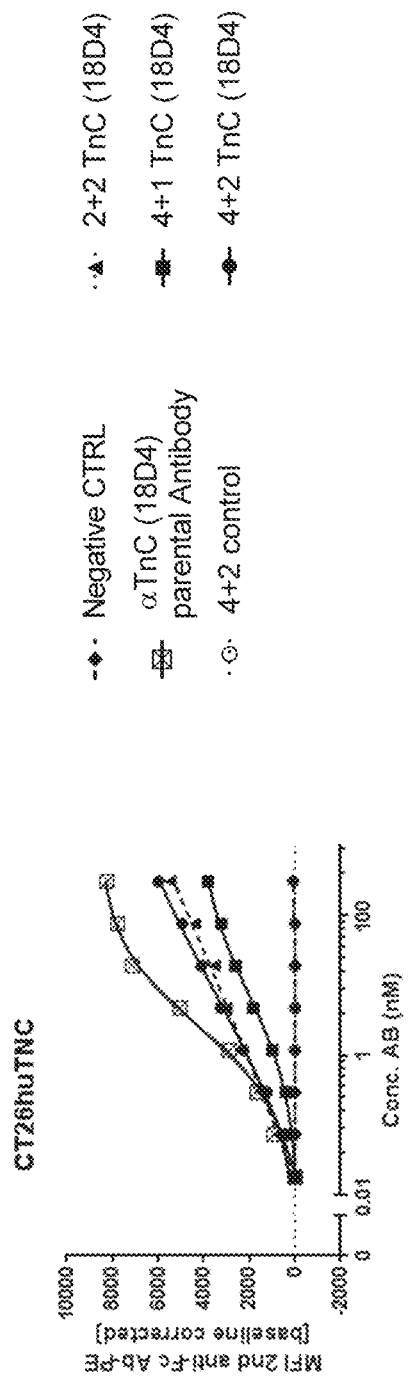
FIG. 10A
FIG. 10B
FIG. 10C

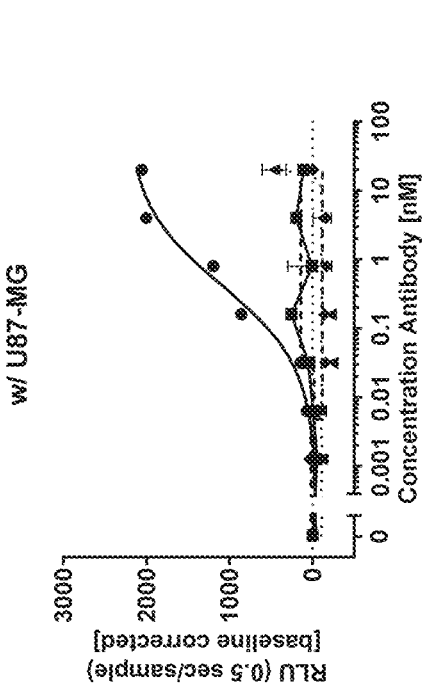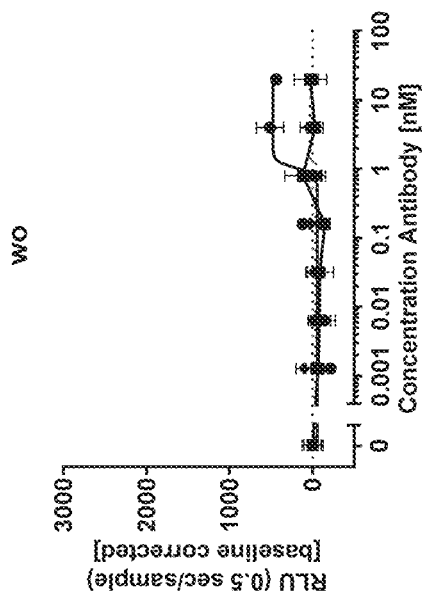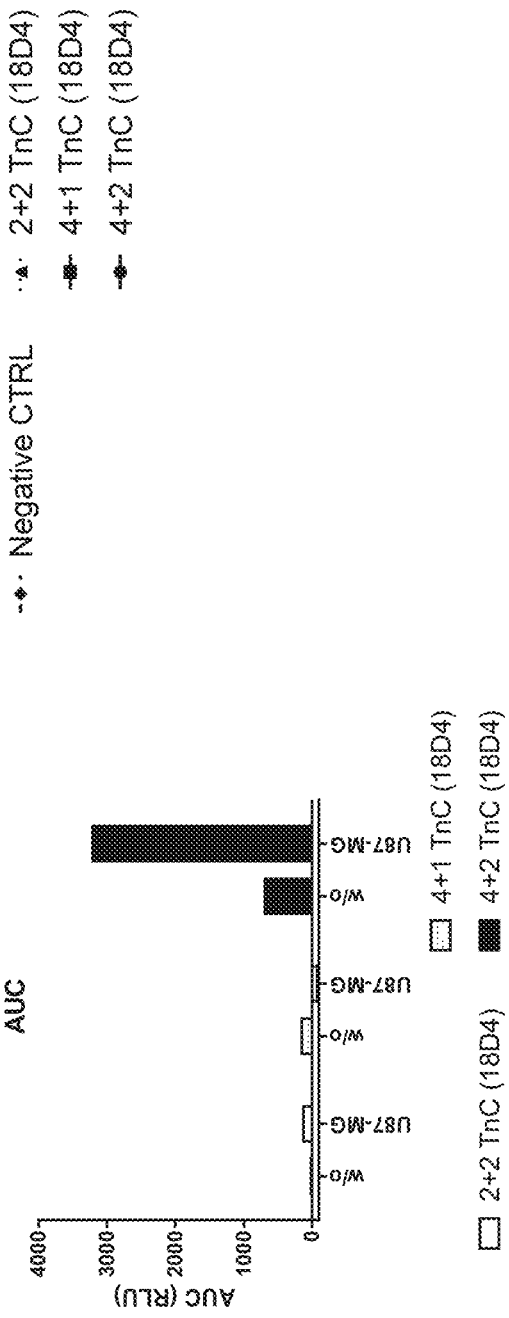
FIG. 12A
FIG. 12B
FIG. 12C

BISPECIFIC ANTIGEN BINDING MOLECULE FOR A COSTIMULATORY TNF RECEPTOR

CROSS REFERENCE TO RELATED APPLICATIONS

This application is a bypass Continuation Application of PCT Application No. PCT/EP2018/057769, filed Mar. 27, 2018, which claims priority to European Application No. 17163561.8, filed Mar. 29, 2017, each of which are incorporated herein by reference in its entirety.

SEQUENCE LISTING

This application contains a Sequence Listing which has been submitted electronically in ASCII format and is hereby incorporated by reference in its entirety. Said ASCII copy, created on Sep. 26, 2019, is named P34209-US_Sequence-_Listing.txt and is 389,159 bytes in size.

FIELD OF THE INVENTION

The invention relates to novel bispecific antigen binding molecules, comprising (a) at least one moiety capable of specific binding to OX40, and (b) at least one moiety capable of specific binding to tenascin C (TnC). The invention further relates to methods of producing these molecules and to methods of using the same.

BACKGROUND

Several members of the tumor necrosis factor receptor (TNFR) family function after initial T cell activation to sustain T cell responses and thus have pivotal roles in the organization and function of the immune system. CD27, 4-1BB (CD137), OX40 (CD134), HVEM, CD30, and GITR can have costimulatory effects on T cells, meaning that they sustain T-cell responses after initial T cell activation (Watts T. H. (2005) Annu. Rev. Immunol. 23, 23-68). The effects of these costimulatory TNFR family members can often be functionally, temporally, or spatially segregated from those of CD28 and from each other. The sequential and transient regulation of T cell activation/survival signals by different costimulators may function to allow longevity of the response while maintaining tight control of T cell survival. Depending on the disease condition, stimulation via costimulatory TNF family members can exacerbate or ameliorate disease. Despite these complexities, stimulation or blockade of TNFR family costimulators shows promise for several therapeutic applications, including cancer, infectious disease, transplantation, and autoimmunity.

Among several costimulatory molecules, the tumor necrosis factor (TNF) receptor family member OX40 (CD134) plays a key role in the survival and homeostasis of effector and memory T cells (Croft M. et al. (2009), Immunological Reviews 229, 173-191). OX40 (CD134) is expressed in several types of cells and regulates immune responses against infections, tumors and self-antigens and its expression has been demonstrated on the surface of T-cells, NKT-cells and NK-cells as well as neutrophils (Baumann R. et al. (2004), Eur. J. Immunol. 34, 2268-2275) and shown to be strictly inducible or strongly upregulated in response to various stimulatory signals. Functional activity of the molecule has been demonstrated in every OX40-expressing cell type suggesting complex regulation of OX40-mediated activity in vivo. Combined with T-cell receptor triggering, OX40 engagement on T-cells by its natural ligand or agonistic antibodies leads to synergistic activation of the PI3K and NFκB signalling pathways (Song J. et al. (2008) J. Immunology 180(11), 7240-7248). In turn, this results in enhanced proliferation, increased cytokine receptor and cytokine production and better survival of activated T-cells. In addition to its co-stimulatory activity in effector CD4$^+$ or CD8$^+$ T-cells, OX40 triggering has been recently shown to inhibit the development and immunosuppressive function of T regulatory cells. This effect is likely to be responsible, at least in part, for the enhancing activity of OX40 on anti-tumor or anti-microbial immune responses. Given that OX40 engagement can expand T-cell populations, promote cytokine secretion, and support T-cell memory, agonists including antibodies and soluble forms of the ligand OX40L have been used successfully in a variety of preclinical tumor models (Weinberg et al. (2000), J. Immunol. 164, 2160-2169).

The available pre-clinical and clinical data clearly demonstrate that there is a high clinical need for effective agonists of costimulatory TNFR family members such as OX40 and 4-1BB that are able to induce and enhance effective endogenous immune responses to cancer. However, almost never are the effects limited to a single cell type or acting via a single mechanism and studies designed to elucidate inter- and intracellular signaling mechanisms have revealed increasing levels of complexity. Thus, there is a need of "targeted" agonists that preferably act on a single cell type. The antigen binding molecules of the invention combine a moiety capable of preferred binding to tumor-specific or tumor-associated targets with a moiety capable of agonistic binding to costimulatory TNF receptors. The antigen binding molecules of this invention may be able to trigger TNF receptors not only effectively, but also very selectively at the desired site thereby reducing undesirable side effects.

Tenascins are a highly conserved family of large multimeric extracellular matrix (ECM) glycoproteins, which is found in vertebrates. Four tenascin paralogues have been identified in mammals, termed Tenascin-C (TnC), tenascin-R, tenascin-X and tenascin-W. Tenascin family proteins have a common primary structure, comprising N-terminal heptad repeats, epidermal growth factor (EGF)-like repeats, fibronectin type III domain repeats and a C-terminal fibrinogen-like globular domain. Via an N-terminal oligomerization domain, individual subunits assemble into trimers or, as is the case for Tenascin-C, even hexamers.

Mammalian TnC monomers typically have 14.5 EGF-like repeats and 8 fibronectin type III domain repeats that are shared by all TnC isoforms. However, up to 9 additional fibronectin type III domain repeats (domains A1 to D) can be independently included or excluded by alternative splicing, giving rise to a large number of TnC isoforms (see e.g., Hsia and Schwarzbauer, J Biol Chem 280, 26641-26644 (2005)).

TnC is transiently expressed in the developing embryo, but virtually absent from adult tissues. It reappears, however, in tissues undergoing remodeling processes, including certain pathological conditions such as wound healing, inflammation and cancer (reviewed in Chiquet-Ehrismann & Chiquet, J Pathol 200, 488-499 (2003)).

Importantly, TnC is highly expressed in the majority of malignant solid tumors, including tumors of the brain, breast, colon, lung, skin and other organs (reviewed in Orend and Chiquet-Ehrismann, Cancer Letters 244, 143-163 (2006)), where it may be expressed by transformed epithelial cells as well as stromal cells in the tumor microenvironment (Yoshida et al., J Pathol 182, 421-428 (1997), Hanamura et al., Int J Cancer 73, 10-15 (1997)). In particular, the "large isoform" of TnC, containing the alternatively spliced domains A1 to D, is expressed in invasive carcinomas while being nearly undetectable in healthy adult tissues (Borsi et al., Int J Cancer 52, 688-692 (1992), Carnemolla et al., Eur J Biochem 205, 561-567 (1992)).

Its expression pattern makes TnC, in particular its alternatively spliced domains, a promising antigen for tumor targeting applications, and accordingly a number of antibodies against several domains of the protein have been developed (see e.g., Brack et al., Clin Cancer Res 12, 3200-3208 (2006) or EP 1 817 345, describing antibodies against the A1 domain of TnC; Silacci et al., Prot Eng Des Sel 19, 471-478 (2006), or EP 1 173 766, describing antibodies against the C domain of TnC; Wang et al., Hybridoma 29, 13-16 (2010), describing an antibody against the D domain of TnC; or Balza et al., FEBS 332, 39-43 (1993), describing several antibodies against different domains of human tenascin). Recently, also antibodies recognizing a specific epitope in the A2 domain of human TnC has been described (WO 2009/089998 and WO 2012/020038).

SUMMARY OF THE INVENTION

The present invention provides a bispecific antigen binding molecule, comprising
(a) at least one moiety capable of specific binding to OX40 comprising an antibody light chain variable region (VL) and an antibody heavy chain variable region (VH), and
(b) at least one moiety capable of specific binding to tenascin C (TnC) comprising an antibody light chain variable region (VL) and an antibody heavy chain variable region (VH).

The novel bispecific antigen binding molecules of the present invention are able to trigger OX40 very selectively at the site where TnC is expressed, due to their binding capability towards a TnC. Side effects may therefore be drastically reduced.

In some embodiments, the bispecific antigen binding molecule additionally comprises
(c) a Fc region composed of a first and a second subunit capable of stable association.

In some embodiments, the moiety capable of specific binding to OX40 binds to a polypeptide comprising, or consisting of, the amino acid sequence of SEQ ID NO:1.

In some embodiments, the moiety capable of specific binding to TnC binds to a polypeptide comprising, or consisting of, the amino acid sequence of SEQ ID NO:39.

In some embodiments, the moiety capable of specific binding to OX40 comprises a heavy chain variable domain (VH) comprising
(i) a CDR-H1 comprising an amino acid sequence selected from the group consisting of SEQ ID NO:2 and SEQ ID NO:3,
(ii) a CDR-H2 comprising an amino acid sequence selected from the group consisting of SEQ ID NO:4 and SEQ ID NO:5, and
(iii) a CDR-H3 comprising an amino acid sequence selected from the group consisting of SEQ ID NO:6, SEQ ID NO:7, SEQ ID NO:8, SEQ ID NO: 9, SEQ ID NO:10, SEQ ID NO:11 and SEQ ID NO:12,
and a light chain variable domain (VL) comprising
(iv) a CDR-L1 comprising an amino acid sequence selected from the group consisting of SEQ ID NO:13, SEQ ID NO:14 and SEQ ID NO:15,
(v) a CDR-L2 comprising an amino acid sequence selected from the group consisting of SEQ ID NO:16, SEQ ID NO:17 and SEQ ID NO:18, and
(vi) a CDR-L3 comprising an amino acid sequence selected from the group consisting of SEQ ID NO:19, SEQ ID NO:20, SEQ ID NO:21, SEQ ID NO:22, SEQ ID NO:23 and SEQ ID NO:24.

In some embodiments, the moiety capable of specific binding to OX40 comprises a heavy chain variable region (VH) comprising an amino acid sequence that is at least about 95%, 96%, 97%, 98%, 99% or 100% identical to an amino acid sequence selected from the group consisting of SEQ ID NO:25, SEQ ID NO: 27, SEQ ID NO:29, SEQ ID NO:31, SEQ ID NO:33, SEQ ID NO:35 and SEQ ID NO:37 and a light chain variable region (VL) comprising an amino acid sequence that is at least about 95%, 96%, 97%, 98%, 99% or 100% identical to an amino acid sequence selected from the group consisting of SEQ ID NO:26, SEQ ID NO: 28, SEQ ID NO:30, SEQ ID NO:32, SEQ ID NO:34, SEQ ID NO:36 and SEQ ID NO:38.

In some embodiments, the moiety capable of specific binding to OX40 comprises
(i) a VH comprising the amino acid sequence of SEQ ID NO:25 and a VL comprising the amino acid sequence of SEQ ID NO:26,
(ii) a VH comprising the amino acid sequence of SEQ ID NO:27 and a VL comprising the amino acid sequence of SEQ ID NO:28,
(iii) a VH comprising the amino acid sequence of SEQ ID NO:29 and a VL comprising the amino acid sequence of SEQ ID NO:30,
(iv) a VH comprising the amino acid sequence of SEQ ID NO:31 and a VL comprising the amino acid sequence of SEQ ID NO:32,
(v) a VH comprising the amino acid sequence of SEQ ID NO:33 and a VL comprising the amino acid sequence of SEQ ID NO:34,
(vi) a VH comprising the amino acid sequence of SEQ ID NO:35 and a VL comprising the amino acid sequence of SEQ ID NO:36, or
(vii) a VH comprising the amino acid sequence of SEQ ID NO:37 and a VL comprising the amino acid sequence of SEQ ID NO:38.

In some embodiments, the moiety capable of specific binding to TnC comprises a VH comprising
(i) a CDR-H1 comprising an amino acid sequence selected from the group consisting of SEQ ID NO:40 and SEQ ID NO:41,
(ii) a CDR-H2 comprising an amino acid sequence selected from the group consisting of SEQ ID NO:42 and SEQ ID NO:43, and
(iii) a CDR-H3 comprising an amino acid sequence selected from the group consisting of SEQ ID NO:44 and SEQ ID NO:45,
and a VL comprising
(iv) a CDR-L1 comprising an amino acid sequence selected from the group consisting of SEQ ID NO:46 and SEQ ID NO:47,
(v) a CDR-L2 comprising an amino acid sequence selected from the group consisting of SEQ ID NO:48 and SEQ ID NO:49, and
(vi) a CDR-L3 comprising an amino acid sequence selected from the group consisting of SEQ ID NO:50 and SEQ ID NO:51.

In some embodiments, the moiety capable of specific binding to TnC comprises a VH comprising an amino acid sequence that is at least about 95%, 96%, 97%, 98%, 99% or 100% identical to an amino acid sequence selected from the group consisting of SEQ ID NO:52 and SEQ ID NO:54 and a VL comprising an amino acid sequence that is at least about 95%, 96%, 97%, 98%, 99% or 100% identical to an amino acid sequence selected from the group consisting of SEQ ID NO:53 and SEQ ID NO:55.

In some embodiments, the moiety capable of specific binding to TnC comprises
(i) a VH comprising the amino acid sequence of SEQ ID NO:52 and a VL comprising the amino acid sequence of SEQ ID NO:53, or
(ii) a VH comprising the amino acid sequence of SEQ ID NO:54 and a VL comprising the amino acid sequence of SEQ ID NO:55.

In some embodiments, the bispecific antigen binding molecule of comprises
(i) at least one moiety capable of specific binding to OX40, comprising a VH comprising an amino acid sequence that is at least about 95%, 96%, 97%, 98%, 99% or 100% identical to the amino acid sequence of SEQ ID NO:25, SEQ ID NO: 27, SEQ ID NO:29, SEQ ID NO:31, SEQ ID NO:33, SEQ ID NO:35 or SEQ ID NO:37 and a VL comprising an amino acid sequence that is at least about 95%, 96%, 97%, 98%, 99% or 100% identical to an amino acid sequence selected from the group consisting of SEQ ID NO:26, SEQ ID NO: 28, SEQ ID NO:30, SEQ ID NO:32, SEQ ID NO:34, SEQ ID NO:36 or SEQ ID NO:38 and
(ii) at least one moiety capable of specific binding to TnC, comprising a VH comprising an amino acid sequence that is at least about 95%, 96%, 97%, 98%, 99% or 100% identical to an amino acid sequence selected from the group consisting of SEQ ID NO:52 or SEQ ID NO:54 and a VL comprising an amino acid sequence that is at least about 95%, 96%, 97%, 98%, 99% or 100% identical to an amino acid sequence selected from the group consisting of SEQ ID NO:53 or SEQ ID NO:55.

In some embodiments, the bispecific antigen binding molecule of comprises
(a) at least one moiety capable of specific binding to OX40, comprising a VH comprising the amino acid sequence of SEQ ID NO: 27 and a VL comprising the amino acid sequence of SEQ ID NO: 28 and
(b) at least one moiety capable of specific binding to TnC, comprising
(i) a VH comprising the amino acid sequence of SEQ ID NO:52 and a VL comprising the amino acid sequence of SEQ ID NO:53, or
(ii) a VH comprising the amino acid sequence of SEQ ID NO:54 and a VL comprising the amino acid sequence of SEQ ID NO:55.

In some embodiments, the Fc region is an IgG, particularly an IgG1 Fc region or an IgG4 Fc region.

In some embodiments, the Fc region comprises one or more amino acid substitution that reduces the binding affinity of the antibody to an Fc receptor and/or effector function.

In some embodiments, the Fc region is of human IgG1h subclass with the amino acid mutations L234A, L235A and P329G (numbering according to Kabat EU index).

In some embodiments, the Fc region comprises a modification promoting the association of the first and second subunit of the Fc region.

In some embodiments, the first subunit of the Fc region comprises knobs and the second subunit of the Fc region comprises holes according to the knobs into holes method.

In some embodiments, the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index).

In some embodiments, the bispecific antigen binding molecule comprises
(a) at least two Fab fragments capable of specific binding to OX40 connected to a Fc region, and
(b) at least one moiety capable of specific binding to TnC comprising an antibody light chain variable region (VL) and an antibody heavy chain variable region (VH), connected to the C-terminus of the Fc region.

In some embodiments, the bispecific antigen binding molecule comprises
(a) two light chains and two heavy chains of an antibody comprising two Fab fragments capable of specific binding to OX40, and a Fc region, and
(b) a VH and a VL of a moiety capable specific binding to TnC, wherein the VH is connected to the C-terminus of one of the two heavy chains of (a), and wherein the VL is connected to the C-terminus of the other of the two heavy chains of (a).

In some embodiments, the bispecific antigen binding molecule comprises
(a) two light chains and two heavy chains of an antibody comprising two Fab fragments capable of specific binding to OX40, and a Fc region, and
(b) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

In some embodiments, the bispecific antigen binding molecule comprises
(a1) two heavy chains, each heavy chain comprising a VH and CH1 domain of a Fab fragment capable of specific binding to OX40 and a Fc region subunit,
(a2) two light chains, each light chain comprising a VL and CL domain of a Fab fragment capable of specific binding to OX40, and
(b) a VH and a VL of a moiety capable specific binding to TnC, wherein the VH is connected to the C-terminus of one of the two heavy chains of (a1), and wherein the VL is connected to the C-terminus of the other of the two heavy chains of (a1).

In some embodiments, the bispecific antigen binding molecule comprises
(a1) two heavy chains, each heavy chain comprising a VH and CH1 domain of a Fab fragment capable of specific binding to OX40, and a Fc region subunit,
(a2) two light chains, each light chain comprising a VL and CL domain of a Fab fragment capable of specific binding to OX40,
(b) two Fab fragments capable of specific binding to TnC, wherein one of the Fab fragments is connected to the C-terminus of one of the two heavy chains of (a1), and the other of the Fab fragments is connected to the C-terminus of the other of the two heavy chains of (a1).

In some embodiments, the two Fab fragments capable of specific binding to TnC are crossover Fab fragments each comprising a VL-CH1 chain and a VH-CL chain, and wherein one of the VL-CH1 chains is connected to the C-terminus of one of the two heavy chains of (a1), and the other of the VL-CH1 chains is connected to the C-terminus of the other of the two heavy chains of (a1).

In some embodiments, the bispecific antigen binding molecule comprises four Fab fragments capable of specific binding to OX40.

In some embodiments, each of the two heavy chains of (a) comprises two VH domains and two CH1 domains of a Fab fragment capable of specific binding to OX40.

In some embodiments, one or more of the Fab fragments capable of specific binding to OX40 comprises a CL domain comprising an arginine (R) at amino acid at position 123 (EU numbering) and a lysine (K) at amino acid at position 124 (EU numbering), and a CH1 domain comprising a glutamic acid (E) at amino acid at position 147 (EU numbering) and a glutamic acid (E) at amino acid at position 213 (EU numbering).

The present invention also provides a bispecific antigen binding molecule comprising two heavy chains, each comprising the amino acid sequence of SEQ ID NO:213, two light chains, each comprising the amino acid sequence of SEQ ID NO:212, and two light chains, each comprising the amino acid sequence of SEQ ID NO:214.

The present invention also provides a bispecific antigen binding molecule comprising two heavy chains, each comprising the amino acid sequence of SEQ ID NO:215, two light chains, each comprising the amino acid sequence of SEQ ID NO:212, and two light chains, each comprising the amino acid sequence of SEQ ID NO:216.

The present invention also provides a bispecific antigen binding molecule comprising a first heavy chain comprising the amino acid sequence of SEQ ID NO:222, a second heavy chain comprising the amino acid sequence of SEQ ID NO:223, and four light chains, each comprising the amino acid sequence of SEQ ID NO:212.

The present invention also provides a bispecific antigen binding molecule comprising two heavy chains, each comprising the amino acid sequence of SEQ ID NO:225, four light chains, each comprising the amino acid sequence of SEQ ID NO:224, and two light chains, each comprising the amino acid sequence of SEQ ID NO:226.

The present invention also provides a polynucleotide encoding the bispecific antigen binding molecule of the present invention.

The present invention also provides an expression vector comprising the polynucleotide of the present invention.

The present invention also provides an host cell comprising the polynucleotide or the expression vector of the present invention.

The present invention also provides a method of producing a bispecific antigen binding molecule, comprising culturing the host cell of the present invention under conditions suitable for the expression of the bispecific antigen binding molecule, and isolating the bispecific antigen binding molecule.

The present invention also provides a pharmaceutical composition comprising the bispecific antigen binding molecule of the present invention and at least one pharmaceutically acceptable excipient.

The present invention also provides the bispecific antigen binding molecule of the present invention, or the pharmaceutical composition of the present invention, for use as a medicament.

The present invention also provides the bispecific antigen binding molecule of the present invention, or the pharmaceutical composition of the present invention, for use
(i) in stimulating T cell response,
(ii) in supporting survival of activated T cells,
(iii) in the treatment of infections,
(iv) in the treatment of cancer,
(v) in delaying progression of cancer, or
(vi) in prolonging the survival of a patient suffering from cancer.

The present invention also provides the bispecific antigen binding molecule of the present invention, or the pharmaceutical composition of the present invention, for use in the treatment of cancer.

The present invention also provides the use of the bispecific antigen binding molecule of the present invention, or the pharmaceutical composition of the present invention, in the manufacture of a medicament for the treatment of cancer.

The present invention also provides a method of treating an individual having cancer comprising administering to the individual an effective amount of the bispecific antigen binding molecule of the present invention, or the pharmaceutical composition of the present invention.

The present invention also provides the bispecific antigen binding molecule of the present invention, or the pharmaceutical composition of the present invention, for use in up-regulating or prolonging cytotoxic T cell activity.

The present invention also provides the use of the bispecific antigen binding molecule of the present invention, or the pharmaceutical composition of the present invention, in the manufacture of a medicament for up-regulating or prolonging cytotoxic T cell activity.

The present invention also provides a method of up-regulating or prolonging cytotoxic T cell activity in an individual having cancer, comprising administering to the individual an effective amount of the bispecific antigen binding molecule of the present invention, or the pharmaceutical composition of the present invention.

In some embodiments in accordance with various aspects of the present invention the individual is a mammal, particularly a human.

BRIEF DESCRIPTION OF THE DRAWINGS

FIG. 4B shows binding of '2+2' molecules comprising anti-OX40 clone 49B4 and anti-TnC clone 11C7, FIG. 4C shows binding of '2+2' molecules comprising anti-OX40 clone 49B4 and anti-TnC clone 18D4, FIG. 4D shows binding of '4+1' molecules comprising anti-OX40 clone 49B4 and anti-TnC clone 18D4, and FIG. 4E shows binding of '4+2' molecules comprising anti-OX40 clone 49B4 and anti-TnC clone 18D4.

FIGS. 6A to 6D show the binding of the bispecific, bivalent anti-OX40, bivalent anti-TnC antigen binding molecules (i.e. 2+2 format) to resting and activated human CD4+ and CD8+ T cells. FIG. 6A shows binding to activated CD4+ T cells, FIG. 6B shows binding to resting CD4+ T cells, FIG. 6C shows binding to activated CD8+ T cells, and FIG. 6D shows binding to resting CD8+ T cells. Binding is shown as the median of fluorescence intensity (MFI) of FITC conjugated anti-human IgG F(ab')$_2$-fragment-specific goat IgG F(ab')2 fragment, which is used as secondary detection antibody. MFI was measured by flow cytometry and baseline corrected by subtracting the MFI of the blank control. The x-axis shows the concentration of the antigen binding molecules. All of the antigen binding molecules comprising an OX40-binding domain bind to activated, OX40 expressing human CD4+ T cells, and to a lower extent to activated human CD8+ T cells. OX40 is not expressed on resting human PBMCs (FIGS. 6B and 6D). After activation, OX40 is up-regulated on CD4+ and CD8+ T cells (FIGS. 6A and 6C). OX40 expression on human CD8+ T cells is lower than on CD4+ T cells.

FIG. 7A shows binding to activated CD4+ T cells, FIG. 7B shows binding to resting CD4+ T cells, FIG. 7C shows binding to activated CD8+ T cells, and FIG. 7D shows binding to resting CD8+ T cells. Binding is shown as the median of fluorescence intensity (MFI) of FITC conjugated anti-human IgG F(ab')$_2$-fragment-specific goat IgG F(ab')2 fragment, which is used as secondary detection antibody. MFI was measured by flow cytometry and baseline corrected by subtracting the MFI of the blank control. The x-axis shows the concentration of the antigen binding molecules. All of the antigen binding molecules comprising an OX40-binding domain bind to activated, OX40 expressing human CD4+ T cells. OX40 is not expressed on resting human PBMCs (FIGS. 7B and 7D). After activation, OX40 is up-regulated on CD4+ and CD8+ T cells (FIGS. 7A and 7C). OX40 expression on human CD8+ T cells is lower than on CD4+ T cells.

FIG. 9A shows binding to WM266-4 cells, which do not express TnC. FIG. 9B shows binding to U87-MG cells, which express TnC. FIG. 9C shows binding to CT26huTnC cells, which express TnC. Binding is shown as the median of fluorescence intensity (MFI) of Fluorescein isothiocyanate (FITC)-labeled anti-human IgG antibody or Phycoerythrin (PE)-labeled anti-human IgG antibody secondary detection antibody, as measured by flow cytometry. The x-axis shows the concentration of antigen binding molecules.

FIGS. 10A to 10C show the binding of the bispecific, tetravalent anti-OX40, monovalent or bivalent anti-TnC antigen binding molecules (i.e. 4+2 or 4+1 format) to WM266-4, U87-MG and CT26huTnC cells. FIG. 10A shows binding to WM266-4 cells, do not express TnC. FIG. 10B shows binding to U87-MG cells, which express TnC. FIG. 10C shows binding to CT26huTnC cells, which express TnC. Binding is shown as the median of fluorescence intensity (MFI) of Fluorescein isothiocyanate (FITC)-labeled anti-human IgG antibody or Phycoerythrin (PE)-labeled anti-human IgG antibody secondary detection antibody, as measured by flow cytometry. The x-axis shows the concentration of the antigen binding molecules.

FIG. 11A shows NFκB activation in OX40$^+$ HeLa reporter cells by antigen binding molecules in the absence of crosslinking. FIG. 11B shows NFκB activation in OX40$^+$ HeLa reporter cells by antigen binding molecules in the presence of crosslinking by anti-human Fc specific secondary antibody. FIG. 11C shows NFκB activation in OX40$^+$ HeLa reporter cells by antigen binding molecules in the presence of crosslinking by U87-MG cells. NF-κB-mediated luciferase activity was characterized by plotting the units of released light (URL), measured during 0.5 s, versus the concentration of the antigen binding molecule (in nM). URLs are emitted due to luciferase-mediated oxidation of luciferin to oxyluciferin. The values were baseline-corrected by subtracting the URLs for a 'blank control' condition. FIG. 11D shows the data of FIGS. 11A to 11C represented as area under the curve (AUC).

FIGS. 12A to 12C show activation of NFκB by the bispecific, tetravalent anti-OX40, monovalent or bivalent anti-TnC antigen binding molecules (i.e. 4+2 or 4+1 format), and bispecific, bivalent anti-OX40, bivalent anti-TnC (i.e. 2+2 format), in the presence or absence of crosslinking by U87-MG cells. FIG. 11A shows NFκB activation in OX40$^+$ HeLa reporter cells by antigen binding molecules in the absence of crosslinking. FIG. 11B shows NFκB activation in OX40$^+$ HeLa reporter cells by antigen binding molecules in the presence of crosslinking by U87-MG cells. NF-κB-mediated luciferase activity was characterized by plotting the units of released light (URL), measured during 0.5 s, versus the concentration of the antigen binding molecule (in nM). URLs are emitted due to luciferase-mediated oxidation of luciferin to oxyluciferin. The values were baseline-corrected by subtracting the URLs for a 'blank control' condition. FIG. 12C shows the data of FIGS. 12A and 12B represented as area under the curve (AUC).

FIG. 13A shows NFκB activation in OX40$^+$ HeLa reporter cells by antigen binding molecules in the absence of crosslinking. FIG. 13B shows NFκB activation in OX40$^+$ HeLa reporter cells by antigen binding molecules in the presence of crosslinking by CT26huTnC cells. NF-κB-mediated luciferase activity was characterized by plotting the units of released light (URL), measured during 0.5 s, versus the concentration of the antigen binding molecule (in nM). URLs are emitted due to luciferase-mediated oxidation of luciferin to oxyluciferin. The values were baseline-corrected by subtracting the URLs for a 'blank control' condition. FIG. 13C shows the data of FIGS. 13A and 13B represented as area under the curve (AUC).

FIG. 14A shows the CD4+ event count, FIG. 14B shows the CD8+ event count, FIG. 14C shows the mean fluorescence intensity (MFI) for CD127 expressed on CD4+ T cells, and FIG. 14D shows the MFI for CD127 expressed on CD8+ T cells. Values were baseline-corrected to values for samples containing only the anti-human CD3.

FIG. 15A shows the percentage of CD4+ CD25+ T cells, FIG. 15B shows the percentage of CD8+ CD25+ T cells, FIG. 15C shows the mean fluorescence intensity (MFI) for CD25 expressed on CD4+ T cells, and FIG. 15D shows the MFI for CD25 expressed on CD8+ T cells. Values were baseline-corrected to values for samples containing only the anti-human CD3.

FIG. 16A shows the percentage of vital, CFSE labelled CD4+ T cells, FIG. 16B shows the percentage of vital, CFSE labelled CD8+ T cells, FIG. 16C shows the mean fluorescence intensity (MFI) for CD127 expressed on CD4+ T cells, and FIG. 16D shows the MFI for CD127 expressed on CD8+ T cells. Values were baseline-corrected to values for samples containing only the anti-human CD3.

DETAILED DESCRIPTION OF THE INVENTION

Definitions

Figure 1:
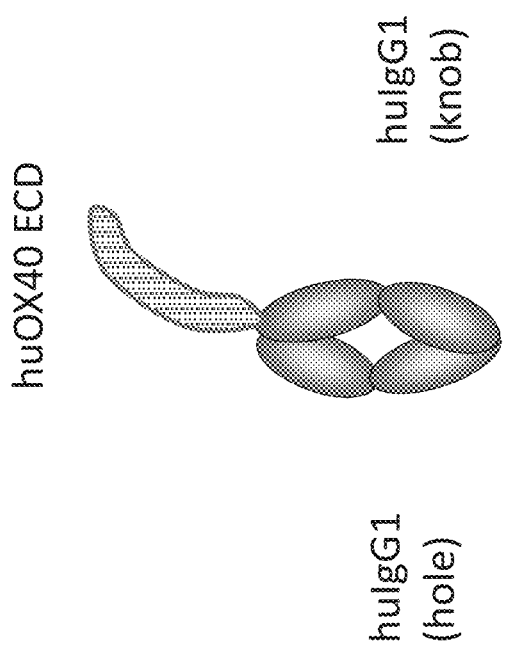
FIG. 1 shows the monomeric form of Fc-linked human OX40 antigen ECD that was used for the preparation of anti-OX40 antibodies.

Unless defined otherwise, technical and scientific terms used herein have the same meaning as generally used in the art to which this invention belongs. For purposes of interpreting this specification, the following definitions will apply and whenever appropriate, terms used in the singular will also include the plural and vice versa.

As used herein, the term "antigen binding molecule" refers in its broadest sense to a molecule that specifically binds an antigenic determinant. Examples of antigen binding molecules are antibodies, antibody fragments and scaffold antigen binding proteins.

As used herein, the term "moiety capable of specific binding to tenascin C (TnC)" or "antigen binding domain capable of specific binding to tenascin C (TnC)" refers to a polypeptide molecule that specifically binds to TnC. In a particular aspect, the antigen binding moiety is able to direct the entity to which it is attached to a target site, for example to a specific type of tumor cell or tumor stroma bearing TnC. Moieties capable of specific binding to a TnC include antibodies and fragments thereof as further defined herein. In addition, moieties capable of specific binding to TnC include scaffold antigen binding proteins as further defined herein, e.g. binding domains which are based on designed repeat proteins or designed repeat domains (see e.g. WO 2002/020565).

In relation to an antibody or fragment thereof, the term "moiety capable of specific binding to tenascin C (TnC)" or "antigen binding domain capable of specific binding to tenascin C (TnC)" refers to the part of the molecule that comprises the area which specifically binds to and is complementary to part or all of TnC. A moiety capable of specific binding to TnC may be provided, for example, by one or more antibody variable domains (also called antibody variable regions). Particularly, a moiety capable of specific binding to TnC comprises an antibody light chain variable region (VL) and an antibody heavy chain variable region (VH). In some embodiments, the "moiety capable of specific binding to tenascin C (TnC)" may be a scFv, a Fab fragment or a cross-Fab fragment, in particular a Fab fragment or a cross-Fab fragment.

The term "moiety capable of specific binding to OX40" or "antigen binding domain capable of specific binding to tenascin OX40" refers to a polypeptide molecule that specifically binds to OX40. In one aspect, the antigen binding moiety is able to activate signaling through OX40. Moieties capable of specific binding to OX40 include antibodies and fragments thereof as further defined herein. In addition, moieties capable of specific binding to OX40 include scaffold antigen binding proteins as further defined herein, e.g. binding domains which are based on designed repeat proteins or designed repeat domains (see e.g. WO 2002/020565). Particularly, a moiety capable of specific binding to OX40 comprises an antibody light chain variable region (VL) and an antibody heavy chain variable region (VH). In a particular aspect, the "moiety capable of specific binding to OX40" may be a Fab fragment, a cross-Fab fragment or a scFv, in particular a Fab fragment or cross-Fab fragment.

The term "antibody" herein is used in the broadest sense and encompasses various antibody structures, including but not limited to monoclonal antibodies, polyclonal antibodies, monospecific and multispecific antibodies (e.g., bispecific antibodies), and antibody fragments so long as they exhibit the desired antigen-binding activity.

The term "monoclonal antibody" as used herein refers to an antibody obtained from a population of substantially homogeneous antibodies, i.e., the individual antibodies comprising the population are identical and/or bind the same epitope, except for possible variant antibodies, e.g. containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen.

The term "monospecific" antibody as used herein denotes an antibody that has one or more binding sites each of which bind to the same epitope of the same antigen. The term "bispecific" means that the antigen binding molecule is able to specifically bind to at least two distinct antigenic determinants. A bispecific antigen binding molecule comprises at least two antigen binding sites, each of which is specific for a different antigenic determinant. In certain embodiments the bispecific antigen binding molecule is capable of simultaneously binding two antigenic determinants, particularly two antigenic determinants expressed on two distinct cells. For example, the antigen binding molecules of the present invention are bispecific, comprising a moiety capable of specific binding to OX40, and a moiety capable of specific binding to TnC.

The term "valent" as used within the current application denotes the presence of a specified number of binding sites in an antigen binding molecule. As such, the terms "bivalent", "tetravalent", and "hexavalent" denote the presence of two binding sites, four binding sites, and six binding sites, respectively, in an antigen binding molecule. Valency of an antigen binding molecule may also be expressed in relation to the number of binding sites for a given antigenic determinant. For example, in some embodiments the antigen binding molecules of the present invention are tetravalent with respect to OX40, and bivalent with respect to TnC (i.e. 4+2).

The terms "full length antibody", "intact antibody", and "whole antibody" are used herein interchangeably to refer to an antibody having a structure substantially similar to a native antibody structure. "Native antibodies" refer to naturally occurring immunoglobulin molecules with varying structures. For example, native IgG-class antibodies are heterotetrameric glycoproteins of about 150,000 daltons, composed of two light chains and two heavy chains that are disulfide-bonded. From N- to C-terminus, each heavy chain has a variable region (VH), also called a variable heavy domain or a heavy chain variable domain, followed by three constant domains (CH1, CH2, and CH3), also called a heavy chain constant region. Similarly, from N- to C-terminus, each light chain has a variable region (VL), also called a variable light domain or a light chain variable domain, followed by a light chain constant domain (CL), also called a light chain constant region. The heavy chain of an antibody may be assigned to one of five types, called α (IgA), δ (IgD), ε (IgE), γ (IgG), or μ (IgM), some of which may be further divided into subtypes, e.g. γ1 (IgG1), γ2 (IgG2), γ3 (IgG3), γ4 (IgG4), α1 (IgA1) and α2 (IgA2). The light chain of an antibody may be assigned to one of two types, called kappa (κ) and lambda (λ), based on the amino acid sequence of its constant domain.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies, triabodies, tetrabodies, cross-Fab fragments; linear antibodies; single-chain antibody molecules (e.g. scFv); and single domain antibodies. For a review of certain antibody fragments, see Hudson et al., Nat Med 9, 129-134 (2003). For a review of scFv fragments, see e.g. Plückthun, in The Pharmacology of Monoclonal Antibodies, vol. 113, Rosenburg and Moore eds., Springer-Verlag, New York, pp. 269-315 (1994); see also WO 93/16185; and U.S. Pat. Nos. 5,571,894 and 5,587,458. For discussion of Fab and F(ab')2 fragments comprising salvage receptor binding epitope residues and having increased in vivo half-life, see U.S. Pat. No. 5,869,046. Diabodies are antibody fragments with two antigen-binding sites that may be bivalent or bispecific, see, for example, EP 404,097; WO 1993/01161; Hudson et al., Nat Med 9, 129-134 (2003); and Hollinger et al., Proc Natl Acad Sci USA 90, 6444-6448 (1993). Triabodies and tetrabodies are also described in Hudson et al., Nat Med 9, 129-134 (2003). Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see e.g. U.S. Pat. No. 6,248,516 B1). Antibody fragments can be made by various techniques, including but not limited to proteolytic digestion of an intact antibody as well as production by recombinant host cells (e.g. E. coli or phage), as described herein.

Papain digestion of intact antibodies produces two identical antigen-binding fragments, called "Fab" fragments containing each the heavy- and light-chain variable domains and also the constant domain of the light chain and the first constant domain (CH1) of the heavy chain. As used herein, Thus, the term "Fab fragment" refers to an antibody fragment comprising a light chain fragment comprising a VL and a constant domain of a light chain (CL), and a VH and a first constant domain (CH1) of a heavy chain. Fab' fragments differ from Fab fragments by the addition of a few residues at the carboxy terminus of the heavy chain CH1 domain including one or more cysteins from the antibody hinge region. Fab'-SH are Fab' fragments wherein the cysteine residue(s) of the constant domains bear a free thiol group. Pepsin treatment yields an F(ab')$_2$ fragment that has two antigen-combining sites (two Fab fragments) and a part of the Fc region. According to the present invention, the term "Fab fragment" also includes "cross-Fab fragments" or "crossover Fab fragments" as defined below.

The term "cross-Fab fragment" or "xFab fragment" or "crossover Fab fragment" refers to a Fab fragment, wherein either the variable regions or the constant regions of the heavy and light chain are exchanged. Two different chain compositions of a cross-Fab molecule are possible and comprised in the bispecific antibodies of the invention: On the one hand, the variable regions of the Fab heavy and light chain are exchanged, i.e. the crossover Fab molecule comprises a peptide chain composed of the light chain variable region (VL) and the heavy chain constant region (CH1), and a peptide chain composed of the heavy chain variable region (VH) and the light chain constant region (CL). This crossover Fab molecule is also referred to as CrossFab$_{(VLVH)}$. On the other hand, when the constant regions of the Fab heavy and light chain are exchanged, the crossover Fab molecule comprises a peptide chain composed of the heavy chain variable region (VH) and the light chain constant region (CL), and a peptide chain composed of the light chain variable region (VL) and the heavy chain constant region (CH1). This crossover Fab molecule is also referred to as CrossFab$_{(CLCH1)}$.

A "single chain Fab fragment" or "scFab" is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CH1-linker-VL-CL, b) VL-CL-linker-VH-CH1, c) VH-CL-linker-VL-CH1 or d) VL-CH1-linker-VH-CL; and wherein said linker is a polypeptide of at least 30 amino acids, preferably between 32 and 50 amino acids. Said single chain Fab fragments are stabilized via the natural disulfide bond between the CL domain and the CH1 domain. In addition, these single chain Fab molecules might be further stabilized by generation of interchain disulfide bonds via insertion of cysteine residues (e.g. position 44 in the variable heavy chain and position 100 in the variable light chain according to Kabat numbering).

A "crossover single chain Fab fragment" or "x-scFab" is a is a polypeptide consisting of an antibody heavy chain variable domain (VH), an antibody constant domain 1 (CH1), an antibody light chain variable domain (VL), an antibody light chain constant domain (CL) and a linker, wherein said antibody domains and said linker have one of the following orders in N-terminal to C-terminal direction: a) VH-CL-linker-VL-CH1 and b) VL-CH1-linker-VH-CL;

wherein VH and VL form together an antigen-binding site which binds specifically to an antigen and wherein said linker is a polypeptide of at least 30 amino acids. In addition, these x-scFab molecules might be further stabilized by generation of interchain disulfide bonds via insertion of cysteine residues (e.g. position 44 in the variable heavy chain and position 100 in the variable light chain according to Kabat numbering).

A "single-chain variable fragment (scFv)" is a fusion protein of the variable regions of the heavy ($V_H$) and light chains ($V_L$) of an antibody, connected with a short linker peptide of ten to about 25 amino acids. The linker is usually rich in glycine for flexibility, as well as serine or threonine for solubility, and can either connect the N-terminus of the $V_H$ with the C-terminus of the $V_L$, or vice versa. This protein retains the specificity of the original antibody, despite removal of the constant regions and the introduction of the linker. scFv antibodies are, e.g. described in Houston, J S., Methods in Enzymol. 203 (1991) 46-96). In addition, antibody fragments comprise single chain polypeptides having the characteristics of a VH, namely being able to assemble together with a VL, or of a VL, namely being able to assemble together with a VH to a functional antigen binding site and thereby providing the antigen binding property of full length antibodies.

"Scaffold antigen binding proteins" are known in the art, for example, fibronectin and designed ankyrin repeat proteins (DARPins) have been used as alternative scaffolds for antigen-binding domains, see, e.g., Gebauer and Skerra, Engineered protein scaffolds as next-generation antibody therapeutics. Curr Opin Chem Biol 13:245-255 (2009) and Stumpp et al., Darpins: A new generation of protein therapeutics. Drug Discovery Today 13: 695-701 (2008). In one aspect of the invention, a scaffold antigen binding protein is selected from the group consisting of CTLA-4 (Evibody), Lipocalins (Anticalin), a Protein A-derived molecule such as Z-domain of Protein A (Affibody), an A-domain (Avimer/Maxibody), a serum transferrin (trans-body); a designed ankyrin repeat protein (DARPin), a variable domain of antibody light chain or heavy chain (single-domain antibody, sdAb), a variable domain of antibody heavy chain (nanobody, aVH), $V_{NAR}$ fragments, a fibronectin (AdNectin), a C-type lectin domain (Tetranectin); a variable domain of a new antigen receptor beta-lactamase ($V_{NAR}$ fragments), a human gamma-crystallin or ubiquitin (Affilin molecules); a kunitz type domain of human protease inhibitors, microbodies such as the proteins from the knottin family, peptide aptamers and fibronectin (adnectin). CTLA-4 (Cytotoxic T Lymphocyte-associated Antigen 4) is a CD28-family receptor expressed on mainly CD4+ T-cells. Its extracellular domain has a variable domain-like Ig fold. Loops corresponding to CDRs of antibodies can be substituted with heterologous sequence to confer different binding properties. CTLA-4 molecules engineered to have different binding specificities are also known as Evibodies (e.g. U.S. Pat. No. 7,166,697B1). Evibodies are around the same size as the isolated variable region of an antibody (e.g. a domain antibody). For further details see Journal of Immunological Methods 248 (1-2), 31-45 (2001). Lipocalins are a family of extracellular proteins which transport small hydrophobic molecules such as steroids, bilins, retinoids and lipids. They have a rigid beta-sheet secondary structure with a number of loops at the open end of the conical structure which can be engineered to bind to different target antigens. Anticalins are between 160-180 amino acids in size, and are derived from lipocalins. For further details see Biochim Biophys Acta 1482: 337-350 (2000), U.S. Pat. No. 7,250,297B1 and US20070224633. An affibody is a scaffold derived from Protein A of *Staphylococcus aureus* which can be engineered to bind to antigen. The domain consists of a three-helical bundle of approximately 58 amino acids. Libraries have been generated by randomization of surface residues. For further details see Protein Eng. Des. Sel. 2004, 17, 455-462 and EP 1641818A1. Avimers are multidomain proteins derived from the A-domain scaffold family. The native domains of approximately 35 amino acids adopt a defined disulfide bonded structure. Diversity is generated by shuffling of the natural variation exhibited by the family of A-domains. For further details see Nature Biotechnology 23(12), 1556-1561 (2005) and Expert Opinion on Investigational Drugs 16(6), 909-917 (June 2007). A transferrin is a monomeric serum transport glycoprotein. Transferrins can be engineered to bind different target antigens by insertion of peptide sequences in a permissive surface loop. Examples of engineered transferrin scaffolds include the Trans-body. For further details see J. Biol. Chem 274, 24066-24073 (1999). Designed Ankyrin Repeat Proteins (DARPins) are derived from Ankyrin which is a family of proteins that mediate attachment of integral membrane proteins to the cytoskeleton. A single ankyrin repeat is a 33 residue motif consisting of two alpha-helices and a beta-turn. They can be engineered to bind different target antigens by randomizing residues in the first alpha-helix and a beta-turn of each repeat. Their binding interface can be increased by increasing the number of modules (a method of affinity maturation). For further details see J. Mol. Biol. 332, 489-503 (2003), PNAS 100(4), 1700-1705 (2003) and J. Mol. Biol. 369, 1015-1028 (2007) and US20040132028A1. A single-domain antibody is an antibody fragment consisting of a single monomeric variable antibody domain. The first single domains were derived from the variable domain of the antibody heavy chain from camelids (nanobodies or $V_H$H fragments). Furthermore, the term single-domain antibody includes an autonomous human heavy chain variable domain (aVH) or $V_{NAR}$ fragments derived from sharks. Fibronectin is a scaffold which can be engineered to bind to antigen. Adnectins consists of a backbone of the natural amino acid sequence of the 10th domain of the 15 repeating units of human fibronectin type III (FN3). Three loops at one end of the .beta.-sandwich can be engineered to enable an Adnectin to specifically recognize a therapeutic target of interest. For further details see Protein Eng. Des. Sel. 18, 435-444 (2005), US20080139791, WO2005056764 and U.S. Pat. No. 6,818,418B1. Peptide aptamers are combinatorial recognition molecules that consist of a constant scaffold protein, typically thioredoxin (TrxA) which contains a constrained variable peptide loop inserted at the active site. For further details see Expert Opin. Biol. Ther. 5, 783-797 (2005). Microbodies are derived from naturally occurring microproteins of 25-50 amino acids in length which contain 3-4 cysteine bridges—examples of microproteins include KalataBI and conotoxin and knottins. The microproteins have a loop which can be engineered to include up to 25 amino acids without affecting the overall fold of the microprotein. For further details of engineered knottin domains, see WO2008098796.

An "antigen binding molecule that binds to the same epitope" as a reference molecule refers to an antigen binding molecule that blocks binding of the reference molecule to its antigen in a competition assay by 50% or more, and conversely, the reference molecule blocks binding of the antigen binding molecule to its antigen in a competition assay by 50% or more.

The term "antigen binding domain" or "antigen-binding site" refers to the part of an antigen binding molecule that comprises the area which specifically binds to and is complementary to part or all of an antigen. Where an antigen is large, an antigen binding molecule may only bind to a particular part of the antigen, which part is termed an epitope. An antigen binding domain may be provided by, for example, one or more variable domains (also called variable regions). Preferably, an antigen binding domain comprises an antibody light chain variable region (VL) and an antibody heavy chain variable region (VH).

As used herein, the term "antigenic determinant" is synonymous with "antigen" and "epitope," and refers to a site (e.g. a contiguous stretch of amino acids or a conformational configuration made up of different regions of non-contiguous amino acids) on a polypeptide macromolecule to which an antigen binding moiety binds, forming an antigen binding moiety-antigen complex. Useful antigenic determinants can be found, for example, on the surfaces of tumor cells, on the surfaces of virus-infected cells, on the surfaces of other diseased cells, on the surface of immune cells, free in blood serum, and/or in the extracellular matrix (ECM). The proteins useful as antigens herein can be any native form the proteins from any vertebrate source, including mammals such as primates (e.g. humans) and rodents (e.g. mice and rats), unless otherwise indicated. In a particular embodiment the antigen is a human protein. Where reference is made to a specific protein herein, the term encompasses the "full-length", unprocessed protein as well as any form of the protein that results from processing in the cell. The term also encompasses naturally occurring variants of the protein, e.g. splice variants or allelic variants.

By "specific binding" is meant that the binding is selective for the antigen and can be discriminated from unwanted or non-specific interactions. The ability of an antigen binding molecule to bind to a specific antigen can be measured either through an enzyme-linked immunosorbent assay (ELISA) or other techniques familiar to one of skill in the art, e.g. Surface Plasmon Resonance (SPR) technique (analyzed on a BIAcore instrument) (Liljeblad et al., Glyco J 17, 323-329 (2000)), and traditional binding assays (Heeley, Endocr Res 28, 217-229 (2002)). In one embodiment, the extent of binding of an antigen binding molecule to an unrelated protein is less than about 10% of the binding of the antigen binding molecule to the antigen as measured, e.g. by SPR. In certain embodiments, a molecule that binds to the antigen has a dissociation constant (Kd) of ≤1 μM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g. from $10^{-9}$ M to $10^{-13}$ M).

"Affinity" or "binding affinity" refers to the strength of the sum total of non-covalent interactions between a single binding site of a molecule (e.g. an antibody) and its binding partner (e.g. an antigen). Unless indicated otherwise, as used herein, "binding affinity" refers to intrinsic binding affinity which reflects a 1:1 interaction between members of a binding pair (e.g. antibody and antigen). The affinity of a molecule X for its partner Y can generally be represented by the dissociation constant (Kd), which is the ratio of dissociation and association rate constants (koff and kon, respectively). Thus, equivalent affinities may comprise different rate constants, as long as the ratio of the rate constants remains the same. Affinity can be measured by common methods known in the art, including those described herein. A particular method for measuring affinity is Surface Plasmon Resonance (SPR).

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "tenascin C (TnC)" refers to any native TnC from any vertebrate source, including mammals such as primates (e.g. humans) non-human primates (e.g. cynomolgus monkeys) and rodents (e.g. mice and rats), unless otherwise indicated. The term encompasses "full-length," unprocessed TnC as well as any form of TnC that results from processing in the cell. The term also encompasses naturally occurring variants of TnC, e.g., splice variants or allelic variants. In one embodiment, the antigen binding molecule of the invention is capable of specific binding to human, mouse and/or cynomolgus TnC. The amino acid sequence of human TnC is shown in UniProt (www.uniprot.org) accession no. P24821 (version 196, SEQ ID NO:39), or NCBI (www.ncbi.nlm.nih.gov/) RefSeq NP_002151.2. The nucleotide and amino acid sequences of C-terminally Avi- and His-tagged human TnC are shown in SEQ ID NOs 167 and 170, respectively. The amino acid sequence of mouse TnC is shown in UniProt (www.uniprot.org) accession no. Q80YX1 (version 125, SEQ ID NO:63), or NCBI (www.ncbi.nlm.nih.gov/) RefSeq NP_035737.2. The nucleotide and amino acid sequences of C-terminally Avi- and His-tagged mouse TnC are shown in SEQ ID NOs 168 and 171, respectively. The nucleotide and amino acid sequences of C-terminally Avi- and His-tagged cynomolgus TnC are shown in SEQ ID NOs 169 and 172, respectively.

In certain embodiments, the antigen binding molecule of the present invention comprises a moiety capable of specific binding to at least one of the domains of TnC selected from the group consisting of A1, A2, A3, A4, B, AD1, AD2, C and D. In some embodiments, a moiety capable of specific binding to TnC binds to the A1 and A4 domains of TnC. In some embodiments, a moiety capable of specific binding to TnC binds to the C domain of TnC.

The term "Fibroblast activation protein (FAP)", also known as Prolyl endopeptidase FAP or Seprase (EC 3.4.21), refers to any native FAP from any vertebrate source, including mammals such as primates (e.g. humans) non-human primates (e.g. cynomolgus monkeys) and rodents (e.g. mice and rats), unless otherwise indicated. The amino acid sequence of human FAP is shown in UniProt (www.uniprot.org) accession no. Q12884 (version 149, SEQ ID NO:81), or NCBI (www.ncbi.nlm.nih.gov/) RefSeq NP_004451.2.

The term "variable region" or "variable domain" refers to the domain of an antibody heavy or light chain that is involved in binding the antigen binding molecule to antigen. The variable domains of the heavy chain and light chain (VH and VL, respectively) of a native antibody generally have similar structures, with each domain comprising four conserved framework regions (FRs) and three hypervariable regions (HVRs). See, e.g., Kindt et al., Kuby Immunology, 6th ed., W.H. Freeman and Co., page 91 (2007). A single VH or VL may be sufficient to confer antigen-binding specificity.

The term "hypervariable region" or "HVR," as used herein refers to each of the regions of an antibody variable domain which are hypervariable in sequence and/or form structurally defined loops ("hypervariable loops"). Generally, native four-chain antibodies comprise six HVRs; three in the VH (H1, H2, H3), and three in the VL (L1, L2, L3). HVRs generally comprise amino acid residues from the hypervariable loops and/or from the "complementarity determining regions" (CDRs), the latter being of highest sequence variability and/or involved in antigen recognition.

Exemplary hypervariable loops occur at amino acid residues 26-32 (L1), 50-52 (L2), 91-96 (L3), 26-32 (H1), 53-55 (H2), and 96-101 (H3). (Chothia and Lesk, *J. Mol. Biol.* 196:901-917 (1987).) Exemplary CDRs (CDR-L1, CDR-L2, CDR-L3, CDR-H1, CDR-H2, and CDR-H3) occur at amino acid residues 24-34 of L1, 50-56 of L2, 89-97 of L3, 31-35B of H1, 50-65 of H2, and 95-102 of H3. (Kabat et al., *Sequences of Proteins of Immunological Interest*, 5th Ed. Public Health Service, National Institutes of Health, Bethesda, Md. (1991).) Hypervariable regions (HVRs) are also referred to as complementarity determining regions (CDRs), and these terms are used herein interchangeably in reference to portions of the variable region that form the antigen binding regions. This particular region has been described by Kabat et al., U.S. Dept. of Health and Human Services, "Sequences of Proteins of Immunological Interest" (1983) and by Chothia et al., *J. Mol. Biol.* 196:901-917 (1987), where the definitions include overlapping or subsets of amino acid residues when compared against each other. Nevertheless, application of either definition to refer to a CDR of an antibody or variants thereof is intended to be within the scope of the term as defined and used herein. The appropriate amino acid residues which encompass the CDRs as defined by each of the above cited references are set forth below in Table A as a comparison. The exact residue numbers which encompass a particular CDR will vary depending on the sequence and size of the CDR. Those skilled in the art can routinely determine which residues comprise a particular CDR given the variable region amino acid sequence of the antibody.

TABLE A

CDR Definitions[1]

| CDR | Kabat | Chothia | AbM[2] |
|---|---|---|---|
| $V_H$ CDR1 | 31-35 | 26-32 | 26-35 |
| $V_H$ CDR2 | 50-65 | 52-58 | 50-58 |
| $V_H$ CDR3 | 95-102 | 95-102 | 95-102 |
| $V_L$ CDR1 | 24-34 | 26-32 | 24-34 |
| $V_L$ CDR2 | 50-56 | 50-52 | 50-56 |
| $V_L$ CDR3 | 89-97 | 91-96 | 89-97 |

[1]Numbering of all CDR definitions in Table A is according to the numbering conventions set forth by Kabat et al. (see below).
[2]"AbM" with a lowercase "b" as used in Table A refers to the CDRs as defined by Oxford Molecular's "AbM" antibody modeling software.

Kabat et al. also defined a numbering system for variable region sequences that is applicable to any antibody. One of ordinary skill in the art can unambiguously assign this system of "Kabat numbering" to any variable region sequence, without reliance on any experimental data beyond the sequence itself. As used herein, "Kabat numbering" refers to the numbering system set forth by Kabat et al., U.S. Dept. of Health and Human Services, "Sequence of Proteins of Immunological Interest" (1983). Unless otherwise specified, references to the numbering of specific amino acid residue positions in an antibody variable region are according to the Kabat numbering system.

With the exception of CDR1 in VH, CDRs generally comprise the amino acid residues that form the hypervariable loops. CDRs also comprise "specificity determining residues," or "SDRs," which are residues that contact antigen. SDRs are contained within regions of the CDRs called abbreviated-CDRs, or a-CDRs. Exemplary a-CDRs (a-CDR-L1, a-CDR-L2, a-CDR-L3, a-CDR-H1, a-CDR-H2, and a-CDR-H3) occur at amino acid residues 31-34 of L1, 50-55 of L2, 89-96 of L3, 31-35B of H1, 50-58 of H2, and 95-102 of H3. (See Almagro and Fransson, *Front. Biosci.* 13:1619-1633 (2008).) Unless otherwise indicated, HVR residues and other residues in the variable domain (e.g., FR residues) are numbered herein according to Kabat et al., supra.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g. $IgG_1$, $IgG_2$, $IgG_3$, $IgG_4$, $IgA_1$, and $IgA_2$. The heavy chain constant domains that correspond to the different classes of immunoglobulins are called α, δ, ε, γ, and μ respectively.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization. Other forms of "humanized antibodies" encompassed by the present invention are those in which the constant region has been additionally modified or changed from that of the original antibody to generate the properties according to the invention, especially in regard to C1q binding and/or Fc receptor (FcR) binding.

A "human" antibody is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

The term "Fc domain" or "Fc region" herein is used to define a C-terminal region of an antibody heavy chain that contains at least a portion of the constant region. The term includes native sequence Fc regions and variant Fc regions. An IgG Fc region comprises an IgG CH2 and an IgG CH3 domain. The "CH2 domain" of a human IgG Fc region usually extends from an amino acid residue at about position 231 to an amino acid residue at about position 340. In one embodiment, a carbohydrate chain is attached to the CH2 domain. The CH2 domain herein may be a native sequence CH2 domain or variant CH2 domain. The "CH3 domain" comprises the stretch of residues C-terminal to a CH2 domain in an Fc region (i.e. from an amino acid residue at about position 341 to an amino acid residue at about position 447 of an IgG). The CH3 region herein may be a native sequence CH3 domain or a variant CH3 domain (e.g. a CH3 domain with an introduced "protuberance" ("knob") in one chain thereof and a corresponding introduced "cavity" ("hole") in the other chain thereof; see U.S. Pat. No.

5,821,333, expressly incorporated herein by reference). Such variant CH3 domains may be used to promote heterodimerization of two non-identical antibody heavy chains as herein described. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., Sequences of Proteins of Immunological Interest, 5th Ed. Public Health Service, National Institutes of Health, Bethesda, Md., 1991.

The "knob-into-hole" technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine). The protuberance and cavity can be made by altering the nucleic acid encoding the polypeptides, e.g. by site-specific mutagenesis, or by peptide synthesis. In a specific embodiment a knob modification comprises the amino acid substitution T366W in one of the two subunits of the Fc domain, and the hole modification comprises the amino acid substitutions T366S, L368A and Y407V in the other one of the two subunits of the Fc domain. In a further specific embodiment, the subunit of the Fc domain comprising the knob modification additionally comprises the amino acid substitution S354C, and the subunit of the Fc domain comprising the hole modification additionally comprises the amino acid substitution Y349C. Introduction of these two cysteine residues results in the formation of a disulfide bridge between the two subunits of the Fc region, thus further stabilizing the dimer (Carter, J Immunol Methods 248, 7-15 (2001)).

A "region equivalent to the Fc region of an immunoglobulin" is intended to include naturally occurring allelic variants of the Fc region of an immunoglobulin as well as variants having alterations which produce substitutions, additions, or deletions but which do not decrease substantially the ability of the immunoglobulin to mediate effector functions (such as antibody-dependent cellular cytotoxicity). For example, one or more amino acids can be deleted from the N-terminus or C-terminus of the Fc region of an immunoglobulin without substantial loss of biological function. Such variants can be selected according to general rules known in the art so as to have minimal effect on activity (see, e.g., Bowie, J. U. et al., Science 247:1306-10 (1990)).

The term "effector functions" refers to those biological activities attributable to the Fc region of an antibody, which vary with the antibody isotype. Examples of antibody effector functions include: C1q binding and complement dependent cytotoxicity (CDC), Fc receptor binding, antibody-dependent cell-mediated cytotoxicity (ADCC), antibody-dependent cellular phagocytosis (ADCP), cytokine secretion, immune complex-mediated antigen uptake by antigen presenting cells, down regulation of cell surface receptors (e.g. B cell receptor), and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; and Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB. FcγRIIA is found on many cells involved in killing (e.g. macrophages, monocytes, neutrophils) and seems able to activate the killing process. FcγRIIB seems to play a role in inhibitory processes and is found on B cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. Fc γ RIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "ADCC" or "antibody-dependent cellular cytotoxicity" is a function mediated by Fc receptor binding and refers to lysis of target cells by an antibody as reported herein in the presence of effector cells. The capacity of the antibody to induce the initial steps mediating ADCC is investigated by measuring their binding to Fcγ receptors expressing cells, such as cells, recombinantly expressing FcγRI and/or FcγRIIA or NK cells (expressing essentially FcγRIIIA). In particular, binding to FcγR on NK cells is measured.

An "activating Fc receptor" is an Fc receptor that following engagement by an Fc region of an antibody elicits signaling events that stimulate the receptor-bearing cell to perform effector functions. Activating Fc receptors include FcγRIIIa (CD16a), FcγRI (CD64), FcγRIIa (CD32), and FcαRI (CD89). A particular activating Fc receptor is human FcγRIIIa (see UniProt accession no. P08637, version 141).

The "Tumor Necrosis factor receptor superfamily" or "TNF receptor superfamily" currently consists of 27 receptors. It is a group of cytokine receptors characterized by the ability to bind tumor necrosis factors (TNFs) via an extracellular cysteine-rich domain (CRD). These pseudorepeats are defined by intrachain disulphides generated by highly conserved cysteine residues within the receptor chains. With the exception of nerve growth factor (NGF), all TNFs are homologous to the archetypal TNF-alpha. In their active form, the majority of TNF receptors form trimeric complexes in the plasma membrane. Accordingly, most TNF receptors contain transmembrane domains (TMDs). Several of these receptors also contain intracellular death domains (DDs) that recruit caspase-interacting proteins following ligand binding to initiate the extrinsic pathway of caspase activation. Other TNF superfamily receptors that lack death domains bind TNF receptor-associated factors and activate intracellular signaling pathways that can lead to proliferation or differentiation. These receptors can also initiate apoptosis, but they do so via indirect mechanisms. In addition to regulating apoptosis, several TNF superfamily receptors are involved in regulating immune cell functions such as B cell homeostasis and activation, natural killer cell activation, and T cell co-stimulation. Several others regulate cell type-specific responses such as hair follicle development and osteoclast development. Members of the TNF receptor superfamily include the following: Tumor necrosis factor receptor 1 (1A) (TNFRSF1A, CD120a), Tumor necrosis factor receptor 2 (1B) (TNFRSF1B, CD120b), Lymphotoxin beta receptor (LTBR, CD18), OX40 (TNFRSF4, CD134), CD40 (Bp50), Fas receptor (Apo-1, CD95, FAS), Decoy receptor 3 (TR6, M68, TNFRSF6B), CD27 (S152, Tp55), CD30 (Ki-1, TNFRSF8), 4-1BB (CD137, TNFRSF9), DR4 (TRAILR1, Apo-2, CD261, TNFRSF10A), DR3 (TRAILR2, CD262, TNFRSF10B), Decoy Receptor 1 (TRAILR3, CD263, TNFRSF10C), Decoy Receptor 2 (TRAILR4, CD264, TNFRSF10D), RANK (CD265, TNFRSF11A), Osteoprotegerin (OCIF, TR1, TNFRSF11B), TWEAK receptor (Fn14, CD266, TNFRSF12A), TACI (CD267, TNFRSF13B), BAFF receptor (CD268, TNFRSF13C), Herpesvirus entry mediator (HVEM, TR2, CD270, TNFRSF14), Nerve growth factor receptor (p75NTR, CD271, NGFR), B-cell maturation antigen (CD269, TNFRSF17), Glucocorticoid-induced TNFR-related (GITR, AITR, CD357, TNFRSF18), TROY (TNFRSF19), DR6 (CD358, TNFRSF21), DR3 (Apo-3, TRAMP, WS-1, TNFRSF25) and Ectodysplasin A2 receptor (XEDAR, EDA2R).

Several members of the tumor necrosis factor receptor (TNFR) family function after initial T cell activation to sustain T cell responses. The term "costimulatory TNF receptor family member" or "costimulatory TNF family receptor" refers to a subgroup of TNF receptor family members, which are able to costimulate proliferation and cytokine production of T-cells. The term refers to any native TNF family receptor from any vertebrate source, including mammals such as primates (e.g. humans), non-human primates (e.g. cynomolgus monkeys) and rodents (e.g. mice and rats), unless otherwise indicated. In specific embodiments of the invention, costimulatory TNF receptor family members are selected from the group consisting of OX40 (CD134), 4-1BB (CD137), CD27, HVEM (CD270), CD30, and GITR, all of which can have costimulatory effects on T cells. More particularly, the antigen binding molecule of the present invention comprises at least moiety capable of specific binding to the costimulatory TNF receptor family member OX40.

Further information, in particular sequences, of the TNF receptor family members may be obtained from publically accessible databases such as Uniprot (www.uniprot.org). For instance, the human costimulatory TNF receptors have the following amino acid sequences: human OX40 (UniProt accession no. P43489, SEQ ID NO:56), human 4-1BB (UniProt accession no. Q07011, SEQ ID NO:57), human CD27 (UniProt accession no. P26842, SEQ ID NO:58), human HVEM (UniProt accession no. Q92956, SEQ ID NO:59), human CD30 (UniProt accession no. P28908, SEQ ID NO:60), and human GITR (UniProt accession no. Q9Y5U5, SEQ ID NO:61).

The term "OX40", as used herein, refers to any native OX40 from any vertebrate source, including mammals such as primates (e.g. humans) and rodents (e.g., mice and rats), unless otherwise indicated. The term encompasses "full-length," unprocessed OX40 as well as any form of OX40 that results from processing in the cell. The term also encompasses naturally occurring variants of OX40, e.g., splice variants or allelic variants. The amino acid sequence of an exemplary human OX40 is shown in SEQ ID NO: 56 (Uniprot P43489, version 112) and the amino acid sequence of an exemplary murine OX40 is shown in SEQ ID NO: 62 (Uniprot P47741, version 101).

The terms "anti-OX40 antibody", "anti-OX40", "OX40 antibody and "an antibody that specifically binds to OX40" refer to an antibody that is capable of binding OX40 with sufficient affinity such that the antibody is useful as a diagnostic and/or therapeutic agent in targeting OX40. In one embodiment, the extent of binding of an anti-OX40 antibody to an unrelated, non-OX40 protein is less than about 10% of the binding of the antibody to OX40 as measured, e.g., by a radioimmunoassay (RIA) or flow cytometry (FACS). In certain embodiments, an antibody that binds to OX40 has a dissociation constant ($K_D$) of $\leq 1$ μM, $\leq 100$ nM, $\leq 10$ nM, $\leq 1$ nM, $\leq 0.1$ nM, $\leq 0.01$ nM, or $\leq 0.001$ nM (e.g. $10^{-6}$ M or less, e.g. from $10^{-68}$M to $10^{-13}$M, e.g., from $10^{-8}$ M to $10^{-10}$ M).

The terms "anti-TnC antibody" and "an antibody that binds to TnC" refer to an antibody that is capable of binding Tenascin-C (TnC) with sufficient affinity such that the antibody is useful as a diagnostic and/or therapeutic agent in targeting TnC. In one embodiment, the extent of binding of an anti-TnC antibody to an unrelated, non-TnC protein is less than about 10% of the binding of the antibody to TnC as measured, e.g., by a radioimmunoassay (RIA). In certain embodiments, an antibody that binds to TnC has a dissociation constant (KD) of ≤1 µM, ≤100 nM, ≤10 nM, ≤5 nM, ≤2 nM, ≤1 nM, ≤0.1 nM, ≤0.01 nM, or ≤0.001 nM (e.g., 10-8 M or less, e.g., from 10-8 M to 10-13 M, e.g., from 10-9 M to 10-13 M, e.g., from 10 nM to 0.1 nM, e.g., from 5 nM to 0.1 nM, e.g., from 2 nM to 0.1 nM). In certain embodiments, an anti-TnC antibody binds to an epitope of TnC that is conserved among TnC from different species. In certain embodiments, an antibody that binds to an epitope of TnC is specific for at least one of the domains selected from the group consisting of A1, A2, A3, A4, B, AD1, AD2, C and D. In certain embodiments an antibody specific for the TnC A1 and TnC A4 domains is provided. In certain embodiments an antibody specific for the TnC C domain is provided.

The term "peptide linker" refers to a peptide comprising one or more amino acids, typically about 2 to 20 amino acids. Peptide linkers are known in the art or are described herein. Suitable, non-immunogenic linker peptides are, for example, $(G_4S)_n$, $(SG_4)_n$ or $G_4(SG_4)_n$ peptide linkers, wherein "n" is generally a number between 1 and 10, typically between 2 and 4, in particular 2, i.e. the peptides selected from the group consisting of GGGGS (SEQ ID NO: 64) GGGGSGGGGS (SEQ ID NO:65), SGGGGSGGGG (SEQ ID NO:66) and GGGGSGGGGSGGGG (SEQ ID NO:68), but also include the sequences GSPGSSSSGS (SEQ ID NO:70), $(G4S)_3$ (SEQ ID NO:67), $(G4S)_4$ (SEQ ID NO:69), GSGSGSGS (SEQ ID NO:71), GSGSGNGS (SEQ ID NO:72), GGSGSGSG (SEQ ID NO:73), GGSGSG (SEQ ID NO:74), GGSG (SEQ ID NO:75), GGSGNGSG (SEQ ID NO:76), GGNGSGSG (SEQ ID NO:77) and GGNGSG (SEQ ID NO:78). Peptide linkers of particular interest are (G4S) (SEQ ID NO:64), $(G_4S)_2$ or GGGGSGGGGS (SEQ ID NO:65) and GSPGSSSSGS (SEQ ID NO:70).

The term "amino acid" as used within this application denotes the group of naturally occurring carboxy α-amino acids comprising alanine (three letter code: ala, one letter code: A), arginine (arg, R), asparagine (asn, N), aspartic acid (asp, D), cysteine (cys, C), glutamine (gln, Q), glutamic acid (glu, E), glycine (gly, G), histidine (his, H), isoleucine (ile, I), leucine (leu, L), lysine (lys, K), methionine (met, M), phenylalanine (phe, F), proline (pro, P), serine (ser, S), threonine (thr, T), tryptophan (trp, W), tyrosine (tyr, Y), and valine (val, V).

By "fused" or "connected" is meant that the components (e.g. a heavy chain of an antibody and a Fab fragment) are linked by peptide bonds, either directly or via one or more peptide linkers.

"Percent (%) amino acid sequence identity" with respect to a reference polypeptide (protein) sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN. SAWI or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary. In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

In certain embodiments, amino acid sequence variants of the antigen binding molecules provided herein are contemplated. For example, it may be desirable to improve the binding affinity and/or other biological properties of the antigen binding molecules. Amino acid sequence variants of the antigen binding molecules may be prepared by introducing appropriate modifications into the nucleotide sequence encoding the molecules, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding. Sites of interest for substitutional mutagenesis include the HVRs and Framework (FRs). Conservative substitutions are provided in Table B under the heading "Preferred Substitutions" and further described below in reference to amino acid side chain classes (1) to (6). Amino acid substitutions may be introduced into the molecule of interest and the products screened for a desired activity, e.g., retained/improved antigen binding, decreased immunogenicity, or improved ADCC or CDC.

TABLE B

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |

TABLE B-continued

| Original Residue | Exemplary Substitutions | Preferred Substitutions |
|---|---|---|
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:
(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

The term "amino acid sequence variants" includes substantial variants wherein there are amino acid substitutions in one or more hypervariable region residues of a parent antigen binding molecule (e.g. a humanized or human antibody). Generally, the resulting variant(s) selected for further study will have modifications (e.g., improvements) in certain biological properties (e.g., increased affinity, reduced immunogenicity) relative to the parent antigen binding molecule and/or will have substantially retained certain biological properties of the parent antigen binding molecule. An exemplary substitutional variant is an affinity matured antibody, which may be conveniently generated, e.g., using phage display-based affinity maturation techniques such as those described herein. Briefly, one or more HVR residues are mutated and the variant antigen binding molecules displayed on phage and screened for a particular biological activity (e.g. binding affinity). In certain embodiments, substitutions, insertions, or deletions may occur within one or more HVRs so long as such alterations do not substantially reduce the ability of the antigen binding molecule to bind antigen. For example, conservative alterations (e.g., conservative substitutions as provided herein) that do not substantially reduce binding affinity may be made in HVRs. A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as Arg, Asp, His, Lys, and Glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody binding molecule complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include bispecific antigen binding molecules of the invention with an N-terminal methionyl residue. Other insertional variants of the molecule include the fusion to the N- or C-terminus to a polypeptide which increases the serum half-life of the bispecific antigen binding molecules.

In certain embodiments, the bispecific antigen binding molecules provided herein are altered to increase or decrease the extent to which the antibody is glycosylated. Glycosylation variants of the molecules may be conveniently obtained by altering the amino acid sequence such that one or more glycosylation sites is created or removed. Where the bispecific antigen binding molecule comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in the antigen binding molecule may be made in order to create variants with certain improved properties. In one aspect, variants of bispecific antigen binding molecules or antibodies of the invention are provided having a carbohydrate structure that lacks fucose attached (directly or indirectly) to an Fc region. Such fucosylation variants may have improved ADCC function, see e.g. US Patent Publication Nos. US 2003/0157108 (Presta, L.) or US 2004/0093621 (Kyowa Hakko Kogyo Co., Ltd). In another aspect, variants of the bispecific antigen binding molecules or antibodies of the invention are provided with bisected oligosaccharides, e.g., in which a biantennary oligosaccharide attached to the Fc region is bisected by GlcNAc. Such variants may have reduced fucosylation and/or improved ADCC function, see for example WO 2003/011878 (Jean-Mairet et al.); U.S. Pat. No. 6,602,684 (Umana et al.); and US 2005/0123546 (Umana et al.). Variants with at least one galactose residue in the oligosaccharide attached to the Fc region are also provided. Such antibody variants may have improved CDC function and are described, e.g., in WO 1997/30087 (Patel et al.); WO 1998/58964 (Raju, S.); and WO 1999/22764 (Raju, S.).

In certain aspects, it may be desirable to create cysteine engineered variants of the bispecific antigen binding molecules of the invention, e.g., "thioMAbs," in which one or more residues of the molecule are substituted with cysteine residues. In particular aspects, the substituted residues occur at accessible sites of the molecule. By substituting those residues with cysteine, reactive thiol groups are thereby positioned at accessible sites of the antibody and may be used to conjugate the antibody to other moieties, such as drug moieties or linker-drug moieties, to create an immunoconjugate. In certain aspects, any one or more of the following residues may be substituted with cysteine: V205 (Kabat numbering) of the light chain; A118 (EU numbering) of the heavy chain; and S400 (EU numbering) of the heavy chain Fc region. Cysteine engineered antigen binding molecules may be generated as described, e.g., in U.S. Pat. No. 7,521,541.

The term "polynucleotide" refers to an isolated nucleic acid molecule or construct, e.g. messenger RNA (mRNA), virally-derived RNA, or plasmid DNA (pDNA). A polynucleotide may comprise a conventional phosphodiester bond or a non-conventional bond (e.g. an amide bond, such as found in peptide nucleic acids (PNA). The term "nucleic acid molecule" refers to any one or more nucleic acid segments, e.g. DNA or RNA fragments, present in a polynucleotide.

By "isolated" nucleic acid molecule or polynucleotide is intended a nucleic acid molecule, DNA or RNA, which has been removed from its native environment. For example, a recombinant polynucleotide encoding a polypeptide contained in a vector is considered isolated for the purposes of the present invention. Further examples of an isolated polynucleotide include recombinant polynucleotides maintained in heterologous host cells or purified (partially or substantially) polynucleotides in solution. An isolated polynucleotide includes a polynucleotide molecule contained in cells that ordinarily contain the polynucleotide molecule, but the polynucleotide molecule is present extrachromosomally or at a chromosomal location that is different from its natural chromosomal location. Isolated RNA molecules include in vivo or in vitro RNA transcripts of the present invention, as well as positive and negative strand forms, and double-stranded forms. Isolated polynucleotides or nucleic acids according to the present invention further include such molecules produced synthetically. In addition, a polynucleotide or a nucleic acid may be or may include a regulatory element such as a promoter, ribosome binding site, or a transcription terminator.

By a nucleic acid or polynucleotide having a nucleotide sequence at least, for example, 95% "identical" to a reference nucleotide sequence of the present invention, it is intended that the nucleotide sequence of the polynucleotide is identical to the reference sequence except that the polynucleotide sequence may include up to five point mutations per each 100 nucleotides of the reference nucleotide sequence. In other words, to obtain a polynucleotide having a nucleotide sequence at least 95% identical to a reference nucleotide sequence, up to 5% of the nucleotides in the reference sequence may be deleted or substituted with another nucleotide, or a number of nucleotides up to 5% of the total nucleotides in the reference sequence may be inserted into the reference sequence. These alterations of the reference sequence may occur at the 5' or 3' terminal positions of the reference nucleotide sequence or anywhere between those terminal positions, interspersed either individually among residues in the reference sequence or in one or more contiguous groups within the reference sequence. As a practical matter, whether any particular polynucleotide sequence is at least 80%, 85%, 90%, 95%, 96%, 97%, 98% or 99% identical to a nucleotide sequence of the present invention can be determined conventionally using known computer programs, such as the ones discussed above for polypeptides (e.g. ALIGN-2).

The term "expression cassette" refers to a polynucleotide generated recombinantly or synthetically, with a series of specified nucleic acid elements that permit transcription of a particular nucleic acid in a target cell. The recombinant expression cassette can be incorporated into a plasmid, chromosome, mitochondrial DNA, plastid DNA, virus, or nucleic acid fragment. Typically, the recombinant expression cassette portion of an expression vector includes, among other sequences, a nucleic acid sequence to be transcribed and a promoter. In certain embodiments, the expression cassette of the invention comprises polynucleotide sequences that encode bispecific antigen binding molecules of the invention or fragments thereof.

The term "vector" or "expression vector" is synonymous with "expression construct" and refers to a DNA molecule that is used to introduce and direct the expression of a specific gene to which it is operably associated in a target cell. The term includes the vector as a self-replicating nucleic acid structure as well as the vector incorporated into the genome of a host cell into which it has been introduced. The expression vector of the present invention comprises an expression cassette. Expression vectors allow transcription of large amounts of stable mRNA. Once the expression vector is inside the target cell, the ribonucleic acid molecule or protein that is encoded by the gene is produced by the cellular transcription and/or translation machinery. In one embodiment, the expression vector of the invention comprises an expression cassette that comprises polynucleotide sequences that encode bispecific antigen binding molecules of the invention or fragments thereof.

The terms "host cell", "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein. A host cell is any type of cellular system that can be used to generate the bispecific antigen binding molecules of the present invention. Host cells include cultured cells, e.g. mammalian cultured cells, such as CHO cells, BHK cells, NS0 cells, SP2/0 cells, YO myeloma cells, P3X63 mouse myeloma cells, PER cells, PER.C6 cells or hybridoma cells, yeast cells, insect cells, and plant cells, to name only a few, but also cells comprised within a transgenic animal, transgenic plant or cultured plant or animal tissue.

An "effective amount" of an agent refers to the amount that is necessary to result in a physiological change in the cell or tissue to which it is administered.

A "therapeutically effective amount" of an agent, e.g. a pharmaceutical composition, refers to an amount effective, at dosages and for periods of time necessary, to achieve the desired therapeutic or prophylactic result. A therapeutically effective amount of an agent for example eliminates, decreases, delays, minimizes or prevents adverse effects of a disease.

An "individual" or "subject" is a mammal. Mammals include, but are not limited to, domesticated animals (e.g. cows, sheep, cats, dogs, and horses), primates (e.g. humans and non-human primates such as monkeys), rabbits, and rodents (e.g. mice and rats). Particularly, the individual or subject is a human.

The term "pharmaceutical composition" refers to a preparation which is in such form as to permit the biological activity of an active ingredient contained therein to be effective, and which contains no additional components which are unacceptably toxic to a subject to which the formulation would be administered.

A "pharmaceutically acceptable excipient" refers to an ingredient in a pharmaceutical composition, other than an active ingredient, which is nontoxic to a subject. A pharmaceutically acceptable excipient includes, but is not limited to, a buffer, a stabilizer, or a preservative.

The term "package insert" is used to refer to instructions customarily included in commercial packages of therapeutic products, that contain information about the indications, usage, dosage, administration, combination therapy, contraindications and/or warnings concerning the use of such therapeutic products.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, the molecules of the invention are used to delay development of a disease or to slow the progression of a disease.

The term "cancer" as used herein refers to proliferative diseases, such as lymphomas, lymphocytic leukemias, lung cancer, non-small cell lung (NSCL) cancer, bronchioloalviolar cell lung cancer, bone cancer, pancreatic cancer, skin cancer, cancer of the head or neck, cutaneous or intraocular melanoma, uterine cancer, ovarian cancer, rectal cancer, cancer of the anal region, stomach cancer, gastric cancer, colon cancer, breast cancer, uterine cancer, carcinoma of the fallopian tubes, carcinoma of the endometrium, carcinoma of the cervix, carcinoma of the vagina, carcinoma of the vulva, Hodgkin's Disease, cancer of the esophagus, cancer of the small intestine, cancer of the endocrine system, cancer of the thyroid gland, cancer of the parathyroid gland, cancer of the adrenal gland, sarcoma of soft tissue, cancer of the urethra, cancer of the penis, prostate cancer, cancer of the bladder, cancer of the kidney or ureter, renal cell carcinoma, carcinoma of the renal pelvis, mesothelioma, hepatocellular cancer, biliary cancer, neoplasms of the central nervous system (CNS), spinal axis tumors, brain stem glioma, glioblastoma multiforme, astrocytomas, schwanomas, ependymonas, medulloblastomas, meningiomas, squamous cell carcinomas, pituitary adenoma and Ewings sarcoma, including refractory versions of any of the above cancers, or a combination of one or more of the above cancers.

Bispecific Antigen Binding Molecules of the Invention

The invention provides novel bispecific antigen binding molecules with particularly advantageous properties such as producibility, stability, binding affinity, biological activity, targeting efficiency and reduced toxicity.

The present invention provides a bispecific antigen binding molecule, comprising
(a) at least one moiety capable of specific binding to OX40 comprising an antibody light chain variable region (VL) and an antibody heavy chain variable region (VH), and
(b) at least one moiety capable of specific binding to tenascin C (TnC) comprising an antibody light chain variable region (VL) and an antibody heavy chain variable region (VH).

In some embodiments, the bispecific antigen binding molecule additionally comprises (c) a Fc region composed of a first and a second subunit capable of stable association.

In a particular aspects, these bispecific antigen binding molecules are characterized by agonistic binding to OX40.

Bispecific Antigen Binding Molecules Binding to OX40

In one aspect, the invention provides bispecific antigen binding molecules, wherein the moiety capable of specific binding to OX40 binds to a polypeptide comprising, or consisting of, the amino acid sequence of SEQ ID NO:1.

In one aspect, provided is a bispecific antigen binding molecule, comprising at least one moiety capable of specific binding to OX40, wherein said moiety comprises a VH comprising
(i) a CDR-H1 comprising an amino acid sequence selected from the group consisting of SEQ ID NO:2 and SEQ ID NO:3,
(ii) a CDR-H2 comprising an amino acid sequence selected from the group consisting of SEQ ID NO:4 and SEQ ID NO:5, and
(iii) a CDR-H3 comprising an amino acid sequence selected from the group consisting of SEQ ID NO:6, SEQ ID NO:7, SEQ ID NO:8, SEQ ID NO: 9, SEQ ID NO:10, SEQ ID NO:11 and SEQ ID NO:12,
and a VL comprising
(iv) a CDR-L1 comprising an amino acid sequence selected from the group consisting of SEQ ID NO:13, SEQ ID NO:14 and SEQ ID NO:15,
(v) a CDR-L2 comprising an amino acid sequence selected from the group consisting of SEQ ID NO:16, SEQ ID NO:17 and SEQ ID NO:18, and
(vi) a CDR-L3 comprising an amino acid sequence selected from the group consisting of SEQ ID NO:19, SEQ ID NO:20, SEQ ID NO:21, SEQ ID NO:22, SEQ ID NO:23 and SEQ ID NO:24.

In particular, provided is a bispecific antigen binding molecule, comprising at least one moiety capable of specific binding to OX40, wherein said moiety comprises
(a) a VH comprising CDR-H1 comprising the amino acid sequence of SEQ ID NO:2, CDR-H2 comprising the amino acid sequence of SEQ ID NO:4, CDR-H3 comprising the amino acid sequence of SEQ ID NO:6 and a VL comprising CDR-L1 comprising the amino acid sequence of SEQ ID NO:13, CDR-L2 comprising the amino acid sequence of SEQ ID NO:16 and CDR-L3 comprising the amino acid sequence of SEQ ID NO:19,
(b) a VH comprising CDR-H1 comprising the amino acid sequence of SEQ ID NO:2, CDR-H2 comprising the amino acid sequence of SEQ ID NO:4, CDR-H3 comprising the amino acid sequence of SEQ ID NO:7 and a VL comprising CDR-L1 comprising the amino acid sequence of SEQ ID NO:13, CDR-L2 comprising the amino acid sequence of SEQ ID NO:16 and CDR-L3 comprising the amino acid sequence of SEQ ID NO:20,
(c) a VH comprising CDR-H1 comprising the amino acid sequence of SEQ ID NO:2, CDR-H2 comprising the amino acid sequence of SEQ ID NO:4, CDR-H3 comprising the amino acid sequence of SEQ ID NO:8 and a VL comprising CDR-L1 comprising the amino acid sequence of SEQ ID NO:13, CDR-L2 comprising the amino acid sequence of SEQ ID NO:16 and CDR-L3 comprising the amino acid sequence of SEQ ID NO:21,
(d) a VH comprising CDR-H1 comprising the amino acid sequence of SEQ ID NO:2, CDR-H2 comprising the amino acid sequence of SEQ ID NO:4, CDR-H3 comprising the amino acid sequence of SEQ ID NO:9 and a VL comprising CDR-L1 comprising the amino acid sequence of SEQ ID NO:13, CDR-L2 comprising the amino acid sequence of SEQ ID NO:16 and CDR-L3 comprising the amino acid sequence of SEQ ID NO:22,
(e) a VH comprising CDR-H1 comprising the amino acid sequence of SEQ ID NO:3, CDR-H2 comprising the amino acid sequence of SEQ ID NO:5, CDR-H3 comprising the amino acid sequence of SEQ ID NO:10 and a VL comprising CDR-L1 comprising the amino acid sequence of SEQ ID NO:14, CDR-L2 comprising the amino acid sequence of SEQ ID NO:17 and CDR-L3 comprising the amino acid sequence of SEQ ID NO:23, (f) a VH comprising CDR-H1 comprising the amino acid sequence of SEQ ID NO:3, CDR-H2 comprising the amino acid sequence of SEQ ID NO:5, CDR-H3 comprising the amino acid sequence of SEQ ID NO:11 and a VL comprising CDR-L1 comprising the amino acid sequence of SEQ ID NO:14, CDR-L2 comprising the amino acid sequence of SEQ ID NO:17 and CDR-L3 comprising the amino acid sequence of SEQ ID NO:23, or (g) a VH comprising CDR-H1 comprising the amino acid sequence of SEQ ID NO:3, CDR-H2 comprising the amino acid sequence of SEQ ID NO:5, CDR-H3 comprising the amino acid sequence of SEQ ID NO:12 and a VL comprising CDR-L1 comprising the amino acid sequence of SEQ ID NO:15, CDR-L2 comprising the amino acid sequence of SEQ ID NO:18 and CDR-L3 comprising the amino acid sequence of SEQ ID NO:24.

In one aspect, the invention provides a bispecific antigen binding molecule, comprising at least one moiety capable of specific binding to OX40, wherein said moiety comprises a VH comprising CDR-H1 comprising the amino acid sequence of SEQ ID NO:2, CDR-H2 comprising the amino acid sequence of SEQ ID NO:4, CDR-H3 comprising the amino acid sequence of SEQ ID NO:7 and a VL comprising CDR-L1 comprising the amino acid sequence of SEQ ID NO:13, CDR-L2 comprising the amino acid sequence of SEQ ID NO:16 and CDR-L3 comprising the amino acid sequence of SEQ ID NO:20.

In another aspect, the invention provides a bispecific antigen binding molecule, wherein the moiety capable of specific binding to OX40 comprises a VH comprising an amino acid sequence that is at least about 95%, 96%, 97%, 98%, 99% or 100% identical to an amino acid sequence selected from the group consisting of SEQ ID NO:25, SEQ ID NO: 27, SEQ ID NO:29, SEQ ID NO:31, SEQ ID NO:33, SEQ ID NO:35 and SEQ ID NO:37 and a VL comprising an amino acid sequence that is at least about 95%, 96%, 97%, 98%, 99% or 100% identical to an amino acid sequence selected from the group consisting of SEQ ID NO:26, SEQ ID NO: 28, SEQ ID NO:30, SEQ ID NO:32, SEQ ID NO:34, SEQ ID NO:36 and SEQ ID NO:38.

Particularly, provided is a bispecific antigen binding molecule, wherein the moiety capable of specific binding to OX40 comprises
(i) a VH comprising the amino acid sequence of SEQ ID NO:25 and a VL comprising the amino acid sequence of SEQ ID NO:26,
(ii) a VH comprising the amino acid sequence of SEQ ID NO:27 and a VL comprising the amino acid sequence of SEQ ID NO:28,
(iii) a VH comprising the amino acid sequence of SEQ ID NO:29 and a VL comprising the amino acid sequence of SEQ ID NO:30,
(iv) a VH comprising the amino acid sequence of SEQ ID NO:31 and a VL comprising the amino acid sequence of SEQ ID NO:32,
(v) a VH comprising the amino acid sequence of SEQ ID NO:33 and a VL comprising the amino acid sequence of SEQ ID NO:34,
(vi) a VH comprising the amino acid sequence of SEQ ID NO:35 and a VL comprising the amino acid sequence of SEQ ID NO:36, or
(vii) a VH comprising the amino acid sequence of SEQ ID NO:37 and a VL comprising the amino acid sequence of SEQ ID NO:38.

In a particular aspect, provided is a bispecific antigen binding molecule, wherein the moiety capable of specific binding to OX40 comprises a VH comprising the amino acid sequence of SEQ ID NO:27 and a VL comprising the amino acid sequence of SEQ ID NO:28.

Bispecific Antigen Binding Molecules Binding to TnC

In one aspect, the invention provides bispecific antigen binding molecules, wherein the moiety capable of specific binding to tenascin C (TnC) binds to a polypeptide comprising, or consisting of, the amino acid sequence of SEQ ID NO:39.

In one aspect, provided is a bispecific antigen binding molecule, comprising at least one moiety capable of specific binding to TnC, wherein said moiety comprises a VH comprising
(i) a CDR-H1 comprising an amino acid sequence selected from the group consisting of SEQ ID NO:40 and SEQ ID NO:41,
(ii) a CDR-H2 comprising an amino acid sequence selected from the group consisting of SEQ ID NO:42 and SEQ ID NO:43, and
(iii) a CDR-H3 comprising an amino acid sequence selected from the group consisting of SEQ ID NO:44 and SEQ ID NO:45,
and a VL comprising
(iv) a CDR-L1 comprising an amino acid sequence selected from the group consisting of SEQ ID NO:46 and SEQ ID NO:47,
(v) a CDR-L2 comprising an amino acid sequence selected from the group consisting of SEQ ID NO:48 and SEQ ID NO:49, and
(vi) a CDR-L3 comprising an amino acid sequence selected from the group consisting of SEQ ID NO:50 and SEQ ID NO:51.

In particular, provided is a bispecific antigen binding molecule, comprising at least one moiety capable of specific binding to TnC, wherein said moiety comprises
(a) a VH comprising CDR-H1 comprising the amino acid sequence of SEQ ID NO:40, CDR-H2 comprising the amino acid sequence of SEQ ID NO:42, CDR-H3 comprising the amino acid sequence of SEQ ID NO:44 and a VL comprising CDR-L1 comprising the amino acid sequence of SEQ ID NO:46, CDR-L2 comprising the amino acid sequence of SEQ ID NO:48 and CDR-L3 comprising the amino acid sequence of SEQ ID NO:50, or
(b) a VH comprising CDR-H1 comprising the amino acid sequence of SEQ ID NO:41, CDR-H2 comprising the amino acid sequence of SEQ ID NO:43, CDR-H3 comprising the amino acid sequence of SEQ ID NO:45 and a VL comprising CDR-L1 comprising the amino acid sequence of SEQ ID NO:47, CDR-L2 comprising the amino acid sequence of SEQ ID NO:49 and CDR-L3 comprising the amino acid sequence of SEQ ID NO:51.

In particular, provided is a bispecific antigen binding molecule, comprising at least one moiety capable of specific binding to TnC, wherein said moiety comprises a VH comprising CDR-H1 comprising the amino acid sequence of SEQ ID NO:40, CDR-H2 comprising the amino acid sequence of SEQ ID NO:42, CDR-H3 comprising the amino acid sequence of SEQ ID NO:44 and a VL comprising CDR-L1 comprising the amino acid sequence of SEQ ID NO:46, CDR-L2 comprising the amino acid sequence of SEQ ID NO:48 and CDR-L3 comprising the amino acid sequence of SEQ ID NO:50.

In another aspect, the invention provides a bispecific antigen binding molecule, wherein the moiety capable of specific binding to TnC comprises a VH comprising an amino acid sequence that is at least about 95%, 96%, 97%, 98%, 99% or 100% identical to an amino acid sequence selected from the group consisting of SEQ ID NO:52 and SEQ ID NO:54 and a VL comprising an amino acid sequence that is at least about 95%, 96%, 97%, 98%, 99% or 100% identical to an amino acid sequence selected from the group consisting of SEQ ID NO:53 and SEQ ID NO:55.

Particularly, provided is a bispecific antigen binding molecule, wherein the moiety capable of specific binding to TnC comprises
  (i) a VH comprising the amino acid sequence of SEQ ID NO:52 and a VL comprising the amino acid sequence of SEQ ID NO:53, or
  (ii) a VH comprising the amino acid sequence of SEQ ID NO:54 and a VL comprising the amino acid sequence of SEQ ID NO:55.

In a particular aspect, provided is a bispecific antigen binding molecule, wherein the moiety capable of specific binding to OX40 comprises a VH comprising the amino acid sequence of SEQ ID NO:52 and a VL comprising the amino acid sequence of SEQ ID NO:53.

Bispecific Antigen Binding Molecules Binding to OX40 and TnC

In a further aspect, provided is a bispecific antigen binding molecule, wherein
(i) the moiety capable of specific binding to OX40 comprises a VH comprising an amino acid sequence that is at least about 95%, 96%, 97%, 98%, 99% or 100% identical to an amino acid sequence selected from the group consisting of SEQ ID NO:25, SEQ ID NO: 27, SEQ ID NO:29, SEQ ID NO:31, SEQ ID NO:33, SEQ ID NO:35 or SEQ ID NO:37 and a VL comprising an amino acid sequence that is at least about 95%, 96%, 97%, 98%, 99% or 100% identical to the amino acid sequence of SEQ ID NO:26, SEQ ID NO: 28, SEQ ID NO:30, SEQ ID NO:32, SEQ ID NO:34, SEQ ID NO:36 or SEQ ID NO:38 and
(ii) the moiety capable of specific binding to TnC comprises a VH comprising an amino acid sequence that is at least about 95%, 96%, 97%, 98%, 99% or 100% identical to an amino acid sequence selected from the group consisting of SEQ ID NO:52 or SEQ ID NO:54 and a VL comprising an amino acid sequence that is at least about 95%, 96%, 97%, 98%, 99% or 100% identical to an amino acid sequence selected from the group consisting of SEQ ID NO:53 or SEQ ID NO:55.

In a particular aspect, provided is a bispecific antigen binding molecule, wherein
(a) the moiety capable of specific binding to OX40 comprises a VH comprising the amino acid sequence of SEQ ID NO:25 and a VL comprising the amino acid sequence of SEQ ID NO:26 and the moiety capable of specific binding to TnC comprises a VH comprising the amino acid sequence of SEQ ID NO:52 and a VL comprising the amino acid sequence of SEQ ID NO:53,
(b) the moiety capable of specific binding to OX40 comprises a VH comprising the amino acid sequence of SEQ ID NO:25 and a VL comprising the amino acid sequence of SEQ ID NO:26 and the moiety capable of specific binding to TnC comprises a VH comprising the amino acid sequence of SEQ ID NO:54 and a VL comprising the amino acid sequence of SEQ ID NO:55,
(c) the moiety capable of specific binding to OX40 comprises a VH comprising the amino acid sequence of SEQ ID NO:27 and a VL comprising the amino acid sequence of SEQ ID NO:28 and the moiety capable of specific binding to TnC comprises a VH comprising the amino acid sequence of SEQ ID NO:52 and a VL comprising the amino acid sequence of SEQ ID NO:53,
(d) the moiety capable of specific binding to OX40 comprises a VH comprising the amino acid sequence of SEQ ID NO:27 and a VL comprising the amino acid sequence of SEQ ID NO:28 and the moiety capable of specific binding to TnC comprises a VH comprising the amino acid sequence of SEQ ID NO:54 and a VL comprising the amino acid sequence of SEQ ID NO:55,
(e) the moiety capable of specific binding to OX40 comprises a VH comprising the amino acid sequence of SEQ ID NO:29 and a VL comprising the amino acid sequence of SEQ ID NO:30 and the moiety capable of specific binding to TnC comprises a VH comprising the amino acid sequence of SEQ ID NO:52 and a VL comprising the amino acid sequence of SEQ ID NO:53,
(f) the moiety capable of specific binding to OX40 comprises a VH comprising the amino acid sequence of SEQ ID NO:29 and a VL comprising the amino acid sequence of SEQ ID NO:30 and the moiety capable of specific binding to TnC comprises a VH comprising the amino acid sequence of SEQ ID NO:54 and a VL comprising the amino acid sequence of SEQ ID NO:55,
(g) the moiety capable of specific binding to OX40 comprises a VH comprising the amino acid sequence of SEQ ID NO:31 and a VL comprising the amino acid sequence of SEQ ID NO:32 and the moiety capable of specific binding to TnC comprises a VH comprising the amino acid sequence of SEQ ID NO:52 and a VL comprising the amino acid sequence of SEQ ID NO:53,
(h) the moiety capable of specific binding to OX40 comprises a VH comprising the amino acid sequence of SEQ ID NO:31 and a VL comprising the amino acid sequence of SEQ ID NO:32 and the moiety capable of specific binding to TnC comprises a VH comprising the amino acid sequence of SEQ ID NO:54 and a VL comprising the amino acid sequence of SEQ ID NO:55,
(i) the moiety capable of specific binding to OX40 comprises a VH comprising the amino acid sequence of SEQ ID NO:33 and a VL comprising the amino acid sequence of SEQ ID NO:34 and the moiety capable of specific binding to TnC comprises a VH comprising the amino acid sequence of SEQ ID NO:52 and a VL comprising the amino acid sequence of SEQ ID NO:53,
(j) the moiety capable of specific binding to OX40 comprises a VH comprising the amino acid sequence of SEQ ID NO:33 and a VL comprising the amino acid sequence of SEQ ID NO:34 and the moiety capable of specific binding to TnC comprises a VH comprising the amino acid sequence of SEQ ID NO:54 and a VL comprising the amino acid sequence of SEQ ID NO:55,
(k) the moiety capable of specific binding to OX40 comprises a VH comprising the amino acid sequence of SEQ ID NO:35 and a VL comprising the amino acid sequence of SEQ ID NO:36 and the moiety capable of specific binding to TnC comprises a VH comprising the amino acid sequence of SEQ ID NO:52 and a VL comprising the amino acid sequence of SEQ ID NO:53,
(l) the moiety capable of specific binding to OX40 comprises a VH comprising the amino acid sequence of SEQ ID NO:35 and a VL comprising the amino acid sequence of SEQ ID NO:36 and the moiety capable of specific binding to TnC comprises a VH comprising the amino acid sequence of SEQ ID NO:54 and a VL comprising the amino acid sequence of SEQ ID NO:55,
(m) the moiety capable of specific binding to OX40 comprises a VH comprising the amino acid sequence of SEQ ID NO:37 and a VL comprising the amino acid sequence of SEQ ID NO:38 and the moiety capable of specific binding to TnC comprises a VH comprising the amino acid sequence of SEQ ID NO:52 and a VL comprising the amino acid sequence of SEQ ID NO:53, or (n) the moiety capable of specific binding to OX40 comprises a VH comprising the amino acid sequence of SEQ ID NO:37 and a VL comprising the amino acid sequence of SEQ ID NO:38 and the moiety capable of specific binding to TnC comprises a VH comprising the amino acid sequence of SEQ ID NO:54 and a VL comprising the amino acid sequence of SEQ ID NO:55.

In a particular aspect, the invention provides a bispecific antigen binding molecule, wherein the moiety capable of specific binding to OX40 comprises a VH comprising the amino acid sequence of SEQ ID NO:27 and a VL comprising the amino acid sequence of SEQ ID NO:28 and the moiety capable of specific binding to TnC comprises a VH comprising the amino acid sequence of SEQ ID NO:52 and a VL comprising the amino acid sequence of SEQ ID NO:53, or the moiety capable of specific binding to OX40 comprises a VH comprising the amino acid sequence of SEQ ID NO:27 and a VL comprising the amino acid sequence of SEQ ID NO:28 and the moiety capable of specific binding to TnC comprises a VH comprising the amino acid sequence of SEQ ID NO:54 and a VL comprising the amino acid sequence of SEQ ID NO:55.

Bispecific, Bivalent Antigen Binding Molecules (2+2 Format)

In one aspect, the invention relates to a bispecific antigen binding molecule, comprising
(a) two moieties capable of specific binding to OX40 comprising an antibody light chain variable region (VL) and an antibody heavy chain variable region (VH),
(b) two moieties capable of specific binding to TnC comprising an antibody light chain variable region (VL) and an antibody heavy chain variable region (VH), and
(c) a Fc region composed of a first and a second subunit capable of stable association.

In one aspect, the bispecific antigen binding molecule is bivalent both for OX40 and for TnC.

In one aspect, the bispecific antigen binding molecule of the invention comprises
(a) two light chains and two heavy chains of an antibody comprising two Fab fragments capable of specific binding to OX40, and a Fc region, and
(b) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

In one aspect, the bispecific antigen binding molecule of the invention comprises
(a) two heavy chains, each heavy chain comprising a VH and CH1 domain of a Fab fragment capable of specific binding to OX40, and a Fc region subunit,
(b) two light chains, each light chain comprising a VL and CL domain of a Fab fragment capable of specific binding to OX40,
(c) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

In some embodiments, the two Fab fragments capable of specific binding to TnC are crossover Fab fragments each comprising a VL-CH1 chain and a VH-CL chain, and wherein one of the VL-CH1 chains is connected to the C-terminus of one of the two heavy chains of (a), and the other of the VL-CH1 chains is connected to the C-terminus of the other of the two heavy chains of (a).

In some embodiments in accordance with various aspects of the present invention, Fab fragments capable of specific binding to TnC are connected to the C-terminus of the heavy chains of (a) via a peptide linker. In some embodiments in accordance with various aspects of the present invention, the VL-CH1 chain of a crossover Fab fragment capable of specific binding to TnC is connected to the C-terminus of one of the two heavy chains of (a) via a peptide linker. In particular embodiments, the peptide linker is (G4S)$_4$ (SEQ ID NO:69).

In a particular aspect, the invention provides a bispecific antigen binding molecule comprising
(a) two heavy chains, each comprising the amino acid sequence of SEQ ID NO:213, a first light chain comprising the amino acid sequence of SEQ ID NO:212, and a second light chain comprising the amino acid sequence of SEQ ID NO:214, or
(b) two heavy chains, each comprising the amino acid sequence of SEQ ID NO:215, a first light chain comprising the amino acid sequence of SEQ ID NO:212, and a second light chain comprising the amino acid sequence of SEQ ID NO:216.

In a particular aspect, the invention provides a bispecific antigen binding molecule comprising
two heavy chains, each comprising the amino acid sequence of SEQ ID NO:213,
two light chains, each comprising the amino acid sequence of SEQ ID NO:212, and
two light chains, each comprising the amino acid sequence of SEQ ID NO:214.

In a particular aspect, the invention provides a bispecific antigen binding molecule comprising
two heavy chains, each comprising the amino acid sequence of SEQ ID NO:215,
two light chains, each comprising the amino acid sequence of SEQ ID NO:212, and
two light chains, each comprising the amino acid sequence of SEQ ID NO:216.

Bispecific Antigen Binding Molecules Having Bivalent or Tetravalent Binding to OX40, and Monovalent Binding to TnC (2+1 and 4+1 Formats)

In one aspect, the bispecific antigen binding molecule is bivalent for OX40 and monovalent for TnC.

In one aspect, the bispecific antigen binding molecule of the invention comprises
(a) two Fab fragments capable of specific binding to OX40 connected to a Fc region, and
(b) a moiety capable of specific binding to TnC comprising an antibody light chain variable region (VL) and an antibody heavy chain variable region (VH) connected to the C-terminus of the Fc region.

In one aspect, the bispecific antigen binding molecule of the invention comprises
(a) two light chains and two heavy chains of an antibody comprising two Fab fragments capable of specific binding to OX40, and a Fc region, and
(b) a VH and a VL of a moiety capable specific binding to TnC, wherein the VH is connected to the C-terminus of one of the two heavy chains of (a), and wherein the VL is connected to the C-terminus of the other of the two heavy chains of (a).

In one aspect, the bispecific antigen binding molecule of the invention comprises
(a) two heavy chains, each heavy chain comprising a VH and CH1 domain of a Fab fragment capable of specific binding to OX40 and a Fc region subunit,
(b) two light chains, each light chain comprising a VL and CL domain of a Fab fragment capable of specific binding to OX40, and
(c) a VH and a VL of a moiety capable specific binding to TnC, wherein the VH is connected to the C-terminus of one of the two heavy chains of (a), and wherein the VL is connected to the C-terminus of the other of the two heavy chains of (a).

In another aspect, the bispecific antigen binding molecule of the invention comprises
(a) two heavy chains, each heavy chain comprising a VH and CH1 domain of a Fab fragment capable of specific binding to OX40 and a Fc region subunit,
(b) two light chains, each light chain comprising a VL and CL domain of a Fab fragment capable of specific binding to OX40, and
(c) a Fab fragment capable specific binding to TnC, wherein the VHCH1 chain or the VLCL chain of the Fab fragment is connected to the C-terminus of one of the two heavy chains of (a).

Bispecific Antigen Binding Molecules Having Tetravalent Binding to OX40, and Monovalent Binding to TnC (4+1 Format)

In one aspect, the bispecific antigen binding molecule is tetravalent for OX40 and monovalent for TnC.

In one aspect, the bispecific antigen binding molecule of the invention comprises
(a) four Fab fragments capable of specific binding to OX40 connected to a Fc region, and
(b) a moiety capable of specific binding to TnC comprising an antibody light chain variable region (VL) and an antibody heavy chain variable region (VH) connected to the C-terminus of the Fc region.

In one aspect, the bispecific antigen binding molecule of the invention comprises
(a) two light chains and two heavy chains of an antibody comprising four Fab fragments capable of specific binding to OX40, and a Fc region, and
(b) a VH and a VL of a moiety capable specific binding to TnC, wherein the VH is connected to the C-terminus of one of the two heavy chains of (a), and wherein the VL is connected to the C-terminus of the other of the two heavy chains of (a).

In one aspect, the bispecific antigen binding molecule of the invention comprises
(a) two heavy chains, each heavy chain comprising two VH domains and two CH1 domains of a Fab fragment capable of specific binding to OX40 and a Fc region subunit,
(b) four light chains, each light chain comprising a VL and CL domain of a Fab fragment capable of specific binding to OX40, and
(c) a VH and a VL of a moiety capable specific binding to TnC, wherein the VH is connected to the C-terminus of one of the two heavy chains of (a), and wherein the VL is connected to the C-terminus of the other of the two heavy chains of (a).

In some embodiments in accordance with various aspects of the present invention, the VH of a moiety capable specific binding to TnC is connected to the C-terminus of one of the two heavy chains of (a) via a peptide linker. In some embodiments in accordance with various aspects of the present invention, the VL of a moiety capable specific binding to TnC is connected to the C-terminus of one of the two heavy chains of (a) via a peptide linker. In particular embodiments, the peptide linker is (G4S)$_4$ (SEQ ID NO:69).

In a particular aspect, the invention provides a bispecific antigen binding molecule comprising a first heavy chain comprising the amino acid sequence of SEQ ID NO:222, a second heavy chain comprising the amino acid sequence of SEQ ID NO:223, and a light chain comprising the amino acid sequence of SEQ ID NO:212.

In a particular aspect, the invention provides a bispecific antigen binding molecule comprising
a first heavy chain comprising the amino acid sequence of SEQ ID NO:222,
a second heavy chain comprising the amino acid sequence of SEQ ID NO:223, and
four light chains, each comprising the amino acid sequence of SEQ ID NO:212.

In one aspect, the bispecific antigen binding molecule of the invention comprises a first and a second heavy chain and four light chains that form a first, a second, a third, a forth, and a fifth antigen binding moiety, wherein the first, the second, the third, and the fourth antigen binding moiety each are capable of specific binding to OX40 and the fifth antigen binding moiety is capable of specific binding to TnC, wherein
(i) the first polypeptide chain comprises in amino (N)-terminal to carboxyl (C)-terminal direction, VH(OX40), CH1, VH(OX40), CH1, CH2, CH3 (Fc knob) and VH(TnC),
(ii) the second polypeptide chain comprises in N-terminal to C-terminal direction, VH(OX40), CH1, VH(OX40), CH1, CH2, CH3 (Fc hole) and VL(TnC), and
(iii) four light chains comprise in N-terminal to C-terminal direction VL(Ox40) and CL.

In another aspect, the bispecific antigen binding molecule of the invention comprises a first and a second heavy chain and four light chains that form a first, a second, a third, a forth, and a fifth antigen binding moiety, wherein the first, the second, the third, and the fourth antigen binding moiety each are capable of specific binding to OX40 and the fifth antigen binding moiety is capable of specific binding to TnC, wherein
(i) the first polypeptide chain comprises in amino (N)-terminal to carboxyl (C)-terminal direction, VH(OX40), CH1, VH(OX40), CH1, CH2, CH3 (Fc knob) and VL(TnC),
(ii) the second polypeptide chain comprises in N-terminal to C-terminal direction, VH(OX40), CH1, VH(OX40), CH1, CH2, CH3 (Fc hole) and VH(TnC), and
(iii) the four light chains comprise in N-terminal to C-terminal direction VL(Ox40) and CL.

Bispecific Antigen Binding Molecules Having Tetravalent Binding to OX40, and Bivalent Binding to TnC (4+2 Format)

In one aspect, the bispecific antigen binding molecule is tetravalent for OX40 and bivalent for TnC.

In one aspect, the bispecific antigen binding molecule of the invention comprises
(a) four Fab fragments capable of specific binding to OX40 connected to a Fc region, and
(b) two moieties capable of specific binding to TnC comprising an antibody light chain variable region (VL) and an antibody heavy chain variable region (VH) connected to the C-terminus of the Fc region.

In one aspect, the bispecific antigen binding molecule of the invention comprises
(a) four light chains and two heavy chains of an antibody comprising four Fab fragments capable of specific binding to OX40, and a Fc region, and (b) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

In one aspect, the bispecific antigen binding molecule of the invention comprises
(a) two heavy chains, each heavy chain comprising two VH domains and two CH1 domains of a Fab fragment capable of specific binding to OX40 and a Fc region subunit,
(b) four light chains, each light chain comprising a VL and CL domain of a Fab fragment capable of specific binding to OX40, and
(c) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

In some embodiments, the two Fab fragments capable of specific binding to TnC are crossover Fab fragments each comprising a VL-CH1 chain and a VH-CL chain, and wherein one of the VL-CH1 chains is connected to the C-terminus of one of the two heavy chains of (a), and the other of the VL-CH1 chains is connected to the C-terminus of the other of the two heavy chains of (a).

In some embodiments in accordance with various aspects of the present invention, Fab fragments capable of specific binding to TnC are connected to the C-terminus of the heavy chains of (a) via a peptide linker. In some embodiments in accordance with various aspects of the present invention, the VL-CH1 chain of a crossover Fab fragment capable of specific binding to TnC is connected to the C-terminus of one of the two heavy chains of (a) via a peptide linker. In particular embodiments, the peptide linker is (G4S)$_4$ (SEQ ID NO:69).

In a particular aspect, the invention provides a bispecific antigen binding molecule comprising two heavy chains, each comprising the amino acid sequence of SEQ ID NO:225, a first light chain comprising the amino acid sequence of SEQ ID NO:224, and a second light chain comprising the amino acid sequence of SEQ ID NO:226.

In a particular aspect, the invention provides a bispecific antigen binding molecule comprising
two heavy chains, each comprising the amino acid sequence of SEQ ID NO:225,
four light chains, each comprising the amino acid sequence of SEQ ID NO:224, and
two light chains, each comprising the amino acid sequence of SEQ ID NO:226.

In one aspect, the bispecific antigen binding molecule of the invention comprises a first and a second heavy chain and six light chains that form a first, a second, a third, a forth, a fifth, and a sixth antigen binding moiety, wherein the first, the second, the third, and the fourth antigen binding moiety each are capable of specific binding to OX40, and wherein the fifth and the sixth antigen binding moiety each are capable of specific binding to TnC, wherein
(i) the first and the second polypeptide chains comprise in amino (N)-terminal to carboxyl (C)-terminal direction, VH(OX40), CH1*, VH(OX40), CH1*, CH2, CH3, VL(TnC) and CH1,
(ii) four light chains comprise in N-terminal to C-terminal direction VL(OX40) and CL*, and
(iii) two light chains comprise in N-terminal to C-terminal direction VH(TnC) and CL and wherein CH1* and CL* comprise amino acid mutations to allow better pairing.

Fc Region Modifications Reducing Fc Receptor Binding and/or Effector Function

In embodiments in accordance with various aspects of the present invention, the bispecific antigen binding molecules further comprise a Fc region composed of a first and a second subunit capable of stable association.

In certain aspects, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

The Fc region confers favorable pharmacokinetic properties to the bispecific antibodies of the invention, including a long serum half-life which contributes to good accumulation in the target tissue and a favorable tissue-blood distribution ratio. At the same time it may, however, lead to undesirable targeting of the bispecific antibodies of the invention to cells expressing Fc receptors rather than to the preferred antigen-bearing cells. Accordingly, in particular embodiments the Fc region of the bispecific antibodies of the invention exhibits reduced binding affinity to an Fc receptor and/or reduced effector function, as compared to a native IgG Fc region, in particular an IgG1 Fc region or an IgG4 Fc region. More particularly, the Fc region is an IgG1 Fc region.

In one such aspect the Fc region (or the bispecific antigen binding molecule of the invention comprising said Fc region) exhibits less than 50%, preferably less than 20%, more preferably less than 10% and most preferably less than 5% of the binding affinity to an Fc receptor, as compared to a native IgG1 Fc region (or the bispecific antigen binding molecule of the invention comprising a native IgG1 Fc region), and/or less than 50%, preferably less than 20%, more preferably less than 10% and most preferably less than 5% of the effector function, as compared to a native IgG1 Fc region (or the bispecific antigen binding molecule of the invention comprising a native IgG1 Fc region). In one aspect, the Fc region (or the bispecific antigen binding molecule of the invention comprising said Fc region) does not substantially bind to an Fc receptor and/or induce effector function. In a particular aspect the Fc receptor is an Fcγ receptor.

In one aspect, the Fc receptor is a human Fc receptor. In one aspect, the Fc receptor is an activating Fc receptor. In a specific aspect, the Fc receptor is an activating human Fcγ receptor, more specifically human FcγRIIIa, FcγRI or FcγRIIa, most specifically human FcγRIIIa. In one aspect, the Fc receptor is an inhibitory Fc receptor. In a specific aspect, the Fc receptor is an inhibitory human Fcγ receptor, more specifically human FcγRIIB. In one aspect the effector function is one or more of CDC, ADCC, ADCP, and cytokine secretion. In a particular aspect, the effector function is ADCC. In one aspect, the Fc region domain exhibits substantially similar binding affinity to neonatal Fc receptor (FcRn), as compared to a native IgG1 Fc region. Substantially similar binding to FcRn is achieved when the Fc region (or the bispecific antigen binding molecule of the invention comprising said Fc region) exhibits greater than about 70%, particularly greater than about 80%, more particularly greater than about 90% of the binding affinity of a native IgG1 Fc region (or the bispecific antigen binding molecule of the invention comprising a native IgG1 Fc region) to FcRn.

In a particular aspect, the Fc region is engineered to have reduced binding affinity to an Fc receptor and/or reduced effector function, as compared to a non-engineered Fc region. In a particular aspect, the Fc region of the bispecific antigen binding molecule of the invention comprises one or more amino acid mutation that reduces the binding affinity of the Fc region to an Fc receptor and/or effector function. Typically, the same one or more amino acid mutation is present in each of the two subunits of the Fc region. In one aspect, the amino acid mutation reduces the binding affinity of the Fc region to an Fc receptor. In another aspect, the amino acid mutation reduces the binding affinity of the Fc region to an Fc receptor by at least 2-fold, at least 5-fold, or at least 10-fold. In one aspect, the bispecific antigen binding molecule of the invention comprising an engineered Fc region exhibits less than 20%, particularly less than 10%, more particularly less than 5% of the binding affinity to an Fc receptor as compared to bispecific antibodies of the invention comprising a non-engineered Fc region. In a particular aspect, the Fc receptor is an Fcγ receptor. In other aspects, the Fc receptor is a human Fc receptor. In one aspect, the Fc receptor is an inhibitory Fc receptor. In a specific aspect, the Fc receptor is an inhibitory human Fcγ receptor, more specifically human FcγRIIB. In some aspects the Fc receptor is an activating Fc receptor. In a specific aspect, the Fc receptor is an activating human Fcγ receptor, more specifically human FcγRIIIa, FcγRI or FcγRIIa, most specifically human FcγRIIIa. Preferably, binding to each of these receptors is reduced. In some aspects, binding affinity to a complement component, specifically binding affinity to C1q, is also reduced. In one aspect, binding affinity to neonatal Fc receptor (FcRn) is not reduced. Substantially similar binding to FcRn, i.e. preservation of the binding affinity of the Fc region to said receptor, is achieved when the Fc region (or the bispecific antigen binding molecule of the invention comprising said Fc region) exhibits greater than about 70% of the binding affinity of a non-engineered form of the Fc region (or the bispecific antigen binding molecule of the invention comprising said non-engineered form of the Fc region) to FcRn. The Fc region, or the bispecific antigen binding molecule of the invention comprising said Fc region, may exhibit greater than about 80% and even greater than about 90% of such affinity. In certain embodiments the Fc region of the bispecific antigen binding molecule of the invention is engineered to have reduced effector function, as compared to a non-engineered Fc region. The reduced effector function can include, but is not limited to, one or more of the following: reduced complement dependent cytotoxicity (CDC), reduced antibody-dependent cell-mediated cytotoxicity (ADCC), reduced antibody-dependent cellular phagocytosis (ADCP), reduced cytokine secretion, reduced immune complex-mediated antigen uptake by antigen-presenting cells, reduced binding to NK cells, reduced binding to macrophages, reduced binding to monocytes, reduced binding to polymorphonuclear cells, reduced direct signaling inducing apoptosis, reduced dendritic cell maturation, or reduced T cell priming.

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581). Certain antibody variants with improved or diminished binding to FcRs are described. (e.g. U.S. Pat. No. 6,737,056; WO 2004/056312, and Shields, R. L. et al., J. Biol. Chem. 276 (2001) 6591-6604).

In one aspect of the invention, the Fc region comprises an amino acid substitution at a position of E233, L234, L235, N297, P331 and P329. In some aspects, the Fc region comprises the amino acid substitutions L234A and L235A ("LALA"). In one such embodiment, the Fc region is an IgG1 Fc region, particularly a human IgG1 Fc region. In one aspect, the Fc region comprises an amino acid substitution at position P329. In a more specific aspect, the amino acid substitution is P329A or P329G, particularly P329G. In one embodiment the Fc region comprises an amino acid substitution at position P329 and a further amino acid substitution selected from the group consisting of E233P, L234A, L235A, L235E, N297A, N297D or P331S. In more particular embodiments the Fc region comprises the amino acid mutations L234A, L235A and P329G ("P329G LALA"). The "P329G LALA" combination of amino acid substitutions almost completely abolishes Fcγ receptor binding of a human IgG1 Fc region, as described in PCT Patent Application No. WO 2012/130831 A1. Said document also describes methods of preparing such mutant Fc regions and methods for determining its properties such as Fc receptor binding or effector functions. such antibody is an IgG1 with mutations L234A and L235A or with mutations L234A, L235A and P329G (numbering according to EU index of Kabat et al, Kabat et al., Sequences of Proteins of Immunological Interest, 5th Ed. Public Health Service, National Institutes of Health, Bethesda, Md., 1991).

In one aspect, the Fc region is an IgG4 Fc region. In a more specific embodiment, the Fc region is an IgG4 Fc region comprising an amino acid substitution at position S228 (Kabat numbering), particularly the amino acid substitution S228P. In a more specific embodiment, the Fc region is an IgG4 Fc region comprising amino acid substitutions L235E and S228P and P329G. This amino acid substitution reduces in vivo Fab arm exchange of IgG4 antibodies (see Stubenrauch et al., Drug Metabolism and Disposition 38, 84-91 (2010)).

Antibodies with increased half lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826). See also Duncan, A. R. and Winter, G., Nature 322 (1988) 738-740; U.S. Pat. Nos. 5,648,260; 5,624,821; and WO 94/29351 concerning other examples of Fc region variants.

Binding to Fc receptors can be easily determined e.g. by ELISA, or by Surface Plasmon Resonance (SPR) using standard instrumentation such as a BIAcore instrument (GE Healthcare), and Fc receptors such as may be obtained by recombinant expression. A suitable such binding assay is described herein. Alternatively, binding affinity of Fc regions or cell activating bispecific antigen binding molecules comprising an Fc region for Fc receptors may be evaluated using cell lines known to express particular Fc receptors, such as human NK cells expressing FcγIIIa receptor. Effector function of an Fc region, or bispecific antibodies of the invention comprising an Fc region, can be measured by methods known in the art. A suitable assay for measuring ADCC is described herein. Other examples of in vitro assays to assess ADCC activity of a molecule of interest are described in U.S. Pat. No. 5,500,362; Hellstrom et al. Proc Natl Acad Sci USA 83, 7059-7063 (1986) and Hellstrom et al., Proc Natl Acad Sci USA 82, 1499-1502 (1985); U.S. Pat. No. 5,821,337; Bruggemann et al., J Exp Med 166, 1351-1361 (1987). Alternatively, non-radioactive assays methods may be employed (see, for example, ACTI™ non-radioactive cytotoxicity assay for flow cytometry (CellTechnology, Inc. Mountain View, Calif.); and CytoTox 96® non-radioactive cytotoxicity assay (Promega, Madison, Wis.)). Useful effector cells for such assays include peripheral blood mononuclear cells (PBMC) and Natural Killer (NK) cells. Alternatively, or additionally, ADCC activity of the molecule of interest may be assessed in vivo, e.g. in a animal model such as that disclosed in Clynes et al., Proc Natl Acad Sci USA 95, 652-656 (1998).

The following section describes preferred aspects of the bispecific antigen binding molecules of the invention comprising Fc region modifications reducing Fc receptor binding and/or effector function. In one aspect, the invention relates to the bispecific antigen binding molecule (a) at least one moiety capable of specific binding to OX40, (b) at least one moiety capable of specific binding to TnC, and (c) a Fc region composed of a first and a second subunit capable of stable association, wherein the Fc region comprises one or more amino acid substitution that reduces the binding affinity of the antibody to an Fc receptor, in particular towards Fcγ receptor. In another aspect, the invention relates to the bispecific antigen binding molecule comprising (a) at least one moiety capable of specific binding to OX40, (b) at least one moiety capable of specific binding to TnC, and (c) a Fc region composed of a first and a second subunit capable of stable association, wherein the Fc region comprises one or more amino acid substitution that reduces effector function. In particular aspect, the Fc region is of human IgG1 subclass with the amino acid mutations L234A, L235A and P329G (numbering according to Kabat EU index).

Fc Region Modifications Promoting Heterodimerization

The bispecific antigen binding molecules of the invention comprise different antigen-binding sites, fused to one or the other of the two subunits of the Fc region, thus the two subunits of the Fc region may be comprised in two non-identical polypeptide chains. Recombinant co-expression of these polypeptides and subsequent dimerization leads to several possible combinations of the two polypeptides. To improve the yield and purity of the bispecific antibodies of the invention in recombinant production, it will thus be advantageous to introduce in the Fc region of the bispecific antigen binding molecules of the invention a modification promoting the association of the desired polypeptides.

Accordingly, in particular aspects the invention relates to the bispecific antigen binding molecule comprising (a) at least one moiety capable of specific binding to OX40, (b) at least one moiety capable of specific binding to TnC, and (c) a Fc region composed of a first and a second subunit capable of stable association, wherein the Fc region comprises a modification promoting the association of the first and second subunit of the Fc region. The site of most extensive protein-protein interaction between the two subunits of a human IgG Fc region is in the CH3 domain of the Fc region. Thus, in one aspect said modification is in the CH3 domain of the Fc region.

In a specific aspect said modification is a so-called "knob-into-hole" modification, comprising a "knob" modification in one of the two subunits of the Fc region and a "hole" modification in the other one of the two subunits of the Fc region. Thus, the invention relates to the bispecific antigen binding molecule comprising (a) at least one moiety capable of specific binding to OX40, (b) at least one moiety capable of specific binding to TnC, and (c) a Fc region composed of a first and a second subunit capable of stable association, wherein the first subunit of the Fc region comprises knobs and the second subunit of the Fc region comprises holes according to the knobs into holes method. In a particular aspect, the first subunit of the Fc region comprises the amino acid substitutions S354C and T366W (EU numbering) and the second subunit of the Fc region comprises the amino acid substitutions Y349C, T366S and Y407V (numbering according to Kabat EU index).

The knob-into-hole technology is described e.g. in U.S. Pat. Nos. 5,731,168; 7,695,936; Ridgway et al., Prot Eng 9, 617-621 (1996) and Carter, J Immunol Meth 248, 7-15 (2001). Generally, the method involves introducing a protuberance ("knob") at the interface of a first polypeptide and a corresponding cavity ("hole") in the interface of a second polypeptide, such that the protuberance can be positioned in the cavity so as to promote heterodimer formation and hinder homodimer formation. Protuberances are constructed by replacing small amino acid side chains from the interface of the first polypeptide with larger side chains (e.g. tyrosine or tryptophan). Compensatory cavities of identical or similar size to the protuberances are created in the interface of the second polypeptide by replacing large amino acid side chains with smaller ones (e.g. alanine or threonine).

Accordingly, in one aspect, in the CH3 domain of the first subunit of the Fc region of the bispecific antigen binding molecules of the invention an amino acid residue is replaced with an amino acid residue having a larger side chain volume, thereby generating a protuberance within the CH3 domain of the first subunit which is positionable in a cavity within the CH3 domain of the second subunit, and in the CH3 domain of the second subunit of the Fc region an amino acid residue is replaced with an amino acid residue having a smaller side chain volume, thereby generating a cavity within the CH3 domain of the second subunit within which the protuberance within the CH3 domain of the first subunit is positionable. The protuberance and cavity can be made by altering the nucleic acid encoding the polypeptides, e.g. by site-specific mutagenesis, or by peptide synthesis. In a specific aspect, in the CH3 domain of the first subunit of the Fc region the threonine residue at position 366 is replaced with a tryptophan residue (T366W), and in the CH3 domain of the second subunit of the Fc region the tyrosine residue at position 407 is replaced with a valine residue (Y407V). In one aspect, in the second subunit of the Fc region additionally the threonine residue at position 366 is replaced with a serine residue (T366S) and the leucine residue at position 368 is replaced with an alanine residue (L368A).

In yet a further aspect, in the first subunit of the Fc region additionally the serine residue at position 354 is replaced with a cysteine residue (S354C), and in the second subunit of the Fc region additionally the tyrosine residue at position 349 is replaced by a cysteine residue (Y349C). Introduction of these two cysteine residues results in formation of a disulfide bridge between the two subunits of the Fc region, further stabilizing the dimer (Carter (2001), J Immunol Methods 248, 7-15). In a particular aspect, the first subunit of the Fc region comprises the amino acid substitutions S354C and T366W (EU numbering) and the second subunit of the Fc region comprises the amino acid substitutions Y349C, T366S and Y407V (numbering according to Kabat EU index).

In an alternative aspect, a modification promoting association of the first and the second subunit of the Fc region comprises a modification mediating electrostatic steering effects, e.g. as described in PCT publication WO 2009/089004. Generally, this method involves replacement of one or more amino acid residues at the interface of the two Fc region subunits by charged amino acid residues so that homodimer formation becomes electrostatically unfavorable but heterodimerization electrostatically favorable.

The C-terminus of the heavy chain of the bispecific antibody as reported herein can be a complete C-terminus ending with the amino acid residues PGK. The C-terminus of the heavy chain can be a shortened C-terminus in which one or two of the C terminal amino acid residues have been removed. In one preferred aspect, the C-terminus of the heavy chain is a shortened C-terminus ending PG. In one aspect of all aspects as reported herein, a bispecific antibody comprising a heavy chain including a C-terminal CH3 domain as specified herein, comprises the C-terminal glycine-lysine dipeptide (G446 and K447, numbering according to Kabat EU index). In one embodiment of all aspects as reported herein, a bispecific antibody comprising a heavy chain including a C-terminal CH3 domain, as specified herein, comprises a C-terminal glycine residue (G446, numbering according to Kabat EU index).

Modifications in the Fab Domains

In one aspect, the invention relates to a bispecific antigen binding molecule comprising (a) a first Fab fragment capable of specific binding to OX40, (b) a second Fab fragment capable of specific binding to TnC, and (c) a Fc region composed of a first and a second subunit capable of stable association, wherein in one of the Fab fragments either the variable domains VH and VL or the constant domains CH1 and CL are exchanged. The bispecific antibodies are prepared according to the Crossmab technology.

Multispecific antibodies with a domain replacement/exchange in one binding arm (CrossMabVH-VL or CrossMabCH-CL) are described in detail in WO2009/080252 and Schaefer, W. et al, PNAS, 108 (2011) 11187-1191. They clearly reduce the byproducts caused by the mismatch of a light chain against a first antigen with the wrong heavy chain against the second antigen (compared to approaches without such domain exchange).

In one aspect, the invention relates to a bispecific antigen binding molecule comprising (a) a first Fab fragment capable of specific binding to OX40, (b) a second Fab fragment capable of specific binding to TnC, and (c) a Fc region composed of a first and a second subunit capable of stable association, wherein in one of the Fab fragments the constant domains CL and CH1 are replaced by each other so that the CH1 domain is part of the light chain and the CL domain is part of the heavy chain. More particularly, in the second Fab fragment capable of specific binding to TnC the constant domains CL and CH1 are replaced by each other so that the CH1 domain is part of the light chain and the CL domain is part of the heavy chain.

In a particular aspect, the invention relates a bispecific antigen binding molecule comprising (a) a first Fab fragment capable of specific binding to OX40, (b) a second Fab fragment capable of specific binding to TnC, wherein the constant domains CL and CH1 are replaced by each other so that the CH1 domain is part of the light chain and the CL domain is part of the heavy chain. Such a molecule is called a monovalent bispecific antigen binding molecule.

In another aspect, the invention relates to a bispecific antigen binding molecule, comprising (a) two light chains and two heavy chains of an antibody comprising two Fab fragments capable of specific binding to OX40 and the Fc region, and (b) two additional Fab fragments capable of specific binding to TnC, wherein said additional Fab fragments are each connected via a peptide linker to the C-terminus of the heavy chains of (a). In a particular aspect, the additional Fab fragments are Fab fragments, wherein the variable domains VL and VH are replaced by each other so that the VH is part of the light chain and the VL is part of the heavy chain.

Thus, in a particular aspect, the invention comprises a bispecific, antigen binding molecule, comprising (a) two light chains and two heavy chains of an antibody comprising two Fab fragments capable of specific binding to OX40 and the Fc region, and (b) two additional Fab fragments capable of specific binding to TnC, wherein said two additional Fab fragments capable of specific binding to a TnC are crossover Fab fragments wherein the variable domains VL and VH are replaced by each other and the VL-CH chains are each connected via a peptide linker to the C-terminus of the heavy chains of (a).

In another aspect, and to further improve correct pairing, the bispecific antigen binding molecule comprising (a) a first Fab fragment capable of specific binding to OX40, (b) a second Fab fragment capable of specific binding to TnC, and (c) a Fc region composed of a first and a second subunit capable of stable association, can contain different charged amino acid substitutions (so-called "charged residues"). These modifications are introduced in the crossed or non-crossed CH1 and CL domains. In a particular aspect, the invention relates to a bispecific antigen binding molecule, wherein in one of CL domains the amino acid at position 123 (EU numbering) has been replaced by arginine (R) and the amino acid at position 124 (EU numbering) has been substituted by lysine (K) and wherein in one of the CH1 domains the amino acids at position 147 (EU numbering) and at position 213 (EU numbering) have been substituted by glutamic acid (E).

More particularly, the invention relates to a bispecific antigen binding molecule comprising a Fab, wherein in the CL domain the amino acid at position 123 (EU numbering) has been replaced by arginine (R) and the amino acid at position 124 (EU numbering) has been substituted by lysine (K), and wherein in the CH1 domain the amino acids at position 147 (EU numbering) and at position 213 (EU numbering) have been substituted by glutamic acid (E).

Accordingly, in some embodiments one or more of the Fab fragments (e.g. Fab fragments capable of specific binding to OX40) of the bispecific antigen binding molecule of the present invention comprise a CL domain comprising an arginine (R) at amino acid at position 123 (EU numbering) and a lysine (K) at amino acid at position 124 (EU numbering), and a CH1 domain comprising a glutamic acid (E) at amino acid at position 147 (EU numbering) and a glutamic acid (E) at amino acid at position 213 (EU numbering).

Polynucleotides

The invention further provides isolated polynucleotides encoding a bispecific antigen binding molecule of the invention as described herein, or a fragment thereof.

The isolated polynucleotides encoding bispecific antigen binding molecules of the invention may be expressed as a single polynucleotide that encodes the entire antigen binding molecule or as multiple (e.g., two or more) polynucleotides that are co-expressed. Polypeptides encoded by polynucleotides that are co-expressed may associate through, e.g., disulfide bonds or other means to form a functional antigen binding molecule. For example, the light chain portion of a moiety capable of specific binding to TnC may be encoded by a separate polynucleotide from the heavy chain portion of the capable of specific binding to TnC. When co-expressed, the heavy chain polypeptides will associate with the light chain polypeptides to form the moiety capable of specific binding to TnC. Similarly, the light chain portion of a moiety capable of specific binding to OX40 may be encoded by a separate polynucleotide from the heavy chain portion of the capable of specific binding to OX40. When co-expressed, the heavy chain polypeptides will associate with the light chain polypeptides to form the moiety capable of specific binding to OX40.

In certain embodiments the polynucleotide or nucleic acid is DNA. In other embodiments, a polynucleotide of the present invention is RNA, for example, in the form of messenger RNA (mRNA). RNA of the present invention may be single stranded or double stranded.

According to another aspect of the invention, there is provided an isolated polynucleotide encoding a bispecific antigen binding molecule as defined herein before or a fusion polypeptide as described herein before. The invention further provides a vector, particularly an expression vector, comprising the isolated polynucleotide of the invention and a host cell comprising the isolated polynucleotide or the vector of the invention. In some embodiments the host cell is a eukaryotic cell, particularly a mammalian cell.

In another aspect, provided is a method for producing the bispecific antigen binding molecule of the invention, comprising the steps of (i) culturing the host cell of the invention under conditions suitable for expression of said antigen binding molecule, and (ii) isolating said bispecific antigen binding molecule. The invention also encompasses a bispecific antigen binding molecule produced by the method of the invention.

Recombinant Methods

Bispecific antigen binding molecules of the invention may be obtained, for example, by solid-state peptide synthesis (e.g. Merrifield solid phase synthesis) or recombinant production. For recombinant production one or more polynucleotide encoding the antigen binding molecule or polypeptide fragments thereof, e.g., as described above, is isolated and inserted into one or more vectors for further cloning and/or expression in a host cell. Such polynucleotide may be readily isolated and sequenced using conventional procedures. In one aspect of the invention, a vector, preferably an expression vector, comprising one or more of the polynucleotides of the invention is provided. Methods which are well known to those skilled in the art can be used to construct expression vectors containing the coding sequence of the bispecific antigen binding molecule (fragment) along with appropriate transcriptional/translational control signals. These methods include in vitro recombinant DNA techniques, synthetic techniques and in vivo recombination/genetic recombination. See, for example, the techniques described in Maniatis et al., MOLECULAR CLONING: A LABORATORY MANUAL, Cold Spring Harbor Laboratory, N.Y. (1989); and Ausubel et al., CURRENT PROTOCOLS IN MOLECULAR BIOLOGY, Greene Publishing Associates and Wiley Interscience, N.Y. (1989). The expression vector can be part of a plasmid, virus, or may be a nucleic acid fragment. The expression vector includes an expression cassette into which the polynucleotide encoding the bispecific antigen binding molecule or polypeptide fragments thereof (i.e. the coding region) is cloned in operable association with a promoter and/or other transcription or translation control elements. As used herein, a "coding region" is a portion of nucleic acid which consists of codons translated into amino acids. Although a "stop codon" (TAG, TGA, or TAA) is not translated into an amino acid, it may be considered to be part of a coding region, if present, but any flanking sequences, for example promoters, ribosome binding sites, transcriptional terminators, introns, 5' and 3' untranslated regions, and the like, are not part of a coding region. Two or more coding regions can be present in a single polynucleotide construct, e.g. on a single vector, or in separate polynucleotide constructs, e.g. on separate (different) vectors. Furthermore, any vector may contain a single coding region, or may comprise two or more coding regions, e.g. a vector of the present invention may encode one or more polypeptides, which are post- or co-translationally separated into the final proteins via proteolytic cleavage. In addition, a vector, polynucleotide, or nucleic acid of the invention may encode heterologous coding regions, either fused or unfused to a polynucleotide encoding the bispecific antigen binding molecule of the invention or polypeptide fragments thereof, or variants or derivatives thereof. Heterologous coding regions include without limitation specialized elements or motifs, such as a secretory signal peptide or a heterologous functional domain. An operable association is when a coding region for a gene product, e.g. a polypeptide, is associated with one or more regulatory sequences in such a way as to place expression of the gene product under the influence or control of the regulatory sequence(s). Two DNA fragments (such as a polypeptide coding region and a promoter associated therewith) are "operably associated" if induction of promoter function results in the transcription of mRNA encoding the desired gene product and if the nature of the linkage between the two DNA fragments does not interfere with the ability of the expression regulatory sequences to direct the expression of the gene product or interfere with the ability of the DNA template to be transcribed. Thus, a promoter region would be operably associated with a nucleic acid encoding a polypeptide if the promoter was capable of effecting transcription of that nucleic acid. The promoter may be a cell-specific promoter that directs substantial transcription of the DNA only in predetermined cells. Other transcription control elements, besides a promoter, for example enhancers, operators, repressors, and transcription termination signals, can be operably associated with the polynucleotide to direct cell-specific transcription.

Suitable promoters and other transcription control regions are disclosed herein. A variety of transcription control regions are known to those skilled in the art. These include, without limitation, transcription control regions, which function in vertebrate cells, such as, but not limited to, promoter and enhancer segments from cytomegaloviruses (e.g. the immediate early promoter, in conjunction with intron-A), simian virus 40 (e.g. the early promoter), and retroviruses (such as, e.g. Rous sarcoma virus). Other transcription control regions include those derived from vertebrate genes such as actin, heat shock protein, bovine growth hormone and rabbit α-globin, as well as other sequences capable of controlling gene expression in eukaryotic cells. Additional suitable transcription control regions include tissue-specific promoters and enhancers as well as inducible promoters (e.g. promoters inducible tetracyclins). Similarly, a variety of translation control elements are known to those of ordinary skill in the art. These include, but are not limited to ribosome binding sites, translation initiation and termination codons, and elements derived from viral systems (particularly an internal ribosome entry site, or IRES, also referred to as a CITE sequence). The expression cassette may also include other features such as an origin of replication, and/or chromosome integration elements such as retroviral long terminal repeats (LTRs), or adeno-associated viral (AAV) inverted terminal repeats (ITRs).

Polynucleotide and nucleic acid coding regions of the present invention may be associated with additional coding regions which encode secretory or signal peptides, which direct the secretion of a polypeptide encoded by a polynucleotide of the present invention. For example, if secretion of the bispecific antigen binding molecule or polypeptide fragments thereof is desired, DNA encoding a signal sequence may be placed upstream of the nucleic acid encoding a bispecific antigen binding molecule of the invention or polypeptide fragments thereof. According to the signal hypothesis, proteins secreted by mammalian cells have a signal peptide or secretory leader sequence which is cleaved from the mature protein once export of the growing protein chain across the rough endoplasmic reticulum has been initiated. Those of ordinary skill in the art are aware that polypeptides secreted by vertebrate cells generally have a signal peptide fused to the N-terminus of the polypeptide, which is cleaved from the translated polypeptide to produce a secreted or "mature" form of the polypeptide. In certain embodiments, the native signal peptide, e.g. an immunoglobulin heavy chain or light chain signal peptide is used, or a functional derivative of that sequence that retains the ability to direct the secretion of the polypeptide that is operably associated with it. Alternatively, a heterologous mammalian signal peptide, or a functional derivative thereof, may be used. For example, the wild-type leader sequence may be substituted with the leader sequence of human tissue plasminogen activator (TPA) or mouse β-glucuronidase.

DNA encoding a short protein sequence that could be used to facilitate later purification (e.g. a histidine tag) or assist in labeling the fusion protein may be included within or at the ends of the polynucleotide encoding a bispecific antigen binding molecule of the invention or polypeptide fragments thereof.

In a further aspect of the invention, a host cell comprising one or more polynucleotides of the invention is provided. In certain embodiments a host cell comprising one or more vectors of the invention is provided. The polynucleotides and vectors may incorporate any of the features, singly or in combination, described herein in relation to polynucleotides and vectors, respectively. In one aspect, a host cell comprises (e.g. has been transformed or transfected with) a vector comprising a polynucleotide that encodes (part of) a bispecific antigen binding molecule of the invention. As used herein, the term "host cell" refers to any kind of cellular system which can be engineered to generate the fusion proteins of the invention or fragments thereof. Host cells suitable for replicating and for supporting expression of antigen binding molecules are well known in the art. Such cells may be transfected or transduced as appropriate with the particular expression vector and large quantities of vector containing cells can be grown for seeding large scale fermenters to obtain sufficient quantities of the antigen binding molecule for clinical applications. Suitable host cells include prokaryotic microorganisms, such as E. coli, or various eukaryotic cells, such as Chinese hamster ovary cells (CHO), human embryonic kidney (HEK) cells, insect cells, or the like. For example, polypeptides may be produced in bacteria in particular when glycosylation is not needed. After expression, the polypeptide may be isolated from the bacterial cell paste in a soluble fraction and can be further purified. In addition to prokaryotes, eukaryotic microbes such as filamentous fungi or yeast are suitable cloning or expression hosts for polypeptide-encoding vectors, including fungi and yeast strains whose glycosylation pathways have been "humanized", resulting in the production of a polypeptide with a partially or fully human glycosylation pattern. See Gerngross, Nat Biotech 22, 1409-1414 (2004), and Li et al., Nat Biotech 24, 210-215 (2006).

Suitable host cells for the expression of (glycosylated) polypeptides are also derived from multicellular organisms (invertebrates and vertebrates). Examples of invertebrate cells include plant and insect cells. Numerous baculoviral strains have been identified which may be used in conjunction with insect cells, particularly for transfection of Spodoptera frugiperda cells. Plant cell cultures can also be utilized as hosts. See e.g. U.S. Pat. Nos. 5,959,177, 6,040,498, 6,420,548, 7,125,978, and 6,417,429 (describing PLANTIBODIES™ technology for producing antibodies in transgenic plants). Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293T cells as described, e.g., in Graham et al., J Gen Virol 36, 59 (1977)), baby hamster kidney cells (BHK), mouse sertoli cells (TM4 cells as described, e.g., in Mather, Biol Reprod 23, 243-251 (1980)), monkey kidney cells (CV1), African green monkey kidney cells (VERO-76), human cervical carcinoma cells (HELA), canine kidney cells (MDCK), buffalo rat liver cells (BRL 3A), human lung cells (W138), human liver cells (Hep G2), mouse mammary tumor cells (MMT 060562), TRI cells (as described, e.g., in Mather et al., Annals N.Y. Acad Sci 383, 44-68 (1982)), MRC 5 cells, and FS4 cells. Other useful mammalian host cell lines include Chinese hamster ovary (CHO) cells, including dhfr-CHO cells (Urlaub et al., Proc Natl Acad Sci USA 77, 4216 (1980)); and myeloma cell lines such as YO, NS0, P3X63 and Sp2/0. For a review of certain mammalian host cell lines suitable for protein production, see, e.g., Yazaki and Wu, Methods in Molecular Biology, Vol. 248 (B. K. C. Lo, ed., Humana Press, Totowa, N.J.), pp. 255-268 (2003). Host cells include cultured cells, e.g., mammalian cultured cells, yeast cells, insect cells, bacterial cells and plant cells, to name only a few, but also cells comprised within a transgenic animal, transgenic plant or cultured plant or animal tissue. In one embodiment, the host cell is a eukaryotic cell, preferably a mammalian cell, such as a Chinese Hamster Ovary (CHO) cell, a human embryonic kidney (HEK) cell or a lymphoid cell (e.g., YO, NS0, Sp20 cell). Standard technologies are known in the art to express foreign genes in these systems. Cells expressing a polypeptide comprising either the heavy or the light chain of an antigen binding domain, may be engineered so as to also express the other of the immunoglobulin chains such that the expressed product is an antigen binding domain that has both a heavy and a light chain.

In another aspect, provided is a method for producing the bispecific antigen binding molecule of the invention, comprising the steps of (i) culturing the host cell of the invention under conditions suitable for expression of said antigen binding molecule, and (ii) isolating said bispecific antigen binding molecule form the host cell or host cell culture medium.

The components of the bispecific antigen binding molecule are genetically fused to each other. Bispecific antigen binding molecules can be designed such that its components are fused directly to each other or indirectly through a linker sequence. The composition and length of the linker may be determined in accordance with methods well known in the art and may be tested for efficacy. Examples of linker sequences between different components of bispecific antigen binding molecules are found in the sequences provided herein. Additional sequences may also be included to incorporate a cleavage site to separate the individual components of the fusion if desired, for example an endopeptidase recognition sequence.

In certain embodiments the moieties capable of specific binding to TnC (e.g. Fab fragments or scFv) forming part of the antigen binding molecule comprise at least an immunoglobulin variable region capable of binding to TnC. Similarly, in certain embodiments, the moieties capable of specific binding to OX40 (e.g. Fab fragments or scFv) forming part of the antigen binding molecule comprise at least an immunoglobulin variable region capable of binding to OX40. Variable regions can form part of and be derived from naturally or non-naturally occurring antibodies and fragments thereof. Methods to produce polyclonal antibodies and monoclonal antibodies are well known in the art (see e.g. Harlow and Lane, "Antibodies, a laboratory manual", Cold Spring Harbor Laboratory, 1988). Non-naturally occurring antibodies can be constructed using solid phase-peptide synthesis, can be produced recombinantly (e.g. as described in U.S. Pat. No. 4,186,567) or can be obtained, for example, by screening combinatorial libraries comprising variable heavy chains and variable light chains (see e.g. U.S. Pat. No. 5,969,108 to McCafferty).

Any animal species of immunoglobulin can be used in the invention. Non-limiting immunoglobulins useful in the present invention can be of murine, primate, or human origin. If the fusion protein is intended for human use, a chimeric form of immunoglobulin may be used wherein the constant regions of the immunoglobulin are from a human. A humanized or fully human form of the immunoglobulin can also be prepared in accordance with methods well known in the art (see e.g. U.S. Pat. No. 5,565,332 to Winter). Humanization may be achieved by various methods including, but not limited to (a) grafting the non-human (e.g., donor antibody) CDRs onto human (e.g. recipient antibody) framework and constant regions with or without retention of critical framework residues (e.g. those that are important for retaining good antigen binding affinity or antibody functions), (b) grafting only the non-human specificity-determining regions (SDRs or a-CDRs; the residues critical for the antibody-antigen interaction) onto human framework and constant regions, or (c) transplanting the entire non-human variable domains, but "cloaking" them with a human-like section by replacement of surface residues. Humanized antibodies and methods of making them are reviewed, e.g., in Almagro and Fransson, Front Biosci 13, 1619-1633 (2008), and are further described, e.g., in Riechmann et al., Nature 332, 323-329 (1988); Queen et al., Proc Natl Acad Sci USA 86, 10029-10033 (1989); U.S. Pat. Nos. 5,821,337, 7,527,791, 6,982,321, and 7,087,409; Jones et al., Nature 321, 522-525 (1986); Morrison et al., Proc Natl Acad Sci 81, 6851-6855 (1984); Morrison and Oi, Adv Immunol 44, 65-92 (1988); Verhoeyen et al., Science 239, 1534-1536 (1988); Padlan, Molec Immun 31(3), 169-217 (1994); Kashmiri et al., Methods 36, 25-34 (2005) (describing SDR (a-CDR) grafting); Padlan, Mol Immunol 28, 489-498 (1991) (describing "resurfacing"); Dall'Acqua et al., Methods 36, 43-60 (2005) (describing "FR shuffling"); and Osbourn et al., Methods 36, 61-68 (2005) and Klimka et al., Br J Cancer 83, 252-260 (2000) (describing the "guided selection" approach to FR shuffling). Particular immunoglobulins according to the invention are human immunoglobulins. Human antibodies and human variable regions can be produced using various techniques known in the art. Human antibodies are described generally in van Dijk and van de Winkel, Curr Opin Pharmacol 5, 368-74 (2001) and Lonberg, Curr Opin Immunol 20, 450-459 (2008). Human variable regions can form part of and be derived from human monoclonal antibodies made by the hybridoma method (see e.g. Monoclonal Antibody Production Techniques and Applications, pp. 51-63 (Marcel Dekker, Inc., New York, 1987)). Human antibodies and human variable regions may also be prepared by administering an immunogen to a transgenic animal that has been modified to produce intact human antibodies or intact antibodies with human variable regions in response to antigenic challenge (see e.g. Lonberg, Nat Biotech 23, 1117-1125 (2005). Human antibodies and human variable regions may also be generated by isolating Fv clone variable region sequences selected from human-derived phage display libraries (see e.g., Hoogenboom et al. in Methods in Molecular Biology 178, 1-37 (O'Brien et al., ed., Human Press, Totowa, N.J., 2001); and McCafferty et al., Nature 348, 552-554; Clackson et al., Nature 352, 624-628 (1991)). Phage typically display antibody fragments, either as single-chain Fv (scFv) fragments or as Fab fragments.

In certain aspects, the moieties capable of specific binding to the relevant target (e.g. Fab fragments or scFv) comprised in the antigen binding molecules of the present invention are engineered to have enhanced binding affinity according to, for example, the methods disclosed in PCT publication WO 2012/020006 (see Examples relating to affinity maturation) or U.S. Pat. Appl. Publ. No. 2004/0132066. The ability of the antigen binding molecules of the invention to bind to a specific antigenic determinant can be measured either through an enzyme-linked immunosorbent assay (ELISA) or other techniques familiar to one of skill in the art, e.g. surface plasmon resonance technique (Liljeblad, et al., Glyco J 17, 323-329 (2000)), and traditional binding assays (Heeley, Endocr Res 28, 217-229 (2002)). Competition assays may be used to identify an antigen binding molecule that competes with a reference antibody for binding to a particular antigen. In certain embodiments, such a competing antigen binding molecule binds to the same epitope (e.g. a linear or a conformational epitope) that is bound by the reference antigen binding molecule. Detailed exemplary methods for mapping an epitope to which an antigen binding molecule binds are provided in Morris (1996) "Epitope Mapping Protocols", in Methods in Molecular Biology vol. 66 (Humana Press, Totowa, N.J.). In an exemplary competition assay, immobilized antigen is incubated in a solution comprising a first labeled antigen binding molecule that binds to the antigen and a second unlabeled antigen binding molecule that is being tested for its ability to compete with the first antigen binding molecule for binding to the antigen. The second antigen binding molecule may be present in a hybridoma supernatant. As a control, immobilized antigen is incubated in a solution comprising the first labeled antigen binding molecule but not the second unlabeled antigen binding molecule. After incubation under conditions permissive for binding of the first antibody to the antigen, excess unbound antibody is removed, and the amount of label associated with immobilized antigen is measured. If the amount of label associated with immobilized antigen is substantially reduced in the test sample relative to the control sample, then that indicates that the second antigen binding molecule is competing with the first antigen binding molecule for binding to the antigen. See Harlow and Lane (1988) Antibodies: A Laboratory Manual ch. 14 (Cold Spring Harbor Laboratory, Cold Spring Harbor, N.Y.).

Bispecific antigen binding molecules of the invention prepared as described herein may be purified by art-known techniques such as high performance liquid chromatography, ion exchange chromatography, gel electrophoresis, affinity chromatography, size exclusion chromatography, and the like. The actual conditions used to purify a particular protein will depend, in part, on factors such as net charge, hydrophobicity, hydrophilicity etc., and will be apparent to those having skill in the art. For affinity chromatography purification an antibody, ligand, receptor or antigen can be used to which the bispecific antigen binding molecule binds. For example, for affinity chromatography purification of fusion proteins of the invention, a matrix with protein A or protein G may be used. Sequential Protein A or G affinity chromatography and size exclusion chromatography can be used to isolate an antigen binding molecule essentially as described in the Examples. The purity of the bispecific antigen binding molecule or fragments thereof can be determined by any of a variety of well-known analytical methods including gel electrophoresis, high pressure liquid chromatography, and the like. For example, the bispecific antigen binding molecule expressed as described in the Examples were shown to be intact and properly assembled as demonstrated by reducing and non-reducing SDS-PAGE.

The invention also encompasses a bispecific antigen binding molecule produced by the methods of the invention.

Assays

The bispecific antigen binding molecules provided herein may be identified, screened for, or characterized for their physical/chemical properties and/or biological activities by various assays known in the art.

1. Affinity Assays

The affinity of the bispecific antigen binding molecule provided herein for OX40 or TnC can be determined in accordance with the methods set forth in the Examples by surface plasmon resonance (SPR), using standard instrumentation such as a BIAcore instrument (GE Healthcare), and receptors or target proteins such as may be obtained by recombinant expression. A specific illustrative and exemplary embodiment for measuring binding affinity is described in Example 4.2. According to one aspect, $K_D$ is measured by surface plasmon resonance using a BIACORE® T200 machine (GE Healthcare) at 25° C.

2. Binding Assays and Other Assays

Binding of the bispecific antigen binding molecule provided herein to the corresponding OX40 and/or TnC expressing cells may be evaluated using cell lines expressing the particular receptor or target antigen, for example by flow cytometry (FACS). In one aspect, fresh peripheral blood mononuclear cells (PBMCs) expressing OX40 are used in the binding assay. These cells are used directly after isolation (naïve PMBCs) or after stimulation (activated PMBCs). In another aspect, activated mouse splenocytes (expressing OX40) can be used to demonstrate binding of the bispecific antigen binding molecule of the invention to the corresponding OX40 expressing cells.

In a further aspect, cancer cell lines expressing TnC were used to demonstrate the binding of the antigen binding molecules to TnC.

In another aspect, competition assays may be used to identify an antigen binding molecule that competes with a specific antibody or antigen binding molecule for binding to TnC or OX40, respectively. In certain embodiments, such a competing antigen binding molecule binds to the same epitope (e.g., a linear or a conformational epitope) that is bound by a specific anti-TnC antibody or a specific anti-OX40 antibody. Detailed exemplary methods for mapping an epitope to which an antibody binds are provided in Morris (1996) "Epitope Mapping Protocols," in *Methods in Molecular Biology* vol. 66 (Humana Press, Totowa, N.J.).

3. Activity Assays

In one aspect, assays are provided for identifying bispecific antigen binding molecules that bind to TnC and to OX40 having biological activity. Biological activity may include, e.g., agonistic signalling through OX40 on cells expressing OX40. Bispecific antigen binding molecules identified by the assays as having such biological activity in vitro are also provided. In particular, a reporter cell assay detecting NF-κB activation in Hela cells expressing human OX40 and co-cultured with TnC-expressing tumor cells is provided (see e.g. Example 5.1).

In certain aspects, bispecific antigen binding molecules of the invention are tested for such biological activity. Assays for detecting the biological activity of the molecules of the invention are those described in Example 5. Furthermore, assays for detecting cell lysis (e.g. by measurement of LDH release), induced apoptosis kinetics (e.g. by measurement of Caspase 3/7 activity) or apoptosis (e.g. using the TUNEL assay) are well known in the art. In addition the biological activity of such complexes can be assessed by evaluating their effects on survival, proliferation and lymphokine secretion of various lymphocyte subsets such as NK cells, NKT-cells or γδ T-cells or assessing their capacity to modulate phenotype and function of antigen presenting cells such as dendritic cells, monocytes/macrophages or B-cells.

Pharmaceutical Compositions, Formulations and Routes of Administration

In a further aspect, the invention provides pharmaceutical compositions comprising any of the bispecific antigen binding molecules provided herein, e.g., for use in any of the below therapeutic methods. In one embodiment, a pharmaceutical composition comprises a bispecific antigen binding molecule and at least one pharmaceutically acceptable excipient. In another embodiment, a pharmaceutical composition comprises any of the bispecific antigen binding molecules provided herein and at least one additional therapeutic agent, e.g., as described below.

Pharmaceutical compositions of the present invention comprise a therapeutically effective amount of one or more bispecific antigen binding molecule dissolved or dispersed in a pharmaceutically acceptable excipient. The phrases "pharmaceutical or pharmacologically acceptable" refers to molecular entities and compositions that are generally non-toxic to recipients at the dosages and concentrations employed, i.e. do not produce an adverse, allergic or other untoward reaction when administered to an animal, such as, for example, a human, as appropriate. The preparation of a pharmaceutical composition that contains at least one bispecific antigen binding molecule and optionally an additional active ingredient will be known to those of skill in the art in light of the present disclosure, as exemplified by Remington's Pharmaceutical Sciences, 18th Ed. Mack Printing Company, 1990, incorporated herein by reference. In particular, the compositions are lyophilized formulations or aqueous solutions. As used herein, "pharmaceutically acceptable excipient" includes any and all solvents, buffers, dispersion media, coatings, surfactants, antioxidants, preservatives (e.g. antibacterial agents, antifungal agents), isotonic agents, salts, stabilizers and combinations thereof, as would be known to one of ordinary skill in the art.

Parenteral compositions include those designed for administration by injection, e.g. subcutaneous, intradermal, intralesional, intravenous, intraarterial intramuscular, intrathecal or intraperitoneal injection. For injection, the bispecific antigen binding molecules of the invention may be formulated in aqueous solutions, preferably in physiologically compatible buffers such as Hanks' solution, Ringer's solution, or physiological saline buffer. The solution may contain formulatory agents such as suspending, stabilizing and/or dispersing agents. Alternatively, the fusion proteins may be in powder form for constitution with a suitable vehicle, e.g., sterile pyrogen-free water, before use. Sterile injectable solutions are prepared by incorporating the fusion proteins or bispecific antigen binding molecules of the invention in the required amount in the appropriate solvent with various of the other ingredients enumerated below, as required. Sterility may be readily accomplished, e.g., by filtration through sterile filtration membranes. Generally, dispersions are prepared by incorporating the various sterilized active ingredients into a sterile vehicle which contains the basic dispersion medium and/or the other ingredients. In the case of sterile powders for the preparation of sterile injectable solutions, suspensions or emulsion, the preferred methods of preparation are vacuum-drying or freeze-drying techniques which yield a powder of the active ingredient plus any additional desired ingredient from a previously sterile-filtered liquid medium thereof. The liquid medium should be suitably buffered if necessary and the liquid diluent first rendered isotonic prior to injection with sufficient saline or glucose. The composition must be stable under the conditions of manufacture and storage, and preserved against the contaminating action of microorganisms, such as bacteria and fungi. It will be appreciated that endotoxin contamination should be kept minimally at a safe level, for example, less that 0.5 ng/mg protein. Suitable pharmaceutically acceptable excipients include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Aqueous injection suspensions may contain compounds which increase the viscosity of the suspension, such as sodium carboxymethyl cellulose, sorbitol, dextran, or the like. Optionally, the suspension may also contain suitable stabilizers or agents which increase the solubility of the compounds to allow for the preparation of highly concentrated solutions. Additionally, suspensions of the active compounds may be prepared as appropriate oily injection suspensions. Suitable lipophilic solvents or vehicles include fatty oils such as sesame oil, or synthetic fatty acid esters, such as ethyl cleats or triglycerides, or liposomes.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in Remington's Pharmaceutical Sciences (18th Ed. Mack Printing Company, 1990). Sustained-release preparations may be prepared. Suitable examples of sustained-release preparations include semipermeable matrices of solid hydrophobic polymers containing the polypeptide, which matrices are in the form of shaped articles, e.g. films, or microcapsules. In particular embodiments, prolonged absorption of an injectable composition can be brought about by the use in the compositions of agents delaying absorption, such as, for example, aluminum monostearate, gelatin or combinations thereof.

Exemplary pharmaceutically acceptable excipients herein further include interstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171, 586 and WO2006/044908, the latter formulations including a histidine-acetate buffer.

In addition to the compositions described previously, the bispecific antigen binding molecules may also be formulated as a depot preparation. Such long acting formulations may be administered by implantation (for example subcutaneously or intramuscularly) or by intramuscular injection. Thus, for example, the bispecific antigen binding molecules may be formulated with suitable polymeric or hydrophobic materials (for example as emulsion in a pharmaceutically acceptable oil) or ion exchange resins, or as sparingly soluble derivatives, for example, as a sparingly soluble salt.

Pharmaceutical compositions comprising the bispecific antigen binding molecules of the invention may be manufactured by means of conventional mixing, dissolving, emulsifying, encapsulating, entrapping or lyophilizing processes. Pharmaceutical compositions may be formulated in conventional manner using one or more physiologically acceptable carriers, diluents, excipients or auxiliaries which facilitate processing of the proteins into preparations that can be used pharmaceutically. Proper formulation is dependent upon the route of administration chosen.

The bispecific antigen binding molecules may be formulated into a composition in a free acid or base, neutral or salt form. Pharmaceutically acceptable salts are salts that substantially retain the biological activity of the free acid or base. These include the acid addition salts, e.g. those formed with the free amino groups of a proteinaceous composition, or which are formed with inorganic acids such as for example, hydrochloric or phosphoric acids, or such organic acids as acetic, oxalic, tartaric or mandelic acid. Salts formed with the free carboxyl groups can also be derived from inorganic bases such as for example, sodium, potassium, ammonium, calcium or ferric hydroxides; or such organic bases as isopropylamine, trimethylamine, histidine or procaine. Pharmaceutical salts tend to be more soluble in aqueous and other protic solvents than are the corresponding free base forms.

The pharmaceutical compositions may also contain more than one active ingredients as necessary for the particular indication being treated, preferably those with complementary activities that do not adversely affect each other. Such active ingredients are suitably present in combination in amounts that are effective for the purpose intended. In one aspect, the pharmaceutical composition comprises a bispecific antigen binding molecule and another active anti-cancer agent.

The formulations to be used for in vivo administration are generally sterile. Sterility may be readily accomplished, e.g., by filtration through sterile filtration membranes.

Therapeutic Methods and Compositions

Any of the bispecific antigen binding molecules provided herein may be used in therapeutic methods. For use in therapeutic methods, the antigen binding molecules of the invention can be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners.

In one aspect, the bispecific antigen binding molecules of the invention are provided for use as a medicament. In further aspects, the bispecific antigen binding molecules of the invention are provided for use in treating a disease, in particular for use in the treatment of cancer. In certain embodiments, the bispecific antigen binding molecules of the invention are provided for use in a method of treatment. In one embodiment, the invention provides a bispecific antigen binding molecule as described herein for use in the treatment of a disease in an individual in need thereof. In certain embodiments, the invention provides a bispecific antigen binding molecule for use in a method of treating an individual having a disease comprising administering to the individual a therapeutically effective amount of the bispecific antigen binding molecule. In certain embodiments the disease to be treated is cancer. In certain embodiments the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. The subject, patient, or "individual" in need of treatment is typically a mammal, more specifically a human.

Also encompassed by the invention is the bispecific antigen binding molecule of the invention, or the pharmaceutical composition of the invention, for use in up-regulating or prolonging cytotoxic T cell activity.

In a further aspect, the invention provides for the use of a bispecific antigen binding molecule of the invention in the manufacture or preparation of a medicament for the treatment of a disease in an individual in need thereof. In one aspect, the medicament is for use in a method of treating a disease comprising administering to an individual having the disease a therapeutically effective amount of the medicament. In certain embodiments the disease to be treated is a proliferative disorder, particularly cancer. Examples of cancers include bladder cancer, brain cancer, head and neck cancer, pancreatic cancer, lung cancer, breast cancer, ovarian cancer, uterine cancer, cervical cancer, endometrial cancer, esophageal cancer, colon cancer, colorectal cancer, rectal cancer, gastric cancer, prostate cancer, blood cancer, skin cancer, squamous cell carcinoma, bone cancer, and kidney cancer. Other cell proliferation disorders that can be treated using a bispecific antigen binding molecule of the present invention include, but are not limited to neoplasms located in the: abdomen, bone, breast, digestive system, liver, pancreas, peritoneum, endocrine glands (adrenal, parathyroid, pituitary, testicles, ovary, thymus, thyroid), eye, head and neck, nervous system (central and peripheral), lymphatic system, pelvic, skin, soft tissue, spleen, thoracic region, and urogenital system. Also included are pre-cancerous conditions or lesions and cancer metastases. In certain embodiments the cancer is chosen from the group consisting of renal cell cancer, skin cancer, lung cancer, colorectal cancer, breast cancer, brain cancer, head and neck cancer. A skilled artisan readily recognizes that in many cases the bispecific antigen binding molecule may not provide a cure but may only provide partial benefit. In some embodiments, a physiological change having some benefit is also considered therapeutically beneficial. Thus, in some embodiments, an amount of bispecific antigen binding molecule that provides a physiological change is considered an "effective amount" or a "therapeutically effective amount". In any of the above embodiments the individual is preferably a mammal, particularly a human.

In a further aspect, the invention provides a method for treating a disease in an individual, comprising administering to said individual a therapeutically effective amount of a bispecific antigen binding molecule of the invention. In one embodiment a composition is administered to said individual, comprising a fusion protein of the invention in a pharmaceutically acceptable form. In certain embodiments the disease to be treated is a proliferative disorder. In a particular embodiment the disease is cancer. In certain embodiments the method further comprises administering to the individual a therapeutically effective amount of at least one additional therapeutic agent, e.g. an anti-cancer agent if the disease to be treated is cancer. An "individual" according to any of the above embodiments may be a mammal, preferably a human.

For the prevention or treatment of disease, the appropriate dosage of a bispecific antigen binding molecule of the invention (when used alone or in combination with one or more other additional therapeutic agents) will depend on the type of disease to be treated, the route of administration, the body weight of the patient, the type of fusion protein, the severity and course of the disease, whether the fusion protein is administered for preventive or therapeutic purposes, previous or concurrent therapeutic interventions, the patient's clinical history and response to the fusion protein, and the discretion of the attending physician. The practitioner responsible for administration will, in any event, determine the concentration of active ingredient(s) in a composition and appropriate dose(s) for the individual subject. Various dosing schedules including but not limited to single or multiple administrations over various time-points, bolus administration, and pulse infusion are contemplated herein.

The bispecific antigen binding molecule is suitably administered to the patient at one time or over a series of treatments. Depending on the type and severity of the disease, about 1 µg/kg to 15 mg/kg (e.g. 0.1 mg/kg-10 mg/kg) of the antigen binding molecule can be an initial candidate dosage for administration to the patient, whether, for example, by one or more separate administrations, or by continuous infusion. One typical daily dosage might range from about 1 μg/kg to 100 mg/kg or more, depending on the factors mentioned above. For repeated administrations over several days or longer, depending on the condition, the treatment would generally be sustained until a desired suppression of disease symptoms occurs. One exemplary dosage of the fusion protein would be in the range from about 0.005 mg/kg to about 10 mg/kg. In other examples, a dose may also comprise from about 1 μg/kg body weight, about 5 μg/kg body weight, about 10 μg/kg body weight, about 50 μg/kg body weight, about 100 μg/kg body weight, about 200 μg/kg body weight, about 350 μg/kg body weight, about 500 μg/kg body weight, about 1 mg/kg body weight, about 5 mg/kg body weight, about 10 mg/kg body weight, about 50 mg/kg body weight, about 100 mg/kg body weight, about 200 mg/kg body weight, about 350 mg/kg body weight, about 500 mg/kg body weight, to about 1000 mg/kg body weight or more per administration, and any range derivable therein. In examples of a derivable range from the numbers listed herein, a range of about 5 mg/kg body weight to about 100 mg/kg body weight, about 5 μg/kg body weight to about 500 mg/kg body weight etc., can be administered, based on the numbers described above. Thus, one or more doses of about 0.5 mg/kg, 2.0 mg/kg, 5.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the bispecific antigen binding molecule). An initial higher loading dose, followed by one or more lower doses may be administered. However, other dosage regimens may be useful. The progress of this therapy is easily monitored by conventional techniques and assays.

The bispecific antigen binding molecule of the invention will generally be used in an amount effective to achieve the intended purpose. For use to treat or prevent a disease condition, the bispecific antigen binding molecules of the invention, or pharmaceutical compositions thereof, are administered or applied in a therapeutically effective amount. Determination of a therapeutically effective amount is well within the capabilities of those skilled in the art, especially in light of the detailed disclosure provided herein.

For systemic administration, a therapeutically effective dose can be estimated initially from in vitro assays, such as cell culture assays. A dose can then be formulated in animal models to achieve a circulating concentration range that includes the $IC_{50}$ as determined in cell culture. Such information can be used to more accurately determine useful doses in humans.

Initial dosages can also be estimated from in vivo data, e.g., animal models, using techniques that are well known in the art. One having ordinary skill in the art could readily optimize administration to humans based on animal data.

Dosage amount and interval may be adjusted individually to provide plasma levels of the bispecific antigen binding molecules which are sufficient to maintain therapeutic effect. Usual patient dosages for administration by injection range from about 0.1 to 50 mg/kg/day, typically from about 0.5 to 1 mg/kg/day. Therapeutically effective plasma levels may be achieved by administering multiple doses each day. Levels in plasma may be measured, for example, by HPLC.

In cases of local administration or selective uptake, the effective local concentration of the bispecific antigen binding molecules may not be related to plasma concentration. One skilled in the art will be able to optimize therapeutically effective local dosages without undue experimentation.

A therapeutically effective dose of the bispecific antigen binding molecules described herein will generally provide therapeutic benefit without causing substantial toxicity. Toxicity and therapeutic efficacy of a fusion protein can be determined by standard pharmaceutical procedures in cell culture or experimental animals. Cell culture assays and animal studies can be used to determine the $LD_{50}$ (the dose lethal to 50% of a population) and the $ED_{50}$ (the dose therapeutically effective in 50% of a population). The dose ratio between toxic and therapeutic effects is the therapeutic index, which can be expressed as the ratio $LD_{50}/ED_{50}$. Bispecific antigen binding molecules that exhibit large therapeutic indices are preferred. In one embodiment, the bispecific antigen binding molecule according to the present invention exhibits a high therapeutic index. The data obtained from cell culture assays and animal studies can be used in formulating a range of dosages suitable for use in humans. The dosage lies preferably within a range of circulating concentrations that include the $ED_{50}$ with little or no toxicity. The dosage may vary within this range depending upon a variety of factors, e.g., the dosage form employed, the route of administration utilized, the condition of the subject, and the like. The exact formulation, route of administration and dosage can be chosen by the individual physician in view of the patient's condition (see, e.g., Fingl et al., 1975, in: The Pharmacological Basis of Therapeutics, Ch. 1, p. 1, incorporated herein by reference in its entirety).

The attending physician for patients treated with the bispecific antigen binding molecules of the invention will know how and when to terminate, interrupt, or adjust administration due to toxicity, organ dysfunction, and the like. Conversely, the attending physician would also know to adjust treatment to higher levels if the clinical response were not adequate (precluding toxicity). The magnitude of an administered dose in the management of the disorder of interest will vary with the severity of the condition to be treated, with the route of administration, and the like. The severity of the condition may, for example, be evaluated, in part, by standard prognostic evaluation methods. Further, the dose and perhaps dose frequency will also vary according to the age, body weight, and response of the individual patient.

Other Agents and Treatments

The bispecific antigen binding molecules of the invention may be administered in combination with one or more other agents in therapy. For instance, a fusion protein of the invention may be co-administered with at least one additional therapeutic agent. The term "therapeutic agent" encompasses any agent that can be administered for treating a symptom or disease in an individual in need of such treatment. Such additional therapeutic agent may comprise any active ingredients suitable for the particular indication being treated, preferably those with complementary activities that do not adversely affect each other. In certain embodiments, an additional therapeutic agent is another anti-cancer agent.

Such other agents are suitably present in combination in amounts that are effective for the purpose intended. The effective amount of such other agents depends on the amount of fusion protein used, the type of disorder or treatment, and other factors discussed above. The bispecific antigen binding molecules are generally used in the same dosages and with administration routes as described herein, or about from 1 to 99% of the dosages described herein, or in any dosage and by any route that is empirically/clinically determined to be appropriate.

Such combination therapies noted above encompass combined administration (where two or more therapeutic agents are included in the same or separate compositions), and separate administration, in which case, administration of the bispecific antigen binding molecule of the invention can occur prior to, simultaneously, and/or following, administration of the additional therapeutic agent and/or adjuvant.

Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper that is pierceable by a hypodermic injection needle). At least one active agent in the composition is a bispecific antigen binding molecule of the invention.

The label or package insert indicates that the composition is used for treating the condition of choice. Moreover, the article of manufacture may comprise (a) a first container with a composition contained therein, wherein the composition comprises a bispecific antigen binding molecule of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition.

Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

TABLE C

Sequences

| SEQ ID NO: | Name | Sequence |
|---|---|---|
| 1 | human OX40 ECD | Uniprot No. P43489, aa 29-214 |
| 2 | OX40(8H9, 49B4, 1G4, 20B7) CDR-H1 | SYAIS |
| 3 | OX40(CLC-563, CLC-564, 17A9) CDR-H1 | SYAMS |
| 4 | OX40(8H9, 49B4, 1G4, 20B7) CDR-H2 | GIIPIFGTANYAQKFQG |
| 5 | OX40(CLC-563, CLC-564, 17A9) CDR-H2 | AISGSGGSTYYADSVKG |
| 6 | OX40(8H9) CDR-H3 | EYGWMDY |
| 7 | OX40(49B4) CDR-H3 | EYYRGPYDY |
| 8 | OX40(1G4) CDR-H3 | EYGSMDY |
| 9 | OX40(20B7) CDR-H3 | VNYPYSYWGDFDY |
| 10 | OX40(CLC-563) CDR-H3 | DVGAFDY |
| 11 | OX40(CLC-564) CDR-H3 | DVGPFDY |
| 12 | OX40(17A9)-CDR-H3 | VFYRGGVSMDY |
| 13 | OX40(8H9, 49B4, 1G4, 20B7) CDR-L1 | RASQSISSWLA |
| 14 | OX40(CLC-563, CLC564) CDR-L1 | RASQSVSSSYLA |
| 15 | OX40(17A9) CDR-L1 | QGDSLRSYYAS |
| 16 | OX40(8H9, 49B4, 1G4, 20B7) CDR-L2 | DASSLES |
| 17 | OX40(CLC-563, CLC564) CDR-L2 | GASSRAT |
| 18 | OX40(17A9) CDR-L2 | GKNNRPS |
| 19 | OX40(8H9) CDR-L3 | QQYLTYSRFT |
| 20 | OX40(49B4) CDR-L3 | QQYSSQPYT |

TABLE C-continued

Sequences

| SEQ ID NO: | Name | Sequence |
|---|---|---|
| 21 | OX40(1G4) CDR-L3 | QQYISYSMLT |
| 22 | OX40(20B7) CDR-L3 | QQYQAFSLT |
| 23 | OX40(CLC-563, CLC-164) CDR-L3 | QQYGSSPLT |
| 24 | OX40(17A9) CDR-L3 | NSRVMPHNRV |
| 25 | OX40(8H9) VH | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAREYGWMDYWGQGTTVTVSS |
| 26 | OX40(8H9) VL | DIQMTQSPSTLSASVGDRVTITCRASQSISSWLAWYQQKPGKAPKLLIYDASSLESGVPSRFSGSGSGTEFTLTISSLQPDDFATYYCQQYLTYSRFTFGQGTKVEIK |
| 27 | OX40(49B4) VH | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAREYYRGPYDYWGQGTTVTVSS |
| 28 | OX40(49B4) VL | DIQMTQSPSTLSASVGDRVTITCRASQSISSWLAWYQQKPGKAPKLLIYDASSLESGVPSRFSGSGSGTEFTLTISSLQPDDFATYYCQQYSSQPYTFGQGTKVEIK |
| 29 | OX40(1G4) VH | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCAREYGSMDYWGQGTTVTVSS |
| 30 | OX40(1G4) VL | DIQMTQSPSTLSASVGDRVTITCRASQSISSWLAWYQQKPGKAPKLLIYDASSLESGVPSRFSGSGSGTEFTLTISSLQPDDFATYYCQQYISYSMLTFGQGTKVEIK |
| 31 | OX40(20B7) VH | QVQLVQSGAEVKKPGSSVKVSCKASGGTFSSYAISWVRQAPGQGLEWMGGIIPIFGTANYAQKFQGRVTITADKSTSTAYMELSSLRSEDTAVYYCARVNYPYSYWGDFDYWGQGTTVTVSS |
| 32 | OX40(20B7) VL | DIQMTQSPSTLSASVGDRVTITCRASQSISSWLAWYQQKPGKAPKLLIYDASSLESGVPSRFSGSGSGTEFTLTISSLQPDDFATYYCQQYQAFSLTFGQGTKVEIK |
| 33 | OX40(CLC-563) VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCALDVGAFDYWGQGALVTVSS |
| 34 | OX40(CLC-563) VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGQGTKVEIK |
| 35 | OX40(CLC-564) VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCAFDVGPFDYWGQGTLVTVSS |
| 36 | OX40(CLC-564) VL | EIVLTQSPGTLSLSPGERATLSCRASQSVSSSYLAWYQQKPGQAPRLLIYGASSRATGIPDRFSGSGSGTDFTLTISRLEPEDFAVYYCQQYGSSPLTFGQGTKVEIK |
| 37 | OX40(17A9) VH | EVQLLESGGGLVQPGGSLRLSCAASGFTFSSYAMSWVRQAPGKGLEWVSAISGSGGSTYYADSVKGRFTISRDNSKNTLYLQMNSLRAEDTAVYYCARVFYRGGVSMDYVVGQGTLVTVSS |

TABLE C-continued

Sequences

| SEQ ID NO: | Name | Sequence |
|---|---|---|
| 38 | OX40(17A9) VL | SSELTQDPAVSVALGQTVRITC<u>QGDSLRSYYAS</u>WYQQKPGQAPVLVIY<u>GKNNRPS</u>GIPDRFSGSSSGNTASLTITGAQAEDEADYYC<u>NSRVMPHNRV</u>FGGGTKLTV |
| 39 | human TnC | Uniprot No. P24821 |
| 40 | TnC(18D4) CDR-H1 | SYAIS |
| 41 | TnC(11C7) CDR-H1 | GFTFSSYAMS |
| 42 | TnC(18D4) CDR-H2 | GIIPIFGTANYAQKFQG |
| 43 | TnC(11C7) CDR-H2 | AISGSGGSTYYADSVKG |
| 44 | TnC(18D4) CDR-H3 | GNFYGGLDY |
| 45 | TnC(11C7) CDR-H3 | TSPRVPLDY |
| 46 | TnC(18D4) CDR-L1 | RASQSISSWLA |
| 47 | TnC(11C7) CDR-L1 | QGDSLRSYYAS |
| 48 | TnC(18D4) CDR-L2 | DASSLES |
| 49 | TnC(11C7) CDR-L2 | GKNNRPS |
| 50 | TnC(18D4) CDR-L3 | QQNKKFPSGT |
| 51 | TnC(11C7) CDR-L3 | NSINSTRNEV |
| 52 | TnC(18D4) VH | QVQLVQSGAEVKKPGSSVKVSCKASGGTFS<u>SYAIS</u>WVRQAPGQGLEWMG<u>GIIPIFGTANYAQKFQG</u>RVTITADKSTSTAYMELSSLRSEDTAVYYCAK<u>GNFYGGLDY</u>WGQGTTVTVSS |
| 53 | TnC(18D4) VL | DIQMTQSPSTLSASVGDRVTITC<u>RASQSISSWLA</u>WYQQKPGKAPKLLIY<u>DASSLES</u>GVPSRFSGSGSGTEFTLTISSLQPDDFATYYC<u>QQNKKFPSGT</u>FGQGTKVEIK |
| 54 | TnC(11C7) VH | EVQLLESGGGLVQPGGSLRLSCAAS<u>GFTFSSYAMS</u>WVRQAPGKGLEWVS<u>AISGSGGSTYYADSVKG</u>RFTISKDNSKNTLYLQMNSLRAEDTAVYYCAK<u>TSPRVPLDY</u>WGQGTLVTVSS |
| 55 | TnC(11C7) VL | SSELTQDPAVSVALGQTVRVTC<u>QGDSLRSYYAS</u>WYQQKPGQAPVLVIY<u>GKNNRPS</u>GIPDRFSGSSSGNTASLTITGAQAEDEADYYC<u>NSINSTRNEV</u>FGGGTKLTVL |
| 56 | human OX40 | UniProt no. P43489 |
| 57 | human 4-1BB | UniProt no. Q07011 |
| 58 | human CD27 | UniProt no. P26842 |
| 59 | human HVEM | UniProt no. Q92956 |
| 60 | human CD30 | UniProt no. P28908 |
| 61 | human GITR | UniProt no. Q9Y5U5 |
| 62 | murine OX40 | UniProt no. P47741 |
| 63 | mouse TnC | Uniprot No. Q80YX1 |
| 64 | Petpide linker G4S | GGGGS |
| 65 | Peptide linker (G4S)$_2$ | GGGGSGGGGS |
| 66 | Peptide linker (SG4)$_2$ | SGGGGSGGGG |
| 67 | Peptide linker (G$_4$S)$_3$ | GGGGSGGGGSGGGGS |

TABLE C-continued

Sequences

| SEQ ID NO: | Name | Sequence |
|---|---|---|
| 68 | Peptide linker G4(SG4)₂ | GGGGSGGGGSGGGG |
| 69 | Peptide linker (G₄S)₄ | GGGGSGGGGSGGGGSGGGGS |
| 70 | Peptide linker | GSPGSSSSGS |
| 71 | Peptide linker | GSGSGSGS |
| 72 | Peptide linker | GSGSGNGS |
| 73 | Peptide linker | GGSGSGSG |
| 74 | Peptide linker | GGSGSG |
| 75 | Peptide linker | GGSG |
| 76 | Peptide linker | GGSGNGSG |
| 77 | Peptide linker | GGNGSGSG |
| 78 | Peptide linker | GGNGSG |
| 79 | cynomolgus OX40 ECD | aa 29-214 |
| 80 | murine OX40 ECD | aa 10-211 |
| 81 | human FAP | UniProt no. Q12884 |
| 82 | nucleotide sequence Fc hole chain | see Table 2 |
| 83 | nucleotide sequence human OX40 antigen Fc knob chain | see Table 2 |
| 84 | nucleotide sequence cynomolgus OX40 antigen Fc knob chain | see Table 2 |
| 85 | nucleotide sequence murine OX40 antigen Fc knob chain | see Table 2 |
| 86 | Fc hole chain | see Table 2 |
| 87 | human OX40 antigen Fc knob chain | see Table 2 |
| 88 | cynomolgus OX40 antigen Fc knob chain | see Table 2 |
| 89 | murine OX40 antigen Fc knob chain | see Table 2 |
| 90 | nucleotide sequence of library DP88-4 | see Table 3 |
| 91 | nucleotide sequence of Fab light chain Vk1_5 | see Table 4 |
| 92 | Fab light chain Vk1_5 | see Table 4 |
| 93 | nucleotide sequence of Fab heavy chain VH1_69 | see Table 4 |
| 94 | Fab heavy chain VH1_69 | see Table 4 |
| 95 | LMB3 | see Table 5 |
| 96 | Vk1_5_L3r_S | see Table 5 |
| 97 | Vk1_5_L3r_SY | see Table 5 |
| 98 | Vk1_5_L3r_SPY | see Table 5 |
| 99 | RJH31 | see Table 5 |

TABLE C-continued

Sequences

| SEQ ID NO: | Name | Sequence |
|---|---|---|
| 100 | RJH32 | see Table 5 |
| 101 | DP88-v4-4 | see Table 5 |
| 102 | DP88-v4-6 | see Table 5 |
| 103 | DP88-v4-8 | see Table 5 |
| 104 | fdseqlong | see Table 5 |
| 105 | (Vk3_20/VH3_23) template | see Table 6 |
| 106 | nucleotide sequence of Fab light chain Vk3_20 | see Table 7 |
| 107 | Fab light chain Vk3_20 | see Table 7 |
| 108 | nucleotide sequence of Fab heavy chain VH3_23 | see Table 7 |
| 109 | Fab heavy chain VH3_23 (DP47) | see Table 7 |
| 110 | MS64 | see Table 8 |
| 111 | DP47CDR3_ba (mod.) | see Table 8 |
| 112 | DP47-v4-4 | see Table 8 |
| 113 | DP47-v4-6 | see Table 8 |
| 114 | DP47-v4-8 | see Table 8 |
| 115 | fdseqlong | see Table 8 |
| 116 | Vl3_19/VH3_23 library template | see Table 9 |
| 117 | nucleotide sequence of Fab light chain Vl3_19 | see Table 10 |
| 118 | Fab light chain Vl3_19 | see Table 10 |
| 119 | LMB3 | see Table 11 |
| 120 | Vl_3_19_L3r_V | see Table 11 |
| 121 | Vl_3_19_L3r_HV | see Table 11 |
| 122 | Vl_3_19_L3r_HLV | see Table 11 |
| 123 | RJH80 | see Table 11 |
| 124 | MS63 | see Table 11 |
| 125 | Nucleotide sequence OX40(8H9) VL | see Table 12 |
| 126 | Nucleotide sequence OX40(8H9) VH | see Table 12 |
| 127 | Nucleotide sequence OX40(49B4) VL | see Table 12 |
| 128 | Nucleotide sequence OX40(49B4) VH | see Table 12 |
| 129 | Nucleotide sequence OX40(1G4) VL | see Table 12 |
| 130 | Nucleotide sequence OX40(1G4) VH | see Table 12 |

TABLE C-continued

Sequences

| SEQ ID NO: | Name | Sequence |
|---|---|---|
| 131 | Nucleotide sequence OX40(20B7) VL | see Table 12 |
| 132 | Nucleotide sequence OX40(20B7) VH | see Table 12 |
| 133 | Nucleotide sequence OX40(CLC-563) VL | see Table 12 |
| 134 | Nucleotide sequence OX40(CLC-563) VH | see Table 12 |
| 135 | Nucleotide sequence OX40(CLC-564) VL | see Table 12 |
| 136 | Nucleotide sequence OX40(CLC-564) VH | see Table 12 |
| 137 | Nucleotide sequence OX40(17A9) VL | see Table 12 |
| 138 | Nucleotide sequence OX40(17A9) VH | see Table 12 |
| 139 | Nucleotide sequence OX40(8B9) light chain in P329GLALA human IgG1 format | see Table 13 |
| 140 | Nucleotide sequence OX40(8B9) heavy chain in P329GLALA human IgG1 format | see Table 13 |
| 141 | OX40(8B9) light chain in P329GLALA human IgG1 format | see Table 13 |
| 142 | OX40(8B9) heavy chain in P329GLALA human IgG1 format | see Table 13 |
| 143 | Nucleotide sequence OX40(49B4) light chain in P329GLALA human IgG1 format | see Table 13 |
| 144 | Nucleotide sequence OX40(49B4) heavy chain in P329GLALA human IgG1 format | see Table 13 |
| 145 | OX40(49B4) light chain in P329GLALA human IgG1 format | see Table 13 |
| 146 | OX40(49B4) heavy chain in P329GLALA human IgG1 format | see Table 13 |
| 147 | Nucleotide sequence OX40(1G4) light chain in P329GLALA human IgG1 format | see Table 13 |
| 148 | Nucleotide sequence OX40(1G4) heavy chain in P329GLALA human IgG1 format | see Table 13 |
| 149 | OX40(1G4) light chain in P329GLALA human IgG1 format | see Table 13 |

TABLE C-continued

Sequences

| SEQ ID NO: | Name | Sequence |
|---|---|---|
| 150 | OX40(1G4) heavy chain in P329GLALA human IgG1 format | see Table 13 |
| 151 | Nucleotide sequence OX40(20B7) light chain in P329GLALA human IgG1 format | see Table 13 |
| 152 | Nucleotide sequence OX40(20B7) heavy chain in P329GLALA human IgG1 format | see Table 13 |
| 153 | OX40(20B7) light chain in P329GLALA human IgG1 format | see Table 13 |
| 154 | OX40(20B7) heavy chain in P329GLALA human IgG1 format | see Table 13 |
| 155 | Nucleotide sequence OX40(CLC-563) light chain in P329GLALA human IgG1 format | see Table 13 |
| 156 | Nucleotide sequence OX40(CLC-563) heavy chain in P329GLALA human IgG1 format | see Table 13 |
| 157 | OX40(CLC-563) light chain in P329GLALA format | see Table 13 human IgG1 |
| 158 | OX40(CLC-563) heavy chain in P329GLALA human IgG1 format | see Table 13 |
| 159 | Nucleotide sequence OX40(CLC-564) light chain in P329GLALA human IgG1 format | see Table 13 |
| 160 | Nucleotide sequence OX40(CLC-564) heavy chain in P329GLALA human IgG1 format | see Table 13 |
| 161 | OX40(CLC-564) light chain in P329GLALA human IgG1 format | see Table 13 |
| 162 | OX40(CLC-564) heavy chain in P329GLALA human IgG1 format | see Table 13 |
| 163 | Nucleotide sequence OX40(17A9) light chain in P329GLALA human IgG1 format | see Table 13 |
| 164 | Nucleotide sequence OX40(17A9) heavy chain in P329GLALA human IgG1 format | see Table 13 |
| 165 | OX40(17A9) light chain in P329GLALA human IgG1 format | see Table 13 |
| 166 | OX40(17A9) heavy chain in P329GLALA human IgG1 format | see Table 13 |

TABLE C-continued

Sequences

| SEQ ID NO: | Name | Sequence |
|---|---|---|
| 167 | Nucleotide sequence human TnC with C-terminal Avi- and His-tags | see Table 15 |
| 168 | Nucleotide sequence mouse TnC with C-terminal Avi- and His-tags | see Table 15 |
| 169 | Nucleotide sequence cynomolgus TnC with C-terminal Avi- and His-tags | see Table 15 |
| 170 | human TnC with C-terminal Avi- and His-tags | see Table 15 |
| 171 | mouse TnC with C-terminal Avi- and His-tags | see Table 15 |
| 172 | cynomolgus TnC with C-terminal Avi- and His-tags | see Table 15 |
| 173 | GST huTnC fn5 A1234 BC fn6 B | see Table 16 |
| 174 | GST huTnC fn5 mu A124 BC hu fn6 B | see Table 16 |
| 175 | GST TnC hu fn5 B-C fn6 B | see Table 16 |
| 176 | GST huTnC fn5 A1234 fn6 B | see Table 16 |
| 177 | huTnC A4 B | see Table 16 |
| 178 | huTnC A1 B | see Table 16 |
| 179 | Nucleotide sequence TnC(18D4) VL | see Table 18 |
| 180 | Nucleotide sequence TnC(18D4) VH | see Table 18 |
| 181 | Nucleotide sequence TnC(11C7) VL | see Table 18 |
| 182 | Nucleotide sequence TnC(11C7) VH | see Table 18 |
| 183 | Nucleotide sequence TnC(18D4) CDR-L1 | see Table 20 |
| 184 | Nucleotide sequence TnC(11C7) CDR-L1 | see Table 20 |
| 185 | Nucleotide sequence TnC(18D4) CDR-L2 | see Table 20 |
| 186 | Nucleotide sequence TnC(11C7) CDR-L2 | see Table 20 |
| 187 | Nucleotide sequence TnC(18D4) CDR-L3 | see Table 20 |
| 188 | Nucleotide sequence TnC(11C7) CDR-L3 | see Table 20 |
| 189 | Nucleotide sequence TnC(18D4) CDR-H1 | see Table 22 |
| 190 | Nucleotide sequence TnC(11C7) CDR-H1 | see Table 22 |
| 191 | Nucleotide sequence TnC(18D4) CDR-H2 | see Table 22 |

TABLE C-continued

Sequences

| SEQ ID NO: | Name | Sequence |
|---|---|---|
| 192 | Nucleotide sequence TnC(11C7) CDR-H2 | see Table 22 |
| 193 | Nucleotide sequence TnC(18D4) CDR-H3 | see Table 22 |
| 194 | Nucleotide sequence TnC(11C7) CDR-H3 | see Table 22 |
| 195 | Nucleotide sequence TnC(18D4) light chain in human IgG1 format | see Table 24 |
| 196 | Nucleotide sequence TnC(18D4) heavy chain in human IgG1 format | see Table 24 |
| 197 | Nucleotide sequence TnC(11C7) light chain in human IgG1 format | see Table 24 |
| 198 | Nucleotide sequence TnC(11C7) heavy chain in human IgG1 format | see Table 24 |
| 199 | TnC(18D4) light chain in human IgG1 format | see Table 25 |
| 200 | TnC(18D4) heavy chain in human IgG1 format | see Table 25 |
| 201 | TnC(11C7) light chain in human IgG1 format | see Table 25 |
| 202 | TnC(11C7) heavy chain in human IgG1 format | see Table 25 |
| 203 | Nucleotide sequence TnC(18D4) heavy chain in P329GLALA human IgG1 format | see Table 26 |
| 204 | Nucleotide sequence TnC(11C7) heavy chain in P329GLALA human IgG1 format | see Table 26 |
| 205 | TnC(18D4) heavy chain in P329GLALA human IgG1 format | see Table 27 |
| 206 | TnC(11C7) heavy chain in P329GLALA human IgG1 format | see Table 27 |
| 207 | Nucleotide sequence LC1 (pCON323) OX40 (49B4) VL/CL | see Table 28 |
| 208 | Nucleotide sequence Heavy chain pETR14728 OX40 (49B4) VHCH1_Fc_PG/LALA TnC (18D4) VHCL | see Table 28 |
| 209 | Nucleotide sequence LC2 pETR14647 TnC (18D4) VLCH1 | see Table 28 |
| 210 | Nucleotide sequence Heavy chain pETR14727 OX40 (49B4) VHCH1_Fc_PG/LALA TnC (11C7) VHCL | see Table 28 |

TABLE C-continued

Sequences

| SEQ ID NO: | Name | Sequence |
|---|---|---|
| 211 | Nucleotide sequence LC2 pETR14648 TnC (11C7) VLCH1 | see Table 28 |
| 212 | LC1 (pCON323) OX40 (49B4) VL/CL | see Table 29 |
| 213 | Heavy chain pETR14728 OX40 (49B4) VHCH1_Fc_PG/LALA TnC (18D4) VHCL | see Table 29 |
| 214 | LC2 pETR14647 TnC (18D4) VLCH1 | see Table 29 |
| 215 | Heavy chain pETR14727 OX40 (49B4) VHCH1_Fc_PG/LALA TnC (11C7) VHCL | see Table 29 |
| 216 | LC2 pETR14648 TnC (11C7) VLCH1 | see Table 29 |
| 217 | Nucleotide sequence HC1 pETR15193 OX40 (49B4) VHCH1_VHCH1_Fc_hole_PG/LALA_TnC (18D4) VL | see Table 31 |
| 218 | Nucleotide sequence HC2 pETR15194 OX40 (49B4) VHCH1_VHCH1_Fc_knob_PG/LALA TnC (18D4) VH | see Table 31 |
| 219 | Nucleotide sequence LC1 pETR14912 OX40 (49B4) VLCL + charges | see Table 31 |
| 220 | Nucleotide sequence HC pETR15206 OX40 (49B4)VHCH1EE_OX40 (49B4)VHCH1EE_Fc_PG/LALA TnC (18D4)VLCH1 | see Table 31 |
| 221 | Nucleotide sequence LC2 pETR15202 TnC (18D4) VHCL | see Table 31 |
| 222 | HC1 pETR15193 OX40 (49B4) VHCH1_VHCH1_Fc_hole_PG/LALA TnC (18D4) VL | see Table 32 |
| 223 | HC2 pETR15194 OX40 (49B4) VHCH1_VHCH1_Fc_knob_PG/LALA TnC (18D4) VH | see Table 32 |
| 224 | LC1 pETR14912 OX40 (49B4) VLCL + charges | see Table 32 |
| 225 | HC pETR15206 OX40 (49B4)VHCH1EE_OX40 (49B4)VHCH1EE_Fc_PG/LALA TnC (18D4)VLCH1 | see Table 32 |
| 226 | LC2 pETR15202 TnC (18D4) VHCL | see Table 32 |

Aspects of the Invention

The following numbered paragraphs (paras) describe aspects of the present invention:

1. A bispecific antigen binding molecule, comprising
   (a) at least one moiety capable of specific binding to OX40, and
   (b) at least one moiety capable of specific binding to tenascin C (TnC).
2. The bispecific antigen binding molecule of para 1, additionally comprising
   (c) a Fc region composed of a first and a second subunit capable of stable association.
3. The bispecific antigen binding molecule of para 1 or para 2, wherein the moiety capable of specific binding to OX40 binds to a polypeptide comprising, or consisting of, the amino acid sequence of SEQ ID NO:1.
4. The bispecific antigen binding molecule of any one of paras 1 to 3, wherein the moiety capable of specific binding to TnC binds to a polypeptide comprising, or consisting of, the amino acid sequence of SEQ ID NO:39.
5. The bispecific antigen binding molecule of any one of paras 1 to 4, wherein the moiety capable of specific binding to OX40 comprises a VH comprising
   (i) a CDR-H1 comprising an amino acid sequence selected from the group consisting of SEQ ID NO:2 and SEQ ID NO:3,
   (ii) a CDR-H2 comprising an amino acid sequence selected from the group consisting of SEQ ID NO:4 and SEQ ID NO:5, and
   (iii) a CDR-H3 comprising an amino acid sequence selected from the group consisting of SEQ ID NO:6, SEQ ID NO:7, SEQ ID NO:8, SEQ ID NO: 9, SEQ ID NO:10, SEQ ID NO:11 and SEQ ID NO:12,
and a VL comprising
   (iv) a CDR-L1 comprising an amino acid sequence selected from the group consisting of SEQ ID NO:13, SEQ ID NO:14 and SEQ ID NO:15,
   (v) a CDR-L2 comprising an amino acid sequence selected from the group consisting of SEQ ID NO:16, SEQ ID NO:17 and SEQ ID NO:18, and
   (vi) a CDR-L3 comprising an amino acid sequence selected from the group consisting of SEQ ID NO:19, SEQ ID NO:20, SEQ ID NO:21, SEQ ID NO:22, SEQ ID NO:23 and SEQ ID NO:24.
6. The bispecific antigen binding molecule of any one of paras 1 to 5, wherein the moiety capable of specific binding to OX40 comprises a VH comprising an amino acid sequence that is at least about 95%, 96%, 97%, 98%, 99% or 100% identical to an amino acid sequence selected from the group consisting of SEQ ID NO:25, SEQ ID NO: 27, SEQ ID NO:29, SEQ ID NO:31, SEQ ID NO:33, SEQ ID NO:35 and SEQ ID NO:37 and a VL comprising an amino acid sequence that is at least about 95%, 96%, 97%, 98%, 99% or 100% identical to an amino acid sequence selected from the group consisting of SEQ ID NO:26, SEQ ID NO: 28, SEQ ID NO:30, SEQ ID NO:32, SEQ ID NO:34, SEQ ID NO:36 and SEQ ID NO:38.
7. The bispecific antigen binding molecule of any one of paras 1 to 6, wherein the moiety capable of specific binding to OX40 comprises
   (i) a VH comprising the amino acid sequence of SEQ ID NO:25 and a VL comprising the amino acid sequence of SEQ ID NO:26,
   (ii) a VH comprising the amino acid sequence of SEQ ID NO:27 and a VL comprising the amino acid sequence of SEQ ID NO:28,
   (iii) a VH comprising the amino acid sequence of SEQ ID NO:29 and a VL comprising the amino acid sequence of SEQ ID NO:30,
   (iv) a VH comprising the amino acid sequence of SEQ ID NO:31 and a VL comprising the amino acid sequence of SEQ ID NO:32,
   (v) a VH comprising the amino acid sequence of SEQ ID NO:33 and a VL comprising the amino acid sequence of SEQ ID NO:34,
   (vi) a VH comprising the amino acid sequence of SEQ ID NO:35 and a VL comprising the amino acid sequence of SEQ ID NO:36, or
   (vii) a VH comprising the amino acid sequence of SEQ ID NO:37 and a VL comprising the amino acid sequence of SEQ ID NO:38.
8. The bispecific antigen binding molecule of any one of paras 1 to 7, wherein the moiety capable of specific binding to TnC comprises a VH comprising
   (i) a CDR-H1 comprising an amino acid sequence selected from the group consisting of SEQ ID NO:40 and SEQ ID NO:41,
   (ii) a CDR-H2 comprising an amino acid sequence selected from the group consisting of SEQ ID NO:42 and SEQ ID NO:43, and
   (iii) a CDR-H3 comprising an amino acid sequence selected from the group consisting of SEQ ID NO:44 and SEQ ID NO:45,
and a VL comprising
   (iv) a CDR-L1 comprising an amino acid sequence selected from the group consisting of SEQ ID NO:46 and SEQ ID NO:47,
   (v) a CDR-L2 comprising an amino acid sequence selected from the group consisting of SEQ ID NO:48 and SEQ ID NO:49, and
   (vi) a CDR-L3 comprising an amino acid sequence selected from the group consisting of SEQ ID NO:50 and SEQ ID NO:51.
9. The bispecific antigen binding molecule of any one of paras 1 to 8, wherein the moiety capable of specific binding to TnC comprises a VH comprising an amino acid sequence that is at least about 95%, 96%, 97%, 98%, 99% or 100% identical to an amino acid sequence selected from the group consisting of SEQ ID NO:52 and SEQ ID NO:54 and a VL comprising an amino acid sequence that is at least about 95%, 96%, 97%, 98%, 99% or 100% identical to an amino acid sequence selected from the group consisting of SEQ ID NO:53 and SEQ ID NO:55.
10. The bispecific antigen binding molecule of any one of paras 1 to 9, wherein the moiety capable of specific binding to TnC comprises
   (i) a VH comprising the amino acid sequence of SEQ ID NO:52 and a VL comprising the amino acid sequence of SEQ ID NO:53, or
   (ii) a VH comprising the amino acid sequence of SEQ ID NO:54 and a VL comprising the amino acid sequence of SEQ ID NO:55.
11. The bispecific antigen binding molecule of any one of paras 1 to 10, comprising
(i) at least one moiety capable of specific binding to OX40, comprising a VH comprising an amino acid sequence that is at least about 95%, 96%, 97%, 98%, 99% or 100% identical to an amino acid sequence selected from the group consisting of SEQ ID NO:25, SEQ ID NO: 27, SEQ ID NO:29, SEQ ID NO:31, SEQ ID NO:33, SEQ ID NO:35 or SEQ ID NO:37 and a VL comprising an amino acid sequence that is at least about 95%, 96%, 97%, 98%, 99% or 100% identical to an amino acid sequence selected from the group consisting of SEQ ID NO:26, SEQ ID NO: 28, SEQ ID NO:30, SEQ ID NO:32, SEQ ID NO:34, SEQ ID NO:36 or SEQ ID NO:38 and (ii) at least one moiety capable of specific binding to TnC, comprising a VH comprising an amino acid sequence that is at least about 95%, 96%, 97%, 98%, 99% or 100% identical to an amino acid sequence selected from the group consisting of SEQ ID NO:52 or SEQ ID NO:54 and a VL comprising an amino acid sequence that is at least about 95%, 96%, 97%, 98%, 99% or 100% identical to an amino acid sequence selected from the group consisting of SEQ ID NO:53 or SEQ ID NO:55.

12. The bispecific antigen binding molecule of any one of paras 1 to 11, comprising (i) at least one moiety capable of specific binding to OX40, comprising a VH comprising the amino acid sequence of SEQ ID NO: 27 and a VL comprising the amino acid sequence of SEQ ID NO: 28 and (ii) at least one moiety capable of specific binding to TnC, comprising a VH comprising the amino acid sequence of SEQ ID NO:52 and a VL comprising the amino acid sequence of SEQ ID NO:53, or a VH comprising the amino acid sequence of SEQ ID NO:54 and a VL comprising the amino acid sequence of SEQ ID NO:55.

13. The bispecific antigen binding molecule of any one of paras 2 to 12, wherein the Fc region is an IgG, particularly an IgG1 Fc region or an IgG4 Fc region.

14. The bispecific antigen binding molecule of any one of paras 2 to 13, wherein the Fc region comprises one or more amino acid substitution that reduces the binding affinity of the antibody to an Fc receptor and/or effector function.

15. The bispecific antigen binding molecule of any one of paras 2 to 14, wherein the Fc region is of human IgG1 subclass with the amino acid mutations L234A, L235A and P329G (numbering according to Kabat EU index).

16. The bispecific antigen binding molecule of any one of paras 2 to 15, wherein the Fc region comprises a modification promoting the association of the first and second subunit of the Fc region.

17. The bispecific antigen binding molecule of any one of paras 2 to 16, wherein the first subunit of the Fc region comprises knobs and the second subunit of the Fc region comprises holes according to the knobs into holes method.

18. The bispecific antibody of any one of paras 2 to 17, wherein the first subunit of the Fc region comprises the amino acid substitutions S354C and T366W (numbering according to Kabat EU index) and the second subunit of the Fc region comprises the amino acid substitutions Y349C, T366S and Y407V (numbering according to Kabat EU index).

19. The bispecific antigen binding molecule of any one of paras 1 to 18, wherein the bispecific antigen binding molecule comprises (a) at least two Fab fragments capable of specific binding to OX40 connected to a Fc region, and (b) at least one moiety capable of specific binding to TnC connected to the C-terminus of the Fc region.

20. The bispecific antigen binding molecule of any one of paras 1 to 19, wherein the bispecific antigen binding molecule comprises (a) two light chains and two heavy chains of an antibody comprising two Fab fragments capable of specific binding to OX40, and a Fc region, and (b) a VH and a VL of a moiety capable specific binding to TnC, wherein the VH is connected to the C-terminus of one of the two heavy chains of (a), and wherein the VL is connected to the C-terminus of the other of the two heavy chains of (a).

21. The bispecific antigen binding molecule of any one of paras 1 to 20, wherein the bispecific antigen binding molecule comprises (a) two light chains and two heavy chains of an antibody comprising two Fab fragments capable of specific binding to OX40, and a Fc region, and (b) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

22. The bispecific antigen binding molecule of any one of paras 1 to 21, wherein the bispecific antigen binding molecule comprises (a) two heavy chains, each heavy chain comprising a VH and CH1 domain of a Fab fragment capable of specific binding to OX40 and a Fc region subunit, (b) two light chains, each light chain comprising a VL and CL domain of a Fab fragment capable of specific binding to OX40, and (c) a VH and a VL of a moiety capable specific binding to TnC, wherein the VH is connected to the C-terminus of one of the two heavy chains of (a), and wherein the VL is connected to the C-terminus of the other of the two heavy chains of (a).

23. The bispecific antigen binding molecule of any one of paras 1 to 19 or para 21, wherein the bispecific antigen binding molecule comprises (a) two heavy chains, each heavy chain comprising a VH and CH1 domain of a Fab fragment capable of specific binding to OX40, and a Fc region subunit, (b) two light chains, each light chain comprising a VL and CL domain of a Fab fragment capable of specific binding to OX40, (c) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

24. The bispecific antigen binding molecule of para 21 or para 23, wherein the two Fab fragments capable of specific binding to TnC are crossover Fab fragments each comprising a VL-CH1 chain and a VH-CL chain, and wherein one of the VL-CH1 chains is connected to the C-terminus of one of the two heavy chains of (a), and the other of the VL-CH1 chains is connected to the C-terminus of the other of the two heavy chains of (a).

25. The bispecific antigen binding molecule of any one of paras 1 to 24, wherein the bispecific antigen binding molecule comprises four Fab fragments capable of specific binding to OX40.

26. The bispecific antigen binding molecule of any one of paras 20 to 25, wherein each of the two heavy chains of (a) comprises two VH domains and two CH1 domains of a Fab fragment capable of specific binding to OX40.

27. The bispecific antigen binding molecule of any one of paras 19 to 26, one or more of the Fab fragments capable of specific binding to OX40 comprises a CL domain comprising an arginine (R) at amino acid at position 123 (EU numbering) and a lysine (K) at amino acid at position 124 (EU numbering), and a CH1 domain comprising a glutamic acid (E) at amino acid at position 147 (EU numbering) and a glutamic acid (E) at amino acid at position 213 (EU numbering).

28. A bispecific antigen binding molecule, comprising
two heavy chains, each comprising the amino acid sequence of SEQ ID NO:213,
two light chains, each comprising the amino acid sequence of SEQ ID NO:212, and
two light chains, each comprising the amino acid sequence of SEQ ID NO:214.

29. A bispecific antigen binding molecule, comprising
two heavy chains, each comprising the amino acid sequence of SEQ ID NO:215,
two light chains, each comprising the amino acid sequence of SEQ ID NO:212, and
two light chains, each comprising the amino acid sequence of SEQ ID NO:216.

30. A bispecific antigen binding molecule, comprising
a first heavy chain comprising the amino acid sequence of SEQ ID NO:222,
a second heavy chain comprising the amino acid sequence of SEQ ID NO:223, and
four light chains, each comprising the amino acid sequence of SEQ ID NO:212.

31. A bispecific antigen binding molecule comprising
two heavy chains, each comprising the amino acid sequence of SEQ ID NO:225,
four light chains, each comprising the amino acid sequence of SEQ ID NO:224, and
two light chains, each comprising the amino acid sequence of SEQ ID NO:226.

32. A polynucleotide encoding the bispecific antigen binding molecule of any one of paras 1 to 31.

33. An expression vector comprising the polynucleotide of para 32.

34. A host cell comprising the polynucleotide of para 32 or the expression vector of para 33.

35. A method of producing a bispecific antigen binding molecule, comprising culturing the host cell of para 34 under conditions suitable for the expression of the bispecific antigen binding molecule, and isolating the bispecific antigen binding molecule.

36. A pharmaceutical composition comprising the bispecific antigen binding molecule of any one of paras 1 to 31 and at least one pharmaceutically acceptable excipient.

37. The bispecific antigen binding molecule of any one of paras 1 to 31, or the pharmaceutical composition of para 36, for use as a medicament.

38. The bispecific antigen binding molecule of any one of paras 1 to 31, or the pharmaceutical composition of para 36, for use
(i) in stimulating T cell response,
(ii) in supporting survival of activated T cells,
(iii) in the treatment of infections,
(iv) in the treatment of cancer,
(v) in delaying progression of cancer, or
(vi) in prolonging the survival of a patient suffering from cancer.

39. The bispecific antigen binding molecule of any one of paras 1 to 31, or the pharmaceutical composition of para 36, for use in the treatment of cancer.

40. Use of the bispecific antigen binding molecule of any one of paras 1 to 31, or the pharmaceutical composition of para 36, in the manufacture of a medicament for the treatment of cancer.

41. A method of treating an individual having cancer comprising administering to the individual an effective amount of the bispecific antigen binding molecule of any one of paras 1 to 31, or the pharmaceutical composition of para 36.

42. The bispecific antigen binding molecule of any one of paras 1 to 31, or the pharmaceutical composition of para 36, for use in up-regulating or prolonging cytotoxic T cell activity.

43. Use of the bispecific antigen binding molecule of any one of paras 1 to 31, or the pharmaceutical composition of para 36, in the manufacture of a medicament for up-regulating or prolonging cytotoxic T cell activity.

44. A method of up-regulating or prolonging cytotoxic T cell activity in an individual having cancer, comprising administering to the individual an effective amount of the bispecific antigen binding molecule of any one of paras 1 to 31, or the pharmaceutical composition of para 36.

EXAMPLES

The following are examples of methods and compositions of the invention. It is understood that various other embodiments may be practiced, given the general description provided above.

Recombinant DNA techniques

Standard methods were used to manipulate DNA as described in Sambrook et al., Molecular cloning: A laboratory manual; Cold Spring Harbor Laboratory Press, Cold Spring Harbor, N.Y., 1989. The molecular biological reagents were used according to the manufacturer's instructions. General information regarding the nucleotide sequences of human immunoglobulin light and heavy chains is given in: Kabat, E. A. et al., (1991) Sequences of Proteins of Immunological Interest, Fifth Ed., NIH Publication No 91-3242.

DNA Sequencing

DNA sequences were determined by double strand sequencing.

Gene Synthesis

Desired gene segments were either generated by PCR using appropriate templates or were synthesized by Geneart AG (Regensburg, Germany) from synthetic oligonucleotides and PCR products by automated gene synthesis. In cases where no exact gene sequence was available, oligonucleotide primers were designed based on sequences from closest homologues and the genes were isolated by RT-PCR from RNA originating from the appropriate tissue. The gene segments flanked by singular restriction endonuclease cleavage sites were cloned into standard cloning/sequencing vectors. The plasmid DNA was purified from transformed bacteria and concentration determined by UV spectroscopy. The DNA sequence of the subcloned gene fragments was confirmed by DNA sequencing. Gene segments were designed with suitable restriction sites to allow sub-cloning into the respective expression vectors. All constructs were designed with a 5'-end DNA sequence coding for a leader peptide which targets proteins for secretion in eukaryotic cells.

Protein Purification

Proteins were purified from filtered cell culture supernatants referring to standard protocols. In brief, antibodies were applied to a Protein A Sepharose column (GE healthcare) and washed with PBS. Elution of antibodies was achieved at pH 2.8 followed by immediate neutralization of the sample. Aggregated protein was separated from monomeric antibodies by size exclusion chromatography (Superdex 200, GE Healthcare) in PBS or in 20 mM Histidine, 150 mM NaCl pH 6.0. Monomeric antibody fractions were pooled, concentrated (if required) using e.g., a MILLIPORE Amicon Ultra (30 MWCO) centrifugal concentrator, frozen and stored at −20° C. or −80° C. Part of the samples were provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) was used according to the manufacturer's instruction. In particular, 10% or 4-12% NuPAGE® Novex® Bis-TRIS Pre-Cast gels (pH 6.4) and a NuPAGE® MES (reduced gels, with NuPAGE® Antioxidant running buffer additive) or MOPS (non-reduced gels) running buffer was used.

Analytical Size Exclusion Chromatography

Size exclusion chromatography (SEC) for the determination of the aggregation and oligomeric state of antibodies was performed by HPLC chromatography. Briefly, Protein A purified antibodies were applied to a Tosoh TSKgel G3000SW column in 300 mM NaCl, 50 mM $KH_2PO_4$/$K_2HPO_4$, pH 7.5 on an Agilent HPLC 1100 system or to a Superdex 200 column (GE Healthcare) in 2×PBS on a Dionex HPLC-System. The eluted protein was quantified by UV absorbance and integration of peak areas. BioRad Gel Filtration Standard 151-1901 served as a standard.

Example 1

Generation of OX40 Antibodies 1.1 Preparation, Purification and Characterization of Antigens and Screening Tools for the Generation of Novel OX40 Binders by Phage Display DNA sequences encoding the ectodomains of human, mouse or cynomolgus OX40 (Table 1) were subcloned in frame with the human IgG1 heavy chain CH2 and CH3 domains on the knob (Merchant et al., Nat Biotechnol (1998) 16, 677-681). An AcTEV protease cleavage site was introduced between an antigen ectodomain and the Fc of human IgG1. An Avi tag for directed biotinylation was introduced at the C-terminus of the antigen-Fc knob. Combination of the antigen-Fc knob chain containing the S354C/T366W mutations, with a Fc hole chain containing the Y349C/T366S/L368A/Y407V mutations allows generation of a heterodimer which includes a single copy of the OX40 ectodomain containing chain, thus creating a monomeric form of Fc-linked antigen (FIG. 1). Table 1 shows the amino acid sequences of the various OX40 ectodomains. Table 2 the cDNA and amino acid sequences of monomeric antigen Fc(kih) fusion molecules as depicted in FIG. 1.

TABLE 1

Amino acid numbering of antigen ectodomains (ECD) and their origin

| SEQ ID NO: | Construct | Origin | ECD |
|---|---|---|---|
| 1 | human OX40 ECD | Synthetized according to P43489 | aa 29-214 |
| 79 | cynomolgus OX40 ECD | Isolated from cynomolgus blood | aa 29-214 |
| 80 | murine OX40 ECD | Synthetized according to P47741 | aa 10-211 |

TABLE 2 cDNA and amino acid sequences of monomeric antigen Fc(kih) fusion molecules (produced by combination of one Fc hole chain with one antigen Fc knob chain)

| SEQ ID NO: | Antigen | Sequence |
|---|---|---|
| 82 | Nucleotide sequence Fc hole chain | GACAAAACTCACACATGCCCACCGTGCCCAGCACCTG AACTCCTGGGGGGACCGTCAGTCTTCCTCTTCCCCCC AAAACCCAAGGACACCCTCATGATCTCCCGGACCCCT GAGGTCACATGCGTGGTGGTGGACGTGAGCCACGAA GACCCTGAGGTCAAGTTCAACTGGTACGTGGACGGC GTGGAGGTGCATAATGCCAAGACAAAGCCGCGGGAG GAGCAGTACAACAGCACGTACCGTGTGGTCAGCGTC CTCACCGTCCTGCACCAGGACTGGCTGAATGGCAAGG AGTACAAGTGCAAGGTCTCCAACAAAGCCCTCCCAG CCCCCATCGAGAAAACCATCTCCAAAGCCAAAGGGC AGCCCCGAGAACCACAGGTGTGCACCCTGCCCCCATC CCGGGATGAGCTGACCAAGAACCAGGTCAGCCTCTC GTGCGCAGTCAAAGGCTTCTATCCCAGCGACATCGCC GTGGAGTGGGAGAGCAATGGGCAGCCGGAGAACAAC TACAAGACCACGCCTCCCGTGCTGGACTCCGACGGCT CCTTCTTCCTCGTGAGCAAGCTCACCGTGGACAAGAG CAGGTGGCAGCAGGGGAACGTCTTCTCATGCTCCGTG ATGCATGAGGCTCTGCACAACCACTACACGCAGAAG AGCCTCTCCCTGTCTCCGGGTAAA |
| 83 | Nucleotide sequence human OX40 antigen Fc knob chain | CTGCACTGCGTGGGCGACACCTACCCCAGCAACGACC GGTGCTGCCACGAGTGCAGACCCGGCAACGGCATGG TGTCCCGGTGCAGCCGGTCCCAGAACACCGTGTGCAG ACCTTGCGGCCCTGGCTTCTACAACGACGTGGTGTCC AGCAAGCCCTGCAAGCCTTGTACCTGGTGCAACCTGC GGAGCGGCAGCGAGCGGAAGCAGCTGTGTACCGCCA CCCAGGATACCGTGTGCCGGTGTAGAGCCGGCACCC AGCCCCTGGACAGCTACAAACCCGGCGTGGACTGCG CCCCTTGCCCTCCTGGCCACTTCAGCCCTGGCGACAA CCAGGCCTGCAAGCCTTGGACCAACTGCACCCTGGCC GGCAAGCACACCCTGCAGCCCGCCAGCAATAGCAGC GACGCCATCTGCGAGGACCGGGATCCTCCTGCCACCC AGCCTCAGGAAACCCAGGGCCCTCCCGCCAGACCCA TCACCGTGCAGCCTACAGAGGCCTGGCCCAGAACCA GCCAGGGGCCTAGCACCAGACCCGTGGAAGTGCCTG |

TABLE 2-continued cDNA and amino acid sequences of monomeric antigen Fc(kih) fusion molecules (produced by combination of one Fc hole chain with one antigen Fc knob chain)

| SEQ ID NO: | Antigen | Sequence |
|---|---|---|
|  |  | GCGGCAGAGCCGTCGACGAACAGTTATATTTTCAGGG CGGCTCACCCAAATCTGCAGACAAAACTCACACATGC CCACCGTGCCCAGCACCTGAACTCCTGGGGGGACCGT CAGTCTTCCTCTTCCCCCCAAAACCCAAGGACACCCT CATGATCTCCCGGACCCCTGAGGTCACATGCGTGGTG GTGGACGTGAGCCACGAAGACCCTGAGGTCAAGTTC AACTGGTACGTGGACGGCGTGGAGGTGCATAATGCC AAGACAAAGCCGCGGGAGGAGCAGTACAACAGCACG TACCGTGTGGTCAGCGTCCTCACCGTCCTGCACCAGG ACTGGCTGAATGGCAAGGAGTACAAGTGCAAGGTCT CCAACAAAGCCCTCCCAGCCCCCATCGAGAAAACCA TCTCCAAAGCCAAAGGGCAGCCCCGAGAACCACAGG TGTACACCCTGCCCCCATGCCGGGATGAGCTGACCAA GAACCAGGTCAGCCTGTGGTGCCTGGTCAAAGGCTTC TATCCCAGCGACATCGCCGTGGAGTGGGAGAGCAAT GGGCAGCCGGAGAACAACTACAAGACCACGCCTCCC GTGCTGGACTCCGACGGCTCCTTCTTCCTCTACAGCA AGCTCACCGTGGACAAGAGCAGGTGGCAGCAGGGGA ACGTCTTCTCATGCTCCGTGATGCATGAGGCTCTGCA CAACCACTACACGCAGAAGAGCCTCTCCCTGTCTCCG GGTAAATCCGGAGGCCTGAACGACATCTTCGAGGCC CAGAAGATTGAATGGCACGAG |
| 84 | Nucleotide sequence cynomolgus OX40 antigen Fc knob chain | CTCCACTGTGTCGGGGACACCTACCCCAGCAACGACC GGTGCTGTCAGGAGTGCAGGCCAGGCAACGGGATGG TGAGCCGCTGCAACCGCTCCCAGAACACGGTGTGCCG TCCGTGCGGGCCCGGCTTCTACAACGACGGTGTCAGC GCCAAGCCCTGCAAGGCCTGCACATGGTGCAACCTCA GAAGTGGGAGTGAGCGGAAACAGCCGTGCACGGCCA CACAGGACACAGTCTGCCGCTGCCGGGCGGGCACCC AGCCCCTGGACAGCTACAAGCCTGGAGTTGACTGTGC CCCCTGCCCTCCAGGGCACTTCTCCCCGGGCGACAAC CAGGCCTGCAAGCCCTGGACCAACTGCACCTTGGCCG GGAAGCACACCCTGCAGCCAGCCAGCAATAGCTCGG ACGCCATCTGTGAGGACAGGGACCCCCCCACCCACAC AGCCCCAGGAGACCCAGGGCCCCCCGGCCAGGCCCA CCACTGTCCAGCCCACTGAAGCCTGGCCCAGAACCTC ACAGAGACCCTCCACCCGGCCCGTGGAGGTCCCCAG GGGCCCTGCGGTCGACGAACAGTTATATTTTCAGGGC GGCTCACCCAAATCTGCAGACAAAACTCACACATGCC CACCGTGCCCAGCACCTGAACTCCTGGGGGGACCGTC AGTCTTCCTCTTCCCCCCAAAACCCAAGGACACCCTC ATGATCTCCCGGACCCCTGAGGTCACATGCGTGGTGG TGGACGTGAGCCACGAAGACCCTGAGGTCAAGTTCA ACTGGTACGTGGACGGCGTGGAGGTGCATAATGCCA AGACAAAGCCGCGGGAGGAGCAGTACAACAGCACGT ACCGTGTGGTCAGCGTCCTCACCGTCCTGCACCAGGA CTGGCTGAATGGCAAGGAGTACAAGTGCAAGGTCTC CAACAAAGCCCTCCCAGCCCCCATCGAGAAAACCAT CTCCAAAGCCAAAGGGCAGCCCCGAGAACCACAGGT GTACACCCTGCCCCCATGCCGGGATGAGCTGACCAAG AACCAGGTCAGCCTGTGGTGCCTGGTCAAAGGCTTCT ATCCCAGCGACATCGCCGTGGAGTGGGAGAGCAATG GGCAGCCGGAGAACAACTACAAGACCACGCCTCCCG TGCTGGACTCCGACGGCTCCTTCTTCCTCTACAGCAA GCTCACCGTGGACAAGAGCAGGTGGCAGCAGGGGAA CGTCTTCTCATGCTCCGTGATGCATGAGGCTCTGCAC AACCACTACACGCAGAAGAGCCTCTCCCTGTCTCCGG GTAAATCCGGAGGCCTGAACGACATCTTCGAGGCCC AGAAGATTGAATGGCACGAG |
| 85 | Nucleotide sequence murine OX40 antigen Fc knob chain | GTGACCGCCAGACGGCTGAACTGCGTGAAGCACACC TACCCCAGCGGCCACAAGTGCTGCAGAGAGTGCCAG CCCGGCCACGGCATGGTGTCCAGATGCGACCACACA CGGGACACCCTGTGCCACCCTTGCGAGACAGGCTTCT ACAACGAGGCCGTGAACTACGATACCTGCAAGCAGT GCACCCAGTGCAACCACAGAAGCGGCAGCGAGCTGA AGCAGAACTGCACCCCCACCCAGGATACCGTGTGCA GATGCAGACCCGGCACCCAGCCCAGACAGGACAGCG GCTACAAGCTGGGCGTGGACTGCGTGCCCTGCCCTCC TGGCCACTTCAGCCCCGGCAACAACCAGGCCTGCAA GCCCTGGACCAACTGCACCCTGAGCGGCAAGCAGAC CAGACACCCCGCCAGCGACAGCCTGGATGCCGTGTG CGAGGACAGAAGCCTGCTGGCCACCCTGCTGTGGGA |

TABLE 2-continued cDNA and amino acid sequences of monomeric antigen Fc(kih) fusion molecules (produced by combination of one Fc hole chain with one antigen Fc knob chain)

| SEQ ID NO: | Antigen | Sequence |
|---|---|---|
| | | GACACAGCGGCCCACCTTCAGACCCACCACCGTGCA<br>GAGCACCACCGTGTGGCCCAGAACCAGCGAGCTGCC<br>CAGTCCTCCTACCCTCGTGACACCTGAGGGCCCCGTC<br>GACGAACAGTTATATTTTCAGGGCGGCTCACCCAAAT<br>CTGCAGACAAAACTCACACATGCCCACCGTGCCCAGC<br>ACCTGAACTCCTGGGGGGACCGTCAGTCTTCCTCTTC<br>CCCCCAAAACCCAAGGACACCCTCATGATCTCCCGGA<br>CCCCTGAGGTCACATGCGTGGTGGTGGACGTGAGCCA<br>CGAAGACCCTGAGGTCAAGTTCAACTGGTACGTGGA<br>CGGCGTGGAGGTGCATAATGCCAAGACAAAGCCGCG<br>GGAGGAGCAGTACAACAGCACGTACCGTGTGGTCAG<br>CGTCCTCACCGTCCTGCACCAGGACTGGCTGAATGGC<br>AAGGAGTACAAGTGCAAGGTCTCCAACAAAGCCCTC<br>CCAGCCCCCATCGAGAAAACCATCTCCAAAGCCAAA<br>GGGCAGCCCCGAGAACCACAGGTGTACACCCTGCCC<br>CCATGCCGGGATGAGCTGACCAAGAACCAGGTCAGC<br>CTGTGGTGCCTGGTCAAAGGCTTCTATCCCAGCGACA<br>TCGCCGTGGAGTGGGAGAGCAATGGGCAGCCGGAGA<br>ACAACTACAAGACCACGCCTCCCGTGCTGGACTCCGA<br>CGGCTCCTTCTTCCTCTACAGCAAGCTCACCGTGGAC<br>AAGAGCAGGTGGCAGCAGGGGAACGTCTTCTCATGC<br>TCCGTGATGCATGAGGCTCTGCACAACCACTACACGC<br>AGAAGAGCCTCTCCCTGTCTCCGGGTAAATCCGGAGG<br>CCTGAACGACATCTTCGAGGCCCAGAAGATTGAATG<br>GCACGAG |
| 86 | Fc hole chain | DKTHTCPPCPAPELLGGPSVFLFPPKPKDTLMISRTPEVT<br>CVVVDVSHEDPEVKFNWYVDGVEVHNAKTKPREEQY<br>NSTYRVVSVLTVLHQDWLNGKEYKCKVSNKALPAPIE<br>KTISKAKGQPREPQVCTLPPSRDELTKNQVSLSCAVKGF<br>YPSDIAVEWESNGQPENNYKTTPPVLDSDGSFFLVSKLT<br>VDKSRWQQGNVFSCSVMHEALHNHYTQKSLSLSPGK |
| 87 | human OX40 antigen Fc knob chain | LHCVGDTYPSNDRCCHECRPGNGMVSRCSRSQNTVCRP<br>CGPGFYNDVVSSKPCKPCTWCNLRSGSERKQLCTATQD<br>TVCRCRAGTQPLDSYKPGVDCAPCPPGHFSPGDNQACK<br>PWTnCTLAGKHTLQPASNSSDAICEDRDPPATQPQETQG<br>PPARPITVQPTEAWPRTSQGPSTRPVEVPGGRAVDEQLY<br>FQGGSPKSADKTHTCPPCPAPELLGGPSVFLFPPKPKDTL<br>MISRTPEVTCVVVDVSHEDPEVKFNWYVDGVEVHNAK<br>TKPREEQYNSTYRVVSVLTVLHQDWLNGKEYKCKVSN<br>KALPAPIEKTISKAKGQPREPQVYTLPPCRDELTKNQVS<br>LWCLVKGFYPSDIAVEWESNGQPENNYKTTPPVLDSDG<br>SFFLYSKLTVDKSRWQQGNVFSCSVMHEALHNHYTQK<br>SLSLSPGKSGGLNDIFEAQKIEWHE |
| 88 | cynomolgus OX40 antigen Fc knob chain | LHCVGDTYPSNDRCCQECRPGNGMVSRCNRSQNTVCR<br>PCGPGFYNDVVSAKPCKACTWCNLRSGSERKQPCTATQ<br>DTVCRCRAGTQPLDSYKPGVDCAPCPPGHFSPGDNQAC<br>KPWTnCTLAGKHTLQPASNSSDAICEDRDPPPTQPQETQ<br>GPPARPTTVQPTEAWPRTSQRPSTRPVEVPRGPAVDEQL<br>YFQGGSPKSADKTHTCPPCPAPELLGGPSVFLFPPKPKD<br>TLMISRTPEVTCVVVDVSHEDPEVKFNWYVDGVEVHN<br>AKTKPREEQYNSTYRVVSVLTVLHQDWLNGKEYKCKV<br>SNKALPAPIEKTISKAKGQPREPQVYTLPPCRDELTKNQ<br>VSLWCLVKGFYPSDIAVEWESNGQPENNYKTTPPVLDS<br>DGSFFLYSKLTVDKSRWQQGNVFSCSVMHEALHNHYT<br>QKSLSLSPGKSGGLNDIFEAQKIEWHE |
| 89 | murine OX40 antigen Fc knob chain | VTARRLNCVKHTYPSGHKCCRECQPGHGMVSRCDHTR<br>DTLCHPCETGFYNEAVNYDTCKQCTQCNHRSGSELKQ<br>NCTPTQDTVCRCRPGTQPRQDSGYKLGVDCVPCPPGHF<br>SPGNNQACKPWTnCTLSGKQTRHPASDSLDAVCEDRSL<br>LATLLWETQRPTFRPTTVQSTTVWPRTSELPSPPTLVTPE<br>GPVDEQLYFQGGSPKSADKTHTCPPCPAPELLGGPSVFL<br>FPPKPKDTLMISRTPEVTCVVVDVSHEDPEVKFNWYVD<br>GVEVHNAKTKPREEQYNSTYRVVSVLTVLHQDWLNGK<br>EYKCKVSNKALPAPIEKTISKAKGQPREPQVYTLPPCRD<br>ELTKNQVSLWCLVKGFYPSDIAVEWESNGQPENNYKTT<br>PPVLDSDGSFFLYSKLTVDKSRWQQGNVFSCSVMHEAL<br>HNHYTQKSLSLSPGKSGGLNDIFEAQKIEWHE |

All OX40-Fc-fusion encoding sequences were cloned into a plasmid vector driving expression of the insert from an MPSV promoter and containing a synthetic polyA signal sequence located at the 3' end of the CDS. In addition, the vector contained an EBV OriP sequence for episomal maintenance of the plasmid.

For preparation of the biotinylated monomeric antigen/Fc fusion molecules, exponentially growing suspension HEK293 EBNA cells were co-transfected with three vectors encoding the two components of fusion protein (knob and hole chains) as well as BirA, an enzyme necessary for the biotinylation reaction. The corresponding vectors were used at a 2:1:0.05 ratio ("antigen ECD-AcTEV-Fc knob":"Fc hole":"BirA").

For protein production in 500 ml shake flasks, 400 million HEK293 EBNA cells were seeded 24 hours before transfection. For transfection cells were centrifuged for 5 minutes at 210 g, and supernatant was replaced by pre-warmed CD CHO medium. Expression vectors were resuspended in 20 mL of CD CHO medium containing 200 μg of vector DNA. After addition of 540 μL of polyethylenimine (PEI), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection, 1 mM valproic acid and 7% Feed were added to the culture. After 7 days of culturing, the cell supernatant was collected by spinning down cells for 15 min at 210 g. The solution was sterile filtered (0.22 μm filter), supplemented with sodium azide to a final concentration of 0.01% (w/v), and kept at 4° C.

Secreted proteins were purified from cell culture supernatants by affinity chromatography using Protein A, followed by size exclusion chromatography. For affinity chromatography, the supernatant was loaded on a HiTrap ProteinA HP column (CV=5 mL, GE Healthcare) equilibrated with 40 mL 20 mM sodium phosphate, 20 mM sodium citrate pH 7.5. Unbound protein was removed by washing with at least 10 column volumes of a buffer containing 20 mM sodium phosphate, 20 mM sodium citrate and 0.5 M sodium chloride (pH 7.5). The bound protein was eluted using a linear pH-gradient of sodium chloride (from 0 to 500 mM) created over 20 column volumes of 20 mM sodium citrate, 0.01% (v/v) Tween-20, pH 3.0. The column was then washed with 10 column volumes of a solution containing 20 mM sodium citrate, 500 mM sodium chloride and 0.01% (v/v) Tween-20, pH 3.0.

The pH of the collected fractions was adjusted by adding 1/40 (v/v) of 2M Tris, pH8.0. The protein was concentrated and filtered prior to loading on a HiLoad Superdex 200 column (GE Healthcare) equilibrated with 2 mM MOPS, 150 mM sodium chloride, 0.02% (w/v) sodium azide solution of pH 7.4.

1.2 Selection of OX40-Specific 8H9, 20B7, 49B4, 1G4, CLC-563, CLC-564 and 17A9 Antibodies from Generic Fab and Common Light Chain Libraries Anti-OX40 antibodies were selected from three different generic phage display libraries: DP88-4 (clones 20B7, 8H9 1G4 and 49B4), the common light chain library Vk3_20/VH3_23 (clones CLC-563 and CLC-564) and lambda-DP47 (clone 17A9).

The DP88-4 library was constructed on the basis of human germline genes using the V-domain pairing Vk1_5 (kappa light chain) and VH1_69 (heavy chain) comprising randomized sequence space in CDR3 of the light chain (L3, 3 different lengths) and CDR3 of the heavy chain (H3, 3 different lengths). Library generation was performed by assembly of 3 PCR-amplified fragments applying splicing by overlapping extension (SOE) PCR. Fragment 1 comprises the 5' end of the antibody gene including randomized L3, fragment 2 is a central constant fragment spanning from L3 to H3 whereas fragment 3 comprises randomized H3 and the 3' portion of the antibody gene. The following primer combinations were used to generate these library fragments for DP88-4 library: fragment 1 (forward primer LMB3 combined with reverse primers Vk1_5_L3r_S or Vk1_5_L3r_SY or Vk1_5_L3r_SPY), fragment 2 (forward primer RJH31 combined with reverse primer RJH32) and fragment 3 (forward primers DP88-v4-4 or DP88-v4-6 or DP88-v4-8 combined with reverse primer fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the gel-purified single fragments as template, parameters were 3 min initial denaturation at 94° C. and 5 cycles of 30 s 94° C., 1 min 58° C., 2 min 72° C. At this stage, outer primers (LMB3 and fdseqlong) were added and additional 20 cycles were performed prior to a terminal elongation for 10 min at 72° C. After assembly of sufficient amounts of full length randomized Fab constructs, they were digested NcoI/NheI and ligated into similarly treated acceptor phagemid vector. Purified ligations were used for ~60 transformations into electrocompetent E. coli TG1. Phagemid particles displaying the Fab library were rescued and purified by PEG/NaCl purification to be used for selections. These library construction steps were repeated three times to obtain a final library size of 4.4×109. Percentages of functional clones, as determined by C-terminal tag detection in dot blot, were 92.6% for the light chain and 93.7% for the heavy chain, respectively.

The common light chain library Vk3_20/VH3_23 was constructed on the basis of human germline genes using the V-domain pairing Vk3_20 (kappa light chain) and VH3_23 (heavy chain) comprising a constant non-randomized common light chain Vk3_20 and randomized sequence space in CDR3 of the heavy chain (H3, 3 different lengths). Library generation was performed by assembly of 2 PCR-amplified fragments applying splicing by overlapping extension (SOE) PCR. Fragment 1 is a constant fragment spanning from L3 to H3 whereas fragment 2 comprises randomized H3 and the 3' portion of the antibody gene. The following primer combinations were used to generate these library fragments for the Vk3_20/VH3_23 common light chain library: fragment 1 (forward primer MS64 combined with reverse primer DP47CDR3_ba (mod.)) and fragment 2 (forward primers DP47-v4-4, DP47-v4-6, DP47-v4-8 combined with reverse primer fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the gel-purified single fragments as template, parameters were 3 min initial denaturation at 94° C. and 5 cycles of 30 s 94° C., 1 min 58° C., 2 min 72° C. At this stage, outer primers (MS64 and fdseqlong) were added and additional 18 cycles were performed prior to a terminal elongation for 10 min at 72° C. After assembly of sufficient amounts of full length randomized VH constructs, they were digested MunI/NotI and ligated into similarly treated acceptor phagemid vector. Purified ligations were used for ~60 transformations into electrocompetent E. coli TG1. Phagemid particles displaying the Fab library were rescued and purified by PEG/NaCl purification to be used for selections. A final library size of 3.75×10⁹ was obtained. Percentages of functional clones, as determined by C-terminal tag detection in dot blot, were 98.9% for the light chain and 89.5% for the heavy chain, respectively.

The lambda-DP47 library was constructed on the basis of human germline genes using the following V-domain pairings: Vl3_19 lambda light chain with VH3_23 heavy chain. The library was randomized in CDR3 of the light chain (L3) and CDR3 of the heavy chain (H3) and was assembled from 3 fragments by "splicing by overlapping extension" (SOE) PCR. Fragment 1 comprises the 5' end of the antibody gene including randomized L3, fragment 2 is a central constant fragment spanning from the end of L3 to the beginning of H3 whereas fragment 3 comprises randomized H3 and the 3' portion of the Fab fragment. The following primer combinations were used to generate library fragments for library: fragment 1 (LMB3—Vl_3_19_L3r_V/Vl_3_19_L3r_HV/Vl_3_19_L3r_HLV), fragment 2 (RJH80—DP47CDR3_ba (mod)) and fragment 3 (DP47-v4-4/DP47-v4-6/DP47-v4-8—fdseqlong). PCR parameters for production of library fragments were 5 min initial denaturation at 94° C., 25 cycles of 60 sec at 94° C., 60 sec at 55° C., 60 sec at 72° C. and terminal elongation for 10 min at 72° C. For assembly PCR, using equimolar ratios of the 3 fragments as template, parameters were 3 min initial denaturation at 94° C. and 5 cycles of 60 sec at 94° C., 60 sec at 55° C., 120 sec at 72° C. At this stage, outer primers were added and additional 20 cycles were performed prior to a terminal elongation for 10 min at 72° C. After assembly of sufficient amounts of full length randomized Fab fragments, they were digested with NcoI/NheI alongside with similarly treated acceptor phagemid vector. 15 ug of Fab library insert were ligated with 13.3 ug of phagemid vector. Purified ligations were used for 60 transformations resulting in 1.5×10⁹ transformants. Phagemid particles displaying the Fab library were rescued and purified by PEG/NaCl purification to be used for selections.

Human OX40 (CD134) as antigen for the phage display selections was transiently expressed as N-terminal monomeric Fc-fusion in HEK EBNA cells and in vivo site-specifically biotinylated via co-expression of BirA biotin ligase at the avi-tag recognition sequence located a the C-terminus of the Fc portion carrying the receptor chain (Fc knob chain).

Selection rounds (biopanning) were performed in solution according to the following pattern:
1. Pre-clearing of ~10¹² phagemid particles on maxisorp plates coated with 10 ug/ml of an unrelated human IgG to deplete the libraries of antibodies recognizing the Fc-portion of the antigen,
2. incubation of the non-binding phagemid particles with 100 nM biotinylated human OX40 for 0.5 h in the presence of 100 nM unrelated non-biotinylated Fc knob-into-hole construct for further depletion of Fc-binders in a total volume of 1 ml,
3. capture of biotinylated hu OX40 and attached specifically binding phage by transfer to 4 wells of a neutravidin pre-coated microtiter plate for 10 min (in rounds 1 & 3),
4. washing of respective wells using 5×PBS/Tween20 and 5×PBS,
5. elution of phage particles by addition of 250 ul 100 mM TEA (triethylamine) per well for 10 min and neutralization by addition of 500 ul 1M Tris/HCl pH 7.4 to the pooled eluates from 4 wells,
6. post-clearing of neutralized eluates by incubation on neutravidin pre-coated microtiter plate with 100 nM biotin-captured Fc knob-into-hole construct for final removal of Fc-binders,
7. re-infection of log-phase E. coli TG1 cells with the supernatant of eluted phage particles, infection with helper phage VCSM13, incubation on a shaker at 30° C. over night and subsequent PEG/NaCl precipitation of phagemid particles to be used in the next selection round.

Selections were carried out over 3 or 4 rounds using constant antigen concentrations of 100 nM. In order to increase the likelihood for binders that are cross-reactive not only to cynomolgus OX40 but also murine OX40, in some selection rounds the murine target was used instead of the human OX40. In rounds 2 and 4, in order to avoid enrichment of binders to neutravidin, capture of antigen: phage complexes was performed by addition of 5.4×10⁷ streptavidin-coated magnetic beads. Specific binders were identified by ELISA as follows: 100 ul of 25 nM biotinylated human OX40 and 10 ug/ml of human IgG were coated on neutravidin plates and maxisorp plates, respectively. Fab-containing bacterial supernatants were added and binding Fabs were detected via their Flag-tags using an anti-Flag/HRP secondary antibody. Clones exhibiting signals on human OX40 and being negative on human IgG were short-listed for further analyses and were also tested in a similar fashion against cynomolgus and murine OX40. They were bacterially expressed in a 0.5 liter culture volume, affinity purified and further characterized by SPR-analysis using BioRad's ProteOn XPR36 biosensor.

Table 3 shows the sequence of generic phage-displayed antibody library (DP88-4), Table 4 provides cDNA and amino acid sequences of library DP88-4 germline template and Table 5 shows the Primer sequences used for generation of DP88-4 germline template.

TABLE 3

Sequence of generic phage-displayed antibody library (DP88-4)

| SEQ ID NO: | Description | Sequence |
|---|---|---|
| 90 | nucleotide sequence of pRJH33 library template DP88-4 library; complete Fab coding region | TGAAATACCTATTGCCTACGGCAGCCGCTGGATTGTTATTACTCG<br>CGGCCCAGCCGGCCATGGCCGACATCCAGATGACCCAGTCTCCT<br>TCCACCCTGTCTGCATCTGTAGGAGACCGTGTCACCATCACTTGC<br>CGTGCCAGTCAGAGTATTAGTAGCTGGTTGGCCTGGTATCAGCA<br>GAAACCAGGGAAAGCCCCTAAGCTCCTGATCTATGATGCCTCCA<br>GTTTGGAAAGTGGGGTCCCATCACGTTTCAGCGGCAGTGGATCC<br>GGGACAGAATTCACTCTCACCATCAGCAGCTTGCAGCCTGATGA<br>TTTTGCAACTTATTACTGCCAACAGTATAATAGTTATTCTACGTT<br>TGGCCAGGGCACCAAAGTCGAGATCAAGCGTACGGTGGCTGCA<br>CCATCTGTCTTCATCTTCCCGCCATCTGATGAGCAGTTGAAATCT<br>GGAACTGCCTCTGTTGTGTGCCTGCTGAATAACTTCTATCCCAGA |

TABLE 3-continued

Sequence of generic phage-displayed antibody library (DP88-4)

| SEQ ID NO: | Description | Sequence |
|---|---|---|
| | comprising PelB leader sequence + Vk1_5 kappa V-domain + CL constant domain for light chain and PelB + VH1_69 V-domain + CH1 constant domain for heavy chain including tags | GAGGCCAAAGTACAGTGGAAGGTGGATAACGCCCTCCAATCGG GTAACTCCCAGGAGAGTGTCACAGAGCAGGACAGCAAGGACAG CACCTACAGCCTCAGCAGCACCCTGACGCTGAGCAAAGCAGACT ACGAGAAACACAAAGTCTACGCCTGCGAAGTCACCCATCAGGG CCTGAGCTCGCCCGTCACAAAGAGCTTCAACAGGGGAGAGTGTG GAGCCGCAGAACAAAAACTCATCTCAGAAGAGGATCTGAATGG AGCCGCAGACTACAAGGACGACGACGACAAGGGTGCCGCATAA TAAGGCGCGCCAATTCTATTTCAAGGAGACAGTCATATGAAATA CCTGCTGCCGACCGCTGCTGCTGGTCTGCTGCTCCTCGCTGCCCA GCCGGCGATGGCCCAGGTGCAATTGGTGCAGTCTGGGGCTGAGG TGAAGAAGCCTGGGTCCTCGGTGAAGGTCTCCTGCAAGGCCTCC GGAGGCACATTCAGCAGCTACGCTATAAGCTGGGTGCGACAGGC CCCTGGACAAGGGCTCGAGTGGATGGGAGGGATCATCCCTATCT TTGGTACAGCAAACTACGCACAGAAGTTCCAGGGCAGGGTCACC ATTACTGCAGACAAATCCACGAGCACAGCCTACATGGAGCTGAG CAGCCTGAGATCTGAGGACACCGCCGTGTATTACTGTGCGAGAC TATCCCCAGGCGGTTACTATGTTATGGATGCCTGGGGCCAAGGG ACCACCGTGACCGTCTCCTCAGCTAGCACCAAAGGCCCATCGGT CTTCCCCCTGGCACCCTCCTCCAAGAGCACCTCTGGGGGCACAG CGGCCCTGGGCTGCCTGGTCAAGGACTACTTCCCCGAACCGGTG ACGGTGTCGTGGAACTCAGGCGCCCTGACCAGCGGCGTGCACAC CTTCCCGGCTGTCCTACAGTCCTCAGGACTCTACTCCCTCAGCAG CGTGGTGACCGTGCCCTCCAGCAGCTTGGGCACCCAGACCTACA TCTGCAACGTGAATCACAAGCCCAGCAACACCAAAGTGGACAA GAAAGTTGAGCCCAAATCTTGTGACGCGGCCGCAAGCACTAGTG CCCATCACCATCACCATCACGCCGCGGCA |

TABLE 4 cDNA and amino acid sequences of library DP88-4 germline template

| SEQ ID NO: | Description | Sequence |
|---|---|---|
| 91 | nucleotide sequence of Fab light chain Vk1_5 | GACATCCAGATGACCCAGTCTCCTTCCACCCTGTCTGC ATCTGTAGGAGACCGTGTCACCATCACTTGCCGTGCCA GTCAGAGTATTAGTAGCTGGTTGGCCTGGTATCAGCAG AAACCAGGGAAAGCCCCTAAGCTCCTGATCTATGATGC CTCCAGTTTGGAAAGTGGGGTCCCATCACGTTTCAGCG GCAGTGGATCCGGGACAGAATTCACTCTCACCATCAGC AGCTTGCAGCCTGATGATTTTGCAACTTATTACTGCCA ACAGTATAATAGTTATTCTACGTTTGGCCAGGGCACCA AAGTCGAGATCAAGCGTACGGTGGCTGCACCATCTGTC TTCATCTTCCCGCCATCTGATGAGCAGTTGAAATCTGG AACTGCCTCTGTTGTGTGCCTGCTGAATAACTTCTATCC CAGAGAGGCCAAAGTACAGTGGAAGGTGGATAACGCC CTCCAATCGGGTAACTCCCAGGAGAGTGTCACAGAGC AGGACAGCAAGGACAGCACCTACAGCCTCAGCAGCAC CCTGACGCTGAGCAAAGCAGACTACGAGAAACACAAA GTCTACGCCTGCGAAGTCACCCATCAGGGCCTGAGCTC GCCCGTCACAAAGAGCTTCAACAGGGGAGAGTGTGGA GCCGCAGAACAAAAACTCATCTCAGAAGAGGATCTGA ATGGAGCCGCAGACTACAAGGACGACGACGACAAGGG TGCCGCA |
| 92 | Fab light chain Vk1_5 | DIQMTQSPSTLSASVGDRVTITCRASQSISSWLAWYQQKP GKAPKLLIYDASSLESGVPSRFSGSGSGTEFTLTISSLQPDD FATYYCQQYNSYSTFGQGTKVEIKRTVAAPSVFIFPPSDE QLKSGTASVVCLLNNFYPREAKVQWKVDNALQSGNSQE SVTEQDSKDSTYSLSSTLTLSKADYEKHKVYACEVTHQG LSSPVTKSFNRGECGAAEQKLISEEDLNGAADYKDDDDK GAA |
| 93 | nucleotide sequence of Fab heavy chain VH1_69 | CAGGTGCAATTGGTGCAGTCTGGGGCTGAGGTGAAGA AGCCTGGGTCCTCGGTGAAGGTCTCCTGCAAGGCCTCC GGAGGCACATTCAGCAGCTACGCTATAAGCTGGGTGC GACAGGCCCCTGGACAAGGGCTCGAGTGGATGGGAGG GATCATCCCTATCTTTGGTACAGCAAACTACGCACAGA AGTTCCAGGGCAGGGTCACCATTACTGCAGACAAATCC ACGAGCACAGCCTACATGGAGCTGAGCAGCCTGAGAT CTGAGGACACCGCCGTGTATTACTGTGCGAGACTATCC |

TABLE 4-continued cDNA and amino acid sequences of library DP88-4 germline template

| SEQ ID NO: | Description | Sequence |
|---|---|---|
| | | CCAGGCGGTTACTATGTTATGGATGCCTGGGGCCAAGG<br>GACCACCGTGACCGTCTCCTCAGCTAGCACCAAAGGCC<br>CATCGGTCTTCCCCCTGGCACCCTCCTCCAAGAGCACC<br>TCTGGGGGCACAGCGGCCCTGGGCTGCCTGGTCAAGG<br>ACTACTTCCCCGAACCGGTGACGGTGTCGTGGAACTCA<br>GGCGCCCTGACCAGCGGCGTGCACACCTTCCCGGCTGT<br>CCTACAGTCCTCAGGACTCTACTCCCTCAGCAGCGTGG<br>TGACCGTGCCCTCCAGCAGCTTGGGCACCCAGACCTAC<br>ATCTGCAACGTGAATCACAAGCCCAGCAACACCAAAG<br>TGGACAAGAAAGTTGAGCCCAAATCTTGTGACGCGGC<br>CGCAAGCACTAGTGCCCATCACCATCACCATCACGCCG<br>CGGCA |
| 94 | Fab heavy chain VH1_69 | QVQLVQSGAEVKKPGSSVKVSCKASGGTFSSYAISWVRQ<br>APGQGLEWMGGIIPIFGTANYAQKFQGRVTITADKSTSTA<br>YMELSSLRSEDTAVYYCARLSPGGYYVMDAWGQGTTVT<br>VSSASTKGPSVFPLAPSSKSTSGGTAALGCLVKDYFPEPV<br>TVSWNSGALTSGVHTFPAVLQSSGLYSLSSVVTVPSSSLG<br>TQTYICNVNHKPSNTKVDKKVEPKSCDAAASTSAHHHH<br>HHAAA |

TABLE 5

Primer sequences used for generation of DP88-4 library

| SEQ ID NO: | Primer name | Primer sequence 5'-3' |
|---|---|---|
| 95 | LMB3 | CAGGAAACAGCTATGACCATGATTAC |
| 96 | Vk1_5_L3r_S | CTCGACTTTGGTGCCCTGGCCAAACGTS<u>BA</u>*A*<sup>TA</sup><u>C</u>*GA*<u>A</u>*TT*<u>A</u>*TA*CTGTTGGCAGTAATAAGTTGCAAAATC<br><u>AT</u><br>underlined: 60% original base and 40% randomization as M.<br>bolded and italic: 60% original base and 40% randomization as N |
| 97 | Vk1_5_L3r_SY | CTCGACTTTGGTGCCCTGGCCAAACGTM*HR*<u>S</u>*GR*<u>A</u>*TA*<u>C</u>*GA*<u>A</u>*TT*<u>A</u>*TA*CTGTTGGCAGTAATAAGTTGCAAAATC<br><u>AT</u><br>underlined: 60% original base and 40% randomization as M.<br>bolded and italic: 60% original base and 40% randomization as N |
| 98 | Vk1_5_L3r_SPY | CTCGACTTTGGTGCCCTGGCCAAACGTM*HH*<u>M</u>*SS*<u>S</u>*GR*<br><u>A</u>*TA*<u>C</u>*GA*<u>A</u>*TT*<u>A</u>*TA*CTGTTGGCAGTAATAAGTTGCAAA<br><u>ATCAT</u><br>underlined: 60% original base and 40% randomization as M.<br>bolded and italic: 60% original base and 40% randomization as N |
| 99 | RJH31 | ACGTTTGGCCAGGGCACCAAAGTCGAG |
| 100 | RJH32 | TCTCGCACAGTAATACACGGCGGTGTCC |
| 101 | DP88-v4-4 | GGACACCGCCGTGTATTACTGTGCGAGA-1-2-2-3-4-<br>GAC-TAC-<br>TGGGGCCAAGGGACCACCGTGACCGTCTCC<br>1: G/D = 20%, E/V/S = 10%, A/P/R/L/T/Y = 5%; 2:<br>G/Y/S = 15%, A/D/T/R/P/L/V/N/W/F/I/E = 4,6%; 3: G/A/Y =<br>20%, P/W/S/D/T = 8%; 4: F = 46%, L/M = 15%, G/I/Y =<br>8%. |
| 102 | DP88-v4-6 | GGACACCGCCGTGTATTACTGTGCGAGA-1-2-2-2-3-<br>4-GAC-TAC-<br>TGGGGCCAAGGGACCACCGTGACCGTCTCC<br>1: G/D = 20%, E/V/S = 10%, A/P/R/L/T/Y = 5%; 2:<br>G/Y/S = 15%, A/D/T/R/P/L/V/N/W/F/I/E = 4,6%; 3: G/A/Y =<br>20%, P/W/S/D/T = 8%; 4: F = 46%, L/M = 15%, G/I/Y =<br>8%. |

TABLE 5-continued

Primer sequences used for generation of DP88-4 library

| SEQ ID NO: | Primer name | Primer sequence 5'-3' |
|---|---|---|
| 103 | DP88-v4-8 | GGACACCGCCGTGTATTACTGTGCGAGA-1-2-2-2-2-2-2-3-4-GAC-TAC-TGGGGCCAAGGGACCACCGTGACCGTCTCC<br>1: G/D = 20%, E/V/S = 10%, A/P/R/L/T/Y = 5%; 2: G/Y/S = 15%, A/D/T/R/P/L/V/N/W/F/I/E = 4,6%; 3: G/A/Y = 20%, P/W/S/D/T = 8%; 4: F = 46%, L/M = 15%, G/I/Y = 8%. |
| 104 | fdseqlong | GACGTTAGTAAATGAATTTTCTGTATGAGG |

Table 6 shows the sequence of generic phage-displayed antibody common light chain library (Vk3_20/VH3_23). Table 7 provides cDNA and amino acid sequences of common light chain library (Vk3_20/VH3_23) germline template and Table 8 shows the Primer sequences used for generation of common light chain library (Vk3_20/VH3_23).

TABLE 6

Sequence of generic phage-displayed antibody common light chain library (Vk3_20/VH3_23) template used for PCR

| SEQ ID NO: | Description | Sequence |
|---|---|---|
| 105 | pRJH110 library template of common light chain library Vk3_20/VH3_23; complete Fab coding region comprising PelB leader sequence + Vk3_20 kappa V-domain + CL constant domain for light chain and PelB + VH3_23 V-domain + CH1 constant domain for heavy chain including tags | ATGAAATACCTATTGCCTACGGCAGCCGCTGGATTGTTATTACTC<br>GCGGCCCAGCCGGCCATGGCCGAAATCGTGTTAACGCAGTCTCC<br>AGGCACCCTGTCTTTGTCTCCAGGGGAAAGAGCCACCCTCTCTT<br>GCAGGGCCAGTCAGAGTGTTAGCAGCAGCTACTTAGCCTGGTAC<br>CAGCAGAAACCTGGCCAGGCTCCCAGGCTCCTCATCTATGGAGC<br>ATCCAGCAGGGCCACTGGCATCCCAGACAGGTTCAGTGGCAGTG<br>GATCCGGGACAGACTTCACTCTCACCATCAGCAGACTGGAGCCT<br>GAAGATTTTGCAGTGTATTACTGTCAGCAGTATGGTAGCTCACC<br>GCTGACGTTCGGCCAGGGGACCAAAGTGGAAATCAAACGTACG<br>GTGGCTGCACCATCTGTCTTCATCTTCCCGCCATCTGATGAGCAG<br>TTGAAATCTGGAACTGCCTCTGTTGTGTGCCTGCTGAATAACTTC<br>TATCCCAGAGAGGCCAAAGTACAGTGGAAGGTGGATAACGCCC<br>TCCAATCGGGTAACTCCCAGGAGAGTGTCACAGAGCAGGACAG<br>CAAGGACAGCACCTACAGCCTCAGCAGCACCCTGACGCTGAGC<br>AAAGCAGACTACGAGAAACACAAAGTCTACGCCTGCGAAGTCA<br>CCCATCAGGGCCTGAGCTCGCCCGTCACAAAGAGCTTCAACAGG<br>GGAGAGTGTGGAGCCGCACATCACCATCACCATCACGGAGCCG<br>CAGACTACAAGGACGACGACGACAAGGGTGCCGCATAATAAGG<br>CGCGCCAATTCTATTTCAAGGAGACAGTCATATGAAATACCTGC<br>TGCCGACCGCTGCTGCTGGTCTGCTGCTCCTCGCTGCCCAGCCGG<br>CGATGGCCGAGGTGCAATTGCTGGAGTCTGGGGGAGGCTTGGTA<br>CAGCCTGGGGGGTCCCTGAGACTCTCCTGTGCAGCCTCCGGATT<br>CACCTTTAGCAGTTATGCCATGAGCTGGGTCCGCCAGGCTCCAG<br>GGAAGGGGCTGGAGTGGGTCTCAGCTATTAGTGGTAGTGGTGGT<br>AGCACATACTACGCAGACTCCGTGAAGGGCCGGTTCACCATCTC<br>CAGAGACAATTCCAAGAACACGCTGTATCTGCAAATGAACAGCC<br>TGAGAGCCGAGGACACGGCCGTATATTACTGTGCGAAACCGTTT<br>CCGTATTTTGACTACTGGGGCCAAGGAACCCTGGTCACCGTCTC<br>GAGTGCTAGCACCAAAGGCCCATCGGTCTTCCCCCTGGCACCCT<br>CCTCCAAGAGCACCTCTGGGGGCACAGCGGCCCTGGGCTGCCTG<br>GTCAAGGACTACTTCCCCGAACCGGTGACGGTGTCGTGGAACTC<br>AGGCGCCCTGACCAGCGGCGTGCACACCTTCCCGGCTGTCCTAC<br>AGTCCTCAGGACTCTACTCCCTCAGCAGCGTGGTGACCGTGCCC<br>TCCAGCAGCTTGGGCACCCAGACCTACATCTGCAACGTGAATCA<br>CAAGCCCAGCAACACCAAAGTGGACAAGAAAGTTGAGCCCAAA<br>TCTTGTGACGCGGCCGCAGAACAAAAACTCATCTCAGAAGAGGA<br>TCTGAATGCCGCGGCA |

TABLE 7 cDNA and amino acid sequences of common light chain library (Vk3_20/VH3_23) germline template

| SEQ ID NO: | Description | Sequence |
|---|---|---|
| 106 | nucleotide sequence of Fab light chain Vk3_20 | GAAATCGTGTTAACGCAGTCTCCAGGCACCCTGTCTTTGT CTCCAGGGGAAAGAGCCACCCTCTCTTGCAGGGCCAGTC AGAGTGTTAGCAGCAGCTACTTAGCCTGGTACCAGCAGA AACCTGGCCAGGCTCCCAGGCTCCTCATCTATGGAGCATC CAGCAGGGCCACTGGCATCCCAGACAGGTTCAGTGGCAG TGGATCCGGGACAGACTTCACTCTCACCATCAGCAGACTG GAGCCTGAAGATTTTGCAGTGTATTACTGTCAGCAGTATG GTAGCTCACCGCTGACGTTCGGCCAGGGGACCAAAGTGG AAATCAAACGTACGGTGGCTGCACCATCTGTCTTCATCTT CCCGCCATCTGATGAGCAGTTGAAATCTGGAACTGCCTCT GTTGTGTGCCTGCTGAATAACTTCTATCCCAGAGAGGCCA AAGTACAGTGGAAGGTGGATAACGCCCTCCAATCGGGTA ACTCCCAGGAGAGTGTCACAGAGCAGGACAGCAAGGACA GCACCTACAGCCTCAGCAGCACCCTGACGCTGAGCAAAG CAGACTACGAGAAACACAAAGTCTACGCCTGCGAAGTCA CCCATCAGGGCCTGAGCTCGCCCGTCACAAAGAGCTTCA ACAGGGGAGAGTGTGGAGCCGCACATCACCATCACCATC ACGGAGCCGCAGACTACAAGGACGACGACGACAAGGGT GCCGCA |
| 107 | Fab light chain Vk3_20 | EIVLTQSPGTLSLSPGERATLSCRASQSVSSSYLAWYQQKPG QAPRLLIYGASSRATGIPDRFSGSGSGTDFTLTISRLEPEDFAV YYCQQYGSSPLTFGQGTKVEIKRTVAAPSVFIFPPSDEQLKS GTASVVCLLNNFYPREAKVQWKVDNALQSGNSQESVTEQD SKDSTYSLSSTLTLSKADYEKHKVYACEVTHQGLSSPVTKSF NRGECGAAHHHHHHGAADYKDDDDKGAA |
| 108 | nucleotide sequence of Fab heavy chain VH3_23 | GAGGTGCAATTGCTGGAGTCTGGGGGAGGCTTGGTACAG CCTGGGGGGTCCCTGAGACTCTCCTGTGCAGCCTCCGGAT TCACCTTTAGCAGTTATGCCATGAGCTGGGTCCGCCAGGC TCCAGGGAAGGGGCTGGAGTGGGTCTCAGCTATTAGTGG TAGTGGTGGTAGCACATACTACGCAGACTCCGTGAAGGG CCGGTTCACCATCTCCAGAGACAATTCCAAGAACACGCTG TATCTGCAGATGAACAGCCTGAGAGCCGAGGACACGGCC GTATATTACTGTGCGAAACCGTTTCCGTATTTTGACTACT GGGGCCAAGGAACCCTGGTCACCGTCTCGAGTGCTAGCA CCAAAGGCCCATCGGTCTTCCCCCTGGCACCCTCCTCCAA GAGCACCTCTGGGGGCACAGCGGCCCTGGGCTGCCTGGT CAAGGACTACTTCCCCGAACCGGTGACGGTGTCGTGGAA CTCAGGCGCCCTGACCAGCGGCGTGCACACCTTCCCGGCT GTCCTACAGTCCTCAGGACTCTACTCCCTCAGCAGCGTGG TGACCGTGCCCTCCAGCAGCTTGGGCACCCAGACCTACAT CTGCAACGTGAATCACAAGCCCAGCAACACCAAAGTGGA CAAGAAAGTTGAGCCCAAATCTTGTGACGCGGCCGCAGA ACAAAAACTCATCTCAGAAGAGGATCTGAATGCCGCGGC A |
| 109 | Fab heavy chain VH3_23 (DP47) | EVQLLESGGGLVQPGGSLRLSCAASGFTFSSYAMSWVRQAP GKGLEWVSAISGSGGSTYYADSVKGRFTISRDNSKNTLYLQ MNSLRAEDTAVYYCAKPFPYFDYWGQGTLVTVSSASTKGP SVFPLAPSSKSTSGGTAALGCLVKDYFPEPVTVSWNSGALTS GVHTFPAVLQSSGLYSLSSVVTVPSSSLGTQTYICNVNHKPS NTKVDKKVEPKSCDAAAEQKLISEEDLNAAA |

TABLE 8

Primer sequences used for generation of common light chain library (Vk3_20/VH3_23)

| SEQ ID NO: | Primer name | Primer sequence 5'-3' |
|---|---|---|
| 110 | MS64 | ACGTTCGGCCAGGGGACCAAAGTGG |
| 111 | DP47CDR3_ba (mod.) | CGCACAGTAATATACGGCCGTGTCC |
| 112 | DP47-v4-4 | CGAGGACACGGCCGTATATTACTGTGCG-5-1-2-2-3-4-GAC-TAC-TGGGGCCAAGGAACCCTGGTCACCGTCTCG |

TABLE 8-continued

Primer sequences used for generation of common light chain library (Vk3_20/VH3_23)

| SEQ ID NO: | Primer name | Primer sequence 5'-3' |
|---|---|---|
| 113 | DP47-v4-6 | CGAGGACACGGCCGTATATTACTGTGCG-5-1-2-2-2-3-4-GAC-TAC-TGGGGCCAAGGAACCCTGGTCACCGTCTCG |
| 114 | DP47-v4-8 | CGAGGACACGGCCGTATATTACTGTGCG-5-1-2-2-2-2-2-3-4-GAC-TAC-TGGGGCCAAGGAACCCTGGTCACCGTCTCG |
| 115 | fdseqlong | GACGTTAGTAAATGAATTTTCTGTATGAGG |

1: G/D = 20%, E/V/S = 10%, A/P/R/L/T/Y = 5%; 2: G/Y/S = 15%, A/D/T/R/P/L/V/N/W/F/I/E = 4,6%; 3: G/A/Y = 20%, P/W/S/D/T = 8%; 4: F = 46%, L/M = 15%, G/I/Y = 8%; 5: K = 70%, R = 30%.

Table 9 shows the sequence of generic phage-displayed lambda-DP47 library (Vl3_19/VH3_23) template used for PCRs. Table 10 provides cDNA and amino acid sequences of lambda-DP47 library (Vl3_19/VH3_23) germline template and Table 11 shows the Primer sequences used for generation of lambda-DP47 library (Vl3_19/VH3_23).

TABLE 9

Sequence of generic phage-displayed lambda-DP47 library (Vl3_19/VH3_23) template used for PCRs

| SEQ ID NO: | Description | Sequence |
|---|---|---|
| 116 | pRJH53 library template of lambda-DP47 library Vl3_19/VH3_23; complete Fab coding region comprising PelB leader sequence + Vl3_19 lambda V-domain + CL constant domain for light chain and PelB + VH3_23 V-domain + CH1 constant domain for heavy chain including tags | ATGAAATACCTATTGCCTACGGCAGCCGCTGGATTGTTATTACTC GCGGCCCAGCCGGCCATGGCCTCGTCTGAGCTGACTCAGGACCC TGCTGTGTCTGTGGCCTTGGGACAGACAGTCAGGATCACATGCC AAGGAGACAGCCTCAGAAGTTATTATGCAAGCTGGTACCAGCAG AAGCCAGGACAGGCCCCTGTACTTGTCATCTATGGTAAAAACAA CCGGCCCTCAGGGATCCCAGACCGATTCTCTGGCTCCAGCTCAG GAAACACAGCTTCCTTGACCATCACTGGGGCTCAGGCGGAAGAT GAGGCTGACTATTACTGTAACTCCCGTGATAGTAGCGGTAATCA TGTGGTATTCGGCGGAGGGACCAAGCTGACCGTCCTAGGACAAC CCAAGGCTGCCCCCAGCGTGACCCTGTTCCCCCCCAGCAGCGAG GAATTGCAGGCCAACAAGGCCACCCTGGTCTGCCTGATCAGCGA CTTCTACCCAGGCGCCGTGACCGTGGCCTGGAAGGCCGACAGCA GCCCCGTGAAGGCCGGCGTGGAGACCACCACCCCCAGCAAGCA GAGCAACAACAAGTACGCCGCCAGCAGCTACCTGAGCCTGACC CCCGAGCAGTGGAAGAGCCACAGGTCCTACAGCTGCCAGGTGA CCCACGAGGGCAGCACCGTGGAGAAAACCGTGGCCCCCACCGA GTGCAGCGGAGCCGCAGAACAAAAACTCATCTCAGAAGAGGAT CTGAATGGAGCCGCAGACTACAAGGACGACGACGACAAGGGTG CCGCATAATAAGGCGCGCCAATTCTATTTCAAGGAGACAGTCAT ATGAAATACCTGCTGCCGACCGCTGCTGCTGGTCTGCTGCTCCTC GCTGCCCAGCCGGCCGATGGCCGAGGTGCAATTGCTGGAGTCTGG GGGAGGCTTGGTACAGCCTGGGGGGTCCCTGAGACTCTCCTGTG CAGCCTCCGGATTCACCTTTAGCAGTTATGCCATGAGCTGGGTCC GCCAGGCTCCAGGGAAGGGGCTGGAGTGGGTCTCAGCTATTAGT GGTAGTGGTGGTAGCACATACTACGCAGACTCCGTGAAGGGCCG GTTCACCATCTCCAGAGACAATTCCAAGAACACGCTGTATCTGC AGATGAACAGCCTGAGAGCCGAGGACACGGCCGTATATTACTGT GCGAAACCGTTTCCGTATTTTGACTACTGGGGCCAAGGAACCCT GGTCACCGTCTCGAGTGCTAGCACCAAAGGCCCATCGGTCTTCC CCCTGGCACCCTCCTCCAAGAGCACCTCTGGGGGCACAGCGGCC CTGGGCTGCCTGGTCAAGGACTACTTCCCCGAACCGGTGACGGT GTCGTGGAACTCAGGCGCCCTGACCAGCGGCGTGCACACCTTCC CGGCTGTCCTACAGTCCTCAGGACTCTACTCCCTCAGCAGCGTG GTGACCGTGCCCTCCAGCAGCTTGGGCACCCAGACCTACATCTG CAACGTGAATCACAAGCCCAGCAACACCAAAGTGGACAAGAAA GTTGAGCCCAAATCTTGTGACGCGGCCGCAAGCACTAGTGCCCA TCACCATCACCATCACGCCGCGGCA |

TABLE 10 cDNA and amino acid sequences of lambda-DP47 library (Vl3_19/VH3_23) germline template

| SEQ ID NO: | Description | Sequence |
|---|---|---|
| 117 | nucleotide sequence of Fab light chain Vl3_19 | TCGTCTGAGCTGACTCAGGACCCTGCTGTGTCTGTGGCCT<br>TGGGACAGACAGTCAGGATCACATGCCAAGGAGACAGCC<br>TCAGAAGTTATTATGCAAGCTGGTACCAGCAGAAGCCAG<br>GACAGGCCCCTGTACTTGTCATCTATGGTAAAAACAACCG<br>GCCCTCAGGGATCCCAGACCGATTCTCTGGCTCCAGCTCA<br>GGAAACACAGCTTCCTTGACCATCACTGGGGCTCAGGCG<br>GAAGATGAGGCTGACTATTACTGTAACTCCCGTGATAGTA<br>GCGGTAATCATGTGGTATTCGGCGGAGGGACCAAGCTGA<br>CCGTCCTAGGACAACCCAAGGCTGCCCCCAGCGTGACCCT<br>GTTCCCCCCCAGCAGCGAGGAATTGCAGGCCAACAAGGC<br>CACCCTGGTCTGCCTGATCAGCGACTTCTACCCAGGCGCC<br>GTGACCGTGGCCTGGAAGGCCGACAGCAGCCCCGTGAAG<br>GCCGGCGTGGAGACCACCACCCCCAGCAAGCAGAGCAAC<br>AACAAGTACGCCGCCAGCAGCTACCTGAGCCTGACCCCC<br>GAGCAGTGGAAGAGCCACAGGTCCTACAGCTGCCAGGTG<br>ACCCACGAGGGCAGCACCGTGGAGAAAACCGTGGCCCCC<br>ACCGAGTGCAGCGGAGCCGCAGAACAAAAACTCATCTCA<br>GAAGAGGATCTGAATGGAGCCGCAGACTACAAGGACGAC<br>GACGACAAGGGTGCCGCA |
| 118 | Fab light chain Vl3_19 | SSELTQDPAVSVALGQTVRITCQGDSLRSYYASWYQQKPGQ<br>APVLVIYGKNNRPSGIPDRFSGSSSGNTASLTITGAQAEDEAD<br>YYCNSRDSSGNHVVFGGGTKLTVLGQPKAAPSVTLFPPSSEE<br>LQANKATLVCLISDFYPGAVTVAWKADSSPVKAGVETTTPS<br>KQSNNKYAASSYLSLTPEQWKSHRSYSCQVTHEGSTVEKTV<br>APTECSGAAEQKLISEEDLNGAADYKDDDDKGAA |
| 108 | nucleotide sequence of Fab heavy chain VH3_23 | see Table 7 |
| 109 | Fab heavy chain VH3_23 (DP47) | see Table 7 |

TABLE 11

Primer sequences used for generation of lambda-DP47 library (Vl3_19/VH3_23)

| SEQ ID NO: | Primer name | Primer sequence 5'-3' |
|---|---|---|
| 119 | LMB3 | CAGGAAACAGCTATGACCATGATTAC |
| 120 | Vl_3_19_L3r_V | GGACGGTCAGCTTGGTCCCTCCGCCGAATAC <u>VHV</u> <u>ATT</u><br><u>ACC</u> <u>GCT</u> <u>ACT</u> <u>ATC</u> <u>ACG</u><br>GGAGTTACAGTAATAGTCAGCCTCATCTTCCGC<br>underlined: 60% original base and 40% randomization as M<br>bold and italic: 60% original base and 40% randomization as N |
| 121 | Vl_3_19_L3r_HV | GGACGGTCAGCTTGGTCCCTCCGCCGAATAC <u>CMM</u><br><u>ATG</u> <u>ATT</u> <u>ACC</u> <u>GCT</u> <u>ACT</u> <u>ATC</u> <u>ACG</u><br>GGAGTTACAGTAATAGTCAGCCTCATCTTCCGC<br>underlined: 60% original base and 40% randomization as M<br>bolded and italic: 60% original base and 40% randomization as N |
| 122 | Vl_3_19_L3r_HLV | GGACGGTCAGCTTGGTCCCTCCGCCGAATAC <u>RHM</u><br><u>VWG</u> <u>ATG</u> <u>ATT</u> <u>ACC</u> <u>GCT</u> <u>ACT</u> <u>ATC</u> <u>ACG</u><br>GGAGTTACAGTAATAGTCAGCCTCATCTTC CGC<br>underlined: 60% original base and 40% randomization as M<br>bolded and italic: 60% original base and 40% randomization as N |
| 123 | RJH80 | TTCGGCGGAGGGACCAAGCTGACCGTCC |
| 124 | MS63 | TTTCGCACAGTAATATACGGCCGTGTCC |

Additional primers used for construction of the lambda-DP47 library, i.e. DP47CDR3_ba (mod.), DP47-v4-4, DP47-v4-6, DP47-v4-8 and fdseqlong, are identical to the primers used for the construction of the common light chain library (Vk3_20/VH3_23) and have already been listed in Table 8.

Clones 8H9, 20B7, 49B4, 1G4, CLC-563, CLC-564 and 17A9 were identified as human OX40-specific binders through the procedure described above. The cDNA sequences of their variable regions are shown in Table 12 below, the corresponding amino acid sequences can be found in Table C.

TABLE 12

Variable region base pair sequences for phage-derived anti-OX40 antibodies. Underlined are the complementarity determining regions (CDRs).

| Clone | SEQ ID NO: | | Sequence |
|---|---|---|---|
| 8H9 | 125 | (VL) | TCGTCTGAGCTGACTCAGGACCCTGCTGTGTCTGTGGCCTTGGGACA GACAGTCAGGATCACATGCCAAGGAGACAGCCTCAGAAGTTATTAT GCAAGCTGGTACCAGCAGAAGCCAGGACAGGCCCCTGTACTTGTCA TCTATGGTAAAAACAACCGGCCCTCAGGGATCCCAGACCGATTCTC TGGCTCCAGCTCAGGAAACACAGCTTCCTTGACCATCACTGGGGCT CAGGCGGAAGATGAGGCTGACTATTACTGTAACTCCCGTGTTATGC CTCATAATCGCGTATTCGGCGGAGGGACCAAGCTGACCGTC |
| | 126 | (VH) | GAGGTGCAATTGTTGGAGTCTGGGGGAGGCTTGGTACAGCCTGGGG GGTCCCTGAGACTCTCCTGTGCAGCCTCCGGATTCACCTTTAGCAGT TATGCCATGAGCTGGGTCCGCCAGGCTCCAGGGAAGGGGCTGGAGT GGGTCTCAGCTATTAGTGGTAGTGGTGGTAGCACATACTACGCAGA CTCCGTGAAGGGCCGGTTCACCATCTCCAGAGACAATTCCAAGAAC ACGCTGTATCTGCAGATGAACAGCCTGAGAGCCGAGGACACGGCCG TATATTACTGTGCGCGTGTTTTCTACCGTGGTGGTGTTTCTATGGAC TACTGGGGCCAAGGAACCCTGGTCACCGTCTCGAGT |
| 49B4 | 127 | (VL) | GACATCCAGATGACCCAGTCTCCTTCCACCCTGTCTGCATCTGTAGG AGACCGTGTCACCATCACTTGCCGTGCCAGTCAGAGTATTAGTAGC TGGTTGGCCTGGTATCAGCAGAAACCAGGGAAAGCCCCTAAGCTCC TGATCTATGATGCCTCCAGTTTGGAAAGTGGGGTCCCATCACGTTTC AGCGGCAGTGGATCCGGGACAGAATTCACTCTCACCATCAGCAGCT TGCAGCCTGATGATTTTGCAACTTATTACTGCCAACAGTATAGTTCG CAGCCGTATACGTTTGGCCAGGGCACCAAAGTCGAGATCAAG |
| | 128 | (VH) | CAGGTGCAATTGGTGCAGTCTGGGGCTGAGGTGAAGAAGCCTGGGT CCTCGGTGAAGGTCTCCTGCAAGGCCTCCGGAGGCACATTCAGCAG CTACGCTATAAGCTGGGTGCGACAGGCCCCTGGACAAGGGCTCGAG TGGATGGGAGGGATCATCCCTATCTTTGGTACAGCAAACTACGCAC AGAAGTTCCAGGGCAGGGTCACCATTACTGCAGACAAATCCACGAG CACAGCCTACATGGAGCTGAGCAGCCTGAGATCTGAGGACACCGCC GTGTATTACTGTGCGAGAGAATACTACCGTGGTCCGTACGACTACT GGGGCCAAGGGACCACCGTGACCGTCTCCTCA |
| 1G4 | 129 | (VL) | GACATCCAGATGACCCAGTCTCCTTCCACCCTGTCTGCATCTGTAGG AGACCGTGTCACCATCACTTGCCGTGCCAGTCAGAGTATTAGTAGC TGGTTGGCCTGGTATCAGCAGAAACCAGGGAAAGCCCCTAAGCTCC TGATCTATGATGCCTCCAGTTTGGAAAGTGGGGTCCCATCACGTTTC AGCGGCAGTGGATCCGGGACAGAATTCACTCTCACCATCAGCAGCT TGCAGCCTGATGATTTTGCAACTTATTACTGCCAACAGTATATTTCG TATTCCATGTTGACGTTTGGCCAGGGCACCAAAGTCGAGATCAAG |
| | 130 | (VH) | CAGGTGCAATTGGTGCAGTCTGGGGCTGAGGTGAAGAAGCCTGGGT CCTCGGTGAAGGTCTCCTGCAAGGCCTCCGGAGGCACATTCAGCAG CTACGCTATAAGCTGGGTGCGACAGGCCCCTGGACAAGGGCTCGAG TGGATGGGAGGGATCATCCCTATCTTTGGTACAGCAAACTACGCAC AGAAGTTCCAGGGCAGGGTCACCATTACTGCAGACAAATCCACGAG CACAGCCTACATGGAGCTGAGCAGCCTGAGATCTGAGGACACCGCC GTGTATTACTGTGCGAGAGAATACGGTTCTATGGACTACTGGGGCC AAGGGACCACCGTGACCGTCTCCTCA |
| 20B7 | 131 | (VL) | GACATCCAGATGACCCAGTCTCCTTCCACCCTGTCTGCATCTGTAGG AGACCGTGTCACCATCACTTGCCGTGCCAGTCAGAGTATTAGTAGC TGGTTGGCCTGGTATCAGCAGAAACCAGGGAAAGCCCCTAAGCTCC TGATCTATGATGCCTCCAGTTTGGAAAGTGGGGTCCCATCACGTTTC AGCGGCAGTGGATCCGGGACAGAATTCACTCTCACCATCAGCAGCT TGCAGCCTGATGATTTTGCAACTTATTACTGCCAACAGTATCAGGCT TTTTCGCTTACGTTTGGCCAGGGCACCAAAGTCGAGATCAAG |
| | 132 | (VH) | CAGGTGCAATTGGTGCAGTCTGGGGCTGAGGTGAAGAAGCCTGGGT CCTCGGTGAAGGTCTCCTGCAAGGCCTCCGGAGGCACATTCAGCAG CTACGCTATAAGCTGGGTGCGACAGGCCCCTGGACAAGGGCTCGAG TGGATGGGAGGGATCATCCCTATCTTTGGTACAGCAAACTACGCAC AGAAGTTCCAGGGCAGGGTCACCATTACTGCAGACAAATCCACGAG CACAGCCTACATGGAGCTGAGCAGCCTGAGATCTGAGGACACCGCC GTGTATTACTGTGCGAGAGTTAACTACCCGTACTCTTACTGGGGTGA CTTCGACTACTGGGGCCAAGGGACCACCGTGACCGTCTCCTCA |
| CLC-563 | 133 | (VL) | GAGATCGTGCTGACCCAGAGCCCCGGCACACTCTCCCTGTCTCCTG GGGAAAGGGCCACCCTTTCATGCAGAGCCAGCCAGTCCGTCTCTAG |

TABLE 12-continued

Variable region base pair sequences for phage-derived anti-OX40 antibodies.
Underlined are the complementarity determining regions (CDRs).

| Clone | SEQ ID NO: | Sequence |
|---|---|---|
|  |  | <u>TAGCTACCTGGCA</u>TGGTATCAGCAGAAGCCAGGACAAGCCCCCGC<br>CTCCTGATTTAC<u>GGCGCTTCCTCTCGGGCAACT</u>GGTATCCCTGACAG<br>GTTCTCAGGGAGCGGAAGCGGAACAGATTTTACCTTGACTATTTCT<br>AGACTGGAGCCAGAGGACTTCGCCGTGTATTACTGT<u>CAGCAGTACG</u><br><u>GTAGTAGCCCCCTCACC</u>TTTGGCCAGGGGACAAAAGTCGAAATCAA<br>G |
|  | 134 (VH) | GAGGTGCAATTGTTGGAGTCTGGGGGAGGCTTGGTACAGCCTGGGG<br>GGTCCCTGAGACTCTCCTGTGCAGCCTCCGGATTCACCTTTAGC<u>AGT</u><br><u>TATGCCATGAGC</u>TGGGTCCGCCAGGCTCCAGGGAAGGGGCTGGAGT<br>GGGTCTC<u>AGCTATTAGTGGTAGTGGTGGTAGCACATACTACGCAGA</u><br><u>CTCCGTGAAGGGC</u>CGGTTCACCATCTCCAGAGACAATTCCAAGAAC<br>ACGCTGTATCTGCAGATGAACAGCCTGAGAGCCGAGGACACGGCCG<br>TATATTACTGTGCGCTT<u>GACGTTGGTGCTTTCGACTAC</u>TGGGGCCAA<br>GGAGCCCTGGTCACCGTCTCGAGT |
| CLC-564 | 135 (VL) | GAGATCGTGCTGACCCAGAGCCCCGGCACACTCTCCCTGTCTCCTG<br>GGGAAAGGGCCACCCTTTCATGC<u>AGAGCCAGCCAGTCCGTCTCTAG</u><br><u>TAGCTACCTGGCA</u>TGGTATCAGCAGAAGCCAGGACAAGCCCCCGC<br>CTCCTGATTTAC<u>GGCGCTTCCTCTCGGGCAACT</u>GGTATCCCTGACAG<br>GTTCTCAGGGAGCGGAAGCGGAACAGATTTTACCTTGACTATTTCT<br>AGACTGGAGCCAGAGGACTTCGCCGTGTATTACTGT<u>CAGCAGTACG</u><br><u>GTAGTAGCCCCCTCACC</u>TTTGGCCAGGGGACAAAAGTCGAAATCAA<br>G |
|  | 136 (VH) | GAGGTGCAATTGTTGGAGTCTGGGGGAGGCTTGGTACAGCCTGGGG<br>GGTCCCTGAGACTCTCCTGTGCAGCCTCCGGATTCACCTTTAGC<u>AGT</u><br><u>TATGCCATGAGC</u>TGGGTCCGCCAGGCTCCAGGGAAGGGGCTGGAGT<br>GGGTCTC<u>AGCTATTAGTGGTAGTGGTGGTAGCACATACTACGCAGA</u><br><u>CTCCGTGAAGGGC</u>CGGTTCACCATCTCCAGAGACAATTCCAAGAAC<br>ACGCTGTATCTGCAGATGAACAGCCTGAGAGCCGAGGACACGGCCG<br>TATATTACTGTGCGTT<u>GACGTTGGTCCGTTCGACTAC</u>TGGGGCCAA<br>GGAACCCTGGTCACCGTCTCGAGT |
| 17A9 | 137 (VL) | TCGTCTGAGCTGACTCAGGACCCTGCTGTGTCTGTGGCCTTGGGACA<br>GACAGTCAGGATCACATGC<u>CAAGGAGACAGCCTCAGAAGTTATTAT</u><br><u>GCAAG</u>CTGGTACCAGCAGAAGCCAGGACAGGCCCCTGTACTTGTCA<br>TCTAT<u>GGTAAAAACAACCGGCCCT</u>CAGGGATCCCAGACCGATTCTC<br>TGGCTCCAGCTCAGGAAACACAGCTTCCTTGACCATCACTGGGGCT<br>CAGGCGGAAGATGAGGCTGACTATTACTGT<u>AACTCCCGTGTTATGC</u><br><u>CTCATAATCGCGT</u>ATTCGGCGGAGGGACCAAGCTGACCGTC |
|  | 138 (VH) | GAGGTGCAATTGTTGGAGTCTGGGGGAGGCTTGGTACAGCCTGGGG<br>GGTCCCTGAGACTCTCCTGTGCAGCCTCCGGATTCACCTTTAGC<u>AGT</u><br><u>TATGCCATGAGC</u>TGGGTCCGCCAGGCTCCAGGGAAGGGGCTGGAGT<br>GGGTCTC<u>AGCTATTAGTGGTAGTGGTGGTAGCACATACTACGCAGA</u><br><u>CTCCGTGAAGGGC</u>CGGTTCACCATCTCCAGAGACAATTCCAAGAAC<br>ACGCTGTATCTGCAGATGAACAGCCTGAGAGCCGAGGACACGGCCG<br>TATATTACTGTGCGCGTGTTTTCTACCGTGGTGGTGTTTCTATGGAC<br><u>TAC</u>TGGGGCCAAGGAACCCTGGTCACCGTCTCGAGT |

1.3 Preparation, Purification and Characterization of Anti-OX40 IgG1 P329G LALA Antibodies The variable regions of heavy and light chain DNA sequences of selected anti-OX40 binders were subcloned in frame with either the constant heavy chain or the constant light chain of human IgG1. The Pro329Gly, Leu234Ala and Leu235Ala mutations have been introduced in the constant region of the knob and hole heavy chains to abrogate binding to Fc gamma receptors according to the method described in International Patent Appl. Publ. No. WO 2012/130831 A1.

The cDNA and amino acid sequences of the anti-OX40 clones are shown in Table 13. All anti-Ox40-Fc-fusion encoding sequences were cloned into a plasmid vector, which drives expression of the insert from an MPSV promoter and contains a synthetic polyA signal sequence located at the 3' end of the CDS. In addition, the vector contains an EBV OriP sequence for episomal maintenance of the plasmid.

TABLE 13

Sequences of anti-OX40 clones in P329GLALA human IgG1 format

| Clone | SEQ ID No. | Sequence |
|---|---|---|
| 8B9 | 139 (nucleotide sequence light chain) | GACATCCAGATGACCCAGTCTCCTTCCACCCTGTCTGCATCTGT<br>AGGAGACCGTGTCACCATCACTTGCCGTGCCAGTCAGAGTATT<br>AGTAGCTGGTTGGCCTGGTATCAGCAGAAACCAGGGAAAGCC<br>CCTAAGCTCCTGATCTATGATGCCTCCAGTTTGGAAAGTGGGG<br>TCCCATCACGTTTCAGCGGCAGTGGATCCGGGACAGAATTCAC |

TABLE 13-continued

Sequences of anti-OX40 clones in P329GLALA human IgG1 format

| Clone | SEQ ID No. | Sequence |
|---|---|---|
|  | 140 (nucleotide sequence heavy chain) | TCTCACCATCAGCAGCTTGCAGCCTGATGATTTTGCAACTTATT ACTGCCAACAGTATTTGACGTATTCGCGGTTTACGTTTGGCCAG GGCACCAAAGTCGAGATCAAGCGTACGGTGGCTGCACCATCTG TCTTCATCTTCCCGCCATCTGATGAGCAGTTGAAATCTGGAACT GCCTCTGTTGTGTGCCTGCTGAATAACTTCTATCCCAGAGAGGC CAAAGTACAGTGGAAGGTGGATAACGCCCTCCAATCGGGTAA CTCCCAGGAGAGTGTCACAGAGCAGGACAGCAAGGACAGCAC CTACAGCCTCAGCAGCACCCTGACGCTGAGCAAAGCAGACTAC GAGAAACACAAAGTCTACGCCTGCGAAGTCACCCATCAGGGC CTGAGCTCGCCCGTCACAAAGAGCTTCAACAGGGGAGAGTGT CAGGTGCAATTGGTGCAGTCTGGGGCTGAGGTGAAGAAGCCTG GGGTCCTCGGTGAAGGTCTCCTGCAAGGCCTCCGGAGGCACATT CAGCAGCTACGCTATAAGCTGGGTGCGACAGGCCCCTGGACAA GGGCTCGAGTGGATGGGAGGGATCATCCCTATCTTTGGTACAG CAAACTACGCACAGAAGTTCCAGGGCAGGGTCACCATTACTGC AGACAAATCCACGAGCACAGCCTACATGGAGCTGAGCAGCCT GAGATCTGAGGACACCGCCGTGTATTACTGTGCGAGAGAATAC GGTTGGATGGACTACTGGGGCCAAGGGACCACCGTGACCGTCT CCTCAGCTAGCACCAAGGGCCCATCGGTCTTCCCCCTGGCACC CTCCTCCAAGAGCACCTCTGGGGGCACAGCGGCCCTGGGCTGC CTGGTCAAGGACTACTTCCCCGAACCGGTGACGGTGTCGTGGA ACTCAGGCGCCCTGACCAGCGGCGTGCACACCTTCCCGGCTGT CCTACAGTCCTCAGGACTCTACTCCCTCAGCAGCGTGGTGACC GTGCCCTCCAGCAGCTTGGGCACCCAGACCTACATCTGCAACG TGAATCACAAGCCCAGCAACACCAAGGTGGACAAGAAAGTTG AGCCCAAATCTTGTGACAAAACTCACACATGCCCACCGTGCCC AGCACCTGAAGCTGCAGGGGGACCGTCAGTCTTCCTCTTCCCC CCAAAACCCAAGGACACCCTCATGATCTCCCGGACCCCTGAGG TCACATGCGTGGTGGTGGACGTGAGCCACGAAGACCCTGAGGT CAAGTTCAACTGGTACGTGGACGGCGTGGAGGTGCATAATGCC AAGACAAAGCCGCGGGAGGAGCAGTACAACAGCACGTACCGT GTGGTCAGCGTCCTCACCGTCCTGCACCAGGACTGGCTGAATG GCAAGGAGTACAAGTGCAAGGTCTCCAACAAAGCCCTCGGCG CCCCCATCGAGAAAACCATCTCCAAAGCCAAAGGGCAGCCCC GAGAACCACAGGTGTACACCCTGCCCCCATCCCGGGATGAGCT GACCAAGAACCAGGTCAGCCTGACCTGCCTGGTCAAAGGCTTC TATCCCAGCGACATCGCCGTGGAGTGGGAGAGCAATGGGCAG CCGGAGAACAACTACAAGACCACGCCTCCCGTGCTGGACTCCG ACGGCTCCTTCTTCCTCTACAGCAAGCTCACCGTGGACAAGAG CAGGTGGCAGCAGGGGAACGTCTTCTCATGCTCCGTGATGCAT GAGGCTCTGCACAACCACTACACGCAGAAGAGCCTCTCCCTGT CTCCGGGTAAA |
|  | 141 (Light chain) | DIQMTQSPSTLSASVGDRVTITCRASQSISSWLAWYQQKPGKAPK LLIYDASSLESGVPSRFSGSGSGTEFTLTISSLQPDDFATYYCQQYL TYSRFTFGQGTKVEIKRTVAAPSVFIFPPSDEQLKSGTASVVCLLN NFYPREAKVQWKVDNALQSGNSQESVTEQDSKDSTYSLSSTLTLS KADYEKHKVYACEVTHQGLSSPVTKSFNRGEC |
|  | 142 (Heavy chain) | QVQLVQSGAEVKKPGSSVKVSCKASGGTFSSYAISWVRQAPGQG LEWMGGIIPIFGTANYAQKFQGRVTITADKSTSTAYMELSSLRSED TAVYYCAREYGWMDYWGQGTTVTVSSASTKGPSVFPLAPSSKST SGGTAALGCLVKDYFPEPVTVSWNSGALTSGVHTFPAVLQSSGL YSLSSVVTVPSSSLGTQTYICNVNHKPSNTKVDKKVEPKSCDKTH TCPPCPAPEAAGGPSVFLFPPKPKDTLMISRTPEVTCVVVDVSHED PEVKFNWYVDGVEVHNAKTKPREEQYNSTYRVVSVLTVLHQDW LNGKEYKCKVSNKALGAPIEKTISKAKGQPREPQVYTLPPSRDEL TKNQVSLTCLVKGFYPSDIAVEWESNGQPENNYKTTPPVLDSDGS FFLYSKLTVDKSRWQQGNVFSCSVMHEALHNHYTQKSLSLSPGK |
| 49B4 | 143 (nucleotide sequence light chain) | GACATCCAGATGACCCAGTCTCCTTCCACCCTGTCTGCATCTGT AGGAGACCGTGTCACCATCACTTGCCGTGCCAGTCAGAGTATT AGTAGCTGGTTGGCCTGGTATCAGCAGAAACCAGGGAAAGCC CCTAAGCTCCTGATCTATGATGCCTCCAGTTTGGAAAGTGGGG TCCCATCACGTTTCAGCGGCAGTGGATCCGGGACAGAATTCAC TCTCACCATCAGCAGCTTGCAGCCTGATGATTTTGCAACTTATT ACTGCCAACAGTATAGTTCGCAGCCTATACGTTTGGCCAGGG CACCAAAGTCGAGATCAAGCGTACGGTGGCTGCACCATCTGTC TTCATCTTCCCGCCATCTGATGAGCAGTTGAAATCTGGAACTGC CTCTGTTGTGTGCCTGCTGAATAACTTCTATCCCAGAGAGGCCA AAGTACAGTGGAAGGTGGATAACGCCCTCCAATCGGGTAACTC CCAGGAGAGTGTCACAGAGCAGGACAGCAAGGACAGCACCTA CAGCCTCAGCAGCACCCTGACGCTGAGCAAAGCAGACTACGA GAAACACAAAGTCTACGCCTGCGAAGTCACCCATCAGGGCCTG AGCTCGCCCGTCACAAAGAGCTTCAACAGGGGAGAGTGT |

TABLE 13-continued

Sequences of anti-OX40 clones in P329GLALA human IgG1 format

| Clone | SEQ ID No. | Sequence |
|---|---|---|
| | 144<br>(nucleotide<br>sequence heavy<br>chain) | CAGGTGCAATTGGTGCAGTCTGGGGCTGAGGTGAAGAAGCCTG<br>GGTCCTCGGTGAAGGTCTCCTGCAAGGCCTCCGGAGGCACATT<br>CAGCAGCTACGCTATAAGCTGGGTGCGACAGGCCCCTGGACAA<br>GGGCTCGAGTGGATGGGAGGGATCATCCCTATCTTTGGTACAG<br>CAAACTACGCACAGAAGTTCCAGGGCAGGGTCACCATTACTGC<br>AGACAAATCCACGAGCACAGCCTACATGGAGCTGAGCAGCCT<br>GAGATCTGAGGACACCGCCGTGTATTACTGTGCGAGAGAATAC<br>TACCGTGGTCCGTACGACTACTGGGGCCAAGGGACCACCGTGA<br>CCGTCTCCTCAGCTAGCACCAAGGGCCCATCGGTCTTCCCCCTG<br>GCACCCTCCTCCAAGAGCACCTCTGGGGGCACAGCGGCCCTGG<br>GCTGCCTGGTCAAGGACTACTTCCCCGAACCGGTGACGGTGTC<br>GTGGAACTCAGGCGCCCTGACCAGCGGCGTGCACACCTTCCCG<br>GCTGTCCTACAGTCCTCAGGACTCTACTCCCTCAGCAGCGTGGT<br>GACCGTGCCCTCCAGCAGCTTGGGCACCCAGACCTACATCTGC<br>AACGTGAATCACAAGCCCAGCAACACCAAGGTGGACAAGAAA<br>GTTGAGCCCAAATCTTGTGACAAAACTCACACATGCCCACCGT<br>GCCCAGCACCTGAAGCTGCAGGGGGACCGTCAGTCTTCCTCTT<br>CCCCCCAAAACCCAAGGACACCCTCATGATCTCCCGGACCCCT<br>GAGGTCACATGCGTGGTGGTGGACGTGAGCCACGAAGACCCT<br>GAGGTCAAGTTCAACTGGTACGTGGACGGCGTGGAGGTGCATA<br>ATGCCAAGACAAAGCCGCGGGAGGAGCAGTACAACAGCACGT<br>ACCGTGTGGTCAGCGTCCTCACCGTCCTGCACCAGGACTGGCT<br>GAATGGCAAGGAGTACAAGTGCAAGGTCTCCAACAAAGCCCT<br>CGGCGCCCCCATCGAGAAAACCATCTCCAAAGCCAAAGGGCA<br>GCCCCGAGAACCACAGGTGTACACCCTGCCCCCATCCCGGGAT<br>GAGCTGACCAAGAACCAGGTCAGCCTGACCTGCCTGGTCAAAG<br>GCTTCTATCCCAGCGACATCGCCGTGGAGTGGGAGAGCAATGG<br>GCAGCCGGAGAACAACTACAAGACCACGCCTCCCGTGCTGGA<br>CTCCGACGGCTCCTTCTTCCTCTACAGCAAGCTCACCGTGGACA<br>AGAGCAGGTGGCAGCAGGGGAACGTCTTCTCATGCTCCGTGAT<br>GCATGAGGCTCTGCACAACCACTACACGCAGAAGAGCCTCTCC<br>CTGTCTCCGGGTAAA |
| | 145<br>(Light chain) | DIQMTQSPSTLSASVGDRVTITCRASQSISSWLAWYQQKPGKAPK<br>LLIYDASSLESGVPSRFSGSGSGTEFTLTISSLQPDDFATYYCQQYS<br>SQPYTFGQGTKVEIKRTVAAPSVFIFPPSDEQLKSGTASVVCLLNN<br>FYPREAKVQWKVDNALQSGNSQESVTEQDSKDSTYSLSSTLTLSK<br>ADYEKHKVYACEVTHQGLSSPVTKSFNRGEC |
| | 146<br>(Heavy chain) | QVQLVQSGAEVKKPGSSVKVSCKASGGTFSSYAISWVRQAPGQG<br>LEWMGGIIPIFGTANYAQKFQGRVTITADKSTSTAYMELSSLRSED<br>TAVYYCAREYYRGPYDYWGQGTTVTVSSASTKGPSVFPLAPSSK<br>STSGGTAALGCLVKDYFPEPVTVSWNSGALTSGVHTFPAVLQSSG<br>LYSLSSVVTVPSSSLGTQTYICNVNHKPSNTKVDKKVEPKSCDKT<br>HTCPPCPAPEAAGGPSVFLFPPKPKDTLMISRTPEVTCVVVDVSHE<br>DPEVKFNWYVDGVEVHNAKTKPREEQYNSTYRVVSVLTVLHQD<br>WLNGKEYKCKVSNKALGAPIEKTISKAKGQPREPQVYTLPPSRDE<br>LTKNQVSLTCLVKGFYPSDIAVEWESNGQPENNYKTTPPVLDSDG<br>SFFLYSKLTVDKSRWQQGNVFSCSVMHEALHNHYTQKSLSLSPG<br>K |
| 1G4 | 147<br>(nucleotide<br>sequence light<br>chain) | GACATCCAGATGACCCAGTCTCCTTCCACCCTGTCTGCATCTGT<br>AGGAGACCGTGTCACCATCACTTGCCGTGCCAGTCAGAGTATT<br>AGTAGCTGGTTGGCCTGGTATCAGCAGAAACCAGGGAAAGCC<br>CCTAAGCTCCTGATCTATGATGCCTCCAGTTTGGAAAGTGGGG<br>TCCCATCACGTTTCAGCGGCAGTGGATCCGGGACAGAATTCAC<br>TCTCACCATCAGCAGCTTGCAGCCTGATGATTTTGCAACTTATT<br>ACTGCCAACAGTATATTTCGTATTCCATGTTGACGTTTGGCCAG<br>GGCACCAAAGTCGAGATCAAGCGTACGGTGGCTGCACCATCTG<br>TCTTCATCTTCCCGCCATCTGATGAGCAGTTGAAATCTGGAACT<br>GCCTCTGTTGTGTGCCTGCTGAATAACTTCTATCCCAGAGAGGC<br>CAAAGTACAGTGGAAGGTGGATAACGCCCTCCAATCGGGTAA<br>CTCCCAGGAGAGTGTCACAGAGCAGGACAGCAAGGACAGCAC<br>CTACAGCCTCAGCAGCACCCTGACGCTGAGCAAAGCAGACTAC<br>GAGAAACACAAAGTCTACGCCTGCGAAGTCACCCATCAGGGC<br>CTGAGCTCGCCCGTCACAAAGAGCTTCAACAGGGGAGAGTGT |
| | 148<br>(nucleotide<br>sequence heavy<br>chain) | CAGGTGCAATTGGTGCAGTCTGGGGCTGAGGTGAAGAAGCCTG<br>GGTCCTCGGTGAAGGTCTCCTGCAAGGCCTCCGGAGGCACATT<br>CAGCAGCTACGCTATAAGCTGGGTGCGACAGGCCCCTGGACAA<br>GGGCTCGAGTGGATGGGAGGGATCATCCCTATCTTTGGTACAG<br>CAAACTACGCACAGAAGTTCCAGGGCAGGGTCACCATTACTGC<br>AGACAAATCCACGAGCACAGCCTACATGGAGCTGAGCAGCCT<br>GAGATCTGAGGACACCGCCGTGTATTACTGTGCGAGAGAATAC<br>GGTTCTATGGACTACTGGGGCCAAGGGACCACCGTGACCGTCT<br>CCTCAGCTAGCACCAAGGGCCCATCGGTCTTCCCCCTGGCACC<br>CTCCTCCAAGAGCACCTCTGGGGGCACAGCGGCCCTGGGCTGC<br>CTGGTCAAGGACTACTTCCCCGAACCGGTGACGGTGTCGTGGA<br>ACTCAGGCGCCCTGACCAGCGGCGTGCACACCTTCCCGGCTGT |

TABLE 13-continued

Sequences of anti-OX40 clones in P329GLALA human IgG1 format

| Clone | SEQ ID No. | Sequence |
|---|---|---|
| | | CCTACAGTCCTCAGGACTCTACTCCCTCAGCAGCGTGGTGACC<br>GTGCCCTCCAGCAGCTTGGGCACCCAGACCTACATCTGCAACG<br>TGAATCACAAGCCCAGCAACACCAAGGTGGACAAGAAAGTTG<br>AGCCCAAATCTTGTGACAAAACTCACACATGCCCACCGTGCCC<br>AGCACCTGAAGCTGCAGGGGGACCGTCAGTCTTCCTCTTCCCC<br>CCAAAACCCAAGGACACCCTCATGATCTCCCGGACCCCTGAGG<br>TCACATGCGTGGTGGTGGACGTGAGCCACGAAGACCCTGAGGT<br>CAAGTTCAACTGGTACGTGGACGGCGTGGAGGTGCATAATGCC<br>AAGACAAAGCCGCGGGAGGAGCAGTACAACAGCACGTACCGT<br>GTGGTCAGCGTCCTCACCGTCCTGCACCAGGACTGGCTGAATG<br>GCAAGGAGTACAAGTGCAAGGTCTCCAACAAAGCCCTCGGCG<br>CCCCCATCGAGAAAACCATCTCCAAAGCCAAAGGGCAGCCCC<br>GAGAACCACAGGTGTACACCCTGCCCCCATCCCGGGATGAGCT<br>GACCAAGAACCAGGTCAGCCTGACCTGCCTGGTCAAAGGCTTC<br>TATCCCAGCGACATCGCCGTGGAGTGGGAGAGCAATGGGCAG<br>CCGGAGAACAACTACAAGACCACGCCTCCCGTGCTGGACTCCG<br>ACGGCTCCTTCTTCCTCTACAGCAAGCTCACCGTGGACAAGAG<br>CAGGTGGCAGCAGGGGAACGTCTTCTCATGCTCCGTGATGCAT<br>GAGGCTCTGCACAACCACTACACGCAGAAGAGCCTCTCCCTGT<br>CTCCGGGTAAA |
| | 149<br>(Light chain) | DIQMTQSPSTLSASVGDRVTITCRASQSISSWLAWYQQKPGKAPK<br>LLIYDASSLESGVPSRFSGSGSGTEFTLTISSLQPDDFATYYCQQYIS<br>YSMLTFGQGTKVEIKRTVAAPSVFIFPPSDEQLKSGTASVVCLLNN<br>FYPREAKVQWKVDNALQSGNSQESVTEQDSKDSTYSLSSTLTLSK<br>ADYEKHKVYACEVTHQGLSSPVTKSFNRGEC |
| | 150<br>(Heavy chain) | QVQLVQSGAEVKKPGSSVKVSCKASGGTFSSYAISWVRQAPGQG<br>LEWMGGIIPIFGTANYAQKFQGRVTITADKSTSTAYMELSSLRSED<br>TAVYYCAREYGSMDYWGQGTTVTVSSASTKGPSVFPLAPSSKST<br>SGGTAALGCLVKDYFPEPVTVSWNSGALTSGVHTFPAVLQSSGL<br>YSLSSVVTVPSSSLGTQTYICNVNHKPSNTKVDKKVEPKSCDKTH<br>TCPPCPAPEAAGGPSVFLFPPKPKDTLMISRTPEVTCVVVDVSHED<br>PEVKFNWYVDGVEVHNAKTKPREEQYNSTYRVVSVLTVLHQDW<br>LNGKEYKCKVSNKALGAPIEKTISKAKGQPREPQVYTLPPSRDEL<br>TKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| 20B7 | 151<br>(nucleotide<br>sequence light<br>chain) | GACATCCAGATGACCCAGTCTCCTTCCACCCTGTCTGCATCTGT<br>AGGAGACCGTGTCACCATCACTTGCCGTGCCAGTCAGAGTATT<br>AGTAGCTGGTTGGCCTGGTATCAGCAGAAACCAGGGAAAGCC<br>CCTAAGCTCCTGATCTATGATGCCTCCAGTTTGGAAAGTGGGG<br>TCCCATCACGTTTCAGCGGCAGTGGATCGGGACAGAATTCAC<br>TCTCACCATCAGCAGCTTGCAGCCTGATGATTTTGCAACTTATT<br>ACTGCCAACAGTATCAGGCTTTTTCGCTTACGTTTGGCCAGGGC<br>ACCAAAGTCGAGATCAAGCGTACGGTGGCTGCACCATCTGTCT<br>TCATCTTCCCGCCATCTGATGAGCAGTTGAAATCTGGAACTGC<br>CTCTGTTGTGTGCCTGCTGAATAACTTCTATCCCAGAGAGGCCA<br>AAGTACAGTGGAAGGTGGATAACGCCCTCCAATCGGGTAACTC<br>CCAGGAGAGTGTCACAGAGCAGGACAGCAAGGACAGCACCTA<br>CAGCCTCAGCAGCACCCTGACGCTGAGCAAAGCAGACTACGA<br>GAAACACAAAGTCTACGCCTGCGAAGTCACCCATCAGGGCCTG<br>AGCTCGCCCGTCACAAAGAGCTTCAACAGGGGAGAGTGT |
| | 152<br>(nucleotide<br>sequence heavy<br>chain) | CAGGTGCAATTGGTGCAGTCTGGGGCTGAGGTGAAGAAGCCTG<br>GGTCCTCGGTGAAGGTCTCCTGCAAGGCCTCCGGAGGCACATT<br>CAGCAGCTACGCTATAAGCTGGGTGCGACAGGCCCCTGGACAA<br>GGGCTCGAGTGGATGGGAGGGATCATCCCTATCTTTGGTACAG<br>CAAACTACGCACAGAAGTTCCAGGGCAGGGTCACCATTACTGC<br>AGACAAATCCACGAGCACAGCCTACATGGAGCTGAGCAGCCT<br>GAGATCTGAGGACACCGCCGTGTATTACTGTGCGAGAGTTAAC<br>TACCCGTACTCTTACTGGGGTGACTTCGACTACTGGGGCCAAG<br>GGACCACCGTGACCGTCTCCTCAGCTAGCACCAAGGGCCCATC<br>GGTCTTCCCCCTGGCACCCTCCTCCAAGAGCACCTCTGGGGGC<br>ACAGCGGCCCTGGGCTGCCTGGTCAAGGACTACTTCCCCGAAC<br>CGGTGACGGTGTCGTGGAACTCAGGCGCCCTGACCAGCGGCGT<br>GCACACCTTCCCGGCTGTCCTACAGTCCTCAGGACTCTACTCCC<br>TCAGCAGCGTGGTGACCGTGCCCTCCAGCAGCTTGGGCACCCA<br>GACCTACATCTGCAACGTGAATCACAAGCCCAGCAACACCAAG<br>GTGGACAAGAAAGTTGAGCCCAAATCTTGTGACAAAACTCACA<br>CATGCCCACCGTGCCCAGCACCTGAAGCTGCAGGGGGACCGTC<br>AGTCTTCCTCTTCCCCCCAAAACCCAAGGACACCCTCATGATCT<br>CCCGGACCCCTGAGGTCACATGCGTGGTGGTGGACGTGAGCCA<br>CGAAGACCCTGAGGTCAAGTTCAACTGGTACGTGGACGGCGTG<br>GAGGTGCATAATGCCAAGACAAAGCCGCGGGAGGAGCAGTAC<br>AACAGCACGTACCGTGTGGTCAGCGTCCTCACCGTCCTGCACC<br>AGGACTGGCTGAATGGCAAGGAGTACAAGTGCAAGGTCTCCA<br>ACAAAGCCCTCGGCGCCCCCATCGAGAAAACCATCTCCAAAGC<br>CAAAGGGCAGCCCCGAGAACCACAGGTGTACACCCTGCCCCC |

TABLE 13-continued

Sequences of anti-OX40 clones in P329GLALA human IgG1 format

| Clone | SEQ ID No. | Sequence |
|---|---|---|
| | | ATCCCGGGATGAGCTGACCAAGAACCAGGTCAGCCTGACCTGC<br>CTGGTCAAAGGCTTCTATCCCAGCGACATCGCCGTGGAGTGGG<br>AGAGCAATGGGCAGCCGGAGAACAACTACAAGACCACGCCTC<br>CCGTGCTGGACTCCGACGGCTCCTTCTTCCTCTACAGCAAGCTC<br>ACCGTGGACAAGAGCAGGTGGCAGCAGGGGAACGTCTTCTCA<br>TGCTCCGTGATGCATGAGGCTCTGCACAACCACTACACGCAGA<br>AGAGCCTCTCCCTGTCTCCGGGTAAA |
| | 153<br>(Light chain) | DIQMTQSPSTLSASVGDRVTITCRASQSISSWLAWYQQKPGKAPK<br>LLIYDASSLESGVPSRFSGSGSGTEFTLTISSLQPDDFATYYCQQYQ<br>AFSLTFGQGTKVEIKRTVAAPSVFIFPPSDEQLKSGTASVVCLLNN<br>FYPREAKVQWKVDNALQSGNSQESVTEQDSKDSTYSLSSTLTLSK<br>ADYEKHKVYACEVTHQGLSSPVTKSFNRGEC |
| | 154<br>(Heavy chain) | QVQLVQSGAEVKKPGSSVKVSCKASGGTFSSYAISWVRQAPGQG<br>LEWMGGIIPIFGTANYAQKFQGRVTITADKSTSTAYMELSSLRSED<br>TAVYYCARVNYPYSYWGDFDYWGQGTTVTVSSASTKGPSVFPL<br>APSSKSTSGGTAALGCLVKDYFPEPVTVSWNSGALTSGVHTFPAV<br>LQSSGLYSLSSVVTVPSSSLGTQTYICNVNHKPSNTKVDKKVEPKS<br>CDKTHTCPPCPAPEAAGGPSVFLFPPKPKDTLMISRTPEVTCVVVD<br>VSHEDPEVKFNWYVDGVEVHNAKTKPREEQYNSTYRVVSVLTV<br>LHQDWLNGKEYKCKVSNKALGAPIEKTISKAKGQPREPQVYTLPP<br>SRDELTKNQVSLTCLVKGFYPSDIAVEWESNGQPENNYKTTPPVL<br>DSDGSFFLYSKLTVDKSRWQQGNVFSCSVMHEALHNHYTQKSLS<br>LSPGK |
| CLC-<br>563 | 155<br>(nucleotide<br>sequence light<br>chain) | GAGATCGTGCTGACCCAGAGCCCCGGCACACTCTCCCTGTCTC<br>CTGGGGAAAGGGCCACCCTTTCATGCAGAGCCAGCCAGTCCGT<br>CTCTAGTAGCTACCTGGCATGGTATCAGCAGAAGCCAGGACAA<br>GCCCCCCGCCTCCTGATTTACGGCGCTTCCTCTCGGGCAACTGG<br>TATCCCTGACAGGTTCTCAGGGAGCGGAAGCGGAACAGATTTT<br>ACCTTGACTATTTCTAGACTGGAGCCAGAGGACTTCGCCGTGT<br>ATTACTGTCAGCAGTACGGTAGTAGCCCCCTCACCTTTGGCCA<br>GGGGACAAAAGTCGAAATCAAGCGTACGGTGGCTGCACCATC<br>TGTCTTCATCTTCCCGCCATCTGATGAGCAGTTGAAATCTGGAA<br>CTGCCTCTGTTGTGTGCCTGCTGAATAACTTCTATCCCAGAGAG<br>GCCAAAGTACAGTGGAAGGTGGATAACGCCCTCCAATCGGGT<br>AACTCCCAGGAGAGTGTCACAGAGCAGGACAGCAAGGACAGC<br>ACCTACAGCCTCAGCAGCACCCTGACGCTGAGCAAAGCAGACT<br>ACGAGAAACACAAAGTCTACGCCTGCGAAGTCACCCATCAGG<br>GCCTGAGCTCGCCCGTCACAAAGAGCTTCAACAGGGGAGAGT<br>GT |
| | 156<br>(nucleotide<br>sequence heavy<br>chain) | GAGGTGCAATTGTTGGAGTCTGGGGGAGGCTTGGTACAGCCTG<br>GGGGGTCCCTGAGACTCTCCTGTGCAGCCTCCGGATTCACCTTT<br>AGCAGTTATGCCATGAGCTGGGTCCGCCAGGCTCCAGGGAAGG<br>GGCTGGAGTGGGTCTCAGCTATTAGTGGTAGTGGTGGTAGCAC<br>ATACTACGCAGACTCCGTGAAGGGCCGGTTCACCATCTCCAGA<br>GACAATTCCAAGAACACGCTGTATCTGCAGATGAACAGCCTGA<br>GAGCCGAGGACACGGCCGTATATTACTGTGCGCTTGACGTTGG<br>TGCTTTCGACTACTGGGGCCAAGGAGCCCTGGTCACCGTCTCG<br>AGTGCTAGCACCAAGGGCCCATCGGTCTTCCCCCTGGCACCCT<br>CCTCCAAGAGCACCTCTGGGGGCACAGCGGCCCTGGGCTGCCT<br>GGTCAAGGACTACTTCCCCGAACCGGTGACGGTGTCGTGGAAC<br>TCAGGCGCCCTGACCAGCGGCGTGCACACCTTCCCGGCTGTCC<br>TACAGTCCTCAGGACTCTACTCCCTCAGCAGCGTGGTGACCGT<br>GCCCTCCAGCAGCTTGGGCACCCAGACCTACATCTGCAACGTG<br>AATCACAAGCCCAGCAACACCAAGGTGGACAAGAAAGTTGAG<br>CCCAAATCTTGTGACAAAACTCACACATGCCCACCGTGCCCAG<br>CACCTGAAGCTGCAGGGGACCGTCAGTCTTCCTCTTCCCCCC<br>AAAACCCAAGGACACCCTCATGATCTCCCGGACCCCTGAGGTC<br>ACATGCGTGGTGGTGGACGTGAGCCACGAAGACCCTGAGGTC<br>AAGTTCAACTGGTACGTGGACGGCGTGGAGGTGCATAATGCCA<br>AGACAAAGCCGCGGGAGGAGCAGTACAACAGCACGTACCGTG<br>TGGTCAGCGTCCTCACCGTCCTGCACCAGGACTGGCTGAATGG<br>CAAGGAGTACAAGTGCAAGGTCTCCAACAAAGCCCTCGGCGC<br>CCCCATCGAGAAAACCATCTCCAAAGCCAAAGGGCAGCCCCG<br>AGAACCACAGGTGTACACCCTGCCCCCATCCCGGGATGAGCTG<br>ACCAAGAACCAGGTCAGCCTGACCTGCCTGGTCAAAGGCTTCT<br>ATCCCAGCGACATCGCCGTGGAGTGGGAGAGCAATGGGCAGC<br>CGGAGAACAACTACAAGACCACGCCTCCCGTGCTGGACTCCGA<br>CGGCTCCTTCTTCCTCTACAGCAAGCTCACCGTGGACAAGAGC<br>AGGTGGCAGCAGGGGAACGTCTTCTCATGCTCCGTGATGCATG<br>AGGCTCTGCACAACCACTACACGCAGAAGAGCCTCTCCCTGTC<br>TCCGGGTAAA |
| | 157<br>(Light chain) | EIVLTQSPGTLSLSPGERATLSCRASQSVSSSYLAWYQQKPGQAPR<br>LLIYGASSRATGIPDRFSGSGSGTDFTLTISRLEPEDFAVYYCQQYG<br>SSPLTFGQGTKVEIKRTVAAPSVFIFPPSDEQLKSGTASVVCLLNNF |

TABLE 13-continued

Sequences of anti-OX40 clones in P329GLALA human IgG1 format

| Clone | SEQ ID No. | Sequence |
|---|---|---|
| | 158<br>(Heavy chain) | YPREAKVQWKVDNALQSGNSQESVTEQDSKDSTYSLSSTLTLSK<br>ADYEKHKVYACEVTHQGLSSPVTKSFNRGEC<br>EVQLLESGGGLVQPGGSLRLSCAASGFTFSSYAMSWVRQAPGKG<br>LEWVSAISGSGGSTYYADSVKGRFTISRDNSKNTLYLQMNSLRAE<br>DTAVYYCALDVGAFDYWGQGALVTVSSASTKGPSVFPLAPSSKS<br>TSGGTAALGCLVKDYFPEPVTVSWNSGALTSGVHTFPAVLQSSGL<br>YSLSSVVTVPSSSLGTQTYICNVNHKPSNTKVDKKVEPKSCDKTH<br>TCPPCPAPEAAGGPSVFLFPPKPKDTLMISRTPEVTCVVVDVSHED<br>PEVKFNWYVDGVEVHNAKTKPREEQYNSTYRVVSVLTVLHQDW<br>LNGKEYKCKVSNKALGAPIEKTISKAKGQPREPQVYTLPPSRDEL<br>TKNQVSLTCLVKGFYPSDIAVEWESNGQPENNYKTTPPVLDSDGS<br>FFLYSKLTVDKSRWQQGNVFSCSVMHEALHNHYTQKSLSLSPGK |
| CLC-564 | 159<br>(nucleotide sequence light chain) | GAGATCGTGCTGACCCAGAGCCCCGGCACACTCTCCCTGTCTC<br>CTGGGGAAAGGGCCACCCTTTCATGCAGAGCCAGCCAGTCCGT<br>CTCTAGTAGCTACCTGGCATGGTATCAGCAGAAGCCAGGACAA<br>GCCCCCCGCCTCCTGATTTACGGCGCTTCCTCTCGGGCAACTGG<br>TATCCCTGACAGGTTCTCAGGGAGCGGAAGCGGAACAGATTTT<br>ACCTTGACTATTTCTAGACTGGAGCCAGAGGACTTCGCCGTGT<br>ATTACTGTCAGCAGTACGGTAGTAGCCCCCTCACCTTTGGCCA<br>GGGGACAAAAGTCGAAATCAAGCGTACGGTGGCTGCACCATC<br>TGTCTTCATCTTCCCGCCATCTGATGAGCAGTTGAAATCTGGAA<br>CTGCCTCTGTTGTGTGCCTGCTGAATAACTTCTATCCCAGAGAG<br>GCCAAAGTACAGTGGAAGGTGGATAACGCCCTCCAATCGGGT<br>AACTCCCAGGAGAGTGTCACAGAGCAGGACAGCAAGGACAGC<br>ACCTACAGCCTCAGCAGCACCCTGACGCTGAGCAAAGCAGACT<br>ACGAGAAACACAAAGTCTACGCCTGCGAAGTCACCCATCAGG<br>GCCTGAGCTCGCCCGTCACAAAGAGCTTCAACAGGGGAGAGT<br>GT |
| | 160<br>(nucleotide sequence heavy chain) | GAGGTGCAATTGTTGGAGTCTGGGGGAGGCTTGGTACAGCCTG<br>GGGGGTCCCTGAGACTCTCCTGTGCAGCCTCCGGATTCACCTTT<br>AGCAGTTATGCCATGAGCTGGGTCCGCCAGGCTCCAGGGAAGG<br>GGCTGGAGTGGGTCTCAGCTATTAGTGGTAGTGGTGGTAGCAC<br>ATACTACGCAGACTCCGTGAAGGGCCGGTTCACCATCTCCAGA<br>GACAATTCCAAGAACACGCTGTATCTGCAGATGAACAGCCTGA<br>GAGCCGAGGACACGGCCGTATATTACTGTGCGTTCGACGTTGG<br>TCCGTTCGACTACTGGGGCCAAGGAACCCTGGTCACCGTCTCG<br>AGTGCTAGCACCAAGGGCCCATCGGTCTTCCCCCTGGCACCCT<br>CCTCCAAGAGCACCTCTGGGGGCACAGCGGCCCTGGGCTGCCT<br>GGTCAAGGACTACTTCCCCGAACCGGTGACGGTGTCGTGGAAC<br>TCAGGCGCCCTGACCAGCGGCGTGCACACCTTCCCGGCTGTCC<br>TACAGTCCTCAGGACTCTACTCCCTCAGCAGCGTGGTGACCGT<br>GCCCTCCAGCAGCTTGGGCACCCAGACCTACATCTGCAACGTG<br>AATCACAAGCCCAGCAACACCAAGGTGGACAAGAAAGTTGAG<br>CCCAAATCTTGTGACAAAACTCACACATGCCCACCGTGCCCAG<br>CACCTGAAGCTGCAGGGGGACCGTCAGTCTTCCTCTTCCCCCC<br>AAAACCCAAGGACACCCTCATGATCTCCCGGACCCCTGAGGTC<br>ACATGCGTGGTGGTGGACGTGAGCCACGAAGACCCTGAGGTC<br>AAGTTCAACTGGTACGTGGACGGCGTGGAGGTGCATAATGCCA<br>AGACAAAGCCGCGGGAGGAGCAGTACAACAGCACGTACCGTG<br>TGGTCAGCGTCCTCACCGTCCTGCACCAGGACTGGCTGAATGG<br>CAAGGAGTACAAGTGCAAGGTCTCCAACAAAGCCCTCGGCGC<br>CCCCATCGAGAAAACCATCTCCAAAGCCAAAGGGCAGCCCCG<br>AGAACCACAGGTGTACACCCTGCCCCCATCCCGGGATGAGCTG<br>ACCAAGAACCAGGTCAGCCTGACCTGCCTGGTCAAAGGCTTCT<br>ATCCCAGCGACATCGCCGTGGAGTGGGAGAGCAATGGGCAGC<br>CGGAGAACAACTACAAGACCACGCCTCCCGTGCTGGACTCCGA<br>CGGCTCCTTCTTCCTCTACAGCAAGCTCACCGTGGACAAGAGC<br>AGGTGGCAGCAGGGGAACGTCTTCTCATGCTCCGTGATGCATG<br>AGGCTCTGCACAACCACTACACGCAGAAGAGCCTCTCCCTGTC<br>TCCGGGTAAA |
| | 161<br>(Light chain) | EIVLTQSPGTLSLSPGERATLSCRASQSVSSSYLAWYQQKPGQAPR<br>LLIYGASSRATGIPDRFSGSGSGTDFTLTISRLEPEDFAVYYCQQYG<br>SSPLTFGQGTKVEIKRTVAAPSVFIFPPSDEQLKSGTASVVCLLNNF<br>YPREAKVQWKVDNALQSGNSQESVTEQDSKDSTYSLSSTLTLSK<br>ADYEKHKVYACEVTHQGLSSPVTKSFNRGEC |
| | 162<br>(Heavy chain) | EVQLLESGGGLVQPGGSLRLSCAASGFTFSSYAMSWVRQAPGKG<br>LEWVSAISGSGGSTYYADSVKGRFTISRDNSKNTLYLQMNSLRAE<br>DTAVYYCAFDVGPFDYWGQGTLVTVSSASTKGPSVFPLAPSSKST<br>SGGTAALGCLVKDYFPEPVTVSWNSGALTSGVHTFPAVLQSSGL<br>YSLSSVVTVPSSSLGTQTYICNVNHKPSNTKVDKKVEPKSCDKTH<br>TCPPCPAPEAAGGPSVFLFPPKPKDTLMISRTPEVTCVVVDVSHED<br>PEVKFNWYVDGVEVHNAKTKPREEQYNSTYRVVSVLTVLHQDW<br>LNGKEYKCKVSNKALGAPIEKTISKAKGQPREPQVYTLPPSRDEL<br>TKNQVSLTCLVKGFYPSDIAVEWESNGQPENNYKTTPPVLDSDGS<br>FFLYSKLTVDKSRWQQGNVFSCSVMHEALHNHYTQKSLSLSPGK |

TABLE 13-continued

Sequences of anti-OX40 clones in P329GLALA human IgG1 format

| Clone | SEQ ID No. | Sequence |
|---|---|---|
| 17A9 | 163 (nucleotide sequence light chain) | TCGTCTGAGCTGACTCAGGACCCTGCTGTGTCTGTGGCCTTGGG ACAGACAGTCAGGATCACATGCCAAGGAGACAGCCTCAGAAG TTATTATGCAAGCTGGTACCAGCAGAAGCCAGGACAGGCCCCT GTACTTGTCATCTATGGTAAAAACAACCGGCCCTCAGGGATCC CAGACCGATTCTCTGGCTCCAGCTCAGGAAACACAGCTTCCTT GACCATCACTGGGGCTCAGGCGGAAGATGAGGCTGACTATTAC TGTAACTCCCGTGTTATGCCTCATAATCGCGTATTCGGCGGAG GGACCAAGCTGACCGTCCTAGGTCAACCCAAGGCTGCCCCCAG CGTGACCCTGTTCCCCCCCAGCAGCGAGGAACTGCAGGCCAAC AAGGCCACCCTGGTCTGCCTGATCAGCGACTTCTACCCAGGCG CCGTGACCGTGGCCTGGAAGGCCGACAGCAGCCCCGTGAAGG CCGGCGTGGAGACCACCACCCCCAGCAAGCAGAGCAACAACA AGTACGCCGCCAGCAGCTACCTGAGCCTGACCCCCGAGCAGTG GAAGAGCCACAGGTCCTACAGCTGCCAGGTGACCCACGAGGG CAGCACCGTGGAGAAAACCGTGGCCCCCACCGAGTGCAGC |
| | 164 (nucleotide sequence heavy chain) | GAGGTGCAATTGTTGGAGTCTGGGGGAGGCTTGGTACAGCCTG GGGGGTCCCTGAGACTCTCCTGTGCAGCCTCCGGATTCACCTTT AGCAGTTATGCCATGAGCTGGGTCCGCCAGGCTCCAGGGAAGG GGCTGGAGTGGGTCTCAGCTATTAGTGGTAGTGGTGGTAGCAC ATACTACGCAGACTCCGTGAAGGGCCGGTTCACCATCTCCAGA GACAATTCCAAGAACACGCTGTATCTGCAGATGAACAGCCTGA GAGCCGAGGACACGGCCGTATATTACTGTGCGCGTGTTTTCTA CCGTGGTGGTGTTTCTATGGACTACTGGGGCCAAGGAACCCTG GTCACCGTCTCGAGTGCTAGCACCAAGGGCCCATCGGTCTTCC CCCTGGCACCCTCCTCCAAGAGCACCTCTGGGGGCACAGCGGC CCTGGGCTGCCTGGTCAAGGACTACTTCCCCGAACCGGTGACG GTGTCGTGGAACTCAGGCGCCCTGACCAGCGGCGTGCACACCT TCCCGGCTGTCCTACAGTCCTCAGGACTCTACTCCCTCAGCAGC GTGGTGACCGTGCCCTCCAGCAGCTTGGGCACCCAGACCTACA TCTGCAACGTGAATCACAAGCCCAGCAACACCAAGGTGGACA AGAAAGTTGAGCCCAAATCTTGTGACAAAACTCACACATGCCC ACCGTGCCCAGCACCTGAAGCTGCAGGGGGACCGTCAGTCTTC CTCTTCCCCCCAAAACCCAAGGACACCCTCATGATCTCCCGGA CCCCTGAGGTCACATGCGTGGTGGTGGACGTGAGCCACGAAGA CCCTGAGGTCAAGTTCAACTGGTACGTGGACGGCGTGGAGGTG CATAATGCCAAGACAAAGCCGCGGGAGGAGCAGTACAACAGC ACGTACCGTGTGGTCAGCGTCCTCACCGTCCTGCACCAGGACT GGCTGAATGGCAAGGAGTACAAGTGCAAGGTCTCCAACAAAG CCCTCGGCGCCCCCATCGAGAAAACCATCTCCAAAGCCAAAGG GCAGCCCCGAGAACCACAGGTGTACACCCTGCCCCCATCCCGG GATGAGCTGACCAAGAACCAGGTCAGCCTGACCTGCCTGGTCA AAGGCTTCTATCCCAGCGACATCGCCGTGGAGTGGGAGAGCAA TGGGCAGCCGGAGAACAACTACAAGACCACGCCTCCCGTGCTG GACTCCGACGGCTCCTTCTTCCTCTACAGCAAGCTCACCGTGG ACAAGAGCAGGTGGCAGCAGGGGAACGTCTTCTCATGCTCCGT GATGCATGAGGCTCTGCACAACCACTACACGCAGAAGAGCCTC TCCCTGTCTCCGGGTAAA |
| | 165 (Light chain) | SSELTQDPAVSVALGQTVRITCQGDSLRSYYASWYQQKPGQAPV LVIYGKNNRPSGIPDRFSGSSSGNTASLTITGAQAEDEADYYCNSR VMPHNRVFGGGTKLTVLGQPKAAPSVTLFPPSSEELQANKATLVC LISDFYPGAVTVAWKADSSPVKAGVETTTPSKQSNNKYAASSYLS LTPEQWKSHRSYSCQVTHEGSTVEKTVAPTECS |
| | 166 (Heavy chain) | EVQLLESGGGLVQPGGSLRLSCAASGFTFSSYAMSWVRQAPGKG LEWVSAISGSGGSTYYADSVKGRFTISRDNSKNTLYLQMNSLRAE DTAVYYCARVFYRGGVSMDYWGQGTLVTVSSASTKGPSVFPLAP SSKSTSGGTAALGCLVKDYFPEPVTVSWNSGALTSGVHTFPAVLQ SSGLYSLSSVVTVPSSSLGTQTYICNVNHKPSNTKVDKKVEPKSCD KTHTCPPCPAPEAAGGPSVFLFPPKPKDTLMISRTPEVTCVVVDVS HEDPEVKFNWYVDGVEVHNAKTKPREEQYNSTYRVVSVLTVLH QDWLNGKEYKCKVSNKALGAPIEKTISKAKGQPREPQVYTLPPSR DELTKNQVSLTCLVKGFYPSDIAVEWESNGQPENNYKTTPPVLDS DGSFFLYSKLTVDKSRWQQGNVFSCSVMHEALHNHYTQKSLSLS PGK |

The anti-Ox40 antibodies were produced by co-transfecting HEK293-EBNA cells with the mammalian expression vectors using polyethylenimine. The cells were transfected with the corresponding expression vectors in a 1:1 ratio ("vector heavy chain":"vector light chain").

For production in 500 mL shake flasks, 400 million HEK293 EBNA cells were seeded 24 hours before transfection. For transfection cells were centrifuged for 5 minutes at 210× g, and the supernatant was replaced by pre-warmed CD CHO medium. Expression vectors (200 μg of total DNA) were mixed in 20 mL CD CHO medium. After addition of 540 μL PEI, the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere. After the incubation, 160 mL of F17 medium was added and cells were cultured for 24 hours. One day after transfection 1 mM valproic acid and 7% Feed with supplements were added. After culturing for 7 days, the supernatant was collected by centrifugation for 15 minutes at 210× g. The solution was sterile filtered (0.22 µm filter), supplemented with sodium azide to a final concentration of 0.01% (w/v), and kept at 4° C.

Purification of antibody molecules from cell culture supernatants was carried out by affinity chromatography using Protein A as described above for purification of antigen Fc fusions.

The protein was concentrated and filtered prior to loading on a HiLoad Superdex 200 column (GE Healthcare) equilibrated with 20 mM Histidine, 140 mM NaCl solution of pH 6.0.

The protein concentration of purified antibodies was determined by measuring the OD at 280 nm, using the molar extinction coefficient calculated on the basis of the amino acid sequence. Purity and molecular weight of the antibodies were analyzed by CE-SDS in the presence and absence of a reducing agent (Invitrogen, USA) using a LabChipGXII (Caliper). The aggregate content of antibody samples was analyzed using a TSKgel G3000 SW XL analytical size-exclusion column (Tosoh) equilibrated in a 25 mM $K_2HPO_4$, 125 mM NaCl, 200 mM L-Arginine Monohydrocloride, 0.02% (w/v) $NaN_3$, pH 6.7 running buffer at 25° C.

Table 14 summarizes the yield and final content of the anti-OX40 P329G LALA IgG1 antibodies.

TABLE 14

Biochemical analysis of anti-OX40 P329G LALA IgG1 clones

| Clone | Yield [mg/l] | Monomer [%] | CE-SDS (non red) | CE-SDS (red) |
|---|---|---|---|---|
| 8H9 P329GLALA IgG1 | 7 | 100 | 1.2% (176 kDa) 96.1% (158 kDa) 1.3% (142 kDa) | 66.9% (54 kDa) 28.9% (25 kDa) |
| 49B4 P329GLALA IgG1 | 7.5 | 100 | 99% (163 kDa) 1% (149 kDa) | 81% (61.7 kDa) 18% (28.9 kDa) |
| 1G4 P329GLALA IgG1 | 1 | 100 | 98.9% (167.4 kDa) 1.1% (151 kDa) | 80% (63.4 kDa) 19% (28.9 kDa) |
| 20B7 P329GLALA IgG1 | 17 | 93 | 97.9% (174 kDa) | 79.8% (65.4 kDa) 19.9% (29.5 kDa) |
| CLC-563 P329GLALA IgG1 | 6.2 | 100 | 97.7% (160 kDa) | 77.7% (60 kDa) 19.8% (26.4 kDa) |
| CLC-564 P329GLALA IgG1 | 13.5 | 100 | 98.4% (155 kDa) | 79.3% (60.1 kDa) 19.8% (26.5 kDa) |
| 17A9 P329GLALA IgG1 | 7.5 | 100 | 98.6% (175 kDa) 1.4% (153 kDa) | 74.1% (61 kDa) 25.5% (38 kDa) |

Example 2

Generation of Tenascin C (TnC) Antibodies 2.1 Preparation, Purification and Characterization of Antigens and Screening Tools for the Generation of Novel TnC Binders by Phage Display The constructs of Table 15 and Table 16 were fused to the C-term of GST, and expressed in *E. coli* BL21(DE3). For site-specific biotinylation, the Avi-tag was added to the C-term of the tenascin sequence, and the BirA biotin ligase was coexpressed on a separate plasmid (Avidity, Colo., USA). Growth medium was 2YT with 100 µg/ml ampicillin and 20 µg/ml chloramphenicol. Biotin was added to a final concentration of 50 µM. Protein Expression was induced with 1 mM IPTG at 22° C. overnight. Cells were harvested by centrifugation, and cell-lysis was performed by sonication in the presence of B-PER reagent (pierce 78260), and 1 mg/ml lysozyme (Sigma L6876). Lysate was centrifuged and cleared lysate was loaded on Glutathione Sepharose columns (GE Healthcare; Product No 17-0756-01). After washing, the TnC molecules were cleaved from the GST via Thrombin (Sigma Aldrich; Product No 10602400001) over night at 4° C. Elution was performed in 50 mM Tris buffer pH 8.0; 200 mM NaCl, 5 mM MgCl2, 1 mM DTT and 10% glycerol. The final purification step was on a gel filtration column (Superdex 75 16/60; GE Healthcare). Samples were flash frozen in liquid nitrogen until processing.

TABLE 15

Sequences of TnC antigens used for cross-species affinity determination

| Antigen | Sequence | SEQ ID NO |
|---|---|---|
| huTnC | ATGTCCCCTATACTAGGTTATTGGAAAATTAAGGGCCT TGTGCAACCCACTCGACTTCTTTTGGAATATCTTGAAG AAAAATATGAAGAGCATTTGTATGAGCGCGATGAAGG TGATAAATGGCGAAACAAAAAGTTTGAATTGGGTTTG GAGTTTCCCAATCTTCCTTATTATATTGATGGTGATGTT AAATTAACACAGTCTATGGCCATCATACGTTATATAGC TGACAAGCACAACATGTTGGGTGGTTGTCCAAAAGAG CGTGCAGAGATTTCAATGCTTGAAGGAGCGGTTTTGGA TATTAGATACGGTGTTTCGAGAATTGCATATAGTAAAG ACTTTGAAACTCTCAAAGTTGATTTTCTTAGCAAGCTA CCTGAAATGCTGAAAATGTTCGAAGATCGTTTATGTCA TAAAACATATTTAAATGGTGATCATGTAACCCATCCTG ACTTCATGTTGTATGACGCTCTTGATGTTGTTTTATACA | 167 |

TABLE 15-continued

Sequences of TnC antigens used for cross-species affinity determination

| Antigen | Sequence | SEQ ID NO |
|---|---|---|
|  | TGGACCCAATGTGCCTGGATGCGTTCCCAAAATTAGTT<br>TGTTTTAAAAAACGTATTGAAGCTATCCCACAAATTGA<br>TAAGTACTTGAAATCCAGCAAGTATATAGCATGGCCTT<br>TGCAGGGCTGGCAAGCCACGTTTGGTGGTGGCGACCAT<br>CCTCCAAAATCGGATGGTTCAACTAGTGGTTCTGGTCA<br>TCACCATCACCATCACTCCGCGGGTCTGGTGCCACGCG<br>GTAGTACTGCAATTGGTATGAAAGAAACCGCTGCTGCT<br>AAATTCGAACGCCAGCACATGGACAGCCCAGATCTGG<br>GTACCGGTGGTGGCTCCGGTATTGAGGGACGCGGGTCC<br>ATGGGATATCGGGGATCCGAGCTGGACACCCCCAAGG<br>ACCTGCAGGTGTCCGAGACAGCCGAGACAAGCCTGAC<br>CCTGCTGTGGAAAACCCCCCTGGCCAAGTTCGACCGGT<br>ACAGACTGAACTACAGCCTGCCCACTGGACAGTGGGT<br>CGGCGTGCAGCTGCCCCGGAACACCACCTCCTACGTGC<br>TGCGGGGCCTGGAACCCGGCCAGGAATACAACGTCCT<br>GCTGACGGCCGAGAAGGGCCGGCACAAGAGCAAGCCC<br>GCCAGAGTGAAGGCCAGCACCGAGCAGGCCCCCGAGC<br>TGGAAAACCTGACCGTGACCGAAGTGGGCTGGGACGG<br>CCTGCGGCTGAACTGGACCGCGGCTGACCAGGCCTATG<br>AGCACTTTATCATTCAGGTGCAGGAGGCCAACAAGGT<br>GGAGGCAGCTCGGAACCTCACCGTGCCTGGCAGCCTTC<br>GGGCTGTGGACATACCGGGCCTCAAGGCTGCTACGCCT<br>TATACAGTCTCCATCTATGGGGTGATCCAGGGCTATAG<br>AACACCAGTGCTCTCTGCTGAGGCCTCCACAGGCGAAA<br>CACCGAACCTGGGCGAAGTGGTGGTGGCGGAAGTGGG<br>TTGGGATGCGCTGAAACTGAACTGGACCGCGCCGGAA<br>GGCGCGTATGAATATTTTTTCATCCAGGTGCAGGAAGC<br>GGATACCGTTGAAGCGGCGCAGAACCTGACCGTTCCG<br>GGCGGTCTGCGTAGCACCGATCTGCCGGGCCTGAAAG<br>CGGCGACCCATTATACCATTACCATCCGTGGGGTGACC<br>CAGGACTTCTCTACCACCCCTCTGAGCGTGGAGGTGCT<br>GACCGAGGAGGTACCCGACATGGGCAACCTGACCGTG<br>ACCGAGGTGTCCTGGGACGCCCTGCGGCTGAACTGGA<br>CCACCCCCGACGGCACCTACGACCAGTTCACAATCCAG<br>GTGCAGGAAGCCGACCAGGTGGAAGAAGCACATAATC<br>TGACCGTTCCGGGTAGCCTGCGTAGCATGGAAATTCCG<br>GGTCTGCGTGCAGGCACCCCGTATACCGTTACCCTGCA<br>TGGTGAAGTTCGTGGTCATAGCACCCGTCCGCTGGCAG<br>TTGAAGTTGTTACCGAAGATCTGCCGCAGCTGGGTGAT<br>CTGGCAGTTAGCGAAGTTGGTTGGGATGGTCTGCGTCT<br>GAATTGGACCGCAGCAGATAATGCATATGAACATTTTG<br>TGATCCAGGTGCAAGAGGTGAATAAAGTTGAAGCAGC<br>CCAGAATCTGACCCTGCCTGGTTCACTGCGTGCAGTTG<br>ATATTCCGGGACTCGAGGCAGCAACCCCGTATCGTGTT<br>AGCATTTATGGTGTTATTCGCGGTTATCGTACACCGGT<br>TCTGAGCGCAGAAGCAAGCACCGCAAAAGAACCGGAA<br>ATTGGTAATCTGAACGTGAGCGATATTACACCGGAATC<br>ATTTAATCTGAGCTGGATGGCAACCGATGGTATTTTTG<br>AAACCTTTACCATCGAGATCATCGATAGCAATCGTCTG<br>CTGGAAACCGTGGAATATAATATTAGCGGTGCAGAAC<br>GTACCGCACATATTAGCGGTCTGCCTCCGAGCACCGAT<br>TTTATTGTTTATCTGAGCGGTCTGGCACCGAGCATTCGT<br>ACCAAAACCATTAGCGCAACCGCAACCACCGAAGCAC<br>TGCCGCTGCTGGAAAATCTGACCATTAGCGATATTAAC<br>CCGTATGGTTTTACCGTTTCATGGATGGCAAGCGAAAA<br>TGCATTTGATAGCTTTCTGGTTACAGTTGTGGATAGCG<br>GTAAACTGCTGGACCCGCAAGAATTTACCCTGAGCGGC<br>ACCCAGCGCAAACTGGAACTGCGTGGTCTGATTACCGG<br>TATTGGTTATGAAGTTATGGTGAGCGGTTTTACCCAGG<br>GTCATCAGACCAAACCGCTGCGTGCAGAAATTGTTACC<br>GAAGCAATGGGTAGCCCGAAAGAAGTTATTTTTTCCGA<br>TATCACCGAGAATTCGGCAACCGTTAGCTGGCGTGCAC<br>CGACCGCACAGGTTGAAAGCTTTCGTATTACCTATGTT<br>CCGATTACCGGTGGCACCCCGAGCATGGTTACAGTTGA<br>TGGCACCAAAACCCAGACCCGTCTGGTTAAACTGATTC<br>CGGGTGTTGAATATCTGGTTAGCATTATTGCCATGAAA<br>GGCTTTGAAGAAAGCGAACCGGTTAGCGGTAGCTTTAC<br>CACAGCTAGCGGCCTGAACGACATCTTCGAGGCTCAG<br>AAAATCGAATGGCACGAAGGTACCCATCACCATCACC<br>ACCACTAA |  |
| muTnC | TATGTCCCCTATACTAGGTTATTGGAAAATTAAGGGCC<br>TTGTGCAACCCACTCGACTTCTTTTGGAATATCTTGAA<br>GAAAAATATGAAGAGCATTTGTATGAGCGCGATGAAG<br>GTGATAAATGGCGAAACAAAAAGTTTGAATTGGGTTT | 168 |

TABLE 15-continued

Sequences of TnC antigens used for cross-species affinity determination

| Antigen | Sequence | SEQ ID NO |
|---|---|---|
| | GGAGTTTCCCAATCTTCCTTATTATATTGATGGTGATGT<br>TAAATTAACACAGTCTATGGCCATCATACGTTATATAG<br>CTGACAAGCACAACATGTTGGGTGGTTGTCCAAAAGA<br>GCGTGCAGAGATTTCAATGCTTGAAGGAGCGGTTTTGG<br>ATATTAGATACGGTGTTTCGAGAATTGCATATAGTAAA<br>GACTTTGAAACTCTCAAAGTTGATTTTCTTAGCAAGCT<br>ACCTGAAATGCTGAAAATGTTCGAAGATCGTTTATGTC<br>ATAAAACATATTTAAATGGTGATCATGTAACCCATCCT<br>GACTTCATGTTGTATGACGCTCTTGATGTTGTTTTATAC<br>ATGGACCCAATGTGCCTGGATGCGTTCCCAAAATTAGT<br>TTGTTTTAAAAAACGTATTGAAGCTATCCCACAAATTG<br>ATAAGTACTTGAAATCCAGCAAGTATATAGCATGGCCT<br>TTGCAGGGCTGGCAAGCCACGTTTGGTGGTGGCGACCA<br>TCCTCCAAAATCGGATGGTTCAACTAGTGGTTCTGGTC<br>ATCACCATCACCATCACTCCGCGGGTCTGGTGCCACGC<br>GGTAGTACTGCAATTGGTATGAAAGAAACCGCTGCTGC<br>TAAATTCGAACGCCAGCACATGGACAGCCCAGATCTG<br>GGTACCGGTGGTGGCTCCGGTATTGAGGGACGCGGGT<br>CCATGGGATATCGGGGATCCGAGCTGGACACCCCCAA<br>GGACCTGCAGGTGTCCGAGACAGCCGAGACAAGCCTG<br>ACCCTGCTGTGGAAAACCCCCCTGGCCAAGTTCGACCG<br>GTACAGACTGAACTACAGCCTGCCCACTGGACAGTGG<br>GTCGGCGTGCAGCTGCCCCGGAACACCACCTCCTACGT<br>GCTGCGGGGCCTGGAACCCGGCCAGGAATACAACGTC<br>CTGCTGACGGCCGAGAAGGGCCGGCACAAGAGCAAGC<br>CCGCCAGAGTGAAGGCCAGCACCGAGGAAGTGCCCAG<br>CCTGGAAAACCTGACCGTGACCGAGGCCGGCTGGGAC<br>GGCCTGCGGCTGAACTGGACCGCCGACGACCTGGCCT<br>ACGAGTACTTCGTGATCCAGGTGCAGGAAGCCAACAA<br>CGTCGAGACAGCCCACAACTTCACCGTGCCCGGCAACC<br>TGAGAGCCGCCGACATCCCCGGCCTGAAGGTGGCCAC<br>ATCCTACCGGGTGTCCATCTACGGCGTGGCCAGGGGCT<br>ACCGGACCCCCGTGCTGTCCGCCGAGACAAGCACCGG<br>CACCACGCCGAACCTGGCGAAGTGACCGTGGCGGAA<br>GTGGGTTGGGATGCGCTGACCCTGAATTGGACCGCACC<br>GGAAGGCGCGTATAAAAACTTTTTCATCCAGGTGCTGG<br>AAGCGGATACCACCCAGACCGTGCAGAACCTGACCGT<br>GCCGGGTGGTCTGCGTAGCGTAGATCTGCCTGGTCTGA<br>AAGCAGCAACCCGCTATTACATTACCCTGCGTGGTGTT<br>ACCCAGGATTTTGGCACCGCACCGCTGAGCGTTGAAGT<br>TCTGACCGAGGATCTGCCGCAGCTGGGTGGTCTGAGCG<br>TTACCGAAGTTAGTTGGGATGGTCTGACCCTGAATTGG<br>ACCACCGATGATCTGGCATATAAACATTTTGTGGTGCA<br>GGTTCAAGAGGCCAATAATGTTGAAGCAGCACAGAAT<br>CTGACCGTTCCGGGTAGCCTGCGTGCAGTTGATATTCC<br>GGGACTGAAAGCCGATACCCCGTATCGTGTTAGCATTT<br>ATGGTGTTATTCAGGGTTATCGTACCCCGATGCTGAGC<br>ACCGATGTTAGCACAGCACGTGAACCGGAAATTGGTA<br>ATCTGAATGTTAGTGATGTGACCCCGAAATCATTTAAT<br>CTGAGCTGGACCGCAACCGATGGTATTTTTGATATGTT<br>TACCATTGAAATTATTGATAGCAATCGCCTGCTGCAGA<br>CCGCAGAACATAACATTAGCGGTGCAGAACGTACCGC<br>ACATATTAGCGGTCTGCCTCCGAGCACCGATTTTATTG<br>TTTATCTGAGCGGTATTGCACCGAGCATTCGTACCAAA<br>ACCATTAGCACCACCGCAACCACCGAAGCACTGACCG<br>CAATGGGTAGCCCGAAAGAAGTGATTTTTAGCGATATT<br>ACCGAAAATAGCGCCACCGTTTCATGGCGTGCACCGAC<br>CGCACAGGTTGAAAGCTTTCGTATTACCTATGTTCCGA<br>TTACCGGTGGCACCCCGAGCATGGTTACCGTTGATGGC<br>ACCAAAACCCAGACCCGTCTGGTTAAACTGATTCCGGG<br>TGTTGAATATCTGGTTAGCATTATTGCCATGAAAGGCT<br>TTGAAGAAAGCGAACCGGTTAGCGGTAGCTTTACCAC<br>AGCTAGCGGCCTGAACGACATCTTCGAGGCTCAGAAA<br>ATCGAATGGCACGAAGGTACCCATCACCATCACCACC<br>ACTAA | |
| cyno TnC | ATGTCCCCTATACTAGGTTATTGGAAAATTAAGGGCCT<br>TGTGCAACCCACTCGACTTCTTTTGGAATATCTTGAAG<br>AAAAATATGAAGAGCATTTGTATGAGCGCGATGAAGG<br>TGATAAATGGCGAAACAAAAAGTTTGAATTGGGTTTG<br>GAGTTTCCCAATCTTCCTTATTATATTGATGGTGATGTT<br>AAATTAACACAGTCTATGGCCATCATACGTTATATAGC<br>TGACAAGCACAACATGTTGGGTGGTTGTCCAAAAGAG<br>CGTGCAGAGATTTCAATGCTTGAAGGAGCGGTTTTGGA<br>TATTAGATACGGTGTTTCGAGAATTGCATATAGTAAAG | 169 |

TABLE 15-continued

Sequences of TnC antigens used for cross-species affinity determination

| Antigen | Sequence | SEQ ID NO |
|---|---|---|
|  | ACTTTGAAACTCTCAAAGTTGATTTTCTTAGCAAGCTA<br>CCTGAAATGCTGAAAATGTTCGAAGATCGTTTATGTCA<br>TAAAACATATTTAAATGGTGATCATGTAACCCATCCTG<br>ACTTCATGTTGTATGACGCTCTTGATGTTGTTTTATACA<br>TGGACCCAATGTGCCTGGATGCGTTCCCAAAATTAGTT<br>TGTTTTAAAAAACGTATTGAAGCTATCCCACAAATTGA<br>TAAGTACTTGAAATCCAGCAAGTATATAGCATGGCCTT<br>TGCAGGGCTGGCAAGCCACGTTTGGTGGTGGCGACCAT<br>CCTCCAAAATCGGATGGTTCAACTAGTGGTTCTGGTCA<br>TCACCATCACCATCACTCCGCGGGTCTGGTGCCACGCG<br>GTAGTACTGCAATTGGTATGAAAGAAACCGCTGCTGCT<br>AAATTCGAACGCCAGCACATGGACAGCCCAGATCTGG<br>GTACCGGTGGTGGCTCCGGTATTGAGGGACGCGGGTCC<br>ATGGGATATCGGGGATCCGAACTGGATACCCCGAAAG<br>ATCTGCGTGTTAGCGAAACCGCAGAAACCAGCCTGAC<br>CCTGTTTTGGAAAACACCGCTGGCAAAATTTGATCGTT<br>ATCGTCTGAATTATAGCCTGCCGACCGGTCAGTGGGTT<br>GGTGTTCAGCTGCCTCGTAATACCACCAGTTATGTTCT<br>GCGTGGTCTGGAACCGGGTCAAGAATATAACGTTCTGC<br>TGACCGCAGAAAAGGTCGTCATAAAAGCAAACCGGC<br>ACGTGTTAAAGCAAGCACCGAACAGGCACCGGAACTG<br>GAAAATCTGACCGTTACCGAAGTTGGCTGGGATGGCCT<br>GCGCCTGAACTGGACGGCTGCGGACCAGGCCTACGAA<br>CACTTCGTTATCCAGGTGCAAGAAGCCAACAAAGTAG<br>AAGCCGCTCAGAATCTGACGGTTCCGGGAAATCTGCGT<br>GCAGTTGATATTCCGGGTCTGAAAGCAGCAACCCCGTA<br>TACCGTTAGCATTTATGGTGTTATTCAGGGTTATCGTAC<br>ACCGGTTCTGAGTGCCGAAGCCAGCACCGGTGAAACC<br>CCGAATCTGGGTGAAGTTATGGTTAGCGAAGTGGGCTG<br>GGATGCACTGAAACTGAATTGGACAGTTCCGGAAGGT<br>GCCTATGAATACTTTTTCATTCAGGTTCAAGAAGCGGA<br>TACCGTTGAAGCCGCTCAGAATCATACCGTTCCGGGTG<br>GTCTGCGTAGCACCGATCTGCCCTGGCCTGAAAGCCGCT<br>ACCCATTACACCATTACCATTCGTGGTGTTACCCAGGA<br>TTTTAGCACCACACCGCTGAGCGTTGAAGTTCTGACAG<br>AAGAACTGCCGCAGCTGGGTGATCTGGCAGTTAGCGA<br>AGTTGGTTGGGATGGTCTGCGTCTGAATTGGACCGCAG<br>CAGATCAGGCATATGAACATTTTGTTATCCAGGTGCAA<br>GAAGTGAACAAAGTTGAAGCAGCACAGAATCTGACCG<br>TTCCGGGTAGCCTGCGTGCAGTTGATATTCCGGGTCTG<br>AAAGCAGCAACCCCGTATACCGTTAGCATTTATGGTGT<br>TATTCGCGGTTATCGTACACCGGTTCTGAGCGCAGAAG<br>CAAGCACCGCAAAAGAACCGGAAATTGGTAATCTGAA<br>CGTGAGCGATATTACACCGGAAAGTTTTAGCCTGAGCT<br>GGACCGCAACCGATGGTATTTTTGAAACCTTTACCATC<br>GAGATCATCGATAGCAATCGTCTGCTGGAAATCGTGGA<br>ATATAACATTAGCGGTCAGAACGTACCGCACATATTA<br>GCGGTCTGCCTCCGAGCACCGATTTTATTGTTTATCTGA<br>GCGGTCTGGCACCGAGCTTTCGTACCAAAACCATTAGC<br>GCAACCGCAACCACCGAAGCACTGACCGCAATGGGTA<br>GCCCGAAAGAAGTGATTTTTAGCGATATTACCGAAAAT<br>AGCGCCACCGTTTCATGGCGTGCACCGACCGCACAGGT<br>TGAAAGCTTTCGTATTACCTATGTTCCGATTACCGGTG<br>GCACCCCGAGCATGGTTACCGTGGATGGCACCAAAAC<br>CCAGACCCGTCTGGTTAAACTGGTTCCGGGTGTTGAAT<br>ATCTGGTGAATATCATTGCCATGAAAGGCTTTGAAGAA<br>AGCGAACCGGTTAGCGGTAGCTTTACCACCGCTAGCGG<br>CCTGAACGACATCTTCGAGGCTCAGAAAATCGAATGG<br>CACGAAGGTACCCATCACCATCACCACCACTAA |  |
| huTnC | MSPILGYWKIKGLVQPTRLLLEYLEEKYEEHLYERDEGD<br>KWRNKKFELGLEFPNLPYYIDGDVKLTQSMAIIRYIADKH<br>NMLGGCPKERAEISMLEGAVLDIRYGVSRIAYSKDFETLK<br>VDFLSKLPEMLKMFEDRLCHKTYLNGDHVTHPDFMLYD<br>ALDVVLYMDPMCLDAFPKLVCFKKRIEAIPQIDKYLKSSK<br>YIAWPLQGWQATFGGGDHPPKSDGSTSGSGHHHHHHSA<br>GLVPRGSTAIGMKETAAAKFERQHMDSPDLGTGGGSGIE | 170 |

TABLE 15-continued

Sequences of TnC antigens used for cross-species affinity determination

| Antigen | Sequence | SEQ ID NO |
|---|---|---|
| | GRGSMGYRGSELDTPKDLQVSETAETSLTLLWKTPLAKF<br>DRYRLNYSLPTGQWVGVQLPRNTTSYVLRGLEPGQEYN<br>VLLTAEKGRHKSKPARVKASTEQAPELENLTVTEVGWD<br>GLRLNWTAADQAYEHFIIQVQEANKVEAARNLTVPGSLR<br>AVDIPGLKAATPYTVSIYGVIQGYRTPVLSAEASTGETPN<br>LGEVVVAEVGWDALKLNWTAPEGAYEYFFIQVQEADTV<br>EAAQNLTVPGGLRSTDLPGLKAATHYTITIRGVTQDFSTT<br>PLSVEVLTEEVPDMGNLTVTEVSWDALRLNWTTPDGTY<br>DQFTIQVQEADQVEEAHNLTVPGSLRSMEIPGLRAGTPYT<br>VTLHGEVRGHSTRPLAVEVVTEDLPQLGDLAVSEVGWD<br>GLRLNWTAADNAYEHFVIQVQEVNKVEAAQNLTLPGSL<br>RAVDIPGLEAATPYRVSIYGVIRGYRTPVLSAEASTAKEPE<br>IGNLNVSDITPESFNLSWMATDGIFETFTIEIIDSNRLLETV<br>EYNISGAERTAHISGLPPSTDFIVYLSGLAPSIRTKTISATA<br>TTEALPLLENLTISDINPYGFTVSWMASENAFDSFLVTVV<br>DSGKLLDPQEFTLSGTQRKLELRGLITGIGYEVMVSGFTQ<br>GHQTKPLRAEIVTEAMGSPKEVIFSDITENSATVSWRAPT<br>AQVESFRITYVPITGGTPSMVTVDGTKTQTRLVKLIPGVE<br>YLVSIIAMKGFEESEPVSGSFTTASGLNDIFEAQKIEWHEG<br>THHHHHH | |
| muTnC | MSPILGYWKIKGLVQPTRLLLEYLEEKYEEHLYERDEGD<br>KWRNKKFELGLEFPNLPYYIDGDVKLTQSMAIIRYIADKH<br>NMLGGCPKERAEISMLEGAVLDIRYGVSRIAYSKDFETLK<br>VDFLSKLPEMLKMFEDRLCHKTYLNGDHVTHPDFMLYD<br>ALDVVLYMDPMCLDAFPKLVCFKKRIEAIPQIDKYLKSSK<br>YIAWPLQGWQATFGGGDHPPKSDGSTSGSGHHHHHHSA<br>GLVPRGSTAIGMKETAAAKFERQHMDSPDLGTGGGSGIE<br>GRGSMGYRGSELDTPKDLQVSETAETSLTLLWKTPLAKF<br>DRYRLNYSLPTGQWVGVQLPRNTTSYVLRGLEPGQEYN<br>VLLTAEKGRHKSKPARVKASTEEVPSLENLTVTEAGWDG<br>LRLNWTADDLAYEYFVIQVQEANNVETAHNFTVPGNLR<br>AADIPGLKVATSYRVSIYGVARGYRTPVLSAETSTGTTPN<br>LGEVTVAEVGWDALTLNWTAPEGAYKNFFIQVLEADTT<br>QTVQNLTVPGGLRSVDLPGLKAATRYYITLRGVTQDFGT<br>APLSVEVLTEDLPQLGGLSVTEVSWDGLTLNWTTDDLAY<br>KHFVVQVQEANNVEAAQNLTVPGSLRAVDIPGLKADTP<br>YRVSIYGVIQGYRTPMLSTDVSTAREPEIGNLNVSDVTPK<br>SFNLSWTATDGIFDMFTIEIIDSNRLLQTAEHNISGAERTA<br>HISGLPPSTDFIVYLSGIAPSIRTKTISTTATTEALTAMGSPK<br>EVIFSDITENSATVSWRAPTAQVESFRITYVPITGGTPSMV<br>TVDGTKTQTRLVKLIPGVEYLVSIIAMKGFEESEPVSGSFT<br>TASGLNDIFEAQKIEWHEGTHHHHHH | 171 |
| cyno TnC | MSPILGYWKIKGLVQPTRLLLEYLEEKYEEHLYERDEGD<br>KWRNKKFELGLEFPNLPYYIDGDVKLTQSMAIIRYIADKH<br>NMLGGCPKERAEISMLEGAVLDIRYGVSRIAYSKDFETLK<br>VDFLSKLPEMLKMFEDRLCHKTYLNGDHVTHPDFMLYD<br>ALDVVLYMDPMCLDAFPKLVCFKKRIEAIPQIDKYLKSSK<br>YIAWPLQGWQATFGGGDHPPKSDGSTSGSGHHHHHHSA<br>GLVPRGSTAIGMKETAAAKFERQHMDSPDLGTGGGSGIE<br>GRGSMGYRGSELDTPKDLRVSETAETSTLFWKTPLAKF<br>DRYRLNYSLPTGQWVGVQLPRNTTSYVLRGLEPGQEYN<br>VLLTAEKGRHKSKPARVKASTEQAPELENLTVTEVGWD<br>GLRLNWTAADQAYEHFVIQVQEANKVEAAQNLTVPGNL<br>RAVDIPGLKAATPYTVSIYGVIQGYRTPVLSAEASTGETP<br>NLGEVMVSEVGWDALKLNWTVPEGAYEYFFIQVQEADT<br>VEAAQNHTVPGGLRSTDLPGLKAATHYTITIRGVTQDFST<br>TPLSVEVLTEELPQLGDLAVSEVGWDGLRLNWTAADQA<br>YEHFVIQVQEVNKVEAAQNLTVPGSLRAVDIPGLKAATP<br>YTVSIYGVIRGYRTPVLSAEASTAKEPEIGNLNVSDITPESF<br>SLSWTATDGIFETFTIEIIDSNRLLEIVEYNISGAERTAHISG<br>LPPSTDFIVYLSGLAPSFRTKTISATATTEALTAMGSPKEVI<br>FSDITENSATVSWRAPTAQVESFRITYVPITGGTPSMVTVD<br>GTKTQTRLVKLVPGVEYLVNIIAMKGFEESEPVSGSFTTA<br>SGLNDIFEAQKIEWHEGTHHHHHH | 172 |

TABLE 16

Sequences of TnC antigens used for affinity determination

| Antigen pETR # batch ID | Protein Sequence | SEQ ID NO: |
|---|---|---|
| GST huTnC fn5 A1234 BC fn6 | MSPILGYWKIKGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI BAWPLQGWQATFGGGDHPPKSDGSTSGSGHHHHHHSAGL VPRGSTAIGMKETAAAKFERQHMDSPDLGTGGGSGIEGR GSMGYRGSELDTPKDLQVSETAETSLTLLWKTPLAKFDR YRLNYSLPTGQWVGVQLPRNTTSYVLRGLEPGQEYNVLL TAEKGRHKSKPARVKASTEQAPELENLTVTEVGWDGLRL NWTAADQAYEHFIIQVQEANKVEAARNLTVPGSLRAVDI PGLKAATPYTVSIYGVIQGYRTPVLSAEASTGETPNLGEV VVAEVGWDALKLNWTAPEGAYEYFFIQVQEADTVEAAQ NLTVPGGLRSTDLPGLKAATHYTITIRGVTQDFSTTPLSVE VLTEEVPDMGNLTVTEVSWDALRLNWTTPDGTYDQFTIQ VQEADQVEEAHNLTVPGSLRSMEIPGLRAGTPYTVTLHGE VRGHSTRPLAVEVVTEDLPQLGDLAVSEVGWDGLRLNW TAADNAYEHFVIQVQEVNKVEAAQNLTLPGSLRAVDIPG LEAATPYRVSIYGVIRGYRTPVLSAEASTAKEPEIGNLNVS DITPESFNLSWMATDGIFETFTIEIIDSNRLLETVEYNISGAE RTAHISGLPPSTDFIVYLSGLAPSIRTKTISATATTEALPLLE NLTISDINPYGFTVSWMASENAFDSFLVTVVDSGKLLDPQ EFTLSGTQRKLELRGLITGIGYEVMVSGFTQGHQTKPLRA EIVTEAMGSPKEVIFSDITENSATVSWRAPTAQVESFRITY VPITGGTPSMVTVDGTKTQTRLVKLIPGVEYLVSIIAMKGF EESEPVSGSFTTASGLNDIFEAQKIEWHEGTHHHHHH | 173 |
| GST huTnC fn5 mu A124 BC fn6 | MSPILGYWKIKGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI AWPLQGWQATFGGGDHPPKSDGSTSGSGHHHHHHSAGL BVPRGSTAIGMKETAAAKFERQHMDSPDLGTGGGSGIEGR GSMGYRGSELDTPKDLQVSETAETSLTLLWKTPLAKFDR YRLNYSLPTGQWVGVQLPRNTTSYVLRGLEPGQEYNVLL TAEKGRHKSKPARVKASTEEVPSLENLTVTEAGWDGLRL NWTADDLAYEYFVIQVQEANNVETAHNFTVPGNLRAADI PGLKVATSYRVSIYGVARGYRTPVLSAETSTGTTPNLGEV TVAEVGWDALTLNWTAPEGAYKNFFIQVLEADTTQTVQ NLTVPGGLRSVDLPGLKAATRYYITLRGVTQDFGTAPLSV EVLTEDLPQLGGLSVTEVSWDGLTLNWTTDDLAYKHFVV QVQEANNVEAAQNLTVPGSLRAVDIPGLKADTPYRVSIY GVIQGYRTPMLSTDVSTAREPEIGNLNVSDVTPKSFNLSW TATDGIFDMFTIEIIDSNRLLQTAEHNISGAERTAHISGLPPS TDFIVYLSGIAPSIRTKTISTTATTEALPLLENLTISDTNPYG FTVSWTASENAFDSFLVTVVDSGKLLDPQEFTLSGTQRKL ELRGLITGIGYEVLVSGFTQGHQTKPLRAETITAMGSPKEV IFSDITENSATVSWRAPTAQVESFRITYVPITGGTPSMVTV DGTKTQTRLVKLIPGVEYLVSIIAMKGFEESEPVSGSFTTA SGLNDIFEAQKIEWHEGTHHHHHH | 174 |
| GST TnC hu fn5 B-C fn6 | MSPILGYWKIKGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI BAWPLQGWQATFGGGDHPPKSDGSTSGSGHHHHHHSAGL VPRGSTAIGMKETAAAKFERQHMDSPDLGTGGGSGIEGR GSMGYRGSELDTPKDLQVSETAETSLTLLWKTPLAKFDR YRLNYSLPTGQWVGVQLPRNTTSYVLRGLEPGQEYNVLL TAEKGRHKSKPARVKASTAKEPEIGNLNVSDITPESFNLS WMATDGIFETFTIEIIDSNRLLETVEYNISGAERTAHISGLP PSTDFIVYLSGLAPSIRTKTISATATTEALPLLENLTISDINP YGFTVSWMASENAFDSFLVTVVDSGKLLDPQEFTLSGTQ RKLELRGLITGIGYEVMVSGFTQGHQTKPLRAEIVTAMGS PKEVIFSDITENSATVSWRAPTAQVESFRITYVPITGGTPSM VTVDGTKTQTRLVKLIPGVEYLVSIIAMKGFEESEPVSGSF TTASGLNDIFEAQKIEWHEGTHHHHHH | 175 |
| GST huTnC fn5 A1234 DFLSKLPEMLKMFEDRLCHKTYLNGDHVTHPDFMLYDAL fn6 B | MSPILGYWKIGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV BDVVLYMDPMCLDAFPKLVCFKKRIEAIPQIDKYLKSSKYI AWPLQGWQATFGGGDHPPKSDGSTSGSGHHHHHHSAGL VPRGSTAIGMKETAAAKFERQHMDSPDLGTGGGSGIEGR GSMGYRGSELDTPKDLQVSETAETSLTLLWKTPLAKFDR YRLNYSLPTGQWVGVQLPRNTTSYVLRGLEPGQEYNVLL TAEKGRHKSKPARVKASTEQAPELENLTVTEVGWDGLRL NWTAADQAYEHFIIQVQEANKVEAARNLTVPGSLRAVDI PGLKAATPYTVSIYGVIQGYRTPVLSAEASTGETPNLGEV VVAEVGWDALKLNWTAPEGAYEYFFIQVQEADTVEAAQ NLTVPGGLRSTDLPGLKAATHYTITIRGVTQDFSTTPLSVE VLTEEVPDMGNLTVTEVSWDALRLNWTTPDGTYDQFTIQ VQEADQVEEAHNLTVPGSLRSMEIPGLRAGTPYTVTLHGE VRGHSTRPLAVEVVTEDLPQLGDLAVSEVGWDGLRLNW TAADNAYEHFVIQVQEVNKVEAAQNLTLPGSLRAVDIPG LEAATPYRVSIYGVIRGYRTPVLSAEASTAKEAMGSPKEVI FSDITENSATVSWRAPTAQVESFRITYVPITGGTPSMVTVD GTKTQTRLVKLIPGVEYLVSIIAMKGFEESEPVSGSFTTAS GLNDIFEAQKIEWHEGTHHHHHH | 176 |
| huTnC A4 B | MSPILGYWKIGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI AWPLQGWQATFGGGDHPPKSDGSTSGSGHHHHHHSAGL VPRGSTAIGMKETAAAKFERQHMDSPDLGTGGGSGIEGR GSMGYRGSEDLPQLGDLAVSEVGWDGLRLNWTAADNA YEHFVIQVQEVNKVEAAQNLTLPGSLRAVDIPGLEAATPY RVSIYGVIRGYRTPVLSAEASTASGLNDIFEAQKIEWHEGT HHHHHH | 177 |
| huTnC A1 B | MSPILGYWKIGLVQPTRLLLEYLEEKYEEHLYERDEGDK WRNKKFELGLEFPNLPYYIDGDVKLTQSMAIIRYIADKHN MLGGCPKERAEISMLEGAVLDIRYGVSRIAYSKDFETLKV DFLSKLPEMLKMFEDRLCHKTYLNGDHVTHPDFMLYDAL DVVLYMDPMCLDAFPKLVCFKKRIEAIPQIDKYLKSSKYI AWPLQGWQATFGGGDHPPKSDGSTSGSGHHHHHHSAGL VPRGSTAIGMKETAAAKFERQHMDSPDLGTGGGSGIEGR GSMGYRGSEQAPELENLTVTEVGWDGLRLNWTAADQAY EHFIIQVQEANKVEAARNLTVPGSLRAVDIPGLKAATPYT VSIYGVIQGYRTPVLSAEASTASGLNDIFEAQKIEWHEGTH HHHHH | 178 |

2.2 Selection of TnC-Specific Antibodies 18D4 and 11C7 from Generic Fab Libraries Anti-TnC antibodies were selected from two different generic phage display libraries: DP88-4 (clone 18D4) and lambda-DP47 (clone 11C7).

Library Construction

The DP88-4 library was constructed on the basis of human germline genes using the V-domain pairing Vk1_5 (kappa light chain) and VH1_69 (heavy chain) comprising randomized sequence space in CDR3 of the light chain (L3, 3 different lengths) and CDR3 of the heavy chain (H3, 3 different lengths). Library generation was performed by assembly of 3 PCR-amplified fragments applying splicing by overlapping extension (SOE) PCR. Fragment 1 comprises the 5' end of the antibody gene including randomized L3, fragment 2 is a central constant fragment spanning from L3 to H3 whereas fragment 3 comprises randomized H3 and the 3' portion of the antibody gene. The following primer combinations were used to generate these library fragments for DP88-4 library: fragment 1 (forward primer LMB3 combined with reverse primers Vk1_5_L3r_S or Vk1_5_L3r_SY or Vk1_5_L3r_SPY), fragment 2 (forward primer RJH31 combined with reverse primer RJH32) and fragment 3 (forward primers DP88-v4-4 or DP88-v4-6 or DP88-v4-8 combined with reverse primer fdseqlong), respectively. PCR parameters for production of library fragments were 5 min initial denaturation at 94° C., 25 cycles of 1 min 94° C., 1 min 58° C., 1 min 72° C. and terminal elongation for 10 min at 72° C. For assembly PCR, using equimolar ratios of the gel-purified single fragments as template, parameters were 3 min initial denaturation at 94° C. and 5 cycles of 30 s 94° C., 1 min 58° C., 2 min 72° C. At this stage, outer primers (LMB3 and fdseqlong) were added and additional 20 cycles were performed prior to a terminal elongation for 10 min at 72° C. After assembly of sufficient amounts of full length randomized Fab constructs, they were digested NcoI/NheI and ligated into similarly treated acceptor phagemid vector. Purified ligations were used for ~60 transformations into electrocompetent *E. coli* TG1. Phagemid particles displaying the Fab library were rescued and purified by PEG/NaCl purification to be used for selections. These library construction steps were repeated three times to obtain a final library size of $4.4 \times 10^9$. Percentages of functional clones, as determined by C-terminal tag detection in dot blot, were 92.6% for the light chain and 93.7% for the heavy chain, respectively.

The lambda-DP47 library was constructed on the basis of human germline genes using the following V-domain pairings: Vl3_19 lambda light chain with VH3_23 heavy chain. The library was randomized in CDR3 of the light chain (L3) and CDR3 of the heavy chain (H3) and was assembled from 3 fragments by "splicing by overlapping extension" (SOE) PCR. Fragment 1 comprises the 5' end of the antibody gene including randomized L3, fragment 2 is a central constant fragment spanning from the end of L3 to the beginning of H3 whereas fragment 3 comprises randomized H3 and the 3' portion of the Fab fragment. The following primer combinations were used to generate library fragments for library: fragment 1 (LMB3—Vl_3_19_L3r_V/Vl_3_19_L3r_HV/Vl_3_19_L3r_HLV), fragment 2 (RJH80—DP47CDR3_ba (mod)) and fragment 3 (DP47-v4-4/DP47-v4-6/DP47-v4-8—fdseqlong). PCR parameters for production of library fragments were 5 min initial denaturation at 94° C., 25 cycles of 60 sec 94° C., 60 sec 55° C., 60 sec 72° C. and terminal elongation for 10 min at 72° C. For assembly PCR, using equimolar ratios of the 3 fragments as template, parameters were 3 min initial denaturation at 94° C. and 5 cycles of 60 s 94° C., 60 sec 55° C., 120 sec 72° C. At this stage, outer primers were added and additional 20 cycles were performed prior to a terminal elongation for 10 min at 72° C. After assembly of sufficient amounts of full length randomized Fab fragments, they were digested with NcoI/NheI alongside with similarly treated acceptor phagemid vector. 15 µg of Fab library insert were ligated with 13.3 µg of phagemid vector. Purified ligations were used for 60 transformations resulting in $1.5 \times 10^9$ transformants. Phagemid particles displaying the Fab library were rescued and purified by PEG/NaCl purification to be used for selections.

Phage Display Selections & ELISA Screening

Human GST-fused TnC fn5 A1234 BC fn6 as antigen for the phage display selections was expressed in *E. coli* and in vivo site-specifically biotinylated via co-expression of BirA biotin ligase at the avi-tag recognition sequence located at the C-terminus of the fusion protein (production of antigens according to Example 2.1, sequences derived from Table 14). This antigen comprises the human TnC extra splice domains A1, A2, A3, A4, B, and C, located between the two fibronectin type III domains 5 and 6. The phage display selections aimed at selecting binders to any of these extra splice domains and determine the domain specificity in a subsequent step by surface plasmon resonance using additional antigen constructs comprising fewer extra splice domains.

Selection rounds (biopanning) were performed in solution according to the following pattern: 1. Pre-clearing of ~$10^{12}$ phagemid particles with an unrelated GST-fusion protein that also carried an avi-tag and His6-tag similar to the TnC target antigen to deplete the libraries of antibodies recognizing the three different tags, 2. incubation of the pre-cleared phagemid particles in the supernatant with 100 nM biotinylated human GST-fused TnC fn5 A1234 BC fn6 for 0.5 hours in the presence of an unrelated non-biotinylated GST-fusion protein for further depletion of tag-binders in a total volume of 1 ml, 3. capture of biotinylated human GST-fused TnC fn5 A1234 BC fn6 and attached specifically binding phage by transfer to 4 wells of a neutravidin pre-coated microtiter plate for 10 minutes (in rounds 1 & 3), 4. washing of respective wells using 5×PBS/Tween20 and 5×PBS, 5. elution of phage particles by addition of 250 µl 100 mM TEA (triethylamine) per well for 10 minutes and neutralization by addition of 500 µl 1 M Tris/HCl pH 7.4 to the pooled eluates from 4 wells, 6. re-infection of log-phase *E. coli* TG1 cells with the supernatant of eluted phage particles, infection with helper phage VCSM13, incubation on a shaker at 30° C. over night and subsequent PEG/NaCl precipitation of phagemid particles to be used in the next selection round. Selections were carried out over 3 rounds using constant antigen concentrations of 100 nM. In round 2, in order to avoid enrichment of binders to neutravidin, capture of antigen: phage complexes was performed by addition of $5.4 \times 10^7$ streptavidin-coated magnetic beads. Specific binders were identified by ELISA after rounds 2 and 3 as follows: 100 µl of 100 nM biotinylated human GST-fused TnC fn5 A1234 BC fn6 were coated on neutravidin plates. Fab-containing bacterial supernatants were added and binding Fabs were detected via their Flag-tags using an anti-Flag/HRP secondary antibody. Clones exhibiting signals on human GST-fused TnC fn5 A1234 BC fn6 and being negative on an unrelated GST-fusion protein carrying the same tags as the target, were short-listed for further analyses. They were bacterially expressed in a 0.5 liter culture volume, affinity purified and further characterized by SPR-analysis using BioRad's ProteOn XPR36 biosensor to test cross-reactivity to murine TnC and to determine which extra splice domains the antibodies recognize.

SPR-Analysis Using BioRad's ProteOn XPR36 Biosensor

Affinities ($K_D$) of selected clones were measured by surface plasmon resonance (SPR) using a ProteOn XPR36 instrument (Biorad) at 25° C. with biotinylated human and murine TnC antigens immobilized on NLC chips by neutravidin capture. Immobilization of antigens (ligand): Recombinant antigens were diluted with PBST (10 mM phosphate, 150 mM sodium chloride pH 7.4, 0.005% Tween 20) to 10 µg/ml, then injected at 30 µl/minute in vertical orientation. Injection of analytes: For 'one-shot kinetics' measurements, injection direction was changed to horizontal orientation, two-fold dilution series of purified Fab were injected simultaneously along separate channels 1-5, with association times of 200 s, and dissociation times of 240 s, respectively. Buffer (PBST) was injected along the sixth channel to provide an "in-line" blank for referencing. Association rate constants (k$_{on}$) and dissociation rate constants (k$_{off}$) were calculated using a simple one-to-one Langmuir binding model in ProteOn Manager v3.1 software by simultaneously fitting the association and dissociation sensorgrams. The equilibrium dissociation constant (K$_D$) was calculated as the ratio k$_{off}$/k$_{on}$. Table 15 lists the equilibrium dissociation constants (K$_D$) of the two selected clones 18D4 and 11C7 for several TnC antigens differing in species and composition of the extra splice domains.

TABLE 17

Equilibrium dissociation constants (K$_D$) for clones 18D4 and 11C7

| Antigen | clone 18D4 K$_D$ [nM] | clone 11C7 K$_D$ [nM] |
|---|---|---|
| GST huTnC fn5 A1234 BC fn6 B | 4.0 | 2.3 |
| GST huTnCfn5 mu A124 BC hu fn6 B | 11.2 | 1.9 |
| GST TnC hu fn5 B-C fn6 B | n.a. | 1.0 |
| GST huTnC fn5 A1234 fn6 B | 5.0 | n.a. |
| huTnC A4 B | 2.0 | n.a. |
| huTnC A1 B | 5.6 | n.a. |

Table 3 shows the sequence of generic phage-displayed DP88-4 library (Vk1_5/VH1_69), Table 4 provides cDNA and amino acid sequences of library DP88-4 germline template and Table 5 shows the Primer sequences used for generation of DP88-4 germline template.

Table 9 shows the sequence of generic phage-displayed lambda-DP47 library (Vl3_19/VH3_23) template used for PCRs. Table 10 provides cDNA and amino acid sequences of lambda-DP47 library (Vl3_19/VH3_23) germline template and Table 11 shows the Primer sequences used for generation of lambda-DP47 library (Vl3_19/VH3_23).

2.3 Cloning of Variable Antibody Domains into Expression Vectors

The variable regions of heavy and light chain DNA sequences of the selected anti-TnC binders (Table 18 to Table 23) were subcloned in frame with either the constant heavy chain or the constant light chain of human IgG1. The antibodies were prepared either as wild type human IgG1 backbone, or as variants containing Pro329Gly, Leu234Ala and Leu235Ala mutations, which have been introduced to abrogate binding to Fc gamma receptors according to the method described in International Patent Appl. Publ. No. WO 2012/130831 A1.

The CDR sequences of the anti-TnC binder are shown in Table 20 to Table 23.
The base pair and amino acid sequences of the anti-TnC IgGs are shown in Table 24 and Table 25. The base pair and amino acid sequences of the anti-TnC P319GLALA IgGs are shown in Table 26 and Table 27. All antibody-encoding sequences were cloned into an expression vector, which drives transcription of the insert with a chimeric MPSV promoter and contains a synthetic polyA signal sequence located at the 3' end of the CDS. In addition, the vector contains an EBV OriP sequence for episomal maintenance of the plasmid.

LCDR3 of clone 11C7 (NSINSTRNEV (SEQ ID NO:51)), as selected by phage display, contains a potential N-glycosylation site, i.e. NST, which can potentially be removed by amino acid substitutions to facilitate production of a homogeneous product. At the same time, binding to the target should be retained. N (position 1) could preferentially be substituted by Q, S or T. Alternatively, S (position 2) could be replaced by P. Alternatively, T (position 3) could be substituted preferentially by G or N or by any other proteinogenic amino acid except for S or C. Whichever substitution(s) would be the best, can be determined empirically by those skilled in the art.

TABLE 18

Variable region base pair sequences for phage-derived anti-TnC antibodies

| Clone | Chain | Base pair sequence | SEQ ID NO |
|---|---|---|---|
| 18D4 | VL | GACATCCAGATGACCCAGTCTCCATCCACCCTGTCTG CATCTGTAGGAGACCGTGTCACCATCACTTGCCGTGC CAGTCAGAGTATTAGTAGCTGGTTGGCCTGGTATCAG CAGAAACCAGGGAAAGCCCCTAAGCTCCTGATCTATG ATGCCTCCAGTTTGGAAAGTGGGGTCCCATCACGTTT CAGCGGCAGTGGATCCGGGACAGAATTCACTCTCACC ATCAGCAGCTTGCAGCCTGATGATTTTGCAACTTATT ACTGCCAACAGAATAAGAAGTTTCCTTCGGGGACGTT TGGCCAGGGCACCAAAGTCGAGATCAAG | 179 |
| | VH | CAGGTGCAATTGGTGCAGTCTGGGGCTGAGGTGAAGA AGCCTGGGTCCTCGGTGAAGGTCTCCTGCAAGGCCTC CGGAGGCACATTCAGCAGCTACGCTATAAGCTGGGTG CGACAGGCCCCTGGACAAGGGCTCGAGTGGATGGGAG GGATCATCCCTATCTTTGGTACAGCAAACTACGCACA GAAGTTCCAGGGCAGGGTCACCATTACTGCAGACAAA TCCACGAGCACAGCCTACATGGAGCTGAGCAGCCTGA GATCTGAGGACACCGCCGTGTATTACTGTGCGAAAGG TAACTTCTACGGTGGTCTGGACTACTGGGGCCAAGGG ACCACCGTGACCGTCTCCTCA | 180 |
| 11C7 | VL | TCGTCTGAGCTGACTCAGGACCCTGCTGTGTCTGTGG CCTTGGGACAGACAGTCAGGGTCACATGCCAAGGAGA CAGCCTCAGAAGTTATTATGCAAGCTGGTACCAGCAG AAGCCAGGACAGGCCCCTGTACTTGTCATCTATGGTA AAAACAACCGGCCCTCAGGGATCCCAGACCGATTCTC TGGCTCCAGCTCAGGAAACACAGCTTCCTTGACCATC ACTGGGGCTCAGGCGGAAGATGAGGCTGACTATTACT GTAACTCCATTAATAGTACTCGTAATGAGGTATTCGG CGGAGGGACCAAGCTGACCGTCCTA | 181 |
| | VH | GAGGTGCAATTGTTGGAGTCTGGGGGAGGCTTGGTAC AGCCTGGGGGGTCCCTGAGACTCTCCTGTGCAGCCTC CGGATTCACCTTTAGCAGTTATGCCATGAGCTGGGTC CGCCAGGCTCCAGGGAAGGGGCTGGAGTGGGTCTCAG CTATTAGCGGTAGTGGTGGTAGCACATACTACGCAGA CTCCGTGAAGGGCCGGTTCACCATCTCCAAAGACAAT TCCAAGAACACGCTGTATCTGCAGATGAACAGCCTGA GAGCCGAGGACACGGCCGTATATTACTGTGCGAAAAC TTCTCCGCGTGTTCCGCTGGACTACTGGGGCCAAGGA ACCCTGGTCACCGTCTCGAGT | 182 |

TABLE 19

Variable region polypeptide sequences for phage-derived anti-TnC antibodies

| Clone | Chain | Polypeptide sequence | SEQ ID NO: |
|---|---|---|---|
| 18D4 | VL | DIQMTQSPSTLSASVGDRVTITCRASQSISSWLAWYQ QKPGKAPKLLIYDASSLESGVPSRFSGSGSGTEFTLT ISSLQPDDFATYYCQQNKKFPSGTFGQGTKVEIK | 53 |
| | VH | QVQLVQSGAEVKKPGSSVKVSCKASGGTFSSYAISWV RQAPGQGLEWMGGIIPIFGTANYAQKFQGRVTITADK STSTAYMELSSLRSEDTAVYYCAKGNFYGGLDYWGQG TTVTVSS | 52 |
| 11C7 | VL | SSELTQDPAVSVALGQTVRVTCQGDSLRSYYASWYQQ KPGQAPVLVIYGKNNRPSGIPDRFSGSSSGNTASLTI TGAQAEDEADYYCNSINSTRNEVFGGGTKLTVL | 55 |
| | VH | EVQLLESGGGLVQPGGSLRLSCAASGFTFSSYAMSWV RQAPGKGLEWVSAISGSGGSTYYADSVKGRFTISKDN | 54 |

TABLE 19-continued

Variable region polypeptide sequences for phage-derived anti-TnC antibodies

| Clone | Chain | Polypeptide sequence | SEQ ID NO: |
|---|---|---|---|
| | | SKNTLYLQMNSLRAEDTAVYYCAKTSPRVPLDYWGQGTLVTVSS | |

TABLE 20

CDR base pairs sequences of the anti-TnC antibody light chains

| clone | SEQ ID NO | LCDR1 | SEQ ID NO | LCDR2 | SEQ ID NO | LCDR3 |
|---|---|---|---|---|---|---|
| 18D4 | 183 | CGTGCCAGTCAGAGTATTAGTAGCTGGTTGGCC | 185 | GATGCCTCCAGTTTGGAAAGT | 187 | CAACAGAATAAGAAGTTTCCTTCGGGGACG |
| 11C7 | 184 | CAAGGAGACAGCCTCAGAAGTTATTATGCAAGC | 186 | GGTAAAAACAACCGGCCCTCA | 188 | AACTCCATTAATAGTACTCGTAATGAGGTA |

TABLE 21

CDR polypeptides sequences of the anti-TnC antibody light chains

| clone | SEQ ID NO | LCDR1 | SEQ ID NO | LCDR2 | SEQ ID NO | LCDR3 |
|---|---|---|---|---|---|---|
| 18D4 | 46 | RASQSISSWLA | 48 | DASSLES | 50 | QQNKKFPSGT |
| 11C7 | 47 | QGDSLRSYYAS | 49 | GKNNRPS | 51 | NSINSTRNEV |

TABLE 22

CDR base pairs sequences of the anti-TnC antibody heavy chains

| clone | SEQ ID NO | HCDR1 | SEQ ID NO | HCDR2 | SEQ ID NO | HCDR3 |
|---|---|---|---|---|---|---|
| 18D4 | 189 | AGCTACGCTATAAGC | 191 | GGGATCATCCCTATCTTTGGTACAGCAAACTACGCACAGAAGTTCCAGGGC | 193 | GGTAACTTCTACGGTGGTCTGGACTAC |
| 11C7 | 190 | GGATTCACCTTTAGCAGTTATGCCATGAGC | 192 | GCTATTAGCGGTAGTGGTGGTAGCACATACTACGCAGACTCCGTGAAGGGC | 194 | ACTTCTCCGCGTGTTCCGCTGGACTAC |

TABLE 23

CDR polypeptide sequences of the anti-TnC antibody heavy chains

| clone | SEQ ID NO | HCDR1 | SEQ ID NO | HCDR2 | SEQ ID NO | HCDR3 |
|---|---|---|---|---|---|---|
| 18D4 | 40 | SYAIS | 42 | GIIPIFGTANYAQKFQG | 44 | GNFYGGLDY |
| 11C7 | 41 | GFTFSSYAMS | 43 | AISGSGGSTYYADSVKG | 45 | TSPRVPLDY |

TABLE 24

Base pair sequences of anti-TnC clones in wild type human IgG1 format

| Clone | Chain | Base pair sequence | SEQ ID NO: |
|---|---|---|---|
| 18D4 | Light chain | GACATCCAGATGACCCAGTCTCCATCCACCCTGTCTGCATCTGTAGGAGACCGTGTCACCATCACTTGCCGTGCCAGTCAGAGTATTAGTAGCTGGTTGGCCTGGTATCAGCAGAAACCAGGGAAAGCCCCTAAGCTCCTGATCTATGATGCCTCCAGTTTGGAAAGTGGGGTCCCATCACGTTTCAGCGGCAGTGGATCCGGGACAGAATTCACTCTCACCATCAGCAGCTTGCAGCCTGATGATTTTGCAACTTATTACTGCCAACAGAATAAGAAGTTTCCTTCGGGGACGTTTGGCCAGGGCACCAAGTCGAGATCAAGCGTACGGTGGCTGCACCATCTGTCTTCATCTTCCCGCCATCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTCAGCAGCACCCTGACGCTGAGCAAAGCAGACTACGAGAAACAAAGTCTACGCCTGCGAAGTCACCCATCAGGGCCTGAGCTCGCCCGTCACAAAGAGCTTCAACAGGGGAGAGTGT | 195 |
| | Heavy chain | CAGGTGCAATTGGTGCAGTCTGGGGCTGAGGTGAAGAAGCCTGGGTCCTCGGTGAAGGTCTCCTGCAAGGCCTCCGGAGGCACATTCAGCAGCTACGCTATAAGCTGGGTGCGACAGGCCCCTGGACAAGGGCTCGAGTGGATGGGAGGGATCATCCCTATCTTTGGTACAGCAAACTACGCACAGAAGTTCCAGGGCAGGGTCACCATTACTGCAGACAAATCCACGAGCACAGCCTACATGGAGCTGAGCAGCCTGAGATCTGAGGACACCGCCGTGTATTACTGTGCGAAAGGTAACTTCTACGGTGGTCTGGACTACTGGGGCCAAGGGACCACCGTGACCGTCTCCTCAGCTAGCACCAAGGGCCCATCGGTCTTCCCCCTGGCACCCTCCTCCAAGAGCACCTCTGGGGGCACAGCGGCCCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTCCCTCAGCAGCGTGGTGACCGTGCCCTCCAGCAGCTTGGGCACCCAGACCTACATCTGCAACGTGAATCACAAGCCCAGCAACACCAAGGTGGACAAGAAAGTTGAGCCCAAATCTTGTGACAAAACTCACACATGCCCACCGTGCCCAGCACCTGAACTCCTGGGGGGACCGTCAGTCTTCCTCTTCCCCCCAAAACCCAAGGACACCCTCATGATCTCCCGGACCCCTGAGGTCACATGCGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCGTGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGGGCAGCCCCGAGAACCACAGGTGTACACCCTGCCCCATCCCGGGATGAGCTGACCAAGAACCAGGTCAGCCTGACCTGCCTGGTCAAAGGCTTCTATCCCAGCGACATCGCCGTGGAGTGGGAGAGCAATGGGCAGCCGGAGAACAACTACAAGACCACGCCTCCCGTGCT | 196 |

TABLE 24-continued

Base pair sequences of anti-TnC clones in wild type human IgG1 format

| Clone | Chain | Base pair sequence | SEQ ID NO: |
|---|---|---|---|
| | | GGACTCCGACGGCTCCTTCTTCCTCTACAGCAAGC TCACCGTGGACAAGAGCAGGTGGCAGCAGGGGA ACGTCTTCTCATGCTCCGTGATGCATGAGGCTCTG CACAACCACTACACGCAGAAGAGCCTCTCCCTGT CTCCGGGTAAA | |
| 11C7 | Light chain | TCGTCTGAGCTGACTCAGGACCCTGCTGTGTCTGT GGCCTTGGGACAGACAGTCAGGGTCACATGCCAA GGAGACAGCCTCAGAAGTTATTATGCAAGCTGGT ACCAGCAGAAGCCAGGACAGGCCCCTGTACTTGT CATCTATGGTAAAAACAACCGGCCCTCAGGGATC CCAGACCGATTCTCTGGCTCCAGCTCAGGAAACA CAGCTTCCTTGACCATCACTGGGGCTCAGGCGGA AGATGAGGCTGACTATTACTGTAACTCCATTAATA GTACTCGTAATGAGGTATTCGGCGGAGGGACCAA GCTGACCGTCCTAGGTCAACCCAAGGCTGCCCCC AGCGTGACCCTGTTCCCCCCCAGCAGCGAGGAAC TGCAGGCCAACAAGGCCACCCTGGTCTGCCTGAT CAGCGACTTCTACCCAGGCGCCGTGACCGTGGCC TGGAAGGCCGACAGCAGCCCCGTGAAGGCCGGCG TGGAGACCACCACCCCCAGCAAGCAGAGCAACAA CAAGTACGCCGCCAGCAGCTACCTGAGCCTGACC CCCGAGCAGTGGAAGAGCCACAGGTCCTACAGCT GCCAGGTGACCCACGAGGGCAGCACCGTGGAGAA AACCGTGGCCCCCACCGAGTGCAGC | 197 |
| | Heavy chain | GAGGTGCAATTGTTGGAGTCTGGGGGAGGCTTGG TACAGCCTGGGGGGTCCCTGAGACTCTCCTGTGCA GCCTCCGGATTCACCTTTAGCAGTTATGCCATGAG CTGGGTCCGCCAGGCTCCAGGGAAGGGGCTGGAG TGGGTCTCAGCTATTAGCGGTAGTGGTGGTAGCA CATACTACGCAGACTCCGTGAAGGGCCGGTTCAC CATCTCCAAAGACAATTCCAAGAACACGCTGTAT CTGCAGATGAACAGCCTGAGAGCCGAGGACACGG CCGTATATTACTGTGCGAAAACTTCTCCGCGTGTT CCGCTGGACTACTGGGGCCAAGGAACCCTGGTCA CCGTCTCGAGTGCTAGCACCAAGGGCCCATCGGT CTTCCCCCTGGCACCCTCCTCCAAGAGCACCTCTG GGGGCACAGCGGCCCTGGGCTGCCTGGTCAAGGA CTACTTCCCCGAACCGGTGACGGTGTCGTGGAACT CAGGCGCCCTGACCAGCGGCGTGCACACCTTCCC GGCTGTCCTACAGTCCTCAGGACTCTACTCCCTCA GCAGCGTGGTGACCGTGCCCTCCAGCAGCTTGGG CACCCAGACCTACATCTGCAACGTGAATCACAAG CCCAGCAACACCAAGGTGGACAAGAAAGTTGAGC CCAAATCTTGTGACAAAACTCACACATGCCCACC GTGCCCAGCACCTGAACTCCTGGGGGGACCGTCA GTCTTCCTCTTCCCCCCAAAACCCAAGGACACCCT CATGATCTCCCGGACCCCTGAGGTCACATGCGTG GTGGTGGACGTGAGCCACGAAGACCCTGAGGTCA AGTTCAACTGGTACGTGGACGGCGTGGAGGTGCA TAATGCCAAGACAAAGCCGCGGGAGGAGCAGTAC AACAGCACGTACCGTGTGGTCAGCGTCCTCACCG TCCTGCACCAGGACTGGCTGAATGGCAAGGAGTA CAAGTGCAAGGTCTCCAACAAAGCCCTCCCAGCC CCCATCGAGAAAACCATCTCCAAAGCCAAAGGGC AGCCCCGAGAACCACAGGTGTACACCCTGCCCCC ATCCCGGGATGAGCTGACCAAGAACCAGGTCAGC CTGACCTGCCTGGTCAAAGGCTTCTATCCCAGCGA CATCGCCGTGGAGTGGGAGAGCAATGGGCAGCCG GAGAACAACTACAAGACCACGCCTCCCGTGCTGG ACTCCGACGGCTCCTTCTTCCTCTACAGCAAGCTC ACCGTGGACAAGAGCAGGTGGCAGCAGGGGAAC GTCTTCTCATGCTCCGTGATGCATGAGGCTCTGCA CAACCACTACACGCAGAAGAGCCTCTCCCTGTCTC CGGGTAAA | 198 |

TABLE 25

Polypeptide sequences of anti-TnC clones in wild type human IgG1 format

| Clone | Chain | Polypeptide sequence | SEQ ID NO: |
|---|---|---|---|
| 18D4 | Light chain | DIQMTQSPSTLSASVGDRVTITCRASQSISSWLAWYQ QKPGKAPKLLIYDASSLESGVPSRFSGSGSGTEFTLT ISSLQPDDFATYYCQQNKKFPSGTFGQGTKVEIKRTV AAPSVFIFPPSDEQLKSGTASVVCLLNNFYPREAKVQ WKVDNALQSGNSQESVTEQDSKDSTYSLSSTLTLSKA DYEKHKVYACEVTHQGLSSPVTKSFNRGEC | 199 |
| | Heavy chain | QVQLVQSGAEVKKPGSSVKVSCKASGGTFSSYAISW VRQAPGQGLEWMGGIIPIFGTANYAQKFQGRVTITA DKSTSTAYMELSSLRSEDTAVYYCAKGNFYGGLDY WGQGTTVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKVE PKSCDKTHTCPPCPAPELLGGPSVFLFPPKPKDTLMI SRTPEVTCVVVDVSHEDPEVKFNWYVDGVEVHNAKT KPREEQYNSTYRVVSVLTVLHQDWLNGKEYKCKVS NKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALH NHYTQKSLSLSPGK | 200 |
| 11C7 | Light chain | SSELTQDPAVSVALGQTVRVTCQGDSLRSYYASWYQ QKPGQAPVLVIYGKNNRPSGIPDRFSGSSSGNTASLT ITGAQAEDEADYYCNSINSTRNEVFGGGTKLTVLGQP KAAPSVTLFPPSSEELQANKATLVCLISDFYPGAVTV AWKADSSPVKAGVETTTPSKQSNNKYAASSYLSLTP EQWKSHRSYSCQVTHEGSTVEKTVAPTECS | 201 |
| | Heavy chain | EVQLLESGGGLVQPGGSLRLSCAASGFTFSSYAMSW VRQAPGKGLEWVSAISGSGGSTYYADSVKGRFTISK DNSKNTLYLQMNSLRAEDTAVYYCAKTSPRVPLDY WGQGTLVTVSSASTKGPSVFPLAPSSKSTSGGTAALG CLVKDYFPEPVTVSWNSGALTSGVHTFPAVLQSSGL YSLSSVVTVPSSSLGTQTYICNVNHKPSNTKVDKKVE PKSCDKTHTCPPCPAPELLGGPSVFLFPPKPKDTLMI SRTPEVTCVVVDVSHEDPEVKFNWYVDGVEVHNAKT KPREEQYNSTYRVVSVLTVLHQDWLNGKEYKCKVS NKALPAPIEKTISKAKGQPREPQVYTLPPSRDELTKN QVSLTCLVKGFYPSDIAVEWESNGQPENNYKTTPPVL DSDGSFFLYSKLTVDKSRWQQGNVFSCSVMHEALH NHYTQKSLSLSPGK | 202 |

TABLE 26

Base pair sequences of anti-TnC clones in P329GLALA human IgG1 format

| Clone | Chain | Base pair sequence | SEQ ID NO: |
|---|---|---|---|
| 18D4 | Light chain | See Table 24 above | 195 |
| | Heavy chain PGLALA | CAGGTGCAATTGGTGCAGTCTGGGGCTGAGGT GAAGAAGCCTGGGTCCTCGGTGAAGGTCTCCT GCAAGGCCTCCGGAGGCACATTCAGCAGCTAC GCTATAAGCTGGGTGCGACAGGCCCCTGGACA AGGGCTCGAGTGGATGGGAGGGATCATCCCTA TCTTTGGTACAGCAAACTACGCACAGAAGTTC CAGGGCAGGGTCACCATTACTGCAGACAAATC CACGAGCACAGCCTACATGGAGCTGAGCAGCC TGAGATCTGAGGACACCGCCGTGTATTACTGT GCGAAAGGTAACTTCTACGGTGGTCTGGACTA CTGGGGCCAAGGGACCACCGTGACCGTCTCCT CAGCTAGCACCAAGGGCCCATCGGTCTTCCCC CTGGCACCCTCCTCCAAGAGCACCTCTGGGGG CACAGCGGCCCTGGGCTGCCTGGTCAAGGACT ACTTCCCCGAACCGGTGACGGTGTCGTGGAAC TCAGGCGCCCTGACCAGCGGCGTGCACACCTT CCCGGCTGTCCTACAGTCCTCAGGACTCTACTC CCTCAGCAGCGTGGTGACCGTGCCCTCCAGCA | 203 |

TABLE 26-continued

Base pair sequences of anti-TnC clones in P329GLALA human IgG1 format

| Clone | Chain | Base pair sequence | |
|---|---|---|---|
| | | GCTTGGGCACCCAGACCTACATCTGCAACGTG<br>AATCACAAGCCCAGCAACACCAAGGTGGACAA<br>GAAAGTTGAGCCCAAATCTTGTGACAAAACTC<br>ACACATGCCCACCGTGCCCAGCACCTGAAGCT<br>GCAGGGGGACCGTCAGTCTTCCTCTTCCCCCCA<br>AAACCCAAGGACACCCTCATGATCTCCCGGAC<br>CCCTGAGGTCACATGCGTGGTGGTGGACGTGA<br>GCCACGAAGACCCTGAGGTCAAGTTCAACTGG<br>TACGTGGACGGCGTGGAGGTGCATAATGCCAA<br>GACAAAGCCGCGGGAGGAGCAGTACAACAGC<br>ACGTACCGTGTGGTCAGCGTCCTCACCGTCCTG<br>CACCAGGACTGGCTGAATGGCAAGGAGTACAA<br>GTGCAAGGTCTCCAACAAAGCCCTCGGCGCCC<br>CCATCGAGAAAACCATCTCCAAAGCCAAAGGG<br>CAGCCCCGAGAACCACAGGTGTACACCCTGCC<br>CCCATCCCGGGATGAGCTGACCAAGAACCAGG<br>TCAGCCTGACCTGCCTGGTCAAAGGCTTCTATC<br>CCAGCGACATCGCCGTGGAGTGGGAGAGCAAT<br>GGGCAGCCGGAGAACAACTACAAGACCACGCC<br>TCCCGTGCTGGACTCCGACGGCTCCTTCTTCCT<br>CTACAGCAAGCTCACCGTGGACAAGAGCAGGT<br>GGCAGCAGGGGAACGTCTTCTCATGCTCCGTG<br>ATGCATGAGGCTCTGCACAACCACTACACGCA<br>GAAGAGCCTCTCCCTGTCTCCGGGTAAA | |
| | Light chain | See Table 24 above | 197 |
| 11C7 | Heavy chain PGLALA | GAGGTGCAATTGTTGGAGTCTGGGGGAGGCTT<br>GGTACAGCCTGGGGGGTCCCTGAGACTCTCCT<br>GTGCAGCCTCCGGATTCACCTTTAGCAGTTATG<br>CCATGAGCTGGGTCCGCCAGGCTCCAGGGAAG<br>GGGCTGGAGTGGGTCTCAGCTATTAGCGGTAG<br>TGGTGGTAGCACATACTACGCAGACTCCGTGA<br>AGGGCCGGTTCACCATCTCCAAAGACAATTCC<br>AAGAACACGCTGTATCTGCAGATGAACAGCCT<br>GAGAGCCGAGGACACGGCCGTATATTACTGTG<br>CGAAAACTTCTCCGCGTGTTCCGCTGGACTACT<br>GGGGCCAAGGAACCCTGGTCACCGTCTCGAGT<br>GCTAGCACCAAGGGCCCATCGGTCTTCCCCCTG<br>GCACCCTCCTCCAAGAGCACCTCTGGGGGCAC<br>AGCGGCCCTGGGCTGCCTGGTCAAGGACTACT<br>TCCCCGAACCGGTGACGGTGTCGTGGAACTCA<br>GGCGCCCTGACCAGCGGCGTGCACACCTTCCC<br>GGCTGTCCTACAGTCCTCAGGACTCTACTCCCT<br>CAGCAGCGTGGTGACCGTGCCCTCCAGCAGCT<br>TGGGCACCCAGACCTACATCTGCAACGTGAAT<br>CACAAGCCCAGCAACACCAAGGTGGACAAGA<br>AAGTTGAGCCCAAATCTTGTGACAAAACTCAC<br>ACATGCCCACCGTGCCCAGCACCTGAAGCTGC<br>AGGGGGACCGTCAGTCTTCCTCTTCCCCCCAAA<br>ACCCAAGGACACCCTCATGATCTCCCGGACCC<br>CTGAGGTCACATGCGTGGTGGTGGACGTGAGC<br>CACGAAGACCCTGAGGTCAAGTTCAACTGGTA<br>CGTGGACGGCGTGGAGGTGCATAATGCCAAGA<br>CAAAGCCGCGGGAGGAGCAGTACAACAGCAC<br>GTACCGTGTGGTCAGCGTCCTCACCGTCCTGCA<br>CCAGGACTGGCTGAATGGCAAGGAGTACAAGT<br>GCAAGGTCTCCAACAAAGCCCTCGGCGCCCCC<br>ATCGAGAAAACCATCTCCAAAGCCAAAGGGCA<br>GCCCCGAGAACCACAGGTGTACACCCTGCCCC<br>CATCCCGGGATGAGCTGACCAAGAACCAGGTC<br>AGCCTGACCTGCCTGGTCAAAGGCTTCTATCCC<br>AGCGACATCGCCGTGGAGTGGGAGAGCAATGG<br>GCAGCCGGAGAACAACTACAAGACCACGCCTC<br>CCGTGCTGGACTCCGACGGCTCCTTCTTCCTCT<br>ACAGCAAGCTCACCGTGGACAAGAGCAGGTGG<br>CAGCAGGGGAACGTCTTCTCATGCTCCGTGAT<br>GCATGAGGCTCTGCACAACCACTACACGCAGA<br>AGAGCCTCTCCCTGTCTCCGGGTAAA | 204 |

TABLE 27

Polypeptide sequences of anti-TnC clones in P329GLALA human IgG1 format.

| Clone | Chain | Polypeptide sequence | SEQ ID NO: |
|---|---|---|---|
| 18D4 | Light chain | See Table 25 above | 199 |
| | Heavy chain | QVQLVQSGAEVKKPGSSVKVSCKASGGTF SSYAISWVRQAPGQGLEWMGGIIPIFGTA NYAQKFQGRVTITADKSTSTAYMELSSLR SEDTAVYYCAKGNFYGGLDYWGQGTTVTV SSASTKGPSVFPLAPSSKSTSGGTAALGC LVKDYFPEPVTVSWNSGALTSGVHTFPAV LQSSGLYSLSSVVTVPSSSLGTQTYICNV NHKPSNTKVDKKVEPKSCDKTHTCPPCPA PEAAGGPSVFLFPPKPKDTLMISRTPEVT CVVVDVSHEDPEVKFNWYVDGVEVHNAKT KPREEQYNSTYRVVSVLTVLHQDWLNGKE YKCKVSNKALGAPIEKTISKAKGQPREPQ VYTLPPSRDELTKNQVSLTCLVKGFYPSD IAVEWESNGQPENNYKTTPPVLDSDGSFF LYSKLTVDKSRWQQGNVFSCSVMHEALHN HYTQKSLSLSPGK | 205 |
| 11C7 | Light chain | See Table 25 above | 201 |
| | Heavy chain | EVQLLESGGGLVQPGGSLRLSCAASGFTF SSYAMSWVRQAPGKGLEWVSAISGSGGST YYADSVKGRFTISKDNSKNTLYLQMNSLR AEDTAVYYCAKTSPRVPLDYWGQGTLVTV SSASTKGPSVFPLAPSSKSTSGGTAALGC LVKDYFPEPVTVSWNSGALTSGVHTFPAV LQSSGLYSLSSVVTVPSSSLGTQTYICNV NHKPSNTKVDKKVEPKSCDKTHTCPPCPA PEAAGGPSVFLFPPKPKDTLMISRTPEVT CVVVDVSHEDPEVKFNWYVDGVEVHNAKT KPREEQYNSTYRVVSVLTVLHQDWLNGKE YKCKVSNKALGAPIEKTISKAKGQPREPQ VYTLPPSRDELTKNQVSLTCLVKGFYPSD IAVEWESNGQPENNYKTTPPVLDSDGSFF LYSKLTVDKSRWQQGNVFSCSVMHEALHN HYTQKSLSLSPGK | 206 |

Example 3

Generation of Bispecific Antibodies Targeting OX40 and Tenascin C (TnC)

3.1 Generation of Bispecific Antibodies Targeting OX40 and Tenascin C (TnC)

Bispecific agonistic OX40 constructs with bivalent binding for OX40, and bivalent binding for TnC (i.e. '2+2' constructs) were prepared.

Figure 2:
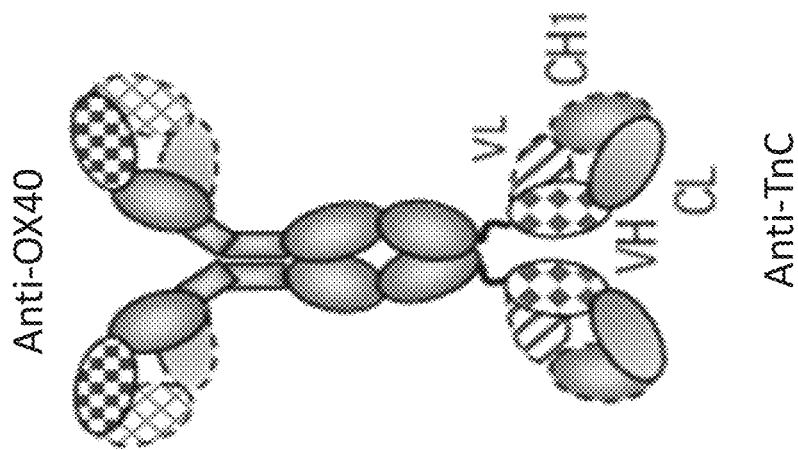
FIG. 2 shows a schematic representation of the bispecific, bivalent anti-OX40, bivalent anti-TnC huIgG1 P329GLALA 2+2 construct.

In this example, the heavy chain (HC) of the construct was comprised of the following components: VHCH1 of anti-OX40 49B4 Fc (P329G/LALA), followed by a (G4S)4 linker and VHCH1 of anti-TnC clone 18D4 or 11C7. The Pro329Gly, Leu234Ala and Leu235Ala mutations have been introduced in the constant region of the heavy chains to abrogate binding to Fc gamma receptors according to the method described in International Patent Appl. Publ. No. WO 2012/130831 A1. This heavy chain fusion was co-expressed with the light chain of the anti-Ox40 49B4 (VLCL) as well as the cross-Fab LC of 18D4 or 11C7 (VLCH1). Crossmab technology was employed for the TnC binding moiety to reduce the formation of wrongly paired light chains (see WO 2010/145792 A1). The resulting bispecific, bivalent construct is depicted in FIG. 2 and the sequences for base pair and amino acid can be found respectively in Table 28 and Table 29.

TABLE 28

Base pair sequences of mature
bispecific anti-Ox40, anti-TnC human IgG1
P329GLALA 2 + 2 format

| Clone | | SEQ ID NO: | Base pair sequence |
|---|---|---|---|
| 2 + 2 (49B4/18D4) | LC1 (pCON323) 49B4 VL/CL | 207 | GACATCCAGATGACCCAGTCTCCTTCCACCCT GTCTGCATCTGTAGGAGACCGTGTCACCATC ACTTGCCGTGCCAGTCAGAGTATTAGTAGCT GGTTGGCCTGGTATCAGCAGAAACCAGGGAA AGCCCCTAAGCTCCTGATCTATGATGCCTCCA GTTTGGAAAGTGGGGTCCCATCACGTTTCAG CGGCAGTGGATCCGGGACAGAATTCACTCTC ACCATCAGCAGCTTGCAGCCTGATGATTTTG CAACTTATTACTGCCAACAGTATAGTTCGCA GCCGTATACGTTTGGCCAGGGCACCAAAGTC GAGATCAAGCGTACGGTGGCTGCACCATCTG TCTTCATCTTCCCGCCATCTGATGAGCAGTTG AAATCTGGAACTGCCTCTGTTGTGTGCCTGCT GAATAACTTCTATCCCAGAGAGGCCAAAGTA CAGTGGAAGGTGGATAACGCCCTCCAATCGG GTAACTCCCAGGAGAGTGTCACAGAGCAGGA CAGCAAGGACAGCACCTACAGCCTCAGCAGC ACCCTGACGCTGAGCAAAGCAGACTACGAGA AACACAAAGTCTACGCCTGCGAAGTCACCCA TCAGGGCCTGAGCTCGCCCGTCACAAAGAGC TTCAACAGGGGAGAGTGT |
| | HC pETR14728 49B4 VHCH1_Fc_PG/ LALA_18D4VHCL | 208 | CAGGTGCAATTGGTGCAGTCTGGGGCTGAGG TGAAGAAGCCTGGGTCCTCGGTGAAGGTCTC CTGCAAGGCCTCCGGAGGCACATTCAGCAGC TACGCTATAAGCTGGGTGCGACAGGCCCCTG GACAAGGGCTCGAGTGGATGGGAGGGATCA TCCCTATCTTTGGTACAGCAAACTACGCACA GAAGTTCCAGGGCAGGGTCACCATTACTGCA GACAAATCCACGAGCACAGCCTACATGGAGC TGAGCAGCCTGAGATCTGAGGACACCGCCGT GTATTACTGTGCGAGAGAATACTACCGTGGT CCGTACGACTACTGGGGCCAAGGGACCACCG TGACCGTCTCCTCAGCTAGCACCAAGGGCCC ATCCGTGTTCCCTCTGGCCCCTTCCAGCAAGT CTACCTCTGGCGGCACAGCCGCTCTGGGCTG CCTCGTGAAGGACTACTTCCCCGAGCCTGTG ACAGTGTCCTGGAACTCTGGCGCCCTGACAT CCGGCGTGCACACCTTTCCAGCTGTGCTGCA GTCCTCCGGCCTGTACTCCCTGTCCTCCGTCG TGACAGTGCCCTCCAGCTCTCTGGGCACCCA GACCTACATCTGCAACGTGAACCACAAGCCC TCCAACACCAAGGTGGACAAGAAGGTGGAA CCCAAGTCCTGCGACAAGACCCACACCTGTC CCCCTTGTCCTGCCCCTGAAGCTGCTGGCGGC CCTAGCGTGTTCCTGTTCCCCCCAAAGCCCAA GGACACCCTGATGATCTCCCGGACCCCCGAA GTGACCTGCGTGGTGGTGGATGTGTCCCACG AGGACCCTGAAGTGAAGTTCAATTGGTACGT GGACGGCGTGGAAGTGCACAATGCCAAGAC CAAGCCTAGAGAGGAACAGTACAACTCCACC TACCGGGTGGTGTCCGTGCTGACCGTGCTGC ACCAGGATTGGCTGAACGGCAAAGAGTACA AGTGCAAGGTGTCCAACAAGGCCCTGGGAGC CCCCATCGAAAAGACCATCTCCAAGGCCAAG GGCCAGCCTCGCGAGCCTCAGGTGTACACCC TGCCCCCTAGCAGAGATGAGCTGACCAAGAA CCAGGTGTCCCTGACCTGTCTCGTGAAAGGC TTCTACCCCTCCGATATCGCCGTGGAATGGG AGAGCAACGGCCAGCCCGAGAACAACTACA AGACCACCCCCCCTGTGCTGGACTCCGACGG CTCATTCTTCCTGTACTCTAAGCTGACAGTGG ACAAGTCCCGGTGGCAGCAGGGCAACGTGTT CTCCTGCTCCGTGATGCACGAGGCCCTGCAC AACCACTACACCCAGAAGTCCCTGTCCCTGT CTCCCGGGGGAGGCGGTGGATCTGGCGGAGG CGGATCCGGTGGTGGCGGTTCCGGGGGCGGT GGATCGCAGGTGCAATTGGTGCAGTCTGGGG CTGAGGTGAAGAAGCCTGGGTCCTCGGTGAA GGTCTCCTGCAAGGCCTCCGGAGGCACATTC AGCAGCTACGCTATAAGCTGGGTGCGACAGG CCCCTGGACAAGGGCTCGAGTGGATGGGAGG GATCATCCCTATCTTTGGTACAGCAAACTAC GCACAGAAGTTCCAGGGCAGGGTCACCATTA |

TABLE 28-continued

Base pair sequences of mature
bispecific anti-Ox40, anti-TnC human IgG1
P329GLALA 2 + 2 format

| Clone | | SEQ ID NO: | Base pair sequence |
|---|---|---|---|
| | | | CTGCAGACAAATCCACGAGCACAGCCTACAT GGAGCTGAGCAGCCTGAGATCTGAGGACACC GCCGTGTATTACTGTGCGAAAGGTAACTTCT ACGGTGGTCTGGACTACTGGGGCCAAGGGAC CACCGTGACCGTCTCCAGCGCTTCTGTGGCC GCTCCCTCCGTGTTCATCTTCCCACCTTCCGA CGAGCAGCTGAAGTCCGGCACTGCCTCTGTC GTGTGCCTGCTGAACAACTTCTACCCTCGGG AAGCCAAGGTGCAGTGGAAAGTGGATAACG CCCTGCAGTCCGGCAACTCCCAGGAATCCGT GACCGAGCAGGACTCCAAGGACAGCACCTAC TCCCTGAGCAGCACCCTGACCCTGTCCAAGG CCGACTACGAGAAGCACAAGGTGTACGCCTG TGAAGTGACCCACCAGGGCCTGTCCAGCCCC GTGACCAAGTCCTTCAACCGGGGCGAGTGCT GA |
| | LC2 pETR14647 18D4 VLCH1 | 209 | GACATCCAGATGACCCAGTCTCCATCCACCC TGTCTGCATCTGTAGGAGACCGTGTCACCAT CACTTGCCGTGCCAGTCAGAGTATTAGTAGC TGGTTGGCCTGGTATCAGCAGAAACCAGGGA AAGCCCCTAAGCTCCTGATCTATGATGCCTCC AGTTTGGAAAGTGGGGTCCCATCACGTTTCA GCGGCAGTGGATCCGGGACAGAATTCACTCT CACCATCAGCAGCTTGCAGCCTGATGATTTT GCAACTTATTACTGCCAACAGAATAAGAAGT TTCCTTCGGGGACGTTTGGCCAGGGCACCAA AGTCGAGATCAAGAGCTCCGCTAGCACCAAG GGCCCCTCCGTGTTTCCTCTGGCCCCCAGCAG CAAGAGCACCTCTGGCGGAACAGCCGCCCTG GGCTGCCTGGTGAAGACTACTTCCCCGAGC CCGTGACCGTGTCCTGGAACTCTGGCGCCCT GACCAGCGGCGTGCACACCTTTCCAGCCGTG CTGCAGAGCAGCGGCCTGTACTCCCTGAGCA GCGTGGTGACAGTGCCCTCCAGCAGCCTGGG CACCCAGACCTACATCTGCAACGTGAACCAC AAGCCCAGCAACACCAAAGTGGACAAGAAG GTGGAACCCAAGAGCTGCGAC |
| 2 + 2 (49B4/11C7) | LC1 pCON323 49B4VLCL | 207 | See above |
| | HC pETR14727 49B4VHCH1_Fc_PG/ LALA_11C7VHCL | 210 | CAGGTGCAATTGGTGCAGTCTGGGGCTGAGG TGAAGAAGCCTGGGTCCTCGGTGAAGGTCTC CTGCAAGGCCTCCGGAGGCACATTCAGCAGC TACGCTATAAGCTGGGTGCGACAGGCCCCTG GACAAGGGCTCGAGTGGATGGGAGGGATCA TCCCTATCTTTGGTACAGCAAACTACGCACA GAAGTTCCAGGGCAGGGTCACCATTACTGCA GACAAATCCACGAGCACAGCCTACATGGAGC TGAGCAGCCTGAGATCTGAGGACACCGCCGT GTATTACTGTGCGAGAGAATACTACCGTGGT CCGTACGACTACTGGGGCCAAGGGACCACCG TGACCGTCTCCTCAGCTAGCACCAAGGGCCC ATCCGTGTTCCCTCTGGCCCCTTCCAGCAAGT CTACCTCTGGCGGCACAGCCGCTCTGGGCTG CCTCGTGAAGGACTACTTCCCCGAGCCTGTG ACAGTGTCCTGGAACTCTGGCGCCCTGACAT CCGGCGTGCACACCTTTCCAGCTGTGCTGCA GTCCTCCGGCCTGTACTCCCTGTCCTCCGTCG TGACAGTGCCCTCCAGCTCTCTGGGCACCCA GACCTACATTTGCAACGTGAACCACAAGCCC TCCAACACCAAGGTGGACAAGAAGGTGGAA CCCAAGTCCTGCGACAAGACCCACACCTGTC CCCCTTGTCCTGCCCCTGAAGCTGCTGGCGGC CCTAGCGTGTTCCTGTTCCCCCCAAAGCCCAA GGACACCCTGATGATCTCCCGGACCCCCGAA GTGACCTGCGTGGTGGTGGATGTGTCCCACG AGGACCCTGAAGTGAAGTTCAATTGGTACGT GGACGGCGTGGAAGTGCACAATGCCAAGAC CAAGCCTAGAGAGGAACAGTACAACTCCACC TACCGGGTGGTGTCCGTGCTGACCGTGCTGC ACCAGGATTGGCTGAACGGCAAAGAGTACA AGTGCAAGGTGTCCAACAAGGCCCTGGGAGC |

TABLE 28-continued

Base pair sequences of mature bispecific anti-Ox40, anti-TnC human IgG1 P329GLALA 2 + 2 format

| Clone | | SEQ ID NO: | Base pair sequence |
|---|---|---|---|
| | | | CCCCATCGAAAAGACCATCTCCAAGGCCAAG GGCCAGCCTCGCGAGCCTCAGGTGTACACCC TGCCCCCTAGCAGAGATGAGCTGACCAAGAA CCAGGTGTCCCTGACCTGTCTCGTGAAAGGC TTCTACCCCTCCGATATCGCCGTGGAATGGG AGAGCAACGGCCAGCCCGAGAACAACTACA AGACCACCCCCCCTGTGCTGGACTCCGACGG CTCATTCTTCCTGTACTCTAAGCTGACAGTGG ACAAGTCCCGGTGGCAGCAGGGCAACGTGTT CTCCTGCTCCGTGATGCACGAGGCCCTGCAC AACCACTACACCCAGAAGTCCCTGTCCCTGT CTCCCGGGGGAGGCGGTGGATCTGGCGGAGG CGGATCCGGTGGTGGCGGTTCCGGGGGCGGT GGATCGGAGGTGCAATTGTTGGAGTCTGGGG GAGGCTTGGTACAGCCTGGGGGGTCCCTGAG ACTCTCCTGTGCAGCCTCCGGATTCACCTTTA GCAGTTATGCCATGAGCTGGGTCCGCCAGGC TCCAGGGAAGGGGCTGGAGTGGGTCTCAGCT ATTAGCGGTAGTGGTGGTAGCACATACTACG CAGACTCCGTGAAGGGCCGGTTCACCATCTC CAAAGACAATTCCAAGAACACGCTGTATCTG CAGATGAACAGCCTGAGAGCCGAGGACACG GCCGTATATTACTGTGCGAAAACTTCTCCGC GTGTTCCGCTGGACTACTGGGGCCAAGGAAC CCTGGTCACCGTCTCGAGCGCTTCTGTGGCCG CTCCCTCCGTGTTCATCTTCCCACCTTCCGAC GAGCAGCTGAAGTCCGGCACTGCCTCTGTCG TGTGCCTGCTGAACAACTTCTACCCTCGGGA AGCCAAGGTGCAGTGGAAAGTGGATAACGC CCTGCAGTCCGGCAACTCCCAGGAATCCGTG ACCGAGCAGGACTCCAAGGACAGCACCTACT CCCTGAGCAGCACCCTGACCCTGTCCAAGGC CGACTACGAGAAGCACAAGGTGTACGCCTGT GAAGTGACCCACCAGGGCCTGTCCAGCCCCG TGACCAAGTCCTTCAACCGGGGCGAGTGC |
| LC2 pETR14648 11C7VLCH1 | | 211 | TCGTCTGAGCTGACTCAGGACCCTGCTGTGTC TGTGGCCTTGGGACAGACAGTCAGGGTCACA TGCCAAGGAGACAGCCTCAGAAGTTATTATG CAAGCTGGTACCAGCAGAAGCCAGGACAGG CCCCTGTACTTGTCATCTATGGTAAAAACAA CCGGCCCTCAGGGATCCCAGACCGATTCTCT GGCTCCAGCTCAGGAAACACAGCTTCCTTGA CCATCACTGGGGCTCAGGCGGAAGATGAGGC TGACTATTACTGTAACTCCATTAATAGTACTC GTAATGAGGTATTCGGCGGAGGGACCAAGCT GACCGTCCTAAGCTCCGCTAGCACCAAGGGC CCCTCCGTGTTCCTCTGGCCCCCAGCAGCAA GAGCACCTCTGGCGGAACAGCCGCCCTGGGC TGCCTGGTGAAAGACTACTTCCCCGAGCCCG TGACCGTGTCCTGGAACTCTGGCGCCCTGAC CAGCGGCGTGCACACCTTTCCAGCCGTGCTG CAGAGCAGCGGCCTGTACTCCCTGAGCAGCG TGGTGACAGTGCCCTCCAGCAGCCTGGGCAC CCAGACCTACATCTGCAACGTGAACCACAAG CCCAGCAACACCAAAGTGGACAAGAAGGTG GAACCCAAGAGCTGCGACTGAT |

TABLE 29

Amino acid sequence of mature bispecific anti-Ox40, anti-TNC human IgG1 P329GLALA 2 + 2 format

| Clone | | SEQ ID NO: | Amino acid sequence |
|---|---|---|---|
| 2 + 2 (49B4/18D4) | LC1 (pCON323) | 212 | DIQMTQSPSTLSASVGDRVTITCRASQSISSWLA WYQQKPGKAPKLLIYDASSLESGVPSRFSGSGS GTEFTLTISSLQPDDFATYYCQQYSSQPYTFGQ GTKVEIKRTVAAPSVFIFPPSDEQLKSGTASVVC |

TABLE 29-continued

Amino acid sequence of mature
bispecific anti-Ox40, anti-TNC human IgG1
P329GLALA 2 + 2 format

| Clone | | SEQ ID NO: | Amino acid sequence |
|---|---|---|---|
| | HC pETR14728 49B4 VHCH1_Fc_PG/ LALA_18D4VHCL) | 213 | LLNNFYPREAKVQWKVDNALQSGNSQESVTE QDSKDSTYSLSSTLTLSKADYEKHKVYACEVT HQGLSSPVTKSFNRGEC QVQLVQSGAEVKKPGSSVKVSCKASGGTFSSY AISWVRQAPGQGLEWMGGIIPIFGTANYAQKF QGRVTITADKSTSTAYMELSSLRSEDTAVYYC AREYYRGPYDYWGQGTTVTVSSASTKGPSVFP LAPSSKSTSGGTAALGCLVKDYFPEPVTVSWNS GALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTPEV TCVVVDVSHEDPEVKFNWYVDGVEVHNAKTK PREEQYNSTYRVVSVLTVLHQDWLNGKEYKC KVSNKALGAPIEKTISKAKGQPREPQVYTLPPS RDELTKNQVSLTCLVKGFYPSDIAVEWESNGQ PENNYKTTPPVLDSDGSFFLYSKLTVDKSRWQ QGNVFSCSVMHEALHNHYTQKSLSLSPGGGGG SGGGGSGGGGSGGGGSQVQLVQSGAEVKKPG SSVKVSCKASGGTFSSYAISWVRQAPGQGLEW MGGIIPIFGTANYAQKFQGRVTITADKSTSTAY MELSSLRSEDTAVYYCAKGNFYGGLDYWGQG TTVTVSSASVAAPSVFIFPPSDEQLKSGTASVVC LLNNFYPREAKVQWKVDNALQSGNSQESVTE QDSKDSTYSLSSTLTLSKADYEKHKVYACEVT HQGLSSPVTKSFNRGEC |
| | LC2 pETR14647 18D4 VLCH1 | 214 | DIQMTQSPSTLSASVGDRVTITCRASQSISSWLA WYQQKPGKAPKLLIYDASSLESGVPSRFSGSGS GTEFTLTISSLQPDDFATYYCQQNKKFPSGTFG QGTKVEIKSSASTKGPSVFPLAPSSKSTSGGTAA LGCLVKDYFPEPVTVSWNSGALTSGVHTFPAV LQSSGLYSLSSVVTVPSSSLGTQTYICNVNHKPS NTKVDKKVEPKSCD |
| 2 + 2 49B4/11C7 | LC (pCON323) | 212 | See above |
| | HC pETR14727 49B4VHCH1_Fc_PG/ LALA_11C7VHCL | 215 | QVQLVQSGAEVKKPGSSVKVSCKASGGTFSSY AISWVRQAPGQGLEWMGGIIPIFGTANYAQKF QGRVTITADKSTSTAYMELSSLRSEDTAVYYC AREYYRGPYDYWGQGTTVTVSSASTKGPSVFP LAPSSKSTSGGTAALGCLVKDYFPEPVTVSWNS GALTSGVHTFPAVLQSSGLYSLSSVVTVPSSSL GTQTYICNVNHKPSNTKVDKKVEPKSCDKTHT CPPCPAPEAAGGPSVFLFPPKPKDTLMISRTPEV TCVVVDVSHEDPEVKFNWYVDGVEVHNAKTK PREEQYNSTYRVVSVLTVLHQDWLNGKEYKC KVSNKALGAPIEKTISKAKGQPREPQVYTLPPS RDELTKNQVSLTCLVKGFYPSDIAVEWESNGQ PENNYKTTPPVLDSDGSFFLYSKLTVDKSRWQ QGNVFSCSVMHEALHNHYTQKSLSLSPGGGGG SGGGGSGGGGSGGGGSEVQLLESGGGLVQPGG SLRLSCAASGFTFSSYAMSWVRQAPGKGLEWV SAISGSGGSTYYADSVKGRFTISKDNSKNTLYL QMNSLRAEDTAVYYCAKTSPRVPLDYWGQGT LVTVSSASVAAPSVFIFPPSDEQLKSGTASVVCL LNNFYPREAKVQWKVDNALQSGNSQESVTEQ DSKDSTYSLSSTLTLSKADYEKHKVYACEVTH QGLSSPVTKSFNRGEC |
| | LC2 pETR14648 11C7VLCH1 | 216 | SSELTQDPAVSVALGQTVRVTCQGDSLRSYYA SWYQQKPGQAPVLVIYGKNNRPSGIPDRFSGSS SGNTASLTITGAQAEDEADYYCNSINSTRNEVF GGGTKLTVLSSASTKGPSVFPLAPSSKSTSGGT AALGCLVKDYFPEPVTVSWNSGALTSGVHTFP AVLQSSGLYSLSSVVTVPSSSLGTQTYICNVNH KPSNTKVDKKVEPKSCD |

All genes were transiently expressed under control of a chimeric MPSV promoter consisting of the MPSV core promoter combined with the CMV promoter enhancer fragment. The expression vector also contains the oriP region for episomal replication in EBNA (Epstein Barr Virus Nuclear Antigen) containing host cells.

The bispecific anti-OX40, anti-TnC 2+2 constructs were produced by co-transfecting HEK293-EBNA cells with the mammalian expression vectors using polyethylenimine. The cells were transfected with the corresponding expression vectors in a 1:1:1 ratio ("vector LC1":"vector HC":"vector LC2").

For a 200 mL production in 500 mL shake flasks, 250 million HEK293 EBNA cells were seeded 24 hours before transfection in Excell media with supplements. For transfection, the cells were centrifuged for 5 minutes at 210× g, and supernatant was replaced by pre-warmed CD-CHO medium. Expression vectors were mixed in 20 mL CD-CHO medium to a final amount of 200 µg DNA. After addition of 540 µL PEI (1 mg/mL), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere and shaking at 165 rpm. After the incubation, 160 mL Excell medium with supplements was added and cells were cultured for 24 hours. At this point the valproic acid concentration is 1 mM (in the media there's as well 5 g/L PepSoy and 6 mM L-Glutamine). 24 h after transfection the cells are supplement with Feed 7 at 12% final volume (24 mL) and 3 g/L glucose (1.2 mL from 500 g/L stock). After culturing for 7 days, the cell supernatant was collected by centrifugation for 45 minutes at 2000-3000× g. The solution was sterile filtered (0.22 µm filter), supplemented with sodium azide to a final concentration of 0.01% (w/v), and stored at 4° C.

Purification of bispecific constructs from cell culture supernatants was carried out by affinity chromatography using MabSelectSure. The protein was concentrated and filtered prior to loading on a HiLoad Superdex 200 column (GE Healthcare) equilibrated with 20 mM Histidine, 140 mM NaCl, 0.01% Tween-20 solution of pH 6.0.

For affinity chromatography, the supernatant was loaded on a ProtA MabSelect Sure column (CV=5 mL, GE Healthcare) equilibrated with 30 mL 20 mM Sodium Citrate, 20 mM Sodium Phosphate, pH 7.5. Unbound protein was removed by washing with 6-10 column volumes of a buffer containing 20 mM sodium phosphate, 20 mM sodium citrate and 0.5 M sodium chloride (pH 7.5). The bound protein was eluted using either a step or a linear pH-gradient of 15 CVs of sodium chloride (from 0 to 100%) of 20 mM Sodium Citrate, 100 mM Sodium Chloride, 100 mM Glycine, 0.01% (v/v) Tween-20, pH 3.0. The column was then washed with 10 column volumes of a solution containing 20 mM Sodium Citrate, 100 mM Sodium Chloride, 100 mM Glycine, 0.01% (v/v) Tween-20, pH 3.0 followed by a re-equilibration step.

The pH of the collected fractions was adjusted by adding 1/10 (v/v) of 0.5 M Na2HPO4, pH 8.0. The protein was concentrated and filtered prior to loading on a HiLoad Superdex 200 column (GE Healthcare) equilibrated with 20 mM Histidine, 140 mM NaCl, pH 6.0, 0.01% Tween20.

The protein concentration of purified bispecific constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM K2HPO4, 125 mM NaCl, 200 mM L-Arginine Monohydrocloride, 0.02% (w/v) NaN3, pH 6.7 running buffer at 25° C. (Table 30).

TABLE 30

Biochemical analysis of bispecific anti-OX40, anti-TnC IgG1 P329G LALA 2 + 2 constructs

| Clone | Yield [mg/l] | Monomer [%] | CE-SDS (non red) | CE-SDS (red) |
|---|---|---|---|---|
| 49B4/TnC 18D4 P329GLALA 2 + 2 (ID7216) | 10.24 | 99.14 0.86% HMW | 94.58% (254 kDa) 5.42% (233 kDa) | 0.73% (347 kDa) 4.51% (118 kDa) 46.88% (94 kDa) 1.99% (32 kDa) 27.6% (29 kDa) 17.44% (27 kDa) 0.85% (19 kDa) |
| 49B4/TnC 11C7 P329GLALA 2 + 2 (ID7215) | 6.52 | 95.14 4.86 HMW | 57.95% (270 kDa)) 18.77% (242 kDa) 0.84% (236 kDa) 2.45% (222 kDa) 11.45% (217 kDa) 3.93% (32 kDa) 4.64% (11.5 kDa) | 0.27% (190 kDa) 2.46% (127 kDa) 0.35% (121 kDa) 54.00% (93 kDa) 10.66% (38 kDa) 1.96% (32 kDa) 30.29% (29 kDa) |

3.2 Generation of Bispecific Antibodies Targeting OX40 and Tenascin C (TnC) (4+1 and 4+2)

Bispecific agonistic OX40 constructs with tetravalent binding for OX40, and monovalent binding for TnC (i.e. '4+1') or bivalent binding for TnC (i.e. '4+2') were prepared. The crossmab technology was applied for the TnC binding moiety in the 4+2 format to reduce the formation of wrongly paired light chains (see WO 2010/145792 A1).

For the 4+1 construct, HC1 of the construct was comprised of the following components: VHCH1_VHCH1 of anti-OX40 49B4_Fc hole (P329G/LALA) followed by a (G4S)4 linker and VL of anti-TnC clone 18D4. HC2 was comprised of VHCH1_VHCH1 of anti-OX40 49B4 followed by Fc knob (P329G/LALA) (G4S)4 linker fused to VH of anti-TnC clone 18D4. The knob into hole technology is described in e.g. in U.S. Pat. Nos. 5,731,168 and 7,695,936 and allows the assembly of the HC1 and HC2. The heavy chain fusion polypeptides were co-expressed with the light chain of the anti-OX40 clone 49B4 (CLVL).

For the 4+2 construct, the HC of the construct is comprised of the following components: VHCH1_VHCH1 of anti-OX40 49B4_Fc (P329G/LALA) followed by a (G4S)4 linker, followed by a crossed Fab unit (VLCH1) of the TnC binding clone 18D4 fused to the C-terminus of the Fc. The heavy chain fusion polypeptides were co-expressed with the light chain (LC1) of the anti-OX40 clone 49B4 (CLVL). The CH and CL of the anti-OX40 Fabs contained charged residues to prevent the generation of Bence Jones proteins and to further stabilize the correct pairing of LC1 to the HCs.

Specifically, the substitutions E123R and Q124K (residues according to EU numbering) were made in the CL domain of the OX40(49B4) VLCL light chain (SEQ ID NO:212), resulting in the light chain sequence SEQ ID NO:224; and the substitutions K147E and K213E (residues according to EU numbering) were made in the CH1 domain of OX40(49B4), resulting in the heavy chain sequence SEQ ID NO:220, In this case the introduction of a knob into hole was not necessary as both HCs contain the same domains. The heavy chain fusion polypeptides and LC1 polypeptides were co-expressed with polypeptide encoding the VH and CL of the anti-TnC binding clone 18D4.

The Pro329Gly, Leu234Ala and Leu235Ala mutations were introduced in the constant region of the heavy chains of the 4+1 and 4+2 constructs to abrogate binding to Fc gamma receptors according to the method described in International Patent Appl. Publ. No. WO 2012/130831 A1.

Figure 3A:
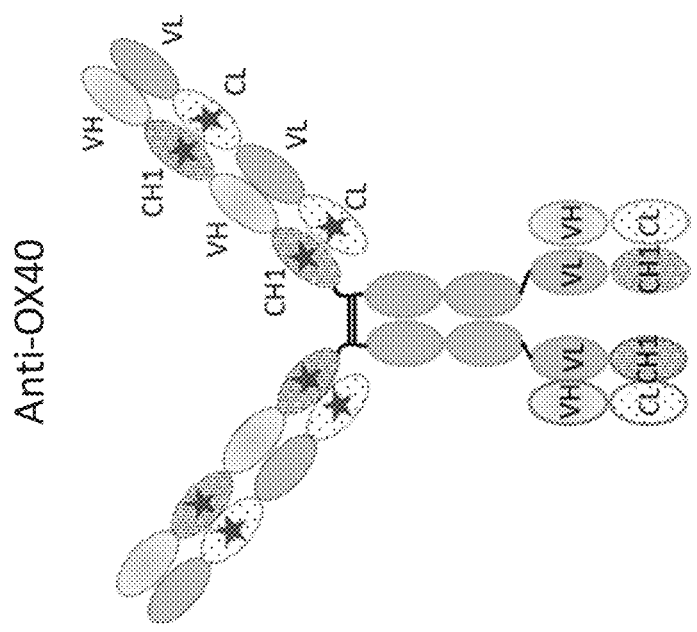
FIG. 3A shows a schematic representation of the bispecific, tetravalent anti-OX40, monovalent anti-TnC huIgG1 P329GLALA kih 4+1 construct.
Figure 3B:
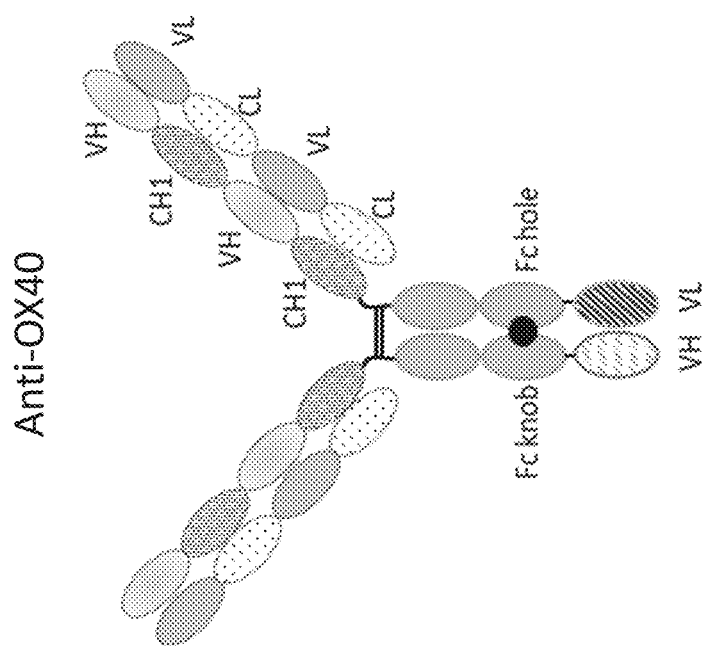
FIG. 3B shows a schematic representation of the bispecific, tetravalent anti-OX40, bivalent anti-TnC huIgG1 P329GLALA 4+2 construct. Charged residues are depicted as stars.
Figure 4A:
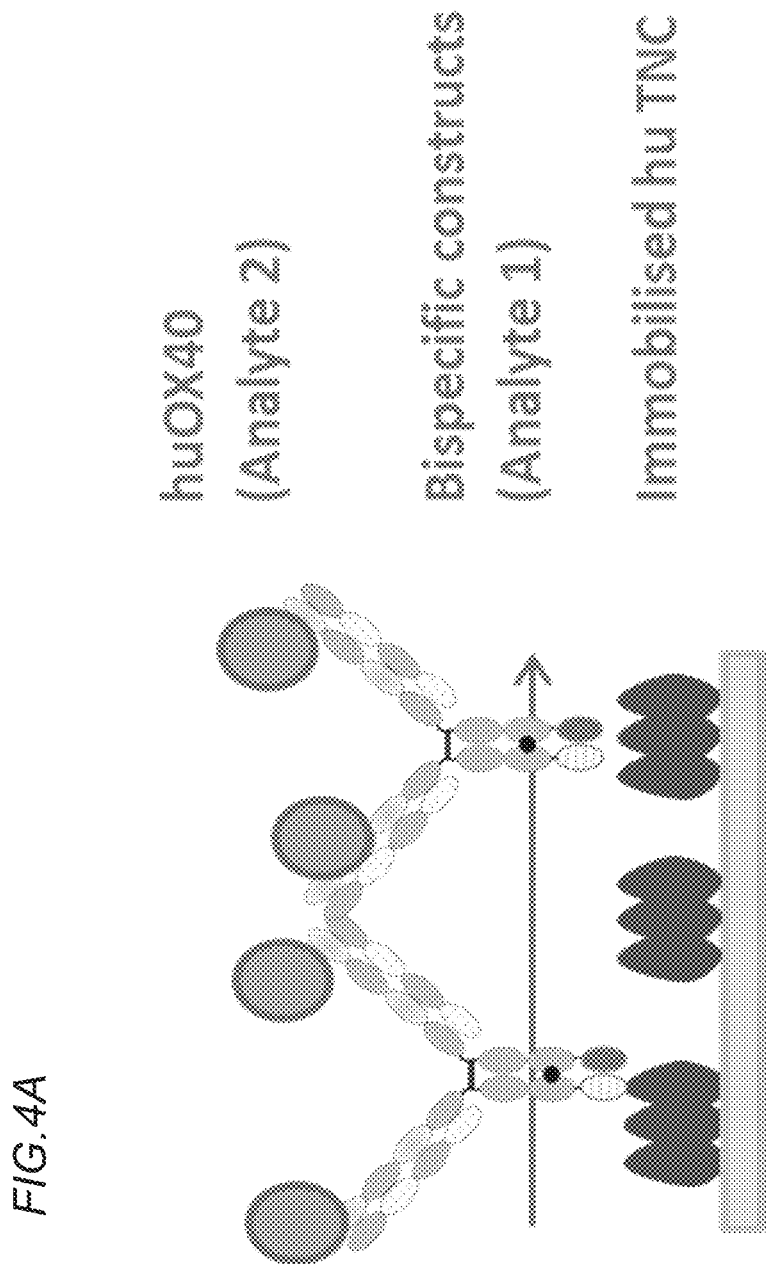
FIG. 4A shows a schematic representation of the set up of the surface plasmon resonance assays for simultaneous binding of human OX40 and human TnC by the bispecific anti-OX40, anti-TnC antigen binding molecules.
Figure 4C:
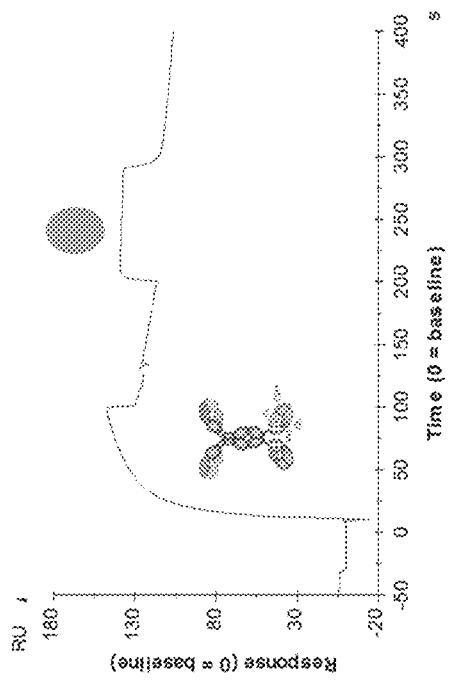
FIGS. 4B to 4E show the binding of the bispecific anti-OX40, anti-TnC antigen binding molecules to recombinant OX40 Fc (kih) receptor and human TnC protein, as assessed by surface plasmon resonance.
Figure 4E:
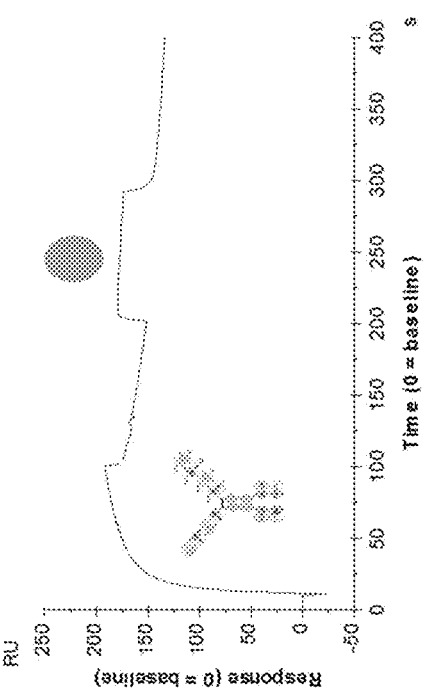
Figure 4B:
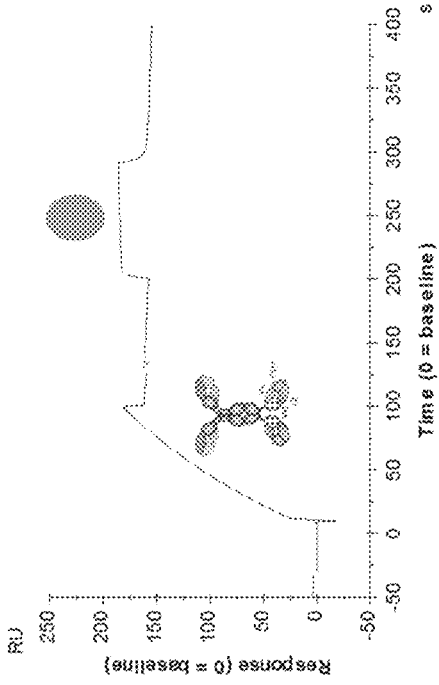
Figure 4D:
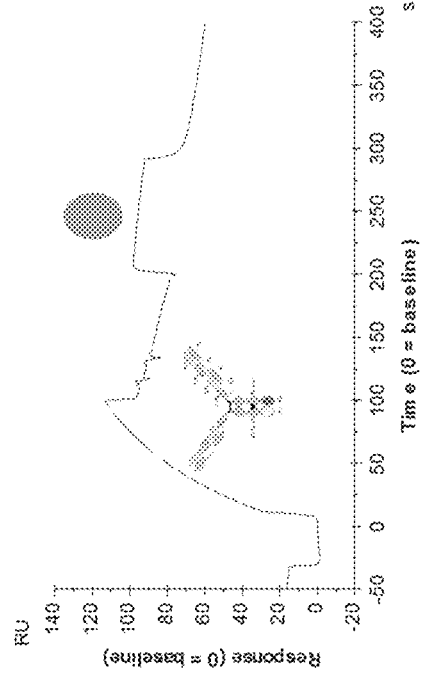
Figure 5:
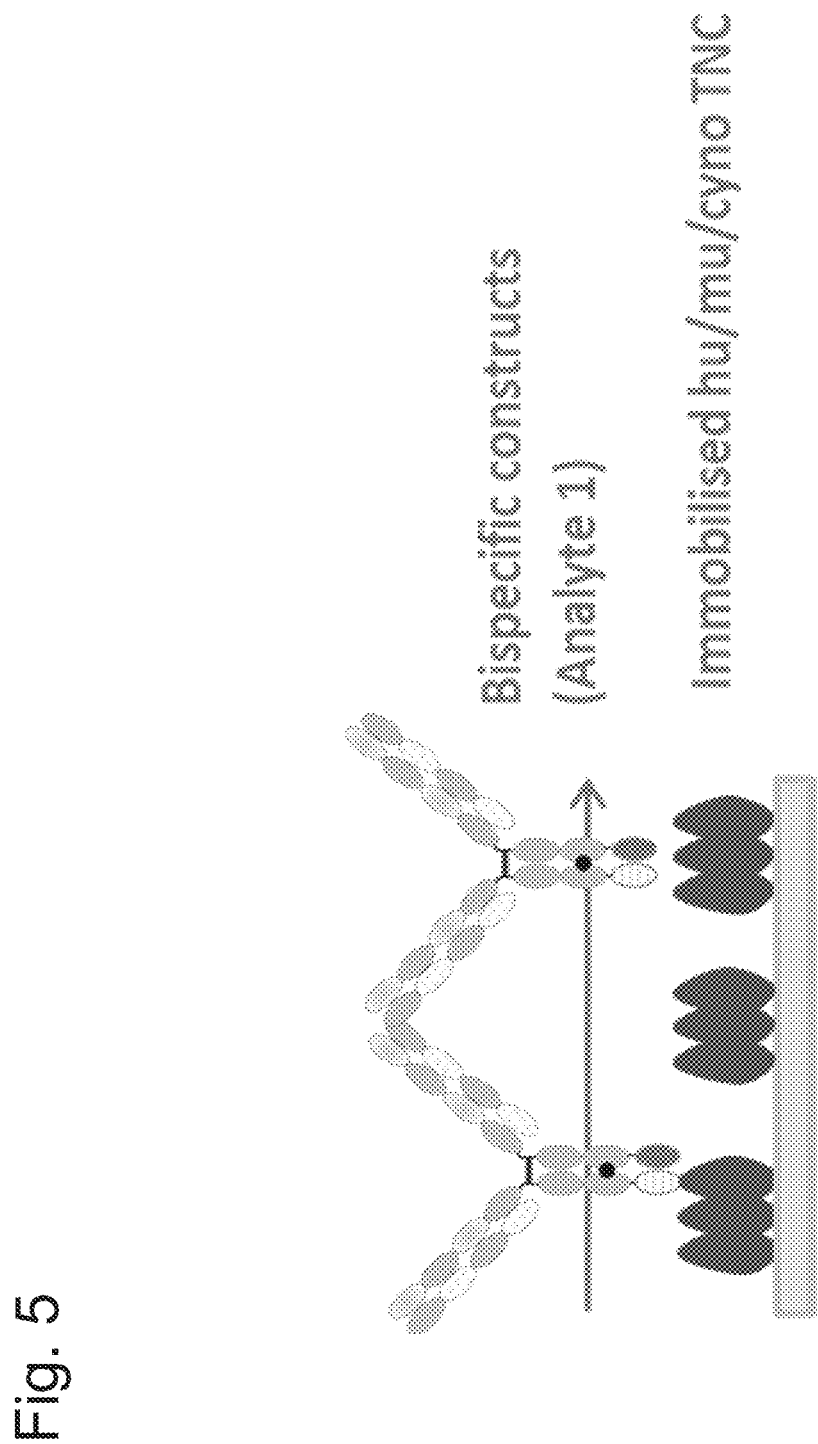
FIG. 5 shows a schematic representation of the set up of the surface plasmon resonance assays for analysis of binding of human TnC, murine TnC and cynomolgus TnC by the bispecific anti-OX40, anti-TnC antigen binding molecules.

The resulting bispecific antigen binding molecules with tetravalent binding for OX40 are depicted in FIG. 3, and the sequences for base pair and amino acids can be found respectively in Table 31 and Table 32.

TABLE 31

Base pair sequences of mature bispecific, tetravalent anti-OX40, monovalent and bivalent anti-TnC huIgG1 P329GLALA molecules

| Clone | | SEQ ID NO: | Base pair sequence |
|---|---|---|---|
| 49B4/TnC 18D4 P329GLALA 4 + 1 (ID7745) | LC1 (pCON323) 49B4 VL/CL | 207 | See Table 28 above |
| | HC1 pETR15193 49B4VHCH1_ VHCH1_Fc_ hole_PG/ LALA_18D4VL | 217 | CAGGTGCAATTGGTGCAGTCTGGGGCTGAGGT GAAGAAGCCTGGGTCCTCGGTGAAGGTCTCCT GCAAGGCCTCCGGAGGCACATTCAGCAGCTAC GCTATAAGCTGGGTGCGACAGGCCCCTGGACA AGGGCTCGAGTGGATGGGAGGGATCATCCCTA TCTTTGGTACAGCAAACTACGCACAGAAGTTC CAGGGCAGGGTCACCATTACTGCAGACAAATC CACGAGCACAGCCTACATGGAGCTGAGCAGCC TGAGATCTGAGGACACCGCCGTGTATTACTGT GCGAGAGAATACTACCGTGGTCCGTACGACTA CTGGGGCCAAGGGACCACCGTGACCGTCTCCT CAGCTAGCACAAAGGGACCTAGCGTGTTCCCC CTGGCCCCCAGCAGCAAGTCTACATCTGGCGG AACAGCCGCCCTGGGCTGCCTCGTGAAGGACT ACTTTCCCGAGCCCGTGACCGTGTCCTGGAAC TCTGGCGCTCTGACAAGCGGCGTGCACACCTT TCCAGCCGTGCTGCAGAGCAGCGGCCTGTACT CTCTGAGCAGCGTCGTGACAGTGCCCAGCAGC TCTCTGGGCACCCAGACCTACATCTGCAACGT GAACCACAAGCCCAGCAACACCAAGGTGGAC AAGAAGGTGGAACCCAAGAGCTGCGACGGCG GAGGGGGATCTGGCGGCGGAGGATCCCAGGT GCAATTGGTGCAGTCTGGGGCTGAGGTGAAGA AGCCTGGGTCCTCGGTGAAGGTCTCCTGCAAG GCCTCCGGAGGCACATTCAGCAGCTACGCTAT AAGCTGGGTGCGACAGGCCCCTGGACAAGGG CTCGAGTGGATGGGAGGGATCATCCCTATCTT TGGTACAGCAAACTACGCACAGAAGTTCCAGG GCAGGGTCACCATTACTGCAGACAAATCCACG AGCACAGCCTACATGGAGCTGAGCAGCCTGAG ATCTGAGGACACCGCCGTGTATTACTGTGCGA GAGAATACTACCGTGGTCCGTACGACTACTGG GGCCAAGGGACCACCGTGACCGTCTCCTCAGC TAGCACCAAGGGCCCATCGGTCTTCCCCCTGG CACCCTCCTCCAAGAGCACCTCTGGGGGCACA GCGGCCCTGGGCTGCCTGGTCAAGGACTACTT CCCCGAACCGGTGACGGTGTCGTGGAACTCAG GCGCCCTGACCAGCGGCGTGCACACCTTCCCG GCTGTCCTACAGTCCTCAGGACTCTACTCCCTC AGCAGCGTGGTGACCGTGCCCTCCAGCAGCTT GGGCACCCAGACCTACATCTGCAACGTGAATC ACAAGCCCAGCAACACCAAGGTGGACAAGAA AGTTGAGCCCAAATCTTGTGACAAAACTCACA CATGCCCACCGTGCCCAGCACCTGAAGCTGCA GGGGGACCGTCAGTCTTCCTCTTCCCCCCAAA ACCCAAGGACACCCTCATGATCTCCCGGACCC CTGAGGTCACATGCGTGGTGGTGGACGTGAGC CACGAAGACCCTGAGGTCAAGTTCAACTGGTA CGTGGACGGCGTGGAGGTGCATAATGCCAAG ACAAAGCCGCGGGAGGAGCAGTACAACAGCA CGTACCGTGTGGTCAGCGTCCTCACCGTCCTG CACCAGGACTGGCTGAATGGCAAGGAGTACA AGTGCAAGGTCTCCAACAAAGCCCTCGGCGCC CCCATCGAGAAAACCATCTCCAAAGCCAAAGG GCAGCCCCGAGAACCACAGGTGTGCACCCTGC CCCCATCCCGGGATGAGCTGACCAAGAACCAG GTCAGCCTCTCGTGCGCAGTCAAAGGCTTCTA TCCCAGCGACATCGCCGTGGAGTGGGAGAGCA ATGGGCAGCCGGAGAACAACTACAAGACCAC GCCTCCCGTGCTGGACTCCGACGGCTCCTTCTT |

TABLE 31-continued

Base pair sequences of mature bispecific,
tetravalent anti-OX40, monovalent and
bivalent anti-TnC huIgG1 P329GLALA molecules

| Clone | SEQ ID NO: | Base pair sequence |
|---|---|---|
| HC2 pETR15194 49B4VHCH1_ VHCH1_Fc_ knob_PG/ LALA_18D4VH | 218 | CCTCGTGAGCAAGCTCACCGTGGACAAGAGCA GGTGGCAGCAGGGGAACGTCTTCTCATGCTCC GTGATGCATGAGGCTCTGCACAACCACTACAC GCAGAAGAGCCTCTCCCTGTCTCCGGGTGGAG GCGGCGGAAGCGGAGGAGGAGGATCCGGCGG CGGAGGTTCCGGAGGCGGTGGATCGGACATCC AGATGACCCAGTCTCCATCCACCCTGTCTGCA TCTGTAGGAGACCGTGTCACCATCACTTGCCG TGCCAGTCAGAGTATTAGTAGCTGGTTGGCCT GGTATCAGCAGAAACCAGGGAAAGCCCCTAA GCTCCTGATCTATGATGCCTCCAGTTTGGAAA GTGGGGTCCCATCACGTTTCAGCGGCAGTGGA TCCGGGACAGAATTCACTCTCACCATCAGCAG CTTGCAGCCTGATGATTTTGCAACTTATTACTG CCAACAGAATAAGAAGTTTCCTTCGGGGACGT TTGGCCAGGGCACCAAAGTCGAGATCAAG CAGGTGCAATTGGTGCAGTCTGGGGCTGAGGT GAAGAAGCCTGGGTCCTCGGTGAAGGTCTCCT GCAAGGCCTCCGGAGGCACATTCAGCAGCTAC GCTATAAGCTGGGTGCGACAGGCCCCTGGACA AGGGCTCGAGTGGATGGGAGGGATCATCCCTA TCTTTGGTACAGCAAACTACGCACAGAAGTTC CAGGGCAGGGTCACCATTACTGCAGACAAATC CACGAGCACAGCCTACATGGAGCTGAGCAGCC TGAGATCTGAGGACACCGCCGTGTATTACTGT GCGAGAGAATACTACGTGGTCCGTACGACTA CTGGGGCCAAGGGACCACCGTGACCGTCTCCT CAGCTAGCACAAAGGGACCTAGCGTGTTCCCC CTGGCCCCCAGCAGCAAGTCTACATCTGGCGG AACAGCCGCCCTGGGCTGCCTCGTGAAGGACT ACTTTCCCGAGCCCGTGACCGTGTCCTGGAAC TCTGGCGCTCTGACAAGCGGCGTGCACACCTT TCCAGCCGTGCTGCAGAGCAGCGGCCTGTACT CTCTGAGCAGCGTCGTGACAGTGCCCAGCAGC TCTCTGGGCACCCAGACCTACATCTGCAACGT GAACCACAAGCCCAGCAACACCAAGGTGGAC AAGAAGGTGGAACCCAAGAGCTGCGACGGCG GAGGGGGATCTGGCGGCGGAGGATCCCAGGT GCAATTGGTGCAGTCTGGGGCTGAGGTGAAGA AGCCTGGGTCCTCGGTGAAGGTCTCCTGCAAG GCCTCCGGAGGCACATTCAGCAGCTACGCTAT AAGCTGGGTGCGACAGGCCCCTGGACAAGGG CTCGAGTGGATGGGAGGGATCATCCCTATCTT TGGTACAGCAAACTACGCACAGAAGTTCCAGG GCAGGGTCACCATTACTGCAGACAAATCCACG AGCACAGCCTACATGGAGCTGAGCAGCCTGAG ATCTGAGGACACCGCCGTGTATTACTGTGCGA GAGAATACTACGTGGTCCGTACGACTACTGG GGCCAAGGGACCACCGTGACCGTCTCCTCAGC TAGCACCAAGGGCCCATCGGTCTTCCCCCTGG CACCCTCCTCCAAGAGCACCTCTGGGGGCACA GCGGCCCTGGGCTGCCTGGTCAAGGACTACTT CCCCGAACCGGTGACGGTGTCGTGGAACTCAG GCGCCCTGACCAGCGGCGTGCACACCTTCCCG GCTGTCCTACAGTCCTCAGGACTCTACTCCCTC AGCAGCGTGGTGACCGTGCCCTCCAGCAGCTT GGGCACCCAGACCTACATCTGCAACGTGAATC ACAAGCCCAGCAACACCAAGGTGGACAAGAA AGTTGAGCCCAAATCTTGTGACAAAACTCACA CATGCCCACCGTGCCCAGCACCTGAAGCTGCA GGGGGACCGTCAGTCTTCCTCTTCCCCCCAAA ACCCAAGGACACCCTCATGATCTCCCGGACCC CTGAGGTCACATGCGTGGTGGTGGACGTGAGC CACGAAGACCCTGAGGTCAAGTTCAACTGGTA CGTGGACGGCGTGGAGGTGCATAATGCCAAG ACAAAGCCGCGGGAGGAGCAGTACAACAGCA CGTACCGTGTGGTCAGCGTCCTCACCGTCCTG CACCAGGACTGGCTGAATGGCAAGGAGTACA AGTGCAAGGTCTCCAACAAAGCCCTCGGCGCC CCCATCGAGAAAACCATCTCCAAAGCCAAAGG GCAGCCCCGAGAACCACAGGTGTACACCCTGC CCCCCTGCAGAGATGAGCTGACCAAGAACCAG GTGTCCCTGTGGTGTCTGGTCAAGGGCTTCTAC |

TABLE 31-continued

Base pair sequences of mature bispecific,
tetravalent anti-OX40, monovalent and
bivalent anti-TnC huIgG1 P329GLALA molecules

| Clone | | SEQ ID NO: | Base pair sequence |
|---|---|---|---|
| | | | CCCAGCGATATCGCCGTGGAGTGGGAGAGCA ACGGCCAGCCTGAGAACAACTACAAGACCAC CCCCCCTGTGCTGGACAGCGACGGCAGCTTCT TCCTGTACTCCAAACTGACCGTGGACAAGAGC CGGTGGCAGCAGGGCAACGTGTTCAGCTGCAG CGTGATGCACGAGGCCCTGCACAACCACTACA CCCAGAAGTCCCTGAGCCTGAGCCCCGGCGGA GGCGGCGGAAGCGGAGGAGGAGGATCCGGTG GTGGCGGTTCCGGGGGCGGTGGATCGCAGGTG CAATTGGTGCAGTCTGGGGCTGAGGTGAAGAA GCCTGGGTCCTCGGTGAAGGTCTCCTGCAAGG CCTCCGGAGGCACATTCAGCAGCTACGCTATA AGCTGGGTGCGACAGGCCCCTGGACAAGGGCT CGAGTGGATGGGAGGGATCATCCCTATCTTTG GTACAGCAAACTACGCACAGAAGTTCCAGGGC AGGGTCACCATTACTGCAGACAAATCCACGAG CACAGCCTACATGGAGCTGAGCAGCCTGAGAT CTGAGGACACCGCCGTGTATTACTGTGCGAAA GGTAACTTCTACGGTGGTCTGGACTACTGGGG CCAAGGGACCACAGTGACCGTAAGCTCC |
| 49B4/TnC 18D4 P329GLALA 4 + 2 (ID8035) | LC1 pETR14912 49B4 VLCL + charges | 219 | GACATCCAGATGACCCAGTCTCCTTCCACCCT GTCTGCATCTGTAGGAGACCGTGTCACCATCA CTTGCCGTGCCAGTCAGAGTATTAGTAGCTGG TTGGCCTGGTATCAGCAGAAACCAGGGAAAGC CCCTAAGCTCCTGATCTATGATGCCTCCAGTTT GGAAAGTGGGGTCCCATCACGTTTCAGCGGCA GTGGATCCGGGACAGAATTCACTCTCACCATC AGCAGCTTGCAGCCTGATGATTTTGCAACTTA TTACTGCCAACAGTATAGTTCGCAGCCGTATA CGTTTGGCCAGGGCACCAAAGTCGAGATCAAG CGTACGGTGGCTGCACCATCTGTCTTCATCTTC CCGCCATCTGATCGGAAGTTGAAATCTGGAAC TGCCTCTGTTGTGTGCCTGCTGAATAACTTCTA TCCCAGAGAGGCCAAAGTACAGTGGAAGGTG GATAACGCCCTCCAATCGGGTAACTCCCAGGA GAGTGTCACAGAGCAGGACAGCAAGGACAGC ACCTACAGCCTCAGCAGCACCCTGACGCTGAG CAAAGCAGACTACGAGAAACACAAAGTCTAC GCCTGCGAAGTCACCCATCAGGGCCTGAGCTC GCCCGTCACAAAGAGCTTCAACAGGGGAGAG TGT |
| | HC pETR15206 49B4VHCH1EE_ 49B4VHCH1EE_ Fc_PG/LALA_ 18D4VLCH1 | 220 | CAGGTGCAGCTGGTGCAGTCTGGCGCCGAAGT GAAGAAACCCGGCAGCAGCGTGAAGGTGTCC TGCAAGGCTTCCGGCGGCACCTTCAGCAGCTA CGCCATTTCTTGGGTGCGCCAGGCCCCTGGAC AGGGCCTGGAATGGATGGGCGGCATCATCCCC ATCTTCGGCACCGCCAACTACGCCCAGAAATT CCAGGGCAGAGTGACCATCACCGCCGACAAG AGCACCAGCACCGCCTACATGGAACTGAGCAG CCTGCGGAGCGAGGACACCGCCGTGTACTACT GCGCCAGAGAGTACTACAGAGGCCCCTACGAC TACTGGGGCCAGGGCACAACCGTGACCGTGTC TAGCGCCAGCACAAAGGGCCCCAGCGTGTTCC CTCTGGCCCCTAGCAGCAAGAGCACATCTGGC GGAACAGCCGCCCTGGGCTGCCTGGTGGAAGA TTACTTCCCCGAGCCCGTGACAGTGTCCTGGA ACTCTGGCGCCCTGACAAGCGGCGTGCACACC TTTCCAGCCGTGCTGCAGAGCAGCGGCCTGTA CTCACTGTCCAGCGTCGTGACTGTGCCCAGCA GCAGCCTGGGAACCCAGACCTACATCTGCAAC GTGAACCACAAGCCCAGCAACACCAAGGTGG ACGAGAAGGTGGAACCCAAGAGCTGCGACGG CGGAGGCGGATCTGGCGGCGGAGGATCCCAG GTGCAGCTGGTGCAGAGCGGAGCTGAAGTGA AAAAGCCTGGCTCCTCCGTGAAAGTGTCTTGT AAAGCCAGCGGCGGCACATTCTCATCCTACGC CATCAGCTGGGTGCGGCAGGCTCCAGGCCAGG GACTGGAATGGATGGGAGGAATTATCCCTATT TTTGGGACAGCCAATTATGCTCAGAAATTTCA GGGGCGCGTGACAATTACAGCCGACAAGTCCA CCTCTACAGCTTATATGGAACTGTCCTCCCTGC GCTCCGAGGATACAGCTGTGTATTATTGTGCC |

TABLE 31-continued

Base pair sequences of mature bispecific,
tetravalent anti-OX40, monovalent and
bivalent anti-TnC huIgG1 P329GLALA molecules

| Clone | SEQ ID NO: | Base pair sequence |
|---|---|---|
| | | CGCGAGTACTACCGGGGACCTTACGATTATTG GGGACAGGGAACCACAGTGACTGTGTCCTCCG CTAGCACCAAGGGACCTTCCGTGTTTCCCCTG GCTCCCAGCTCCAAGTCTACCTCTGGGGGCAC AGCTGCTCTGGGATGTCTGGTGGAAGATTATT TTCCTGAACCTGTGACCGTGTCATGGAACAGC GGAGCCCTGACCTCCGGGGTGCACACATTCCC TGCTGTGCTGCAGTCCTCCGGCCTGTATAGCCT GAGCAGCGTCGTGACCGTGCCTTCCAGCTCTC TGGGCACACAGACATATATCTGTAATGTGAAT CACAAACCCTCTAATACCAAAGTGGATGAGAA AGTGGAACCTAAGTCCTGCGACAAGACCCACA CCTGTCCCCCTTGTCCTGCCCCTGAAGCTGCTG GCGGCCCATCTGTGTTTCTGTTCCCCCCAAAGC CCAAGGACACCCTGATGATCAGCCGGACCCCC GAAGTGACCTGCGTGGTGGTGGATGTGTCCCA CGAGGACCCAGAAGTGAAGTTCAATTGGTACG TGGACGGCGTGGAAGTGCACAACGCCAAGAC CAAGCCGCGGGAAGAACAGTACAACAGCACC TACCGGGTGGTGTCCGTGCTGACAGTGCTGCA CCAGGACTGGCTGAACGGCAAAGAGTACAAG TGCAAGGTGTCCAACAAGGCCCTGGGAGCCCC CATCGAGAAACCATCAGCAAGGCCAAGGGC CAGCCCCGCGAACCTCAGGTGTACACCCTGCC CCCAAGCAGGGACGAGCTGACCAAGAACCAG GTGTCCCTGACCTGTCTCGTGAAGGGCTTCTAC CCCTCCGATATCGCCGTGGAATGGGAGAGCAA CGGCCAGCCCGAGAACAACTACAAGACCACC CCCCCTGTGCTGGACAGCGACGGCTCATTCTT CCTGTACTCCAAGCTGACCGTGGACAAGAGCC GGTGGCAGCAGGGCAACGTGTTCAGCTGCAGC GTGATGCACGAGGCCCTGCACAACCACTACAC ACAGAAGTCTCTGAGCCTGAGCCCTGGCGGAG GGGGAGGATCTGGGGGAGGCGGAAGTGGGGG AGGGGGTTCCGGAGGCGGTGGATCGGACATCC AGATGACCCAGTCTCCATCCACCCTGTCTGCA TCTGTAGGAGACCGTGTCACCATCACTTGCCG TGCCAGTCAGAGTATTAGTAGCTGGTTGGCCT GGTATCAGCAGAAACCAGGGAAAGCCCCTAA GCTCCTGATCTATGATGCCTCCAGTTTGGAAA GTGGGGTCCCATCACGTTTCAGCGGCAGTGGA TCCGGGACAGAATTCACTCTCACCATCAGCAG CTTGCAGCCTGATGATTTTGCAACTTATTACTG CCAACAGAATAAGAAGTTTCCTTCGGGGACGT TTGGCCAGGGCACCAAAGTCGAGATCAAGTCT AGCGCTTCCACCAAGGGCCCCTCAGTGTTCCC ACTGGCACCATCCAGCAAGTCCACAAGCGGAG GAACCGCCGCTCTGGGCTGTCTCGTGAAAGAC TACTTTCCAGAGCCAGTGACCGTGTCCTGGAA TAGTGGCGCTCTGACTTCTGGCGTGCACACTTT CCCCGCAGTGCTGCAGAGTTCTGGCCTGTACT CCCTGAGTAGCGTCGTGACAGTGCCCTCCTCT AGCCTGGGCACTCAGACTTACATCTGCAATGT GAATCATAAGCCTTCCAACACAAAAGTGGACA AAAAGTGGAACCCAAATCTTGC |
| LC2 pETR15202 18D4 VHCL | 221 | CAGGTGCAATTGGTGCAGTCTGGGGCTGAGGT GAAGAAGCCTGGGTCCTCGGTGAAGGTCTCCT GCAAGGCCTCCGGAGGCACATTCAGCAGCTAC GCTATAAGCTGGGTGCGACAGGCCCCTGGACA AGGGCTCGAGTGGATGGGAGGGATCATCCCTA TCTTTGGTACAGCAAACTACGCACAGAAGTTC CAGGGCAGGGTCACCATTACTGCAGACAAATC CACGAGCACAGCCTACATGGAGCTGAGCAGCC TGAGATCTGAGGACACCGCCGTGTATTACTGT GCGAAAGGTAACTTCTACGGTGGTCTGGACTA CTGGGGCCAAGGGACCACCGTGACCGTCTCCT CAGCTAGCGTGGCCGCTCCCTCCGTGTTCATCT TCCCACCTTCCGACGAGCAGCTGAAGTCCGGC ACCGCTTCTGTCGTGTGCCTGCTGAACAACTTC TACCCCCCGCGAGGCCAAGGTGCAGTGGAAGGT GGACAACGCCCTGCAGTCCGGCAACAGCCAG GAATCCGTGACCGAGCAGGACTCCAAGGACA GCACCTACTCCCTGTCCTCCACCCTGACCCTGT |

TABLE 31-continued

Base pair sequences of mature bispecific, tetravalent anti-OX40, monovalent and bivalent anti-TnC huIgG1 P329GLALA molecules

| Clone | SEQ ID NO: | Base pair sequence |
|---|---|---|
| | | CCAAGGCCGACTACGAGAAGCACAAGGTGTA CGCCTGCGAAGTGACCCACCAGGGCCTGTCTA GCCCCGTGACCAAGTCTTTCAACCGGGGCGAG TGC |

TABLE 32

Amino acid sequences of mature bispecific, tetravalent anti-OX40, monovalent and bivalent anti-TnC huIgG1 P329GLALA molecules

| Clone | | SEQ ID NO: | Amino acid sequence |
|---|---|---|---|
| 49B4/TnC 18D4 P329GLALA 4 + 1 (ID7745) | LC 49B4 VL/CL (pCON323) | 212 | See Table 29 above |
| | HC1 pETR15193 49B4VHCH1_ VHCH1_Fc_ hole_PG/ LALA_18D4VL | 222 | QVQLVQSGAEVKKPGSSVKVSCKASGGTFSS YAISWVRQAPGQGLEWMGGIIPIFGTANYAQ KFQGRVTITADKSTSTAYMELSSLRSEDTAVY YCAREYYRGPYDYWGQGTTVTVSSASTKGPS VFPLAPSSKSTSGGTAALGCLVKDYFPEPVTV SWNSGALTSGVHTFPAVLQSSGLYSLSSVVTV PSSSLGTQTYICNVNHKPSNTKVDKKVEPKSC DGGGGSGGGGSQVQLVQSGAEVKKPGSSVK VSCKASGGTFSSYAISWVRQAPGQGLEWMG GIIPIFGTANYAQKFQGRVTITADKSTSTAYME LSSLRSEDTAVYYCAREYYRGPYDYWGQGT TVTVSSASTKGPSVFPLAPSSKSTSGGTAALG CLVKDYFPEPVTVSWNSGALTSGVHTFPAVL QSSGLYSLSSVVTVPSSSLGTQTYICNVNHKPS NTKVDKKVEPKSCDKTHTCPPCPAPEAAGGP SVFLFPPKPKDTLMISRTPEVTCVVVDVSHED PEVKFNWYVDGVEVHNAKTKPREEQYNSTY RVVSVLTVLHQDWLNGKEYKCKVSNKALGA PIEKTISKAKGQPREPQVCTLPPSRDELTKNQV SLSCAVKGFYPSDIAVEWESNGQPENNYKTTP PVLDSDGSFFLVSKLTVDKSRWQQGNVFSCS VMHEALHNHYTQKSLSLSPGGGGSGGGGS GGGGSGGGGSDIQMTQSPSTLSASVGDRVTIT CRASQSISSWLAWYQQKPGKAPKLLIYDASSL ESGVPSRFSGSGSGTEFTLTISSLQPDDFATYY CQQNKKFPSGTFGQGTKVEIK |
| | HC2 pETR15194 49B4VHCH1_ VHCH1_Fc_ knob_PG/ LALA_18D4VH | 223 | QVQLVQSGAEVKKPGSSVKVSCKASGGTFSS YAISWVRQAPGQGLEWMGGIIPIFGTANYAQ KFQGRVTITADKSTSTAYMELSSLRSEDTAVY YCAREYYRGPYDYWGQGTTVTVSSASTKGPS VFPLAPSSKSTSGGTAALGCLVKDYFPEPVTV SWNSGALTSGVHTFPAVLQSSGLYSLSSVVTV PSSSLGTQTYICNVNHKPSNTKVDKKVEPKSC DGGGGSGGGGSQVQLVQSGAEVKKPGSSVK VSCKASGGTFSSYAISWVRQAPGQGLEWMG GIIPIFGTANYAQKFQGRVTITADKSTSTAYME LSSLRSEDTAVYYCAREYYRGPYDYWGQGT TVTVSSASTKGPSVFPLAPSSKSTSGGTAALG CLVKDYFPEPVTVSWNSGALTSGVHTFPAVL QSSGLYSLSSVVTVPSSSLGTQTYICNVNHKPS NTKVDKKVEPKSCDKTHTCPPCPAPEAAGGP SVFLFPPKPKDTLMISRTPEVTCVVVDVSHED PEVKFNWYVDGVEVHNAKTKPREEQYNSTY RVVSVLTVLHQDWLNGKEYKCKVSNKALGA PIEKTISKAKGQPREPQVYTLPPCRDELTKNQ VSLWCLVKGFYPSDIAVEWESNGQPENNYKT TPPVLDSDGSFFLYSKLTVDKSRWQQGNVFS CSVMHEALHNHYTQKSLSLSPGGGGSGGGG SGGGGSGGGGSQVQLVQSGAEVKKPGSSV KVSCKASGGTFSSYAISWVRQAPGQGLEWM GGIIPIFGTANYAQKFQGRVTITADKSTSTAY MELSSLRSEDTAVYYCAKGNFYGGLDYWGQ GTTVTVSS |

TABLE 32-continued

Amino acid sequences of mature bispecific, tetravalent anti-OX40, monovalent and bivalent anti-TnC huIgG1 P329GLALA molecules

| Clone | | SEQ ID NO: | Amino acid sequence |
|---|---|---|---|
| 49B4/TnC 18D4 P329GLALA 4 + 2 (ID8035) | LC1 pETR14912 49B4 VLCL + charges | 224 | DIQMTQSPSTLSASVGDRVTITCRASQSISSWL AWYQQKPGKAPKLLIYDASSLESGVPSRFSGS GSGTEFTLTISSLQPDDFATYYCQQYSSQPYTF GQGTKVEIKRTVAAPSVFIFPPSDRKLKSGTAS VVCLLNNFYPREAKVQWKVDNALQSGNSQE SVTEQDSKDSTYSLSSTLTLSKADYEKHKVY ACEVTHQGLSSPVTKSFNRGEC |
| | HC pETR15206 49B4VHCH1EE_ 49B4VHCH1EE_ Fc_PG/LALA_ 18D4VLCH1 | 225 | QVQLVQSGAEVKKPGSSVKVSCKASGGTFSS YAISWVRQAPGQGLEWMGGIIPIFGTANYAQ KFQGRVTITADKSTSTAYMELSSLRSEDTAVY YCAREYYRGPYDYWGQGTTVTVSSASTKGPS VFPLAPSSKSTSGGTAALGCLVEDYFPEPVTV SWNSGALTSGVHTFPAVLQSSGLYSLSSVVTV PSSSLGTQTYICNVNHKPSNTKVDEKVEPKSC DGGGGSGGGGSQVQLVQSGAEVKKPGSSVK VSCKASGGTFSSYAISWVRQAPGQGLEWMG GIIPIFGTANYAQKFQGRVTITADKSTSTAYME LSSLRSEDTAVYYCAREYYRGPYDYWGQGT TVTVSSASTKGPSVFPLAPSSKSTSGGTAALG CLVEDYFPEPVTVSWNSGALTSGVHTFPAVL QSSGLYSLSSVVTVPSSSLGTQTYICNVNHKPS NTKVDEKVEPKSCDKTHTCPPCPAPEAAGGP SVFLFPPKPKDTLMISRTPEVTCVVVDVSHED PEVKFNWYVDGVEVHNAKTKPREEQYNSTY RVVSVLTVLHQDWLNGKEYKCKVSNKALGA PIEKTISKAKGQPREPQVYTLPPSRDELTKNQV SLTCLVKGFYPSDIAVEWESNGQPENNYKTTP PVLDSDGSFFLYSKLTVDKSRWQQGNVFSCS VMHEALHNHYTQKSLSLSPGGGGGSGGGGS GGGGSGGGGSDIQMTQSPSTLSASVGDRVTIT CRASQSISSWLAWYQQKPGKAPKLLIYDASSL ESGVPSRFSGSGSGTEFTLTISSLQPDDFATYY CQQNKKFPSGTFGQGTKVEIKSSASTKGPSVF PLAPSSKSTSGGTAALGCLVKDYFPEPVTVSW NSGALTSGVHTFPAVLQSSGLYSLSSVVTVPS SSLGTQTYICNVNHKPSNTKVDKKVEPKSC |
| | LC2 pETR15202 18D4 VHCL | 226 | QVQLVQSGAEVKKPGSSVKVSCKASGGTFSS YAISWVRQAPGQGLEWMGGIIPIFGTANYAQ KFQGRVTITADKSTSTAYMELSSLRSEDTAVY YCAKGNFYGGLDYWGQGTTVTVSSASVAAP SVFIFPPSDEQLKSGTASVVCLLNNFYPREAK VQWKVDNALQSGNSQESVTEQDSKDSTYSLS STLTLSKADYEKHKVYACEVTHQGLSSPVTK SFNRGEC |

All genes were transiently expressed under control of a chimeric MPSV promoter consisting of the MPSV core promoter combined with the CMV promoter enhancer fragment. The expression vector also contains the oriP region for episomal replication in EBNA (Epstein Barr Virus Nuclear Antigen) containing host cells.

The bispecific anti-OX40, anti-TnC constructs were produced by co-transfecting HEK293-EBNA cells with the mammalian expression vectors using polyethylenimine. The cells were transfected with the corresponding expression vectors in a 1:1:4 ratio ("vector heavy chain":"vector light chain1":"vector light chain2" for 4+2) and 1:1:4 ("vector heavy chain1": "vector heavy chain2": "vector light chain" for 4+1).

For a 200 mL production in 500 mL shake flasks, 250 million HEK293 EBNA cells were seeded 24 hours before transfection in Excell media with supplements. For transfection, the cells were centrifuged for 5 minutes at 210× g, and supernatant was replaced by pre-warmed CD-CHO medium. Expression vectors were mixed in 20 mL CD-CHO medium to a final amount of 200 µg DNA. After addition of 540 µL PEI (1 mg/mL), the solution was vortexed for 15 seconds and incubated for 10 minutes at room temperature. Afterwards, cells were mixed with the DNA/PEI solution, transferred to a 500 mL shake flask and incubated for 3 hours at 37° C. in an incubator with a 5% $CO_2$ atmosphere and shaking at 165 rpm. After the incubation, 160 mL Excell medium with supplements was added and cells were cultured for 24 hours. At this point the valproic acid concentration is 1 mM (in the media there's as well 5 g/L PepSoy and 6 mM L-Glutamine). 24 h after transfection the cells are supplement with Feed 7 at 12% final volume (24 mL) and 3 g/L glucose (1.2 mL from 500 g/L stock). After culturing for 7 days, the cell supernatant was collected by centrifugation for 45 minutes at 2000-3000× g. The solution was sterile filtered (0.22 µm filter), supplemented with sodium azide to a final concentration of 0.01% (w/v), and kept at 4° C.

For affinity chromatography, the supernatant was loaded on a ProtA MabSelect Sure column (CV=5 mL, GE Healthcare) equilibrated with 30 mL 20 mM Sodium Citrate, 20 mM Sodium Phosphate, pH 7.5. Unbound protein was removed by washing with 6-10 column volumes of a buffer containing 20 mM sodium phosphate, 20 mM sodium citrate, pH 7.5. The bound protein was eluted using a step elution with 8 CV of 20 mM Sodium Citrate, 100 mM Sodium Chloride, 100 mM Glycine, pH 3.0

The pH of the collected fractions was adjusted by adding 1/10 (v/v) of 0.5 M Na2HPO4, pH8.0. The protein was concentrated and filtered prior to loading on a HiLoad Superdex 200 column (GE Healthcare) equilibrated with 20 mM Histidine, 140 mM NaCl, 0.01% Tween20, pH 6.0.

The protein concentration of purified bispecific tetravalent 4+1 and 4+2 constructs was determined by measuring the OD at 280 nm, using the molar extinction coefficient calculated on the basis of the amino acid sequence. Purity and molecular weight of the bispecific constructs were analyzed by CE-SDS in the presence and absence of a reducing agent (Invitrogen, USA) using a LabChipGXII (Caliper). The aggregate content of bispecific constructs was analyzed using a TSKgel G3000 SW XL analytical size-exclusion column (Tosoh) equilibrated in a 25 mM K2HPO4, 125 mM NaCl, 200 mM L-Arginine Monohydrocloride, 0.02% (w/v) NaN3, pH 6.7 running buffer at 25° C.

TABLE 33

Biochemical analysis of bispecific tetravalent anti-Ox40, anti-TnC IgG1 P329G LALA 4 + 1 and 4 + 2 constructs.

| Clone | Yield [mg/l] | Monomer [%] | CE-SDS (non red) | CE-SDS (red) |
|---|---|---|---|---|
| 49B4/TnC 18D4 P329GLALA 4 + 1 (ID7745) | 8.68 | 97.87 1.82 HMW | 93.12% (258 kDa) 4.73% (250 kDa) 0.33% (223 kDa) 1.82% (155 kDa) | 1.23% (140 kDa) 0.96% (119 kDa) 61.37% (108 kDa) 1.79% (36 kDa) 3.67% (33.5 kDa) 30.97% (31 kDa) |
| 49B4/TnC 18D4 P329GLALA 4 + 2 (ID8035) | 9.41 | 99.19 0.81 HMW | 0.37% (783 kDa) 99.63% (334 kDa) | 3.73% (150 kDa) 30.25 (125 kDa) 0.32% (33 kDa) 0.62% (31 kDa) 65% (30 kDa) |

3.3 Determination of the Aggregation Temperature of Anti-OX40, Anti-TnC 2+2, 4+1 and 4+2 Constructs For direct comparison of all formats the thermal stability was monitored by Static Light Scattering (SLS) and by measuring the intrinsic protein fluorescence in response to applied temperature stress. 30 mg of filtered protein sample with a protein concentration of 1 mg/ml was applied in duplicate to an Optim 2 instrument (Avacta Analytical Ltd). The temperature was ramped from 25 to 85° C. at 0.1° C./min, with the radius and total scattering intensity being collected. For determination of intrinsic protein fluorescence the sample was excited at 266 nm and emission was collected between 275 nm and 460 nm.

TABLE 34

Aggregation temperatures for the bispecific, anti-OX40, anti-TnC 2 + 2, 4 + 1 and 4 + 2 constructs

| construct | 49B4/TnC 18D4 P329GLALA 2 + 2 | 49B4/TnC 11C7 P329GLALA 2 + 2 | 49B4/TnC 18D4 P329GLALA 4 + 1 | 49B4/TnC 18D4 P329GLALA 4 + 2 |
|---|---|---|---|---|
| Tagg (° C.) | 56 | 45 | 54 | 57 |

Example 4

Binding of Bispecific Antibodies Targeting OX40 and Tenascin C (TnC)

4.1 Analysis of Simultaneous Binding to OX40 and TnC by Surface Plasmon Resonance Analysis The capacity of binding simultaneously human Ox40 Fc(kih) and human TnC was assessed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Biotinylated human TnC was directly coupled to a flow cell of a streptavidin (SA) sensor chip. Immobilization levels up to 1000 resonance units (RU) were used.

The bispecific antibodies targeting OX40 and TnC were passed over the chip surface at a concentration of 250 nM, at a flow rate of 30 μL/minute for 90 seconds, and dissociation was set to zero seconds. Human OX40 was injected as second analyte with a flow rate of 30 μL/minute for 90 seconds at a concentration of 250 nM, and dissociation was monitored for 120 seconds. Bulk refractive index differences were corrected for by subtracting the response obtained in a reference flow cell, where no protein was immobilized.

All of the bispecific antigen binding molecules were able to bind simultaneously to human OX40 and human TnC (FIGS. 4B to 4E).

4.2 Analysis of Binding to Human, Murine and Cynomolgus TnC by Surface Plasmon Resonance Analysis The capacity of the bispecific constructs to bind human, murine and cynomolgus TnC was analysed by surface plasmon resonance (SPR). All SPR experiments were performed on a Biacore T200 at 25° C. with HBS-EP as running buffer (0.01 M HEPES pH 7.4, 0.15 M NaCl, 3 mM EDTA, 0.005% Surfactant P20, Biacore, Freiburg/Germany).

Biotinylated human, murine or cynomolgus TnC molecules were immobilised on a SA chip to reach an immobilization level of 10 resonance units (RU).

Following immobilisation, the bispecific molecules or control molecules were immediately passed over the chip surface at concentrations ranging from 0.05-50 nM, at a flow rate of 30 μL/minute for 120 seconds and a dissociation phase of 180 seconds. The surface was regenerated using 10 mM glycine pH2.1. Bulk refractive index differences were corrected for by subtracting the response obtained in a reference flow cell, where no TnC was immobilized. Affinity/Avidity was determined under these experimental conditions using the Langmuir 1:1 curve fitting. For bivalent binding the same 1:1 fitting was used leading to an apparent KD value. For construct 49B4/11C7 (2+2), binding to cyno and muTNC was so weak that it was classified as "no binding".

TABLE 35

K<sub>D</sub> values for binding of the indicated bispecific antibodies targeting OX40 and TnC for human, murine and cynomolgus TnC

| Antigen binding molecule | huTnC KD (nM) | cynoTnC KD (nM) | muTnC KD (nM) |
|---|---|---|---|
| 49B4/18D4 2 + 2 | 0.11 | 0.28 | 0.3 |
| 49B4/11C7 2 + 2 | 5.85 | No binding | No binding |
| 49B4/18D4 4 + 1 | 15.1 | 36.3 | 15.6 |
| 49B4/18D4 4 + 2 | 0.18 | 0.4 | 0.65 |

4.3 Analysis of Binding to Human Ox40 Expressing Cells: Naïve and Activated Human Peripheral Mononuclear Blood Leukocytes (PBMC)

Buffy coats were obtained from the Zurich blood donation center. To isolate fresh peripheral blood mononuclear cells (PBMCs) the buffy coat was diluted with an equal volume of DPBS (Gibco by Life Technologies, Cat. No. 14190 326). 50 mL polypropylene centrifuge tubes (TPP, Cat.-No. 91050) were supplied with 15 mL Histopaque 1077 (SIGMA Life Science, Cat.-No. 10771, polysucrose and sodium diatrizoate, adjusted to a density of 1.077 g/mL) and the buffy coat solution was layered above the Histopaque 1077. The tubes were centrifuged for 30 min at 400× g, at room temperature, with low acceleration and no break. Subsequently the PBMCs were collected from the interphase, washed three times with DPBS and resuspended in T cell medium consisting of RPMI 1640 medium (Gibco by Life Technology, Cat. No. 42401-042) supplemented with 10% Fetal Bovine Serum (FBS, Gibco by Life Technology, Cat. No. 16000-044, Lot 941273, gamma-irradiated, mycoplasma-free and heat inactivated at 56° C. for 35 min), 1% (v/v) GlutaMAX I (GIBCO by Life Technologies, Cat. No. 35050 038), 1 mM Sodium-Pyruvat (SIGMA, Cat. No. S8636), 1% (v/v) MEM non-essential amino acids (SIGMA, Cat.-No. M7145) and 50 µM β-Mercaptoethanol (SIGMA, M3148).

PBMCs were used in experiments either directly after isolation (for analysis of binding to resting human PBMCs), or following stimulation to provide for high expression of human OX40 expression on the cell surface of T cells (for analysis of binding to activated human PBMCs). For stimulations, naïve PBMCs were cultured for four days in T cell medium supplied with 200 U/mL Proleukin (Novartis) and 2 ug/mL PHA-L (Sigma-Aldrich, L2769-10) in 6-well tissue culture plate and then 1 day on pre-coated 6-well tissue culture plates [2 ug/mL] anti-human CD3 (clone OKT3, eBioscience, Ca. No. 16-0037-85) and [2 ug/mL] anti-human CD28 (clone CD28.2, eBioscience, Cat No. 16-0289-85] in T cell medium supplied with 200 U/mL Proleukin at 37° C. and 5% $CO_2$.

For detection of OX40, naïve human PBMC and activated human PBMC were mixed. To enable distinction of naïve from activated human PBMC naïve cells were labeled prior to the binding assay using the eFluor670 cell proliferation dye (eBioscience, Cat.-No. 65-0840-85).

For labeling, cells were harvested, washed with pre-warmed (37° C.) DPBS and adjusted to a cell density of $1\times10^7$ cells/mL in DPBS. eFluor670 cell proliferation dye (eBioscience, Cat.-No. 65-0840-85) was added to the suspension of naïve human PBMC at a final concentration of 2.5 mM and a final cell density of $0.5\times10^7$ cells/mL in DPBS. Cells were then incubated for 10 min at room temperature in the dark. To stop the labeling reaction, 4 mL heat inactivated FBS was added and cells were washed three times with T cell medium. A 2:1 mixture of $1\times10^5$ resting eFluor670 labeled human PBMC and $0.5\times10^5$ unlabeled activated human PBMC were then added to each well of round-bottomed suspension cell 96-well plates (Greiner bio-one, cellstar, Cat. No. 650185).

Cells were stained for 120 minutes at 4° C. in the dark in 50 µL/well 4° C. FACS buffer containing different amounts of the indicated antigen binding molecules. After three washes with 4° C. FACS buffer, cells were stained for 45 minutes at 4° C. in the dark in 25 µL/well 4° C. FACS buffer containing a mixture of fluorescently labeled anti-human CD4 (clone RPA-T4, mouse IgG1 k, BioLegend, Cat.-No. 300532), anti-human CD8 (clone RPa-T8, mouse IgG1k, BioLegend, Cat.-No. 3010441) and Fluorescein isothiocyanate (FITC)-conjugated AffiniPure anti-human IgG Fcγ-fragment-specific goat IgG F(ab')₂ fragment (Jackson ImmunoResearch, Cat.-No. 109-096-098).

Cells were then resuspended in 85 FACS-buffer containing 0.2 µg/mL DAPI (Santa Cruz Biotec, Cat. No. Sc-3598) and acquired the same day using 5-laser LSR-Fortessa (BD Bioscience with DIVA software).

As shown in FIGS. 6A to 6D and FIGS. 7A to 7D, none of the antigen binding molecules specific for OX40 bound to resting human CD4+ T-cells or CD8+ T-cells, which do not express OX40 at the cell surface. By contrast, all of the bispecific anti-OX40, anti-TnC molecules displayed binding to activated CD8⁺ or CD4⁺ T-cells, which express OX40. Binding to CD4+ T-cells was much stronger than that to CD8+ T cells. Activated human CD8⁺ T cells express OX40 at a much lower level than the level of expression by activated CD4⁺ T cells. Expression levels for OX40 are depended on the kinetics and strength of stimulation and conditions were here optimized for OX40 expression on CD4+ T cells but not for CD8+ T cells. Thus, only a small amount of OX40 expression was induced on CD8+ T cells.

The bispecific anti-OX40, anti-TnC molecules were found to vary in their strength of binding. As shown in Table 36 as can be seen in FIG. 7A, the 4+2 molecules with tetravalent binding for OX40 bound more strongly and with higher avidity than the bivalent 2+2 molecules.

Figure 7A:
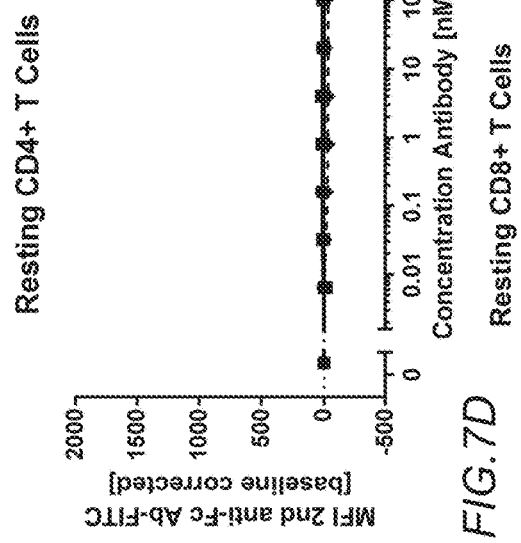
FIGS. 7A to 7D show the binding of the bispecific, tetravalent anti-OX40, monovalent or bivalent anti-TnC antigen binding molecules (i.e. 4+2 or 4+1 format) to resting and activated human CD4+ and CD8+ T cells.
Figure 7B:
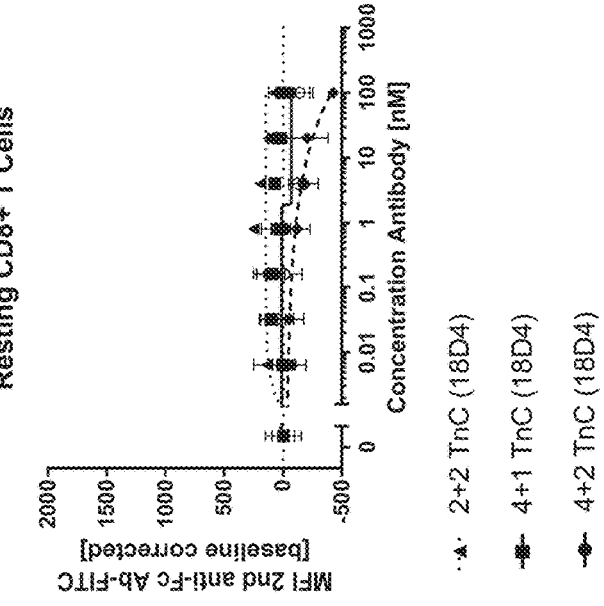
Figure 7C:
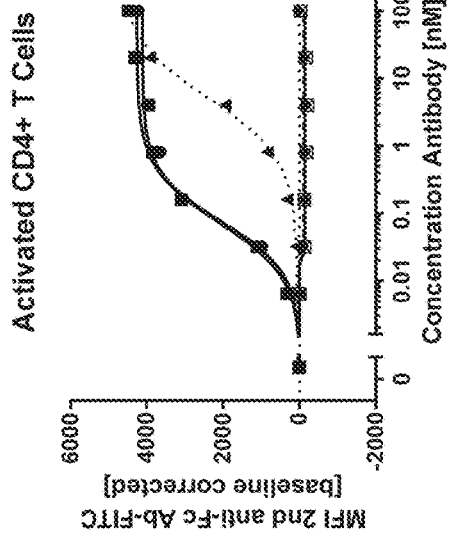
Figure 7D:
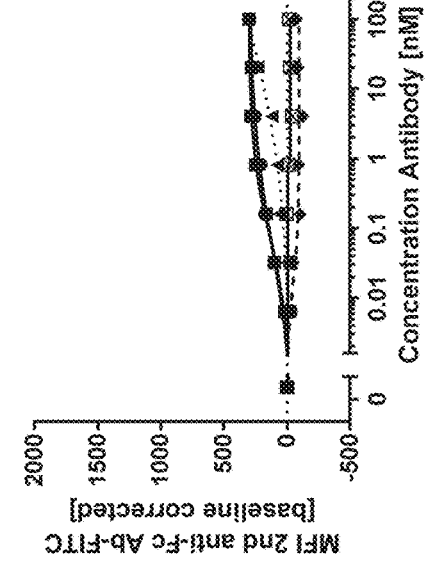

The results also suggested that the presence of a TnC-binding moiety did not influence binding to OX40 binding for the tetravalent OX40 binders (see e.g. FIG. 6A and FIG. 7A).

4.4 Binding to Human TnC-Expressing and TnC-Negative Tumor Cells

Binding of the bispecific anti-OX40, anti-TnC molecules to TnC expressed at the cell surface was analysed using TnC-expressing U87-MG cells (ATCC HTB-14), and CT26 cell line transfected to stably express human TnC (designated 'CT26huTnC' cells). The specificity of binding was analysed using TnC-negative cell line WM-266-4 (ATCC CRL-1676).

To allow the tumor cells to be distinguished, WM266-4 cells were pre-labeled with PKH-26 Red Fluorescence Cell linker Kit (Sigma, Cat-No. PKH26GL). Cells were harvested and washed three times with RPMI 1640 medium. The cells were then stained for 5 minutes at room temperature in the dark at a final cell density of $0.5\times10^7$ cells in freshly prepared PKH26-Red-stain solution (at a final concentration of 1 nM, in diluent C (provided with the PKH-26 Red Fluorescence Cell linker Kit)). Excess FBS was added to stop labeling reaction and cell were washed four times with RPMI 1640 medium supplemented with 10% (v/v) FBS, 1% (v/v) GlutaMAX-I to remove excess dye.

For the detection of binding of antigen binding molecules to the different cell types, 0.5–2×10⁵ PkH26 labeled WM266-4 and/or unlabeled U87-MG cells or CT26huTnC cells were added to wells of round-bottomed suspension cell 96-well plates (Greiner bio-one, cellstar, Cat. No. 650185). Cells were then stained for 60 to 120 minutes at 4° C. in the dark in 50 4/well 4° C. FACS buffer (DPBS (Gibco by Life Technologies, Cat. No. 14190 326) w/BSA (0.1% v/w, Sigma-Aldrich, Cat. No. A9418) containing titrated antigen binding molecules. After three washes with excess FACS buffer, cells were stained for 30-60 minutes at 4° C. in the dark in 25 μL/well 4° C. FACS buffer containing Fluorescein isothiocyanate (FITC)-conjugated AffiniPure anti-human IgG Fcγ-fragment-specific goat IgG F(ab')2 fragment (Jackson ImmunoResearch, Cat-No. 109-096-098) or Phycoerythrin (PE)-conjugated AffiniPure anti-human IgG Fcγ-fragment-specific goat IgG F(ab')2 fragment (Jackson ImmunoResearch, Cat.-No. 109-116-098) as indicated. Expression of TnC and FAP on tumor cells was determined using the anti-FAP antibody (Calbiochem, moIgG1, OP188) or anti-TnC antibody (US Biological, moIgG1, T2550-20D), and detected using the secondary antibody FITC-labeled anti-mouse IgG antibody (Dako, Code K0078 (Quifikit)).

For discrimination of live and dead cells two methods were used. Non-fixed cells were acquired the same day in 85 μL/well FACS-buffer containing 0.2 μg/mL DAPI (Santa Cruz Biotec, Cat. No. Sc-3598) running a 5-laser LSR-Fortessa (BD Bioscience with DIVA software). In some cases, however, dead cells were labeled prior to the binding assay with Fixable Viability Dye eFluor® 660 (eBioscience 65-0864-18) or with Zombie Aqua' Fixable Viability Kit (BioLegend 423102) according to manufacturer's instructions to allow for subsequent formalin fixation of cells and over-night acquisition on a on a MACS Quant Analyzer 10 or on a 5-laser LSR_Fortessa (BD Bioscience with DIVA software). Briefly, cells were washed once with DPBS (Gibco by Life Technologies, Cat. No. 14190 326) and were incubated for 30 minutes at dark/4° C. at a cell concentration of 1×10⁶ cell/mL in DPBS containing Viability Dye eFluor® 660 [1 ug/mL]. Alternatively, cells were washed once with DPBS and were incubated for 15 minutes at dark/4° C. at a cell concentration of 1×10⁶ cell/mL in DPBS containing Zombie Aqua™ Viability Dye [1:800 dilution]. Cells were subsequently washed once with DPBS to remove excess dye before primary antigen binding molecules were added to the cells and the cells were incubated as described above. The cells were subsequently fixed for 15 minutes at 4° C. in formalin solution (1-2.5% (v/v) in DPBS, Sigma HT501320) before measurement.

Figure 8:
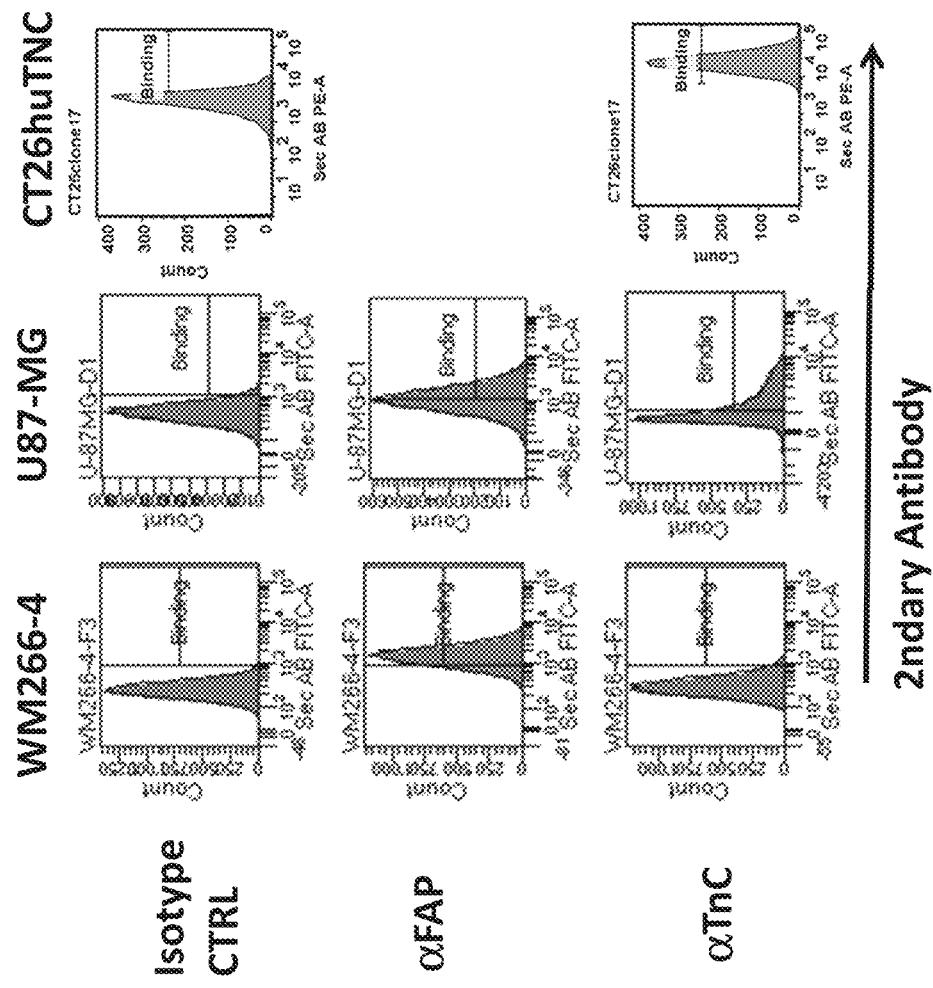
FIG. 8 shows expression of human FAP and human TnC on WM226-4, U87-MG and CT26huTnC cells, as determined by flow cytometry. WM266-4 cells are shown to express FAP but not TnC. U87-MG cells are shown to express FAP and TnC. CT26huTnC cells are shown to express TnC.

As shown in FIG. 8, TnC expression was detected on U87-MG cells (at a low level), and at high levels on CT26huTnC cells, but not on WM-266-4 cells. FAP expression was detected on WM-266-4 and U87-MG cells.

Figure 9B:
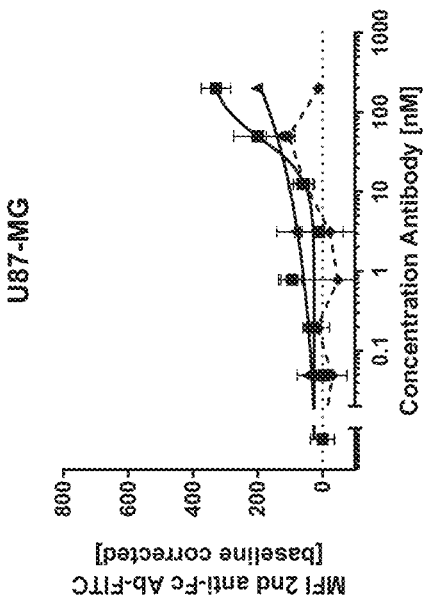
FIGS. 9A to 9C show the binding of the bispecific, bivalent anti-OX40, bivalent anti-TnC antigen binding molecules (i.e. 2+2 format) to WM266-4, U87-MG and CT26huTnC cells.
Figure 9A:
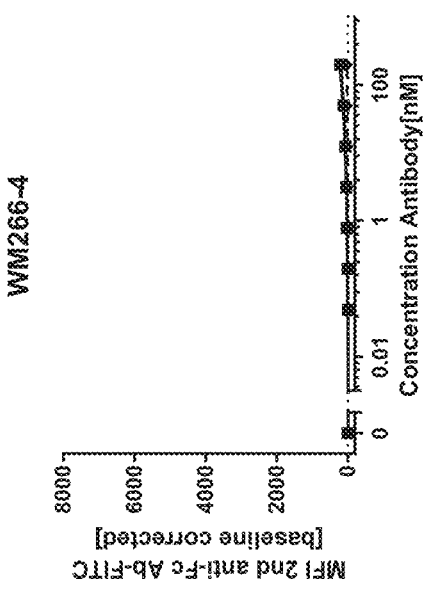
Figure 9C:
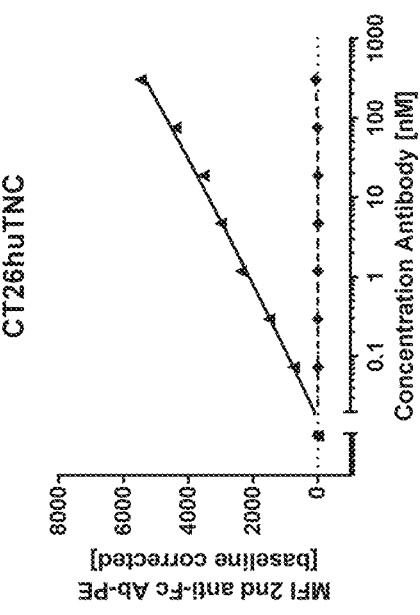

As shown in FIG. 9, the bispecific, bivalent anti-OX40 (clone 49B4), bivalent anti-TnC (clone 11C7 or clone 18D4) antigen binding molecules do not display binding to WM-266-4 cells (FIG. 9A). The bivalent anti-OX40, bivalent anti-TnC clone 18D4 antigen binding molecules displayed binding to TnC on U87-MG cells (FIG. 9B), and strong binding to CT26huTnC cells (FIG. 9C; filled triangles).

As shown in FIG. 10, the parental bivalent anti-TnC antibody clone18D4 (FIG. 10B; square with a cross) showed strong binding to TnC on U87-MG cells, and strong binding to CT26huTnC cells (FIG. 10C; square with a cross). Bivalent anti-OX40, bivalent anti-TnC clone 18D4 and tetravalent anti-OX40, bivalent anti-TnC clone 18D4 molecules were shown to bind to CT26huTnC cells less strongly than the parental bivalent anti-TnC antibody clone18D4 (FIG. 10C; filled triangle and filled circle vs. square with a cross), suggesting that expression of the molecule at the C-terminus of the antigen binding molecule decreases binding to TnC. Stabilization by introduction of charges was able to slightly increase binding to TnC by the N-terminally-expressed bivalent anti-TnC (FIG. 10C; filled circle vs filled triangle). Bivalent anti-OX40, bivalent anti-TnC clone 18D4 and tetravalent anti-OX40, bivalent anti-TnC clone 18D4 molecules were shown to bind to CT26huTnC cells more strongly than tetravalent anti-OX40, monovalent anti-TnC clone 18D4 molecules (FIG. 10C; filled square vs filled triangle and filled circle). The anti-TnC antigen binding molecules did not show binding to the TnC-negative WM-226-4 cells (FIG. 10A)

Table 36 shows the EC50 values for binding of the indicated antigen binding molecules to WM266-4, U87-MG and CT26huTnC cells.

TABLE 36

EC50 values for binding of aOx40 binder 49B9 in different bispecific human IgG1 P329GLALA formats to cell surface human TnC and human Ox40

| EC50 (nM) | 2 + 2 TnC (11C7) | 2 + 2 TnC (18D4) | 4 + 1 TnC (18D4) | 4 + 2 TnC (18D4) | αTnC (18D4) |
|---|---|---|---|---|---|
| OX40⁺ Cells | 4.22 | 6.59 | 0.08 | 0.08 | (—) |
| CT26huTnC TnC⁺ Cells | | n.c. | 7.73 | 8.63 | 2.69 |
| U87MG TnC⁺ Cells | n.c. | n.c. | n.c. | 44.26 | 8.21 | n.c. = curve was not to fit, no EC$_{50}$ calculation possible.

Example 5

Biological Activity of Bispecific Antigen Binding Molecules Targeting OX40 and TnC 5.1 HeLa Cells Expressing Human OX40 and Reporter Gene NF-κB-Luciferase Agonstic binding of Ox40 to its ligand induces downstream signaling via activation of nuclear factor kappa B (NFκB) (A. D. Weinberg et al., J. Leukoc. Biol. 2004, 75(6), 962-972). The recombinant reporter cell line HeLa_hOX40_NFκB_Luc1 expressing human OX40 on its surface was generated. This cell line harbors a reporter plasmid containing the luciferase gene under the control of an NFκB-sensitive enhancer segment. Binding and activation of OX40 induces dose-dependent activation of NFκB, which then translocates to the nucleus, where it binds to the NFκB-sensitive enhancer of the reporter plasmid to increase expression of the luciferase protein. Luciferase catalyzes luciferin-oxidation resulting in oxyluciferin, which emits light. This can be detected and quantified using a luminometer. Thus, the HeLa_hOx40_NFκB_Luc1 reporter cells can be used to analyse the ability of anti-OX40 molecules to induce NFκB activation as a measure for bioactivity.

Adherent HeLa_hOx40_NFκB_Luc1 cells were harvested using cell dissociation buffer (Invitrogen, Cat.-No. 13151-014) for 10 minutes at 37° C. Cells were washed once with DPBS and were adjusted to a cell density of 1.33×10⁵ in assay media comprising of MEM (Invitrogen, Cat.-No. 22561-021), 10% (v/v) heat-inactivated FBS, 1 mM Sodium-Pyruvate and 1% (v/v) non-essential amino acids. Cells were seeded at a density of 0.2×10⁵ cells per well in a sterile, white 96-well flat-bottomed tissue culture plate with lid (greiner bio-one, Cat. No. 655083) and incubated overnight at 37° C. in a 5% $CO_2$ atmosphere, in an incubator (Hera Cell 150).

The next day, HeLa_hOx40_NFkB_Luc1 cells were stimulated for 5-6 hours by adding assay medium containing various titrated bispecific antigen binding molecules targeting OX40 in a P329GLALA huIgG1 format. To analyse the effect of hyper-crosslinking on bioactivity, 25 µL/well of medium containing secondary antibody anti-human IgG Fcγ-fragment-specific goat IgG F(ab')$_2$ fragment (Jackson ImmunoResearch, 109-006-098) was added in a or 1:2 ratio (2 times more secondary antibody than the primary anti-OX40 P329GLALA huIgG1 antigen binding molecule). Hyper-crosslinking of the constructs by cell surface TnC+ cells was tested by adding 25 µL/well of medium containing TnC+ tumor cells (U87-MG or CT26huTnC cells) in a 4 to 1 ratio (four times as many TnC+ tumor cells as reporter cells per well).

After incubation, assay supernatant was aspirated and plates washed two times with DPBS. Quantification of light emission was performed using the luciferase 100 assay system and the reporter lysis buffer (both Promega, Cat.-No. E4550 and Cat-No: E3971) according to manufacturer's instructions. Briefly, cells were lysed for 10 minutes at –20° C. by addition of 30 uL per well 1× lysis buffer. Cells were thawed for 20 minutes at 37° C. before 90 uL luciferase assay reagent was added per well. Light emission was quantified immediately with a SpectraMax M5/M5e microplate reader (Molecular Devices, USA) or on a Spark® 10M multimode microplate reader (Tecan trading AG) using 500 ms integration time, without any filter to collect all wavelengths. Emitted relative light units (RLU) were corrected by basal luminescence of HeLa_hOx40_NFkB_Luc1 cells and were plotted against the logarithmic primary antibody concentration using Prism4 or 6 (GraphPad Software, USA). Curves were fitted to the data using the inbuilt sigmoidal dose response.

Figure 11A:
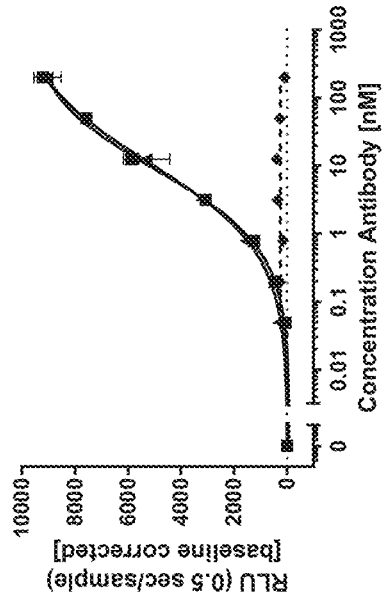
FIGS. 11A to 11D show activation of NFκB by the bispecific, bivalent anti-OX40, bivalent anti-TnC antigen binding molecules (i.e. 2+2 format), in the presence or absence of crosslinking.
Figure 11B:
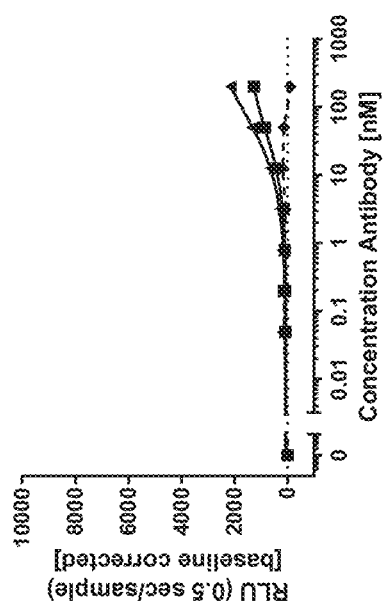
Figure 11C:
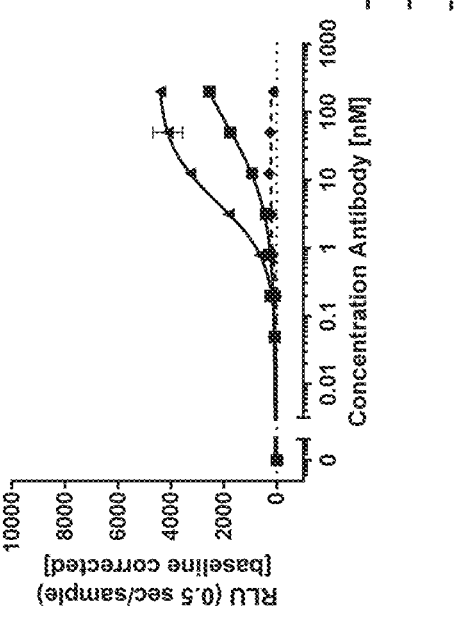
Figure 11D:
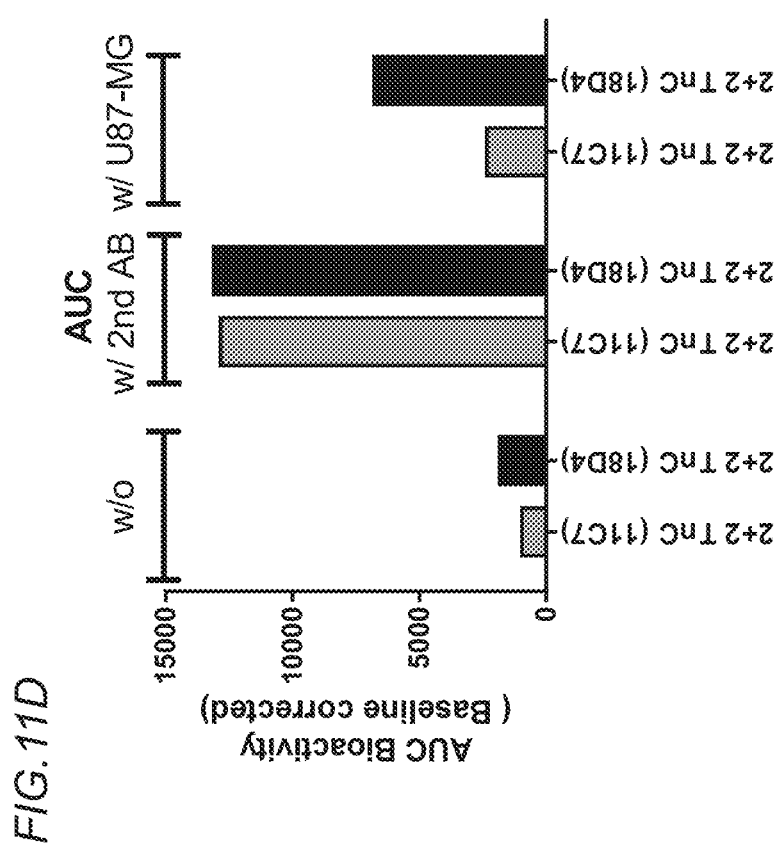

As shown in FIG. 11, all of the bivalent anti-OX40 antigen binding 2+2 molecules induced limited NFkB activation (FIG. 11A). Crosslinking by anti-human Fc specific secondary antibody strongly enhanced bioactivity independently of the targeting moiety (FIG. 11B). TnC-expressing tumor cells increased induction of NFκB-mediated luciferase-activation when TnC targeted molecules were used (FIGS. 11C and 11D; filled squares and filled triangles).

Figure 13A:
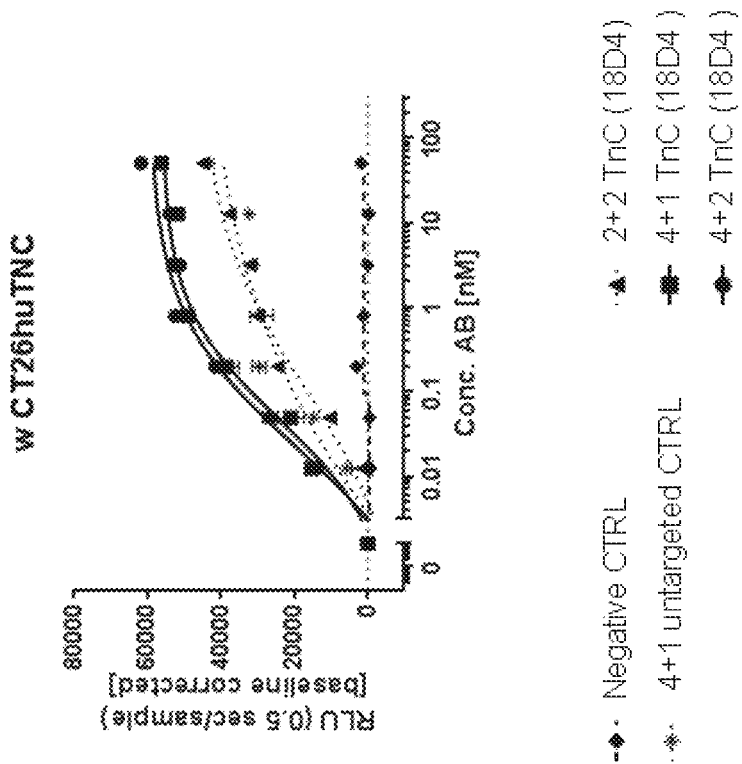
FIGS. 13A to 13C show activation of NFκB by the bispecific, tetravalent anti-OX40, monovalent or bivalent anti-TnC antigen binding molecules (i.e. 4+2 or 4+1 format), and bispecific, bivalent anti-OX40, bivalent anti-TnC (i.e. 2+2 format), in the presence or absence of crosslinking by CT26huTnC cells.
Figure 13B:

As shown in FIG. 12 and FIG. 13, all of the anti-OX40 antigen binding molecules induced limited NFkB activation (FIGS. 12A and 13A). Crosslinking by U87-MG cells enhanced bioactivity when TnC-targeted antigen binding molecules were used (FIG. 12B). As expected, all TnC targeted molecules caused a much higher induction of NFkB when crosslinked with CT26huTnC cell line as compared to crosslinking by U87-MG cells (compare FIG. 12B with FIG. 13B).

The area under the curve of the respective plotted dose-response curves was determined as an indicator of the agonistic capacity of each antigen binding molecule.

As shown in FIG. 12C, the tetravalent anti-OX40, bivalent anti-TnC (clone 18D4) 4+2 molecule induced the most NFkB activation in the presence of cross-linking by U87-MG cells (which express intermediate levels of surface TnC), and only a low level of agonism was detected by cross-linking by U87-MG cells with the equivalent tetravalent anti-OX40, monovalent anti-TnC (clone 18D4) 4+1 molecule. This finding is in agreement with the finding that the 4+2 molecules bind to U87-MG cells to a greater extent than the 4+1 molecules—see FIG. 10C.

Figure 13C:
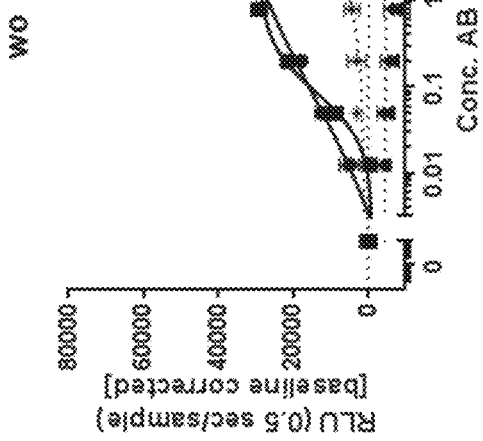
Figure 14A:
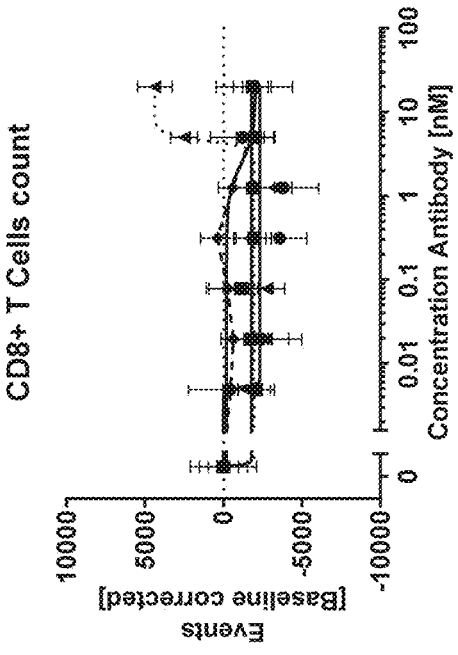
FIGS. 14A to 14D show rescue of suboptimal TCR restimulation of preactivated CD4 T cells with plate-immobilized the bispecific, tetravalent anti-OX40, monovalent or bivalent anti-TnC antigen binding molecules (i.e. 4+2 or 4+1 format), and bispecific, bivalent anti-OX40, bivalent anti-TnC (i.e. 2+2 format), in the presence of crosslinking by U87-MG cells.
Figure 14B:
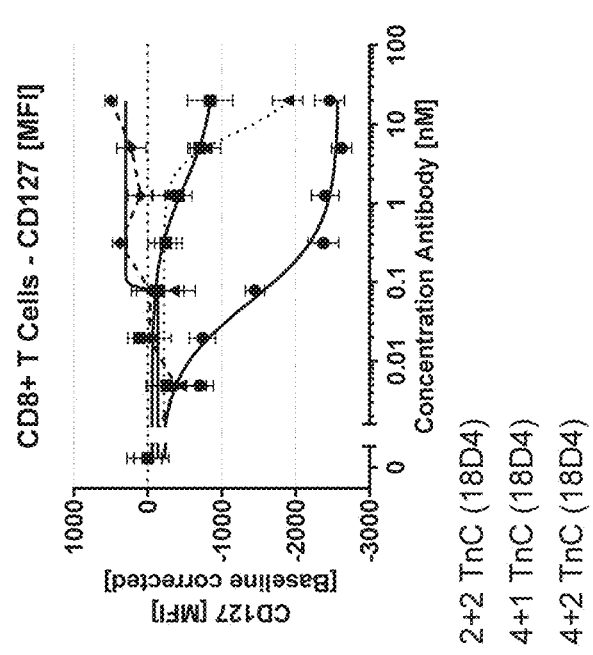
Figure 14C:
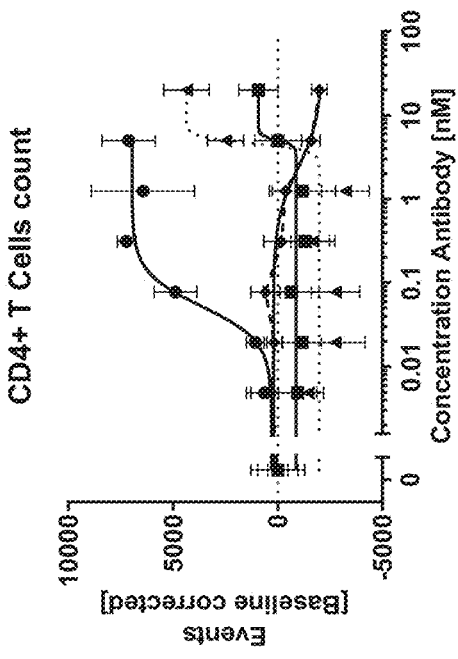
Figure 14D:
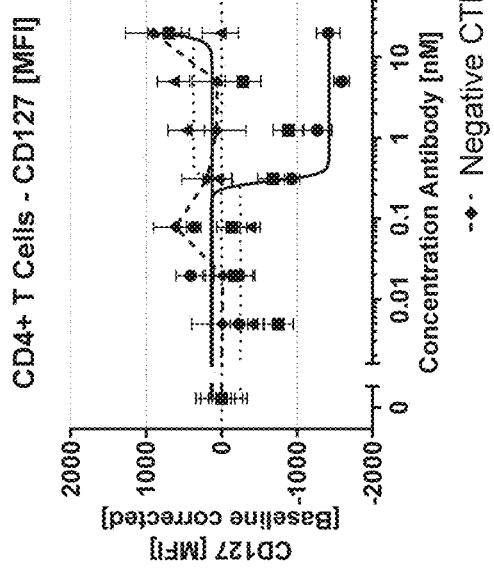
Figure 15A:
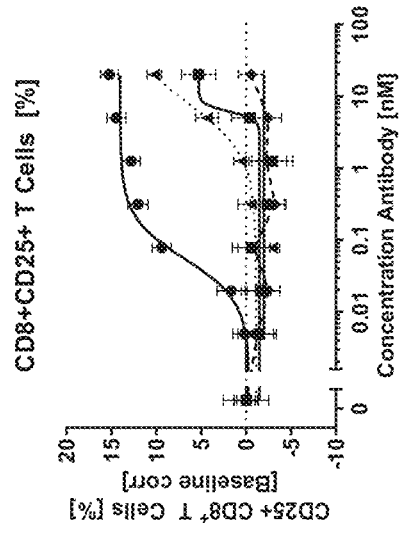
FIGS. 15A to 15D show rescue of suboptimal TCR restimulation of preactivated CD4 T cells with plate-immobilized the bispecific, tetravalent anti-OX40, monovalent or bivalent anti-TnC antigen binding molecules (i.e. 4+2 or 4+1 format), and bispecific, bivalent anti-OX40, bivalent anti-TnC (i.e. 2+2 format), in the presence of crosslinking by U87-MG cells.
Figure 15B:
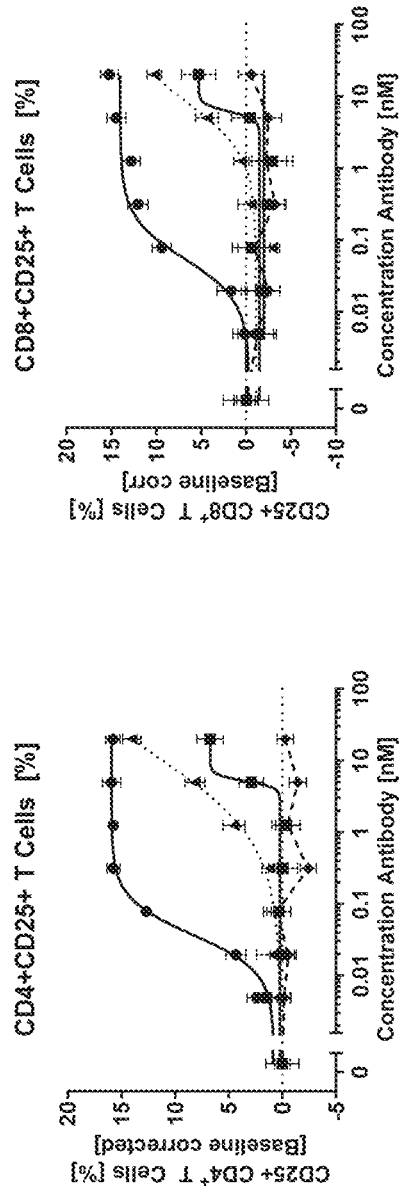
Figure 15C:
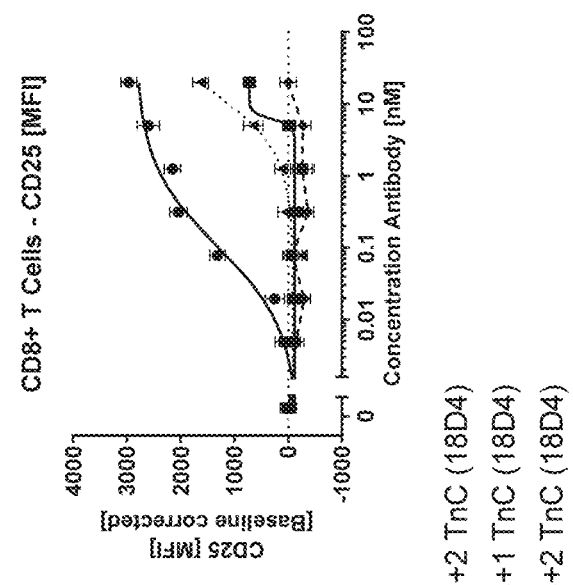
Figure 15D:
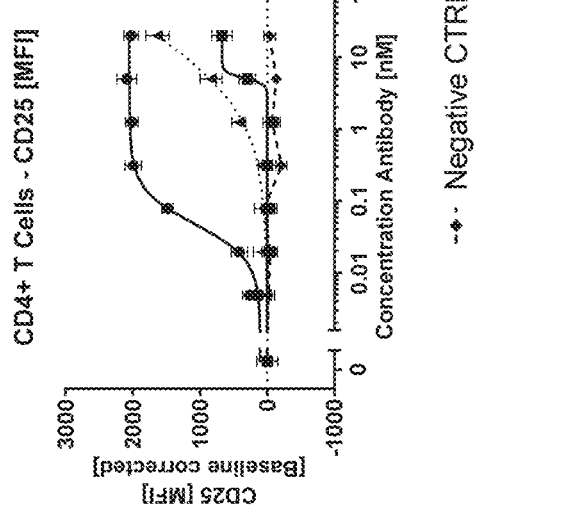
Figure 16A:
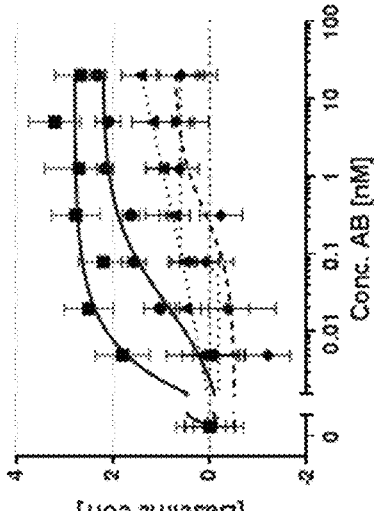
FIGS. 16A to 16D show rescue of suboptimal TCR restimulation of preactivated CD4 T cells with plate-immobilized the bispecific, tetravalent anti-OX40, monovalent or bivalent anti-TnC antigen binding molecules (i.e. 4+2 or 4+1 format), and bispecific, bivalent anti-OX40, bivalent anti-TnC (i.e. 2+2 format), in the presence of crosslinking by CT26huTnC cells.
Figure 16B:
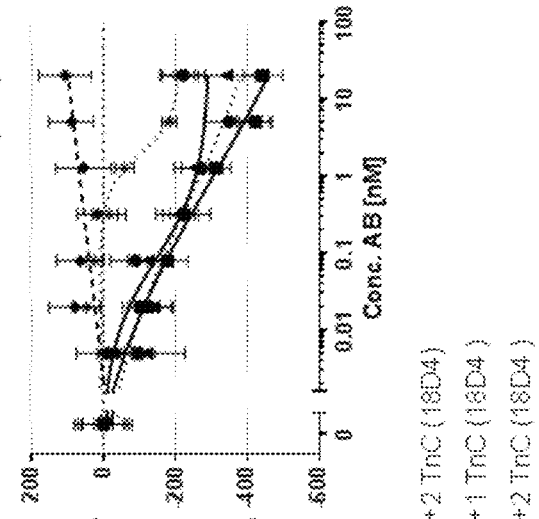
Figure 16C:
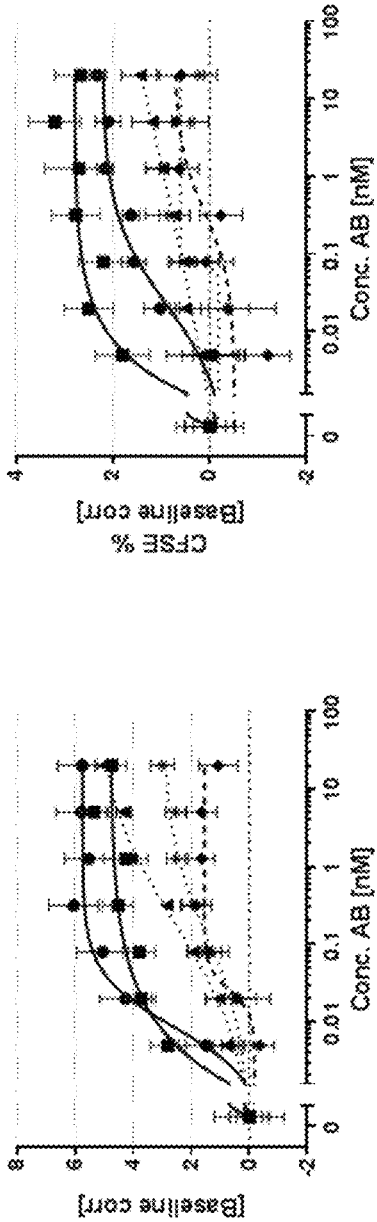
Figure 16D:
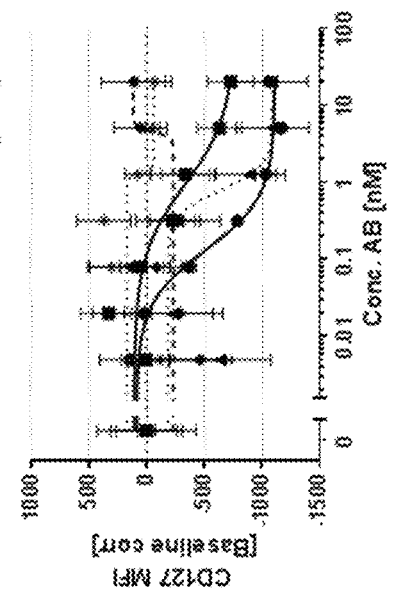

However, as shown in FIGS. 13B and 13C, when CT26huTnC cell line was used, both the tetravalent anti-OX40, bivalent anti-TnC (clone 18D4) 4+2 molecule and the tetravalent anti-OX40, monovalent anti-TnC (clone 18D4) 4+1 molecule induced very strong NFkB activation, and to a similar extent. It is also clear from FIGS. 13B and 13C that the bivalent anti-OX40, bivalent anti-TnC (clone 18D4) 2+2 molecule induced a lower level of NFkB activation as compared to the tetravalent anti-OX40, bivalent anti-TnC (clone 18D4) 4+2 and tetravalent anti-OX40, monovalent anti-TnC (clone 18D4) 4+1 molecules.

This latter finding suggests that hypercrosslinking by TnC, as well as high valency for OX40, are important for the agonist function of the OX40 antigen binding molecules.

5.2 OX40 Mediated Costimulation of Suboptimally TCR Triggered Resting Human PBMC and Hypercrosslinking by Cell Surface TnC Ligation of OX40 provides a synergistic co-stimulatory signal promoting division and survival of T-cells following suboptimal T-cell receptor (TCR) stimulation (M. Croft et al., Immunol. Rev. 2009, 229(1), 173-191). Additionally, production of several cytokines and surface expression of T-cell activation markers is increased following ligation of OX40 (I. Gramaglia et al., J. Immunol. 1998, 161(12), 6510-6517; S. M. Jensen et al., Seminars in Oncology 2010, 37(5), 524-532).

The bispecific anti-OX40, anti-TnC antigen binding molecules were analysed for their ability to rescue suboptimal TCR stimulation of resting human PBMC cells. Human PBMC preparations contain (1) resting, OX40-negative CD4+ and CD8+ T cells and (2) antigen presenting cells with various Fc-receptor molecules on their cell surface e.g. B cells and monocytes. Anti-human CD3 antibody of human IgG1 isotype binds through its Fc to the Fc-γ receptor molecules and trigger a prolonged TCR activation on resting OX40-negative CD4+ and CD8+ T cells. These cells then start to express OX40 within several hours. Functional agonistic compounds against OX40 can signal via the OX40 receptor present on activated CD8+ and CD4+ T cells and support TCR-mediated stimulation.

Resting eFluor670- or CFSE-labelled (Cell Trace CFSE proliferation Kit, Thermo Fischer, C34554) human PBMCs were stimulated for four days with a suboptimal concentration of anti-CD3 antibody in the presence of irradiated U87-MG or CT26huTnC cells and titrated anti-OX40 antigen binding molecules. The effects on T-cell survival, proliferation and differentiation were analysed by monitoring total cell counts and eFluor670/CFSE dilution in living cells by flow cytometry. Additionally, cells were co-stained with fluorescently-labeled antibodies against T-cell activation marker CD25 and the maturation marker CD127.

U87-MG or CT26huTnC cells were harvested using cell dissociation buffer (Invitrogen, Cat.-No. 13151-014) for 10 minutes at 37° C. Cells were washed once with DPBS. U87-MG or CT26huTnC cells were cultured at a density of $0.2 \times 10^5$ cells per well in T cell media in a sterile 96-well round bottom adhesion tissue culture plate (TPP, Cat. No. 92097) overnight at 37° C. and 5% $CO_2$ in an incubator (Hera Cell 150). The next day they were irradiated in an xRay irradiator using a dose of 4500 RAD to prevent later overgrowth of human PBMC by the tumor cell line.

Human PBMCs were isolated by ficoll density centrifugation and were labeled with eFluor670 as described in Example 4.3. Alternatively, the PBMCs were labelled with CFSE, for labeling cells were harvested, washed with pre-warmed (37° C.) DPBS and adjusted to a cell density of $1 \times 10^7$ cells/mL in DPBS. CFSE (Cell Trace CFSE proliferation Kit, Thermo Fischer, Cat.-No. C34554) was added to the suspension of naïve human PBMC at a final concentration of 0.2 µM and a final cell density of $0.5 \times 10^7$ cells/mL in DPBS. Cells were then incubated for 10 min at 37° C. in the dark. To stop the labeling reaction 4 mL heat inactivated FBS were added and cells were washed three times with T cell medium. Cells were added to each well at a density of $0.6 \times 10^5$ cells per well. Anti-human CD3 antibody (clone V9, human IgG1) at a final concentration of 10 nM, and the indicated anti-OX40 antigen binding molecules were added at the indicated concentrations. Cells were activated for four days at 37° C. and 5% $CO_2$ in an incubator (Hera Cell 150). Cells were subsequently surface-stained with fluorescent dye-conjugated antibodies anti-human CD4 (clone RPA-T4, BioLegend, Cat.-No. 300532), CD8 (clone RPa-T8, BioLegend, Cat.-No. 3010441), anti-CD25 (clone M-A251, BioLegend, Cat.-No. 356112) and anti-CD127 (clone A019D5, BioLegend, Cat.-No. 351324) for 20 min at 4° C. Cell pellets were washed once with FACS buffer. Cells were finally resuspended in 85 µL/well FACS-buffer containing 0.2 µg/mL DAPI (Santa Cruz Biotec, Cat. No. Sc-3598) and acquired the same day using 5-laser LSR-Fortessa (BD Bioscience with DIVA software).

In some cases, cells were washed once with DPBS and were incubated for 15 minutes at dark/4° C. at a cell concentration of $1 \times 10^6$ cell/mL in DPBS containing Zombie Aqua™ Viability Dye [1:800 dilution]. Cells were washed once with DPBS to remove excess and surface staining with fluorescent dye-conjugated antibodies was performed as described above. Cells were fixed for 30 minutes/4° C. in formalin solution (1% (v/v) in DPBS, Sigma HT501320) before measurement. Plates were finally resuspended in 100 µL/well FACS-buffer and acquired the same day using 5-laser LSR-Fortessa (BD Bioscience with DIVA software).

The results of the experiments are shown in FIGS. 14 to 16.

Hyper-crosslinking of the TnC-targeted 4+2 (filled circle) anti-OX40 antigen binding molecules by culture in the presence of U87-MG cells strongly promoted proliferation and maturation (FIG. 14) and induced an enhanced activated (CD25+) phenotype (FIG. 15) in human CD4+ and CD8+ T cells. Hyper-crosslinking of the TnC targeted 4+2 (filled circle) anti-OX40 antigen binding molecules by culture in the presence of CT26huTnC cells strongly promoted proliferation and maturation (FIG. 16) in human CD4+ and CD8+ T cells. The tetravalent anti-OX40, bivalent anti-TnC 4+2 molecules (filled circle) were clearly superior in their ability to rescue suboptimal TCR stimulation, as compared to bivalent anti-OX40, bivalent anti-TnC 2+2 molecules (filled triangle) and tetravalent anti-OX40, monovalent anti-TnC 4+1 molecules (filled square).

Tetravalent anti-OX40, monovalent anti-TnC 4+1 molecules (filled square) were shown to have reduced ability to rescue suboptimal TCR stimulation as compared to bivalent anti-OX40, bivalent anti-TnC 2+2 molecules (filled triangle). This may be explained by the reduced affinity of monomeric N-terminally fused anti-TnC (18D4) molecules for TnC as compared to bivalent molecules. However, only a small degree of crosslinking by cell surface TnC can be expected from N terminal fused anti-TnC (18D4) binders due to steric hindrance.

The results suggest that for optimal OX40 agonism in T cells, not only sufficient oligomerization of the OX40 receptor is required (e.g. through tetravalency for OX40), but also, cell surface immobilization of OX40 receptor oligomers is necessary.

The invention claimed is:

1. A bispecific antigen binding molecule, comprising
   (a) at least one moiety capable of specific binding to OX40 comprising an antibody light chain variable region (VL) comprising the amino acid sequence of SEQ ID NO:28 and an antibody heavy chain variable region (VH) comprising the amino acid sequence of SEQ ID NO:27, and
   (b) at least one moiety capable of specific binding to tenascin C (TnC) comprising (i) a VH comprising the amino acid sequence of SEQ ID NO:52 and a VL comprising the amino acid sequence of SEQ ID NO:53, or (ii) a VH comprising the amino acid sequence of SEQ ID NO:54 and a VL comprising the amino acid sequence of SEQ ID NO:55, connected to the C-terminus of the Fc region, and
   (c) an Fc region composed of a first and a second subunit capable of stable association, wherein the Fc region is of human IgG1 subclass with the amino acid mutations L234A, L235A and P329G (numbering according to Kabat EU index).

2. The bispecific antigen binding molecule of claim 1, wherein the Fc region comprises a modification promoting the association of the first and second subunit of the Fc region.

3. The bispecific antigen binding molecule of claim 1, wherein the bispecific antigen binding molecule comprises
   (a) two heavy chains, each heavy chain comprising a VH and CH1 domain of a Fab fragment capable of specific binding to OX40, and a Fc region subunit,
   (b) two light chains, each light chain comprising a VL and CL domain of a Fab fragment capable of specific binding to OX40, and
   (c) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

4. The bispecific antigen binding molecule of claim 1, wherein the bispecific antigen binding molecule comprises four Fab fragments capable of specific binding to OX40.

5. The bispecific antigen binding molecule of claim 1, wherein the bispecific antigen binding molecule comprises
   (a) two heavy chains, each heavy chain comprising two VH domains and two CH1 domains of a Fab fragment capable of specific binding to OX40 and a Fc region subunit,
   (b) four light chains, each light chain comprising a VL and CL domain of a Fab fragment capable of specific binding to OX40, and
   (c) a VH and a VL of a moiety capable specific binding to TnC, wherein the VH is connected to the C-terminus of one of the two heavy chains of (a), and wherein the VL is connected to the C-terminus of the other of the two heavy chains of (a).

6. The bispecific antigen binding molecule of claim 1, wherein the bispecific antigen binding molecule comprises
   (a) two heavy chains, each heavy chain comprising two VH domains and two CH1 domains of a Fab fragment capable of specific binding to OX40 and a Fc region subunit,
   (b) four light chains, each light chain comprising a VL and CL domain of a Fab fragment capable of specific binding to OX40, and
   (c) two Fab fragments capable of specific binding to TnC, wherein one of the Fab fragments is connected to the C-terminus of one of the two heavy chains of (a), and the other of the Fab fragments is connected to the C-terminus of the other of the two heavy chains of (a).

7. A pharmaceutical composition comprising the bispecific antigen binding molecule of claim 1 and at least one pharmaceutically acceptable excipient.

8. A method of treating an individual having cancer comprising administering to the individual an effective amount of the bispecific antigen binding molecule of claim 1.

9. A polynucleotide encoding the bispecific antigen binding molecule of claim 1.

10. An expression vector comprising the polynucleotide of claim 9.

11. A host cell comprising the expression vector of claim 10.

12. A method of producing a bispecific antigen binding molecule, comprising culturing the host cell of claim 11 under conditions suitable for the expression of the bispecific antigen binding molecule, and isolating the bispecific antigen binding molecule.

13. A bispecific antigen binding molecule, selected from the group consisting of
   (i) a bispecific antigen binding molecule comprising two heavy chains, each comprising the amino acid sequence of SEQ ID NO:213, two light chains, each comprising the amino acid sequence of SEQ ID NO:212, and two light chains, each comprising the amino acid sequence of SEQ ID NO:214,
   (ii) a bispecific antigen binding molecule comprising two heavy chains, each comprising the amino acid sequence of SEQ ID NO:215, two light chains, each comprising the amino acid sequence of SEQ ID NO:212, and two light chains, each comprising the amino acid sequence of SEQ ID NO:216,
   (iii) a bispecific antigen binding molecule comprising a first heavy chain comprising the amino acid sequence of SEQ ID NO:222, a second heavy chain comprising the amino acid sequence of SEQ ID NO:223, and four light chains, each comprising the amino acid sequence of SEQ ID NO:212, and
   (iv) a bispecific antigen binding molecule comprising two heavy chains, each comprising the amino acid sequence of SEQ ID NO:225, four light chains, each comprising the amino acid sequence of SEQ ID NO:224, and two light chains, each comprising the amino acid sequence of SEQ ID NO:226.

* * * * *

SEQUENCE LISTING

```
<160> NUMBER OF SEQ ID NOS: 226

<210> SEQ ID NO 1
<211> LENGTH: 186
<212> TYPE: PRT
<213> ORGANISM: Homo sapiens

<400> SEQUENCE: 1

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
    50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
    130                 135                 140
```

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
            165                 170                 175

Arg Pro Val Glu Val Pro Gly Gly Arg Ala
        180                 185

<210> SEQ ID NO 2
<211> LENGTH: 5
<212> TYPE: PRT
<213> ORGANISM: Artificial sequence
<220> FEATURE:
<223> OTHER INFORMATION: OX40(8H9,49B4,1G4, 20B7)  CDR-H1

<400> SEQUENCE: 2

Ser Tyr Ala Ile Ser
1               5

<210> SEQ ID NO 3
<211> LENGTH: 5
<212> TYPE: PRT
<213> ORGANISM: Artificial sequence
<220> FEATURE:
<223> OTHER INFORMATION: OX40(CLC-563, CLC-564, 17A9)  CDR-H1

<400> SEQUENCE: 3

Ser Tyr Ala Met Ser
1               5

<210> SEQ ID NO 4
<211> LENGTH: 17
<212> TYPE: PRT
<213> ORGANISM: Artificial sequence
<220> FEATURE:
<223> OTHER INFORMATION: OX40(8H9,49B4,1G4, 20B7)  CDR-H2

<400> SEQUENCE: 4

Gly Ile Ile Pro Ile Phe Gly Thr Ala Asn Tyr Ala Gln Lys Phe Gln
1               5                   10                  15

Gly

<210> SEQ ID NO 5
<211> LENGTH: 17
<212> TYPE: PRT
<213> ORGANISM: Artificial sequence
<220> FEATURE:
<223> OTHER INFORMATION: OX40(CLC-563, CLC-564, 17A9)  CDR-H2

<400> SEQUENCE: 5

Ala Ile Ser Gly Ser Gly Gly Ser Thr Tyr Tyr Ala Asp Ser Val Lys
1               5                   10                  15

Gly

<210> SEQ ID NO 6
<211> LENGTH: 7
<212> TYPE: PRT
<213> ORGANISM: Artificial sequence
<220> FEATURE:
<223> OTHER INFORMATION: OX40(8H9)  CDR-H3

<400> SEQUENCE: 6

Glu Tyr Gly Trp Met Asp Tyr
1               5

```
<210> SEQ ID NO 7
<211> LENGTH: 9
<212> TYPE: PRT
<213> ORGANISM: Artificial sequence
<220> FEATURE:
<223> OTHER INFORMATION: OX40(49B4)  CDR-H3

<400> SEQUENCE: 7

Glu Tyr Tyr Arg Gly Pro Tyr Asp Tyr
1               5

<210> SEQ ID NO 8
<211> LENGTH: 7
<212> TYPE: PRT
<213> ORGANISM: Artificial sequence
<220> FEATURE:
<223> OTHER INFORMATION: OX40(1G4)  CDR-H3

<400> SEQUENCE: 8

Glu Tyr Gly Ser Met Asp Tyr
1               5

<210> SEQ ID NO 9
<211> LENGTH: 13
<212> TYPE: PRT
<213> ORGANISM: Artificial sequence
<220> FEATURE:
<223> OTHER INFORMATION: OX40(20B7)  CDR-H3

<400> SEQUENCE: 9

Val Asn Tyr Pro Tyr Ser Tyr Trp Gly Asp Phe Asp Tyr
1               5                   10

<210> SEQ ID NO 10
<211> LENGTH: 7
<212> TYPE: PRT
<213> ORGANISM: Artificial sequence
<220> FEATURE:
<223> OTHER INFORMATION: OX40(CLC-563)  CDR-H3

<400> SEQUENCE: 10

Asp Val Gly Ala Phe Asp Tyr
1               5

<210> SEQ ID NO 11
<211> LENGTH: 7
<212> TYPE: PRT
<213> ORGANISM: Artificial sequence
<220> FEATURE:
<223> OTHER INFORMATION: OX40(CLC-564)  CDR-H3

<400> SEQUENCE: 11

Asp Val Gly Pro Phe Asp Tyr
1               5

<210> SEQ ID NO 12
<211> LENGTH: 11
<212> TYPE: PRT
<213> ORGANISM: Artificial sequence
<220> FEATURE:
<223> OTHER INFORMATION: OX40(17A9)-CDR-H3

<400> SEQUENCE: 12

Val Phe Tyr Arg Gly Gly Val Ser Met Asp Tyr
1               5                   10

<210> SEQ ID NO 13
```

```
<211> LENGTH: 11
<212> TYPE: PRT
<213> ORGANISM: Artificial sequence
<220> FEATURE:
<223> OTHER INFORMATION: OX40(8H9,49B4,1G4, 20B7)  CDR-L1

<400> SEQUENCE: 13

Arg Ala Ser Gln Ser Ile Ser Ser Trp Leu Ala
1               5                   10

<210> SEQ ID NO 14
<211> LENGTH: 12
<212> TYPE: PRT
<213> ORGANISM: Artificial sequence
<220> FEATURE:
<223> OTHER INFORMATION: OX40(CLC-563, CLC564)  CDR-L1

<400> SEQUENCE: 14

Arg Ala Ser Gln Ser Val Ser Ser Ser Tyr Leu Ala
1               5                   10

<210> SEQ ID NO 15
<211> LENGTH: 11
<212> TYPE: PRT
<213> ORGANISM: Artificial sequence
<220> FEATURE:
<223> OTHER INFORMATION: OX40(17A9) CDR-L1

<400> SEQUENCE: 15

Gln Gly Asp Ser Leu Arg Ser Tyr Tyr Ala Ser
1               5                   10

<210> SEQ ID NO 16
<211> LENGTH: 7
<212> TYPE: PRT
<213> ORGANISM: Artificial sequence
<220> FEATURE:
<223> OTHER INFORMATION: OX40(8H9,49B4,1G4, 20B7)  CDR-L2

<400> SEQUENCE: 16

Asp Ala Ser Ser Leu Glu Ser
1               5

<210> SEQ ID NO 17
<211> LENGTH: 7
<212> TYPE: PRT
<213> ORGANISM: Artificial sequence
<220> FEATURE:
<223> OTHER INFORMATION: OX40(CLC-563, CLC564)  CDR-L2

<400> SEQUENCE: 17

Gly Ala Ser Ser Arg Ala Thr
1               5

<210> SEQ ID NO 18
<211> LENGTH: 7
<212> TYPE: PRT
<213> ORGANISM: Artificial sequence
<220> FEATURE:
<223> OTHER INFORMATION: OX40(17A9) CDR-L2

<400> SEQUENCE: 18

Gly Lys Asn Asn Arg Pro Ser
1               5

<210> SEQ ID NO 19
<211> LENGTH: 10
```

<212> TYPE: PRT
<213> ORGANISM: Artificial sequence
<220> FEATURE:
<223> OTHER INFORMATION: OX40(8H9) CDR-L3

<400> SEQUENCE: 19

Gln Gln Tyr Leu Thr Tyr Ser Arg Phe Thr
1               5                   10

<210> SEQ ID NO 20
<211> LENGTH: 9
<212> TYPE: PRT
<213> ORGANISM: Artificial sequence
<220> FEATURE:
<223> OTHER INFORMATION: OX40(49B4) CDR-L3

<400> SEQUENCE: 20

Gln Gln Tyr Ser Ser Gln Pro Tyr Thr
1               5

<210> SEQ ID NO 21
<211> LENGTH: 10
<212> TYPE: PRT
<213> ORGANISM: Artificial sequence
<220> FEATURE:
<223> OTHER INFORMATION: OX40(1G4) CDR-L3

<400> SEQUENCE: 21

Gln Gln Tyr Ile Ser Tyr Ser Met Leu Thr
1               5                   10

<210> SEQ ID NO 22
<211> LENGTH: 9
<212> TYPE: PRT
<213> ORGANISM: Artificial sequence
<220> FEATURE:
<223> OTHER INFORMATION: OX40(20B7) CDR-L3

<400> SEQUENCE: 22

Gln Gln Tyr Gln Ala Phe Ser Leu Thr
1               5

<210> SEQ ID NO 23
<211> LENGTH: 9
<212> TYPE: PRT
<213> ORGANISM: Artificial sequence
<220> FEATURE:
<223> OTHER INFORMATION: OX40(CLC-563, CLC-164) CDR-L3

<400> SEQUENCE: 23

Gln Gln Tyr Gly Ser Ser Pro Leu Thr
1               5

<210> SEQ ID NO 24
<211> LENGTH: 10
<212> TYPE: PRT
<213> ORGANISM: Artificial sequence
<220> FEATURE:
<223> OTHER INFORMATION: OX40(17A9) CDR-L3

<400> SEQUENCE: 24

Asn Ser Arg Val Met Pro His Asn Arg Val
1               5                   10

<210> SEQ ID NO 25
<211> LENGTH: 116
<212> TYPE: PRT

```
<213> ORGANISM: Artificial sequence
<220> FEATURE:
<223> OTHER INFORMATION: OX40(8H9) VH

<400> SEQUENCE: 25

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110

Thr Val Ser Ser
        115

<210> SEQ ID NO 26
<211> LENGTH: 108
<212> TYPE: PRT
<213> ORGANISM: Artificial sequence
<220> FEATURE:
<223> OTHER INFORMATION: OX40(8H9) VL

<400> SEQUENCE: 26

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Leu Thr Tyr Ser Arg
                85                  90                  95

Phe Thr Phe Gly Gln Gly Thr Lys Val Glu Ile Lys
            100                 105

<210> SEQ ID NO 27
<211> LENGTH: 118
<212> TYPE: PRT
<213> ORGANISM: Artificial sequence
<220> FEATURE:
<223> OTHER INFORMATION: OX40(49B4) VH

<400> SEQUENCE: 27

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45
```

```
Gly Gly Ile Ile Pro Ile Phe Gly Thr Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Tyr Arg Gly Pro Tyr Asp Tyr Trp Gly Gln Gly Thr
            100                 105                 110

Thr Val Thr Val Ser Ser
            115

<210> SEQ ID NO 28
<211> LENGTH: 107
<212> TYPE: PRT
<213> ORGANISM: Artificial sequence
<220> FEATURE:
<223> OTHER INFORMATION: OX40(49B4) VL

<400> SEQUENCE: 28

Asp Ile Gln Met Thr Gln Ser Pro Ser Thr Leu Ser Ala Ser Val Gly
 1               5                  10                  15

Asp Arg Val Thr Ile Thr Cys Arg Ala Ser Gln Ser Ile Ser Ser Trp
                 20                  25                  30

Leu Ala Trp Tyr Gln Gln Lys Pro Gly Lys Ala Pro Lys Leu Leu Ile
             35                  40                  45

Tyr Asp Ala Ser Ser Leu Glu Ser Gly Val Pro Ser Arg Phe Ser Gly
 50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Gln Tyr Ser Ser Gln Pro Tyr
                 85                  90                  95

Thr Phe Gly Gln Gly Thr Lys Val Glu Ile Lys
            100                 105

<210> SEQ ID NO 29
<211> LENGTH: 116
<212> TYPE: PRT
<213> ORGANISM: Artificial sequence
<220> FEATURE:
<223> OTHER INFORMATION: OX40(1G4) VH

<400> SEQUENCE: 29

Gln Val Gln Leu Val Gln Ser Gly Ala Glu Val Lys Lys Pro Gly Ser
 1               5                  10                  15

Ser Val Lys Val Ser Cys Lys Ala Ser Gly Gly Thr Phe Ser Ser Tyr
                 20                  25                  30

Ala Ile Ser Trp Val Arg Gln Ala Pro Gly Gln Gly Leu Glu Trp Met
             35                  40                  45

Gly Gly Ile Ile Pro Ile Phe Gly Thr Ala Asn Tyr Ala Gln Lys Phe
         50                  55                  60

Gln Gly Arg Val Thr Ile Thr Ala Asp Lys Ser Thr Ser Thr Ala Tyr
 65                  70                  75                  80

Met Glu Leu Ser Ser Leu Arg Ser Glu Asp Thr Ala Val Tyr Tyr Cys
                 85                  90                  95

Ala Arg Glu Tyr Gly Ser Met Asp Tyr Trp Gly Gln Gly Thr Thr Val
            100                 105                 110

Thr Val Ser Ser
```

<210> SEQ ID NO 30
<211> LENGTH: 108
<212> TYPE: PRT
<213> ORGANISM: Artificial sequence
<220> FEATURE:
<223> OTHER INFORMATION: OX40(1G4) VL

<400> SEQUENCE: 30

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Met
                85                  90                  95

Leu Thr Phe Gly Gln Gly Thr Lys Val Glu Ile Lys
            100                 105

<210> SEQ ID NO 31
<211> LENGTH: 122
<212> TYPE: PRT
<213> ORGANISM: Artificial sequence
<220> FEATURE:
<223> OTHER INFORMATION: OX40(20B7) VH

<400> SEQUENCE: 31

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Tyr Pro Tyr Ser Tyr Trp Gly Asp Phe Asp Tyr Trp
            100                 105                 110

Gly Gln Gly Thr Thr Val Thr Val Ser Ser
        115                 120

<210> SEQ ID NO 32
<211> LENGTH: 107
<212> TYPE: PRT
<213> ORGANISM: Artificial sequence
<220> FEATURE:
<223> OTHER INFORMATION: OX40(20B7) VL

<400> SEQUENCE: 32

Asp Ile Gln Met Thr Gln Ser Pro Ser Thr Leu Ser Ala Ser Val Gly
1               5                   10                  15

-continued

```
Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ala Phe Ser Leu
                85                  90                  95

Thr Phe Gly Gln Gly Thr Lys Val Glu Ile Lys
            100                 105
```

<210> SEQ ID NO 33
<211> LENGTH: 116
<212> TYPE: PRT
<213> ORGANISM: Artificial sequence
<220> FEATURE:
<223> OTHER INFORMATION: OX40(CLC-563) VH

<400> SEQUENCE: 33

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Asp Val Gly Ala Phe Asp Tyr Trp Gly Gln Gly Ala Leu Val
            100                 105                 110

Thr Val Ser Ser
        115
```

<210> SEQ ID NO 34
<211> LENGTH: 108
<212> TYPE: PRT
<213> ORGANISM: Artificial sequence
<220> FEATURE:
<223> OTHER INFORMATION: OX40(CLC-563) VL

<400> SEQUENCE: 34

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
```

```
                    85                  90                  95

Leu Thr Phe Gly Gln Gly Thr Lys Val Glu Ile Lys
            100                 105

<210> SEQ ID NO 35
<211> LENGTH: 116
<212> TYPE: PRT
<213> ORGANISM: Artificial sequence
<220> FEATURE:
<223> OTHER INFORMATION: OX40(CLC-564)  VH

<400> SEQUENCE: 35

Glu Val Gln Leu Leu Glu Ser Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Phe Asp Val Gly Pro Phe Asp Tyr Trp Gly Gln Gly Thr Leu Val
            100                 105                 110

Thr Val Ser Ser
        115

<210> SEQ ID NO 36
<211> LENGTH: 108
<212> TYPE: PRT
<213> ORGANISM: Artificial sequence
<220> FEATURE:
<223> OTHER INFORMATION: OX40(CLC-564)  VL

<400> SEQUENCE: 36

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys
            100                 105

<210> SEQ ID NO 37
<211> LENGTH: 120
<212> TYPE: PRT
<213> ORGANISM: Artificial sequence
<220> FEATURE:
<223> OTHER INFORMATION: OX40(17A9)  VH

<400> SEQUENCE: 37
```

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Phe Tyr Arg Gly Gly Val Ser Met Asp Tyr Trp Gly Gln
            100                 105                 110

Gly Thr Leu Val Thr Val Ser Ser
            115                 120

<210> SEQ ID NO 38
<211> LENGTH: 106
<212> TYPE: PRT
<213> ORGANISM: Artificial sequence
<220> FEATURE:
<223> OTHER INFORMATION: OX40(17A9)  VL

<400> SEQUENCE: 38

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Val Met Pro His Asn Arg
                85                  90                  95

Val Phe Gly Gly Gly Thr Lys Leu Thr Val
            100                 105

<210> SEQ ID NO 39
<211> LENGTH: 2201
<212> TYPE: PRT
<213> ORGANISM: Homo sapiens

<400> SEQUENCE: 39

Met Gly Ala Met Thr Gln Leu Leu Ala Gly Val Phe Leu Ala Phe Leu
1               5                   10                  15

Ala Leu Ala Thr Glu Gly Gly Val Leu Lys Lys Val Ile Arg His Lys
            20                  25                  30

Arg Gln Ser Gly Val Asn Ala Thr Leu Pro Glu Glu Asn Gln Pro Val
        35                  40                  45

Val Phe Asn His Val Tyr Asn Ile Lys Leu Pro Val Gly Ser Gln Cys
    50                  55                  60

Ser Val Asp Leu Glu Ser Ala Ser Gly Glu Lys Asp Leu Ala Pro Pro
65                  70                  75                  80
```

-continued

```
Ser Glu Pro Ser Glu Ser Phe Gln Glu His Thr Val Asp Gly Glu Asn
            85                  90                  95
Gln Ile Val Phe Thr His Arg Ile Asn Ile Pro Arg Arg Ala Cys Gly
            100                 105                 110
Cys Ala Ala Ala Pro Asp Val Lys Glu Leu Leu Ser Arg Leu Glu Glu
            115                 120                 125
Leu Glu Asn Leu Val Ser Ser Leu Arg Glu Gln Cys Thr Ala Gly Ala
        130                 135                 140
Gly Cys Cys Leu Gln Pro Ala Thr Gly Arg Leu Asp Thr Arg Pro Phe
145                 150                 155                 160
Cys Ser Gly Arg Gly Asn Phe Ser Thr Glu Gly Cys Gly Cys Val Cys
                165                 170                 175
Glu Pro Gly Trp Lys Gly Pro Asn Cys Ser Glu Pro Glu Cys Pro Gly
            180                 185                 190
Asn Cys His Leu Arg Gly Arg Cys Ile Asp Gly Gln Cys Ile Cys Asp
            195                 200                 205
Asp Gly Phe Thr Gly Glu Asp Cys Ser Gln Leu Ala Cys Pro Ser Asp
        210                 215                 220
Cys Asn Asp Gln Gly Lys Cys Val Asn Gly Val Cys Ile Cys Phe Glu
225                 230                 235                 240
Gly Tyr Ala Gly Ala Asp Cys Ser Arg Glu Ile Cys Pro Val Pro Cys
                245                 250                 255
Ser Glu Glu His Gly Thr Cys Val Asp Gly Leu Cys Val Cys His Asp
            260                 265                 270
Gly Phe Ala Gly Asp Asp Cys Asn Lys Pro Leu Cys Leu Asn Asn Cys
        275                 280                 285
Tyr Asn Arg Gly Arg Cys Val Glu Asn Glu Cys Val Cys Asp Glu Gly
        290                 295                 300
Phe Thr Gly Glu Asp Cys Ser Glu Leu Ile Cys Pro Asn Asp Cys Phe
305                 310                 315                 320
Asp Arg Gly Arg Cys Ile Asn Gly Thr Cys Tyr Cys Glu Glu Gly Phe
                325                 330                 335
Thr Gly Glu Asp Cys Gly Lys Pro Thr Cys Pro His Ala Cys His Thr
            340                 345                 350
Gln Gly Arg Cys Glu Glu Gly Gln Cys Val Cys Asp Glu Gly Phe Ala
        355                 360                 365
Gly Val Asp Cys Ser Glu Lys Arg Cys Pro Ala Asp Cys His Asn Arg
        370                 375                 380
Gly Arg Cys Val Asp Gly Arg Cys Glu Cys Asp Asp Gly Phe Thr Gly
385                 390                 395                 400
Ala Asp Cys Gly Glu Leu Lys Cys Pro Asn Gly Cys Ser Gly His Gly
                405                 410                 415
Arg Cys Val Asn Gly Gln Cys Val Cys Asp Glu Gly Tyr Thr Gly Glu
            420                 425                 430
Asp Cys Ser Gln Leu Arg Cys Pro Asn Asp Cys His Ser Arg Gly Arg
        435                 440                 445
Cys Val Glu Gly Lys Cys Val Cys Glu Gln Gly Phe Lys Gly Tyr Asp
        450                 455                 460
Cys Ser Asp Met Ser Cys Pro Asn Asp Cys His Gln His Gly Arg Cys
465                 470                 475                 480
Val Asn Gly Met Cys Val Cys Asp Asp Gly Tyr Thr Gly Glu Asp Cys
                485                 490                 495
Arg Asp Arg Gln Cys Pro Arg Asp Cys Ser Asn Arg Gly Leu Cys Val
```

-continued

```
                500                 505                 510
Asp Gly Gln Cys Val Cys Glu Asp Gly Phe Thr Gly Pro Asp Cys Ala
            515                 520                 525
Glu Leu Ser Cys Pro Asn Asp Cys His Gly Gln Gly Arg Cys Val Asn
            530                 535                 540
Gly Gln Cys Val Cys His Glu Gly Phe Met Gly Lys Asp Cys Lys Glu
545                 550                 555                 560
Gln Arg Cys Pro Ser Asp Cys His Gly Gln Gly Arg Cys Val Asp Gly
                565                 570                 575
Gln Cys Ile Cys His Glu Gly Phe Thr Gly Leu Asp Cys Gly Gln His
            580                 585                 590
Ser Cys Pro Ser Asp Cys Asn Asn Leu Gly Gln Cys Val Ser Gly Arg
            595                 600                 605
Cys Ile Cys Asn Glu Gly Tyr Ser Gly Glu Asp Cys Ser Glu Val Ser
610                 615                 620
Pro Pro Lys Asp Leu Val Val Thr Glu Val Thr Glu Thr Val Asn
625                 630                 635                 640
Leu Ala Trp Asp Asn Glu Met Arg Val Thr Glu Tyr Leu Val Val Tyr
                645                 650                 655
Thr Pro Thr His Glu Gly Gly Leu Glu Met Gln Phe Arg Val Pro Gly
                660                 665                 670
Asp Gln Thr Ser Thr Ile Ile Gln Glu Leu Glu Pro Gly Val Glu Tyr
            675                 680                 685
Phe Ile Arg Val Phe Ala Ile Leu Glu Asn Lys Lys Ser Ile Pro Val
            690                 695                 700
Ser Ala Arg Val Ala Thr Tyr Leu Pro Ala Pro Glu Gly Leu Lys Phe
705                 710                 715                 720
Lys Ser Ile Lys Glu Thr Ser Val Glu Val Glu Trp Asp Pro Leu Asp
                725                 730                 735
Ile Ala Phe Glu Thr Trp Glu Ile Ile Phe Arg Asn Met Asn Lys Glu
                740                 745                 750
Asp Glu Gly Glu Ile Thr Lys Ser Leu Arg Arg Pro Glu Thr Ser Tyr
            755                 760                 765
Arg Gln Thr Gly Leu Ala Pro Gly Gln Glu Tyr Glu Ile Ser Leu His
            770                 775                 780
Ile Val Lys Asn Asn Thr Arg Gly Pro Gly Leu Lys Arg Val Thr Thr
785                 790                 795                 800
Thr Arg Leu Asp Ala Pro Ser Gln Ile Glu Val Lys Asp Val Thr Asp
                805                 810                 815
Thr Thr Ala Leu Ile Thr Trp Phe Lys Pro Leu Ala Glu Ile Asp Gly
                820                 825                 830
Ile Glu Leu Thr Tyr Gly Ile Lys Asp Val Pro Gly Asp Arg Thr Thr
            835                 840                 845
Ile Asp Leu Thr Glu Asp Glu Asn Gln Tyr Ser Ile Gly Asn Leu Lys
            850                 855                 860
Pro Asp Thr Glu Tyr Glu Val Ser Leu Ile Ser Arg Arg Gly Asp Met
865                 870                 875                 880
Ser Ser Asn Pro Ala Lys Glu Thr Phe Thr Thr Gly Leu Asp Ala Pro
                885                 890                 895
Arg Asn Leu Arg Arg Val Ser Gln Thr Asp Asn Ser Ile Thr Leu Glu
            900                 905                 910
Trp Arg Asn Gly Lys Ala Ala Ile Asp Ser Tyr Arg Ile Lys Tyr Ala
            915                 920                 925
```

```
Pro Ile Ser Gly Gly Asp His Ala Glu Val Asp Val Pro Lys Ser Gln
    930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Glu Asp Lys Glu Ser Asn Pro
            965                 970                 975

Ala Thr Ile Asn Ala Ala Thr Glu Leu Asp Thr Pro Lys Asp Leu Gln
            980                 985                 990

Val Ser Glu Thr Ala Glu Thr Ser Leu Thr Leu Leu Trp Lys Thr Pro
        995                 1000                1005

Leu Ala Lys Phe Asp Arg Tyr Arg Leu Asn Tyr Ser Leu Pro Thr
    1010                1015                1020

Gly Gln Trp Val Gly Val Gln Leu Pro Arg Asn Thr Thr Ser Tyr
    1025                1030                1035

Val Leu Arg Gly Leu Glu Pro Gly Gln Glu Tyr Asn Val Leu Leu
    1040                1045                1050

Thr Ala Glu Lys Gly Arg His Lys Ser Lys Pro Ala Arg Val Lys
    1055                1060                1065

Ala Ser Thr Glu Gln Ala Pro Glu Leu Glu Asn Leu Thr Val Thr
    1070                1075                1080

Glu Val Gly Trp Asp Gly Leu Arg Leu Asn Trp Thr Ala Ala Asp
    1085                1090                1095

Gln Ala Tyr Glu His Phe Ile Ile Gln Val Gln Glu Ala Asn Lys
    1100                1105                1110

Val Glu Ala Ala Arg Asn Leu Thr Val Pro Gly Ser Leu Arg Ala
    1115                1120                1125

Val Asp Ile Pro Gly Leu Lys Ala Ala Thr Pro Tyr Thr Val Ser
    1130                1135                1140

Ile Tyr Gly Val Ile Gln Gly Tyr Arg Thr Pro Val Leu Ser Ala
    1145                1150                1155

Glu Ala Ser Thr Gly Glu Thr Pro Asn Leu Gly Glu Val Val Val
    1160                1165                1170

Ala Glu Val Gly Trp Asp Ala Leu Lys Leu Asn Trp Thr Ala Pro
    1175                1180                1185

Glu Gly Ala Tyr Glu Tyr Phe Phe Ile Gln Val Gln Glu Ala Asp
    1190                1195                1200

Thr Val Glu Ala Ala Gln Asn Leu Thr Val Pro Gly Gly Leu Arg
    1205                1210                1215

Ser Thr Asp Leu Pro Gly Leu Lys Ala Ala Thr His Tyr Thr Ile
    1220                1225                1230

Thr Ile Arg Gly Val Thr Gln Asp Phe Ser Thr Thr Pro Leu Ser
    1235                1240                1245

Val Glu Val Leu Thr Glu Val Pro Asp Met Gly Asn Leu Thr
    1250                1255                1260

Val Thr Glu Val Ser Trp Asp Ala Leu Arg Leu Asn Trp Thr Thr
    1265                1270                1275

Pro Asp Gly Thr Tyr Asp Gln Phe Thr Ile Gln Val Gln Glu Ala
    1280                1285                1290

Asp Gln Val Glu Glu Ala His Asn Leu Thr Val Pro Gly Ser Leu
    1295                1300                1305

Arg Ser Met Glu Ile Pro Gly Leu Arg Ala Gly Thr Pro Tyr Thr
    1310                1315                1320
```

```
Val Thr Leu His Gly Glu Val Arg Gly His Ser Thr Arg Pro Leu
1325                1330                1335

Ala Val Glu Val Val Thr Glu Asp Leu Pro Gln Leu Gly Asp Leu
1340                1345                1350

Ala Val Ser Glu Val Gly Trp Asp Gly Leu Arg Leu Asn Trp Thr
1355                1360                1365

Ala Ala Asp Asn Ala Tyr Glu His Phe Val Ile Gln Val Gln Glu
1370                1375                1380

Val Asn Lys Val Glu Ala Ala Gln Asn Leu Thr Leu Pro Gly Ser
1385                1390                1395

Leu Arg Ala Val Asp Ile Pro Gly Leu Glu Ala Ala Thr Pro Tyr
1400                1405                1410

Arg Val Ser Ile Tyr Gly Val Ile Arg Gly Tyr Arg Thr Pro Val
1415                1420                1425

Leu Ser Ala Glu Ala Ser Thr Ala Lys Glu Pro Glu Ile Gly Asn
1430                1435                1440

Leu Asn Val Ser Asp Ile Thr Pro Glu Ser Phe Asn Leu Ser Trp
1445                1450                1455

Met Ala Thr Asp Gly Ile Phe Glu Thr Phe Thr Ile Glu Ile Ile
1460                1465                1470

Asp Ser Asn Arg Leu Leu Glu Thr Val Glu Tyr Asn Ile Ser Gly
1475                1480                1485

Ala Glu Arg Thr Ala His Ile Ser Gly Leu Pro Pro Ser Thr Asp
1490                1495                1500

Phe Ile Val Tyr Leu Ser Gly Leu Ala Pro Ser Ile Arg Thr Lys
1505                1510                1515

Thr Ile Ser Ala Thr Ala Thr Thr Glu Ala Leu Pro Leu Leu Glu
1520                1525                1530

Asn Leu Thr Ile Ser Asp Ile Asn Pro Tyr Gly Phe Thr Val Ser
1535                1540                1545

Trp Met Ala Ser Glu Asn Ala Phe Asp Ser Phe Leu Val Thr Val
1550                1555                1560

Val Asp Ser Gly Lys Leu Leu Asp Pro Gln Glu Phe Thr Leu Ser
1565                1570                1575

Gly Thr Gln Arg Lys Leu Glu Leu Arg Gly Leu Ile Thr Gly Ile
1580                1585                1590

Gly Tyr Glu Val Met Val Ser Gly Phe Thr Gln Gly His Gln Thr
1595                1600                1605

Lys Pro Leu Arg Ala Glu Ile Val Thr Glu Ala Glu Pro Glu Val
1610                1615                1620

Asp Asn Leu Leu Val Ser Asp Ala Thr Pro Asp Gly Phe Arg Leu
1625                1630                1635

Ser Trp Thr Ala Asp Glu Gly Val Phe Asp Asn Phe Val Leu Lys
1640                1645                1650

Ile Arg Asp Thr Lys Lys Gln Ser Glu Pro Leu Glu Ile Thr Leu
1655                1660                1665

Leu Ala Pro Glu Arg Thr Arg Asp Ile Thr Gly Leu Arg Glu Ala
1670                1675                1680

Thr Glu Tyr Glu Ile Glu Leu Tyr Gly Ile Ser Lys Gly Arg Arg
1685                1690                1695

Ser Gln Thr Val Ser Ala Ile Ala Thr Thr Ala Met Gly Ser Pro
1700                1705                1710

Lys Glu Val Ile Phe Ser Asp Ile Thr Glu Asn Ser Ala Thr Val
```

-continued

```
            1715                1720                1725

Ser Trp Arg Ala Pro Thr Ala Gln Val Glu Ser Phe Arg Ile Thr
            1730                1735                1740

Tyr Val Pro Ile Thr Gly Gly Thr Pro Ser Met Val Thr Val Asp
            1745                1750                1755

Gly Thr Lys Thr Gln Thr Arg Leu Val Lys Leu Ile Pro Gly Val
            1760                1765                1770

Glu Tyr Leu Val Ser Ile Ile Ala Met Lys Gly Phe Glu Glu Ser
            1775                1780                1785

Glu Pro Val Ser Gly Ser Phe Thr Thr Ala Leu Asp Gly Pro Ser
            1790                1795                1800

Gly Leu Val Thr Ala Asn Ile Thr Asp Ser Glu Ala Leu Ala Arg
            1805                1810                1815

Trp Gln Pro Ala Ile Ala Thr Val Asp Ser Tyr Val Ile Ser Tyr
            1820                1825                1830

Thr Gly Glu Lys Val Pro Glu Ile Thr Arg Thr Val Ser Gly Asn
            1835                1840                1845

Thr Val Glu Tyr Ala Leu Thr Asp Leu Glu Pro Ala Thr Glu Tyr
            1850                1855                1860

Thr Leu Arg Ile Phe Ala Glu Lys Gly Pro Gln Lys Ser Ser Thr
            1865                1870                1875

Ile Thr Ala Lys Phe Thr Thr Asp Leu Asp Ser Pro Arg Asp Leu
            1880                1885                1890

Thr Ala Thr Glu Val Gln Ser Glu Thr Ala Leu Leu Thr Trp Arg
            1895                1900                1905

Pro Pro Arg Ala Ser Val Thr Gly Tyr Leu Leu Val Tyr Glu Ser
            1910                1915                1920

Val Asp Gly Thr Val Lys Glu Val Ile Val Gly Pro Asp Thr Thr
            1925                1930                1935

Ser Tyr Ser Leu Ala Asp Leu Ser Pro Ser Thr His Tyr Thr Ala
            1940                1945                1950

Lys Ile Gln Ala Leu Asn Gly Pro Leu Arg Ser Asn Met Ile Gln
            1955                1960                1965

Thr Ile Phe Thr Thr Ile Gly Leu Leu Tyr Pro Phe Pro Lys Asp
            1970                1975                1980

Cys Ser Gln Ala Met Leu Asn Gly Asp Thr Thr Ser Gly Leu Tyr
            1985                1990                1995

Thr Ile Tyr Leu Asn Gly Asp Lys Ala Glu Ala Leu Glu Val Phe
            2000                2005                2010

Cys Asp Met Thr Ser Asp Gly Gly Gly Trp Ile Val Phe Leu Arg
            2015                2020                2025

Arg Lys Asn Gly Arg Glu Asn Phe Tyr Gln Asn Trp Lys Ala Tyr
            2030                2035                2040

Ala Ala Gly Phe Gly Asp Arg Arg Glu Glu Phe Trp Leu Gly Leu
            2045                2050                2055

Asp Asn Leu Asn Lys Ile Thr Ala Gln Gly Gln Tyr Glu Leu Arg
            2060                2065                2070

Val Asp Leu Arg Asp His Gly Glu Thr Ala Phe Ala Val Tyr Asp
            2075                2080                2085

Lys Phe Ser Val Gly Asp Ala Lys Thr Arg Tyr Lys Leu Lys Val
            2090                2095                2100

Glu Gly Tyr Ser Gly Thr Ala Gly Asp Ser Met Ala Tyr His Asn
            2105                2110                2115
```

```
Gly Arg Ser Phe Ser Thr Phe Asp Lys Asp Thr Asp Ser Ala Ile
    2120            2125                2130

Thr Asn Cys Ala Leu Ser Tyr Lys Gly Ala Phe Trp Tyr Arg Asn
    2135            2140                2145

Cys His Arg Val Asn Leu Met Gly Arg Tyr Gly Asp Asn Asn His
    2150            2155                2160

Ser Gln Gly Val Asn Trp Phe His Trp Lys Gly His Glu His Ser
    2165            2170                2175

Ile Gln Phe Ala Glu Met Lys Leu Arg Pro Ser Asn Phe Arg Asn
    2180            2185                2190

Leu Glu Gly Arg Arg Lys Arg Ala
    2195            2200

<210> SEQ ID NO 40
<211> LENGTH: 5
<212> TYPE: PRT
<213> ORGANISM: Artificial Sequence
<220> FEATURE:
<223> OTHER INFORMATION: TnC(18D4) CDR-H1

<400> SEQUENCE: 40

Ser Tyr Ala Ile Ser
1               5

<210> SEQ ID NO 41
<211> LENGTH: 10
<212> TYPE: PRT
<213> ORGANISM: Artificial Sequence
<220> FEATURE:
<223> OTHER INFORMATION: TnC(11C7) CDR-H1

<400> SEQUENCE: 41

Gly Phe Thr Phe Ser Ser Tyr Ala Met Ser
1               5                   10

<210> SEQ ID NO 42
<211> LENGTH: 17
<212> TYPE: PRT
<213> ORGANISM: Artificial Sequence
<220> FEATURE:
<223> OTHER INFORMATION: TnC(18D4) CDR-H2

<400> SEQUENCE: 42

Gly Ile Ile Pro Ile Phe Gly Thr Ala Asn Tyr Ala Gln Lys Phe Gln
1               5                   10                  15

Gly

<210> SEQ ID NO 43
<211> LENGTH: 17
<212> TYPE: PRT
<213> ORGANISM: Artificial Sequence
<220> FEATURE:
<223> OTHER INFORMATION: TnC(11C7) CDR-H2

<400> SEQUENCE: 43

Ala Ile Ser Gly Ser Gly Gly Ser Thr Tyr Tyr Ala Asp Ser Val Lys
1               5                   10                  15

Gly

<210> SEQ ID NO 44
<211> LENGTH: 9
<212> TYPE: PRT
```

```
<213> ORGANISM: Artificial Sequence
<220> FEATURE:
<223> OTHER INFORMATION: TnC(18D4) CDR-H3

<400> SEQUENCE: 44

Gly Asn Phe Tyr Gly Gly Leu Asp Tyr
1               5

<210> SEQ ID NO 45
<211> LENGTH: 9
<212> TYPE: PRT
<213> ORGANISM: Artificial Sequence
<220> FEATURE:
<223> OTHER INFORMATION: TnC(11C7) CDR-H3

<400> SEQUENCE: 45

Thr Ser Pro Arg Val Pro Leu Asp Tyr
1               5

<210> SEQ ID NO 46
<211> LENGTH: 11
<212> TYPE: PRT
<213> ORGANISM: Artificial Sequence
<220> FEATURE:
<223> OTHER INFORMATION: TnC(18D4) CDR-L1

<400> SEQUENCE: 46

Arg Ala Ser Gln Ser Ile Ser Ser Trp Leu Ala
1               5                   10

<210> SEQ ID NO 47
<211> LENGTH: 11
<212> TYPE: PRT
<213> ORGANISM: Artificial Sequence
<220> FEATURE:
<223> OTHER INFORMATION: TnC(11C7) CDR-L1

<400> SEQUENCE: 47

Gln Gly Asp Ser Leu Arg Ser Tyr Tyr Ala Ser
1               5                   10

<210> SEQ ID NO 48
<211> LENGTH: 7
<212> TYPE: PRT
<213> ORGANISM: Artificial Sequence
<220> FEATURE:
<223> OTHER INFORMATION: TnC(18D4) CDR-L2

<400> SEQUENCE: 48

Asp Ala Ser Ser Leu Glu Ser
1               5

<210> SEQ ID NO 49
<211> LENGTH: 7
<212> TYPE: PRT
<213> ORGANISM: Artificial Sequence
<220> FEATURE:
<223> OTHER INFORMATION: TnC(11C7) CDR-L2

<400> SEQUENCE: 49

Gly Lys Asn Asn Arg Pro Ser
1               5

<210> SEQ ID NO 50
<211> LENGTH: 10
<212> TYPE: PRT
<213> ORGANISM: Artificial Sequence
```

```
<220> FEATURE:
<223> OTHER INFORMATION: TnC(18D4)  CDR-L3

<400> SEQUENCE: 50

Gln Gln Asn Lys Lys Phe Pro Ser Gly Thr
1               5                   10

<210> SEQ ID NO 51
<211> LENGTH: 10
<212> TYPE: PRT
<213> ORGANISM: Artificial Sequence
<220> FEATURE:
<223> OTHER INFORMATION: TnC(11C7)  CDR-L3

<400> SEQUENCE: 51

Asn Ser Ile Asn Ser Thr Arg Asn Glu Val
1               5                   10

<210> SEQ ID NO 52
<211> LENGTH: 118
<212> TYPE: PRT
<213> ORGANISM: Artificial Sequence
<220> FEATURE:
<223> OTHER INFORMATION: TnC(18D4) VH

<400> SEQUENCE: 52

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser
        115

<210> SEQ ID NO 53
<211> LENGTH: 108
<212> TYPE: PRT
<213> ORGANISM: Artificial Sequence
<220> FEATURE:
<223> OTHER INFORMATION: TnC(18D4) VL

<400> SEQUENCE: 53

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80
```

```
Asp Asp Phe Ala Thr Tyr Tyr Cys Gln Gln Asn Lys Lys Phe Pro Ser
                85                  90                  95
Gly Thr Phe Gly Gln Gly Thr Lys Val Glu Ile Lys
            100                 105

<210> SEQ ID NO 54
<211> LENGTH: 118
<212> TYPE: PRT
<213> ORGANISM: Artificial Sequence
<220> FEATURE:
<223> OTHER INFORMATION: TnC(11C7) VH

<400> SEQUENCE: 54

Glu Val Gln Leu Leu Glu Ser Gly Gly Gly Leu Val Gln Pro Gly Gly
1               5                   10                  15
Ser Leu Arg Leu Ser Cys Ala Ala Ser Gly Phe Thr Phe Ser Ser Tyr
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Lys Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Thr Ser Pro Arg Val Pro Leu Asp Tyr Trp Gly Gln Gly Thr
            100                 105                 110
Leu Val Thr Val Ser Ser
        115

<210> SEQ ID NO 55
<211> LENGTH: 107
<212> TYPE: PRT
<213> ORGANISM: Artificial Sequence
<220> FEATURE:
<223> OTHER INFORMATION: TnC(11C7) VL

<400> SEQUENCE: 55

Ser Ser Glu Leu Thr Gln Asp Pro Ala Val Ser Val Ala Leu Gly Gln
1               5                   10                  15
Thr Val Arg Val Thr Cys Gln Gly Asp Ser Leu Arg Ser Tyr Tyr Ala
            20                  25                  30
Ser Trp Tyr Gln Gln Lys Pro Gly Gln Ala Pro Val Leu Val Ile Tyr
        35                  40                  45
Gly Lys Asn Asn Arg Pro Ser Gly Ile Pro Asp Arg Phe Ser Gly Ser
    50                  55                  60
Ser Ser Gly Asn Thr Ala Ser Leu Thr Ile Thr Gly Ala Gln Ala Glu
65                  70                  75                  80
Asp Glu Ala Asp Tyr Tyr Cys Asn Ser Ile Asn Ser Thr Arg Asn Glu
                85                  90                  95
Val Phe Gly Gly Gly Thr Lys Leu Thr Val Leu
            100                 105

<210> SEQ ID NO 56
<211> LENGTH: 277
<212> TYPE: PRT
<213> ORGANISM: Homo sapiens

<400> SEQUENCE: 56
```

Met Cys Val Gly Ala Arg Arg Leu Gly Arg Gly Pro Cys Ala Ala Leu
1               5                   10                  15

Leu Leu Leu Gly Leu Gly Leu Ser Thr Val Thr Gly Leu His Cys Val
                20                  25                  30

Gly Asp Thr Tyr Pro Ser Asn Asp Arg Cys Cys His Glu Cys Arg Pro
            35                  40                  45

Gly Asn Gly Met Val Ser Arg Cys Ser Arg Ser Gln Asn Thr Val Cys
        50                  55                  60

Arg Pro Cys Gly Pro Gly Phe Tyr Asn Asp Val Val Ser Ser Lys Pro
65                  70                  75                  80

Cys Lys Pro Cys Thr Trp Cys Asn Leu Arg Ser Gly Ser Glu Arg Lys
                85                  90                  95

Gln Leu Cys Thr Ala Thr Gln Asp Thr Val Cys Arg Cys Arg Ala Gly
            100                 105                 110

Thr Gln Pro Leu Asp Ser Tyr Lys Pro Gly Val Asp Cys Ala Pro Cys
        115                 120                 125

Pro Pro Gly His Phe Ser Pro Gly Asp Asn Gln Ala Cys Lys Pro Trp
130                 135                 140

Thr Asn Cys Thr Leu Ala Gly Lys His Thr Leu Gln Pro Ala Ser Asn
145                 150                 155                 160

Ser Ser Asp Ala Ile Cys Glu Asp Arg Asp Pro Pro Ala Thr Gln Pro
                165                 170                 175

Gln Glu Thr Gln Gly Pro Pro Ala Arg Pro Ile Thr Val Gln Pro Thr
            180                 185                 190

Glu Ala Trp Pro Arg Thr Ser Gln Gly Pro Ser Thr Arg Pro Val Glu
        195                 200                 205

Val Pro Gly Gly Arg Ala Val Ala Ala Ile Leu Gly Leu Gly Leu Val
210                 215                 220

Leu Gly Leu Leu Gly Pro Leu Ala Ile Leu Leu Ala Leu Tyr Leu Leu
225                 230                 235                 240

Arg Arg Asp Gln Arg Leu Pro Pro Asp Ala His Lys Pro Pro Gly Gly
                245                 250                 255

Gly Ser Phe Arg Thr Pro Ile Gln Glu Glu Gln Ala Asp Ala His Ser
            260                 265                 270

Thr Leu Ala Lys Ile
        275

<210> SEQ ID NO 57
<211> LENGTH: 255
<212> TYPE: PRT
<213> ORGANISM: Homo sapiens

<400> SEQUENCE: 57

Met Gly Asn Ser Cys Tyr Asn Ile Val Ala Thr Leu Leu Leu Val Leu
1               5                   10                  15

Asn Phe Glu Arg Thr Arg Ser Leu Gln Asp Pro Cys Ser Asn Cys Pro
                20                  25                  30

Ala Gly Thr Phe Cys Asp Asn Asn Arg Asn Gln Ile Cys Ser Pro Cys
            35                  40                  45

Pro Pro Asn Ser Phe Ser Ser Ala Gly Gly Gln Arg Thr Cys Asp Ile
        50                  55                  60

Cys Arg Gln Cys Lys Gly Val Phe Arg Thr Arg Lys Glu Cys Ser Ser
65                  70                  75                  80

Thr Ser Asn Ala Glu Cys Asp Cys Thr Pro Gly Phe His Cys Leu Gly

```
            85                  90                  95
Ala Gly Cys Ser Met Cys Glu Gln Asp Cys Lys Gln Gly Gln Glu Leu
            100                 105                 110

Thr Lys Lys Gly Cys Lys Asp Cys Cys Phe Gly Thr Phe Asn Asp Gln
            115                 120                 125

Lys Arg Gly Ile Cys Arg Pro Trp Thr Asn Cys Ser Leu Asp Gly Lys
            130                 135                 140

Ser Val Leu Val Asn Gly Thr Lys Glu Arg Asp Val Val Cys Gly Pro
145                 150                 155                 160

Ser Pro Ala Asp Leu Ser Pro Gly Ala Ser Ser Val Thr Pro Pro Ala
            165                 170                 175

Pro Ala Arg Glu Pro Gly His Ser Pro Gln Ile Ile Ser Phe Phe Leu
            180                 185                 190

Ala Leu Thr Ser Thr Ala Leu Leu Phe Leu Leu Phe Phe Leu Thr Leu
            195                 200                 205

Arg Phe Ser Val Val Lys Arg Gly Arg Lys Lys Leu Leu Tyr Ile Phe
            210                 215                 220

Lys Gln Pro Phe Met Arg Pro Val Gln Thr Thr Gln Glu Glu Asp Gly
225                 230                 235                 240

Cys Ser Cys Arg Phe Pro Glu Glu Glu Glu Gly Gly Cys Glu Leu
            245                 250                 255

<210> SEQ ID NO 58
<211> LENGTH: 260
<212> TYPE: PRT
<213> ORGANISM: Homo sapiens

<400> SEQUENCE: 58

Met Ala Arg Pro His Pro Trp Trp Leu Cys Val Leu Gly Thr Leu Val
1               5                   10                  15

Gly Leu Ser Ala Thr Pro Ala Pro Lys Ser Cys Pro Glu Arg His Tyr
            20                  25                  30

Trp Ala Gln Gly Lys Leu Cys Cys Gln Met Cys Glu Pro Gly Thr Phe
            35                  40                  45

Leu Val Lys Asp Cys Asp Gln His Arg Lys Ala Ala Gln Cys Asp Pro
            50                  55                  60

Cys Ile Pro Gly Val Ser Phe Ser Pro Asp His His Thr Arg Pro His
65                  70                  75                  80

Cys Glu Ser Cys Arg His Cys Asn Ser Gly Leu Leu Val Arg Asn Cys
            85                  90                  95

Thr Ile Thr Ala Asn Ala Glu Cys Ala Cys Arg Asn Gly Trp Gln Cys
            100                 105                 110

Arg Asp Lys Glu Cys Thr Glu Cys Asp Pro Leu Pro Asn Pro Ser Leu
            115                 120                 125

Thr Ala Arg Ser Ser Gln Ala Leu Ser Pro His Pro Gln Pro Thr His
            130                 135                 140

Leu Pro Tyr Val Ser Glu Met Leu Glu Ala Arg Thr Ala Gly His Met
145                 150                 155                 160

Gln Thr Leu Ala Asp Phe Arg Gln Leu Pro Ala Arg Thr Leu Ser Thr
            165                 170                 175

His Trp Pro Pro Gln Arg Ser Leu Cys Ser Ser Asp Phe Ile Arg Ile
            180                 185                 190

Leu Val Ile Phe Ser Gly Met Phe Leu Val Phe Thr Leu Ala Gly Ala
            195                 200                 205
```

```
Leu Phe Leu His Gln Arg Arg Lys Tyr Arg Ser Asn Lys Gly Glu Ser
            210                 215                 220

Pro Val Glu Pro Ala Glu Pro Cys His Tyr Ser Cys Pro Arg Glu Glu
225                 230                 235                 240

Glu Gly Ser Thr Ile Pro Ile Gln Glu Asp Tyr Arg Lys Pro Glu Pro
                245                 250                 255

Ala Cys Ser Pro
            260

<210> SEQ ID NO 59
<211> LENGTH: 283
<212> TYPE: PRT
<213> ORGANISM: Homo sapiens

<400> SEQUENCE: 59

Met Glu Pro Pro Gly Asp Trp Gly Pro Pro Trp Arg Ser Thr Pro
1               5                   10                  15

Lys Thr Asp Val Leu Arg Leu Val Leu Tyr Leu Thr Phe Leu Gly Ala
                20                  25                  30

Pro Cys Tyr Ala Pro Ala Leu Pro Ser Cys Lys Glu Asp Glu Tyr Pro
            35                  40                  45

Val Gly Ser Glu Cys Cys Pro Lys Cys Ser Pro Gly Tyr Arg Val Lys
50                  55                  60

Glu Ala Cys Gly Glu Leu Thr Gly Thr Val Cys Glu Pro Cys Pro Pro
65                  70                  75                  80

Gly Thr Tyr Ile Ala His Leu Asn Gly Leu Ser Lys Cys Leu Gln Cys
                85                  90                  95

Gln Met Cys Asp Pro Ala Met Gly Leu Arg Ala Ser Arg Asn Cys Ser
            100                 105                 110

Arg Thr Glu Asn Ala Val Cys Gly Cys Ser Pro Gly His Phe Cys Ile
        115                 120                 125

Val Gln Asp Gly Asp His Cys Ala Ala Cys Arg Ala Tyr Ala Thr Ser
    130                 135                 140

Ser Pro Gly Gln Arg Val Gln Lys Gly Gly Thr Glu Ser Gln Asp Thr
145                 150                 155                 160

Leu Cys Gln Asn Cys Pro Pro Gly Thr Phe Ser Pro Asn Gly Thr Leu
                165                 170                 175

Glu Glu Cys Gln His Gln Thr Lys Cys Ser Trp Leu Val Thr Lys Ala
            180                 185                 190

Gly Ala Gly Thr Ser Ser Ser His Trp Val Trp Trp Phe Leu Ser Gly
        195                 200                 205

Ser Leu Val Ile Val Ile Val Cys Ser Thr Val Gly Leu Ile Ile Cys
    210                 215                 220

Val Lys Arg Arg Lys Pro Arg Gly Asp Val Val Lys Val Ile Val Ser
225                 230                 235                 240

Val Gln Arg Lys Arg Gln Glu Ala Glu Gly Glu Ala Thr Val Ile Glu
                245                 250                 255

Ala Leu Gln Ala Pro Pro Asp Val Thr Thr Val Ala Val Glu Glu Thr
            260                 265                 270

Ile Pro Ser Phe Thr Gly Arg Ser Pro Asn His
        275                 280

<210> SEQ ID NO 60
<211> LENGTH: 595
<212> TYPE: PRT
<213> ORGANISM: Homo sapiens
```

<400> SEQUENCE: 60

```
Met Arg Val Leu Leu Ala Ala Leu Gly Leu Leu Phe Leu Gly Ala Leu
1               5                   10                  15

Arg Ala Phe Pro Gln Asp Arg Pro Phe Glu Asp Thr Cys His Gly Asn
            20                  25                  30

Pro Ser His Tyr Tyr Asp Lys Ala Val Arg Arg Cys Cys Tyr Arg Cys
        35                  40                  45

Pro Met Gly Leu Phe Pro Thr Gln Gln Cys Pro Gln Arg Pro Thr Asp
    50                  55                  60

Cys Arg Lys Gln Cys Glu Pro Asp Tyr Tyr Leu Asp Glu Ala Asp Arg
65              70                  75                  80

Cys Thr Ala Cys Val Thr Cys Ser Arg Asp Asp Leu Val Glu Lys Thr
                85                  90                  95

Pro Cys Ala Trp Asn Ser Ser Arg Val Cys Glu Cys Arg Pro Gly Met
                100                 105                 110

Phe Cys Ser Thr Ser Ala Val Asn Ser Cys Ala Arg Cys Phe Phe His
        115                 120                 125

Ser Val Cys Pro Ala Gly Met Ile Val Lys Phe Pro Gly Thr Ala Gln
    130                 135                 140

Lys Asn Thr Val Cys Glu Pro Ala Ser Pro Gly Val Ser Pro Ala Cys
145                 150                 155                 160

Ala Ser Pro Glu Asn Cys Lys Glu Pro Ser Ser Gly Thr Ile Pro Gln
                165                 170                 175

Ala Lys Pro Thr Pro Val Ser Pro Ala Thr Ser Ser Ala Ser Thr Met
                180                 185                 190

Pro Val Arg Gly Gly Thr Arg Leu Ala Gln Glu Ala Ala Ser Lys Leu
                195                 200                 205

Thr Arg Ala Pro Asp Ser Pro Ser Ser Val Gly Arg Pro Ser Ser Asp
210                 215                 220

Pro Gly Leu Ser Pro Thr Gln Pro Cys Pro Glu Gly Ser Gly Asp Cys
225                 230                 235                 240

Arg Lys Gln Cys Glu Pro Asp Tyr Tyr Leu Asp Glu Ala Gly Arg Cys
                245                 250                 255

Thr Ala Cys Val Ser Cys Ser Arg Asp Asp Leu Val Glu Lys Thr Pro
                260                 265                 270

Cys Ala Trp Asn Ser Ser Arg Thr Cys Glu Cys Arg Pro Gly Met Ile
                275                 280                 285

Cys Ala Thr Ser Ala Thr Asn Ser Cys Ala Arg Cys Val Pro Tyr Pro
                290                 295                 300

Ile Cys Ala Ala Glu Thr Val Thr Lys Pro Gln Asp Met Ala Glu Lys
305                 310                 315                 320

Asp Thr Thr Phe Glu Ala Pro Pro Leu Gly Thr Gln Pro Asp Cys Asn
                325                 330                 335

Pro Thr Pro Glu Asn Gly Glu Ala Pro Ala Ser Thr Ser Pro Thr Gln
                340                 345                 350

Ser Leu Leu Val Asp Ser Gln Ala Ser Lys Thr Leu Pro Ile Pro Thr
                355                 360                 365

Ser Ala Pro Val Ala Leu Ser Ser Thr Gly Lys Pro Val Leu Asp Ala
                370                 375                 380

Gly Pro Val Leu Phe Trp Val Ile Leu Val Leu Val Val Val Val Gly
385                 390                 395                 400

Ser Ser Ala Phe Leu Leu Cys His Arg Arg Ala Cys Arg Lys Arg Ile
```

```
                    405                 410                 415
Arg Gln Lys Leu His Leu Cys Tyr Pro Val Gln Thr Ser Gln Pro Lys
            420                 425                 430

Leu Glu Leu Val Asp Ser Arg Pro Arg Ser Ser Thr Gln Leu Arg
        435                 440                 445

Ser Gly Ala Ser Val Thr Glu Pro Val Ala Glu Arg Gly Leu Met
450                 455                 460

Ser Gln Pro Leu Met Glu Thr Cys His Ser Val Gly Ala Ala Tyr Leu
465                 470                 475                 480

Glu Ser Leu Pro Leu Gln Asp Ala Ser Pro Ala Gly Gly Pro Ser Ser
            485                 490                 495

Pro Arg Asp Leu Pro Glu Pro Arg Val Ser Thr Glu His Thr Asn Asn
            500                 505                 510

Lys Ile Glu Lys Ile Tyr Ile Met Lys Ala Asp Thr Val Ile Val Gly
            515                 520                 525

Thr Val Lys Ala Glu Leu Pro Glu Gly Arg Gly Leu Ala Gly Pro Ala
        530                 535                 540

Glu Pro Glu Leu Glu Glu Leu Glu Ala Asp His Thr Pro His Tyr
545                 550                 555                 560

Pro Glu Gln Glu Thr Glu Pro Pro Leu Gly Ser Cys Ser Asp Val Met
                565                 570                 575

Leu Ser Val Glu Glu Gly Lys Glu Asp Pro Leu Pro Thr Ala Ala
            580                 585                 590

Ser Gly Lys
        595

<210> SEQ ID NO 61
<211> LENGTH: 241
<212> TYPE: PRT
<213> ORGANISM: Homo sapiens

<400> SEQUENCE: 61

Met Ala Gln His Gly Ala Met Gly Ala Phe Arg Ala Leu Cys Gly Leu
1               5                   10                  15

Ala Leu Leu Cys Ala Leu Ser Leu Gly Gln Arg Pro Thr Gly Gly Pro
            20                  25                  30

Gly Cys Gly Pro Gly Arg Leu Leu Leu Gly Thr Gly Thr Asp Ala Arg
        35                  40                  45

Cys Cys Arg Val His Thr Thr Arg Cys Cys Arg Asp Tyr Pro Gly Glu
    50                  55                  60

Glu Cys Cys Ser Glu Trp Asp Cys Met Cys Val Gln Pro Glu Phe His
65                  70                  75                  80

Cys Gly Asp Pro Cys Cys Thr Thr Cys Arg His His Pro Cys Pro Pro
            85                  90                  95

Gly Gln Gly Val Gln Ser Gln Gly Lys Phe Ser Phe Gly Phe Gln Cys
            100                 105                 110

Ile Asp Cys Ala Ser Gly Thr Phe Ser Gly Gly His Glu Gly His Cys
        115                 120                 125

Lys Pro Trp Thr Asp Cys Thr Gln Phe Gly Phe Leu Thr Val Phe Pro
    130                 135                 140

Gly Asn Lys Thr His Asn Ala Val Cys Val Pro Gly Ser Pro Pro Ala
145                 150                 155                 160

Glu Pro Leu Gly Trp Leu Thr Val Val Leu Leu Ala Val Ala Ala Cys
                165                 170                 175
```

Val Leu Leu Leu Thr Ser Ala Gln Leu Gly Leu His Ile Trp Gln Leu
                180                 185                 190

Arg Ser Gln Cys Met Trp Pro Arg Glu Thr Gln Leu Leu Leu Glu Val
            195                 200                 205

Pro Pro Ser Thr Glu Asp Ala Arg Ser Cys Gln Phe Pro Glu Glu Glu
        210                 215                 220

Arg Gly Glu Arg Ser Ala Glu Glu Lys Gly Arg Leu Gly Asp Leu Trp
225                 230                 235                 240

Val

<210> SEQ ID NO 62
<211> LENGTH: 272
<212> TYPE: PRT
<213> ORGANISM: Mus musculus

<400> SEQUENCE: 62

Met Tyr Val Trp Val Gln Gln Pro Thr Ala Leu Leu Leu Ala Leu
1               5                   10                  15

Thr Leu Gly Val Thr Ala Arg Arg Leu Asn Cys Val Lys His Thr Tyr
                20                  25                  30

Pro Ser Gly His Lys Cys Cys Arg Glu Cys Gln Pro Gly His Gly Met
            35                  40                  45

Val Ser Arg Cys Asp His Thr Arg Asp Thr Leu Cys His Pro Cys Glu
        50                  55                  60

Thr Gly Phe Tyr Asn Glu Ala Val Asn Tyr Asp Thr Cys Lys Gln Cys
65                  70                  75                  80

Thr Gln Cys Asn His Arg Ser Gly Ser Glu Leu Lys Gln Asn Cys Thr
                85                  90                  95

Pro Thr Gln Asp Thr Val Cys Arg Cys Arg Pro Gly Thr Gln Pro Arg
            100                 105                 110

Gln Asp Ser Gly Tyr Lys Leu Gly Val Asp Cys Val Pro Cys Pro Pro
        115                 120                 125

Gly His Phe Ser Pro Gly Asn Asn Gln Ala Cys Lys Pro Trp Thr Asn
130                 135                 140

Cys Thr Leu Ser Gly Lys Gln Thr Arg His Pro Ala Ser Asp Ser Leu
145                 150                 155                 160

Asp Ala Val Cys Glu Asp Arg Ser Leu Leu Ala Thr Leu Leu Trp Glu
                165                 170                 175

Thr Gln Arg Pro Thr Phe Arg Pro Thr Thr Val Gln Ser Thr Thr Val
            180                 185                 190

Trp Pro Arg Thr Ser Glu Leu Pro Ser Pro Thr Leu Val Thr Pro
        195                 200                 205

Glu Gly Pro Ala Phe Ala Val Leu Leu Gly Leu Gly Leu Gly Leu Leu
        210                 215                 220

Ala Pro Leu Thr Val Leu Leu Ala Leu Tyr Leu Leu Arg Lys Ala Trp
225                 230                 235                 240

Arg Leu Pro Asn Thr Pro Lys Pro Cys Trp Gly Asn Ser Phe Arg Thr
                245                 250                 255

Pro Ile Gln Glu Glu His Thr Asp Ala His Phe Thr Leu Ala Lys Ile
            260                 265                 270

<210> SEQ ID NO 63
<211> LENGTH: 2110
<212> TYPE: PRT
<213> ORGANISM: Mus musculus

```
<400> SEQUENCE: 63

Met Gly Ala Val Thr Trp Leu Leu Pro Gly Ile Phe Leu Ala Leu Phe
1               5                   10                  15

Ala Leu Thr Pro Glu Gly Gly Val Leu Lys Lys Ile Ile Arg His Lys
            20                  25                  30

Arg Glu Ser Gly Leu Asn Met Thr Leu Pro Glu Asn Gln Pro Val
        35                  40                  45

Val Phe Asn His Ile Tyr Asn Ile Lys Leu Pro Met Gly Ser Gln Cys
    50                  55                  60

Ser Val Asp Leu Glu Ser Ala Ser Gly Glu Lys Asp Leu Thr Pro Thr
65                  70                  75                  80

Pro Glu Ser Ser Gly Ser Phe Gln Glu His Thr Val Asp Gly Glu Asn
                85                  90                  95

Gln Ile Val Phe Thr His Arg Ile Asn Ile Pro Arg Arg Ala Cys Gly
                100                 105                 110

Cys Ala Ala Ala Pro Asp Val Lys Glu Leu Leu Ser Arg Leu Glu Glu
            115                 120                 125

Leu Glu Leu Leu Val Ser Ser Leu Arg Glu Gln Cys Thr Met Gly Thr
            130                 135                 140

Gly Cys Cys Leu Gln Pro Ala Glu Gly Arg Leu Asp Thr Arg Pro Phe
145                 150                 155                 160

Cys Ser Gly Arg Gly Asn Phe Ser Ala Glu Cys Gly Cys Val Cys
                165                 170                 175

Glu Pro Gly Trp Lys Gly Pro Asn Cys Ser Glu Pro Asp Cys Pro Gly
            180                 185                 190

Asn Cys Asn Leu Arg Gly Gln Cys Leu Asp Gly Gln Cys Ile Cys Asp
        195                 200                 205

Glu Gly Phe Thr Gly Glu Asp Cys Ser Gln Leu Ala Cys Pro Asn Asp
    210                 215                 220

Cys Asn Asp Gln Gly Arg Cys Val Asn Gly Val Cys Val Cys Phe Glu
225                 230                 235                 240

Gly Tyr Ala Gly Pro Asp Cys Gly Leu Glu Val Cys Pro Val Pro Cys
                245                 250                 255

Ser Glu Glu His Gly Met Cys Val Asp Gly Arg Cys Val Cys Lys Asp
            260                 265                 270

Gly Phe Ala Gly Glu Asp Cys Asn Glu Pro Leu Cys Leu Asn Asn Cys
        275                 280                 285

Tyr Asn Arg Gly Arg Cys Val Glu Asn Glu Cys Val Cys Asp Glu Gly
    290                 295                 300

Phe Thr Gly Glu Asp Cys Ser Glu Leu Ile Cys Pro Asn Asp Cys Phe
305                 310                 315                 320

Asp Arg Gly Arg Cys Ile Asn Gly Thr Cys Tyr Cys Glu Glu Gly Phe
                325                 330                 335

Thr Gly Glu Asp Cys Gly Glu Leu Thr Cys Pro Asn Asp Cys Gln Gly
            340                 345                 350

Arg Gly Gln Cys Glu Glu Gly Gln Cys Val Cys Asn Glu Gly Phe Ala
        355                 360                 365

Gly Ala Asp Cys Ser Glu Lys Arg Cys Pro Ala Asp Cys His His Arg
    370                 375                 380

Gly Arg Cys Leu Asn Gly Gln Cys Glu Cys Asp Asp Gly Phe Thr Gly
385                 390                 395                 400

Ala Asp Cys Gly Asp Leu Gln Cys Pro Asn Gly Cys Ser Gly His Gly
                405                 410                 415
```

```
Arg Cys Val Asn Gly Gln Cys Val Cys Asp Glu Gly Tyr Thr Gly Glu
            420                 425                 430

Asp Cys Ser Gln Arg Arg Cys Pro Asn Asp Cys His Asn Arg Gly Leu
            435                 440                 445

Cys Val Gln Gly Lys Cys Ile Cys Glu Gln Gly Phe Lys Gly Phe Asp
            450                 455                 460

Cys Ser Glu Met Ser Cys Pro Asn Asp Cys His Gln His Gly Arg Cys
465                 470                 475                 480

Val Asn Gly Met Cys Ile Cys Asp Asp Tyr Thr Gly Glu Asp Cys
                    485                 490                 495

Arg Asp Arg Arg Cys Pro Arg Asp Cys Ser Gln Arg Gly Arg Cys Val
            500                 505                 510

Asp Gly Gln Cys Ile Cys Glu Asp Gly Phe Thr Gly Pro Asp Cys Ala
            515                 520                 525

Glu Leu Ser Cys Pro Ser Asp Cys His Gly His Gly Arg Cys Val Asn
            530                 535                 540

Gly Gln Cys Ile Cys His Glu Gly Phe Thr Gly Lys Asp Cys Lys Glu
545                 550                 555                 560

Gln Arg Cys Pro Ser Asp Cys His Gly Gln Gly Arg Cys Glu Asp Gly
            565                 570                 575

Gln Cys Ile Cys His Glu Gly Phe Thr Gly Leu Asp Cys Gly Gln Arg
            580                 585                 590

Ser Cys Pro Asn Asp Cys Ser Asn Gln Gly Gln Cys Val Ser Gly Arg
            595                 600                 605

Cys Ile Cys Asn Glu Gly Tyr Thr Gly Ile Asp Cys Ser Glu Val Ser
            610                 615                 620

Pro Pro Lys Asp Leu Ile Val Thr Glu Val Thr Glu Thr Val Asn
625                 630                 635                 640

Leu Ala Trp Asp Asn Glu Met Arg Val Thr Glu Tyr Leu Ile Met Tyr
                    645                 650                 655

Thr Pro Thr His Ala Asp Gly Leu Glu Met Gln Phe Arg Val Pro Gly
                    660                 665                 670

Asp Gln Thr Ser Thr Thr Ile Arg Glu Leu Glu Pro Gly Val Glu Tyr
                    675                 680                 685

Phe Ile Arg Val Phe Ala Ile Leu Glu Asn Lys Arg Ser Ile Pro Val
            690                 695                 700

Ser Ala Arg Val Ala Thr Tyr Leu Pro Ala Pro Glu Gly Leu Lys Phe
705                 710                 715                 720

Lys Ser Ile Lys Glu Thr Ser Val Glu Val Glu Trp Asp Pro Leu Asp
                    725                 730                 735

Ile Ala Phe Glu Thr Trp Glu Ile Ile Phe Arg Asn Met Asn Lys Glu
                    740                 745                 750

Asp Glu Gly Glu Ile Thr Lys Ser Leu Arg Arg Pro Glu Thr Ser Tyr
                    755                 760                 765

Arg Gln Thr Gly Leu Ala Pro Gly Gln Glu Tyr Glu Ile Ser Leu His
            770                 775                 780

Ile Val Lys Asn Asn Thr Arg Gly Pro Gly Leu Lys Lys Val Thr Thr
785                 790                 795                 800

Thr Arg Leu Asp Ala Pro Ser His Ile Glu Val Lys Asp Val Thr Asp
                    805                 810                 815

Thr Thr Ala Leu Ile Thr Trp Phe Lys Pro Leu Ala Glu Ile Asp Ser
                    820                 825                 830
```

Ile Glu Leu Ser Tyr Gly Ile Lys Asp Val Pro Gly Asp Arg Thr Thr
        835                 840                 845

Ile Asp Leu Thr His Glu Asp Asn Gln Tyr Ser Ile Gly Asn Leu Arg
        850                 855                 860

Pro Asp Thr Glu Tyr Glu Val Ser Leu Ile Ser Arg Arg Val Asp Met
865                 870                 875                 880

Ala Ser Asn Pro Ala Lys Glu Thr Phe Ile Thr Gly Leu Asp Ala Pro
                885                 890                 895

Arg Asn Leu Arg Arg Val Ser Gln Thr Asp Asn Ser Ile Thr Leu Glu
                900                 905                 910

Trp Arg Asn Val Lys Ala Asp Ile Asp Ser Tyr Arg Ile Lys Tyr Ala
                915                 920                 925

Pro Ile Ser Gly Gly Asp His Ala Glu Ile Asp Val Pro Lys Ser Gln
        930                 935                 940

Gln Ala Thr Thr Lys Thr Thr Leu Thr Gly Leu Arg Pro Gly Thr Glu
945                 950                 955                 960

Tyr Gly Ile Gly Val Ser Ala Val Lys Gly Asp Lys Glu Ser Asp Pro
                965                 970                 975

Ala Thr Ile Asn Ala Ala Thr Glu Ile Asp Ala Pro Lys Asp Leu Arg
        980                 985                 990

Val Ser Glu Thr Thr Gln Asp Ser Leu Thr Phe Phe Trp Thr Thr Pro
        995                 1000                1005

Leu Ala Lys Phe Asp Arg Tyr Arg Leu Asn Tyr Ser Leu Pro Thr
        1010                1015                1020

Gly Gln Ser Met Glu Val Gln Leu Pro Lys Asp Ala Thr Ser His
        1025                1030                1035

Val Leu Thr Asp Leu Glu Pro Gly Gln Glu Tyr Thr Val Leu Leu
        1040                1045                1050

Ile Ala Glu Lys Gly Arg His Lys Ser Lys Pro Ala Arg Val Lys
        1055                1060                1065

Ala Ser Thr Glu Glu Val Pro Ser Leu Glu Asn Leu Thr Val Thr
        1070                1075                1080

Glu Ala Gly Trp Asp Gly Leu Arg Leu Asn Trp Thr Ala Asp Asp
        1085                1090                1095

Leu Ala Tyr Glu Tyr Phe Val Ile Gln Val Gln Glu Ala Asn Asn
        1100                1105                1110

Val Glu Thr Ala His Asn Phe Thr Val Pro Gly Asn Leu Arg Ala
        1115                1120                1125

Ala Asp Ile Pro Gly Leu Lys Val Ala Thr Ser Tyr Arg Val Ser
        1130                1135                1140

Ile Tyr Gly Val Ala Arg Gly Tyr Arg Thr Pro Val Leu Ser Ala
        1145                1150                1155

Glu Thr Ser Thr Gly Thr Thr Pro Asn Leu Gly Glu Val Thr Val
        1160                1165                1170

Ala Glu Val Gly Trp Asp Ala Leu Thr Leu Asn Trp Thr Ala Pro
        1175                1180                1185

Glu Gly Ala Tyr Lys Asn Phe Phe Ile Gln Val Leu Glu Ala Asp
        1190                1195                1200

Thr Thr Gln Thr Val Gln Asn Leu Thr Val Pro Gly Gly Leu Arg
        1205                1210                1215

Ser Val Asp Leu Pro Gly Leu Lys Ala Ala Thr Arg Tyr Tyr Ile
        1220                1225                1230

Thr Leu Arg Gly Val Thr Gln Asp Phe Gly Thr Ala Pro Leu Ser

```
        1235                1240                1245

Val Glu Val Leu Thr Glu Asp Leu Pro Gln Leu Gly Gly Leu Ser
    1250                1255                1260

Val Thr Glu Val Ser Trp Asp Gly Leu Thr Leu Asn Trp Thr Thr
    1265                1270                1275

Asp Asp Leu Ala Tyr Lys His Phe Val Gln Val Gln Glu Ala
    1280                1285                1290

Asn Asn Val Glu Ala Ala Gln Asn Leu Thr Val Pro Gly Ser Leu
    1295                1300                1305

Arg Ala Val Asp Ile Pro Gly Leu Lys Ala Asp Thr Pro Tyr Arg
    1310                1315                1320

Val Ser Ile Tyr Gly Val Ile Gln Gly Tyr Arg Thr Pro Met Leu
    1325                1330                1335

Ser Thr Asp Val Ser Thr Ala Arg Glu Pro Glu Ile Gly Asn Leu
    1340                1345                1350

Asn Val Ser Asp Val Thr Pro Lys Ser Phe Asn Leu Ser Trp Thr
    1355                1360                1365

Ala Thr Asp Gly Ile Phe Asp Met Phe Thr Ile Glu Ile Ile Asp
    1370                1375                1380

Ser Asn Arg Leu Leu Gln Thr Ala Glu His Asn Ile Ser Gly Ala
    1385                1390                1395

Glu Arg Thr Ala His Ile Ser Gly Leu Pro Pro Ser Thr Asp Phe
    1400                1405                1410

Ile Val Tyr Leu Ser Gly Ile Ala Pro Ser Ile Arg Thr Lys Thr
    1415                1420                1425

Ile Ser Thr Thr Ala Thr Thr Glu Ala Leu Pro Leu Leu Glu Asn
    1430                1435                1440

Leu Thr Ile Ser Asp Thr Asn Pro Tyr Gly Phe Thr Val Ser Trp
    1445                1450                1455

Thr Ala Ser Glu Asn Ala Phe Asp Ser Phe Leu Val Thr Val Val
    1460                1465                1470

Asp Ser Gly Lys Leu Leu Asp Pro Gln Glu Phe Thr Leu Ser Gly
    1475                1480                1485

Thr Gln Arg Lys Leu Glu Leu Arg Gly Leu Ile Thr Gly Ile Gly
    1490                1495                1500

Tyr Glu Val Leu Val Ser Gly Phe Thr Gln Gly His Gln Thr Lys
    1505                1510                1515

Pro Leu Arg Ala Glu Thr Ile Thr Glu Ala Glu Pro Glu Val Asp
    1520                1525                1530

Asn Leu Leu Val Ser Asp Ala Thr Pro Asp Gly Phe Arg Leu Ser
    1535                1540                1545

Trp Thr Ala Asp Glu Gly Ile Phe Asp Ser Phe Val Ile Arg Ile
    1550                1555                1560

Arg Asp Thr Lys Lys Gln Ser Glu Pro Gln Glu Ile Ser Leu Pro
    1565                1570                1575

Ser Pro Glu Arg Thr Arg Asp Ile Thr Gly Leu Arg Glu Ala Thr
    1580                1585                1590

Glu Tyr Glu Ile Glu Leu Tyr Gly Ile Ser Arg Gly Arg Arg Ser
    1595                1600                1605

Gln Pro Val Ser Ala Ile Ala Thr Thr Ala Met Gly Ser Pro Lys
    1610                1615                1620

Glu Ile Met Phe Ser Asp Ile Thr Glu Asn Ala Ala Thr Val Ser
    1625                1630                1635
```

```
Trp Arg Ala Pro Thr Ala Gln Val Glu Ser Phe Arg Ile Thr Tyr
1640                1645                1650

Val Pro Met Thr Gly Gly Ala Pro Ser Met Val Thr Val Asp Gly
1655                1660                1665

Thr Asp Thr Glu Thr Arg Leu Val Lys Leu Thr Pro Gly Val Glu
1670                1675                1680

Tyr Arg Val Ser Val Ile Ala Met Lys Gly Phe Glu Glu Ser Asp
1685                1690                1695

Pro Val Ser Gly Thr Leu Ile Thr Ala Leu Asp Gly Pro Ser Gly
1700                1705                1710

Leu Leu Ile Ala Asn Ile Thr Asp Ser Glu Ala Leu Ala Met Trp
1715                1720                1725

Gln Pro Ala Ile Ala Thr Val Asp Ser Tyr Val Ile Ser Tyr Thr
1730                1735                1740

Gly Glu Arg Val Pro Glu Val Thr Arg Thr Val Ser Gly Asn Thr
1745                1750                1755

Val Glu Tyr Glu Leu His Asp Leu Glu Pro Ala Thr Glu Tyr Ile
1760                1765                1770

Leu Ser Ile Phe Ala Glu Lys Gly Gln Gln Lys Ser Ser Thr Ile
1775                1780                1785

Ala Thr Lys Phe Thr Thr Asp Leu Asp Ser Pro Arg Glu Phe Thr
1790                1795                1800

Ala Thr Glu Val Gln Ser Glu Thr Ala Leu Leu Thr Trp Arg Pro
1805                1810                1815

Pro Arg Ala Ser Val Thr Gly Tyr Leu Leu Val Tyr Glu Ser Val
1820                1825                1830

Asp Gly Thr Val Lys Glu Val Ile Val Gly Pro Asp Thr Thr Ser
1835                1840                1845

Tyr Ser Leu Ala Asp Leu Ser Pro Ser Thr His Tyr Ser Ala Arg
1850                1855                1860

Ile Gln Ala Leu Ser Gly Ser Leu Arg Ser Lys Leu Ile Gln Thr
1865                1870                1875

Ile Phe Thr Thr Ile Gly Leu Leu Tyr Pro Phe Pro Arg Asp Cys
1880                1885                1890

Ser Gln Ala Met Leu Asn Gly Asp Thr Thr Ser Gly Leu Tyr Thr
1895                1900                1905

Ile Tyr Ile Asn Gly Asp Lys Thr Gln Ala Leu Glu Val Tyr Cys
1910                1915                1920

Asp Met Thr Ser Asp Gly Gly Trp Ile Val Phe Leu Arg Arg
1925                1930                1935

Lys Asn Gly Arg Glu Asp Phe Tyr Arg Asn Trp Lys Ala Tyr Ala
1940                1945                1950

Ala Gly Phe Gly Asp Arg Arg Glu Glu Phe Trp Leu Gly Leu Asp
1955                1960                1965

Asn Leu Ser Lys Ile Thr Ala Gln Gly Gln Tyr Glu Leu Arg Val
1970                1975                1980

Asp Leu Gln Asp His Gly Glu Ser Ala Tyr Ala Val Tyr Asp Arg
1985                1990                1995

Phe Ser Val Gly Asp Ala Lys Ser Arg Tyr Lys Leu Lys Val Glu
2000                2005                2010

Gly Tyr Ser Gly Thr Ala Gly Asp Ser Met Asn Tyr His Asn Gly
2015                2020                2025
```

```
Arg Ser Phe Ser Thr Tyr Asp Lys Asp Thr Asp Ser Ala Ile Thr
    2030            2035            2040

Asn Cys Ala Leu Ser Tyr Lys Gly Ala Phe Trp Tyr Lys Asn Cys
    2045            2050            2055

His Arg Val Asn Leu Met Gly Arg Tyr Gly Asp Asn Asn His Ser
    2060            2065            2070

Gln Gly Val Asn Trp Phe His Trp Lys Gly His Glu Tyr Ser Ile
    2075            2080            2085

Gln Phe Ala Glu Met Lys Leu Arg Pro Ser Asn Phe Arg Asn Leu
    2090            2095            2100

Glu Gly Arg Arg Lys Arg Ala
    2105            2110
```

<210> SEQ ID NO 64
<211> LENGTH: 5
<212> TYPE: PRT
<213> ORGANISM: Artificial Sequence
<220> FEATURE:
<223> OTHER INFORMATION: Petpide linker G4S

<400> SEQUENCE: 64

```
Gly Gly Gly Gly Ser
1               5
```

<210> SEQ ID NO 65
<211> LENGTH: 10
<212> TYPE: PRT
<213> ORGANISM: Artificial Sequence
<220> FEATURE:
<223> OTHER INFORMATION: Peptide linker (G4S)2

<400> SEQUENCE: 65

```
Gly Gly Gly Gly Ser Gly Gly Gly Gly Ser
1               5                   10
```

<210> SEQ ID NO 66
<211> LENGTH: 10
<212> TYPE: PRT
<213> ORGANISM: Artificial Sequence
<220> FEATURE:
<223> OTHER INFORMATION: Peptide linker (SG4)2

<400> SEQUENCE: 66

```
Ser Gly Gly Gly Gly Ser Gly Gly Gly Gly
1               5                   10
```

<210> SEQ ID NO 67
<211> LENGTH: 15
<212> TYPE: PRT
<213> ORGANISM: Artificial Sequence
<220> FEATURE:
<223> OTHER INFORMATION: Peptide linker (G4S)3

<400> SEQUENCE: 67

```
Gly Gly Gly Gly Ser Gly Gly Gly Gly Ser Gly Gly Gly Gly Ser
1               5                   10                  15
```

<210> SEQ ID NO 68
<211> LENGTH: 14
<212> TYPE: PRT
<213> ORGANISM: Artificial Sequence
<220> FEATURE:
<223> OTHER INFORMATION: Peptide linker G4(SG4)2

<400> SEQUENCE: 68

```
Gly Gly Gly Gly Ser Gly Gly Gly Gly
1               5                   10
```

<210> SEQ ID NO 69
<211> LENGTH: 20
<212> TYPE: PRT
<213> ORGANISM: Artificial Sequence
<220> FEATURE:
<223> OTHER INFORMATION: Peptide linker (G4S)4

<400> SEQUENCE: 69

```
Gly Gly Gly Gly Ser Gly Gly Gly Gly Ser Gly Gly Gly Gly Ser Gly
1               5                   10                  15
Gly Gly Gly Ser
            20
```

<210> SEQ ID NO 70
<211> LENGTH: 10
<212> TYPE: PRT
<213> ORGANISM: Artificial Sequence
<220> FEATURE:
<223> OTHER INFORMATION: Peptide linker GSPGSSSSGS

<400> SEQUENCE: 70

```
Gly Ser Pro Gly Ser Ser Ser Ser Gly Ser
1               5                   10
```

<210> SEQ ID NO 71
<211> LENGTH: 8
<212> TYPE: PRT
<213> ORGANISM: Artificial Sequence
<220> FEATURE:
<223> OTHER INFORMATION: Peptide linker GSGSGSGS

<400> SEQUENCE: 71

```
Gly Ser Gly Ser Gly Ser Gly Ser
1               5
```

<210> SEQ ID NO 72
<211> LENGTH: 8
<212> TYPE: PRT
<213> ORGANISM: Artificial Sequence
<220> FEATURE:
<223> OTHER INFORMATION: Peptide linker GSGSGNGS

<400> SEQUENCE: 72

```
Gly Ser Gly Ser Gly Asn Gly Ser
1               5
```

<210> SEQ ID NO 73
<211> LENGTH: 8
<212> TYPE: PRT
<213> ORGANISM: Artificial Sequence
<220> FEATURE:
<223> OTHER INFORMATION: Peptide linker GGSGSGSG

<400> SEQUENCE: 73

```
Gly Gly Ser Gly Ser Gly Ser Gly
1               5
```

<210> SEQ ID NO 74
<211> LENGTH: 6
<212> TYPE: PRT
<213> ORGANISM: Artificial Sequence
<220> FEATURE:
<223> OTHER INFORMATION: Peptide linker GGSGSG

<400> SEQUENCE: 74

Gly Gly Ser Gly Ser Gly
1               5

<210> SEQ ID NO 75
<211> LENGTH: 4
<212> TYPE: PRT
<213> ORGANISM: Artificial Sequence
<220> FEATURE:
<223> OTHER INFORMATION: Peptide linkeer GGSG

<400> SEQUENCE: 75

Gly Gly Ser Gly
1

<210> SEQ ID NO 76
<211> LENGTH: 8
<212> TYPE: PRT
<213> ORGANISM: Artificial Sequence
<220> FEATURE:
<223> OTHER INFORMATION: Peptide linker GGSGNGSG

<400> SEQUENCE: 76

Gly Gly Ser Gly Asn Gly Ser Gly
1               5

<210> SEQ ID NO 77
<211> LENGTH: 8
<212> TYPE: PRT
<213> ORGANISM: Artificial Sequence
<220> FEATURE:
<223> OTHER INFORMATION: Peptide linker GGNGSGSG

<400> SEQUENCE: 77

Gly Gly Asn Gly Ser Gly Ser Gly
1               5

<210> SEQ ID NO 78
<211> LENGTH: 6
<212> TYPE: PRT
<213> ORGANISM: Artificial Sequence
<220> FEATURE:
<223> OTHER INFORMATION: Peptide linker GGNGSG

<400> SEQUENCE: 78

Gly Gly Asn Gly Ser Gly
1               5

<210> SEQ ID NO 79
<211> LENGTH: 186
<212> TYPE: PRT
<213> ORGANISM: cynomolgus

<400> SEQUENCE: 79

Leu His Cys Val Gly Asp Thr Tyr Pro Ser Asn Asp Arg Cys Cys Gln
1               5                   10                  15

Glu Cys Arg Pro Gly Asn Gly Met Val Ser Arg Cys Asn Arg Ser Gln
            20                  25                  30

Asn Thr Val Cys Arg Pro Cys Gly Pro Gly Phe Tyr Asn Asp Val Val
        35                  40                  45

Ser Ala Lys Pro Cys Lys Ala Cys Thr Trp Cys Asn Leu Arg Ser Gly
    50                  55                  60

Ser Glu Arg Lys Gln Pro Cys Thr Ala Thr Gln Asp Thr Val Cys Arg

```
              65                  70                  75                  80
Cys Arg Ala Gly Thr Gln Pro Leu Asp Ser Tyr Lys Pro Gly Val Asp
                85                  90                  95

Cys Ala Pro Cys Pro Gly His Phe Ser Pro Gly Asp Asn Gln Ala
            100                 105                 110

Cys Lys Pro Trp Thr Asn Cys Thr Leu Ala Gly Lys His Thr Leu Gln
            115                 120                 125

Pro Ala Ser Asn Ser Ser Asp Ala Ile Cys Glu Asp Arg Asp Pro Pro
            130                 135                 140

Pro Thr Gln Pro Gln Glu Thr Gln Gly Pro Pro Ala Arg Pro Thr Thr
145                 150                 155                 160

Val Gln Pro Thr Glu Ala Trp Pro Arg Thr Ser Gln Arg Pro Ser Thr
                165                 170                 175

Arg Pro Val Glu Val Pro Arg Gly Pro Ala
                180                 185

<210> SEQ ID NO 80
<211> LENGTH: 192
<212> TYPE: PRT
<213> ORGANISM: Mus musculus

<400> SEQUENCE: 80

Val Thr Ala Arg Arg Leu Asn Cys Val Lys His Thr Tyr Pro Ser Gly
1               5                   10                  15

His Lys Cys Cys Arg Glu Cys Gln Pro Gly His Gly Met Val Ser Arg
                20                  25                  30

Cys Asp His Thr Arg Asp Thr Leu Cys His Pro Cys Glu Thr Gly Phe
            35                  40                  45

Tyr Asn Glu Ala Val Asn Tyr Asp Thr Cys Lys Gln Cys Thr Gln Cys
        50                  55                  60

Asn His Arg Ser Gly Ser Glu Leu Lys Gln Asn Cys Thr Pro Thr Gln
65                  70                  75                  80

Asp Thr Val Cys Arg Cys Arg Pro Gly Thr Gln Pro Arg Gln Asp Ser
                85                  90                  95

Gly Tyr Lys Leu Gly Val Asp Cys Val Pro Cys Pro Pro Gly His Phe
            100                 105                 110

Ser Pro Gly Asn Asn Gln Ala Cys Lys Pro Trp Thr Asn Cys Thr Leu
            115                 120                 125

Ser Gly Lys Gln Thr Arg His Pro Ala Ser Asp Ser Leu Asp Ala Val
        130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
            180                 185                 190

<210> SEQ ID NO 81
<211> LENGTH: 760
<212> TYPE: PRT
<213> ORGANISM: Homo sapiens

<400> SEQUENCE: 81

Met Lys Thr Trp Val Lys Ile Val Phe Gly Val Ala Thr Ser Ala Val
1               5                   10                  15

Leu Ala Leu Leu Val Met Cys Ile Val Leu Arg Pro Ser Arg Val His
```

-continued

```
             20                  25                  30
Asn Ser Glu Glu Asn Thr Met Arg Ala Leu Thr Leu Lys Asp Ile Leu
         35                  40                  45
Asn Gly Thr Phe Ser Tyr Lys Thr Phe Phe Pro Asn Trp Ile Ser Gly
     50                  55                  60
Gln Glu Tyr Leu His Gln Ser Ala Asp Asn Asn Ile Val Leu Tyr Asn
 65                  70                  75                  80
Ile Glu Thr Gly Gln Ser Tyr Thr Ile Leu Ser Asn Arg Thr Met Lys
                 85                  90                  95
Ser Val Asn Ala Ser Asn Tyr Gly Leu Ser Pro Asp Arg Gln Phe Val
            100                 105                 110
Tyr Leu Glu Ser Asp Tyr Ser Lys Leu Trp Arg Tyr Ser Tyr Thr Ala
        115                 120                 125
Thr Tyr Tyr Ile Tyr Asp Leu Ser Asn Gly Glu Phe Val Arg Gly Asn
    130                 135                 140
Glu Leu Pro Arg Pro Ile Gln Tyr Leu Cys Trp Ser Pro Val Gly Ser
145                 150                 155                 160
Lys Leu Ala Tyr Val Tyr Gln Asn Asn Ile Tyr Leu Lys Gln Arg Pro
                165                 170                 175
Gly Asp Pro Pro Phe Gln Ile Thr Phe Asn Gly Arg Glu Asn Lys Ile
            180                 185                 190
Phe Asn Gly Ile Pro Asp Trp Val Tyr Glu Glu Met Leu Ala Thr
        195                 200                 205
Lys Tyr Ala Leu Trp Trp Ser Pro Asn Gly Lys Phe Leu Ala Tyr Ala
    210                 215                 220
Glu Phe Asn Asp Thr Asp Ile Pro Val Ile Ala Tyr Ser Tyr Tyr Gly
225                 230                 235                 240
Asp Glu Gln Tyr Pro Arg Thr Ile Asn Ile Pro Tyr Pro Lys Ala Gly
                245                 250                 255
Ala Lys Asn Pro Val Val Arg Ile Phe Ile Ile Asp Thr Thr Tyr Pro
            260                 265                 270
Ala Tyr Val Gly Pro Gln Glu Val Pro Val Pro Ala Met Ile Ala Ser
        275                 280                 285
Ser Asp Tyr Tyr Phe Ser Trp Leu Thr Trp Val Thr Asp Glu Arg Val
    290                 295                 300
Cys Leu Gln Trp Leu Lys Arg Val Gln Asn Val Ser Val Leu Ser Ile
305                 310                 315                 320
Cys Asp Phe Arg Glu Asp Trp Gln Thr Trp Asp Cys Pro Lys Thr Gln
                325                 330                 335
Glu His Ile Glu Glu Ser Arg Thr Gly Trp Ala Gly Gly Phe Phe Val
            340                 345                 350
Ser Thr Pro Val Phe Ser Tyr Asp Ala Ile Ser Tyr Tyr Lys Ile Phe
        355                 360                 365
Ser Asp Lys Asp Gly Tyr Lys His Ile His Tyr Ile Lys Asp Thr Val
    370                 375                 380
Glu Asn Ala Ile Gln Ile Thr Ser Gly Lys Trp Glu Ala Ile Asn Ile
385                 390                 395                 400
Phe Arg Val Thr Gln Asp Ser Leu Phe Tyr Ser Ser Asn Glu Phe Glu
                405                 410                 415
Glu Tyr Pro Gly Arg Arg Asn Ile Tyr Arg Ile Ser Ile Gly Ser Tyr
            420                 425                 430
Pro Pro Ser Lys Lys Cys Val Thr Cys His Leu Arg Lys Glu Arg Cys
        435                 440                 445
```

```
Gln Tyr Tyr Thr Ala Ser Phe Ser Asp Tyr Ala Lys Tyr Tyr Ala Leu
    450                 455                 460

Val Cys Tyr Gly Pro Gly Ile Pro Ile Ser Thr Leu His Asp Gly Arg
465                 470                 475                 480

Thr Asp Gln Glu Ile Lys Ile Leu Glu Glu Asn Lys Glu Leu Glu Asn
                485                 490                 495

Ala Leu Lys Asn Ile Gln Leu Pro Lys Glu Glu Ile Lys Lys Leu Glu
            500                 505                 510

Val Asp Glu Ile Thr Leu Trp Tyr Lys Met Ile Leu Pro Pro Gln Phe
        515                 520                 525

Asp Arg Ser Lys Lys Tyr Pro Leu Leu Ile Gln Val Tyr Gly Gly Pro
    530                 535                 540

Cys Ser Gln Ser Val Arg Ser Val Phe Ala Val Asn Trp Ile Ser Tyr
545                 550                 555                 560

Leu Ala Ser Lys Glu Gly Met Val Ile Ala Leu Val Asp Gly Arg Gly
                565                 570                 575

Thr Ala Phe Gln Gly Asp Lys Leu Leu Tyr Ala Val Tyr Arg Lys Leu
            580                 585                 590

Gly Val Tyr Glu Val Asp Gln Ile Thr Ala Val Arg Lys Phe Ile
        595                 600                 605

Glu Met Gly Phe Ile Asp Glu Lys Arg Ile Ala Ile Trp Gly Trp Ser
    610                 615                 620

Tyr Gly Gly Tyr Val Ser Ser Leu Ala Leu Ala Ser Gly Thr Gly Leu
625                 630                 635                 640

Phe Lys Cys Gly Ile Ala Val Ala Pro Val Ser Ser Trp Glu Tyr Tyr
                645                 650                 655

Ala Ser Val Tyr Thr Glu Arg Phe Met Gly Leu Pro Thr Lys Asp Asp
            660                 665                 670

Asn Leu Glu His Tyr Lys Asn Ser Thr Val Met Ala Arg Ala Glu Tyr
        675                 680                 685

Phe Arg Asn Val Asp Tyr Leu Leu Ile His Gly Thr Ala Asp Asp Asn
    690                 695                 700

Val His Phe Gln Asn Ser Ala Gln Ile Ala Lys Ala Leu Val Asn Ala
705                 710                 715                 720

Gln Val Asp Phe Gln Ala Met Trp Tyr Ser Asp Gln Asn His Gly Leu
                725                 730                 735

Ser Gly Leu Ser Thr Asn His Leu Tyr Thr His Met Thr His Phe Leu
            740                 745                 750

Lys Gln Cys Phe Ser Leu Ser Asp
    755                 760

<210> SEQ ID NO 82
<211> LENGTH: 681
<212> TYPE: DNA
<213> ORGANISM: Artificial Sequence
<220> FEATURE:
<223> OTHER INFORMATION: Nucleotide sequence Fc hole chain

<400> SEQUENCE: 82
gacaaaactc acacatgccc accgtgccca gcacctgaac tcctgggggg accgtcagtc    60
ttcctcttcc ccccaaaacc caaggacacc ctcatgatct cccggacccc tgaggtcaca   120
tgcgtggtgg tggacgtgag ccacgaagac cctgaggtca agttcaactg gtacgtggac   180
ggcgtggagg tgcataatgc caagacaaag ccgcgggagg agcagtacaa cagcacgtac   240
```

```
cgtgtggtca gcgtcctcac cgtcctgcac caggactggc tgaatggcaa ggagtacaag      300
tgcaaggtct ccaacaaagc cctcccagcc cccatcgaga aaaccatctc caaagccaaa      360
gggcagcccc gagaaccaca ggtgtgcacc ctgcccccat cccgggatga gctgaccaag      420
aaccaggtca gcctctcgtg cgcagtcaaa ggcttctatc ccagcgacat cgccgtggag      480
tgggagagca atgggcagcc ggagaacaac tacaagacca cgcctcccgt gctggactcc      540
gacggctcct tcttcctcgt gagcaagctc accgtggaca gagcaggtg gcagcagggg      600 aacgtcttct catgctccgt gatgcatgag gctctgcaca accactacac gcagaagagc      660
ctctccctgt ctccgggtaa a                                              681
```

```
<210> SEQ ID NO 83
<211> LENGTH: 1335
<212> TYPE: DNA
<213> ORGANISM: Artificial Sequence
<220> FEATURE:
<223> OTHER INFORMATION: nucleotide sequence human OX40 antigen Fc knob
      chain

<400> SEQUENCE: 83
```

```
ctgcactgcg tgggcgacac ctaccccagc aacgaccggt gctgccacga gtgcagaccc       60
ggcaacggca tggtgtcccg cgtgcagccg gtcccagaaca ccgtgtgcag accttgcggc     120
cctggcttct acaacgacgt ggtgtccagc aagcccctgca agccttgtac ctggtgcaac     180
ctgcggagcg gcagcgagcg gaagcagctg tgtaccgcca cccaggatac cgtgtgccgg     240
tgtagagccg gcacccagcc cctggacagc tacaaacccg gcgtggactg cgcccccttgc    300 cctcctggcc acttcagccc tggcgacaac caggcctgca agccttggac caactgcacc     360
ctggccggca gcacaccct gcagccgcc agcaatagca gcgacgccat ctgcgaggac       420
cgggatcctc ctgccaccca gcctcaggaa acccagggcc ctcccgccag acccatcacc     480
gtgcagccta cagaggcctg gcccagaacc agcaggggc ctagcaccag acccgtggaa      540
gtgcctggcg gcagagccgt cgacgaacag ttatattttc agggcggctc acccaaatct     600
gcagacaaaa ctcacacatg cccaccgtgc ccagcacctg aactcctggg gggaccgtca     660
gtcttcctct tccccccaaa acccaaggac accctcatga tctcccggac ccctgaggtc     720
acatgcgtgg tggtggacgt gagccacgaa gaccctgagg tcaagttcaa ctggtacgtg     780
gacggcgtgg aggtgcataa tgccaagaca aagccgcggg aggagcagta caacagcacg     840
taccgtgtgg tcagcgtcct caccgtcctg caccaggact ggctgaatgg caaggagtac     900
aagtgcaagg tctccaacaa agccctccca gcccccatcg agaaaccat ctccaaagcc      960 aaagggcagc cccgagaacc acaggtgtac accctgcccc catgccggga tgagctgacc    1020
aagaaccagg tcagcctgtg tgtgctggtc aaaggcttct atcccagcga catcgccgtg    1080
gagtgggaga gcaatgggca gccggagaac aactacaaga ccacgcctcc cgtgctggac    1140
tccgacggct ccttcttcct ctacagcaag ctcaccgtgg acaagagcag gtggcagcag    1200
gggaacgtct tctcatgctc cgtgatgcat gaggctctgc acaaccacta cacgcagaag    1260
agcctctccc tgtctccggg taaatccgga ggcctgaacg acatcttcga ggcccagaag    1320
attgaatggc acgag                                                   1335
```

```
<210> SEQ ID NO 84
<211> LENGTH: 1335
<212> TYPE: DNA
<213> ORGANISM: Artificial Sequence
<220> FEATURE:
```

<223> OTHER INFORMATION: nucleotide sequence cynomolgus OX40 antigen Fc
      knob chain

<400> SEQUENCE: 84

| | | |
|---|---|---|
| ctccactgtg tcggggacac ctaccccagc aacgaccggt gctgtcagga gtgcaggcca | 60 |
| ggcaacggga tggtgagccg ctgcaaccgc tcccagaaca cggtgtgccg tccgtgcggg | 120 |
| cccggcttct acaacgacgt ggtcagcgcc aagccctgca aggcctgcac atggtgcaac | 180 |
| ctcagaagtg ggagtgagcg gaaacagccg tgcacggcca cacaggacac agtctgccgc | 240 |
| tgccgggcgg gcacccagcc cctggacagc tacaagcctg gagttgactg tgcccctgc | 300 |
| cctccagggc acttctcccc gggcgacaac caggcctgca gccctggac caactgcacc | 360 |
| ttggccggga agcacaccct gcagccagcc agcaatagct cggacgccat ctgtgaggac | 420 |
| agggaccccc cacccacaca gccccaggag acccagggcc cccggccag gcccaccact | 480 |
| gtccagccca ctgaagcctg gccagaacc tcacagagac cctccacccg gccgtggag | 540 |
| gtccccaggg gccctgcggt cgacgaacag ttatattttc agggcggctc acccaaatct | 600 |
| gcagacaaaa ctcacacatg cccaccgtgc ccagcacctg aactcctggg gggaccgtca | 660 |
| gtcttcctct tccccccaaa acccaaggac accctcatga tctcccggac ccctgaggtc | 720 |
| acatgcgtgg tggtggacgt gagccacgaa gaccctgagg tcaagttcaa ctggtacgtg | 780 |
| gacggcgtgg aggtgcataa tgccaagaca agccgcggg aggagcagta acagcacg | 840 |
| taccgtgtgg tcagcgtcct caccgtcctg caccaggact ggctgaatgg caaggagtac | 900 |
| aagtgcaagg tctccaacaa agccctccca gccccatcg agaaaaccat ctccaaagcc | 960 |
| aaagggcagc cccgagaacc acaggtgtac accctgcccc catgccggga tgagctgacc | 1020 |
| aagaaccagg tcagcctgtg cgtgcctggtc aaaggcttct atcccagcga catcgccgtg | 1080 |
| gagtgggaga gcaatgggca gccggagaac aactacaaga ccacgcctcc cgtgctggac | 1140 |
| tccgacggct ccttcttcct ctacagcaag ctcaccgtgg acaagagcag gtggcagcag | 1200 |
| gggaacgtct tctcatgctc cgtgatgcat gaggctctgc acaaccacta cacgcagaag | 1260 |
| agcctctccc tgtctccggg taaatccgga ggcctgaacg acatcttcga ggcccagaag | 1320 |
| attgaatggc acgag | 1335 |

<210> SEQ ID NO 85
<211> LENGTH: 1353
<212> TYPE: DNA
<213> ORGANISM: Artificial Sequence
<220> FEATURE:
<223> OTHER INFORMATION: nucleotide sequence murine OX40 antigen Fc knob
      chain

<400> SEQUENCE: 85

| | | |
|---|---|---|
| gtgaccgcca gacggctgaa ctgcgtgaag cacacctacc ccagcggcca caagtgctgc | 60 |
| agagagtgcc agcccggcca cggcatggtg tccagatgcg accacacacg ggacaccctg | 120 |
| tgccacccct gcgagacagg cttctacaac gaggccgtga ctacgatac ctgcaagcag | 180 |
| tgcacccagt gcaaccacag aagcggcagc gagctgaagc agaactgcac ccccacccag | 240 |
| gataccgtgt gcagatgcag accggcacc cagcccagac aggacagcgg ctacaagctg | 300 |
| ggcgtggact gcgtgccctg ccctcctggc cacttcagcc ccggcaacaa ccaggcctgc | 360 |
| aagccctgga ccaactgcac cctgagcggc aagcagacca gacacccgc cagcgacagc | 420 |
| ctggatgccg tgtgcgagga cagaagcctg ctggccaccc tgctgtggga cacacagcgg | 480 |
| cccaccttca gacccaccac cgtgcagagc accaccgtgt ggcccagaac cagcgagctg | 540 |

```
cccagtcctc ctaccctcgt gacacctgag ggccccgtcg acgaacagtt atattttcag    600
ggcggctcac ccaaatctgc agacaaaact cacacatgcc caccgtgccc agcacctgaa    660
ctcctggggg gaccgtcagt cttcctcttc cccccaaaac ccaaggacac cctcatgatc    720
tcccggaccc ctgaggtcac atgcgtggtg gtggacgtga gccacgaaga ccctgaggtc    780
aagttcaact ggtacgtgga cggcgtggag gtgcataatg ccaagacaaa gccgcgggag    840
gagcagtaca acagcacgta ccgtgtggtc agcgtcctca ccgtcctgca ccaggactgg    900
ctgaatggca aggagtacaa gtgcaaggtc tccaacaaag ccctcccagc ccccatcgag    960
aaaaccatct ccaaagccaa agggcagccc cgagaaccac aggtgtacac cctgccccca   1020 tgcccgggatg agctgaccaa gaaccaggtc agcctgtggt gcctggtcaa aggcttctat   1080
cccagcgaca tcgccgtgga gtgggagagc aatgggcagc cggagaacaa ctacaagacc   1140
acgcctcccg tgctggactc cgacggctcc ttcttcctct acagcaagct caccgtggac   1200
aagagcaggt ggcagcaggg gaacgtcttc tcatgctccg tgatgcatga ggctctgcac   1260
aaccactaca cgcagaagag cctctccctg tctccgggta aatccggagg cctgaacgac   1320
atcttcgagg cccagaagat tgaatggcac gag                                 1353
```

<210> SEQ ID NO 86
<211> LENGTH: 227
<212> TYPE: PRT
<213> ORGANISM: Artificial Sequence
<220> FEATURE:
<223> OTHER INFORMATION: Fc hole chain

<400> SEQUENCE: 86

```
Asp Lys Thr His Thr Cys Pro Pro Cys Pro Ala Pro Glu Leu Leu Gly
1               5                   10                  15

Gly Pro Ser Val Phe Leu Phe Pro Pro Lys Pro Lys Asp Thr Leu Met
            20                  25                  30

Ile Ser Arg Thr Pro Glu Val Thr Cys Val Val Val Asp Val Ser His
        35                  40                  45

Glu Asp Pro Glu Val Lys Phe Asn Trp Tyr Val Asp Gly Val Glu Val
    50                  55                  60

His Asn Ala Lys Thr Lys Pro Arg Glu Glu Gln Tyr Asn Ser Thr Tyr
65                  70                  75                  80

Arg Val Val Ser Val Leu Thr Val Leu His Gln Asp Trp Leu Asn Gly
                85                  90                  95

Lys Glu Tyr Lys Cys Lys Val Ser Asn Lys Ala Leu Pro Ala Pro Ile
            100                 105                 110

Glu Lys Thr Ile Ser Lys Ala Lys Gly Gln Pro Arg Glu Pro Gln Val
        115                 120                 125

Cys Thr Leu Pro Pro Ser Arg Asp Glu Leu Thr Lys Asn Gln Val Ser
    130                 135                 140

Leu Ser Cys Ala Val Lys Gly Phe Tyr Pro Ser Asp Ile Ala Val Glu
145                 150                 155                 160

Trp Glu Ser Asn Gly Gln Pro Glu Asn Asn Tyr Lys Thr Thr Pro Pro
                165                 170                 175

Val Leu Asp Ser Asp Gly Ser Phe Phe Leu Val Ser Lys Leu Thr Val
            180                 185                 190

Asp Lys Ser Arg Trp Gln Gln Gly Asn Val Phe Ser Cys Ser Val Met
        195                 200                 205

His Glu Ala Leu His Asn His Tyr Thr Gln Lys Ser Leu Ser Leu Ser
```

Pro Gly Lys
225

<210> SEQ ID NO 87
<211> LENGTH: 445
<212> TYPE: PRT
<213> ORGANISM: Artificial Sequence
<220> FEATURE:
<223> OTHER INFORMATION: human OX40 antigen Fc knob chain

<400> SEQUENCE: 87

Leu His Cys Val Gly Asp Thr Tyr Pro Ser Asn Asp Arg Cys Cys His
1               5                   10                  15

Glu Cys Arg Pro Gly Asn Gly Met Val Ser Arg Cys Ser Arg Ser Gln
            20                  25                  30

Asn Thr Val Cys Arg Pro Cys Gly Pro Gly Phe Tyr Asn Asp Val Val
        35                  40                  45

Ser Ser Lys Pro Cys Lys Pro Cys Thr Trp Cys Asn Leu Arg Ser Gly
50                  55                  60

Ser Glu Arg Lys Gln Leu Cys Thr Ala Thr Gln Asp Thr Val Cys Arg
65                  70                  75                  80

Cys Arg Ala Gly Thr Gln Pro Leu Asp Ser Tyr Lys Pro Gly Val Asp
                85                  90                  95

Cys Ala Pro Cys Pro Pro Gly His Phe Ser Pro Gly Asp Asn Gln Ala
            100                 105                 110

Cys Lys Pro Trp Thr Asn Cys Thr Leu Ala Gly Lys His Thr Leu Gln
        115                 120                 125

Pro Ala Ser Asn Ser Ser Asp Ala Ile Cys Glu Asp Arg Asp Pro Pro
130                 135                 140

Ala Thr Gln Pro Gln Glu Thr Gln Gly Pro Pro Ala Arg Pro Ile Thr
145                 150                 155                 160

Val Gln Pro Thr Glu Ala Trp Pro Arg Thr Ser Gln Gly Pro Ser Thr
                165                 170                 175

Arg Pro Val Glu Val Pro Gly Gly Arg Ala Val Asp Glu Gln Leu Tyr
            180                 185                 190

Phe Gln Gly Gly Ser Pro Lys Ser Ala Asp Lys Thr His Thr Cys Pro
        195                 200                 205

Pro Cys Pro Ala Pro Glu Leu Leu Gly Gly Pro Ser Val Phe Leu Phe
210                 215                 220

Pro Pro Lys Pro Lys Asp Thr Leu Met Ile Ser Arg Thr Pro Glu Val
225                 230                 235                 240

Thr Cys Val Val Val Asp Val Ser His Glu Asp Pro Glu Val Lys Phe
                245                 250                 255

Asn Trp Tyr Val Asp Gly Val Glu Val His Asn Ala Lys Thr Lys Pro
            260                 265                 270

Arg Glu Glu Gln Tyr Asn Ser Thr Tyr Arg Val Val Ser Val Leu Thr
        275                 280                 285

Val Leu His Gln Asp Trp Leu Asn Gly Lys Glu Tyr Lys Cys Lys Val
    290                 295                 300

Ser Asn Lys Ala Leu Pro Ala Pro Ile Glu Lys Thr Ile Ser Lys Ala
305                 310                 315                 320

Lys Gly Gln Pro Arg Glu Pro Gln Val Tyr Thr Leu Pro Pro Cys Arg
                325                 330                 335

Asp Glu Leu Thr Lys Asn Gln Val Ser Leu Trp Cys Leu Val Lys Gly

```
                    340                 345                 350
Phe Tyr Pro Ser Asp Ile Ala Val Glu Trp Glu Ser Asn Gly Gln Pro
                355                 360                 365
Glu Asn Asn Tyr Lys Thr Thr Pro Pro Val Leu Asp Ser Asp Gly Ser
            370                 375                 380
Phe Phe Leu Tyr Ser Lys Leu Thr Val Asp Lys Ser Arg Trp Gln Gln
385                 390                 395                 400
Gly Asn Val Phe Ser Cys Ser Val Met His Glu Ala Leu His Asn His
                405                 410                 415
Tyr Thr Gln Lys Ser Leu Ser Leu Ser Pro Gly Lys Ser Gly Gly Leu
            420                 425                 430
Asn Asp Ile Phe Glu Ala Gln Lys Ile Glu Trp His Glu
        435                 440                 445

<210> SEQ ID NO 88
<211> LENGTH: 445
<212> TYPE: PRT
<213> ORGANISM: Artificial Sequence
<220> FEATURE:
<223> OTHER INFORMATION: cynomolgus OX40 antigen Fc knob chain

<400> SEQUENCE: 88

Leu His Cys Val Gly Asp Thr Tyr Pro Ser Asn Asp Arg Cys Cys Gln
1               5                   10                  15
Glu Cys Arg Pro Gly Asn Gly Met Val Ser Arg Cys Asn Arg Ser Gln
            20                  25                  30
Asn Thr Val Cys Arg Pro Cys Gly Pro Gly Phe Tyr Asn Asp Val Val
        35                  40                  45
Ser Ala Lys Pro Cys Lys Ala Cys Thr Trp Cys Asn Leu Arg Ser Gly
    50                  55                  60
Ser Glu Arg Lys Gln Pro Cys Thr Ala Thr Gln Asp Thr Val Cys Arg
65                  70                  75                  80
Cys Arg Ala Gly Thr Gln Pro Leu Asp Ser Tyr Lys Pro Gly Val Asp
                85                  90                  95
Cys Ala Pro Cys Pro Pro Gly His Phe Ser Pro Gly Asp Asn Gln Ala
            100                 105                 110
Cys Lys Pro Trp Thr Asn Cys Thr Leu Ala Gly Lys His Thr Leu Gln
        115                 120                 125
Pro Ala Ser Asn Ser Ser Asp Ala Ile Cys Glu Asp Arg Asp Pro Pro
    130                 135                 140
Pro Thr Gln Pro Gln Glu Thr Gln Gly Pro Pro Ala Arg Pro Thr Thr
145                 150                 155                 160
Val Gln Pro Thr Glu Ala Trp Pro Arg Thr Ser Gln Arg Pro Ser Thr
                165                 170                 175
Arg Pro Val Glu Val Pro Arg Gly Pro Ala Val Asp Glu Gln Leu Tyr
            180                 185                 190
Phe Gln Gly Gly Ser Pro Lys Ser Ala Asp Lys Thr His Thr Cys Pro
        195                 200                 205
Pro Cys Pro Ala Pro Glu Leu Leu Gly Gly Pro Ser Val Phe Leu Phe
    210                 215                 220
Pro Pro Lys Pro Lys Asp Thr Leu Met Ile Ser Arg Thr Pro Glu Val
225                 230                 235                 240
Thr Cys Val Val Val Asp Val Ser His Glu Asp Pro Glu Val Lys Phe
                245                 250                 255
Asn Trp Tyr Val Asp Gly Val Glu Val His Asn Ala Lys Thr Lys Pro
```

```
                 260                 265                 270
Arg Glu Glu Gln Tyr Asn Ser Thr Tyr Arg Val Val Ser Val Leu Thr
            275                 280                 285

Val Leu His Gln Asp Trp Leu Asn Gly Lys Glu Tyr Lys Cys Lys Val
        290                 295                 300

Ser Asn Lys Ala Leu Pro Ala Pro Ile Glu Lys Thr Ile Ser Lys Ala
305                 310                 315                 320

Lys Gly Gln Pro Arg Glu Pro Gln Val Tyr Thr Leu Pro Pro Cys Arg
                325                 330                 335

Asp Glu Leu Thr Lys Asn Gln Val Ser Leu Trp Cys Leu Val Lys Gly
            340                 345                 350

Phe Tyr Pro Ser Asp Ile Ala Val Glu Trp Glu Ser Asn Gly Gln Pro
        355                 360                 365

Glu Asn Asn Tyr Lys Thr Thr Pro Pro Val Leu Asp Ser Asp Gly Ser
        370                 375                 380

Phe Phe Leu Tyr Ser Lys Leu Thr Val Asp Lys Ser Arg Trp Gln Gln
385                 390                 395                 400

Gly Asn Val Phe Ser Cys Ser Val Met His Glu Ala Leu His Asn His
                405                 410                 415

Tyr Thr Gln Lys Ser Leu Ser Leu Ser Pro Gly Lys Ser Gly Gly Leu
            420                 425                 430

Asn Asp Ile Phe Glu Ala Gln Lys Ile Glu Trp His Glu
        435                 440                 445

<210> SEQ ID NO 89
<211> LENGTH: 451
<212> TYPE: PRT
<213> ORGANISM: Artificial Sequence
<220> FEATURE:
<223> OTHER INFORMATION: murine OX40 antigen Fc knob chain

<400> SEQUENCE: 89

Val Thr Ala Arg Arg Leu Asn Cys Val Lys His Thr Tyr Pro Ser Gly
1               5                   10                  15

His Lys Cys Cys Arg Glu Cys Gln Pro Gly His Gly Met Val Ser Arg
            20                  25                  30

Cys Asp His Thr Arg Asp Thr Leu Cys His Pro Cys Glu Thr Gly Phe
        35                  40                  45

Tyr Asn Glu Ala Val Asn Tyr Asp Thr Cys Lys Gln Cys Thr Gln Cys
    50                  55                  60

Asn His Arg Ser Gly Ser Glu Leu Lys Gln Asn Cys Thr Pro Thr Gln
65                  70                  75                  80

Asp Thr Val Cys Arg Cys Arg Pro Gly Thr Gln Pro Arg Gln Asp Ser
                85                  90                  95

Gly Tyr Lys Leu Gly Val Asp Cys Val Pro Cys Pro Pro Gly His Phe
            100                 105                 110

Ser Pro Gly Asn Asn Gln Ala Cys Lys Pro Trp Thr Asn Cys Thr Leu
        115                 120                 125

Ser Gly Lys Gln Thr Arg His Pro Ala Ser Asp Ser Leu Asp Ala Val
    130                 135                 140

Cys Glu Asp Arg Ser Leu Leu Ala Thr Leu Leu Trp Glu Thr Gln Arg
145                 150                 155                 160

Pro Thr Phe Arg Pro Thr Thr Val Gln Ser Thr Thr Val Trp Pro Arg
                165                 170                 175

Thr Ser Glu Leu Pro Ser Pro Pro Thr Leu Val Thr Pro Glu Gly Pro
```

```
            180                 185                 190
Val Asp Glu Gln Leu Tyr Phe Gln Gly Gly Ser Pro Lys Ser Ala Asp
        195                 200                 205

Lys Thr His Thr Cys Pro Pro Cys Pro Ala Pro Glu Leu Leu Gly Gly
    210                 215                 220

Pro Ser Val Phe Leu Phe Pro Pro Lys Pro Lys Asp Thr Leu Met Ile
225                 230                 235                 240

Ser Arg Thr Pro Glu Val Thr Cys Val Val Val Asp Val Ser His Glu
                245                 250                 255

Asp Pro Glu Val Lys Phe Asn Trp Tyr Val Asp Gly Val Glu Val His
            260                 265                 270

Asn Ala Lys Thr Lys Pro Arg Glu Glu Gln Tyr Asn Ser Thr Tyr Arg
        275                 280                 285

Val Val Ser Val Leu Thr Val Leu His Gln Asp Trp Leu Asn Gly Lys
    290                 295                 300

Glu Tyr Lys Cys Lys Val Ser Asn Lys Ala Leu Pro Ala Pro Ile Glu
305                 310                 315                 320

Lys Thr Ile Ser Lys Ala Lys Gly Gln Pro Arg Glu Pro Gln Val Tyr
                325                 330                 335

Thr Leu Pro Pro Cys Arg Asp Glu Leu Thr Lys Asn Gln Val Ser Leu
            340                 345                 350

Trp Cys Leu Val Lys Gly Phe Tyr Pro Ser Asp Ile Ala Val Glu Trp
        355                 360                 365

Glu Ser Asn Gly Gln Pro Glu Asn Asn Tyr Lys Thr Thr Pro Pro Val
    370                 375                 380

Leu Asp Ser Asp Gly Ser Phe Phe Leu Tyr Ser Lys Leu Thr Val Asp
385                 390                 395                 400

Lys Ser Arg Trp Gln Gln Gly Asn Val Phe Ser Cys Ser Val Met His
                405                 410                 415

Glu Ala Leu His Asn His Tyr Thr Gln Lys Ser Leu Ser Leu Ser Pro
            420                 425                 430

Gly Lys Ser Gly Gly Leu Asn Asp Ile Phe Glu Ala Gln Lys Ile Glu
        435                 440                 445

Trp His Glu
    450

<210> SEQ ID NO 90
<211> LENGTH: 1613
<212> TYPE: DNA
<213> ORGANISM: Artificial Sequence
<220> FEATURE:
<223> OTHER INFORMATION: nucleotide sequence of library DP88-4

<400> SEQUENCE: 90
tgaaatacct attgcctacg gcagccgctg gattgttatt actcgcggcc cagccggcca      60
tggccgacat ccagatgacc cagtctcctt ccaccctgtc tgcatctgta ggagaccgtg     120
tcaccatcac ttgccgtgcc agtcagagta ttagtagctg gttggcctgg tatcagcaga     180
aaccagggaa agcccctaag ctcctgatct atgatgcctc cagtttggaa agtggggtcc     240
catcacgttt cagcggcagt ggatccggga cagaattcac tctcaccatc agcagcttgc     300
agcctgatga ttttgcaact tattactgcc aacagtataa tagttattct acgtttggcc     360
agggcaccaa agtcgagatc aagcgtacgg tggctcacc atctgtcttc atcttcccgc     420
catctgatga gcagttgaaa tctggaactg cctctgttgt gtgcctgctg aataacttct     480
```

```
atcccagaga ggccaaagta cagtggaagg tggataacgc cctccaatcg ggtaactccc    540
aggagagtgt cacagagcag gacagcaagg acagcaccta cagcctcagc agcaccctga    600
cgctgagcaa agcagactac gagaaacaca agtctacgc ctgcgaagtc acccatcagg    660
gcctgagctc gcccgtcaca aagagcttca cagggagaga gtgtggagcc gcagaacaaa    720
aactcatctc agaagaggat ctgaatggag ccgcagacta caaggacgac gacgacaagg    780
gtgccgcata taaggcgcg ccaattctat ttcaaggaga cagtcatatg aaatacctgc    840
tgccgaccgc tgctgctggt ctgctgctcc tcgctgccca gccggcgatg gcccaggtgc    900
aattggtgca gtctggggct gaggtgaaga agcctgggtc ctcggtgaag gtctcctgca    960
aggcctccgg aggcacattc agcagctacg ctataagctg ggtgcgacag gcccctggac   1020
aagggctcga gtggatggga gggatcatcc ctatctttgg tacagcaaac tacgcacaga   1080
agttccaggg cagggtcacc attactgcag acaaatccac gagcacagcc tacatggagc   1140
tgagcagcct gagatctgag gacaccgccg tgtattactg tgcgagacta tcccaggcg    1200
gttactatgt tatggatgcc tggggccaag ggaccaccgt gaccgtctcc tcagctagca   1260
ccaaaggccc atcggtcttc cccctggcac cctcctccaa gagcacctct ggggggcacag   1320
cggcctgggg ctgcctggtc aaggactact ccccgaacc ggtgacggtg tcgtggaact   1380
caggcgccct gaccagcggc gtgcacacct tcccggctgt cctacagtcc tcaggactct   1440
actccctcag cagcgtggtg accgtgccct ccagcagctt gggcacccag acctacatct   1500
gcaacgtgaa tcacaagccc agcaacacca agtggacaa gaaagttgag cccaaatctt   1560
gtgacgcggc cgcaagcact agtgcccatc accatcacca tcacgccgcg gca           1613

<210> SEQ ID NO 91
<211> LENGTH: 723
<212> TYPE: DNA
<213> ORGANISM: Artificial Sequence
<220> FEATURE:
<223> OTHER INFORMATION: nucleotide sequence of Fab light chain Vk1_5

<400> SEQUENCE: 91
gacatccaga tgacccagtc tccttccacc ctgtctgcat ctgtaggaga ccgtgtcacc     60
atcacttgcc gtgccagtca gagtattagt agctggttgg cctggtatca gcagaaacca    120
gggaaagccc ctaagctcct gatctatgat gcctccagtt tggaaagtgg ggtcccatca    180
cgtttcagcg gcagtggatc cgggacagaa ttcactctca ccatcagcag cttgcagcct    240
gatgattttg caacttatta ctgccaacag tataatagtt attctacgtt tggccagggc    300
accaaagtcg agatcaagcg tacggtggct gcaccatctg tcttcatctt cccgccatct    360
gatgagcagt tgaaatctgg aactgcctct gttgtgtgcc tgctgaataa cttctatccc    420
agagaggcca agtacagtg gaaggtggat aacgccctcc aatcgggtaa ctcccaggag    480
agtgtcacag agcaggacag caaggacagc acctacagcc tcagcagcac cctgacgctg    540
agcaaagcag actacgagaa acacaaagtc tacgcctgcg aagtcaccca tcagggcctg    600
agctcgcccg tcacaaagag cttcaacagg ggagagtgtg agccgcagaa caaaaaactc    660
atctcagaag aggatctgaa tggagccgca gactacaagg acgacgacga caagggtgcc    720
gca                                                                  723

<210> SEQ ID NO 92
<211> LENGTH: 241
<212> TYPE: PRT
<213> ORGANISM: Artificial Sequence
```

<220> FEATURE:
<223> OTHER INFORMATION: Fab light chain Vk1_5

<400> SEQUENCE: 92

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Asn Ser Tyr Ser Thr
                85                  90                  95

Phe Gly Gln Gly Thr Lys Val Glu Ile Lys Arg Thr Val Ala Ala Pro
            100                 105                 110

Ser Val Phe Ile Phe Pro Pro Ser Asp Glu Gln Leu Lys Ser Gly Thr
        115                 120                 125

Ala Ser Val Val Cys Leu Leu Asn Asn Phe Tyr Pro Arg Glu Ala Lys
    130                 135                 140

Val Gln Trp Lys Val Asp Asn Ala Leu Gln Ser Gly Asn Ser Gln Glu
145                 150                 155                 160

Ser Val Thr Glu Gln Asp Ser Lys Asp Ser Thr Tyr Ser Leu Ser Ser
                165                 170                 175

Thr Leu Thr Leu Ser Lys Ala Asp Tyr Glu Lys His Lys Val Tyr Ala
            180                 185                 190

Cys Glu Val Thr His Gln Gly Leu Ser Ser Pro Val Thr Lys Ser Phe
        195                 200                 205

Asn Arg Gly Glu Cys Gly Ala Ala Glu Gln Lys Leu Ile Ser Glu Glu
    210                 215                 220

Asp Leu Asn Gly Ala Ala Asp Tyr Lys Asp Asp Asp Lys Gly Ala
225                 230                 235                 240

Ala

<210> SEQ ID NO 93
<211> LENGTH: 720
<212> TYPE: DNA
<213> ORGANISM: Artificial Sequence
<220> FEATURE:
<223> OTHER INFORMATION: nucleotide sequence of Fab heavy chain VH1_69

<400> SEQUENCE: 93
caggtgcaat tggtgcagtc tggggctgag gtgaagaagc ctgggtcctc ggtgaaggtc     60
tcctgcaagg cctccggagg cacattcagc agctacgcta taagctgggt gcgacaggcc    120
cctggacaag ggctcgagtg gatgggaggg atcatcccta tctttggtac agcaaactac    180
gcacagaagt tccagggcag ggtcaccatt actgcagaca aatccacgag cacagcctac    240
atggagctga gcagcctgag atctgaggac accgccgtgt attactgtgc gagactatcc    300
ccaggcggtt actatgttat ggatgcctgg ggccaaggga ccaccgtgac cgtctcctca    360
gctagcacca aggcccatc ggtcttcccc ctggcaccct cctccaagag cacctctggg    420
ggcacagcgg ccctgggctg cctggtcaag gactacttcc ccgaaccggt gacggtgtcg    480
tggaactcag gcgccctgac cagcggcgtg cacaccttcc cggctgtcct acagtcctca    540

```
ggactctact ccctcagcag cgtggtgacc gtgccctcca gcagcttggg cacccagacc    600
tacatctgca acgtgaatca caagcccagc aacaccaaag tggacaagaa agttgagccc    660
aaatcttgtg acgcggccgc aagcactagt gcccatcacc atcaccatca cgccgcggca    720
```

<210> SEQ ID NO 94
<211> LENGTH: 240
<212> TYPE: PRT
<213> ORGANISM: Artificial Sequence
<220> FEATURE:
<223> OTHER INFORMATION: Fab heavy chain VH1_69

<400> SEQUENCE: 94

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Leu Ser Pro Gly Gly Tyr Tyr Val Met Asp Ala Trp Gly Gln
            100                 105                 110

Gly Thr Thr Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Ala Ala Ala Ser Thr Ser Ala His His His His His Ala Ala Ala
225                 230                 235                 240
```

<210> SEQ ID NO 95
<211> LENGTH: 26
<212> TYPE: DNA
<213> ORGANISM: Artificial Sequence
<220> FEATURE:
<223> OTHER INFORMATION: LMB3 Primer

<400> SEQUENCE: 95

```
caggaaacag ctatgaccat gattac                                          26
```

<210> SEQ ID NO 96
<211> LENGTH: 71
<212> TYPE: DNA
<213> ORGANISM: Artificial Sequence
<220> FEATURE:
<223> OTHER INFORMATION: Vk1_5_L3r_S Primer

<400> SEQUENCE: 96
ctcgactttg gtgccctggc caaacgtsba atacgaatta tactgttggc agtaataagt    60
tgcaaaatca t    71

<210> SEQ ID NO 97
<211> LENGTH: 74
<212> TYPE: DNA
<213> ORGANISM: Artificial Sequence
<220> FEATURE:
<223> OTHER INFORMATION: Vk1_5_L3r_SY Primer

<400> SEQUENCE: 97
ctcgactttg gtgccctggc caaacgtmhr sgratacgaa ttatactgtt ggcagtaata    60
agttgcaaaa tcat    74

<210> SEQ ID NO 98
<211> LENGTH: 77
<212> TYPE: DNA
<213> ORGANISM: Artificial Sequence
<220> FEATURE:
<223> OTHER INFORMATION: Vk1_5_L3r_SPY

<400> SEQUENCE: 98
ctcgactttg gtgccctggc caaacgtmhh msssgratac gaattatact gttggcagta    60
ataagttgca aaatcat    77

<210> SEQ ID NO 99
<211> LENGTH: 27
<212> TYPE: DNA
<213> ORGANISM: Artificial Sequence
<220> FEATURE:
<223> OTHER INFORMATION: RJH31 Primer

<400> SEQUENCE: 99
acgtttggcc agggcaccaa agtcgag    27

<210> SEQ ID NO 100
<211> LENGTH: 28
<212> TYPE: DNA
<213> ORGANISM: Artificial Sequence
<220> FEATURE:
<223> OTHER INFORMATION: RJH32 Primer

<400> SEQUENCE: 100
tctcgcacag taatacacgg cggtgtcc    28

<210> SEQ ID NO 101
<211> LENGTH: 64
<212> TYPE: DNA
<213> ORGANISM: Artificial Sequence
<220> FEATURE:
<223> OTHER INFORMATION: DP88-v4-4

<400> SEQUENCE: 101
ggacaccgcc gtgtattact gtgcgagaga ctactggggc caagggacca ccgtgaccgt    60
ctcc    64

<210> SEQ ID NO 102
<211> LENGTH: 64
<212> TYPE: DNA

```
<213> ORGANISM: Artificial Sequence
<220> FEATURE:
<223> OTHER INFORMATION: DP88-v4-6

<400> SEQUENCE: 102
ggacaccgcc gtgtattact gtgcgagaga ctactggggc caagggacca ccgtgaccgt    60
ctcc                                                                  64

<210> SEQ ID NO 103
<211> LENGTH: 64
<212> TYPE: DNA
<213> ORGANISM: Artificial Sequence
<220> FEATURE:
<223> OTHER INFORMATION: DP88-v4-8

<400> SEQUENCE: 103
ggacaccgcc gtgtattact gtgcgagaga ctactggggc caagggacca ccgtgaccgt    60
ctcc                                                                  64

<210> SEQ ID NO 104
<211> LENGTH: 30
<212> TYPE: DNA
<213> ORGANISM: Artificial Sequence
<220> FEATURE:
<223> OTHER INFORMATION: fdseqlong Primer

<400> SEQUENCE: 104
gacgttagta aatgaatttt ctgtatgagg                                      30

<210> SEQ ID NO 105
<211> LENGTH: 1596
<212> TYPE: DNA
<213> ORGANISM: Artificial Sequence
<220> FEATURE:
<223> OTHER INFORMATION: (Vk3_20/VH3_23) template

<400> SEQUENCE: 105
atgaaatacc tattgcctac ggcagccgct ggattgttat tactcgcggc ccagccggcc    60
atggccgaaa tcgtgttaac gcagtctcca ggcaccctgt ctttgtctcc aggggaaaga   120
gccaccctct cttgcagggc cagtcagagt gttagcagca gctacttagc ctggtaccag   180
cagaaacctg gccaggctcc caggctcctc atctatggag catccagcag ggccactggc   240
atcccagaca ggttcagtgg cagtggatcc gggacagact tcactctcac catcagcaga   300
ctggagcctg aagattttgc agtgtattac tgtcagcagt atggtagctc accgctgacg   360
ttcggccagg ggaccaaagt ggaaatcaaa cgtacggtgg ctgcaccatc tgtcttcatc   420
ttcccgccat ctgatgagca gttgaaatct ggaactgcct ctgttgtgtg cctgctgaat   480
aacttctatc ccagagaggc caaagtacag tggaaggtgg ataacgccct ccaatcgggt   540
aactcccagg agagtgtcac agagcaggac agcaaggaca gcacctacag cctcagcagc   600
accctgacgc tgagcaaagc agactacgag aaacacaaag tctacgcctg cgaagtcacc   660
catcagggcc tgagctcgcc cgtcacaaag agcttcaaca ggggagagtg tggagccgca   720
catcaccatc accatcacgg agccgcagac tacaaggacg acgacgacaa gggtgccgca   780
taataaggcg cgccaattct atttcaagga cagtcata tgaaatacct gctgccgacc   840
gctgctgctg gtctgctgct cctcgctgcc cagccggcga tggccgaggt gcaattgctg   900
gagtctgggg gaggcttggt acagcctggg gggtccctga ctctcctgtg cagcctcc    960 ggattcacct ttagcagtta tgccatgagc tgggtccgcc aggctccagg aaggggctg   1020
```

```
gagtgggtct cagctattag tggtagtggt ggtagcacat actacgcaga ctccgtgaag    1080
ggccggttca ccatctccag agacaattcc aagaacacgc tgtatctgca gatgaacagc    1140
ctgagagccg aggacacggc cgtatattac tgtgcgaaac cgtttccgta ttttgactac    1200
tggggccaag gaaccctggt caccgtctcg agtgctagca ccaaaggccc atcggtcttc    1260
cccctggcac cctcctccaa gagcacctct ggggggcacag cggccctggg ctgcctggtc    1320
aaggactact ccccgaacc ggtgacggtg tcgtggaact caggcgccct gaccagcggc    1380
gtgcacacct tcccggctgt cctacagtcc tcaggactct actccctcag cagcgtggtg    1440
accgtgccct ccagcagctt gggcacccag acctacatct gcaacgtgaa tcacaagccc    1500
agcaacacca agtggacaa gaaagttgag cccaaatctt gtgacgcggc cgcagaacaa    1560
aaactcatct cagaagagga tctgaatgcc gcggca                              1596
```

<210> SEQ ID NO 106
<211> LENGTH: 714
<212> TYPE: DNA
<213> ORGANISM: Artificial Sequence
<220> FEATURE:
<223> OTHER INFORMATION: Fab light chain Vk3_20

<400> SEQUENCE: 106

```
gaaatcgtgt taacgcagtc tccaggcacc ctgtctttgt ctccagggga aagagccacc     60
ctctcttgca gggccagtca gagtgttagc agcagctact tagcctggta ccagcagaaa    120
cctggccagg ctcccaggct cctcatctat ggagcatcca gcagggccac tggcatccca    180
gacaggttca gtggcagtgg atccgggaca gacttcactc tcaccatcag cagactggag    240
cctgaagatt ttgcagtgta ttactgtcag cagtatggta gctcaccgct gacgttcggc    300
caggggacca agtggaaat caaacgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgtggagc cgcacatcac    660
catcaccatc acgagccgc agactacaag gacgacgacg acaagggtgc cgca           714
```

<210> SEQ ID NO 107
<211> LENGTH: 238
<212> TYPE: PRT
<213> ORGANISM: Artificial Sequence
<220> FEATURE:
<223> OTHER INFORMATION: Fab light chain Vk3_20

<400> SEQUENCE: 107

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80
```

```
Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys Gly Ala Ala His His His His His His
    210                 215                 220

Gly Ala Ala Asp Tyr Lys Asp Asp Asp Lys Gly Ala Ala
225                 230                 235
```

<210> SEQ ID NO 108
<211> LENGTH: 711
<212> TYPE: DNA
<213> ORGANISM: Artificial Sequence
<220> FEATURE:
<223> OTHER INFORMATION: Fab heavy chain VH3_23

<400> SEQUENCE: 108

```
gaggtgcaat tgctggagtc tgggggaggc ttggtacagc ctggggggtc cctgagactc        60
tcctgtgcag cctccggatt cacctttagc agttatgcca tgagctgggt ccgccaggct       120
ccagggaagg ggctggagtg ggtctcagct attagtggta gtggtggtag cacatactac       180
gcagactccg tgaagggccg gttcaccatc tccagagaca attccaagaa cacgctgtat       240
ctgcagatga acagcctgag agccgaggac acggccgtat attactgtgc gaaaccgttt       300
ccgtattttg actactgggg ccaaggaacc ctggtcaccg tctcgagtgc tagcaccaaa       360
ggcccatcgg tcttccccct ggcaccctcc tccaagagca cctctggggg cacagcggcc       420
ctgggctgcc tggtcaagga ctacttcccc gaaccggtga cggtgtcgtg gaactcaggc       480
gccctgacca gcggcgtgca caccttcccg gctgtcctac agtcctcagg actctactcc       540
ctcagcagcg tggtgaccgt gccctccagc agcttgggca cccagaccta catctgcaac       600
gtgaatcaca agcccagcaa caccaaagtg gacaagaaag ttgagcccaa atcttgtgac       660
gcggccgcag aacaaaaact catctcagaa gaggatctga atgccgcggc a                711
```

<210> SEQ ID NO 109
<211> LENGTH: 237
<212> TYPE: PRT
<213> ORGANISM: Artificial Sequence
<220> FEATURE:
<223> OTHER INFORMATION: Fab heavy chain VH3_23 (DP47)

<400> SEQUENCE: 109

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
                20                  25                  30
Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Pro Phe Pro Tyr Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Ala Ala Ala Glu
    210                 215                 220

Gln Lys Leu Ile Ser Glu Glu Asp Leu Asn Ala Ala Ala
225                 230                 235
```

```
<210> SEQ ID NO 110
<211> LENGTH: 25
<212> TYPE: DNA
<213> ORGANISM: Artificial Sequence
<220> FEATURE:
<223> OTHER INFORMATION: MS64 Primer

<400> SEQUENCE: 110
acgttcggcc aggggaccaa agtgg                                          25

<210> SEQ ID NO 111
<211> LENGTH: 25
<212> TYPE: DNA
<213> ORGANISM: Artificial Sequence
<220> FEATURE:
<223> OTHER INFORMATION: DP47CDR3_ba Primer

<400> SEQUENCE: 111
cgcacagtaa tatacggccg tgtcc                                          25

<210> SEQ ID NO 112
<211> LENGTH: 64
<212> TYPE: DNA
<213> ORGANISM: Artificial Sequence
<220> FEATURE:
<223> OTHER INFORMATION: DP47-v4-4

<400> SEQUENCE: 112
cgaggacacg gccgtatatt actgtgcgga ctactggggc caaggaaccc tggtcaccgt    60
ctcg                                                                64
```

<210> SEQ ID NO 113
<211> LENGTH: 64
<212> TYPE: DNA
<213> ORGANISM: Artificial Sequence
<220> FEATURE:
<223> OTHER INFORMATION: DP47-v4-6

<400> SEQUENCE: 113

```
cgaggacacg gccgtatatt actgtgcgga ctactggggc caaggaaccc tggtcaccgt    60
ctcg                                                                 64
```

<210> SEQ ID NO 114
<211> LENGTH: 64
<212> TYPE: DNA
<213> ORGANISM: Artificial Sequence
<220> FEATURE:
<223> OTHER INFORMATION: DP47-v4-8

<400> SEQUENCE: 114

```
cgaggacacg gccgtatatt actgtgcgga ctactggggc caaggaaccc tggtcaccgt    60
ctcg                                                                 64
```

<210> SEQ ID NO 115
<211> LENGTH: 30
<212> TYPE: DNA
<213> ORGANISM: Artificial Sequence
<220> FEATURE:
<223> OTHER INFORMATION: fdseqlong

<400> SEQUENCE: 115

```
gacgttagta aatgaatttt ctgtatgagg                                     30
```

<210> SEQ ID NO 116
<211> LENGTH: 1605
<212> TYPE: DNA
<213> ORGANISM: Artificial Sequence
<220> FEATURE:
<223> OTHER INFORMATION: Vl3_19/VH3_23 library template

<400> SEQUENCE: 116

```
atgaaatacc tattgcctac ggcagccgct ggattgttat tactcgcggc ccagccggcc    60
atggcctcgt ctgagctgac tcaggaccct gctgtgtctg tggccttggg acagacagtc   120
aggatcacat gccaaggaga cagcctcaga agttattatg caagctggta ccagcagaag   180
ccaggacagg ccctgtact tgtcatctat ggtaaaaaca accggccctc agggatccca   240
gaccgattct ctggctccag ctcaggaaac acagcttcct tgaccatcac tggggctcag   300
gcggaagatg aggctgacta ttactgtaac tcccgtgata gtagcggtaa tcatgtggta   360
ttcggcggag ggaccaagct gaccgtccta ggacaaccca aggctgcccc cagcgtgacc   420
ctgttccccc ccagcagcga ggaattgcag ccaacaaggg ccaccctggt ctgcctgatc   480
agcgacttct acccaggcgc cgtgaccgtg gcctggaagg ccgacagcag ccccgtgaag   540
gccggcgtgg agaccaccac ccccagcaag cagagcaaca caagtacgc cgccagcagc   600 tacctgagcc tgaccccga gcagtggaag agccacaggt cctacagctg ccaggtgacc   660
cacgagggca gcaccgtgga aaaaccgtg gcccccaccg agtgcagcgg agccgcagaa   720
caaaaactca tctcagaaga ggatctgaat ggagccgcag actacaagga cgacgacgac   780
aagggtgccg cataataagg cgcgccaatt ctatttcaag agacagtca tatgaaatac   840 ctgctgccga ccgctgctgc tggtctgctg ctcctcgctg cccagccggc gatggccgag   900
```

```
gtgcaattgc tggagtctgg gggaggcttg gtacagcctg gggggtccct gagactctcc    960
tgtgcagcct ccggattcac ctttagcagt tatgccatga gctgggtccg ccaggctcca   1020
gggaaggggc tggagtgggt ctcagctatt agtggtagtg gtggtagcac atactacgca   1080
gactccgtga agggccggtt caccatctcc agagacaatt ccaagaacac gctgtatctg   1140
cagatgaaca gcctgagagc cgaggacacg gccgtatatt actgtgcgaa accgtttccg   1200
tattttgact actggggcca aggaaccctg gtcaccgtct cgagtgctag caccaaaggc   1260
ccatcggtct tccccctggc accctcctcc aagagcacct ctgggggcac agcggccctg   1320
ggctgcctgg tcaaggacta cttccccgaa ccggtgacgg tgtcgtggaa ctcaggcgcc   1380
ctgaccagcg gcgtgcacac cttcccggct gtcctacagt cctcaggact ctactccctc   1440
agcagcgtgg tgaccgtgcc ctccagcagc ttgggcaccc agacctacat ctgcaacgtg   1500
aatcacaagc ccagcaacac caaagtggac aagaaagttg agcccaaatc ttgtgacgcg   1560
gccgcaagca ctagtgccca tcaccatcac catcacgccg cggca                  1605

<210> SEQ ID NO 117
<211> LENGTH: 726
<212> TYPE: DNA
<213> ORGANISM: Artificial Sequence
<220> FEATURE:
<223> OTHER INFORMATION: Fab light chain V13_19

<400> SEQUENCE: 117
tcgtctgagc tgactcagga ccctgctgtg tctgtggcct tgggacagac agtcaggatc     60
acatgccaag gagacagcct cagaagttat tatgcaagct ggtaccagca gaagccagga    120
caggcccctg tacttgtcat ctatggtaaa aacaaccggc cctcagggat cccagaccga    180
ttctctggct ccagctcagg aaacacagct tccttgacca tcactggggc tcaggcggaa    240
gatgaggctg actattactg taactcccgt gatagtagcg gtaatcatgt ggtattcggc    300
ggagggacca agctgaccgt cctaggacaa cccaaggctg cccccagcgt gaccctgttc    360
ccccccagca gcgaggaatt gcaggccaac aaggccaccc tggtctgcct gatcagcgac    420
ttctacccag gcgccgtgac cgtggcctgg aaggccgaca gcagcccgt gaaggccggc    480 gtggagacca ccaccccag caagcagagc aacaacaagt acgccgccag cagctacctg    540
agcctgaccc ccgagcagtg gaagagccac aggtcctaca gctgccaggt gacccacgag    600
ggcagcaccg tggagaaaac cgtggccccc accgagtgca cggagccgc agaacaaaaa    660 ctcatctcag aagaggatct gaatggagcc gcagactaca aggacgacga cgacaagggt    720
gccgca                                                              726

<210> SEQ ID NO 118
<211> LENGTH: 242
<212> TYPE: PRT
<213> ORGANISM: Artificial Sequence
<220> FEATURE:
<223> OTHER INFORMATION: Fab light chain V13_19

<400> SEQUENCE: 118

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45
```

```
Gly Lys Asn Asn Arg Pro Ser Gly Ile Pro Asp Arg Phe Ser Gly Ser
 50                  55                  60

Ser Ser Gly Asn Thr Ala Ser Leu Thr Ile Thr Gly Ala Gln Ala Glu
 65                  70                  75                  80

Asp Glu Ala Asp Tyr Tyr Cys Asn Ser Arg Asp Ser Ser Gly Asn His
                 85                  90                  95

Val Val Phe Gly Gly Gly Thr Lys Leu Thr Val Leu Gly Gln Pro Lys
            100                 105                 110

Ala Ala Pro Ser Val Thr Leu Phe Pro Pro Ser Ser Glu Glu Leu Gln
        115                 120                 125

Ala Asn Lys Ala Thr Leu Val Cys Leu Ile Ser Asp Phe Tyr Pro Gly
    130                 135                 140

Ala Val Thr Val Ala Trp Lys Ala Asp Ser Ser Pro Val Lys Ala Gly
145                 150                 155                 160

Val Glu Thr Thr Thr Pro Ser Lys Gln Ser Asn Asn Lys Tyr Ala Ala
                165                 170                 175

Ser Ser Tyr Leu Ser Leu Thr Pro Glu Gln Trp Lys Ser His Arg Ser
            180                 185                 190

Tyr Ser Cys Gln Val Thr His Glu Gly Ser Thr Val Glu Lys Thr Val
        195                 200                 205

Ala Pro Thr Glu Cys Ser Gly Ala Ala Glu Gln Lys Leu Ile Ser Glu
    210                 215                 220

Glu Asp Leu Asn Gly Ala Ala Asp Tyr Lys Asp Asp Asp Asp Lys Gly
225                 230                 235                 240

Ala Ala

<210> SEQ ID NO 119
<211> LENGTH: 26
<212> TYPE: DNA
<213> ORGANISM: Artificial Sequence
<220> FEATURE:
<223> OTHER INFORMATION: LMB3 lambda-DP47 library

<400> SEQUENCE: 119
caggaaacag ctatgaccat gattac                                       26

<210> SEQ ID NO 120
<211> LENGTH: 85
<212> TYPE: DNA
<213> ORGANISM: Artificial Sequence
<220> FEATURE:
<223> OTHER INFORMATION: Vl_3_19_L3r_V lambda-DP47 library

<400> SEQUENCE: 120
ggacggtcag cttggtccct ccgccgaata cvhvattacc gctactatca cgggagttac    60
agtaatagtc agcctcatct tccgc                                         85

<210> SEQ ID NO 121
<211> LENGTH: 88
<212> TYPE: DNA
<213> ORGANISM: Artificial Sequence
<220> FEATURE:
<223> OTHER INFORMATION: Vl_3_19_L3r_HV lambda-DP47

<400> SEQUENCE: 121
ggacggtcag cttggtccct ccgccgaata ccmmatgatt accgctacta tcacgggagt    60
tacagtaata gtcagcctca tcttccgc                                      88
```

<210> SEQ ID NO 122
<211> LENGTH: 91
<212> TYPE: DNA
<213> ORGANISM: Artificial Sequence
<220> FEATURE:
<223> OTHER INFORMATION: Vl_3_19_L3r_HLV lambda-DP47

<400> SEQUENCE: 122

```
ggacggtcag cttggtccct ccgccgaata crhmvwgatg attaccgcta ctatcacggg      60
agttacagta atagtcagcc tcatcttccg c                                     91
```

<210> SEQ ID NO 123
<211> LENGTH: 28
<212> TYPE: DNA
<213> ORGANISM: Artificial Sequence
<220> FEATURE:
<223> OTHER INFORMATION: RJH80 lambda-DP47

<400> SEQUENCE: 123

```
ttcggcggag ggaccaagct gaccgtcc                                         28
```

<210> SEQ ID NO 124
<211> LENGTH: 28
<212> TYPE: DNA
<213> ORGANISM: Artificial Sequence
<220> FEATURE:
<223> OTHER INFORMATION: MS63

<400> SEQUENCE: 124

```
tttcgcacag taatatacgg ccgtgtcc                                         28
```

<210> SEQ ID NO 125
<211> LENGTH: 318
<212> TYPE: DNA
<213> ORGANISM: Artificial Sequence
<220> FEATURE:
<223> OTHER INFORMATION: DNA (8H9 ) VL

<400> SEQUENCE: 125

```
tcgtctgagc tgactcagga ccctgctgtg tctgtggcct tgggacagac agtcaggatc      60
acatgccaag gagacagcct cagaagttat tatgcaagct ggtaccagca gaagccagga     120
caggcccctg tacttgtcat ctatggtaaa acaaccggc cctcaggat cccagaccga      180 ttctctggct ccagctcagg aaacacagct tccttgacca tcactggggc tcaggcggaa     240
gatgaggctg actattactg taactcccgt gttatgcctc ataatcgcgt attcggcgga     300
gggaccaagc tgaccgtc                                                   318
```

<210> SEQ ID NO 126
<211> LENGTH: 360
<212> TYPE: DNA
<213> ORGANISM: Artificial Sequence
<220> FEATURE:
<223> OTHER INFORMATION: DNA (8H9) VH

<400> SEQUENCE: 126

```
gaggtgcaat tgttggagtc tgggggaggc ttggtacagc ctgggggtc cctgagactc       60 tcctgtgcag cctccggatt cacctttagc agttatgcca tgagctgggt ccgccaggct     120
ccagggaagg ggctggagtg ggtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gcgtgttttc     300
```
taccgtggtg gtgtttctat ggactactgg ggccaaggaa ccctggtcac cgtctcgagt    360

<210> SEQ ID NO 127
<211> LENGTH: 321
<212> TYPE: DNA
<213> ORGANISM: Artificial Sequence
<220> FEATURE:
<223> OTHER INFORMATION: DNA (49B4) VL

<400> SEQUENCE: 127
gacatccaga tgacccagtc tccttccacc ctgtctgcat ctgtaggaga ccgtgtcacc     60
atcacttgcc gtgccagtca gagtattagt agctggttgg cctggtatca gcagaaacca    120
gggaaagccc ctaagctcct gatctatgat gcctccagtt tggaaagtgg ggtcccatca    180
cgtttcagcg gcagtggatc cgggacagaa ttcactctca ccatcagcag cttgcagcct    240
gatgattttg caacttatta ctgccaacag tatagttcgc agccgtatac gtttggccag    300
ggcaccaaag tcgagatcaa g                                              321

<210> SEQ ID NO 128
<211> LENGTH: 354
<212> TYPE: DNA
<213> ORGANISM: Artificial Sequence
<220> FEATURE:
<223> OTHER INFORMATION: DNA (49B4) VH

<400> SEQUENCE: 128
caggtgcaat tggtgcagtc tggggctgag gtgaagaagc ctgggtcctc ggtgaaggtc     60
tcctgcaagg cctccggagg cacattcagc agctacgcta taagctgggt gcgacaggcc    120
cctggacaag gctcgagtg gatgggaggg atcatcccta tctttggtac agcaaactac    180
gcacagaagt tccagggcag ggtcaccatt actgcagaca atccacgag cacagcctac    240 atggagctga gcagcctgag atctgaggac accgccgtgt attactgtgc gagagaatac    300
taccgtggtc cgtacgacta ctggggccaa gggaccaccg tgaccgtctc ctca          354

<210> SEQ ID NO 129
<211> LENGTH: 324
<212> TYPE: DNA
<213> ORGANISM: Artificial Sequence
<220> FEATURE:
<223> OTHER INFORMATION: DNA (1G4) VL

<400> SEQUENCE: 129
gacatccaga tgacccagtc tccttccacc ctgtctgcat ctgtaggaga ccgtgtcacc     60
atcacttgcc gtgccagtca gagtattagt agctggttgg cctggtatca gcagaaacca    120
gggaaagccc ctaagctcct gatctatgat gcctccagtt tggaaagtgg ggtcccatca    180
cgtttcagcg gcagtggatc cgggacagaa ttcactctca ccatcagcag cttgcagcct    240
gatgattttg caacttatta ctgccaacag tatatttcgt attccatgtt gacgtttggc    300
cagggcacca agtcgagat caag                                            324

<210> SEQ ID NO 130
<211> LENGTH: 348
<212> TYPE: DNA
<213> ORGANISM: Artificial Sequence
<220> FEATURE:
<223> OTHER INFORMATION: DNA (1G4) VH

<400> SEQUENCE: 130

| | |
|---|---|
| caggtgcaat tggtgcagtc tggggctgag gtgaagaagc ctgggtcctc ggtgaaggtc | 60 |
| tcctgcaagg cctccggagg cacattcagc agctacgcta taagctgggt gcgacaggcc | 120 |
| cctggacaag ggctcgagtg gatgggaggg atcatcccta tctttggtac agcaaactac | 180 |
| gcacagaagt tccagggcag ggtcaccatt actgcagaca atccacgag cacagcctac | 240 |
| atggagctga gcagcctgag atctgaggac accgccgtgt attactgtgc gagagaatac | 300 |
| ggttctatgg actactgggg ccaagggacc accgtgaccg tctcctca | 348 |

<210> SEQ ID NO 131
<211> LENGTH: 321
<212> TYPE: DNA
<213> ORGANISM: Artificial Sequence
<220> FEATURE:
<223> OTHER INFORMATION: DNA (20B7) VL

<400> SEQUENCE: 131

| | |
|---|---|
| gacatccaga tgacccagtc tccttccacc ctgtctgcat ctgtaggaga ccgtgtcacc | 60 |
| atcacttgcc gtgccagtca gagtattagt agctggttgg cctggtatca gcagaaacca | 120 |
| gggaaagccc ctaagctcct gatctatgat gcctccagtt tggaaagtgg ggtcccatca | 180 |
| cgtttcagcg gcagtggatc cgggacagaa ttcactctca ccatcagcag cttgcagcct | 240 |
| gatgattttg caacttatta ctgccaacag tatcaggctt tttcgcttac gtttggccag | 300 |
| ggcaccaaag tcgagatcaa g | 321 |

<210> SEQ ID NO 132
<211> LENGTH: 366
<212> TYPE: DNA
<213> ORGANISM: Artificial Sequence
<220> FEATURE:
<223> OTHER INFORMATION: DNA (20B7) VH

<400> SEQUENCE: 132

| | |
|---|---|
| caggtgcaat tggtgcagtc tggggctgag gtgaagaagc ctgggtcctc ggtgaaggtc | 60 |
| tcctgcaagg cctccggagg cacattcagc agctacgcta taagctgggt gcgacaggcc | 120 |
| cctggacaag ggctcgagtg gatgggaggg atcatcccta tctttggtac agcaaactac | 180 |
| gcacagaagt tccagggcag ggtcaccatt actgcagaca atccacgag cacagcctac | 240 |
| atggagctga gcagcctgag atctgaggac accgccgtgt attactgtgc gagagttaac | 300 |
| tacccgtact cttactgggg tgacttcgac tactggggcc aagggaccac cgtgaccgtc | 360 |
| tcctca | 366 |

<210> SEQ ID NO 133
<211> LENGTH: 324
<212> TYPE: DNA
<213> ORGANISM: Artificial Sequence
<220> FEATURE:
<223> OTHER INFORMATION: DNA (CLC-563) VL

<400> SEQUENCE: 133

| | |
|---|---|
| gagatcgtgc tgacccagag ccccggcaca ctctccctgt ctcctgggga agggccacc | 60 |
| ctttcatgca gagccagcca gtccgtctct agtagctacc tggcatggta tcagcagaag | 120 |
| ccaggacaag ccccccgcct cctgatttac ggcgcttcct ctcgggcaac tggtatccct | 180 |
| gacaggttct cagggagcgg aagcggaaca gattttacct tgactatttc tagactggag | 240 |
| ccagaggact tcgccgtgta ttactgtcag cagtacggta gtagcccct cacctttggc | 300 |
| caggggacaa aagtcgaaat caag | 324 |

<210> SEQ ID NO 134
<211> LENGTH: 348
<212> TYPE: DNA
<213> ORGANISM: Artificial Sequence
<220> FEATURE:
<223> OTHER INFORMATION: DNA (CLC-563) VH

<400> SEQUENCE: 134

```
gaggtgcaat tgttggagtc tggggggaggc ttggtacagc ctggggggtc cctgagactc    60
tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gcttgacgtt   300
ggtgctttcg actactgggg ccaaggagcc ctggtcaccg tctcgagt              348
```

<210> SEQ ID NO 135
<211> LENGTH: 324
<212> TYPE: DNA
<213> ORGANISM: Artificial Sequence
<220> FEATURE:
<223> OTHER INFORMATION: DNA (CLC-564) VL

<400> SEQUENCE: 135

```
gagatcgtgc tgacccagag ccccggcaca ctctccctgt ctcctgggga aagggccacc    60
ctttcatgca gagccagcca gtccgtctct agtagctacc tggcatggta tcagcagaag   120
ccaggacaag ccccccgcct cctgatttac ggcgcttcct ctcgggcaac tggtatccct   180
gacaggttct cagggagcgg aagcggaaca gatttaccct tgactatttc tagactggag   240
ccagaggact cgccgtgta ttactgtcag cagtacggta gtagcccct cacctttggc   300
caggggacaa aagtcgaaat caag                                          324
```

<210> SEQ ID NO 136
<211> LENGTH: 348
<212> TYPE: DNA
<213> ORGANISM: Artificial Sequence
<220> FEATURE:
<223> OTHER INFORMATION: DNA (CLC-564) VH

<400> SEQUENCE: 136

```
gaggtgcaat tgttggagtc tggggggaggc ttggtacagc ctggggggtc cctgagactc    60
tcctgtgcag cctccggatt cacctttagc agttatgcca tgagctgggt ccgccaggct   120
ccagggaagg ggctggagtg ggtctcagct attagtggta gtggtggtag cacatactac   180
gcagactccg tgaagggccg gttcaccatc tccagagaca attccaagaa cacgctgtat   240
ctgcagatga acagcctgag agccgaggac acggccgtat attactgtgc gttcgacgtt   300
ggtccgttcg actactgggg ccaaggaacc ctggtcaccg tctcgagt              348
```

<210> SEQ ID NO 137
<211> LENGTH: 318
<212> TYPE: DNA
<213> ORGANISM: Artificial Sequence
<220> FEATURE:
<223> OTHER INFORMATION: DNA (17A9) VL

<400> SEQUENCE: 137

```
tcgtctgagc tgactcagga ccctgctgtg tctgtggcct tgggacagac agtcaggatc    60
```

| acatgccaag gagacagcct cagaagttat tatgcaagct ggtaccagca gaagccagga | 120 |
| caggcccctg tacttgtcat ctatggtaaa acaaccggc cctcaggat cccagaccga | 180 |
| ttctctggct ccagctcagg aaacacagct tccttgacca tcactggggc tcaggcggaa | 240 |
| gatgaggctg actattactg taactcccgt gttatgcctc ataatcgcgt attcggcgga | 300 |
| gggaccaagc tgaccgtc | 318 |

<210> SEQ ID NO 138
<211> LENGTH: 360
<212> TYPE: DNA
<213> ORGANISM: Artificial Sequence
<220> FEATURE:
<223> OTHER INFORMATION: DNA (17A9) VH

<400> SEQUENCE: 138

| gaggtgcaat tgttggagtc tgggggaggc ttggtacagc ctgggggtc cctgagactc | 60 |
| tcctgtgcag cctccggatt cacctttagc agttatgcca tgagctgggt ccgccaggct | 120 |
| ccagggaagg ggctggagtg gtctcagct attagtggta gtggtggtag cacatactac | 180 |
| gcagactccg tgaagggccg gttcaccatc tccagagaca attccaagaa cacgctgtat | 240 |
| ctgcagatga acagcctgag agccgaggac acggccgtat attactgtgc gcgtgttttc | 300 |
| taccgtggtg gtgttttctat ggactactgg ggccaaggaa ccctggtcac cgtctcgagt | 360 |

<210> SEQ ID NO 139
<211> LENGTH: 645
<212> TYPE: DNA
<213> ORGANISM: Artificial Sequence
<220> FEATURE:
<223> OTHER INFORMATION: DNA 8H9 P329GLALA IgG1 light chain

<400> SEQUENCE: 139

| gacatccaga tgacccagtc tccttccacc ctgtctgcat ctgtaggaga ccgtgtcacc | 60 |
| atcacttgcc gtgccagtca gagtattagt agctggttgg cctggtatca gcagaaacca | 120 |
| gggaaagccc ctaagctcct gatctatgat gcctccagtt tggaaagtgg ggtcccatca | 180 |
| cgtttcagcg gcagtggatc cgggacagaa ttcactctca ccatcagcag cttgcagcct | 240 |
| gatgattttg caacttatta ctgccaacag tatttgacgt attcgcggtt tacgtttggc | 300 |
| cagggcacca agtcgagat caagcgtacg gtggctgcac catctgtctt catcttcccg | 360 |
| ccatctgatg agcagttgaa atctggaact gcctctgttg tgtgcctgct gaataacttc | 420 |
| tatcccagag aggccaaagt acagtggaag gtggataacg ccctccaatc gggtaactcc | 480 |
| caggagagtg tcacagagca ggacagcaag gacagcacct acagcctcag cagcaccctg | 540 |
| acgctgagca agcagactac gagaaacac aaagtctacg cctgcgaagt cacccatcag | 600 |
| ggcctgagct cgcccgtcac aaagagcttc aacagggag agtgt | 645 |

<210> SEQ ID NO 140
<211> LENGTH: 1338
<212> TYPE: DNA
<213> ORGANISM: Artificial Sequence
<220> FEATURE:
<223> OTHER INFORMATION: DNA 8H9 P329GLALA IgG1 heavy chain

<400> SEQUENCE: 140

| caggtgcaat tggtgcagtc tggggctgag gtgaagaagc ctgggtcctc ggtgaaggtc | 60 |
| tcctgcaagg cctccggagg cacattcagc agctacgcta aagctgggt gcgacaggcc | 120 |
| cctggacaag ggctcgagtg gatgggaggg atcatcccta tctttggtac agcaaactac | 180 |

```
gcacagaagt tccagggcag ggtcaccatt actgcagaca atccacgag cacagcctac    240 atggagctga gcagcctgag atctgaggac accgccgtgt attactgtgc gagagaatac    300
ggttggatgg actactgggg ccaagggacc accgtgaccg tctcctcagc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg aactcaggc    480 gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagctg caggggggacc gtcagtcttc    720 ctcttcccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cggcgccccc atcgagaaaa ccatctccaa agccaaaggg    1020
cagccccgag aaccacaggt gtacaccctg cccccatccc gggatgagct gaccaagaac    1080
caggtcagcc tgacctgcct ggtcaaaggc ttctatccca gcgacatcgc cgtggagtgg    1140
gagagcaatg ggcagccgga gaacaactac aagaccacgc ctcccgtgct ggactccgac    1200
ggctccttct cctctacag caagctcacc gtggacaaga gcaggtggca gcaggggaac    1260
gtcttctcat gctccgtgat gcatgaggct ctgcacaacc actacacgca gaagagcctc    1320
tccctgtctc cgggtaaa                                                  1338
```

<210> SEQ ID NO 141
<211> LENGTH: 215
<212> TYPE: PRT
<213> ORGANISM: Artificial Sequence
<220> FEATURE:
<223> OTHER INFORMATION: 8H9 P329GLALA IgG1 light chain

<400> SEQUENCE: 141

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Leu Thr Tyr Ser Arg
                85                  90                  95

Phe Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
```

```
                145                 150                 155                 160
Gln Glu Ser Val Thr Glu Gln Asp Ser Lys Asp Ser Thr Tyr Ser Leu
                    165                 170                 175

Ser Ser Thr Leu Thr Leu Ser Lys Ala Asp Tyr Glu Lys His Lys Val
                180                 185                 190

Tyr Ala Cys Glu Val Thr His Gln Gly Leu Ser Ser Pro Val Thr Lys
                195                 200                 205

Ser Phe Asn Arg Gly Glu Cys
            210                 215

<210> SEQ ID NO 142
<211> LENGTH: 446
<212> TYPE: PRT
<213> ORGANISM: Artificial Sequence
<220> FEATURE:
<223> OTHER INFORMATION: 8H9 P329GLALA IgG1 Heavy chain

<400> SEQUENCE: 142

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Trp Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
```

```
                290                 295                 300
Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
                340                 345                 350

Ser Arg Asp Glu Leu Thr Lys Asn Gln Val Ser Leu Thr Cys Leu Val
                355                 360                 365

Lys Gly Phe Tyr Pro Ser Asp Ile Ala Val Glu Trp Glu Ser Asn Gly
                370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
                420                 425                 430

Asn His Tyr Thr Gln Lys Ser Leu Ser Leu Ser Pro Gly Lys
                435                 440                 445

<210> SEQ ID NO 143
<211> LENGTH: 642
<212> TYPE: DNA
<213> ORGANISM: Artificial Sequence
<220> FEATURE:
<223> OTHER INFORMATION: DNA 49B4 P329GLALA IgG1 light chain

<400> SEQUENCE: 143
gacatccaga tgacccagtc tccttccacc ctgtctgcat ctgtaggaga ccgtgtcacc      60
atcacttgcc gtgccagtca gagtattagt agctggttgg cctggtatca gcagaaacca     120
gggaaagccc ctaagctcct gatctatgat gcctccagtt tggaaagtgg ggtcccatca     180
cgtttcagcg gcagtggatc cgggacagaa ttcactctca ccatcagcag cttgcagcct     240
gatgattttg caacttatta ctgccaacag tatagttcgc agccgtatac gtttggccag     300
ggcaccaaag tcgagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag caccctgacg     540
ctgagcaaag cagactacga gaaacacaaa gtctacgcct gcgaagtcac ccatcagggc     600
ctgagctcgc ccgtcacaaa gagcttcaac aggggagagt gt                        642

<210> SEQ ID NO 144
<211> LENGTH: 1344
<212> TYPE: DNA
<213> ORGANISM: Artificial Sequence
<220> FEATURE:
<223> OTHER INFORMATION: DNA 49B4 P329GLALA IgG1 heavy chain

<400> SEQUENCE: 144
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag ggctcgagtg gatgggaggg atcatcccta tctttggtac agcaaactac     180
gcacagaagt tccagggcag ggtcaccatt actgcagaca atccacgag cacagcctac     240
```

```
atggagctga gcagcctgag atctgaggac accgccgtgt attactgtgc gagagaatac      300
taccgtggtc cgtacgacta ctggggccaa gggaccaccg tgaccgtctc ctcagctagc      360
accaagggcc catcggtctt ccccctggca ccctcctcca agagcacctc tgggggcaca      420
gcggccctgg gctgcctggt caaggactac ttccccgaac cggtgacggt gtcgtggaac      480
tcaggcgccc tgaccagcgg cgtgcacacc ttcccggctg tcctacagtc ctcaggactc      540
tactccctca gcagcgtggt gaccgtgccc tccagcagct gggcaccca gacctacatc      600 tgcaacgtga atcacaagcc cagcaacacc aaggtggaca agaaagttga gcccaaatct      660
tgtgacaaaa ctcacacatg cccaccgtgc ccagcacctg aagctgcagg ggaccgtca       720 gtcttcctct tccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca agccgcggg aggagcagta caacagcacg       900
taccgtgtgg tcagcgtcct caccgtcctg caccaggact ggctgaatgg caaggagtac      960
aagtgcaagg tctccaacaa agccctcggc gcccccatcg agaaaaccat ctccaaagcc     1020
aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctacagcaag ctcaccgtgg acaagagcag gtggcagcag     1260
gggaacgtct tctcatgctc cgtgatgcat gaggctctgc acaaccacta cacgcagaag     1320
agcctctccc tgtctccggg taaa                                           1344
```

<210> SEQ ID NO 145
<211> LENGTH: 214
<212> TYPE: PRT
<213> ORGANISM: Artificial Sequence
<220> FEATURE:
<223> OTHER INFORMATION: 49B4 P329GLALA IgG1 light chain

<400> SEQUENCE: 145

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser

```
                165                 170                 175
Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
            195                 200                 205

Phe Asn Arg Gly Glu Cys
        210

<210> SEQ ID NO 146
<211> LENGTH: 448
<212> TYPE: PRT
<213> ORGANISM: Artificial Sequence
<220> FEATURE:
<223> OTHER INFORMATION: 49B4 heavy chain

<400> SEQUENCE: 146

Gln Val Gln Leu Val Gln Ser Gly Ala Glu Val Lys Lys Pro Gly Ser
1               5                  10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
```

```
                    305                 310                 315                 320
             Lys Cys Lys Val Ser Asn Lys Ala Leu Gly Ala Pro Ile Glu Lys Thr
                             325                 330                 335

Ile Ser Lys Ala Lys Gly Gln Pro Arg Glu Pro Gln Val Tyr Thr Leu
                             340                 345                 350

Pro Pro Ser Arg Asp Glu Leu Thr Lys Asn Gln Val Ser Leu Thr Cys
                             355                 360                 365

Leu Val Lys Gly Phe Tyr Pro Ser Asp Ile Ala Val Glu Trp Glu Ser
                     370                 375                 380

Asn Gly Gln Pro Glu Asn Asn Tyr Lys Thr Thr Pro Pro Val Leu Asp
             385                 390                 395                 400

Ser Asp Gly Ser Phe Phe Leu Tyr Ser Lys Leu Thr Val Asp Lys Ser
                             405                 410                 415

Arg Trp Gln Gln Gly Asn Val Phe Ser Cys Ser Val Met His Glu Ala
                             420                 425                 430

Leu His Asn His Tyr Thr Gln Lys Ser Leu Ser Leu Ser Pro Gly Lys
                             435                 440                 445
```

<210> SEQ ID NO 147
<211> LENGTH: 645
<212> TYPE: DNA
<213> ORGANISM: Artificial Sequence
<220> FEATURE:
<223> OTHER INFORMATION: DNA 1G4 P329GLALA IgG1 light chain

<400> SEQUENCE: 147

```
gacatccaga tgacccagtc tccttccacc ctgtctgcat ctgtaggaga ccgtgtcacc      60
atcacttgcc gtgccagtca gagtattagt agctggttgg cctggtatca gcagaaacca     120
gggaaagccc ctaagctcct gatctatgat gcctccagtt tggaaagtgg ggtcccatca     180
cgtttcagcg gcagtggatc cgggacagaa ttcactctca ccatcagcag cttgcagcct     240
gatgattttg caacttatta ctgccaacag tatatttcgt attccatgtt gacgtttggc     300
cagggcacca agtcgagat caagcgtacg gtggctgcac catctgtctt catcttcccg     360
ccatctgatg agcagttgaa atctggaact gcctctgttg tgtgcctgct gaataacttc     420
tatcccagag aggccaaagt acagtggaag gtggataacg ccctccaatc gggtaactcc     480
caggagagtg tcacagagca ggacagcaag gacagcacct acagcctcag cagcaccctg     540
acgctgagca agcagactac gagaaacac aaagtctacg cctgcgaagt cacccatcag     600
ggcctgagct cgcccgtcac aaagagcttc aacaggggag agtgt                    645
```

<210> SEQ ID NO 148
<211> LENGTH: 1338
<212> TYPE: DNA
<213> ORGANISM: Artificial Sequence
<220> FEATURE:
<223> OTHER INFORMATION: DNA 1G4 P329GLALA IgG1 heavy chain

<400> SEQUENCE: 148

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggaggg atcatccta tctttggtac agcaaactac     180
gcacagaagt tccagggcag ggtcaccatt actgcagaca aatccacgag cacagcctac     240
atggagctga gcagcctgag atctgaggac accgccgtgt attactgtgc gagagaatac     300
ggttctatgg actactgggg ccaagggacc accgtgaccg tctcctcagc tagcaccaag     360
```

```
ggcccatcgg tcttcccct ggcaccctcc tccaagagca cctctgggggg cacagcggcc      420 ctgggctgcc tggtcaagga ctacttcccc gaaccggtga cggtgtcgtg aactcaggc       480 gccctgacca gcggcgtgca caccttcccg gctgtcctac agtcctcagg actctactcc     540
ctcagcagcg tggtgaccgt gccctccagc agcttgggca cccagaccta catctgcaac     600
gtgaatcaca gcccagcaac accaaggtg gacaagaaag ttgagcccaa atcttgtgac      660
aaaactcaca catgcccacc gtgcccagca cctgaagctg caggggggacc gtcagtcttc    720 ctcttcccc caaaacccaa ggacaccctc atgatctccc ggaccccctga ggtcacatgc    780 gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cggcgcccccc atcgagaaaa ccatctccaa agccaaaggg   1020
cagccccgag aaccacaggt gtacaccctg ccccccatccc gggatgagct gaccaagaac  1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcagggggaac 1260 gtcttctcat gctccgtgat gcatgaggct ctgcacaacc actacacgca gaagagcctc   1320
tccctgtctc cgggtaaa                                                  1338

<210> SEQ ID NO 149
<211> LENGTH: 215
<212> TYPE: PRT
<213> ORGANISM: Artificial Sequence
<220> FEATURE:
<223> OTHER INFORMATION: 1G4 P329GLALA IgG1 light chain

<400> SEQUENCE: 149

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ile Ser Tyr Ser Met
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
```

-continued

```
                180                 185                 190
Tyr Ala Cys Glu Val Thr His Gln Gly Leu Ser Ser Pro Val Thr Lys
            195                 200                 205

Ser Phe Asn Arg Gly Glu Cys
    210             215

<210> SEQ ID NO 150
<211> LENGTH: 446
<212> TYPE: PRT
<213> ORGANISM: Artificial Sequence
<220> FEATURE:
<223> OTHER INFORMATION: 1G4 P329GLALA IgG1 heavy chain

<400> SEQUENCE: 150

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Gly Ser Met Asp Tyr Trp Gly Gln Gly Thr Thr Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
```

```
                    325                 330                 335
Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
            370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445

<210> SEQ ID NO 151
<211> LENGTH: 642
<212> TYPE: DNA
<213> ORGANISM: Artificial sequence
<220> FEATURE:
<223> OTHER INFORMATION: DNA 20B7 P329GLALA IgG1 light chain

<400> SEQUENCE: 151
gacatccaga tgacccagtc tccttccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatcaggctt tttcgcttac gtttggccag   300
ggcaccaaag tcgagatcaa gcgtacggtg gctgcaccat ctgtcttcat cttcccgcca   360
tctgatgagc agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga gaaacacaaa gtctacgcct gcgaagtcac ccatcagggc   600
ctgagctcgc ccgtcacaaa gagcttcaac aggggagagt gt                      642

<210> SEQ ID NO 152
<211> LENGTH: 1356
<212> TYPE: DNA
<213> ORGANISM: Artificial Sequence
<220> FEATURE:
<223> OTHER INFORMATION: DNA 20B7 P329GLALA IgG1 heavy chain

<400> SEQUENCE: 152
caggtgcaat ggtgcagtc tggggctgag gtgaagaagc ctgggtcctc ggtgaaggtc     60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gagagttaac   300
tacccgtact cttactgggg tgacttcgac tactggggcc aagggaccac cgtgaccgtc   360
tcctcagcta gcaccaaggg cccatcggtc ttccccctgg cacctcctc caagagcacc    420
```

```
tctgggggca cagcggccct gggctgcctg gtcaaggact acttccccga accggtgacg    480
gtgtcgtgga actcaggcgc cctgaccagc ggcgtgcaca ccttcccggc tgtcctacag    540
tcctcaggac tctactccct cagcagcgtg gtgaccgtgc cctccagcag cttgggcacc    600
cagacctaca tctgcaacgt gaatcacaag cccagcaaca ccaaggtgga caagaaagtt    660
gagcccaaat cttgtgacaa aactcacaca tgcccaccgt gcccagcacc tgaagctgca    720
gggggaccgt cagtcttcct cttccccccca aaacccaagg acaccctcat gatctcccgg    780
acccctgagg tcacatgcgt ggtggtggac gtgagccacg aagaccctga ggtcaagttc    840
aactggtacg tggacggcgt ggaggtgcat aatgccaaga caaagccgcg ggaggagcag    900
tacaacagca cgtaccgtgt ggtcagcgtc ctcaccgtcc tgcaccagga ctggctgaat    960
ggcaaggagt acaagtgcaa ggtctccaac aaagccctcg cgccccccat cgagaaaacc    1020
atctccaaag ccaaagggca gccccgagaa ccacaggtgt acaccctgcc cccatcccgg    1080
gatgagctga ccaagaacca ggtcagcctg acctgcctgg tcaaaggctt ctatcccagc    1140
gacatcgccg tggagtggga gagcaatggg cagccggaga acaactacaa gaccacgcct    1200
cccgtgctgg actccgacgg ctccttcttc ctctacagca agctcaccgt ggacaagagc    1260
aggtggcagc aggggaacgt cttctcatgc tccgtgatgc atgaggctct gcacaaccac    1320
tacacgcaga gagcctctcc cctgtctccg ggtaaa    1356
```

<210> SEQ ID NO 153
<211> LENGTH: 214
<212> TYPE: PRT
<213> ORGANISM: Artificial
<220> FEATURE:
<223> OTHER INFORMATION: 20B7 P329GLALA IgG1 Light chain

<400> SEQUENCE: 153

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Gln Ala Phe Ser Leu
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
```

```
              195                 200                 205
Phe Asn Arg Gly Glu Cys
    210

<210> SEQ ID NO 154
<211> LENGTH: 452
<212> TYPE: PRT
<213> ORGANISM: Artificial
<220> FEATURE:
<223> OTHER INFORMATION: 20B7 P329GLALA IgG1 heavy chain

<400> SEQUENCE: 154

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Val Asn Tyr Pro Tyr Ser Tyr Trp Gly Asp Phe Asp Tyr Trp
            100                 105                 110

Gly Gln Gly Thr Thr Val Thr Val Ser Ser Ala Ser Thr Lys Gly Pro
        115                 120                 125

Ser Val Phe Pro Leu Ala Pro Ser Ser Lys Ser Thr Ser Gly Gly Thr
    130                 135                 140

Ala Ala Leu Gly Cys Leu Val Lys Asp Tyr Phe Pro Glu Pro Val Thr
145                 150                 155                 160

Val Ser Trp Asn Ser Gly Ala Leu Thr Ser Gly Val His Thr Phe Pro
                165                 170                 175

Ala Val Leu Gln Ser Ser Gly Leu Tyr Ser Leu Ser Ser Val Val Thr
            180                 185                 190

Val Pro Ser Ser Ser Leu Gly Thr Gln Thr Tyr Ile Cys Asn Val Asn
        195                 200                 205

His Lys Pro Ser Asn Thr Lys Val Asp Lys Lys Val Glu Pro Lys Ser
    210                 215                 220

Cys Asp Lys Thr His Thr Cys Pro Pro Cys Pro Ala Pro Glu Ala Ala
225                 230                 235                 240

Gly Gly Pro Ser Val Phe Leu Phe Pro Pro Lys Pro Lys Asp Thr Leu
                245                 250                 255

Met Ile Ser Arg Thr Pro Glu Val Thr Cys Val Val Val Asp Val Ser
            260                 265                 270

His Glu Asp Pro Glu Val Lys Phe Asn Trp Tyr Val Asp Gly Val Glu
        275                 280                 285

Val His Asn Ala Lys Thr Lys Pro Arg Glu Glu Gln Tyr Asn Ser Thr
    290                 295                 300

Tyr Arg Val Val Ser Val Leu Thr Val Leu His Gln Asp Trp Leu Asn
305                 310                 315                 320

Gly Lys Glu Tyr Lys Cys Lys Val Ser Asn Lys Ala Leu Gly Ala Pro
                325                 330                 335

Ile Glu Lys Thr Ile Ser Lys Ala Lys Gly Gln Pro Arg Glu Pro Gln
```

```
              340                 345                 350
Val Tyr Thr Leu Pro Pro Ser Arg Asp Glu Leu Thr Lys Asn Gln Val
            355                 360                 365

Ser Leu Thr Cys Leu Val Lys Gly Phe Tyr Pro Ser Asp Ile Ala Val
        370                 375                 380

Glu Trp Glu Ser Asn Gly Gln Pro Glu Asn Asn Tyr Lys Thr Thr Pro
385                 390                 395                 400

Pro Val Leu Asp Ser Asp Gly Ser Phe Phe Leu Tyr Ser Lys Leu Thr
                405                 410                 415

Val Asp Lys Ser Arg Trp Gln Gln Gly Asn Val Phe Ser Cys Ser Val
            420                 425                 430

Met His Glu Ala Leu His Asn His Tyr Thr Gln Lys Ser Leu Ser Leu
        435                 440                 445

Ser Pro Gly Lys
    450
```

<210> SEQ ID NO 155
<211> LENGTH: 645
<212> TYPE: DNA
<213> ORGANISM: Artificial
<220> FEATURE:
<223> OTHER INFORMATION: DNA CLC-563 P329GLALA IgG1 light chain

<400> SEQUENCE: 155

```
gagatcgtgc tgacccagag ccccggcaca ctctccctgt ctcctgggga agggccacc      60
ctttcatgca gagccagcca gtccgtctct agtagctacc tggcatggta tcagcagaag    120
ccaggacaag cccccgcct cctgatttac ggcgcttcct ctcgggcaac tggtatccct     180
gacaggttct cagggagcgg aagcggaaca gattttacct tgactatttc tagactggag    240
ccagaggact tcgccgtgta ttactgtcag cagtacggta gtagcccct cacctttggc     300
caggggacaa agtcgaaat caagcgtacg gtggctgcac catctgtctt catcttcccg     360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca agcagcta cgagaaacac aaagtctacg cctgcgaagt cacccatcag      600
ggcctgagct cgcccgtcac aaagagcttc aacaggggag agtgt                    645
```

<210> SEQ ID NO 156
<211> LENGTH: 1338
<212> TYPE: DNA
<213> ORGANISM: Artificial
<220> FEATURE:
<223> OTHER INFORMATION: DNA CLC-563 P329GLALA IgG1 heavy chain

<400> SEQUENCE: 156

```
gaggtgcaat tgttggagtc tgggggaggc ttggtacagc ctgggggtc cctgagactc      60
tcctgtgcag cctccggatt caccttagc agttatgcca tgagctgggt ccgccaggct    120
ccagggaagg gctgagtg gtctcagct attagtggta gtggtggtag cacatactac      180
gcagactccg tgaagggccg gttcaccatc tccagagaca attccaagaa cacgctgtat    240
ctgcagatga acagcctgag agccgaggac acggccgtat attactgtgc gcttgacgtt    300
ggtgctttcg actactgggg ccaaggagcc ctggtcaccg tctcgagtgc tagcaccaag    360
ggcccatcgg tcttccccct ggcacccttc tccaagagca cctctggggg cacagcggcc    420
```

```
ctgggctgcc tggtcaagga ctacttcccc gaaccggtga cggtgtcgtg gaactcaggc    480
gccctgacca gcggcgtgca caccttcccg gctgtcctac agtcctcagg actctactcc    540
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagctg caggggggacc gtcagtcttc    720 ctcttccccc caaaacccaa ggacaccctc atgatctccc ggacccctga ggtcacatgc    780
gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cggcgccccc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc tcccgtgctg gactccgac   1200 ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338

<210> SEQ ID NO 157
<211> LENGTH: 215
<212> TYPE: PRT
<213> ORGANISM: Artificial
<220> FEATURE:
<223> OTHER INFORMATION: CLC-563 P329GLALA IgG1 light chain

<400> SEQUENCE: 157

Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
```

```
                195                 200                 205

Ser Phe Asn Arg Gly Glu Cys
    210                 215

<210> SEQ ID NO 158
<211> LENGTH: 446
<212> TYPE: PRT
<213> ORGANISM: Artificial
<220> FEATURE:
<223> OTHER INFORMATION: CLC-563 P329GLALA IgG1 heavy chain

<400> SEQUENCE: 158

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Leu Asp Val Gly Ala Phe Asp Tyr Trp Gly Gln Gly Ala Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
```

```
                340             345             350
Ser Arg Asp Glu Leu Thr Lys Asn Gln Val Ser Leu Thr Cys Leu Val
            355                 360                 365

Lys Gly Phe Tyr Pro Ser Asp Ile Ala Val Glu Trp Glu Ser Asn Gly
        370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
            435                 440                 445
```

<210> SEQ ID NO 159
<211> LENGTH: 645
<212> TYPE: DNA
<213> ORGANISM: Artificial
<220> FEATURE:
<223> OTHER INFORMATION: DNA CLC-564 P329GLALA IgG1 light chain

<400> SEQUENCE: 159

```
gagatcgtgc tgacccagag ccccggcaca ctctccctgt ctcctgggga agggccacc      60
ctttcatgca gagccagcca gtccgtctct agtagctacc tggcatggta tcagcagaag    120
ccaggacaag ccccccgcct cctgatttac ggcgcttcct ctcgggcaac tggtatccct    180
gacaggttct cagggagcgg aagcggaaca gattttacct tgactatttc tagactggag    240
ccagaggact cgccgtgta ttactgtcag cagtacggta gtagccccct cacctttggc    300
cagggggacaa aagtcgaaat caagcgtacg gtggctgcac catctgtctt catcttcccg    360
ccatctgatg agcagttgaa atctggaact gcctctgttg tgtgcctgct gaataacttc    420
tatcccagag aggccaaagt acagtggaag gtggataacg ccctccaatc gggtaactcc    480
caggagagtg tcacagagca ggacagcaag gacagcacct acagcctcag cagcaccctg    540
acgctgagca aagcagacta cgagaaacac aaagtctacg cctgcgaagt cacccatcag    600
ggcctgagct cgcccgtcac aaagagcttc aacaggggag agtgt                    645
```

<210> SEQ ID NO 160
<211> LENGTH: 1338
<212> TYPE: DNA
<213> ORGANISM: Artificial
<220> FEATURE:
<223> OTHER INFORMATION: DNA CLC-564 P329GLALA IgG1 heavy chain

<400> SEQUENCE: 160

```
gaggtgcaat tgttggagtc tgggggaggc ttggtacagc ctgggggtc cctgagactc       60
tcctgtgcag cctccggatt cacctttagc agttatgcca tgagctgggt ccgccaggct    120
ccagggaagg ggctggagtg gtctcagct attagtggta gtggtggtag cacatactac    180
gcagactccg tgaagggccg gttcaccatc tccagagaca attccaagaa cacgctgtat    240
ctgcagatga acagcctgag agccgaggac acggccgtat attactgtgc gttcgacgtt    300
ggtccgttcg actactgggg ccaaggaacc ctggtcaccg tctcgagtgc tagcaccaag    360
ggcccatcgg tcttccccct ggcaccctcc tccaagagca cctctggggg cacagcggcc    420
ctgggctgcc tggtcaagga ctacttcccc gaaccggtga cggtgtcgtg aactcaggc    480
gccctgacca gcggcgtgca caccttcccg gctgtcctac agtcctcagg actctactcc    540
```

```
ctcagcagcg tggtgaccgt gccctccagc agcttgggca cccagaccta catctgcaac    600
gtgaatcaca agcccagcaa caccaaggtg gacaagaaag ttgagcccaa atcttgtgac    660
aaaactcaca catgcccacc gtgcccagca cctgaagctg caggggggacc gtcagtcttc    720
```
```
ctcttccccc caaaacccaa ggacaccctc atgatctccc ggaccctga ggtcacatgc    780 gtggtggtgg acgtgagcca cgaagaccct gaggtcaagt tcaactggta cgtggacggc    840
gtggaggtgc ataatgccaa gacaaagccg cgggaggagc agtacaacag cacgtaccgt    900
gtggtcagcg tcctcaccgt cctgcaccag gactggctga atggcaagga gtacaagtgc    960
aaggtctcca acaaagccct cggcgccccc atcgagaaaa ccatctccaa agccaaaggg   1020
cagccccgag aaccacaggt gtacaccctg cccccatccc gggatgagct gaccaagaac   1080
caggtcagcc tgacctgcct ggtcaaaggc ttctatccca gcgacatcgc cgtggagtgg   1140
gagagcaatg ggcagccgga gaacaactac aagaccacgc ctcccgtgct ggactccgac   1200
ggctccttct tcctctacag caagctcacc gtggacaaga gcaggtggca gcaggggaac   1260
gtcttctcat gctccgtgat gcatgaggct ctgcacaacc actacacgca gaagagcctc   1320
tccctgtctc cgggtaaa                                                 1338
```

<210> SEQ ID NO 161
<211> LENGTH: 215
<212> TYPE: PRT
<213> ORGANISM: Artificial
<220> FEATURE:
<223> OTHER INFORMATION: CLC-564 P329GLALA IgG1 light chain

<400> SEQUENCE: 161

```
Glu Ile Val Leu Thr Gln Ser Pro Gly Thr Leu Ser Leu Ser Pro Gly
1               5                   10                  15

Glu Arg Ala Thr Leu Ser Cys Arg Ala Ser Gln Ser Val Ser Ser Ser
            20                  25                  30

Tyr Leu Ala Trp Tyr Gln Gln Lys Pro Gly Gln Ala Pro Arg Leu Leu
        35                  40                  45

Ile Tyr Gly Ala Ser Ser Arg Ala Thr Gly Ile Pro Asp Arg Phe Ser
    50                  55                  60

Gly Ser Gly Ser Gly Thr Asp Phe Thr Leu Thr Ile Ser Arg Leu Glu
65                  70                  75                  80

Pro Glu Asp Phe Ala Val Tyr Tyr Cys Gln Gln Tyr Gly Ser Ser Pro
                85                  90                  95

Leu Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
            210                 215
```

<210> SEQ ID NO 162
<211> LENGTH: 446
<212> TYPE: PRT
<213> ORGANISM: Artificial
<220> FEATURE:
<223> OTHER INFORMATION: CLC-564 P329GLALA IgG1 heavy chain

<400> SEQUENCE: 162

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Phe Asp Val Gly Pro Phe Asp Tyr Trp Gly Gln Gly Thr Leu Val
            100                 105                 110

Thr Val Ser Ser Ala Ser Thr Lys Gly Pro Ser Val Phe Pro Leu Ala
        115                 120                 125

Pro Ser Ser Lys Ser Thr Ser Gly Gly Thr Ala Ala Leu Gly Cys Leu
    130                 135                 140

Val Lys Asp Tyr Phe Pro Glu Pro Val Thr Val Ser Trp Asn Ser Gly
145                 150                 155                 160

Ala Leu Thr Ser Gly Val His Thr Phe Pro Ala Val Leu Gln Ser Ser
                165                 170                 175

Gly Leu Tyr Ser Leu Ser Ser Val Val Thr Val Pro Ser Ser Ser Leu
            180                 185                 190

Gly Thr Gln Thr Tyr Ile Cys Asn Val Asn His Lys Pro Ser Asn Thr
        195                 200                 205

Lys Val Asp Lys Lys Val Glu Pro Lys Ser Cys Asp Lys Thr His Thr
    210                 215                 220

Cys Pro Pro Cys Pro Ala Pro Glu Ala Ala Gly Gly Pro Ser Val Phe
225                 230                 235                 240

Leu Phe Pro Pro Lys Pro Lys Asp Thr Leu Met Ile Ser Arg Thr Pro
                245                 250                 255

Glu Val Thr Cys Val Val Val Asp Val Ser His Glu Asp Pro Glu Val
            260                 265                 270

Lys Phe Asn Trp Tyr Val Asp Gly Val Glu Val His Asn Ala Lys Thr
        275                 280                 285

Lys Pro Arg Glu Glu Gln Tyr Asn Ser Thr Tyr Arg Val Val Ser Val
    290                 295                 300

Leu Thr Val Leu His Gln Asp Trp Leu Asn Gly Lys Glu Tyr Lys Cys
305                 310                 315                 320

Lys Val Ser Asn Lys Ala Leu Gly Ala Pro Ile Glu Lys Thr Ile Ser
                325                 330                 335

Lys Ala Lys Gly Gln Pro Arg Glu Pro Gln Val Tyr Thr Leu Pro Pro
            340                 345                 350

Ser Arg Asp Glu Leu Thr Lys Asn Gln Val Ser Leu Thr Cys Leu Val
```

```
                355                 360                 365
Lys Gly Phe Tyr Pro Ser Asp Ile Ala Val Glu Trp Glu Ser Asn Gly
    370                 375                 380

Gln Pro Glu Asn Asn Tyr Lys Thr Thr Pro Pro Val Leu Asp Ser Asp
385                 390                 395                 400

Gly Ser Phe Phe Leu Tyr Ser Lys Leu Thr Val Asp Lys Ser Arg Trp
                405                 410                 415

Gln Gln Gly Asn Val Phe Ser Cys Ser Val Met His Glu Ala Leu His
            420                 425                 430

Asn His Tyr Thr Gln Lys Ser Leu Ser Leu Ser Pro Gly Lys
        435                 440                 445

<210> SEQ ID NO 163
<211> LENGTH: 639
<212> TYPE: DNA
<213> ORGANISM: Artificial
<220> FEATURE:
<223> OTHER INFORMATION: DNA 17A9 P329GLALA IgG1 light chain

<400> SEQUENCE: 163
tcgtctgagc tgactcagga ccctgctgtg tctgtggcct tgggacagac agtcaggatc      60
acatgccaag agacagcct cagaagttat tatgcaagct ggtaccagca gaagccagga     120
caggcccctg tacttgtcat ctatggtaaa acaaccggc cctcagggat cccagaccga     180
ttctctggct ccagctcagg aaacacagct tccttgacca tcactggggc tcaggcggaa     240
gatgaggctg actattactg taactcccgt gttatgcctc ataatcgcgt attcggcgga     300
gggaccaagc tgaccgtcct aggtcaaccc aaggctgccc cagcgtgac cctgttcccc     360 cccagcagcg aggaactgca ggccaacaag gccaccctgg tctgcctgat cagcgacttc     420
tacccaggcg ccgtgaccgt ggcctggaag gcgacagca ccccgtgaa ggccggcgtg     480 gagaccacca ccccagcaa gcagagcaac aacaagtacg ccgccagcag ctacctgagc     540
ctgacccccg agcagtggaa gagccacagg tcctacagct gccaggtgac ccacgagggc     600
agcaccgtgg agaaaaccgt ggccccacc gagtgcagc                            639

<210> SEQ ID NO 164
<211> LENGTH: 1350
<212> TYPE: DNA
<213> ORGANISM: Artificial
<220> FEATURE:
<223> OTHER INFORMATION: DNA 17A9 P329GLALA IgG1 heavy chain

<400> SEQUENCE: 164
gaggtgcaat tgttggagtc tgggggaggc ttggtacagc ctgggggtc cctgagactc      60 tcctgtgcag cctccggatt cacctttagc agttatgcca tgagctgggt ccgccaggct     120
ccagggaagg gctggagtg gtctcagct attagtggta gtggtggtag cacatactac     180
gcagactccg tgaagggccg gttcaccatc tccagagaca attccaagaa cacgctgtat     240
ctgcagatga acagcctgag agccgaggac acggccgtat attactgtgc gcgtgttttc     300
taccgtggtg gtgttttctat ggactactgg ggccaaggaa ccctggtcac cgtctcgagt     360
gctagcacca agggcccatc ggtcttcccc ctggcaccct cctccaagag cacctctggg     420
ggcacagcgg ccctgggctg cctggtcaag gactacttcc ccgaaccggt gacggtgtcg     480
tggaactcag gcgccctgac cagcggcgtg cacaccttcc cggctgtcct acagtcctca     540
ggactctact ccctcagcag cgtggtgacc gtgccctcca gcagcttggg cacccagacc     600
```

```
tacatctgca acgtgaatca caagcccagc aacaccaagg tggacaagaa agttgagccc    660
aaatcttgtg acaaaactca cacatgccca ccgtgcccag cacctgaagc tgcagggga    720 ccgtcagtct tcctcttccc cccaaaaccc aaggacaccc tcatgatctc ccggacccct    780
gaggtcacat gcgtggtggt ggacgtgagc cacgaagacc ctgaggtcaa gttcaactgg    840
tacgtggacg gcgtggaggt gcataatgcc aagacaaagc cgcgggagga gcagtacaac    900
agcacgtacc gtgtggtcag cgtcctcacc gtcctgcacc aggactggct gaatggcaag    960
gagtacaagt gcaaggtctc caacaaagcc ctcggcgccc ccatcgagaa aaccatctcc   1020
aaagccaaag gcagccccg agaaccacag gtgtacaccc tgcccccatc ccgggatgag    1080
ctgaccaaga accaggtcag cctgacctgc ctggtcaaag gcttctatcc cagcgacatc    1140
gccgtggagt gggagagcaa tgggcagccg gagaacaact acaagaccac gcctcccgtg   1200
ctggactccg acggctcctt cttcctctac agcaagctca ccgtggacaa gagcaggtgg   1260
cagcagggga acgtcttctc atgctccgtg atgcatgagg ctctgcacaa ccactacacg   1320
cagaagagcc tctccctgtc tccgggtaaa                                    1350
```

<210> SEQ ID NO 165
<211> LENGTH: 213
<212> TYPE: PRT
<213> ORGANISM: Artificial
<220> FEATURE:
<223> OTHER INFORMATION: 17A9 P329GLALA IgG1 light chain

<400> SEQUENCE: 165

```
Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Val Met Pro His Asn Arg
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210
```

-continued

```
<210> SEQ ID NO 166
<211> LENGTH: 450
<212> TYPE: PRT
<213> ORGANISM: Artificial
<220> FEATURE:
<223> OTHER INFORMATION: 17A9 P329GLALA IgG1 heavy chain

<400> SEQUENCE: 166
```

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Val Phe Tyr Arg Gly Gly Val Ser Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Ala Ala Gly Gly
225                 230                 235                 240

Pro Ser Val Phe Leu Phe Pro Pro Lys Pro Lys Asp Thr Leu Met Ile
                245                 250                 255

Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Gly Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Asp Glu Leu Thr Lys Asn Gln Val Ser Leu
        355                 360                 365

Thr Cys Leu Val Lys Gly Phe Tyr Pro Ser Asp Ile Ala Val Glu Trp

```
              370                 375                 380
Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly Lys
    450

<210> SEQ ID NO 167
<211> LENGTH: 3102
<212> TYPE: DNA
<213> ORGANISM: Artificial Sequence
<220> FEATURE:
<223> OTHER INFORMATION: Nucleotide sequence human TnC with C-terminal
      Avi- and His-tags

<400> SEQUENCE: 167
atgtccccta ctactaggtta ttggaaaatt aagggccttg tgcaacccac tcgacttctt     60
ttggaatatc ttgaagaaaa atatgaagag catttgtatg agcgcgatga aggtgataaa    120
tggcgaaaca aaaagtttga attgggtttg gagtttccca atcttcctta ttatattgat    180
ggtgatgtta aattaacaca gtctatggcc atcatacgtt atatagctga caagcacaac    240
atgttgggtg ttgtccaaa agagcgtgca gagatttcaa tgcttgaagg agcggttttg    300
gatattagat acgtgtttc gagaattgca tatagtaaag actttgaaac tctcaaagtt    360
gattttctta gcaagctacc tgaaatgctg aaaatgttcg aagatcgttt atgtcataaa    420
acatatttaa atggtgatca tgtaacccat cctgacttca tgttgtatga cgctcttgat    480
gttgttttat acatggaccc aatgtgcctg atgcgttcc caaaattagt ttgttttaaa    540
aaacgtattg aagctatccc acaaattgat aagtacttga atccagcaa gtatatagca    600 tggcctttgc agggctggca agccacgttt ggtggtggcg accatcctcc aaaatcggat    660
ggttcaacta gtggttctgg tcatcaccat caccatcact ccgcgggtct ggtgccacgc    720
ggtagtactg caattggtat gaaagaaacc gctgctgcta aattcgaacg ccagcacatg    780
gacagcccag atctgggtac cggtggtggc tccggtattg agggacgcgg gtccatggga    840
tatcggggat ccgagctgga cacccccaag gacctgcagg tgtccgagac agccgagaca    900
agcctgaccc tgctgtggaa accccctg gccaagttcg accggtacag actgaactac    960
agcctgccca ctggacagtg ggtcggcgtg cagctgcccc ggaacaccac ctcctacgtg   1020
ctgcggggcc tggaacccgg ccaggaatac aacgtcctgc tgacggccga aagggccgg   1080 cacaagagca gcccgccag agtgaaggcc agcaccgagc aggcccccga gctggaaaac   1140
ctgaccgtga ccgaagtggg ctgggacggc ctgcggctga actggaccgc ggctgaccag   1200
gcctatgagc actttatcat tcaggtgcag gaggccaaca aggtggaggc agctcggaac   1260
ctcaccgtgc ctggcagcct tcgggctgtg acataccgg cctcaaggc tgctacgcct   1320 tatacagtct ccatctatgg ggtgatccag ggctatagaa accagtgct ctctgctgag   1380 gcctccacag gcgaaacacc gaacctgggc gaagtggtgg tggcggaagt gggttgggat   1440
gcgctgaaac tgaactggac cgcgccgaa ggcgcgtatg aatatttttt catccaggtg   1500
caggaagcgg ataccgttga agcggcgcag aacctgaccg ttccgggcgg tctgcgtagc   1560
```

```
accgatctgc cgggcctgaa agcggcgacc cattatacca ttaccatccg tggggtgacc    1620
caggacttct ctaccacccc tctgagcgtg gaggtgctga ccgaggaggt acccgacatg    1680
ggcaacctga ccgtgaccga ggtgtcctgg gacgccctgc ggctgaactg gaccaccccc    1740
gacggcacct acgaccagtt cacaatccag gtgcaggaag ccgaccaggt ggaagaagca    1800
cataatctga ccgttccggg tagcctgcgt agcatggaaa ttccgggtct gcgtgcaggc    1860
accccgtata ccgttaccct gcatggtgaa gttcgtggtc atagcacccg tccgctggca    1920
gttgaagttg ttaccgaaga tctgccgcag ctgggtgatc tggcagttag cgaagttggt    1980
tgggatggtc tgcgtctgaa ttggaccgca gcagataatg catatgaaca ttttgtgatc    2040
caggtgcaag aggtgaataa agttgaagca gcccagaatc tgaccctgcc tggttcactg    2100
cgtgcagttg atattccggg actcgaggca gcaaccccgt atcgtgttag catttatggt    2160
gttattcgcg gttatcgtac accggttctg agcgcagaag caagcaccgc aaaagaaccg    2220
gaaattggta atctgaacgt gagcgatatt acaccggaat catttaatct gagctggatg    2280
gcaaccgatg gtattttga aacctttacc atcgagatca tcgatagcaa tcgtctgctg    2340
gaaaccgtgg aatataatat tagcggtgca gaacgtaccg cacatattag cggtctgcct    2400
ccgagcaccg attttattgt ttatctgagc ggtctggcac cgagcattcg taccaaaacc    2460
attagcgcaa ccgcaaccac cgaagcactg ccgctgctgg aaaatctgac cattagcgat    2520
attaacccgt atggttttac cgtttcatgg atggcaagcg aaaatgcatt tgatagcttt    2580
ctggttacag ttgtggatag cggtaaactg ctggacccgc aagaatttac cctgagcggc    2640
acccagcgca aactggaact gcgtggtctg attaccggta ttggttatga agttatggtg    2700
agcggtttta cccagggtca tcagaccaaa ccgctgcgtg cagaaattgt taccgaagca    2760
atgggtagcc cgaaagaagt tattttttcc gatatcaccg agaattcggc aaccgttagc    2820
tggcgtgcac cgaccgcaca ggttgaaagc tttcgtatta cctatgttcc gattaccggt    2880
ggcaccccga gcatggttac agttgatggc accaaaaccc agaccgtctc tggttaaactg    2940 attccgggtg ttgaatatct ggttagcatt attgccatga aaggctttga agaaagcgaa    3000
ccggttagcg gtagctttac cacagctagc ggcctgaacg acatcttcga ggctcagaaa    3060
atcgaatggc acgaaggtac ccatcaccat caccaccact aa                      3102
```

<210> SEQ ID NO 168
<211> LENGTH: 2566
<212> TYPE: DNA
<213> ORGANISM: Artificial Sequence
<220> FEATURE:
<223> OTHER INFORMATION: Nucleotide sequence mouse TnC with C-terminal
      Avi- and His-tags

<400> SEQUENCE: 168

```
tatgtcccct atactaggtt attggaaaat taagggcctt gtgcaaccca ctcgacttct     60
tttggaatat cttgaagaaa aatatgaaga gcatttgtat gagcgcgatg aaggtgataa    120
atggcgaaac aaaaagtttg aattgggttt ggagtttccc aatcttcctt attatattga    180
tggtgatgtt aaattaacac agtctatggc catcatacgt tatatagctg acaagcacaa    240
catgttgggt ggttgtccaa agagcgtgc agagatttca atgcttgaag gagcggtttt    300
ggatattaga tacggtgttt cgagaattgc atatagtaaa gactttgaaa ctctcaaagt    360
tgattttctt agcaagctac ctgaaatgct gaaaatgttc gaagatcgtt tatgtcataa    420 aacatatttta aatggtgatc atgtaaccca tcctgacttc atgttgtatg acgctcttga    480
```

```
tgttgtttta tacatggacc caatgtgcct ggatgcgttc ccaaaattag tttgttttaa    540
aaaacgtatt gaagctatcc cacaaattga taagtacttg aaatccagca agtatatagc    600
atggcctttg cagggctggc aagccacgtt tggtggtggc gaccatcctc caaaatcgga    660
tggttcaact agtggttctg gtcatcacca tcaccatcac tccgcgggtc tggtgccacg    720
cggtagtact gcaattggta tgaaagaaac cgctgctgct aaattcgaac gccagcacat    780
ggacagccca gatctgggta ccggtggtgg ctccggtatt gagggacgcg gtccatggga    840
atatcgggga tccgagctgg acacccccaa ggacctgcag gtgtccgaga cagccgagac    900
aagcctgacc ctgctgtgga aaccccccct ggccaagttc gaccggtaca gactgaacta    960
cagcctgccc actggacagt gggtcggcgt gcagctgccc cggaacacca cctcctacgt   1020
gctgcgggc ctggaacccg ccaggaata acgtcctg ctgacggccg agaagggccg   1080
gcacaagagc aagcccgcca gagtgaaggc cagcaccgag aagtgccca gcctggaaaa   1140
cctgaccgtg accgaggccg gctgggacgg cctgcggctg aactggaccg ccgacgacct   1200
ggcctacgag tacttcgtga tccaggtgca ggaagccaac aacgtcgaga cagcccacaa   1260
cttcaccgtg cccggcaacc tgagagccgc cgacatcccc ggcctgaagg tggccacatc   1320
ctaccgggtg tccatctacg gcgtggccag gggctaccgg acccccgtgc tgtccgccga   1380
gacaagcacc ggcaccacgc cgaacctggg cgaagtgacc gtggcggaag tgggttggga   1440
tgcgctgacc ctgaattgga ccgcaccgga aggcgcgtat aaaaacttt tcatccaggt   1500
gctggaagcg gataccaccc agaccgtgca gaacctgacc gtgccgggtg gtctgcgtag   1560
cgtagatctg cctggtctga aagcagcaac ccgctattac attaccctgc gtggtgttac   1620
ccaggatttt ggcaccgcac cgctgagcgt tgaagttctg accgaggatc tgccgcagct   1680
gggtggtctg agcgttaccg aagttagttg ggatggtctg accctgaatt ggaccaccga   1740
tgatctggca tataaacatt ttgtggtgca ggttcaagag gccaataatg ttgaagcagc   1800
acagaatctg accgttccgg gtagcctgcg tgcagttgat attccgggac tgaaagccga   1860
taccccgtat cgtgttagca tttatggtgt tattcagggt tatcgtaccc cgatgctgag   1920
caccgatgtt agcacagcac gtgaaccgga aattggtaat ctgaatgtta gtgatgtgac   1980
cccgaaaatca tttaatctga gctggaccgc aaccgatggt attttgata tgtttaccat   2040
tgaaattatt gatagcaatc gcctgctgca gaccgcagaa cataacatta gcggtgcaga   2100
acgtaccgca catattagcg gtctgcctcc gagcaccgat tttattgttt atctgagcgg   2160
tattgcaccg agcattcgta ccaaaaccat tagcaccacc gcaaccaccg aagcactgac   2220
cgcaatgggt agcccgaaag aagtgatttt tagcgatatt accgaaaata gcgccaccgt   2280
ttcatggcgt gcaccgaccg cacaggttga aagctttcgt attacctatg ttccgattac   2340
cggtggcacc ccgagcatgg ttaccgttga tggcaccaaa acccagaccc gtctggttaa   2400
actgattccg ggtgttgaat atctggttag cattattgcc atgaaaggct ttgaagaaag   2460
cgaaccggtt agcggtagct ttaccacagc tagcggcctg aacgacatct tcgaggctca   2520
gaaaatcgaa tggcacgaag gtacccatca ccatcaccac cactaa              2566
```

<210> SEQ ID NO 169  
<211> LENGTH: 2565  
<212> TYPE: DNA  
<213> ORGANISM: Artificial Sequence  
<220> FEATURE:  
<223> OTHER INFORMATION: Nucleotide sequence cynomolgus TnC with  
        C-terminal Avi- and His-tags

<400> SEQUENCE: 169

```
atgtcccctc tactaggtta ttggaaaatt aagggccttg tgcaacccac tcgacttctt      60
ttggaatatc ttgaagaaaa atatgaagag catttgtatg agcgcgatga aggtgataaa     120
tggcgaaaca aaaagtttga attgggtttg gagtttccca atcttcctta ttatattgat     180
ggtgatgtta aattaacaca gtctatggcc atcatacgtt atatagctga caagcacaac     240
atgttgggtg gttgtccaaa agagcgtgca gagatttcaa tgcttgaagg agcggttttg     300
gatattagat acggtgtttc gagaattgca tatagtaaag actttgaaac tctcaaagtt     360
gattttctta gcaagctacc tgaaatgctg aaaatgttcg aagatcgttt atgtcataaa     420
acatatttaa atggtgatca tgtaacccat cctgacttca tgttgtatga cgctcttgat     480
gttgttttat acatggaccc aatgtgcctg gatgcgttcc caaaattagt ttgttttaaa     540
aaacgtattg aagctatccc acaaattgat aagtacttga atccagcaa gtatatagca     600
tggcctttgc agggctggca agccacgttt ggtggtggcg accatcctcc aaaatcggat     660
ggttcaacta gtggttctgg tcatcaccat caccatcact ccgcgggtct ggtgccacgc     720
ggtagtactg caattggtat gaaagaaacc gctgctgcta aattcgaacg ccagcacatg     780
gacagcccag atctgggtac cggtggtggc tccggtattg agggacgcgg gtccatggga     840
tatcggggat ccgaactgga taccccgaaa gatctgcgtg ttagcgaaac cgcagaaacc     900
agcctgaccc tgttttggaa aacaccgctg gcaaaatttg atcgttatcg tctgaattat     960
agcctgccga ccggtcagtg ggttggtgtt cagctgcctc gtaataccac cagttatgtt    1020
ctgcgtggtc tggaaccggg tcaagaatat aacgttctgc tgaccgcaga aaaaggtcgt    1080
cataaaagca aaccggcacg tgttaaagca agcaccgaac aggcaccgga actggaaaat    1140
ctgaccgtta ccgaagttgg ctgggatggc ctgcgcctga actggacggc tgcggaccag    1200
gcctacgaac acttcgttat ccaggtgcaa gaagccaaca agtagaagc cgctcagaat    1260
ctgacggttc cgggaaatct gcgtgcagtt gatattccgg gtctgaaagc agcaaccccg    1320
tataccgtta gcatttatgg tgttattcag ggttatcgta caccggttct gagtgccgaa    1380
gccagcaccg gtgaaacccc gaatctgggt gaagttatgg ttagcgaagt gggctgggat    1440
gcactgaaac tgaattggac agttccggaa ggtgcctatg aatactttt cattcaggtt    1500
caagaagcgg ataccgttga agccgctcag aatcataccg ttccgggtgg tctgcgtagc    1560
accgatctgc ctggcctgaa agccgctacc cattacacca ttaccattcg tggtgttacc    1620
caggatttta gcaccacacc gctgagcgtt gaagttctga cagaagaact gccgcagctg    1680
ggtgatctgg cagttagcga agttggttgg gatggtctgc gtctgaattg accgcagca    1740
gatcaggcat atgaacattt tgttatccag gtgcaagaag tgaacaaagt tgaagcagca    1800
cagaatctga ccgttccggg tagcctgcgt gcagttgata ttccgggtct gaaagcagca    1860
accccgtata ccgttagcat ttatggtgtt attcgcggtt atcgtacacc ggttctgagc    1920
gcagaagcaa gcaccgcaaa agaaccggaa attggtaatc tgaacgtgag cgatattaca    1980
ccggaaagtt ttagcctgag ctggaccgca accgatggta ttttgaaac ctttaccatc    2040
gagatcatcg atagcaatcg tctgctggaa atcgtggaat ataacattag cggtgcagaa    2100
cgtaccgcac atattagcgg tctgcctccg agcaccgatt ttattgttta tctgagcggt    2160
ctggcaccga gctttcgtac caaaaccatt agcgcaaccg caaccaccga agcactgacc    2220
gcaatgggta gcccgaaaga agtgattttt agcgatatta ccgaaaatag cgccaccgtt    2280
```

-continued

```
tcatggcgtg caccgaccgc acaggttgaa agctttcgta ttacctatgt tccgattacc    2340
ggtggcaccc cgagcatggt taccgtggat ggcaccaaaa cccagacccg tctggttaaa    2400
ctggttccgg tgttgaata tctggtgaat atcattgcca tgaaaggctt tgaagaaagc    2460
gaaccggtta gcggtagctt taccaccgct agcggcctga acgacatctt cgaggctcag    2520
aaaatcgaat ggcacgaagg tacccatcac catcaccacc actaa    2565
```

<210> SEQ ID NO 170
<211> LENGTH: 1033
<212> TYPE: PRT
<213> ORGANISM: Artificial Sequence
<220> FEATURE:
<223> OTHER INFORMATION: human TnC with C-terminal Avi- and His-tags

<400> SEQUENCE: 170

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320
```

```
Ser Leu Pro Thr Gly Gln Trp Val Gly Val Gln Leu Pro Arg Asn Thr
            325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
            355                 360                 365

Lys Ala Ser Thr Glu Gln Ala Pro Glu Leu Glu Asn Leu Thr Val Thr
            370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
            405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
            435                 440                 445

Ile Gln Gly Tyr Arg Thr Pro Val Leu Ser Ala Glu Ala Ser Thr Gly
            450                 455                 460

Glu Thr Pro Asn Leu Gly Glu Val Val Val Ala Glu Val Gly Trp Asp
465                 470                 475                 480

Ala Leu Lys Leu Asn Trp Thr Ala Pro Glu Gly Ala Tyr Glu Tyr Phe
            485                 490                 495

Phe Ile Gln Val Gln Glu Ala Asp Thr Val Glu Ala Ala Gln Asn Leu
            500                 505                 510

Thr Val Pro Gly Gly Leu Arg Ser Thr Asp Leu Pro Gly Leu Lys Ala
            515                 520                 525

Ala Thr His Tyr Thr Ile Thr Ile Arg Gly Val Thr Gln Asp Phe Ser
            530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
            565                 570                 575

Trp Thr Thr Pro Asp Gly Thr Tyr Asp Gln Phe Thr Ile Gln Val Gln
            580                 585                 590

Glu Ala Asp Gln Val Glu Glu Ala His Asn Leu Thr Val Pro Gly Ser
            595                 600                 605

Leu Arg Ser Met Glu Ile Pro Gly Leu Arg Ala Gly Thr Pro Tyr Thr
            610                 615                 620

Val Thr Leu His Gly Glu Val Arg Gly His Ser Thr Arg Pro Leu Ala
625                 630                 635                 640

Val Glu Val Val Thr Glu Asp Leu Pro Gln Leu Gly Asp Leu Ala Val
            645                 650                 655

Ser Glu Val Gly Trp Asp Gly Leu Arg Leu Asn Trp Thr Ala Ala Asp
            660                 665                 670

Asn Ala Tyr Glu His Phe Val Ile Gln Val Gln Glu Val Asn Lys Val
            675                 680                 685

Glu Ala Ala Gln Asn Leu Thr Leu Pro Gly Ser Leu Arg Ala Val Asp
            690                 695                 700

Ile Pro Gly Leu Glu Ala Ala Thr Pro Tyr Arg Val Ser Ile Tyr Gly
705                 710                 715                 720

Val Ile Arg Gly Tyr Arg Thr Pro Val Leu Ser Ala Glu Ala Ser Thr
            725                 730                 735
```

Ala Lys Glu Pro Glu Ile Gly Asn Leu Asn Val Ser Asp Ile Thr Pro
            740                 745                 750

Glu Ser Phe Asn Leu Ser Trp Met Ala Thr Asp Gly Ile Phe Glu Thr
        755                 760                 765

Phe Thr Ile Glu Ile Asp Ser Asn Arg Leu Leu Glu Thr Val Glu
    770                 775                 780

Tyr Asn Ile Ser Gly Ala Glu Arg Thr Ala His Ile Ser Gly Leu Pro
785                 790                 795                 800

Pro Ser Thr Asp Phe Ile Val Tyr Leu Ser Gly Leu Ala Pro Ser Ile
                805                 810                 815

Arg Thr Lys Thr Ile Ser Ala Thr Ala Thr Thr Glu Ala Leu Pro Leu
                820                 825                 830

Leu Glu Asn Leu Thr Ile Ser Asp Ile Asn Pro Tyr Gly Phe Thr Val
                835                 840                 845

Ser Trp Met Ala Ser Glu Asn Ala Phe Asp Ser Phe Leu Val Thr Val
        850                 855                 860

Val Asp Ser Gly Lys Leu Leu Asp Pro Gln Glu Phe Thr Leu Ser Gly
865                 870                 875                 880

Thr Gln Arg Lys Leu Glu Leu Arg Gly Leu Ile Thr Gly Ile Gly Tyr
                885                 890                 895

Glu Val Met Val Ser Gly Phe Thr Gln Gly His Gln Thr Lys Pro Leu
            900                 905                 910

Arg Ala Glu Ile Val Thr Glu Ala Met Gly Ser Pro Lys Glu Val Ile
            915                 920                 925

Phe Ser Asp Ile Thr Glu Asn Ser Ala Thr Val Ser Trp Arg Ala Pro
        930                 935                 940

Thr Ala Gln Val Glu Ser Phe Arg Ile Thr Tyr Val Pro Ile Thr Gly
945                 950                 955                 960

Gly Thr Pro Ser Met Val Thr Val Asp Gly Thr Lys Thr Gln Thr Arg
                965                 970                 975

Leu Val Lys Leu Ile Pro Gly Val Glu Tyr Leu Val Ser Ile Ile Ala
                980                 985                 990

Met Lys Gly Phe Glu Glu Ser Glu Pro Val Ser Gly Ser Phe Thr Thr
            995                 1000                1005

Ala Ser Gly Leu Asn Asp Ile Phe Glu Ala Gln Lys Ile Glu Trp
    1010                1015                1020

His Glu Gly Thr His His His His His His
1025                1030

<210> SEQ ID NO 171
<211> LENGTH: 854
<212> TYPE: PRT
<213> ORGANISM: Artificial Sequence
<220> FEATURE:
<223> OTHER INFORMATION: mouse TnC with C-terminal Avi- and His-tags

<400> SEQUENCE: 171

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

-continued

```
Leu Thr Gln Ser Met Ala Ile Ile Arg Tyr Ile Ala Asp Lys His Asn
 65                  70                  75                  80

Met Leu Gly Gly Cys Pro Lys Glu Arg Ala Glu Ile Ser Met Leu Glu
                 85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Glu Val Pro Ser Leu Glu Asn Leu Thr Val Thr
370                 375                 380

Glu Ala Gly Trp Asp Gly Leu Arg Leu Asn Trp Thr Ala Asp Asp Leu
385                 390                 395                 400

Ala Tyr Glu Tyr Phe Val Ile Gln Val Gln Glu Ala Asn Asn Val Glu
                405                 410                 415

Thr Ala His Asn Phe Thr Val Pro Gly Asn Leu Arg Ala Ala Asp Ile
            420                 425                 430

Pro Gly Leu Lys Val Ala Thr Ser Tyr Arg Val Ser Ile Tyr Gly Val
        435                 440                 445

Ala Arg Gly Tyr Arg Thr Pro Val Leu Ser Ala Glu Thr Ser Thr Gly
450                 455                 460

Thr Thr Pro Asn Leu Gly Glu Val Thr Val Ala Glu Val Gly Trp Asp
465                 470                 475                 480

Ala Leu Thr Leu Asn Trp Thr Ala Pro Glu Gly Ala Tyr Lys Asn Phe
```

```
                       485                 490                495
Phe Ile Gln Val Leu Glu Ala Asp Thr Thr Gln Thr Val Gln Asn Leu
                    500                 505                 510

Thr Val Pro Gly Gly Leu Arg Ser Val Asp Leu Pro Gly Leu Lys Ala
                515                 520                 525

Ala Thr Arg Tyr Tyr Ile Thr Leu Arg Gly Val Thr Gln Asp Phe Gly
            530                 535                 540

Thr Ala Pro Leu Ser Val Glu Val Leu Thr Glu Asp Leu Pro Gln Leu
545                 550                 555                 560

Gly Gly Leu Ser Val Thr Glu Val Ser Trp Asp Gly Leu Thr Leu Asn
                565                 570                 575

Trp Thr Thr Asp Asp Leu Ala Tyr Lys His Phe Val Val Gln Val Gln
                580                 585                 590

Glu Ala Asn Asn Val Glu Ala Ala Gln Asn Leu Thr Val Pro Gly Ser
                595                 600                 605

Leu Arg Ala Val Asp Ile Pro Gly Leu Lys Ala Asp Thr Pro Tyr Arg
            610                 615                 620

Val Ser Ile Tyr Gly Val Ile Gln Gly Tyr Arg Thr Pro Met Leu Ser
625                 630                 635                 640

Thr Asp Val Ser Thr Ala Arg Glu Pro Glu Ile Gly Asn Leu Asn Val
                645                 650                 655

Ser Asp Val Thr Pro Lys Ser Phe Asn Leu Ser Trp Thr Ala Thr Asp
                660                 665                 670

Gly Ile Phe Asp Met Phe Thr Ile Glu Ile Asp Ser Asn Arg Leu
            675                 680                 685

Leu Gln Thr Ala Glu His Asn Ile Ser Gly Ala Glu Arg Thr Ala His
            690                 695                 700

Ile Ser Gly Leu Pro Pro Ser Thr Asp Phe Ile Val Tyr Leu Ser Gly
705                 710                 715                 720

Ile Ala Pro Ser Ile Arg Thr Lys Thr Ile Ser Thr Thr Ala Thr Thr
                725                 730                 735

Glu Ala Leu Thr Ala Met Gly Ser Pro Lys Glu Val Ile Phe Ser Asp
            740                 745                 750

Ile Thr Glu Asn Ser Ala Thr Val Ser Trp Arg Ala Pro Thr Ala Gln
            755                 760                 765

Val Glu Ser Phe Arg Ile Thr Tyr Val Pro Ile Thr Gly Gly Thr Pro
            770                 775                 780

Ser Met Val Thr Val Asp Gly Thr Lys Thr Gln Thr Arg Leu Val Lys
785                 790                 795                 800

Leu Ile Pro Gly Val Glu Tyr Leu Val Ser Ile Ile Ala Met Lys Gly
                805                 810                 815

Phe Glu Glu Ser Glu Pro Val Ser Gly Ser Phe Thr Thr Ala Ser Gly
            820                 825                 830

Leu Asn Asp Ile Phe Glu Ala Gln Lys Ile Glu Trp His Glu Gly Thr
            835                 840                 845

His His His His His His
    850

<210> SEQ ID NO 172
<211> LENGTH: 854
<212> TYPE: PRT
<213> ORGANISM: Artificial Sequence
<220> FEATURE:
<223> OTHER INFORMATION: cynomolgus TnC with C-terminal Avi- and
      His-tags
```

<400> SEQUENCE: 172

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Arg Val Ser Glu Thr Ala Glu Thr Ser Leu Thr Leu
    290                 295                 300

Phe Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Gln Ala Pro Glu Leu Glu Asn Leu Thr Val Thr
    370                 375                 380

Glu Val Gly Trp Asp Gly Leu Arg Leu Asn Trp Thr Ala Ala Asp Gln
385                 390                 395                 400

Ala Tyr Glu His Phe Val Ile Gln Val Gln Glu Ala Asn Lys Val Glu

```
            405                 410                 415
Ala Ala Gln Asn Leu Thr Val Pro Gly Asn Leu Arg Ala Val Asp Ile
            420                 425                 430
Pro Gly Leu Lys Ala Ala Thr Pro Tyr Thr Val Ser Ile Tyr Gly Val
            435                 440                 445
Ile Gln Gly Tyr Arg Thr Pro Val Leu Ser Ala Glu Ala Ser Thr Gly
            450                 455                 460
Glu Thr Pro Asn Leu Gly Glu Val Met Val Ser Glu Val Gly Trp Asp
465                 470                 475                 480
Ala Leu Lys Leu Asn Trp Thr Val Pro Glu Gly Ala Tyr Glu Tyr Phe
            485                 490                 495
Phe Ile Gln Val Gln Glu Ala Asp Thr Val Glu Ala Ala Gln Asn His
            500                 505                 510
Thr Val Pro Gly Gly Leu Arg Ser Thr Asp Leu Pro Gly Leu Lys Ala
            515                 520                 525
Ala Thr His Tyr Thr Ile Thr Ile Arg Gly Val Thr Gln Asp Phe Ser
            530                 535                 540
Thr Thr Pro Leu Ser Val Glu Val Leu Thr Glu Glu Leu Pro Gln Leu
545                 550                 555                 560
Gly Asp Leu Ala Val Ser Glu Val Gly Trp Asp Gly Leu Arg Leu Asn
            565                 570                 575
Trp Thr Ala Ala Asp Gln Ala Tyr Glu His Phe Val Ile Gln Val Gln
            580                 585                 590
Glu Val Asn Lys Val Glu Ala Ala Gln Asn Leu Thr Val Pro Gly Ser
            595                 600                 605
Leu Arg Ala Val Asp Ile Pro Gly Leu Lys Ala Ala Thr Pro Tyr Thr
            610                 615                 620
Val Ser Ile Tyr Gly Val Ile Arg Gly Tyr Arg Thr Pro Val Leu Ser
625                 630                 635                 640
Ala Glu Ala Ser Thr Ala Lys Glu Pro Glu Ile Gly Asn Leu Asn Val
            645                 650                 655
Ser Asp Ile Thr Pro Glu Ser Phe Ser Leu Ser Trp Thr Ala Thr Asp
            660                 665                 670
Gly Ile Phe Glu Thr Phe Thr Ile Glu Ile Ile Asp Ser Asn Arg Leu
            675                 680                 685
Leu Glu Ile Val Glu Tyr Asn Ile Ser Gly Ala Glu Arg Thr Ala His
            690                 695                 700
Ile Ser Gly Leu Pro Pro Ser Thr Asp Phe Ile Val Tyr Leu Ser Gly
705                 710                 715                 720
Leu Ala Pro Ser Phe Arg Thr Lys Thr Ile Ser Ala Thr Ala Thr Thr
            725                 730                 735
Glu Ala Leu Thr Ala Met Gly Ser Pro Lys Glu Val Ile Phe Ser Asp
            740                 745                 750
Ile Thr Glu Asn Ser Ala Thr Val Ser Trp Arg Ala Pro Thr Ala Gln
            755                 760                 765
Val Glu Ser Phe Arg Ile Thr Tyr Val Pro Ile Thr Gly Gly Thr Pro
            770                 775                 780
Ser Met Val Thr Val Asp Gly Thr Lys Thr Gln Thr Arg Leu Val Lys
785                 790                 795                 800
Leu Val Pro Gly Val Glu Tyr Leu Val Asn Ile Ile Ala Met Lys Gly
            805                 810                 815
Phe Glu Glu Ser Glu Pro Val Ser Gly Ser Phe Thr Thr Ala Ser Gly
            820                 825                 830
```

Leu Asn Asp Ile Phe Glu Ala Gln Lys Ile Glu Trp His Glu Gly Thr
                835                 840                 845

His His His His His His
    850

<210> SEQ ID NO 173
<211> LENGTH: 1033
<212> TYPE: PRT
<213> ORGANISM: Artificial Sequence
<220> FEATURE:
<223> OTHER INFORMATION: GST huTnC fn5 A1234 BC fn6 B

<400> SEQUENCE: 173

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Lys Phe Glu
                245                 250                 255

Arg Gln His Met Asp Ser Pro Asp Leu Gly Thr Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

```
Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
            355                 360                 365

Lys Ala Ser Thr Glu Gln Ala Pro Glu Leu Glu Asn Leu Thr Val Thr
            370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
            420                 425                 430

Pro Gly Leu Lys Ala Ala Thr Pro Tyr Thr Val Ser Ile Tyr Gly Val
            435                 440                 445

Ile Gln Gly Tyr Arg Thr Pro Val Leu Ser Ala Glu Ala Ser Thr Gly
            450                 455                 460

Glu Thr Pro Asn Leu Gly Glu Val Val Ala Glu Val Gly Trp Asp
465                 470                 475                 480

Ala Leu Lys Leu Asn Trp Thr Ala Pro Glu Gly Ala Tyr Glu Tyr Phe
                485                 490                 495

Phe Ile Gln Val Gln Glu Ala Asp Thr Val Glu Ala Ala Gln Asn Leu
            500                 505                 510

Thr Val Pro Gly Gly Leu Arg Ser Thr Asp Leu Pro Gly Leu Lys Ala
            515                 520                 525

Ala Thr His Tyr Thr Ile Thr Ile Arg Gly Val Thr Gln Asp Phe Ser
            530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
            580                 585                 590

Glu Ala Asp Gln Val Glu Glu Ala His Asn Leu Thr Val Pro Gly Ser
            595                 600                 605

Leu Arg Ser Met Glu Ile Pro Gly Leu Arg Ala Gly Thr Pro Tyr Thr
            610                 615                 620

Val Thr Leu His Gly Glu Val Arg Gly His Ser Thr Arg Pro Leu Ala
625                 630                 635                 640

Val Glu Val Val Thr Glu Asp Leu Pro Gln Leu Gly Asp Leu Ala Val
                645                 650                 655

Ser Glu Val Gly Trp Asp Gly Leu Arg Leu Asn Trp Thr Ala Ala Asp
            660                 665                 670

Asn Ala Tyr Glu His Phe Val Ile Gln Val Gln Glu Val Asn Lys Val
            675                 680                 685

Glu Ala Ala Gln Asn Leu Thr Leu Pro Gly Ser Leu Arg Ala Val Asp
            690                 695                 700

Ile Pro Gly Leu Glu Ala Ala Thr Pro Tyr Arg Val Ser Ile Tyr Gly
705                 710                 715                 720

Val Ile Arg Gly Tyr Arg Thr Pro Val Leu Ser Ala Glu Ala Ser Thr
                725                 730                 735

Ala Lys Glu Pro Glu Ile Gly Asn Leu Asn Val Ser Asp Ile Thr Pro
            740                 745                 750
```

```
Glu Ser Phe Asn Leu Ser Trp Met Ala Thr Asp Gly Ile Phe Glu Thr
            755                 760                 765

Phe Thr Ile Glu Ile Ile Asp Ser Asn Arg Leu Leu Glu Thr Val Glu
    770                 775                 780

Tyr Asn Ile Ser Gly Ala Glu Arg Thr Ala His Ile Ser Gly Leu Pro
785                 790                 795                 800

Pro Ser Thr Asp Phe Ile Val Tyr Leu Ser Gly Leu Ala Pro Ser Ile
                805                 810                 815

Arg Thr Lys Thr Ile Ser Ala Thr Ala Thr Thr Glu Ala Leu Pro Leu
            820                 825                 830

Leu Glu Asn Leu Thr Ile Ser Asp Ile Asn Pro Tyr Gly Phe Thr Val
                835                 840                 845

Ser Trp Met Ala Ser Glu Asn Ala Phe Asp Ser Phe Leu Val Thr Val
850                 855                 860

Val Asp Ser Gly Lys Leu Leu Asp Pro Gln Glu Phe Thr Leu Ser Gly
865                 870                 875                 880

Thr Gln Arg Lys Leu Glu Leu Arg Gly Leu Ile Thr Gly Ile Gly Tyr
                885                 890                 895

Glu Val Met Val Ser Gly Phe Thr Gln Gly His Gln Thr Lys Pro Leu
                900                 905                 910

Arg Ala Glu Ile Val Thr Glu Ala Met Gly Ser Pro Lys Glu Val Ile
            915                 920                 925

Phe Ser Asp Ile Thr Glu Asn Ser Ala Thr Val Ser Trp Arg Ala Pro
            930                 935                 940

Thr Ala Gln Val Glu Ser Phe Arg Ile Thr Tyr Val Pro Ile Thr Gly
945                 950                 955                 960

Gly Thr Pro Ser Met Val Thr Val Asp Gly Thr Lys Thr Gln Thr Arg
                965                 970                 975

Leu Val Lys Leu Ile Pro Gly Val Glu Tyr Leu Val Ser Ile Ile Ala
                980                 985                 990

Met Lys Gly Phe Glu Glu Ser Glu Pro Val Ser Gly Ser Phe Thr Thr
            995                 1000                1005

Ala Ser Gly Leu Asn Asp Ile Phe Glu Ala Gln Lys Ile Glu Trp
    1010                1015                1020

His Glu Gly Thr His His His His His His
1025                1030

<210> SEQ ID NO 174
<211> LENGTH: 941
<212> TYPE: PRT
<213> ORGANISM: Artificial Sequence
<220> FEATURE:
<223> OTHER INFORMATION: GST huTnCfn5 mu A124 BC hu fn6 B

<400> SEQUENCE: 174

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80
```

```
Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

Leu Leu Thr Ala Glu Lys Gly Arg His Lys Ser Lys Pro Ala Arg Val
        355                 360                 365

Lys Ala Ser Thr Glu Glu Val Pro Ser Leu Glu Asn Leu Thr Val Thr
    370                 375                 380

Glu Ala Gly Trp Asp Gly Leu Arg Leu Asn Trp Thr Ala Asp Asp Leu
385                 390                 395                 400

Ala Tyr Glu Tyr Phe Val Ile Gln Val Gln Glu Ala Asn Asn Val Glu
                405                 410                 415

Thr Ala His Asn Phe Thr Val Pro Gly Asn Leu Arg Ala Ala Asp Ile
            420                 425                 430

Pro Gly Leu Lys Val Ala Thr Ser Tyr Arg Val Ser Ile Tyr Gly Val
        435                 440                 445

Ala Arg Gly Tyr Arg Thr Pro Val Leu Ser Ala Glu Thr Ser Thr Gly
    450                 455                 460

Thr Thr Pro Asn Leu Gly Glu Val Thr Val Ala Glu Val Gly Trp Asp
465                 470                 475                 480

Ala Leu Thr Leu Asn Trp Thr Ala Pro Glu Gly Ala Tyr Lys Asn Phe
                485                 490                 495

Phe Ile Gln Val Leu Glu Ala Asp Thr Thr Gln Thr Val Gln Asn Leu
```

```
                  500                 505                 510
Thr Val Pro Gly Gly Leu Arg Ser Val Asp Leu Pro Gly Leu Lys Ala
            515                 520                 525
Ala Thr Arg Tyr Tyr Ile Thr Leu Arg Gly Val Thr Gln Asp Phe Gly
            530                 535                 540
Thr Ala Pro Leu Ser Val Glu Val Leu Thr Glu Asp Leu Pro Gln Leu
545                 550                 555                 560
Gly Gly Leu Ser Val Thr Glu Val Ser Trp Asp Gly Leu Thr Leu Asn
                565                 570                 575
Trp Thr Thr Asp Asp Leu Ala Tyr Lys His Phe Val Gln Val Gln
            580                 585                 590
Glu Ala Asn Asn Val Glu Ala Ala Gln Asn Leu Thr Val Pro Gly Ser
            595                 600                 605
Leu Arg Ala Val Asp Ile Pro Gly Leu Lys Ala Asp Thr Pro Tyr Arg
            610                 615                 620
Val Ser Ile Tyr Gly Val Ile Gln Gly Tyr Arg Thr Pro Met Leu Ser
625                 630                 635                 640
Thr Asp Val Ser Thr Ala Arg Glu Pro Glu Ile Gly Asn Leu Asn Val
                645                 650                 655
Ser Asp Val Thr Pro Lys Ser Phe Asn Leu Ser Trp Thr Ala Thr Asp
                660                 665                 670
Gly Ile Phe Asp Met Phe Thr Ile Glu Ile Asp Ser Asn Arg Leu
            675                 680                 685
Leu Gln Thr Ala Glu His Asn Ile Ser Gly Ala Glu Arg Thr Ala His
            690                 695                 700
Ile Ser Gly Leu Pro Pro Ser Thr Asp Phe Ile Val Tyr Leu Ser Gly
705                 710                 715                 720
Ile Ala Pro Ser Ile Arg Thr Lys Thr Ile Ser Thr Ala Thr Thr
            725                 730                 735
Glu Ala Leu Pro Leu Leu Glu Asn Leu Thr Ile Ser Asp Thr Asn Pro
            740                 745                 750
Tyr Gly Phe Thr Val Ser Trp Thr Ala Ser Glu Asn Ala Phe Asp Ser
            755                 760                 765
Phe Leu Val Thr Val Asp Ser Gly Lys Leu Leu Asp Pro Gln Glu
770                 775                 780
Phe Thr Leu Ser Gly Thr Gln Arg Lys Leu Glu Leu Arg Gly Leu Ile
785                 790                 795                 800
Thr Gly Ile Gly Tyr Glu Val Leu Val Ser Gly Phe Thr Gln Gly His
                805                 810                 815
Gln Thr Lys Pro Leu Arg Ala Glu Thr Ile Thr Ala Met Gly Ser Pro
            820                 825                 830
Lys Glu Val Ile Phe Ser Asp Ile Thr Glu Asn Ser Ala Thr Val Ser
            835                 840                 845
Trp Arg Ala Pro Thr Ala Gln Val Glu Ser Phe Arg Ile Thr Tyr Val
            850                 855                 860
Pro Ile Thr Gly Gly Thr Pro Ser Met Val Thr Val Asp Gly Thr Lys
865                 870                 875                 880
Thr Gln Thr Arg Leu Val Lys Leu Ile Pro Gly Val Glu Tyr Leu Val
                885                 890                 895
Ser Ile Ile Ala Met Lys Gly Phe Glu Glu Ser Glu Pro Val Ser Gly
            900                 905                 910
Ser Phe Thr Thr Ala Ser Gly Leu Asn Asp Ile Phe Glu Ala Gln Lys
            915                 920                 925
```

Ile Glu Trp His Glu Gly Thr His His His His His
930                935                940

<210> SEQ ID NO 175
<211> LENGTH: 668
<212> TYPE: PRT
<213> ORGANISM: Artificial Sequence
<220> FEATURE:
<223> OTHER INFORMATION: GST TnC hu fn5 B-C fn6 B

<400> SEQUENCE: 175

Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Asp His Pro Pro Lys Ser Asp Gly Ser Thr Ser
    210                 215                 220

Gly Ser Gly His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Leu Asp Thr
        275                 280                 285

Pro Lys Asp Leu Gln Val Ser Glu Thr Ala Glu Thr Ser Leu Thr Leu
    290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
            340                 345                 350

```
Leu Leu Thr Ala Glu Lys Gly Arg His Lys Ser Lys Pro Ala Arg Val
            355                 360                 365

Lys Ala Ser Thr Ala Lys Glu Pro Glu Ile Gly Asn Leu Asn Val Ser
        370                 375                 380

Asp Ile Thr Pro Glu Ser Phe Asn Leu Ser Trp Met Ala Thr Asp Gly
385                 390                 395                 400

Ile Phe Glu Thr Phe Thr Ile Glu Ile Asp Ser Asn Arg Leu Leu
                405                 410                 415

Glu Thr Val Glu Tyr Asn Ile Ser Gly Ala Glu Arg Thr Ala His Ile
            420                 425                 430

Ser Gly Leu Pro Pro Ser Thr Asp Phe Ile Val Tyr Leu Ser Gly Leu
        435                 440                 445

Ala Pro Ser Ile Arg Thr Lys Thr Ile Ser Ala Thr Ala Thr Glu
450                 455                 460

Ala Leu Pro Leu Leu Glu Asn Leu Thr Ile Ser Asp Ile Asn Pro Tyr
465                 470                 475                 480

Gly Phe Thr Val Ser Trp Met Ala Ser Glu Asn Ala Phe Asp Ser Phe
                485                 490                 495

Leu Val Thr Val Val Asp Ser Gly Lys Leu Leu Asp Pro Gln Glu Phe
            500                 505                 510

Thr Leu Ser Gly Thr Gln Arg Lys Leu Glu Leu Arg Gly Leu Ile Thr
        515                 520                 525

Gly Ile Gly Tyr Glu Val Met Val Ser Gly Phe Thr Gln Gly His Gln
530                 535                 540

Thr Lys Pro Leu Arg Ala Glu Ile Val Thr Ala Met Gly Ser Pro Lys
545                 550                 555                 560

Glu Val Ile Phe Ser Asp Ile Thr Glu Asn Ser Ala Thr Val Ser Trp
                565                 570                 575

Arg Ala Pro Thr Ala Gln Val Glu Ser Phe Arg Ile Thr Tyr Val Pro
            580                 585                 590

Ile Thr Gly Gly Thr Pro Ser Met Val Thr Val Asp Gly Thr Lys Thr
        595                 600                 605

Gln Thr Arg Leu Val Lys Leu Ile Pro Gly Val Glu Tyr Leu Val Ser
610                 615                 620

Ile Ile Ala Met Lys Gly Phe Glu Glu Ser Glu Pro Val Ser Gly Ser
625                 630                 635                 640

Phe Thr Thr Ala Ser Gly Leu Asn Asp Ile Phe Glu Ala Gln Lys Ile
                645                 650                 655

Glu Trp His Glu Gly Thr His His His His His
            660                 665
```

<210> SEQ ID NO 176
<211> LENGTH: 853
<212> TYPE: PRT
<213> ORGANISM: Artificial Sequence
<220> FEATURE:
<223> OTHER INFORMATION: GST huTnC fn5 A1234 fn6 B

<400> SEQUENCE: 176

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45
```

```
Gly Leu Glu Phe Pro Asn Leu Pro Tyr Tyr Ile Asp Gly Asp Val Lys
 50                  55                  60

Leu Thr Gln Ser Met Ala Ile Ile Arg Tyr Ile Ala Asp Lys His Asn
 65                      70                  75                  80

Met Leu Gly Gly Cys Pro Lys Glu Arg Ala Glu Ile Ser Met Leu Glu
                     85                  90                  95

Gly Ala Val Leu Asp Ile Arg Tyr Gly Val Ser Arg Ile Ala Tyr Ser
                100                 105                 110

Lys Asp Phe Glu Thr Leu Lys Val Asp Phe Leu Ser Lys Leu Pro Glu
            115                 120                 125

Met Leu Lys Met Phe Glu Asp Arg Leu Cys His Lys Thr Tyr Leu Asn
        130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
                180                 185                 190

Leu Lys Ser Ser Lys Tyr Ile Ala Trp Pro Leu Gln Gly Trp Gln Ala
            195                 200                 205

Thr Phe Gly Gly Gly Asp His Pro Pro Lys Ser Asp Gly Ser Thr Ser
        210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
                260                 265                 270

Ile Glu Gly Arg Gly Ser Met Gly Tyr Arg Gly Ser Glu Leu Asp Thr
            275                 280                 285

Pro Lys Asp Leu Gln Val Ser Glu Thr Ala Glu Thr Ser Leu Thr Leu
        290                 295                 300

Leu Trp Lys Thr Pro Leu Ala Lys Phe Asp Arg Tyr Arg Leu Asn Tyr
305                 310                 315                 320

Ser Leu Pro Thr Gly Gln Trp Val Gly Val Gln Leu Pro Arg Asn Thr
                325                 330                 335

Thr Ser Tyr Val Leu Arg Gly Leu Glu Pro Gly Gln Glu Tyr Asn Val
                340                 345                 350

Leu Leu Thr Ala Glu Lys Gly Arg His Lys Ser Lys Pro Ala Arg Val
            355                 360                 365

Lys Ala Ser Thr Glu Gln Ala Pro Glu Leu Glu Asn Leu Thr Val Thr
        370                 375                 380

Glu Val Gly Trp Asp Gly Leu Arg Leu Asn Trp Thr Ala Ala Asp Gln
385                 390                 395                 400

Ala Tyr Glu His Phe Ile Ile Gln Val Gln Glu Ala Asn Lys Val Glu
                405                 410                 415

Ala Ala Arg Asn Leu Thr Val Pro Gly Ser Leu Arg Ala Val Asp Ile
                420                 425                 430

Pro Gly Leu Lys Ala Ala Thr Pro Tyr Thr Val Ser Ile Tyr Gly Val
            435                 440                 445

Ile Gln Gly Tyr Arg Thr Pro Val Leu Ser Ala Glu Ala Ser Thr Gly
        450                 455                 460
```

Glu Thr Pro Asn Leu Gly Glu Val Val Ala Val Gly Trp Asp
465                 470                 475                 480

Ala Leu Lys Leu Asn Trp Thr Ala Pro Glu Gly Ala Tyr Glu Tyr Phe
                485                 490                 495

Phe Ile Gln Val Gln Glu Ala Asp Thr Val Glu Ala Ala Gln Asn Leu
            500                 505                 510

Thr Val Pro Gly Gly Leu Arg Ser Thr Asp Leu Pro Gly Leu Lys Ala
        515                 520                 525

Ala Thr His Tyr Thr Ile Thr Ile Arg Gly Val Thr Gln Asp Phe Ser
    530                 535                 540

Thr Thr Pro Leu Ser Val Glu Val Leu Thr Glu Glu Val Pro Asp Met
545                 550                 555                 560

Gly Asn Leu Thr Val Thr Glu Val Ser Trp Asp Ala Leu Arg Leu Asn
                565                 570                 575

Trp Thr Thr Pro Asp Gly Thr Tyr Asp Gln Phe Thr Ile Gln Val Gln
            580                 585                 590

Glu Ala Asp Gln Val Glu Ala His Asn Leu Thr Val Pro Gly Ser
        595                 600                 605

Leu Arg Ser Met Glu Ile Pro Gly Leu Arg Ala Gly Thr Pro Tyr Thr
    610                 615                 620

Val Thr Leu His Gly Glu Val Arg Gly His Ser Thr Arg Pro Leu Ala
625                 630                 635                 640

Val Glu Val Val Thr Glu Asp Leu Pro Gln Leu Gly Asp Leu Ala Val
                645                 650                 655

Ser Glu Val Gly Trp Asp Gly Leu Arg Leu Asn Trp Thr Ala Ala Asp
            660                 665                 670

Asn Ala Tyr Glu His Phe Val Ile Gln Val Gln Glu Val Asn Lys Val
        675                 680                 685

Glu Ala Ala Gln Asn Leu Thr Leu Pro Gly Ser Leu Arg Ala Val Asp
    690                 695                 700

Ile Pro Gly Leu Glu Ala Ala Thr Pro Tyr Arg Val Ser Ile Tyr Gly
705                 710                 715                 720

Val Ile Arg Gly Tyr Arg Thr Pro Val Leu Ser Ala Glu Ala Ser Thr
                725                 730                 735

Ala Lys Glu Ala Met Gly Ser Pro Lys Glu Val Ile Phe Ser Asp Ile
            740                 745                 750

Thr Glu Asn Ser Ala Thr Val Ser Trp Arg Ala Pro Thr Ala Gln Val
        755                 760                 765

Glu Ser Phe Arg Ile Thr Tyr Val Pro Ile Thr Gly Gly Thr Pro Ser
    770                 775                 780

Met Val Thr Val Asp Gly Thr Lys Thr Gln Thr Arg Leu Val Lys Leu
785                 790                 795                 800

Ile Pro Gly Val Glu Tyr Leu Val Ser Ile Ile Ala Met Lys Gly Phe
                805                 810                 815

Glu Glu Ser Glu Pro Val Ser Gly Ser Phe Thr Thr Ala Ser Gly Leu
            820                 825                 830

Asn Asp Ile Phe Glu Ala Gln Lys Ile Glu Trp His Glu Gly Thr His
        835                 840                 845

His His His His His
        850

<210> SEQ ID NO 177
<211> LENGTH: 400
<212> TYPE: PRT

<213> ORGANISM: Artificial Sequence
<220> FEATURE:
<223> OTHER INFORMATION: huTnC A4 B

<400> SEQUENCE: 177

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Asp Leu Pro
        275                 280                 285

Gln Leu Gly Asp Leu Ala Val Ser Glu Val Gly Trp Asp Gly Leu Arg
290                 295                 300

Leu Asn Trp Thr Ala Ala Asp Asn Ala Tyr Glu His Phe Val Ile Gln
305                 310                 315                 320

Val Gln Glu Val Asn Lys Val Glu Ala Ala Gln Asn Leu Thr Leu Pro
                325                 330                 335

Gly Ser Leu Arg Ala Val Asp Ile Pro Gly Leu Glu Ala Ala Thr Pro
            340                 345                 350

Tyr Arg Val Ser Ile Tyr Gly Val Ile Arg Gly Tyr Arg Thr Pro Val
        355                 360                 365

Leu Ser Ala Glu Ala Ser Thr Ala Ser Gly Leu Asn Asp Ile Phe Glu
370                 375                 380

Ala Gln Lys Ile Glu Trp His Glu Gly Thr His His His His His His
```

385 390 395 400

<210> SEQ ID NO 178
<211> LENGTH: 400
<212> TYPE: PRT
<213> ORGANISM: Artificial Sequence
<220> FEATURE:
<223> OTHER INFORMATION: huTnC A1 B

<400> SEQUENCE: 178

```
Met Ser Pro Ile Leu Gly Tyr Trp Lys Ile Lys Gly Leu Val Gln Pro
1               5                   10                  15

Thr Arg Leu Leu Leu Glu Tyr Leu Glu Glu Lys Tyr Glu Glu His Leu
            20                  25                  30

Tyr Glu Arg Asp Glu Gly Asp Lys Trp Arg Asn Lys Lys Phe Glu Leu
        35                  40                  45

Gly Leu Glu Phe Pro Asn Leu Pro Tyr Tyr Ile Asp Gly Asp Val Lys
    50                  55                  60

Leu Thr Gln Ser Met Ala Ile Ile Arg Tyr Ile Ala Asp Lys His Asn
65                  70                  75                  80

Met Leu Gly Gly Cys Pro Lys Glu Arg Ala Glu Ile Ser Met Leu Glu
                85                  90                  95

Gly Ala Val Leu Asp Ile Arg Tyr Gly Val Ser Arg Ile Ala Tyr Ser
            100                 105                 110

Lys Asp Phe Glu Thr Leu Lys Val Asp Phe Leu Ser Lys Leu Pro Glu
        115                 120                 125

Met Leu Lys Met Phe Glu Asp Arg Leu Cys His Lys Thr Tyr Leu Asn
    130                 135                 140

Gly Asp His Val Thr His Pro Asp Phe Met Leu Tyr Asp Ala Leu Asp
145                 150                 155                 160

Val Val Leu Tyr Met Asp Pro Met Cys Leu Asp Ala Phe Pro Lys Leu
                165                 170                 175

Val Cys Phe Lys Lys Arg Ile Glu Ala Ile Pro Gln Ile Asp Lys Tyr
            180                 185                 190

Leu Lys Ser Ser Lys Tyr Ile Ala Trp Pro Leu Gln Gly Trp Gln Ala
        195                 200                 205

Thr Phe Gly Gly Gly Asp His Pro Pro Lys Ser Asp Gly Ser Thr Ser
    210                 215                 220

Gly Ser Gly His His His His His His Ser Ala Gly Leu Val Pro Arg
225                 230                 235                 240

Gly Ser Thr Ala Ile Gly Met Lys Glu Thr Ala Ala Ala Lys Phe Glu
                245                 250                 255

Arg Gln His Met Asp Ser Pro Asp Leu Gly Thr Gly Gly Gly Ser Gly
            260                 265                 270

Ile Glu Gly Arg Gly Ser Met Gly Tyr Arg Gly Ser Glu Gln Ala Pro
        275                 280                 285

Glu Leu Glu Asn Leu Thr Val Thr Glu Val Gly Trp Asp Gly Leu Arg
    290                 295                 300

Leu Asn Trp Thr Ala Ala Asp Gln Ala Tyr Glu His Phe Ile Ile Gln
305                 310                 315                 320

Val Gln Glu Ala Asn Lys Val Glu Ala Ala Arg Asn Leu Thr Val Pro
                325                 330                 335

Gly Ser Leu Arg Ala Val Asp Ile Pro Gly Leu Lys Ala Ala Thr Pro
            340                 345                 350

Tyr Thr Val Ser Ile Tyr Gly Val Ile Gln Gly Tyr Arg Thr Pro Val
```

```
                355                 360                 365
Leu Ser Ala Glu Ala Ser Thr Ala Ser Gly Leu Asn Asp Ile Phe Glu
    370                 375                 380

Ala Gln Lys Ile Glu Trp His Glu Gly Thr His His His His His
385                 390                 395                 400

<210> SEQ ID NO 179
<211> LENGTH: 324
<212> TYPE: DNA
<213> ORGANISM: Artificial Sequence
<220> FEATURE:
<223> OTHER INFORMATION: Nucleotide sequence TnC(18D4) VL

<400> SEQUENCE: 179
gacatccaga tgacccagtc tccatccacc ctgtctgcat ctgtaggaga ccgtgtcacc    60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag aataagaagt tccttcgggg acgtttggc    300 cagggcacca aagtcgagat caag                                           324

<210> SEQ ID NO 180
<211> LENGTH: 354
<212> TYPE: DNA
<213> ORGANISM: Artificial Sequence
<220> FEATURE:
<223> OTHER INFORMATION: Nucleotide sequence TnC(18D4) VH

<400> SEQUENCE: 180
caggtgcaat ggtgcagtc tggggctgag gtgaagaagc ctgggtcctc ggtgaaggtc    60
tcctgcaagg cctccggagg cacattcagc agctacgcta taagctgggt gcgacaggcc   120
cctggacaag gctcgagtg gatgggaggg atcatcccta tctttggtac agcaaactac   180
gcacagaagt tccagggcag ggtcaccatt actgcagaca aatccacgag cacagcctac   240
atggagctga gcagcctgag atctgaggac accgccgtgt attactgtgc gaaaggtaac   300
ttctacggtg gtctggacta ctggggccaa gggaccaccg tgaccgtctc ctca          354

<210> SEQ ID NO 181
<211> LENGTH: 321
<212> TYPE: DNA
<213> ORGANISM: Artificial Sequence
<220> FEATURE:
<223> OTHER INFORMATION: Nucleotide sequence TnC(11C7) VL

<400> SEQUENCE: 181
tcgtctgagc tgactcagga ccctgctgtg tctgtggcct tgggacagac agtcagggtc    60
acatgccaag agacagcct cagaagttat tatgcaagct ggtaccagca gaagccagga   120
caggcccctg tacttgtcat ctatggtaaa acaaccggc cctcagggat cccagaccga    180
ttctctggct ccagctcagg aaacacagct tccttgacca tcactggggc tcaggcggaa   240
gatgaggctg actattactg taactccatt aatagtactc gtaatgaggt attcggcgga   300
gggaccaagc tgaccgtcct a                                              321

<210> SEQ ID NO 182
<211> LENGTH: 354
<212> TYPE: DNA
<213> ORGANISM: Artificial Sequence
```

```
<220> FEATURE:
<223> OTHER INFORMATION: Nucleotide sequence TnC(11C7)  VH

<400> SEQUENCE: 182
gaggtgcaat tgttggagtc tgggggaggc ttggtacagc ctgggggtc cctgagactc    60 tcctgtgcag cctccggatt cacctttagc agttatgcca tgagctgggt ccgccaggct   120
ccagggaagg ggctggagtg ggtctcagct attagcggta gtggtggtag cacatactac   180
gcagactccg tgaagggccg gttcaccatc tccaaagaca attccaagaa cacgctgtat   240
ctgcagatga acagcctgag agccgaggac acggccgtat attactgtgc gaaaacttct   300
ccgcgtgttc cgctggacta ctggggccaa ggaaccctgg tcaccgtctc gagt          354

<210> SEQ ID NO 183
<211> LENGTH: 33
<212> TYPE: DNA
<213> ORGANISM: Artificial Sequence
<220> FEATURE:
<223> OTHER INFORMATION: Nucleotide sequence TnC(18D4)  CDR-L1

<400> SEQUENCE: 183
cgtgccagtc agagtattag tagctggttg gcc                                 33

<210> SEQ ID NO 184
<211> LENGTH: 33
<212> TYPE: DNA
<213> ORGANISM: Artificial Sequence
<220> FEATURE:
<223> OTHER INFORMATION: Nucleotide sequence TnC(11C7)  CDR-L1

<400> SEQUENCE: 184
caaggagaca gcctcagaag ttattatgca agc                                 33

<210> SEQ ID NO 185
<211> LENGTH: 21
<212> TYPE: DNA
<213> ORGANISM: Artificial Sequence
<220> FEATURE:
<223> OTHER INFORMATION: Nucleotide sequence TnC(18D4)  CDR-L2

<400> SEQUENCE: 185
gatgcctcca gtttggaaag t                                              21

<210> SEQ ID NO 186
<211> LENGTH: 21
<212> TYPE: DNA
<213> ORGANISM: Artificial Sequence
<220> FEATURE:
<223> OTHER INFORMATION: Nucleotide sequence TnC(11C7)  CDR-L2

<400> SEQUENCE: 186
ggtaaaaaca accggccctc a                                              21

<210> SEQ ID NO 187
<211> LENGTH: 30
<212> TYPE: DNA
<213> ORGANISM: Artificial Sequence
<220> FEATURE:
<223> OTHER INFORMATION: Nucleotide sequence TnC(18D4)  CDR-L3

<400> SEQUENCE: 187
caacagaata agaagtttcc ttcggggacg                                     30

<210> SEQ ID NO 188
```

```
<211> LENGTH: 30
<212> TYPE: DNA
<213> ORGANISM: Artificial Sequence
<220> FEATURE:
<223> OTHER INFORMATION: Nucleotide sequence TnC(11C7)  CDR-L3

<400> SEQUENCE: 188
aactccatta atagtactcg taatgaggta                                      30

<210> SEQ ID NO 189
<211> LENGTH: 15
<212> TYPE: DNA
<213> ORGANISM: Artificial Sequence
<220> FEATURE:
<223> OTHER INFORMATION: Nucleotide sequence TnC(18D4)  CDR-H1

<400> SEQUENCE: 189
agctacgcta taagc                                                      15

<210> SEQ ID NO 190
<211> LENGTH: 30
<212> TYPE: DNA
<213> ORGANISM: Artificial Sequence
<220> FEATURE:
<223> OTHER INFORMATION: Nucleotide sequence TnC(11C7)  CDR-H1

<400> SEQUENCE: 190
ggattcacct ttagcagtta tgccatgagc                                      30

<210> SEQ ID NO 191
<211> LENGTH: 51
<212> TYPE: DNA
<213> ORGANISM: Artificial Sequence
<220> FEATURE:
<223> OTHER INFORMATION: Nucleotide sequence TnC(18D4)  CDR-H2

<400> SEQUENCE: 191
gggatcatcc ctatctttgg tacagcaaac tacgcacaga gttccaggg c               51

<210> SEQ ID NO 192
<211> LENGTH: 51
<212> TYPE: DNA
<213> ORGANISM: Artificial Sequence
<220> FEATURE:
<223> OTHER INFORMATION: Nucleotide sequence TnC(11C7)  CDR-H2

<400> SEQUENCE: 192
gctattagcg gtagtggtgg tagcacatac tacgcagact ccgtgaaggg c              51

<210> SEQ ID NO 193
<211> LENGTH: 27
<212> TYPE: DNA
<213> ORGANISM: Artificial Sequence
<220> FEATURE:
<223> OTHER INFORMATION: Nucleotide sequence TnC(18D4)  CDR-H3

<400> SEQUENCE: 193
ggtaacttct acggtggtct ggactac                                         27

<210> SEQ ID NO 194
<211> LENGTH: 27
<212> TYPE: DNA
<213> ORGANISM: Artificial Sequence
<220> FEATURE:
<223> OTHER INFORMATION: Nucleotide sequence TnC(11C7)  CDR-H3

<400> SEQUENCE: 194
```
acttctccgc gtgttccgct ggactac                                            27

<210> SEQ ID NO 195
<211> LENGTH: 645
<212> TYPE: DNA
<213> ORGANISM: Artificial Sequence
<220> FEATURE:
<223> OTHER INFORMATION: Nucleotide sequence TnC(18D4) light chain in
      human IgG1 format

<400> SEQUENCE: 195

```
gacatccaga tgacccagtc tccatccacc ctgtctgcat ctgtaggaga ccgtgtcacc   60
atcacttgcc gtgccagtca gagtattagt agctggttgg cctggtatca gcagaaacca  120
gggaaagccc ctaagctcct gatctatgat gcctccagtt tggaaagtgg ggtcccatca  180
cgtttcagcg gcagtggatc cgggacagaa ttcactctca ccatcagcag cttgcagcct  240
gatgattttg caacttatta ctgccaacag aataagaagt ttccttcggg gacgtttggc  300
cagggcacca aagtcgagat caagcgtacg gtggctgcac catctgtctt catcttcccg  360
ccatctgatg agcagttgaa atctggaact gcctctgttg tgtgcctgct gaataacttc  420
tatcccagag aggccaaagt acagtggaag gtggataacg ccctccaatc gggtaactcc  480
caggagagtg tcacagagca ggacagcaag acagcacct acagcctcag cagcaccctg   540
acgctgagca agcagacta cgagaaacac aaagtctacg cctgcgaagt cacccatcag  600
ggcctgagct cgcccgtcac aaagagcttc aacaggggag agtgt                  645
```

<210> SEQ ID NO 196
<211> LENGTH: 1344
<212> TYPE: DNA
<213> ORGANISM: Artificial Sequence
<220> FEATURE:
<223> OTHER INFORMATION: Nucleotide sequence TnC(18D4) heavy chain in
      human IgG1 format

<400> SEQUENCE: 196

```
caggtgcaat tggtgcagtc tggggctgag gtgaagaagc ctgggtcctc ggtgaaggtc   60
tcctgcaagg cctccggagg cacattcagc agctacgcta taagctgggt gcgacaggcc  120
cctggacaag gctcgagtg gatgggaggg atcatcccta tctttggtac agcaaactac  180
gcacagaagt tccagggcag ggtcaccatt actgcagaca atccacgag cacagcctac  240
atggagctga gcagcctgag atctgaggac accgccgtgt attactgtgc gaaaggtaac  300
ttctacggtg gtctggacta ctggggccaa gggaccaccg tgaccgtctc ctcagctagc  360
accaagggcc catcggtctt cccctggca ccctcctcca agagcacctc tgggggcaca  420
gcggccctgg gctgcctggt caaggactac ttccccgaac cggtgacggt gtcgtggaac  480
tcaggcgccc tgaccagcgg cgtgcacacc ttcccggctg tcctacagtc ctcaggactc  540
tactccctca gcagcgtggt gaccgtgccc tccagcagct gggcaccca gacctacatc  600
tgcaacgtga atcacaagcc cagcaacacc aaggtggaca gaaagttga gcccaaatct  660
tgtgacaaaa ctcacacatg cccaccgtgc ccagcacctg aactcctggg gggaccgtca  720
gtcttcctct tccccccaaa acccaaggac accctcatga tctcccggac ccctgaggtc  780
acatgcgtgg tggtggacgt gagccacgaa gaccctgagg tcaagttcaa ctggtacgtg  840
gacggcgtgg aggtgcataa tgccaagaca aagccgcggg aggagcagta caacagcacg  900
taccgtgtgg tcagcgtcct caccgtcctg caccaggact ggctgaatgg caaggagtac  960
```

```
aagtgcaagg tctccaacaa agccctccca gcccccatcg agaaaaccat ctccaaagcc   1020
aaagggcagc cccgagaacc acaggtgtac accctgcccc catcccggga tgagctgacc   1080
aagaaccagg tcagcctgac ctgcctggtc aaaggcttct atcccagcga catcgccgtg   1140
gagtgggaga gcaatgggca gccggagaac aactacaaga ccacgcctcc cgtgctggac   1200
tccgacggct ccttcttcct ctacagcaag ctcaccgtgg acaagagcag gtggcagcag   1260
gggaacgtct tctcatgctc cgtgatgcat gaggctctgc acaaccacta cacgcagaag   1320
agcctctccc tgtctccggg taaa                                          1344

<210> SEQ ID NO 197
<211> LENGTH: 639
<212> TYPE: DNA
<213> ORGANISM: Artificial Sequence
<220> FEATURE:
<223> OTHER INFORMATION: Nucleotide sequence TnC(11C7) light chain in
      human IgG1 format

<400> SEQUENCE: 197
tcgtctgagc tgactcagga ccctgctgtg tctgtggcct tgggacagac agtcagggtc     60
acatgccaag agacagcctc agaagttat tatgcaagct ggtaccagca gaagccagga    120
caggcccctg tacttgtcat ctatggtaaa acaaccggc cctcagggat cccagaccga    180
ttctctggct ccagctcagg aaacacagct tccttgacca tcactggggc tcaggcggaa    240
gatgaggctg actattactg taactccatt aatagtactc gtaatgaggt attcggcgga    300
gggaccaagc tgaccgtcct aggtcaaccc aaggctgccc cagcgtgac cctgttcccc    360 cccagcagcg aggaactgca ggccaacaag gccaccctgg tctgcctgat cagcgacttc    420
tacccaggcg ccgtgaccgt ggcctggaag gccgacagca gccccgtgaa ggccggcgtg    480
gagaccacca cccccagcaa gcagagcaac aacaagtacg ccgccagcag ctacctgagc    540
ctgacccccg agcagtggaa gagccacagg tcctacagct gccaggtgac ccacgagggc    600
agcaccgtgg agaaaaccgt ggccccccacc gagtgcagc                          639

<210> SEQ ID NO 198
<211> LENGTH: 1344
<212> TYPE: DNA
<213> ORGANISM: Artificial Sequence
<220> FEATURE:
<223> OTHER INFORMATION: Nucleotide sequence TnC(11C7) heavy chain in
      human IgG1 format

<400> SEQUENCE: 198
gaggtgcaat tgttggagtc tgggggaggc ttggtacagc ctgggggtc cctgagactc      60 tcctgtgcag cctccggatt caccttagc agttatgcca tgagctgggt ccgccaggct    120
ccagggaagg ggctggagtg gtctcagct attagcggta gtggtggtag cacatactac    180
gcagactccg tgaagggccg gttcaccatc tccaaagaca attccaagaa cacgctgtat    240
ctgcagatga acagcctgag agccgaggac acggccgtat attactgtgc gaaaacttct    300
ccgcgtgttc cgctggacta ctggggccaa ggaaccctgg tcaccgtctc gagtgctagc    360
accaagggcc catcggtctt ccccctggca ccctcctcca agagcacctc tgggggcaca    420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc    600 tgcaacgtga atcacaagcc cagcaacacc aaggtggaca gaaagttga gcccaaatct    660
```

```
tgtgacaaaa ctcacacatg cccaccgtgc ccagcacctg aactcctggg gggaccgtca      720
gtcttcctct ccccccaaa acccaaggac accctcatga tctcccggac ccctgaggtc      780
acatgcgtgg tggtggacgt gagccacgaa gaccctgagg tcaagttcaa ctggtacgtg      840
gacggcgtgg aggtgcataa tgccaagaca aagccgcggg aggagcagta caacagcacg      900
taccgtgtgg tcagcgtcct caccgtcctg caccaggact ggctgaatgg caaggagtac      960
aagtgcaagg tctccaacaa agccctccca gcccccatcg agaaaaccat ctccaaagcc     1020
aaagggcagc cccgagaacc acaggtgtac accctgcccc catcccggga tgagctgacc     1080
aagaaccagg tcagcctgac ctgcctggtc aaaggcttct atcccagcga catcgccgtg     1140
gagtgggaga gcaatgggca gccggagaac aactacaaga ccacgcctcc cgtgctggac     1200
tccgacggct ccttcttcct ctacagcaag ctcaccgtgg acaagagcag gtggcagcag     1260
gggaacgtct tctcatgctc cgtgatgcat gaggctctgc acaaccacta cacgcagaag     1320
agcctctccc tgtctccggg taaa                                            1344

<210> SEQ ID NO 199
<211> LENGTH: 215
<212> TYPE: PRT
<213> ORGANISM: Artificial Sequence
<220> FEATURE:
<223> OTHER INFORMATION: TnC(18D4) light chain in human IgG1 format

<400> SEQUENCE: 199

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Asn Lys Lys Phe Pro Ser
                85                  90                  95

Gly Thr Phe Gly Gln Gly Thr Lys Val Glu Ile Lys Arg Thr Val Ala
            100                 105                 110

Ala Pro Ser Val Phe Ile Phe Pro Pro Ser Asp Glu Gln Leu Lys Ser
        115                 120                 125

Gly Thr Ala Ser Val Val Cys Leu Leu Asn Asn Phe Tyr Pro Arg Glu
    130                 135                 140

Ala Lys Val Gln Trp Lys Val Asp Asn Ala Leu Gln Ser Gly Asn Ser
145                 150                 155                 160

Gln Glu Ser Val Thr Glu Gln Asp Ser Lys Asp Ser Thr Tyr Ser Leu
                165                 170                 175

Ser Ser Thr Leu Thr Leu Ser Lys Ala Asp Tyr Glu Lys His Lys Val
            180                 185                 190

Tyr Ala Cys Glu Val Thr His Gln Gly Leu Ser Ser Pro Val Thr Lys
        195                 200                 205

Ser Phe Asn Arg Gly Glu Cys
    210                 215

<210> SEQ ID NO 200
```

```
<211> LENGTH: 448
<212> TYPE: PRT
<213> ORGANISM: Artificial Sequence
<220> FEATURE:
<223> OTHER INFORMATION: TnC(18D4) heavy chain in human IgG1 format

<400> SEQUENCE: 200
```

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Leu Leu Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Pro Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

```
Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 201
<211> LENGTH: 213
<212> TYPE: PRT
<213> ORGANISM: Artificial Sequence
<220> FEATURE:
<223> OTHER INFORMATION: TnC(11C7) light chain in human IgG1 format

<400> SEQUENCE: 201

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ile Asn Ser Thr Arg Asn Glu
                85                  90                  95

Val Phe Gly Gly Gly Thr Lys Leu Thr Val Leu Gly Gln Pro Lys Ala
            100                 105                 110

Ala Pro Ser Val Thr Leu Phe Pro Pro Ser Ser Glu Glu Leu Gln Ala
        115                 120                 125

Asn Lys Ala Thr Leu Val Cys Leu Ile Ser Asp Phe Tyr Pro Gly Ala
    130                 135                 140

Val Thr Val Ala Trp Lys Ala Asp Ser Ser Pro Val Lys Ala Gly Val
145                 150                 155                 160

Glu Thr Thr Thr Pro Ser Lys Gln Ser Asn Asn Lys Tyr Ala Ala Ser
                165                 170                 175

Ser Tyr Leu Ser Leu Thr Pro Glu Gln Trp Lys Ser His Arg Ser Tyr
            180                 185                 190

Ser Cys Gln Val Thr His Glu Gly Ser Thr Val Glu Lys Thr Val Ala
        195                 200                 205

Pro Thr Glu Cys Ser
    210

<210> SEQ ID NO 202
<211> LENGTH: 448
<212> TYPE: PRT
<213> ORGANISM: Artificial Sequence
<220> FEATURE:
<223> OTHER INFORMATION: TnC(11C7) heavy chain in human IgG1 format

<400> SEQUENCE: 202

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
```

```
            20                  25                  30
Ala Met Ser Trp Val Arg Gln Ala Pro Gly Lys Gly Leu Glu Trp Val
        35                  40                  45
Ser Ala Ile Ser Gly Ser Gly Gly Ser Thr Tyr Tyr Ala Asp Ser Val
    50                  55                  60
Lys Gly Arg Phe Thr Ile Ser Lys Asp Asn Ser Lys Asn Thr Leu Tyr
65                  70                  75                  80
Leu Gln Met Asn Ser Leu Arg Ala Glu Asp Thr Ala Val Tyr Tyr Cys
                85                  90                  95
Ala Lys Thr Ser Pro Arg Val Pro Leu Asp Tyr Trp Gly Gln Gly Thr
            100                 105                 110
Leu Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
    130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Lys Val Glu Pro Lys Ser Cys Asp Lys Thr
    210                 215                 220
His Thr Cys Pro Pro Cys Pro Ala Pro Glu Leu Leu Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
    290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Pro Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
    370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Lys
        435                 440                 445
```

<210> SEQ ID NO 203
<211> LENGTH: 1344
<212> TYPE: DNA
<213> ORGANISM: Artificial Sequence
<220> FEATURE:
<223> OTHER INFORMATION: Nucleotide sequence TnC(18D4) heavy chain in P329GLALA human IgG1 format

<400> SEQUENCE: 203

```
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag ggctcgagtg gatgggaggg atcatcccta tctttggtac agcaaactac     180
gcacagaagt tccagggcag ggtcaccatt actgcagaca atccacgag cacagcctac     240
atggagctga gcagcctgag atctgaggac accgccgtgt attactgtgc gaaaggtaac     300
ttctacggtg gtctggacta ctggggccaa gggaccaccg tgaccgtctc ctcagctagc     360
accaagggcc catcggtctt ccccctggca ccctcctcca gagcacctc tgggggcaca     420
gcggccctgg gctgcctggt caaggactac ttccccgaac cggtgacggt gtcgtggaac     480
tcaggcgccc tgaccagcgg cgtgcacacc ttcccggctg tcctacagtc ctcaggactc     540
tactccctca gcagcgtggt gaccgtgccc tccagcagct gggcaccca gacctacatc     600
tgcaacgtga atcacaagcc cagcaacacc aaggtggaca gaaagttga gcccaaatct     660
tgtgacaaaa ctcacacatg cccaccgtgc ccagcacctg aagctgcagg gggaccgtca     720
gtcttcctct tccccccaaa acccaaggac accctcatga tctcccggac ccctgaggtc     780
acatgcgtgg tggtggacgt gagccacgaa gaccctgagg tcaagttcaa ctggtacgtg     840
gacggcgtgg aggtgcataa tgccaagaca agccgcggg aggagcagta caacagcacg     900
taccgtgtgg tcagcgtcct caccgtcctg caccaggact ggctgaatgg caaggagtac     960
aagtgcaagg tctccaacaa agccctcggc gccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                           1344
```

<210> SEQ ID NO 204
<211> LENGTH: 1344
<212> TYPE: DNA
<213> ORGANISM: Artificial Sequence
<220> FEATURE:
<223> OTHER INFORMATION: Nucleotide sequence TnC(11C7) heavy chain in P329GLALA human IgG1 format

<400> SEQUENCE: 204

```
gaggtgcaat tgttggagtc tggggggaggc ttggtacagc ctgggggtc cctgagactc      60
tcctgtgcag cctccggatt caccttagc agttatgcca tgagctgggt ccgccaggct     120
ccagggaagg ggctggagtg ggtctcagct attagcggta gtggtggtag cacatactac     180
gcagactccg tgaagggccg gttcaccatc tccaaagaca attccaagaa cacgctgtat     240
ctgcagatga acagcctgag agccgaggac acggccgtat attactgtgc gaaaacttct     300
```

```
ccgcgtgttc cgctggacta ctggggccaa ggaaccctgg tcaccgtctc gagtgctagc    360
accaagggcc catcggtctt ccccctggca cctcctcca agagcacctc tgggggcaca      420
gcggccctgg gctgcctggt caaggactac ttccccgaac cggtgacggt gtcgtggaac    480
tcaggcgccc tgaccagcgg cgtgcacacc ttcccggctg tcctacagtc ctcaggactc    540
tactccctca gcagcgtggt gaccgtgccc tccagcagct gggcaccca gacctacatc     600
tgcaacgtga atcacaagcc cagcaacacc aaggtggaca agaaagttga gcccaaatct    660
tgtgacaaaa ctcacacatg cccaccgtgc ccagcacctg aagctgcagg gggaccgtca    720
gtcttcctct tccccccaaa acccaaggac accctcatga tctcccggac ccctgaggtc    780
acatgcgtgg tggtggacgt gagccacgaa gaccctgagg tcaagttcaa ctggtacgtg    840
gacggcgtgg aggtgcataa tgccaagaca aagccgcggg aggagcagta caacagcacg    900
taccgtgtgg tcagcgtcct caccgtcctg caccaggact ggctgaatgg caaggagtac    960
aagtgcaagg tctccaacaa agccctcggc gccccatcg agaaaaccat ctccaaagcc    1020
aaagggcagc cccgagaacc acaggtgtac accctgcccc catcccggga tgagctgacc    1080
aagaaccagg tcagcctgac ctgcctggtc aaaggcttct atcccagcga catcgccgtg    1140
gagtgggaga gcaatgggca gccggagaac aactacaaga ccacgcctcc cgtgctggac    1200
tccgacggct ccttcttcct ctacagcaag ctcaccgtgg acaagagcag gtggcagcag    1260
gggaacgtct tctcatgctc cgtgatgcat gaggctctgc acaaccacta cacgcagaag    1320
agcctctccc tgtctccggg taaa                                           1344
```

<210> SEQ ID NO 205
<211> LENGTH: 448
<212> TYPE: PRT
<213> ORGANISM: Artificial Sequence
<220> FEATURE:
<223> OTHER INFORMATION: TnC(18D4) heavy chain in P329GLALA human IgG1
      format

<400> SEQUENCE: 205

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Gly Leu Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

```
Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
            195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
            245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
            275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
            325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
            355                 360                 365

Leu Val Lys Gly Phe Tyr Pro Ser Asp Ile Ala Val Glu Trp Glu Ser
            370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
            405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
            435                 440                 445

<210> SEQ ID NO 206
<211> LENGTH: 448
<212> TYPE: PRT
<213> ORGANISM: Artificial Sequence
<220> FEATURE:
<223> OTHER INFORMATION: TnC(11C7) heavy chain in P329GLALA human IgG1
      format

<400> SEQUENCE: 206

Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
            35                  40                  45

Ser Ala Ile Ser Gly Ser Gly Gly Ser Thr Tyr Tyr Ala Asp Ser Val
            50                  55                  60

Lys Gly Arg Phe Thr Ile Ser Lys Asp Asn Ser Lys Asn Thr Leu Tyr
65                  70                  75                  80

Leu Gln Met Asn Ser Leu Arg Ala Glu Asp Thr Ala Val Tyr Tyr Cys
```

```
                    85                  90                  95
Ala Lys Thr Ser Pro Arg Val Pro Leu Asp Tyr Trp Gly Gln Gly Thr
                100                 105                 110

Leu Val Thr Val Ser Ser Ala Ser Thr Lys Gly Pro Ser Val Phe Pro
            115                 120                 125

Leu Ala Pro Ser Ser Lys Ser Thr Ser Gly Gly Thr Ala Ala Leu Gly
        130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
210                 215                 220

His Thr Cys Pro Pro Cys Pro Ala Pro Glu Ala Ala Gly Gly Pro Ser
225                 230                 235                 240

Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
        370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Lys
        435                 440                 445

<210> SEQ ID NO 207
<211> LENGTH: 642
<212> TYPE: DNA
<213> ORGANISM: Artificial Sequence
<220> FEATURE:
<223> OTHER INFORMATION: Nucleotide sequence LC1 (pCON323) OX40 (49B4)
      VL/CL

<400> SEQUENCE: 207
```

```
gacatccaga tgacccagtc tccttccacc ctgtctgcat ctgtaggaga ccgtgtcacc      60
atcacttgcc gtgccagtca gagtattagt agctggttgg cctggtatca gcagaaacca     120
gggaaagccc ctaagctcct gatctatgat gcctccagtt tggaaagtgg ggtcccatca     180
cgtttcagcg gcagtggatc cgggacagaa ttcactctca ccatcagcag cttgcagcct     240
gatgattttg caacttatta ctgccaacag tatagttcgc agccgtatac gtttggccag     300
ggcaccaaag tcgagatcaa gcgtacggtg gctgcaccat ctgtcttcat cttcccgcca     360
tctgatgagc agttgaaatc tggaactgcc tctgttgtgt gcctgctgaa taacttctat     420
cccagagagg ccaaagtaca gtggaaggtg gataacgccc tccaatcggg taactcccag     480
gagagtgtca cagagcagga cagcaaggac agcacctaca gcctcagcag cacccctgacg    540 ctgagcaaag cagactacga aaacacaaa gtctacgcct gcgaagtcac ccatcagggc      600
ctgagctcgc ccgtcacaaa gagcttcaac aggggagagt gt                       642

<210> SEQ ID NO 208
<211> LENGTH: 2079
<212> TYPE: DNA
<213> ORGANISM: Artificial Sequence
<220> FEATURE:
<223> OTHER INFORMATION: Nucleotide sequence Heavy chain pETR14728 OX40
      (49B4) VHCH1_Fc_PGLALA_TnC (18D4) VHCL

<400> SEQUENCE: 208
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc    120
cctggacaag gctcgagtg gatgggaggg atcatcccta tctttggtac agcaaactac     180
gcacagaagt tccagggcag ggtcaccatt actgcagaca aatccacgag cacagcctac    240
atggagctga gcagcctgag atctgaggac accgccgtgt attactgtgc gagagaatac    300
taccgtggtc cgtacgacta ctggggccaa gggaccaccg tgaccgtctc ctcagctagc    360
accaagggcc catccgtgtt ccctctggcc ccttccagca gtctacctc tggcggcaca    420 gccgctctgg gctgcctcgt gaaggactac ttccccgagc ctgtgacagt gtcctggaac    480
tctggcgccc tgacatccgg cgtgcacacc tttccagctg tgctgcagtc ctccggcctg    540
tactccctgt cctccgtcgt gacagtgccc tccagctctc tgggcaccca gacctacatc    600
tgcaacgtga accacaagcc ctccaacacc aaggtggaca gaaggtgga acccaagtcc     660 tgcgacaaga cccacacctg tcccccttgt cctgcccctg aagctgctgg cggccctagc    720
gtgttcctgt tcccccaaa gcccaaggac accctgatga tctcccggac ccccgaagtg    780
acctgcgtgg tggtggatgt gtcccacgag gaccctgaag tgaagttcaa ttggtacgtg    840
gacggcgtgg aagtgcacaa tgccaagacc aagcctagag gaacagta caactccacc      900 taccgggtgg tgtccgtgct gaccgtgctg caccaggatt ggctgaacgg caaagagtac    960
aagtgcaagg tgtccaacaa ggccctggga gcccccatcg aaaagaccat ctccaaggcc  1020
aagggccagc ctcgcgagcc tcaggtgtac accctgcccc ctagcagaga tgagctgacc  1080
aagaaccagg tgtccctgac ctgtctcgtg aaaggcttct accctccga tatcgccgtg   1140 gaatgggaga gcaacggcca gcccgagaac aactacaaga ccacccccc tgtgctggac   1200 tccgacggct cattcttcct gtactctaag ctgacagtgg acaagtcccg gtggcagcag  1260
ggcaacgtgt tctcctgctc cgtgatgcac gaggccctgc acaaccacta cacccagaag  1320
tccctgtccc tgtctcccgg gggaggcggt ggatctggcg gaggcggatc cggtggtggc  1380
```

|  |  |
|---|---|
| ggttccgggg gcggtggatc gcaggtgcaa ttggtgcagt ctggggctga ggtgaagaag | 1440 |
| cctgggtcct cggtgaaggt ctcctgcaag gcctccggag gcacattcag cagctacgct | 1500 |
| ataagctggg tgcgacaggc ccctggacaa gggctcgagt ggatgggagg gatcatccct | 1560 |
| atctttggta cagcaaacta cgcacagaag ttccagggca gggtcaccat tactgcagac | 1620 |
| aaatccacga gcacagccta catggagctg agcagcctga gatctgagga caccgccgtg | 1680 |
| tattactgtg cgaaaggtaa cttctacggt ggtctggact actggggcca agggaccacc | 1740 |
| gtgaccgtct ccagcgcttc tgtggccgct ccctccgtgt tcatcttccc accttccgac | 1800 |
| gagcagctga agtccggcac tgcctctgtc gtgtgcctgc tgaacaactt ctaccctcgg | 1860 |
| gaagccaagg tgcagtggaa agtggataac gccctgcagt ccggcaactc ccaggaatcc | 1920 |
| gtgaccgagc aggactccaa ggacagcacc tactccctga gcagcaccct gaccctgtcc | 1980 |
| aaggccgact acgagaagca caaggtgtac gcctgtgaag tgacccacca gggcctgtcc | 2040 |
| agccccgtga ccaagtcctt caaccggggc gagtgctga | 2079 |

<210> SEQ ID NO 209
<211> LENGTH: 642
<212> TYPE: DNA
<213> ORGANISM: Artificial Sequence
<220> FEATURE:
<223> OTHER INFORMATION: Nucleotide sequence LC2 pETR14647 TnC (18D4) VLCH1

<400> SEQUENCE: 209

|  |  |
|---|---|
| gacatccaga tgacccagtc tccatccacc ctgtctgcat ctgtaggaga ccgtgtcacc | 60 |
| atcacttgcc gtgccagtca gagtattagt agctggttgg cctggtatca gcagaaacca | 120 |
| gggaaagccc ctaagctcct gatctatgat gcctccagtt tggaaagtgg ggtcccatca | 180 |
| cgtttcagcg gcagtggatc cgggacagaa ttcactctca ccatcagcag cttgcagcct | 240 |
| gatgattttg caacttatta ctgccaacag aataagaagt ttccttcggg gacgtttggc | 300 |
| cagggcacca aagtcgagat caagagctcc gctagcacca agggcccctc cgtgtttcct | 360 |
| ctggccccca gcagcaagag cacctctggc ggaacagccg ccctgggctg cctggtgaaa | 420 |
| gactacttcc ccgagcccgt gaccgtgtcc tggaactctg gcgccctgac cagcggcgtg | 480 |
| cacacctttc cagccgtgct gcagagcagc ggcctgtact ccctgagcag cgtggtgaca | 540 |
| gtgccctcca gcagctggg cacccagacc tacatctgca acgtgaacca caagcccagc | 600 |
| aacaccaaag tggacaagaa ggtggaaccc aagagctgcg ac | 642 |

<210> SEQ ID NO 210
<211> LENGTH: 2076
<212> TYPE: DNA
<213> ORGANISM: Artificial Sequence
<220> FEATURE:
<223> OTHER INFORMATION: Nucleotide sequence Heavy chain pETR14727 OX40 (49B4) VHCH1_Fc_PG/LALA_TnC (11C7) VHCL

<400> SEQUENCE: 210

|  |  |
|---|---|
| caggtgcaat tggtgcagtc tggggctgag gtgaagaagc tgggtcctc ggtgaaggtc | 60 |
| tcctgcaagg cctccggagg cacattcagc agctacgcta aagctgggt gcgacaggcc | 120 |
| cctggacaag ggctcgagtg gatgggaggg atcatcccta tctttggtac agcaaactac | 180 |
| gcacagaagt tccagggcag ggtcaccatt actgcagaca aatccacgag cacagcctac | 240 |
| atggagctga gcagcctgag atctgaggac accgccgtgt attactgtgc gagagaatac | 300 |
| taccgtggtc cgtacgacta ctggggccaa gggaccaccg tgaccgtctc ctcagctagc | 360 |

```
accaagggcc catccgtgtt ccctctggcc ccttccagca agtctacctc tggcggcaca    420
gccgctctgg gctgcctcgt gaaggactac ttccccgagc ctgtgacagt gtcctggaac    480
tctggcgccc tgacatccgg cgtgcacacc tttccagctg tgctgcagtc ctccggcctg    540
tactccctgt cctccgtcgt gacagtgccc tccagctctc tgggcaccca gacctacatt    600
tgcaacgtga accacaagcc ctccaacacc aaggtggaca gaaggtggaa acccaagtcc    660
tgcgacaaga cccacacctg tccccttgt cctgccctg aagctgctgg cggccctagc      720
gtgttcctgt tccccccaaa gcccaaggac accctgatga tctcccggac ccccgaagtg    780
acctgcgtgt ggtggatgt gtcccacgag gaccctgaag tgaagttcaa ttggtacgtg     840
gacggcgtgg aagtgcacaa tgccaagacc aagcctagag aggaacagta caactccacc    900
taccgggtgg tgtccgtgct gaccgtgctg caccaggatt ggctgaacgg caaagagtac    960
aagtgcaagg tgtccaacaa ggccctggga gcccccatcg aaaagaccat ctccaaggcc    1020
aagggccagc ctcgcgagcc tcaggtgtac accctgcccc ctagcagaga tgagctgacc    1080
aagaaccagg tgtccctgac ctgtctcgtg aaaggcttct accctccga tatcgccgtg     1140 gaatgggaga gcaacggcca gcccgagaac aactacaaga ccaccccccc tgtgctggac    1200
tccgacggct cattcttcct gtactctaag ctgacagtgg acaagtcccg gtggcagcag    1260
ggcaacgtgt tctcctgctc cgtgatgcac gaggccctgc acaaccacta cacccagaag    1320
tccctgtccc tgtctcccgg gggaggcggt ggatctggcg gaggcggatc cggtggtggc    1380
ggttccgggg gcggtggatc ggaggtgcaa ttgttggagt ctggggggag cttggtacag    1440 cctgggggt ccctgagact ctcctgtgca gcctccggat tcacctttag cagttatgcc     1500
atgagctggg tccgccaggc tccagggaag gggctgagt gggtctcagc tattagcggt    1560
agtggtggta gcacatacta cgcagactcc gtgaagggcc ggttcaccat ctccaaagac    1620
aattccaaga acacgctgta tctgcagatg aacagcctga gccgagga cacggccgta     1680 tattactgtg cgaaaacttc tccgcgtgtt ccgctggact actggggcca aggaaccctg    1740
gtcaccgtct cgagcgcttc tgtggccgct ccctccgtgt tcatcttccc accttccgac    1800
gagcagctga gtccggcac tgcctctgtc gtgtgcctgc tgaacaactt ctaccctcgg    1860
gaagccaagg tgcagtggaa agtggataac gccctgcagt ccggcaactc ccaggaatcc    1920
gtgaccgagc aggactccaa ggacagcacc tactccctga gcagcaccct gaccctgtcc    1980
aaggccgact acgagaagca caaggtgtac gcctgtgaag tgacccacca gggcctgtcc    2040
agccccgtga ccaagtcctt caaccggggc gagtgc                              2076
```

<210> SEQ ID NO 211
<211> LENGTH: 643
<212> TYPE: DNA
<213> ORGANISM: Artificial Sequence
<220> FEATURE:
<223> OTHER INFORMATION: Nucleotide sequence LC2 pETR14648 TnC (11C7)
    VLCH1

<400> SEQUENCE: 211

```
tcgtctgagc tgactcagga ccctgctgtg tctgtggcct gggacagac agtcagggtc     60 acatgccaag agacagcct cagaagttat tatgcaagct ggtaccagca gaagccagga    120
caggcccctg tacttgtcat ctatggtaaa aacaaccggc cctcagggat cccagaccga    180
ttctctggct ccagctcagg aaacacagct tccttgacca tcactggggc tcaggcggaa    240
gatgaggctg actattactg taactccatt aatagtactc gtaatgaggt attcggcgga    300
```

```
gggaccaagc tgaccgtcct aagctccgct agcaccaagg gcccctccgt gtttcctctg    360
gcccccagca gcaagagcac ctctggcgga acagccgccc tgggctgcct ggtgaaagac    420
tacttccccg agcccgtgac cgtgtcctgg aactctggcg ccctgaccag cggcgtgcac    480 accttttccag ccgtgctgca gagcagcggc ctgtactccc tgagcagcgt ggtgacagtg    540
ccctccagca gcctgggcac ccagacctac atctgcaacg tgaaccacaa gcccagcaac    600
accaaagtgg acaagaaggt ggaacccaag agctgcgact gat                       643
```

<210> SEQ ID NO 212
<211> LENGTH: 214
<212> TYPE: PRT
<213> ORGANISM: Artificial Sequence
<220> FEATURE:
<223> OTHER INFORMATION: LC1 (pCON323) OX40 (49B4) VL/CL

<400> SEQUENCE: 212

```
Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
            20                  25                  30

Leu Ala Trp Tyr Gln Gln Lys Pro Gly Lys Ala Pro Lys Leu Leu Ile
        35                  40                  45

Tyr Asp Ala Ser Ser Leu Glu Ser Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
            100                 105                 110

Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210
```

<210> SEQ ID NO 213
<211> LENGTH: 692
<212> TYPE: PRT
<213> ORGANISM: Artificial Sequence
<220> FEATURE:
<223> OTHER INFORMATION: Heavy chain pETR14728 OX40 (49B4)
      VHCH1_Fc_PG/LALA_TnC (18D4) VHCL

<400> SEQUENCE: 213

```
Gln Val Gln Leu Val Gln Ser Gly Ala Glu Val Lys Lys Pro Gly Ser
1               5                   10                  15
```

-continued

```
Ser Val Lys Val Ser Cys Lys Ala Ser Gly Thr Phe Ser Ser Tyr
            20                  25                  30
Ala Ile Ser Trp Val Arg Gln Ala Pro Gly Gln Gly Leu Glu Trp Met
        35                  40                  45
Gly Gly Ile Ile Pro Ile Phe Gly Thr Ala Asn Tyr Ala Gln Lys Phe
50                  55                  60
Gln Gly Arg Val Thr Ile Thr Ala Asp Lys Ser Thr Ser Thr Ala Tyr
65                  70                  75                  80
Met Glu Leu Ser Ser Leu Arg Ser Glu Asp Thr Ala Val Tyr Tyr Cys
                85                  90                  95
Ala Arg Glu Tyr Tyr Arg Gly Pro Tyr Asp Tyr Trp Gly Gln Gly Thr
            100                 105                 110
Thr Val Thr Val Ser Ser Ala Ser Thr Lys Gly Pro Ser Val Phe Pro
        115                 120                 125
Leu Ala Pro Ser Ser Lys Ser Thr Ser Gly Gly Thr Ala Ala Leu Gly
130                 135                 140
Cys Leu Val Lys Asp Tyr Phe Pro Glu Pro Val Thr Val Ser Trp Asn
145                 150                 155                 160
Ser Gly Ala Leu Thr Ser Gly Val His Thr Phe Pro Ala Val Leu Gln
                165                 170                 175
Ser Ser Gly Leu Tyr Ser Leu Ser Ser Val Val Thr Val Pro Ser Ser
            180                 185                 190
Ser Leu Gly Thr Gln Thr Tyr Ile Cys Asn Val Asn His Lys Pro Ser
        195                 200                 205
Asn Thr Lys Val Asp Lys Val Glu Pro Lys Ser Cys Asp Lys Thr
210                 215                 220
His Thr Cys Pro Pro Cys Pro Ala Pro Glu Ala Ala Gly Gly Pro Ser
225                 230                 235                 240
Val Phe Leu Phe Pro Pro Lys Pro Lys Asp Thr Leu Met Ile Ser Arg
                245                 250                 255
Thr Pro Glu Val Thr Cys Val Val Val Asp Val Ser His Glu Asp Pro
            260                 265                 270
Glu Val Lys Phe Asn Trp Tyr Val Asp Gly Val Glu Val His Asn Ala
        275                 280                 285
Lys Thr Lys Pro Arg Glu Glu Gln Tyr Asn Ser Thr Tyr Arg Val Val
290                 295                 300
Ser Val Leu Thr Val Leu His Gln Asp Trp Leu Asn Gly Lys Glu Tyr
305                 310                 315                 320
Lys Cys Lys Val Ser Asn Lys Ala Leu Gly Ala Pro Ile Glu Lys Thr
                325                 330                 335
Ile Ser Lys Ala Lys Gly Gln Pro Arg Glu Pro Gln Val Tyr Thr Leu
            340                 345                 350
Pro Pro Ser Arg Asp Glu Leu Thr Lys Asn Gln Val Ser Leu Thr Cys
        355                 360                 365
Leu Val Lys Gly Phe Tyr Pro Ser Asp Ile Ala Val Glu Trp Glu Ser
370                 375                 380
Asn Gly Gln Pro Glu Asn Asn Tyr Lys Thr Thr Pro Pro Val Leu Asp
385                 390                 395                 400
Ser Asp Gly Ser Phe Phe Leu Tyr Ser Lys Leu Thr Val Asp Lys Ser
                405                 410                 415
Arg Trp Gln Gln Gly Asn Val Phe Ser Cys Ser Val Met His Glu Ala
            420                 425                 430
Leu His Asn His Tyr Thr Gln Lys Ser Leu Ser Leu Ser Pro Gly Gly
```

```
                    435                 440                 445
        Gly Gly Gly Ser Gly Gly Gly Ser Gly Gly Gly Ser Gly Gly
            450                 455                 460

Gly Gly Ser Gln Val Gln Leu Val Gln Ser Gly Ala Glu Val Lys Lys
        465                 470                 475                 480

Pro Gly Ser Ser Val Lys Val Ser Cys Lys Ala Ser Gly Gly Thr Phe
                        485                 490                 495

Ser Ser Tyr Ala Ile Ser Trp Val Arg Gln Ala Pro Gly Gln Gly Leu
                    500                 505                 510

Glu Trp Met Gly Gly Ile Ile Pro Ile Phe Gly Thr Ala Asn Tyr Ala
                515                 520                 525

Gln Lys Phe Gln Gly Arg Val Thr Ile Thr Ala Asp Lys Ser Thr Ser
            530                 535                 540

Thr Ala Tyr Met Glu Leu Ser Ser Leu Arg Ser Glu Asp Thr Ala Val
        545                 550                 555                 560

Tyr Tyr Cys Ala Lys Gly Asn Phe Tyr Gly Gly Leu Asp Tyr Trp Gly
                        565                 570                 575

Gln Gly Thr Thr Val Thr Val Ser Ser Ala Ser Val Ala Ala Pro Ser
                    580                 585                 590

Val Phe Ile Phe Pro Pro Ser Asp Glu Gln Leu Lys Ser Gly Thr Ala
                595                 600                 605

Ser Val Val Cys Leu Leu Asn Asn Phe Tyr Pro Arg Glu Ala Lys Val
            610                 615                 620

Gln Trp Lys Val Asp Asn Ala Leu Gln Ser Gly Asn Ser Gln Glu Ser
        625                 630                 635                 640

Val Thr Glu Gln Asp Ser Lys Asp Ser Thr Tyr Ser Leu Ser Ser Thr
                        645                 650                 655

Leu Thr Leu Ser Lys Ala Asp Tyr Glu Lys His Lys Val Tyr Ala Cys
                    660                 665                 670

Glu Val Thr His Gln Gly Leu Ser Ser Pro Val Thr Lys Ser Phe Asn
                675                 680                 685

Arg Gly Glu Cys
            690

<210> SEQ ID NO 214
<211> LENGTH: 214
<212> TYPE: PRT
<213> ORGANISM: Artificial Sequence
<220> FEATURE:
<223> OTHER INFORMATION: LC2 pETR14647 TnC (18D4) VLCH1

<400> SEQUENCE: 214

Asp Ile Gln Met Thr Gln Ser Pro Ser Thr Leu Ser Ala Ser Val Gly
        1               5                   10                  15

Asp Arg Val Thr Ile Thr Cys Arg Ala Ser Gln Ser Ile Ser Ser Trp
                    20                  25                  30

Leu Ala Trp Tyr Gln Gln Lys Pro Gly Lys Ala Pro Lys Leu Leu Ile
                35                  40                  45

Tyr Asp Ala Ser Ser Leu Glu Ser Gly Val Pro Ser Arg Phe Ser Gly
            50                  55                  60

Ser Gly Ser Gly Thr Glu Phe Thr Leu Thr Ile Ser Ser Leu Gln Pro
        65                  70                  75                  80

Asp Asp Phe Ala Thr Tyr Tyr Cys Gln Gln Asn Lys Lys Phe Pro Ser
                        85                  90                  95

Gly Thr Phe Gly Gln Gly Thr Lys Val Glu Ile Lys Ser Ser Ala Ser
```

```
                      100                 105                 110
Thr Lys Gly Pro Ser Val Phe Pro Leu Ala Pro Ser Ser Lys Ser Thr
                  115                 120                 125

Ser Gly Gly Thr Ala Ala Leu Gly Cys Leu Val Lys Asp Tyr Phe Pro
            130                 135                 140

Glu Pro Val Thr Val Ser Trp Asn Ser Gly Ala Leu Thr Ser Gly Val
145                 150                 155                 160

His Thr Phe Pro Ala Val Leu Gln Ser Ser Gly Leu Tyr Ser Leu Ser
                165                 170                 175

Ser Val Val Thr Val Pro Ser Ser Ser Leu Gly Thr Gln Thr Tyr Ile
            180                 185                 190

Cys Asn Val Asn His Lys Pro Ser Asn Thr Lys Val Asp Lys Lys Val
                195                 200                 205

Glu Pro Lys Ser Cys Asp
    210

<210> SEQ ID NO 215
<211> LENGTH: 692
<212> TYPE: PRT
<213> ORGANISM: Artificial Sequence
<220> FEATURE:
<223> OTHER INFORMATION: Heavy chain pETR14727 OX40 (49B4)
      VHCH1_Fc_PG/LALA_TnC (11C7) VHCL

<400> SEQUENCE: 215

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Lys Thr
    210                 215                 220

His Thr Cys Pro Pro Cys Pro Ala Pro Glu Ala Ala Gly Gly Pro Ser
225                 230                 235                 240
```

```
Val Phe Leu Phe Pro Pro Lys Pro Lys Asp Thr Leu Met Ile Ser Arg
                245                 250                 255

Thr Pro Glu Val Thr Cys Val Val Val Asp Val Ser His Glu Asp Pro
            260                 265                 270

Glu Val Lys Phe Asn Trp Tyr Val Asp Gly Val Glu Val His Asn Ala
        275                 280                 285

Lys Thr Lys Pro Arg Glu Glu Gln Tyr Asn Ser Thr Tyr Arg Val Val
    290                 295                 300

Ser Val Leu Thr Val Leu His Gln Asp Trp Leu Asn Gly Lys Glu Tyr
305                 310                 315                 320

Lys Cys Lys Val Ser Asn Lys Ala Leu Gly Ala Pro Ile Glu Lys Thr
                325                 330                 335

Ile Ser Lys Ala Lys Gly Gln Pro Arg Glu Pro Gln Val Tyr Thr Leu
            340                 345                 350

Pro Pro Ser Arg Asp Glu Leu Thr Lys Asn Gln Val Ser Leu Thr Cys
        355                 360                 365

Leu Val Lys Gly Phe Tyr Pro Ser Asp Ile Ala Val Glu Trp Glu Ser
    370                 375                 380

Asn Gly Gln Pro Glu Asn Asn Tyr Lys Thr Thr Pro Pro Val Leu Asp
385                 390                 395                 400

Ser Asp Gly Ser Phe Phe Leu Tyr Ser Lys Leu Thr Val Asp Lys Ser
                405                 410                 415

Arg Trp Gln Gln Gly Asn Val Phe Ser Cys Ser Val Met His Glu Ala
            420                 425                 430

Leu His Asn His Tyr Thr Gln Lys Ser Leu Ser Leu Ser Pro Gly Gly
        435                 440                 445

Gly Gly Gly Ser Gly Gly Gly Ser Gly Gly Gly Gly Ser Gly Gly
    450                 455                 460

Gly Gly Ser Glu Val Gln Leu Leu Glu Ser Gly Gly Gly Leu Val Gln
465                 470                 475                 480

Pro Gly Gly Ser Leu Arg Leu Ser Cys Ala Ala Ser Gly Phe Thr Phe
                485                 490                 495

Ser Ser Tyr Ala Met Ser Trp Val Arg Gln Ala Pro Gly Lys Gly Leu
            500                 505                 510

Glu Trp Val Ser Ala Ile Ser Gly Ser Gly Gly Ser Thr Tyr Tyr Ala
        515                 520                 525

Asp Ser Val Lys Gly Arg Phe Thr Ile Ser Lys Asp Asn Ser Lys Asn
    530                 535                 540

Thr Leu Tyr Leu Gln Met Asn Ser Leu Arg Ala Glu Asp Thr Ala Val
545                 550                 555                 560

Tyr Tyr Cys Ala Lys Thr Ser Pro Arg Val Pro Leu Asp Tyr Trp Gly
                565                 570                 575

Gln Gly Thr Leu Val Thr Val Ser Ser Ala Ser Val Ala Ala Pro Ser
            580                 585                 590

Val Phe Ile Phe Pro Pro Ser Asp Glu Gln Leu Lys Ser Gly Thr Ala
        595                 600                 605

Ser Val Val Cys Leu Leu Asn Asn Phe Tyr Pro Arg Glu Ala Lys Val
    610                 615                 620

Gln Trp Lys Val Asp Asn Ala Leu Gln Ser Gly Asn Ser Gln Glu Ser
625                 630                 635                 640

Val Thr Glu Gln Asp Ser Lys Asp Ser Thr Tyr Ser Leu Ser Ser Thr
                645                 650                 655

Leu Thr Leu Ser Lys Ala Asp Tyr Glu Lys His Lys Val Tyr Ala Cys
```

```
                       660                 665                 670
Glu Val Thr His Gln Gly Leu Ser Ser Pro Val Thr Lys Ser Phe Asn
            675                 680                 685
Arg Gly Glu Cys
        690

<210> SEQ ID NO 216
<211> LENGTH: 213
<212> TYPE: PRT
<213> ORGANISM: Artificial Sequence
<220> FEATURE:
<223> OTHER INFORMATION: LC2 pETR14648 TnC (11C7) VLCH1

<400> SEQUENCE: 216

Ser Ser Glu Leu Thr Gln Asp Pro Ala Val Ser Val Ala Leu Gly Gln
1               5                   10                  15

Thr Val Arg Val Thr Cys Gln Gly Asp Ser Leu Arg Ser Tyr Tyr Ala
            20                  25                  30

Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Ile Asn Ser Thr Arg Asn Glu
                85                  90                  95

Val Phe Gly Gly Gly Thr Lys Leu Thr Val Leu Ser Ser Ala Ser Thr
            100                 105                 110

Lys Gly Pro Ser Val Phe Pro Leu Ala Pro Ser Ser Lys Ser Thr Ser
        115                 120                 125

Gly Gly Thr Ala Ala Leu Gly Cys Leu Val Lys Asp Tyr Phe Pro Glu
    130                 135                 140

Pro Val Thr Val Ser Trp Asn Ser Gly Ala Leu Thr Ser Gly Val His
145                 150                 155                 160

Thr Phe Pro Ala Val Leu Gln Ser Ser Gly Leu Tyr Ser Leu Ser Ser
                165                 170                 175

Val Val Thr Val Pro Ser Ser Ser Leu Gly Thr Gln Thr Tyr Ile Cys
            180                 185                 190

Asn Val Asn His Lys Pro Ser Asn Thr Lys Val Asp Lys Lys Val Glu
        195                 200                 205

Pro Lys Ser Cys Asp
    210

<210> SEQ ID NO 217
<211> LENGTH: 2421
<212> TYPE: DNA
<213> ORGANISM: Artificial Sequence
<220> FEATURE:
<223> OTHER INFORMATION: Nucleotide sequence HC1 pETR15193 OX40 (49B4)
      VHCH1_VHCH1_Fc_hole_PG/LALA_TnC (18D4) VL

<400> SEQUENCE: 217
caggtgcaat tggtgcagtc tggggctgag gtgaagaagc ctgggtcctc ggtgaaggtc      60
tcctgcaagg cctccggagg cacattcagc agctacgcta taagctgggt gcgacaggcc     120
cctggacaag gctcgagtg gatgggaggg atcatcccta tctttggtac agcaaactac     180
gcacagaagt tccagggcag ggtcaccatt actgcagaca atccaccgag cacagcctac     240
```

| | |
|---|---|
| atggagctga gcagcctgag atctgaggac accgccgtgt attactgtgc gagagaatac | 300 |
| taccgtggtc cgtacgacta ctggggccaa gggaccaccg tgaccgtctc ctcagctagc | 360 |
| acaaagggac ctagcgtgtt ccccctggcc cccagcagca agtctacatc tggcggaaca | 420 |
| gccgccctgg gctgcctcgt gaaggactac tttcccgagc ccgtgaccgt gtcctggaac | 480 |
| tctggcgctc tgacaagcgg cgtgcacacc tttccagccg tgctgcagag cagcggcctg | 540 |
| tactctctga gcagcgtcgt gacagtgccc agcagctctc tgggcaccca gacctacatc | 600 |
| tgcaacgtga accacaagcc cagcaacacc aaggtggaca gaaggtgga cccaagagc | 660 |
| tgcgacggcg agggggatc tggcggcgga ggatcccagg tgcaattggt gcagtctggg | 720 |
| gctgaggtga agaagcctgg gtcctcggtg aaggtctcct gcaaggcctc cggaggcaca | 780 |
| ttcagcagct acgctataag ctgggtgcga caggcccctg acaagggct cgagtggatg | 840 |
| ggagggatca tccctatctt tggtacagca aactacgcac agaagttcca gggcagggtc | 900 |
| accattactg cagacaaatc cacgagcaca gcctacatgg agctgagcag cctgagatct | 960 |
| gaggacaccg ccgtgtatta ctgtgcgaga gaatactacc gtggtccgta cgactactgg | 1020 |
| ggccaaggga ccaccgtgac cgtctcctca gctagcacca agggcccatc ggtcttcccc | 1080 |
| ctggcaccct cctccaagag cacctctggg ggcacagcgg ccctgggctg cctggtcaag | 1140 |
| gactacttcc ccgaaccggt gacggtgtcg tggaactcag gcgccctgac cagcggcgtg | 1200 |
| cacaccttcc cggctgtcct acagtcctca ggactctact ccctcagcag cgtggtgacc | 1260 |
| gtgccctcca gcagcttggg cacccagacc tacatctgca acgtgaatca caagcccagc | 1320 |
| aacaccaagg tggacaagaa agttgagccc aaatcttgtg acaaaactca cacatgccca | 1380 |
| ccgtgcccag cacctgaagc tgcaggggga ccgtcagtct tcctcttccc cccaaaaccc | 1440 |
| aaggacaccc tcatgatctc ccggaccccct gaggtcacat gcgtggtggt ggacgtgagc | 1500 |
| cacgaagacc ctgaggtcaa gttcaactgg tacgtggacg gcgtggaggt gcataatgcc | 1560 |
| aagacaaagc cgcggggagga gcagtacaac agcacgtacc gtgtggtcag cgtcctcacc | 1620 |
| gtcctgcacc aggactggct gaatggcaag gagtacaagt gcaaggtctc caacaaagcc | 1680 |
| ctcggcgccc ccatcgagaa aaccatctcc aaagccaaag gcagccccg agaaccacag | 1740 |
| gtgtgcaccc tgcccccatc ccgggatgag ctgaccaaga accaggtcag cctctcgtgc | 1800 |
| gcagtcaaag cttctatcc cagcgacatc gccgtggagt gggagagcaa tgggcagccg | 1860 |
| gagaacaact acaagaccac gcctcccgtg ctggactccg acggctcctt cttcctcgtg | 1920 |
| agcaagctca ccgtggacaa gagcaggtgg cagcagggga acgtcttctc atgctccgtg | 1980 |
| atgcatgagg ctctgcacaa ccactacacg cagaagagcc tctccctgtc tccgggtgga | 2040 |
| ggcggcggaa gcgaggagg aggatccggc ggcggaggtt ccggaggcgg tggatcggac | 2100 |
| atccagatga cccagtctcc atccaccctg tctgcatctg taggagaccg tgtcaccatc | 2160 |
| acttgccgtg ccagtcagag tattagtagc tggttggcct ggtatcagca gaaaccaggg | 2220 |
| aaagcccta agctcctgat ctatgatgcc tccagtttgg aaagtggggt cccatcacgt | 2280 |
| ttcagcggca gtggatccgg gacagaattc actctcacca tcagcagctt gcagcctgat | 2340 |
| gattttgcaa cttattactg ccaacagaat aagaagttc cttcggggac gtttggccag | 2400 |
| ggcaccaaag tcgagatcaa g | 2421 |

<210> SEQ ID NO 218
<211> LENGTH: 2451
<212> TYPE: DNA
<213> ORGANISM: Artificial Sequence
<220> FEATURE:
<223> OTHER INFORMATION: Nucleotide sequence HC2 pETR15194 OX40 (49B4)
    VHCH1_VHCH1_Fc_knob_PG/LALA_ TnC (18D4) VH

<400> SEQUENCE: 218

| | | | | | |
|---|---|---|---|---|---|
| caggtgcaat | tggtgcagtc | tggggctgag | gtgaagaagc | ctgggtcctc | ggtgaaggtc | 60 |
| tcctgcaagg | cctccggagg | cacattcagc | agctacgcta | taagctgggt | gcgacaggcc | 120 |
| cctggacaag | ggctcgagtg | gatgggaggg | atcatccctatctttggtac | agcaaactac | 180 |
| gcacagaagt | tccagggcag | ggtcaccatt | actgcagaca | aatccacgag | cacagcctac | 240 |
| atggagctga | gcagcctgag | atctgaggac | accgccgtgt | attactgtgc | gagagaatac | 300 |
| taccgtggtc | cgtacgacta | ctggggccaa | gggaccaccg | tgaccgtctc | ctcagctagc | 360 |
| acaaagggac | ctagcgtgtt | cccctggcc | ccagcagca | agtctacatc | tggcggaaca | 420 |
| gccgccctgg | gctgcctcgt | gaaggactac | tttcccgagc | ccgtgaccgt | gtcctggaac | 480 |
| tctggcgctc | tgacaagcgg | cgtgcacacc | tttccagccg | tgctgcagag | cagcggcctg | 540 |
| tactctctga | gcagcgtcgt | gacagtgccc | agcagctctc | tgggcaccca | gacctacatc | 600 |
| tgcaacgtga | accacaagcc | cagcaacacc | aaggtggaca | gaaggtgga | acccaagagc | 660 |
| tgcgacggcg | gaggggatc | tggcggcgga | ggatcccagg | tgcaattggt | gcagtctggg | 720 |
| gctgaggtga | agaagcctgg | gtcctcggtg | aaggtctcct | gcaaggcctc | cggaggcaca | 780 |
| ttcagcagct | acgctataag | ctgggtgcga | caggcccctg | acaagggct | cgagtggatg | 840 |
| ggagggatca | tccctatctt | tggtacagca | aactacgcac | agaagttcca | gggcagggtc | 900 |
| accattactg | cagacaaatc | cacgagcaca | gcctacatgg | agctgagcag | cctgagatct | 960 |
| gaggacaccg | ccgtgtatta | ctgtgcgaga | gaatactacc | gtggtccgta | cgactactgg | 1020 |
| ggccaaggga | ccaccgtgac | cgtctcctca | gctagcacca | agggcccatc | ggtcttcccc | 1080 |
| ctggcaccct | cctccaagag | cacctctggg | ggcacagcgg | ccctgggctg | cctggtcaag | 1140 |
| gactacttcc | ccgaaccggt | gacggtgtcg | tggaactcag | gcgccctgac | cagcggcgtg | 1200 |
| cacaccttcc | cggctgtcct | acagtcctca | ggactctact | ccctcagcag | cgtggtgacc | 1260 |
| gtgccctcca | gcagcttggg | cacccagacc | tacatctgca | acgtgaatca | caagcccagc | 1320 |
| aacaccaagg | tggacaagaa | agttgagccc | aaatcttgtg | acaaaactca | cacatgccca | 1380 |
| ccgtgcccag | cacctgaagc | tgcaggggga | ccgtcagtct | tcctcttccc | cccaaaaccc | 1440 |
| aaggacaccc | tcatgatctc | ccggacccct | gaggtcacat | gcgtggtggt | ggacgtgagc | 1500 |
| cacgaagacc | ctgaggtcaa | gttcaactgg | tacgtggacg | gcgtggaggt | gcataatgcc | 1560 |
| aagacaaagc | cgcgggagga | gcagtacaac | agcacgtacc | gtgtggtcag | cgtcctcacc | 1620 |
| gtcctgcacc | aggactggct | gaatggcaag | gagtacaagt | gcaaggtctc | caacaaagcc | 1680 |
| ctcggcgccc | ccatcgagaa | aaccatctcc | aaagccaaag | ggcagccccg | agaaccacag | 1740 |
| gtgtacaccc | tgcccccctg | cagagatgag | ctgaccaaga | accaggtgtc | cctgtggtgt | 1800 |
| ctggtcaagg | gcttctaccc | cagcgatatc | gccgtggagt | gggagagcaa | cggccagcct | 1860 |
| gagaacaact | acaagaccac | ccccctgtg | ctggacagcg | acggcagctt | cttcctgtac | 1920 |
| tccaaactga | ccgtggacaa | gagccggtgg | cagcagggca | acgtgttcag | ctgcagcgtg | 1980 |
| atgcacgagg | ccctgcacaa | ccactacacc | cagaagtccc | tgagcctgag | ccccggcgga | 2040 |
| ggcggcggaa | gcggaggagg | aggatccggt | ggtggcggtt | ccgggggcgg | tggatcgcag | 2100 |
| gtgcaattgg | tgcagtctgg | ggctgaggtg | aagaagcctg | gtcctcggt | gaaggtctcc | 2160 |
| tgcaaggcct | ccggaggcac | attcagcagc | tacgctataa | gctgggtgcg | acaggcccct | 2220 |

```
ggacaagggc tcgagtggat gggagggatc atccctatct ttggtacagc aaactacgca    2280
cagaagttcc agggcagggt caccattact gcagacaaat ccacgagcac agcctacatg    2340
gagctgagca gcctgagatc tgaggacacc gccgtgtatt actgtgcgaa aggtaacttc    2400
tacggtggtc tggactactg gggccaaggg accacagtga ccgtaagctc c             2451
```

<210> SEQ ID NO 219
<211> LENGTH: 642
<212> TYPE: DNA
<213> ORGANISM: Artificial Sequence
<220> FEATURE:
<223> OTHER INFORMATION: Nucleotide sequence LC1 pETR14912 OX40 (49B4)
      VLCL + charges

<400> SEQUENCE: 219

```
gacatccaga tgacccagtc tccttccacc ctgtctgcat ctgtaggaga ccgtgtcacc     60
atcacttgcc gtgccagtca gagtattagt agctggttgg cctggtatca gcagaaacca   120
gggaaagccc ctaagctcct gatctatgat gcctccagtt tggaaagtgg ggtcccatca   180
cgtttcagcg gcagtggatc cgggacagaa ttcactctca ccatcagcag cttgcagcct   240
gatgattttg caacttatta ctgccaacag tatagttcgc agccgtatac gtttggccag   300
ggcaccaaag tcgagatcaa gcgtacggtg gctgcaccat ctgtcttcat cttcccgcca   360
tctgatcgga agttgaaatc tggaactgcc tctgttgtgt gcctgctgaa taacttctat   420
cccagagagg ccaaagtaca gtggaaggtg gataacgccc tccaatcggg taactcccag   480
gagagtgtca cagagcagga cagcaaggac agcacctaca gcctcagcag caccctgacg   540
ctgagcaaag cagactacga aaacacaaa gtctacgcct gcgaagtcac ccatcagggc    600
ctgagctcgc ccgtcacaaa gagcttcaac aggggagagt gt                       642
```

<210> SEQ ID NO 220
<211> LENGTH: 2736
<212> TYPE: DNA
<213> ORGANISM: Artificial Sequence
<220> FEATURE:
<223> OTHER INFORMATION: Nucleotide sequence HC pETR15206 OX40
      (49B4)VHCH1EE_OX40(49B4)VHCH1EE_Fc_PG/LALA_TnC (18D4)VLCH1

<400> SEQUENCE: 220

```
caggtgcagc tggtgcagtc tggcgccgaa gtgaagaaac ccggcagcag cgtgaaggtg     60
tcctgcaagg cttccggcgg caccttcagc agctacgcca tttcttgggt gcgccaggcc   120
cctggacagg gctggaatg gatgggcggc atcatcccca tcttcggcac cgccaactac   180
gcccagaaat ccagggcag agtgaccatc accgccgaca agagcaccag caccgcctac   240
atggaactga gcagcctgcg gagcgaggac accgccgtgt actactgcgc cagagagtac   300
tacagaggcc cctacgacta ctggggccag ggcacaaccg tgaccgtgtc tagcgccagc   360
acaaagggcc cagcgtgtt ccctctggcc cctagcagca gagcacatc tggcggaaca   420 gccgccctgg gctgcctggt ggaagattac ttccccgagc ccgtgacagt gtcctggaac   480
tctggcgccc tgacaagcgg cgtgcacacc tttccagccg tgctgcagag cagcggcctg   540
tactcactgt ccagcgtcgt gactgtgccc agcagcagcc tgggaaccca gacctacatc   600
tgcaacgtga accacaagcc cagcaacacc aaggtggacg agaaggtgga acccaagagc   660
tgcgacggcg gaggcggatc tggcggcgga ggatcccagg tgcagctggt gcagagcgga   720
gctgaagtga aaagcctgg ctcctccgtg aaagtgtctt gtaaagccag cggcggcaca   780
```

```
ttctcatcct acgccatcag ctgggtgcgg caggctccag gccagggact ggaatggatg    840
ggaggaatta tccctatttt tgggacagcc aattatgctc agaaatttca ggggcgcgtg    900
acaattacag ccgacaagtc cacctctaca gcttatatgg aactgtcctc cctgcgctcc    960
gaggatacag ctgtgtatta ttgtgcccgc gagtactacc ggggaccttc gattattgg    1020 ggacagggaa ccacagtgac tgtgtcctcc gctagcacca agggaccttc cgtgtttccc   1080
ctggctccca gctccaagtc tacctctggg gcacagctg ctctgggatg tctggtggaa    1140
gattattttc ctgaacctgt gaccgtgtca tggaacagcg gagccctgac ctccggggtg   1200
cacacattcc ctgctgtgct gcagtcctcc ggcctgtata gcctgagcag cgtcgtgacc   1260
gtgccttcca gctctctggg cacacagaca tatatctgta atgtgaatca caaaccctct   1320
aataccaaag tggatgagaa agtgaacct aagtcctgcg acaagaccca cctgtccc     1380 ccttgtcctg cccctgaagc tgctggcggc ccatctgtgt ttctgttccc cccaaagccc   1440
aaggacaccc tgatgatcag ccggaccccc gaagtgacct gcgtggtggt ggatgtgtcc   1500
cacgaggacc cagaagtgaa gttcaattgg tacgtggacg gcgtggaagt gcacaacgcc   1560
aagaccaagc cgcgggaaga acagtacaac agcacctacc gggtggtgtc cgtgctgaca   1620
gtgctgcacc aggactggct gaacggcaaa gagtacaagt gcaaggtgtc caacaaggcc   1680
ctggagcccc catcgagaa aaccatcagc aaggccaagg ccagccccg cgaacctcag    1740 gtgtacaccc tgcccccaag cagggacgag ctgaccaaga accaggtgtc cctgacctgt   1800
ctcgtgaagg gcttctaccc ctccgatatc gccgtggaat gggagagcaa cggccagccc   1860
gagaacaact acaagaccac ccccctgtg ctggacagcg acggctcatt cttcctgtac    1920
tccaagctga ccgtggacaa gagccggtgg cagcagggca acgtgttcag ctgcagcgtg   1980
atgcacgagg ccctgcacaa ccactacaca cagaagtctc tgagcctgag ccctggcgga   2040 ggggaggat ctggggagg cggaagtggg ggagggggtt ccggaggcgg tggatcggac    2100
atccagatga cccagtctcc atccaccctg tctgcatctg taggagaccg tgtcaccatc   2160
acttgccgtg ccagtcagag tattagtagc tggttggcct ggtatcagca gaaaccaggg   2220
aaagccccta agctcctgat ctatgatgcc tccagtttgg aaagtggggt cccatcacgt   2280
ttcagcggca gtggatccgg gacagaattc actctcacca tcagcagctt gcagcctgat   2340 gatttttgcaa cttattactg ccaacagaat aagaagtttc cttcggggac gtttggccag   2400
ggcaccaaag tcgagatcaa gtctagcgct tccaccaagg cccctcagt gttcccactg    2460 gcaccatcca gcaagtccac aagcggagga accgccgctc tgggctgtct cgtgaaagac   2520
tactttccag agccagtgac cgtgtcctgg aatagtggcg ctctgacttc tggcgtgcac   2580 actttcccg cagtgctgca gagttctggc ctgtactccc tgagtagcgt cgtgacagtg   2640
ccctcctcta gcctgggcac tcagacttac atctgcaatg tgaatcataa gccttccaac   2700 acaaagtgg acaaaaagt ggaacccaaa tcttgc                               2736
```

<210> SEQ ID NO 221
<211> LENGTH: 675
<212> TYPE: DNA
<213> ORGANISM: Artificial Sequence
<220> FEATURE:
<223> OTHER INFORMATION: Nucleotide sequence LC2 pETR15202 TnC (18D4)
      VHCL

<400> SEQUENCE: 221

```
caggtgcaat tggtgcagtc tggggctgag gtgaagaagc ctgggtcctc ggtgaaggtc     60
```

-continued

```
tcctgcaagg cctccggagg cacattcagc agctacgcta taagctgggt gcgacaggcc    120
cctggacaag ggctcgagtg gatgggaggg atcatccccta tctttggtac agcaaactac   180
gcacagaagt tccagggcag ggtcaccatt actgcagaca atccacgag cacagcctac     240 atggagctga gcagcctgag atctgaggac accgccgtgt attactgtgc gaaaggtaac    300
ttctacggtg gtctggacta ctggggccaa gggaccaccg tgaccgtctc ctcagctagc    360
gtggccgctc cctccgtgtt catcttccca ccttccgacg agcagctgaa gtccggcacc    420
gcttctgtcg tgtgcctgct gaacaacttc taccccgcg aggccaaggt gcagtggaag     480
gtggacaacg ccctgcagtc cggcaacagc caggaatccg tgaccgagca ggactccaag   540
gacagcacct actccctgtc ctccaccctg accctgtcca aggccgacta cgagaagcac    600
aaggtgtacg cctgcgaagt gacccaccag ggcctgtcta gccccgtgac caagtctttc    660
aaccggggcg agtgc                                                     675
```

<210> SEQ ID NO 222
<211> LENGTH: 807
<212> TYPE: PRT
<213> ORGANISM: Artificial Sequence
<220> FEATURE:
<223> OTHER INFORMATION: HC1 pETR15193 OX40 (49B4)
    VHCH1_VHCH1_Fc_hole_PG/LALA_TnC (18D4) VL

<400> SEQUENCE: 222

```
Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly
    210                 215                 220

Gly Gly Ser Gly Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
```

```
                  245                 250                 255
Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
            275                 280                 285

Thr Ala Asn Tyr Ala Gln Lys Phe Gln Gly Arg Val Thr Ile Thr Ala
            290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
                340                 345                 350

Thr Lys Gly Pro Ser Val Phe Pro Leu Ala Pro Ser Ser Lys Ser Thr
            355                 360                 365

Ser Gly Gly Thr Ala Ala Leu Gly Cys Leu Val Lys Asp Tyr Phe Pro
        370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Leu Gly Thr Gln Thr Tyr Ile
            420                 425                 430

Cys Asn Val Asn His Lys Pro Ser Asn Thr Lys Val Asp Lys Lys Val
            435                 440                 445

Glu Pro Lys Ser Cys Asp Lys Thr His Thr Cys Pro Pro Cys Pro Ala
450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
            515                 520                 525

Tyr Asn Ser Thr Tyr Arg Val Val Ser Val Leu Thr Val Leu His Gln
            530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
                565                 570                 575

Arg Glu Pro Gln Val Cys Thr Leu Pro Pro Ser Arg Asp Glu Leu Thr
            580                 585                 590

Lys Asn Gln Val Ser Leu Ser Cys Ala Val Lys Gly Phe Tyr Pro Ser
            595                 600                 605

Asp Ile Ala Val Glu Trp Glu Ser Asn Gly Gln Pro Glu Asn Asn Tyr
            610                 615                 620

Lys Thr Thr Pro Pro Val Leu Asp Ser Asp Gly Ser Phe Phe Leu Val
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670
```

Ser Leu Ser Leu Ser Pro Gly Gly Gly Gly Ser Gly Gly Gly
              675                 680                 685

Ser Gly Gly Gly Gly Ser Gly Gly Gly Ser Asp Ile Gln Met Thr
    690                 695                 700

Gln Ser Pro Ser Thr Leu Ser Ala Ser Val Gly Asp Arg Val Thr Ile
705                 710                 715                 720

Thr Cys Arg Ala Ser Gln Ser Ile Ser Ser Trp Leu Ala Trp Tyr Gln
                725                 730                 735

Gln Lys Pro Gly Lys Ala Pro Lys Leu Leu Ile Tyr Asp Ala Ser Ser
                740                 745                 750

Leu Glu Ser Gly Val Pro Ser Arg Phe Ser Gly Ser Gly Ser Gly Thr
                755                 760                 765

Glu Phe Thr Leu Thr Ile Ser Ser Leu Gln Pro Asp Asp Phe Ala Thr
                770                 775                 780

Tyr Tyr Cys Gln Gln Asn Lys Lys Phe Pro Ser Gly Thr Phe Gly Gln
785                 790                 795                 800

Gly Thr Lys Val Glu Ile Lys
                805

<210> SEQ ID NO 223
<211> LENGTH: 817
<212> TYPE: PRT
<213> ORGANISM: Artificial Sequence
<220> FEATURE:
<223> OTHER INFORMATION: HC2 pETR15194 OX40 (49B4)
      VHCH1_VHCH1_Fc_knob_PG/LALA_ TnC (18D4) VH

<400> SEQUENCE: 223

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Lys Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Ser Val Val Thr Val Pro Ser Ser
            180                 185                 190

Ser Leu Gly Thr Gln Thr Tyr Ile Cys Asn Val Asn His Lys Pro Ser
        195                 200                 205

Asn Thr Lys Val Asp Lys Lys Val Glu Pro Lys Ser Cys Asp Gly Gly

```
                210                 215                 220
Gly Gly Ser Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
                260                 265                 270

Pro Gly Gln Gly Leu Glu Trp Met Gly Gly Ile Ile Pro Ile Phe Gly
                275                 280                 285

Thr Ala Asn Tyr Ala Gln Lys Phe Gln Gly Arg Val Thr Ile Thr Ala
290                 295                 300

Asp Lys Ser Thr Ser Thr Ala Tyr Met Glu Leu Ser Ser Leu Arg Ser
305                 310                 315                 320

Glu Asp Thr Ala Val Tyr Tyr Cys Ala Arg Glu Tyr Tyr Arg Gly Pro
                325                 330                 335

Tyr Asp Tyr Trp Gly Gln Gly Thr Thr Val Thr Val Ser Ser Ala Ser
                340                 345                 350

Thr Lys Gly Pro Ser Val Phe Pro Leu Ala Pro Ser Ser Lys Ser Thr
                355                 360                 365

Ser Gly Gly Thr Ala Ala Leu Gly Cys Leu Val Lys Asp Tyr Phe Pro
370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
                420                 425                 430

Cys Asn Val Asn His Lys Pro Ser Asn Thr Lys Val Asp Lys Lys Val
                435                 440                 445

Glu Pro Lys Ser Cys Asp Lys Thr His Thr Cys Pro Pro Cys Pro Ala
                450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
                500                 505                 510

Asp Gly Val Glu Val His Asn Ala Lys Thr Lys Pro Arg Glu Glu Gln
                515                 520                 525

Tyr Asn Ser Thr Tyr Arg Val Val Ser Val Leu Thr Val Leu His Gln
                530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
                565                 570                 575

Arg Glu Pro Gln Val Tyr Thr Leu Pro Pro Cys Arg Asp Glu Leu Thr
                580                 585                 590

Lys Asn Gln Val Ser Leu Trp Cys Leu Val Lys Gly Phe Tyr Pro Ser
                595                 600                 605

Asp Ile Ala Val Glu Trp Glu Ser Asn Gly Gln Pro Glu Asn Asn Tyr
                610                 615                 620

Lys Thr Thr Pro Pro Val Leu Asp Ser Asp Gly Ser Phe Phe Leu Tyr
625                 630                 635                 640
```

-continued

```
Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
                660                 665                 670

Ser Leu Ser Leu Ser Pro Gly Gly Gly Gly Ser Gly Gly Gly Gly
            675                 680                 685

Ser Gly Gly Gly Gly Ser Gly Gly Gly Gly Ser Gln Val Gln Leu Val
690                 695                 700

Gln Ser Gly Ala Glu Val Lys Lys Pro Gly Ser Ser Val Lys Val Ser
705                 710                 715                 720

Cys Lys Ala Ser Gly Gly Thr Phe Ser Ser Tyr Ala Ile Ser Trp Val
                725                 730                 735

Arg Gln Ala Pro Gly Gln Gly Leu Glu Trp Met Gly Gly Ile Ile Pro
                740                 745                 750

Ile Phe Gly Thr Ala Asn Tyr Ala Gln Lys Phe Gln Gly Arg Val Thr
                755                 760                 765

Ile Thr Ala Asp Lys Ser Thr Ser Thr Ala Tyr Met Glu Leu Ser Ser
            770                 775                 780

Leu Arg Ser Glu Asp Thr Ala Val Tyr Tyr Cys Ala Lys Gly Asn Phe
785                 790                 795                 800

Tyr Gly Gly Leu Asp Tyr Trp Gly Gln Gly Thr Thr Val Thr Val Ser
                805                 810                 815

Ser

<210> SEQ ID NO 224
<211> LENGTH: 214
<212> TYPE: PRT
<213> ORGANISM: Artificial Sequence
<220> FEATURE:
<223> OTHER INFORMATION: LC1 pETR14912 OX40 (49B4) VLCL + charges

<400> SEQUENCE: 224

Asp Ile Gln Met Thr Gln Ser Pro Ser Thr Leu Ser Ala Ser Val Gly
1               5                   10                  15

Asp Arg Val Thr Ile Thr Cys Arg Ala Ser Gln Ser Ile Ser Ser Trp
                20                  25                  30

Leu Ala Trp Tyr Gln Gln Lys Pro Gly Lys Ala Pro Lys Leu Leu Ile
            35                  40                  45

Tyr Asp Ala Ser Ser Leu Glu Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Gln Tyr Ser Ser Gln Pro Tyr
                85                  90                  95

Thr Phe Gly Gln Gly Thr Lys Val Glu Ile Lys Arg Thr Val Ala Ala
                100                 105                 110

Pro Ser Val Phe Ile Phe Pro Pro Ser Asp Arg Lys Leu Lys Ser Gly
            115                 120                 125

Thr Ala Ser Val Val Cys Leu Leu Asn Asn Phe Tyr Pro Arg Glu Ala
        130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175
```

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210

<210> SEQ ID NO 225
<211> LENGTH: 912
<212> TYPE: PRT
<213> ORGANISM: Artificial Sequence
<220> FEATURE:
<223> OTHER INFORMATION: HC pETR15206 OX40
      (49B4)VHCH1EE_OX40(49B4)VHCH1EE_Fc_PG/LALA_TnC (18D4)VLCH1

<400> SEQUENCE: 225

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Glu Tyr Tyr Arg Gly Pro Tyr Asp Tyr Trp Gly Gln Gly Thr
            100                 105                 110

Thr Val Thr Val Ser Ser Ala Ser Thr Lys Gly Pro Ser Val Phe Pro
        115                 120                 125

Leu Ala Pro Ser Ser Lys Ser Thr Ser Gly Gly Thr Ala Ala Leu Gly
    130                 135                 140

Cys Leu Val Glu Asp Tyr Phe Pro Glu Pro Val Thr Val Ser Trp Asn
145                 150                 155                 160

Ser Gly Ala Leu Thr Ser Gly Val His Thr Phe Pro Ala Val Leu Gln
                165                 170                 175

Ser Ser Gly Leu Tyr Ser Leu Ser Val Val Thr Val Pro Ser Ser Ser
            180                 185                 190

Ser Leu Gly Thr Gln Thr Tyr Ile Cys Asn Val Asn His Lys Pro Ser
        195                 200                 205

Asn Thr Lys Val Asp Glu Lys Val Glu Pro Lys Ser Cys Asp Gly Gly
    210                 215                 220

Gly Gly Ser Gly Gly Gly Gly Ser Gln Val Gln Leu Val Gln Ser Gly
225                 230                 235                 240

Ala Glu Val Lys Lys Pro Gly Ser Ser Val Lys Val Ser Cys Lys Ala
                245                 250                 255

Ser Gly Gly Thr Phe Ser Ser Tyr Ala Ile Ser Trp Val Arg Gln Ala
            260                 265                 270

Pro Gly Gln Gly Leu Glu Trp Met Gly Gly Ile Ile Pro Ile Phe Gly
        275                 280                 285

Thr Ala Asn Tyr Ala Gln Lys Phe Gln Gly Arg Val Thr Ile Thr Ala
    290                 295                 300

Asp Lys Ser Thr Ser Thr Ala Tyr Met Glu Leu Ser Ser Leu Arg Ser
305                 310                 315                 320

```
Glu Asp Thr Ala Val Tyr Tyr Cys Ala Arg Glu Tyr Arg Gly Pro
            325                 330                 335

Tyr Asp Tyr Trp Gly Gln Gly Thr Thr Val Thr Val Ser Ser Ala Ser
        340                 345                 350

Thr Lys Gly Pro Ser Val Phe Pro Leu Ala Pro Ser Ser Lys Ser Thr
            355                 360                 365

Ser Gly Gly Thr Ala Ala Leu Gly Cys Leu Val Glu Asp Tyr Phe Pro
    370                 375                 380

Glu Pro Val Thr Val Ser Trp Asn Ser Gly Ala Leu Thr Ser Gly Val
385                 390                 395                 400

His Thr Phe Pro Ala Val Leu Gln Ser Ser Gly Leu Tyr Ser Leu Ser
                405                 410                 415

Ser Val Val Thr Val Pro Ser Ser Ser Leu Gly Thr Gln Thr Tyr Ile
            420                 425                 430

Cys Asn Val Asn His Lys Pro Ser Asn Thr Lys Val Asp Glu Lys Val
        435                 440                 445

Glu Pro Lys Ser Cys Asp Lys Thr His Thr Cys Pro Pro Cys Pro Ala
    450                 455                 460

Pro Glu Ala Ala Gly Gly Pro Ser Val Phe Leu Phe Pro Pro Lys Pro
465                 470                 475                 480

Lys Asp Thr Leu Met Ile Ser Arg Thr Pro Glu Val Thr Cys Val Val
                485                 490                 495

Val Asp Val Ser His Glu Asp Pro Glu Val Lys Phe Asn Trp Tyr Val
            500                 505                 510

Asp Gly Val Glu Val His Asn Ala Lys Thr Lys Pro Arg Glu Glu Gln
        515                 520                 525

Tyr Asn Ser Thr Tyr Arg Val Val Ser Val Leu Thr Val Leu His Gln
    530                 535                 540

Asp Trp Leu Asn Gly Lys Glu Tyr Lys Cys Lys Val Ser Asn Lys Ala
545                 550                 555                 560

Leu Gly Ala Pro Ile Glu Lys Thr Ile Ser Lys Ala Lys Gly Gln Pro
                565                 570                 575

Arg Glu Pro Gln Val Tyr Thr Leu Pro Pro Ser Arg Asp Glu Leu Thr
            580                 585                 590

Lys Asn Gln Val Ser Leu Thr Cys Leu Val Lys Gly Phe Tyr Pro Ser
        595                 600                 605

Asp Ile Ala Val Glu Trp Glu Ser Asn Gly Gln Pro Glu Asn Asn Tyr
    610                 615                 620

Lys Thr Thr Pro Pro Val Leu Asp Ser Asp Gly Ser Phe Phe Leu Tyr
625                 630                 635                 640

Ser Lys Leu Thr Val Asp Lys Ser Arg Trp Gln Gln Gly Asn Val Phe
                645                 650                 655

Ser Cys Ser Val Met His Glu Ala Leu His Asn His Tyr Thr Gln Lys
            660                 665                 670

Ser Leu Ser Leu Ser Pro Gly Gly Gly Gly Ser Gly Gly Gly Gly
        675                 680                 685

Ser Gly Gly Gly Gly Ser Gly Gly Gly Gly Ser Asp Ile Gln Met Thr
    690                 695                 700

Gln Ser Pro Ser Thr Leu Ser Ala Ser Val Gly Asp Arg Val Thr Ile
705                 710                 715                 720

Thr Cys Arg Ala Ser Gln Ser Ile Ser Ser Trp Leu Ala Trp Tyr Gln
                725                 730                 735
```

Gln Lys Pro Gly Lys Ala Pro Lys Leu Leu Ile Tyr Asp Ala Ser Ser
                740                 745                 750

Leu Glu Ser Gly Val Pro Ser Arg Phe Ser Gly Ser Gly Ser Gly Thr
            755                 760                 765

Glu Phe Thr Leu Thr Ile Ser Ser Leu Gln Pro Asp Asp Phe Ala Thr
770                 775                 780

Tyr Tyr Cys Gln Gln Asn Lys Lys Phe Pro Ser Gly Thr Phe Gly Gln
785                 790                 795                 800

Gly Thr Lys Val Glu Ile Lys Ser Ser Ala Ser Thr Lys Gly Pro Ser
                805                 810                 815

Val Phe Pro Leu Ala Pro Ser Ser Lys Ser Thr Ser Gly Gly Thr Ala
            820                 825                 830

Ala Leu Gly Cys Leu Val Lys Asp Tyr Phe Pro Glu Pro Val Thr Val
        835                 840                 845

Ser Trp Asn Ser Gly Ala Leu Thr Ser Gly Val His Thr Phe Pro Ala
    850                 855                 860

Val Leu Gln Ser Ser Gly Leu Tyr Ser Leu Ser Ser Val Val Thr Val
865                 870                 875                 880

Pro Ser Ser Ser Leu Gly Thr Gln Thr Tyr Ile Cys Asn Val Asn His
                885                 890                 895

Lys Pro Ser Asn Thr Lys Val Asp Lys Lys Val Glu Pro Lys Ser Cys
            900                 905                 910

<210> SEQ ID NO 226
<211> LENGTH: 225
<212> TYPE: PRT
<213> ORGANISM: Artificial Sequence
<220> FEATURE:
<223> OTHER INFORMATION: LC2 pETR15202 TnC (18D4) VHCL

<400> SEQUENCE: 226

Gln Val Gln Leu Val Gln Ser Gly Ala Glu Val Lys Lys Pro Gly Ser
1               5                   10                  15

Ser Val Lys Val Ser Cys Lys Ala Ser Gly Gly Thr Phe Ser Ser Tyr
            20                  25                  30

Ala Ile Ser Trp Val Arg Gln Ala Pro Gly Gln Gly Leu Glu Trp Met
        35                  40                  45

Gly Gly Ile Ile Pro Ile Phe Gly Thr Ala Asn Tyr Ala Gln Lys Phe
    50                  55                  60

Gln Gly Arg Val Thr Ile Thr Ala Asp Lys Ser Thr Ser Thr Ala Tyr
65                  70                  75                  80

Met Glu Leu Ser Ser Leu Arg Ser Glu Asp Thr Ala Val Tyr Tyr Cys
                85                  90                  95

Ala Lys Gly Asn Phe Tyr Gly Leu Asp Tyr Trp Gly Gln Gly Thr
            100                 105                 110

Thr Val Thr Val Ser Ser Ala Ser Val Ala Ala Pro Ser Val Phe Ile
        115                 120                 125

Phe Pro Pro Ser Asp Glu Gln Leu Lys Ser Gly Thr Ala Ser Val Val
    130                 135                 140

Cys Leu Leu Asn Asn Phe Tyr Pro Arg Glu Ala Lys Val Gln Trp Lys
145                 150                 155                 160

Val Asp Asn Ala Leu Gln Ser Gly Asn Ser Gln Glu Ser Val Thr Glu
                165                 170                 175

Gln Asp Ser Lys Asp Ser Thr Tyr Ser Leu Ser Ser Thr Leu Thr Leu
            180                 185                 190

```
Ser Lys Ala Asp Tyr Glu Lys His Lys Val Tyr Ala Cys Glu Val Thr
            195                 200                 205

His Gln Gly Leu Ser Ser Pro Val Thr Lys Ser Phe Asn Arg Gly Glu
    210                 215                 220

Cys
225
```